US012479854B2

(12) United States Patent
Shen et al.

(10) Patent No.: US 12,479,854 B2
(45) **Date of Patent: *Nov. 25, 2025**

(54) SPIROPYRROLIDINE DERIVED ANTIVIRAL AGENTS

(71) Applicant: Enanta Pharmaceuticals, Inc., Watertown, MA (US)

(72) Inventors: Ruichao Shen, Belmont, MA (US); Yong He, Lexington, MA (US); Xuechao Xing, Wilmington, MA (US); Matthew C. Rhodes, Boston, MA (US); Joseph D. Panarese, Newton, MA (US); Samuel Bartlett, Brighton, MA (US); Wei Li, Lexington, MA (US); Hui Cao, Belmont, MA (US); Jiajun Zhang, Cambridge, MA (US); Xiaowen Peng, Sudbury, MA (US); Guoqiang Wang, Belmont, MA (US); Yat Sun Or, Waltham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 896 days.

This patent is subject to a terminal disclaimer.

(21) Appl. No.: 17/720,603

(22) Filed: Apr. 14, 2022

(65) Prior Publication Data

US 2023/0122228 A1 Apr. 20, 2023

Related U.S. Application Data

(63) Continuation-in-part of application No. 17/479,248, filed on Sep. 20, 2021, now Pat. No. 11,325,916.

(60) Provisional application No. 63/324,367, filed on Mar. 28, 2022, provisional application No. 63/227,206, filed on Jul. 29, 2021.

(51) Int. Cl.

| | |
|---|---|
| ***C07D 487/10*** | (2006.01) |
| ***A61K 9/00*** | (2006.01) |
| ***A61P 11/00*** | (2006.01) |
| ***A61P 31/14*** | (2006.01) |

(52) U.S. Cl.

CPC .......... *C07D 487/10* (2013.01); *A61K 9/0019* (2013.01); *A61K 9/0073* (2013.01); *A61P 11/00* (2018.01); *A61P 31/14* (2018.01)

(58) Field of Classification Search

CPC ...... A61K 31/404; A61P 31/14; C07D 487/10

See application file for complete search history.

(56) References Cited

U.S. PATENT DOCUMENTS

| | | | |
|---|---|---|---|
| 8,088,815 | B2 | 1/2012 | Bartkovitz et al. |
| 8,222,288 | B2 | 7/2012 | Wang et al. |
| 8,222,425 | B2 | 7/2012 | Britt et al. |
| 8,372,802 | B2 | 2/2013 | Gai et al. |
| 8,546,416 | B2 | 10/2013 | Ambarkhane et al. |
| 9,290,757 | B2 | 3/2016 | Madison |
| 9,309,284 | B2 | 4/2016 | Chang et al. |
| 9,428,739 | B2 | 8/2016 | Colt et al. |
| 9,474,759 | B2 | 10/2016 | Chang et al. |
| 9,591,858 | B2 | 3/2017 | Valles et al. |
| 9,828,342 | B2 | 11/2017 | Home et al. |
| 9,975,885 | B2 | 5/2018 | St. John et al. |
| 10,017,463 | B2 | 7/2018 | Hedstrom et al. |
| 10,023,879 | B2 | 7/2018 | Flynn et al. |
| 10,093,915 | B2 | 10/2018 | Wu et al. |
| 10,130,701 | B2 | 11/2018 | Bickerton et al. |
| 10,196,444 | B2 | 2/2019 | Jarjour et al. |
| 10,590,084 | B2 | 3/2020 | Buckman et al. |
| 10,934,261 | B2 | 3/2021 | Buckman et al. |
| 10,959,969 | B1 | 3/2021 | Johnson |
| 11,013,779 | B2 | 5/2021 | Chang et al. |
| 11,021,513 | B2 | 6/2021 | Schinazi et al. |

(Continued)

FOREIGN PATENT DOCUMENTS

| | | | |
|---|---|---|---|
| CN | 114057624 | A | 2/2022 |
| CN | 115894504 | A | 4/2023 |

(Continued)

OTHER PUBLICATIONS

PubChem, SID 332063528, Deposited Apr. 10, 2017. [Retrieved on Feb. 21, 2024] online at https://pubchem.ncbi.nlm.nih.gov/substance/332063528.

(Continued)

*Primary Examiner* — Theodore R. Howell

(74) *Attorney, Agent, or Firm* — Edgar W. Harlan; Carolyn S. Elmore; Elmore Patent Law Group, P.C.

(57) ABSTRACT

The present invention discloses compounds of Formula (I), and pharmaceutically acceptable salts, thereof:

(I)

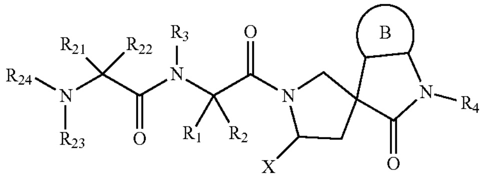

which inhibit coronavirus replication activity. The invention further relates to pharmaceutical compositions comprising a compound of Formula (I) or a pharmaceutically acceptable salt thereof, and methods of treating or preventing a coronavirus infection in a subject in need thereof, comprising administering to the subject a therapeutically effective amount of a compound of Formula (I) or a pharmaceutically acceptable salt thereof.

22 Claims, No Drawings

(56) References Cited

U.S. PATENT DOCUMENTS

| | | | |
|---|---|---|---|
| 11,033,600 | B2 | 6/2021 | Chang et al. |
| 11,045,546 | B1 | 6/2021 | Kelly et al. |
| 11,058,763 | B2 | 7/2021 | Zhang et al. |
| 11,058,779 | B2 | 7/2021 | Lu et al. |
| 11,124,497 | B1 | 9/2021 | Arnold et al. |
| 11,174,231 | B1 | 11/2021 | Arnold et al. |
| 11,207,370 | B2 | 12/2021 | Schinazi et al. |
| 11,319,325 | B1 | 5/2022 | Zhang et al. |
| 11,325,916 | B1 | 5/2022 | Shen et al. |
| 11,339,170 | B1 | 5/2022 | Gao et al. |
| 11,352,363 | B1 | 6/2022 | Wang et al. |
| 11,358,953 | B2 | 6/2022 | Panarese et al. |
| 11,384,090 | B2 | 7/2022 | Wang et al. |
| 11,858,945 | B2 | 1/2024 | Panarese et al. |
| 11,912,714 | B2 | 2/2024 | Cao et al. |
| 11,919,910 | B2 | 3/2024 | Wang et al. |
| 2005/0143320 | A1 | 6/2005 | Yang et al. |
| 2006/0014821 | A1 | 1/2006 | He et al. |
| 2008/0125430 | A1 | 5/2008 | Wang et al. |
| 2009/0137818 | A1 | 5/2009 | Hilgenfeld et al. |
| 2010/0272681 | A1 | 10/2010 | Farmer et al. |
| 2010/0317661 | A1 | 12/2010 | Wang et al. |
| 2013/0072500 | A1 | 3/2013 | Banka et al. |
| 2013/0072686 | A1 | 3/2013 | Cadieux et al. |
| 2013/0172327 | A1 | 7/2013 | Grundl et al. |
| 2014/0148494 | A1 | 5/2014 | Wang et al. |
| 2014/0243341 | A1 | 8/2014 | Chang et al. |
| 2014/0378680 | A1 | 12/2014 | Wang et al. |
| 2015/0133368 | A1 | 5/2015 | Chang et al. |
| 2015/0336928 | A1 | 11/2015 | Fang et al. |
| 2016/0014821 | A1 | 1/2016 | Toebes |
| 2017/0044183 | A1 | 2/2017 | Lim et al. |
| 2017/0066718 | A1 | 3/2017 | Takahashi et al. |
| 2020/0230198 | A1 | 7/2020 | Chang et al. |
| 2021/0355111 | A1 | 11/2021 | Arnold et al. |
| 2022/0033383 | A1 | 2/2022 | Panarese et al. |
| 2022/0041652 | A1 | 2/2022 | Panarese et al. |
| 2022/0048944 | A1 | 2/2022 | Panarese et al. |
| 2022/0162216 | A1 | 5/2022 | Wang et al. |
| 2022/0162231 | A1 | 5/2022 | Wang et al. |
| 2022/0380377 | A1 | 12/2022 | Zhang et al. |
| 2022/0402926 | A1 | 12/2022 | Zhang et al. |
| 2023/0051320 | A1 | 2/2023 | Ren et al. |
| 2023/0103494 | A1 | 4/2023 | Wang et al. |
| 2023/0115107 | A1 | 4/2023 | Gao et al. |
| 2023/0122228 | A1 | 4/2023 | Shen et al. |
| 2023/0151019 | A1 | 5/2023 | Cao et al. |
| 2023/0159545 | A1 | 5/2023 | Panarese et al. |
| 2023/0159546 | A1 | 5/2023 | Kass et al. |
| 2023/0174531 | A1 | 6/2023 | Panarese et al. |
| 2023/0174542 | A1 | 6/2023 | Panarese et al. |
| 2023/0203048 | A1 | 6/2023 | Wang et al. |
| 2023/0295175 | A1 | 9/2023 | Zhu et al. |
| 2023/0331734 | A1 | 10/2023 | Cao et al. |
| 2024/0132512 | A1 | 4/2024 | Zhu et al. |
| 2024/0327334 | A1 | 10/2024 | Gao et al. |

FOREIGN PATENT DOCUMENTS

| | | | |
|---|---|---|---|
| EP | 4159211 | A1 | 4/2023 |
| EP | 4209494 | A1 | 7/2023 |
| GB | 2595975 | A | 12/2021 |
| WO | 0059929 | A1 | 10/2000 |
| WO | 0208244 | A2 | 1/2002 |
| WO | 2004101742 | A3 | 6/2005 |
| WO | 2005113580 | A1 | 12/2005 |
| WO | 2006061714 | A2 | 6/2006 |
| WO | 2006061714 | A3 | 8/2006 |
| WO | 2007038138 | A2 | 4/2007 |
| WO | 2008144507 | A2 | 11/2008 |
| WO | 2012099454 | A1 | 7/2012 |
| WO | 2013049382 | A1 | 5/2013 |
| WO | 2013166319 | A1 | 11/2013 |
| WO | 2017222935 | A1 | 12/2017 |
| WO | 2018023054 | A1 | 2/2018 |
| WO | 2018042343 | A2 | 3/2018 |
| WO | 2019086142 | A1 | 5/2019 |
| WO | 2020221826 | A1 | 11/2020 |
| WO | 2021205296 | A1 | 10/2021 |
| WO | 2021206876 | A1 | 10/2021 |
| WO | 2021206877 | A1 | 10/2021 |
| WO | 2021207409 | A2 | 10/2021 |
| WO | 2021226546 | A1 | 11/2021 |
| WO | 2021250648 | A1 | 12/2021 |
| WO | 2021252491 | A1 | 12/2021 |
| WO | 2021252644 | A1 | 12/2021 |
| WO | 2022013684 | A1 | 1/2022 |
| WO | 2022020242 | A1 | 1/2022 |
| WO | 2022020711 | A1 | 1/2022 |
| WO | 2022021841 | A1 | 2/2022 |
| WO | 2022070048 | A1 | 4/2022 |
| WO | 2022109363 | A1 | 5/2022 |
| WO | 2022159644 | A1 | 7/2022 |
| WO | 2022235605 | A1 | 11/2022 |
| WO | 2022251615 | A1 | 12/2022 |
| WO | 2022256434 | A1 | 12/2022 |
| WO | 2023086350 | A1 | 5/2023 |
| WO | 2023086400 | A1 | 5/2023 |
| WO | 2023109926 | A1 | 6/2023 |
| WO | 2023125825 | A1 | 7/2023 |
| WO | 2024076680 | A1 | 4/2024 |

OTHER PUBLICATIONS

U.S. Appl. No. 18/372,732, filed Sep. 26, 2023.

Cao, Hui et al., U.S. Appl. No. 17/983,501, filed Nov. 9, 2022.

Gao, X. et al., U.S. Appl. No. 17/720,654, filed Apr. 14, 2022.

Kass, Jorden et al., U.S. Appl. No. 17/989,103, filed Nov. 17, 2022.

Panarese, Joseph D. et al., U.S. Appl. No. 17/983,484, filed Nov. 9, 2022.

Panarese, Joseph D. et al., U.S. Appl. No. 18/075,567, filed Dec. 6, 2022.

Panarese, Joseph D. et al., U.S. Appl. No. 18/102,850, filed Jan. 30, 2023.

PubChem, SID 160923150, deposited Mar. 4, 2013.

PubChem, SID 267351747, deposited Dec. 11, 2015.

Shen, Ruichao et al., U.S. Appl. No. 17/479,248, filed Sep. 20, 2021.

Wang, Guoqiang et al., U.S. Appl. No. 17/531,874, filed Nov. 22, 2021.

Wang, Guoqiang et al., U.S. Appl. No. 17/983,474, filed Nov. 9, 2022.

Zhang, Jiajun et al., U.S. Appl. No. 17/479,669, filed Sep. 20, 2021.

PubChem, SID 367622864, May 25, 2018.

PubChem, SID 326247498, deposited Jan. 25, 2017, 1-7.

Anonymous, "Nirmatrelvir", Cortellis Database, Retrieved from the Internet: URL:https://www.cortellis.com/drugdiscovery/entity/drug/1126756/product?ent=qR5ruNw5&updateHistoryPage=5&orderBy=_score:desc, Nov. 8, 2022, 3 pgs.

Anonymous, "Pfizer Initiates Phase 1 Study of Novel Oral Antiviral Therapeutic Agent Against SARS-CoV-2 Science Products Stories Newsroom About", Retrieved from the Internet: URL:https://www.pfizer.com/news/press-release/press-release-detail/pfizer-initiatesphase-1-study-novel-oral-antiviral [retrieved on Nov. 11, 2022] 9 pgs.

Chia, C.S. B. "Novel Coronavirus Main Protease Di- and Tripeptide Inhibitors for Treating COVID-19", ACS Med. Chem. Lett., 13(9), URL:https://pubs.acs.org/doi/pdf/10.1021/acsmedchemlett.2c00332, Aug. 8, 2022, 1388-1389.

Chuck, C-P et al., "Design, synthesis and crystallographic analysis of nitrile-based broad-spectrum peptidomimetic inhibitors for coronavirus 3C-like proteases", Euro. J. Med. Chem., 59, https://doi.org/10.1016/j.ejmech.2012.10.053, Jan. 2013, 1-6.

Efremov, I. et al., "Discovery and Optimization of a Novel Spiropyrrolidine Inhibitor of B-Secretase (BACE1) through Fragment-Based Drug Design", J. Med. Chem., vol. 55, Apr. 2, 2012, 9069-9088.

Halford, B. "Pfizer unveils its oral SARS-00V-2 inhibitor—The antiviral candidate is the first orally administered compound to enter clinical trials that targets the virus's main protease", Chem. & Eng. News, online at https://cen.acs.org/acs-news/acs-meeting-news/Pfizer-unveils-oral-SARS-CoV/99/i13, (a version appeared in 99(13)), Apr. 7, 2021, 2 pgs.

(56) References Cited

OTHER PUBLICATIONS

Halford, B. "Pfizer's novel COVID-19 antiviral heads to clinical trials—The small molecule targets coronavirus 3CL protease and is active against multiple coronaviruses in cell studies", Chem. & Eng. News, online at https://cen.acs.org/pharmaceuticals/drug-discovery/Pfizers-novel-COVID-19-antiviral/98/web/2020/09, Sep. 17, 2020, 2 pgs.
Kelemen, A. et al., "Spiro[pyrrolidine-3,3'-oxindoles] and Their Indoline Analogues as New 5-HT6 Receptor Chemotypes", Molecules, 22, DOI: 10.3390/molecules22122221, Dec. 14, 2017, 1-25.
Konno, S. et al., "3CL Protease Inhibitors with an Electrophilic Arylketone Moiety as Anti-SARS-CoV-2 Agents", J. Medicinal Chemistry, https://doi.org/10.1021/acs.jmedchem.1c00665, Jul. 27, 2021, pp. 1-14.
Lee., C. et al., "Structural Basis of Inhibition Specificities of 3C and 3C-like Proteases by Zinc-coordinating and Peptidomimetic Compounds", J. Biological Chem., 284(12), Mar. 20, 2009, 7646-7655.
Mandadapu, S. et al., "Macrocyclic Inhibitors of 3c and 3C-Like Proteases of Picornavirus, Norovirus, and Coronavirus", Bioorg. & Med. Chem. Lett., 23, http:lfdx.doi.org/10.1016/j.bmcl.2013.05.021, May 16, 2013, 3709-3712.
Marti, Christiane "Novel Approach to Spiro-Pyrrolidine-Oxindoles and its Application to the Synthesis of (+−)-Horsfiline and (−)-Spirotryprostatin", ETH Library, Doctoral Thesis, https://doi.org/10.3929/ethz-a-004489068, 2003, 1-2, 23-25.
Owen, D. "Oral inhibitors of the 1-12 SARS-CoV-2 main protease for the treatment of COVID-19", 261st Am. Chem. Soc. (ACS) Natl Meet, Apr. 16, 2021, 1 pg.
Thanigaimalai, P. et al., "Design, synthesis, and biological evaluation of novel dipeptide-type SARS-CoV 3CL protease inhibitors: Structure-activity relationship study", Euro J. Med. Chem., 65, DOI: 10.1016/J.EJMECH.2013.05.005, May 20, 2013, 436-447.
Wang, Y. et al., "Inhibition of Enterovirus 71 Replication by an a-Hydroxy-Nitrile Derivative NK-1.9k", Antiviral Res., 141, Jan. 5, 2017, 91-100.
Xu, J. et al., "Green Oxidation of Indoles Using Halide Catalysis", Nature Communications, 10:4754, https://doi.org/10.1038/s41467-019-12768-4, Oct. 18, 2019, 1-11.
Yang, S. et al., "Synthesis, Crystal Structure, Structure-Activity Relationships, and Antiviral Activity of a Potent SARS Coronavirus 3CL Protease Inhibitor", J. Med. Chem., 49, Jul. 14, 2006, 4971-4980.
Zhang, L. et al., "a-Ketoamides as Broad-Spectrum Inhibitors of Coronavirus and Enterovirus Replication: Structue-Based Design, Synthesis, and Activity Assessment", J. Med. Chem., 63, https://dx.doi.org/10.1021/acs,jmedchem.9b01828, 2020, 4562-4578.
Zhou, L. et al., "An Overview of Spirooxindole as a Promising Scaffold for Novel Drug Discovery", Expert Opinion on Drug Discovery, 15(5), Feb. 2020, 603-625.
Ziarani, G. et al., "Synthesis of Spiro-Fused Heterocyclic Scaffolds Through Multicomponent Reactions Involving Isatin", ARKIVOC, 2016 (i), http://dx.doi.org/10.3998/ark.5550190.p009.385, 2016, 1, 14-16.
"1-(2-oxospiro[1H-indole-3,3'-pyrrolidine]-1'-yl)-4-pyridin-2-ylbutane-1,4-dione", Pubchem CID 145894940. Create Date: Feb. 12, 2020. Date Accessed: Jun. 9, 2023, 2 pgs.
Bafna, K. , et al., "Structural Similarity of SARS-CoV2 Mpro and HCV NS3/4A Proteases Suggests New Approaches for Identifying Existing Drugs Useful as COVID-19 Therapeutics", , ChemRxiv online at DOI: 10.26434/chem rxiv.12153615. v1.
Baker, J. D, et al., "A drug repurposing screen identifies hepatitis C antivirals as inhibitors of the SARS-CoV-2 main 1 protease", BioRxiv. Preprint. avail at https://doi.org/10.1101/2020.07.10.197889, Jul. 10, 2020.
Dai, W. , et al., "Structure-based design of antiviral drug candidates targeting the SARS-CoV-2 main protease", Science, 368(6497), DOI: 10.1126/science. abb4489, 1331-1334.
Owen, D. R, et al., "An oral SARS-CoV-2 Mpro inhibitor clinical candidate for the treatment of COVID-19", Science, 374(6575), doi: 10.1126/science.abl4784, Dec. 24, 2021, 1586-1593.
Vandyck, K. , et al., "Considerations for the discovery and development of 3-chymotrypsin-like cysteine protease inhibitors targeting SARS-CoV-2 infection", Current Opinion in Virology, 49, DOI: 10.1016/j.coviro.2021.04.006, 36-40.
Zhai, Y. , et al., "Cyanohydrin as an Anchoring Group for Potent and Selective Inhibitors of Enterovirus 71 3C Protease", J. Med. Chem., 58, 9414-9420.
Chen, L. , et al., "Design, Synthesis, Characterization, and Biological Activities of Novel Spirooxindole Analogues Containing Hydantoin, Thiohydantoin, Urea, and Thiourea Moieties", J. Agric. Food Chem., 68(39)https://doi.org/10.1021/acs.jafc.0c04488, 10618-10625.
U.S. Appl. No. 18/654,530, filed May 3, 2024.
U.S. Appl. No. 18/402,901, filed Jan. 3, 2024.
U.S. Appl. No. 18/390,287, filed Dec. 20, 2023.
Pellegrini, "Synthesis of the Oxindole Alkaloid (—)-Horsfiline", Tetrahedron Asymmetry 5(10), Oct. 1994, 1979-1992.

SPIROPYRROLIDINE DERIVED ANTIVIRAL AGENTS

RELATED APPLICATIONS

This application is a continuation-in-part of U.S. application Ser. No. 17/479,248, filed on Sep. 20, 2021, which claims the benefit of U.S. Provisional Application No. 63/227,206, filed on Jul. 29, 2021. This application also claims priority to U.S. Provisional Application No. 63/324,367, filed on Mar. 28, 2022. The entire teachings of the above applications are incorporated herein by reference.

TECHNICAL FIELD

The invention relates to compounds and methods of inhibiting coronavirus replication activity by contacting the 3C-Like protease (sometimes referred to as "3CLpro", "Main protease", or "Mpro") with a therapeutically effective amount of a 3C-Like protease inhibitor. The invention further relates to pharmaceutical compositions containing the coronavirus 3C-Like protease inhibitor in a mammal by administering effective amounts of such coronavirus 3C-Like protease inhibitor.

BACKGROUND OF THE INVENTION

Coronaviruses are family of single-stranded, positive-strand RNA viruses with viral envelopes, classified within the Nidovirales order. The coronavirus family comprises pathogens of humans and many animal species, including horses, cattle, pigs, birds, cats and monkeys, and have been known for more than 60 years. The isolation of the prototype murine coronavirus strain JHM, for example, was reported in 1949. Coronaviruses are common viruses that generally cause mild to moderate upper-respiratory tract illnesses in humans and are named for the crown-like spikes on their envelope surface. There are four major sub-groups known as alpha, beta, gamma and delta coronaviruses, with the first coronaviruses identified in the mid-1960s. The coronaviruses known to infect humans include alpha coronaviruses 229E and NL63; and beta coronaviruses OC43, HKU1, SARS-CoV (the coronavirus that causes severe acute respiratory syndrome, or SARS), and MERS-CoV (the coronavirus that causes Middle East Respiratory Syndrome, or MERS). People are commonly infected with human coronaviruses 229E, NL63, 0C43 and HKU1, and symptoms usually include mild to moderate upper-respiratory tract illnesses of short duration, such as runny nose, cough, sore throat and fever. Occasionally human coronaviruses result in lower-respiratory tract illnesses, such as pneumonia, although this is more common in people with cardiopulmonary disease or compromised immune systems, or in the elderly. Transmission of the common human coronaviruses is not fully understood. However, it is likely that human coronaviruses spread from an infected person to others through the air by coughing and sneezing, and through close personal contact, such as touching or shaking hands. These viruses may also spread by touching contaminated objects or surfaces then touching the mouth, nose, or eyes.

Coronaviruses are enveloped, positive-sense, single-stranded RNA viruses. The genomic RNA of CoVs has a 5'-cap structure and 3'-poly-A tail and contains at least 6 open reading frames (ORFs). The first ORF (ORF 1a/b) directly translates two polyproteins: pp1a and pp1ab. These polyproteins are processed by papain-like proteases and a 3C-Like protease (3CLpro), also known as the main protease (Mpro), into 16 non-structural proteins. These non-structural proteins engage in the production of subgenomic RNAs that encode four structural proteins, namely envelope, membrane, spike, and nucleocapsid proteins, among other accessory proteins. As a result, it is understood that 3C-Like protease has a critical role in the coronavirus life cycle.

3CLpro is a cysteine protease involved in most cleavage events within the precursor polyprotein. Active 3CLpro is a homodimer containing two protomers and features a Cys-His dyad located in between domains I and II. 3CLpro is conserved among coronaviruses and several common features are shared among the substrates of 3CLpro in different coronaviruses. As there is no human homolog of 3CLpro, it is an ideal antiviral target. Although compounds have been reported to inhibit 3CLpro activity, they have not been approved as coronavirus therapies. (Refer to WO2004101742 A2, US 2005/0143320 A1, US 2006/0014821 A1, US 2009/0137818 A1, WO2013/049382 A2, WO2013/166319 A1, WO2018042343, WO2018023054, WO2005113580, and WO2006061714).

More effective therapies for coronavirus infections are needed due to this high unmet clinical need. This invention provides compounds which inhibit the coronavirus lifecycle and methods for preparation and use of these compounds. These compounds are useful for treating or preventing coronavirus infections and decreasing occurrence of disease complications such as organ failure or death.

SUMMARY OF THE INVENTION

The present invention relates to novel antiviral compounds, pharmaceutical compositions comprising such compounds, as well as methods to treat or prevent viral (particularly coronavirus) infection in a subject in need of such therapy with said compounds. Compounds of the present invention inhibit the protein(s) encoded by a coronavirus or interfere with the life cycle of a coronavirus and are also useful as antiviral agents. In addition, the present invention provides processes for the preparation of said compounds.

The present invention provides compounds represented by Formula (I), and pharmaceutically acceptable salts, esters and prodrugs thereof, (I)

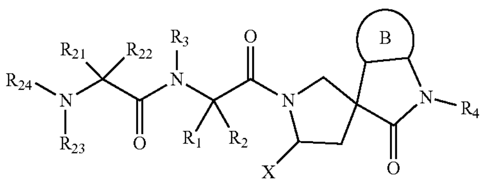

wherein:

$R_1$, $R_2$, $R_3$, $R_{21}$, $R_{22}$, and $R_{23}$ are each independently selected from:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

Alternatively, $R_1$ and $R_2$ are taken together with the carbon atom to which they are attached to form an optionally substituted 3- to 8-membered carbocyclic ring or an optionally substituted 3- to 8-membered heterocyclic ring.

Alternatively, $R_1$ and $R_3$ are taken together with the atoms to which they are attached to form an optionally substituted 3- to 8-membered heterocyclic ring.

Alternatively, $R_{21}$ and $R_3$ are taken together with the intervening atoms to form an optionally substituted 4- to 8-membered heterocyclic ring.

Alternatively, $R_{22}$ is absent and $R_{21}$ and $R_3$ are taken together with the intervening atoms to form an optionally substituted 4- to 8-membered partially unsaturated heterocyclic ring or an optionally substituted 5- to 6-membered heteroaryl ring.

Alternatively, $R_{21}$ and $R_{22}$ are taken together with the carbon atom to which they are attached to form an optionally substituted 3- to 8-membered carbocyclic ring or an optionally substituted 3- to 8-membered heterocyclic ring.

$R_{24}$ is selected from:
1) —C(O)$R_{25}$;
2) —C(O)O$R_{25}$;
3) —C(O)N$R_{13}R_{14}$;
4) —S$(O)_2R_{25}$;
5) Hydrogen;
6) Optionally substituted —$C_1$-$C_8$ alkyl;
7) Optionally substituted —$C_2$-$C_8$ alkenyl;
8) Optionally substituted —$C_2$-$C_8$ alkynyl;
9) Optionally substituted —$C_3$-$C_{12}$ cycloalkyl;
10) Optionally substituted 3- to 12-membered heterocycloalkyl;
11) Optionally substituted aryl;
12) Optionally substituted arylalkyl;
13) Optionally substituted heteroaryl;
14) Optionally substituted heteroarylalkyl;
15) —(CO)(CO)N$R_{13}R_{14}$;
16) —(CO)(CO)$R_{25}$;
17) —S$(O)_2$N$R_{13}R_{14}$;
18) —C(S)$R_{25}$; and
19) —C(S)N$R_{13}R_{14}$;

Alternatively, $R_{23}$ and $R_{24}$ are taken together with the nitrogen atom to which they are attached to form an optionally substituted 3- to 12-membered heterocyclic ring, or an optionally substituted 5- to 12-membered heteroaryl ring;

$R_{25}$ is selected from:
1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_{12}$ cycloalkyl;
5) Optionally substituted 3- to 12-membered heterocycloalkyl;
6) Optionally substituted aryl;
7) Optionally substituted arylalkyl;
8) Optionally substituted heteroaryl; and
9) Optionally substituted heteroarylalkyl;

$R_4$ is hydrogen, optionally substituted —$C_1$-$C_4$ alkyl, optionally substituted —$C_2$-$C_4$ alkenyl, optionally substituted —$C_3$-$C_6$ cycloalkyl, optionally substituted arylalkyl, optionally substituted heteroarylalkyl, halogen, —CN, —OH, or a prodrug moiety;

B is an optionally substituted aryl or optionally substituted heteroaryl;

alternatively, one of $R_{21}$ and $R_{24}$ is L-, wherein L is a saturated or unsaturated linker of 4 to 20 atoms in length which is attached to B;

X is selected from:
1) —CN;
2) —C(O)$R_{15}$;
3) —CH(OH)S$O_3R_{16}$;
4) —C(O)N$R_{13}R_{14}$;
5) —C(O)C(O)N$R_{13}R_{14}$;
6) —CH═CH—C(O)O$R_{25}$,
7) —CH═CH—C(O)N$R_{13}R_{14}$,
8) —CH═CH—S$(O)_2$N$R_{13}R_{14}$,
9) —B$(OR_{13})_2$;
10) —C≡C$R_{13}$;
11) —C≡C—C(O)O$R_{25}$;
12) —C≡C—C(O)N$R_{13}R_{14}$;
13) —C≡C—S$(O)_2$N$R_{13}R_{14}$;
14) —$(CR_{13}R_{14})_w$—CN; and
15) —$(CR_{13}R_{14})_w$—(C═O)—$R_{25}$;

w is 1, 2, 3, 4, or 5;

$R_{13}$ and $R_{14}$ each independently selected from:
1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

Alternatively, $R_{13}$ and $R_{14}$ are taken together with the nitrogen atom to which they are attached to form an optionally substituted 3- to 8-membered heterocyclic ring;

$R_{15}$ is hydrogen, hydroxy, optionally substituted —$C_1$-$C_8$ alkyl, optionally substituted aryl, optionally substituted heteroaryl, optionally substituted arylalkyl or optionally substituted heteroarylalkyl; and $R_{16}$ is hydrogen or $Na^+$.

DETAILED DESCRIPTION OF THE INVENTION

In one embodiment of the present invention is a compound of Formula (I) as described above, or a pharmaceutically acceptable salt thereof.

In certain embodiments of the compounds of Formula (I), $R_4$ is hydrogen, optionally substituted —$C_1$-$C_4$ alkyl, optionally substituted —$C_2$-$C_4$ alkenyl, or optionally substituted —$C_3$-$C_6$ cycloalkyl; X is selected from:
1) —CN;
2) —C(O)$R_{15}$;
3) —CH(OH)S$O_3R_{16}$;
4) —C(O)N$R_{13}R_{14}$; and
5) —C(O)C(O)N$R_{13}R_{14}$;

$R_{24}$ is selected from:
1) —C(O)$R_{25}$;
2) —C(O)O$R_{25}$;
3) —C(O)N$R_{13}R_{14}$;
4) —S$(O)_2R_{25}$;
5) Hydrogen;
6) Optionally substituted —$C_1$-$C_8$ alkyl;
7) Optionally substituted —$C_2$-$C_8$ alkenyl;
8) Optionally substituted —$C_2$-$C_8$ alkynyl;
9) Optionally substituted —$C_3$-$C_8$ cycloalkyl;
10) Optionally substituted 3- to 8-membered heterocycloalkyl;
11) Optionally substituted aryl;
12) Optionally substituted arylalkyl;

13) Optionally substituted heteroaryl; and

14) Optionally substituted heteroarylalkyl;

$R_{25}$ is selected from:

1) Optionally substituted —$C_1$-$C_8$ alkyl;

2) Optionally substituted —$C_2$-$C_8$ alkenyl;

3) Optionally substituted —$C_2$-$C_8$ alkynyl;

4) Optionally substituted —$C_3$-$C_8$ cycloalkyl;

5) Optionally substituted 3- to 8-membered heterocycloalkyl;

6) Optionally substituted aryl;

7) Optionally substituted arylalkyl;

8) Optionally substituted heteroaryl; and

9) Optionally substituted heteroarylalkyl;

and $R_{15}$ is hydrogen, hydroxy, or optionally substituted —$C_1$-$C_8$ alkyl.

In one embodiment of the present invention, the compound of Formula (I) is represented by Formula (I-A) or Formula (I-B), or a pharmaceutically acceptable salt, ester or prodrug thereof:

(I-A)

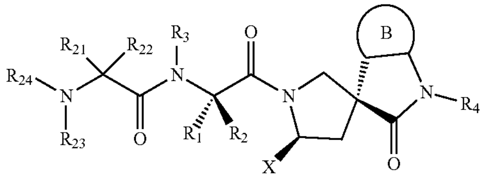

(I-B)

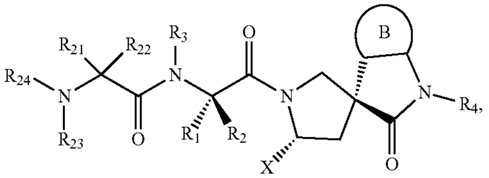

wherein B, X, $R_1$, $R_2$, $R_3$, $R_4$, $R_{21}$, $R_{22}$, $R_{23}$, and $R_{24}$ are as previously defined.

In a preferred embodiment, the compound of Formula (I) has the stereochemistry shown in Formula (I-A).

In one embodiment of the present invention, the compound of Formula (I) is represented by Formula (II), or a pharmaceutically acceptable salt, ester or prodrug thereof:

(II)

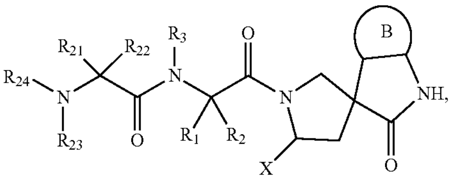

wherein B, X, $R_1$, $R_2$, $R_3$, $R_{21}$, $R_{22}$, $R_{23}$, and $R_{24}$ are as previously defined.

In one embodiment of the present invention, the compound of Formula (I) is represented by Formula (II-A) or Formula (II-B), or a pharmaceutically acceptable salt, ester or prodrug thereof:

(II-A)

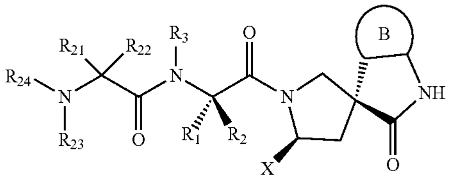

(II-B)

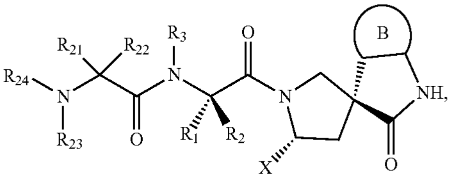

wherein B, X, $R_1$, $R_2$, $R_3$, $R_{21}$, $R_{22}$, $R_{23}$, and $R_{24}$ are as previously defined.

In certain embodiments of the compounds of Formula (I), $R_1$ is hydrogen, optionally substituted —$C_1$-$C_6$ alkyl; optionally substituted —$C_3$-$C_6$ cycloalkyl; optionally substituted aryl; optionally substituted arylalkyl; or optionally substituted heteroarylalkyl.

In certain embodiments, $R_1$ is —$C_1$-$C_6$-alkyl, preferably branched —$C_3$-$C_6$-alkyl, such as isobutyl or neopentyl. In certain embodiments, $R_1$ is optionally substituted benzyl.

In certain embodiments, $R_1$ is optionally substituted —$C_1$-$C_6$-alkyl, preferably $R_1$ is 2-fluoro-2-methylpropyl, or cyclopropylmethyl.

In certain embodiments of the compounds of Formula (I), $R_2$ is hydrogen or optionally substituted —$C_1$-$C_4$ alkyl; optionally substituted —$C_3$-$C_6$ cycloalkyl; optionally substituted aryl; optionally substituted arylalkyl; or optionally substituted heteroarylalkyl. In certain embodiments, $R_2$ is hydrogen.

In certain embodiments of the compounds of Formula (I), $R_3$ is hydrogen or optionally substituted —$C_1$-$C_4$ alkyl; $R_4$ is hydrogen or optionally substituted —$C_1$-$C_4$ alkyl.

In certain embodiments of the compounds of Formula (I), $R_3$ is hydrogen, -Me, -Et, —Pr, -i-Pr, -allyl, —$CF_3$, —$CD_3$ or cyclopropyl.

In certain embodiments of the compounds of Formula (I), $R_4$ is hydrogen, -Me, -Et, —Pr, -i-Pr, -allyl, —$CF_3$ or cyclopropyl.

In certain embodiments, $R_3$ and $R_4$ are each independently hydrogen or methyl.

In certain embodiments of the compounds of Formula (I), X is —CN.

In certain embodiments of the compounds of Formula (I), X is —C(O)H.

In certain embodiments of the compounds of Formula (I), X is —$C(O)CH_2OH$, —$C(O)CH_2Cl$ or —$C(O)CH_2F$.

In certain embodiments of the compounds of Formula (I), X is —C(O)CHFCl.

In certain embodiments of the compounds of Formula (I), X is —$C(O)C(O)NR_{13}R_{14}$, wherein $R_{13}$ and $R_{14}$ are as previously defined.

In certain embodiments of the compounds of Formula (I), X is —$C{\equiv}CR_{13}$, wherein $R_{13}$ is as previously defined. Preferably, $R_{13}$ is hydrogen.

In certain embodiments of the compounds of Formula (I), $R_{21}$ is hydrogen, optionally substituted —$C_1$-$C_4$ alkyl; optionally substituted —$C_3$-$C_6$ cycloalkyl; optionally substituted aryl; optionally substituted heteroaryl; optionally substituted arylalkyl; or optionally substituted heteroarylalkyl. In certain embodiments, $R_{21}$ is optionally substituted phenyl, optionally substituted benzyl, optionally substituted methyl, t-butyl, isopropyl, neopentyl,

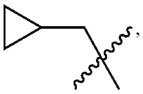,
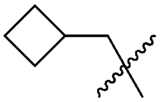, or
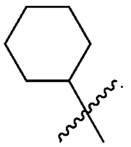.

In certain embodiments of the compounds of Formula (I), $R_{22}$ is hydrogen or optionally substituted $-C_1$-$C_4$ alkyl; optionally substituted $-C_3$-$C_6$ cycloalkyl; optionally substituted aryl; optionally substituted heteroaryl; optionally substituted arylalkyl; optionally substituted heteroarylalkyl. In certain embodiments, $R_{22}$ is hydrogen.

In certain embodiments of the compounds of Formula (I), $R_1$ and $R_{21}$ are each independently $C_1$-$C_4$ alkyl substituted with one or more fluorine atoms; $C_3$-$C_6$ cycloalkyl substituted with one or more fluorine atoms; aryl substituted with one or more fluorine atoms; heteroaryl substituted with one or more fluorine atoms; arylalkyl substituted with one or more fluorine atoms; or heteroarylalkyl substituted with one or more fluorine atoms. Each of the foregoing groups can be substituted with a number of fluorine atoms ranging from 1 to the maximum number possible, i.e., replacement of all hydrogen atoms with fluorine atoms. In certain embodiments, $R_1$ and $R_{21}$ are each independently $-CF_3$, $-CF_2-CF_3$, $-CH_2CH(CF_3)_2$,

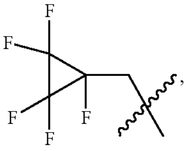, or
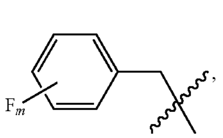, wherein m is 1, 2, 3, 4, or 5.

In certain embodiments of the compounds of Formula (I), $R_{23}$ is hydrogen or optionally substituted $-C_1$-$C_4$ alkyl. In certain embodiments $R_{23}$ is hydrogen.

In certain embodiments of the compounds of Formula (I), $R_{24}$ is $-C(O)R_{25}$, $-C(O)OR_{25}$, or $-C(O)NR_{13}R_{14}$, wherein $R_{13}$, $R_{14}$, and $R_{25}$ are as previously defined.

In certain embodiments of the compounds of Formula (I), $R_2$ is hydrogen, $R_3$ is hydrogen, $R_4$ is hydrogen, and $R_{22}$ is hydrogen.

In certain embodiments of the compounds of Formula (I), $R_4$ is hydrogen or optionally substituted $-C_1$-$C_4$ alkyl, such as methyl; $R_{23}$ is hydrogen or optionally substituted $-C_1$-$C_4$ alkyl, such as methyl; and $R_{24}$ is $-C(O)R_{25}$, $-C(O)OR_{25}$, or $-C(O)NR_{13}R_{14}$, wherein $R_{13}$, $R_{14}$, and $R_{25}$ are previously defined.

In certain embodiments of the compounds of Formula (I), $R_4$ is cyano-$C_1$-$C_4$ alkyl, cyano-$C_3$-$C_6$ cycloalkyl, hydroxy-$C_1$-$C_4$ alkyl, or optionally substituted hydroxy-$C_3$-$C_6$ cycloalkyl, wherein each of the foregoing is optionally further substituted.

In certain embodiments of the compounds of Formula (I), $R_4$ is a prodrug moiety, wherein said prodrug moiety is an amino acid residue, preferably a naturally occurring L-amino acid residue.

In certain embodiments of the compounds of Formula (I), $R_4$ is a prodrug moiety selected from the group consisting of:

1) $-C(O)R_{25}$;
2) $-S(O)_2R_{25}$;
3) $-P(O)(R_{25})_2$;
4) $-C(O)OR_{25}$;
5) $-S(O)_2OR_{25}$; and
6) $-P(O)(OR_{25})_2$, wherein each $R_{25}$ is the same or different.

In certain embodiments of the compounds of Formula (I), $R_4$ is a prodrug moiety selected from the group consisting of:

1) $-CHR_{13}O(CO)R_{25}$;
2) $-CHR_{13}O(CO)CH(NH_2)R_{25}$;
3) $-CHR_{13}O(CO)OR_{25}$; and
4) $-CHR_{13}O(PO)(OR_{14})_2$, wherein each $R_{14}$ is the same or different.

In certain embodiments of the compounds of Formula (I), $R_2$ is hydrogen, $R_3$ is methyl, $R_4$ is hydrogen or a prodrug moiety, $R_{22}$ is hydrogen, $R_{23}$ is hydrogen, and $R_{24}$ is $-C(O)R_{25}$, $-C(O)OR_{25}$, or $-C(O)NR_{13}R_{14}$, wherein $R_{13}$, $R_{14}$, and $R_{25}$ are as previously defined.

In certain embodiments of the compounds of Formula (I), $R_2$ is hydrogen, $R_3$ and $R_4$ are independently hydrogen or optionally substituted $-C_1$-$C_4$ alkyl, such as methyl; $R_{23}$ is hydrogen, and $R_{24}$ is $-C(O)R_{25}$, $-C(O)OR_{25}$, or $-C(O)NR_{13}R_{14}$, wherein $R_{13}$, $R_{14}$, and $R_{25}$ are as previously defined.

In certain embodiments of the compounds of Formula (I), $R_{24}$ is $-C(O)R_{25}$; $C(O)OR_{25}$; or $-S(O)_2R_{25}$; and $R_{25}$ is selected from the following groups by removal of a hydrogen atom, and $R_{25}$ is optionally substituted:

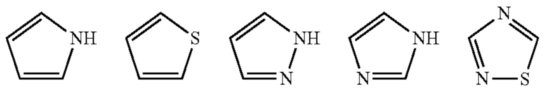
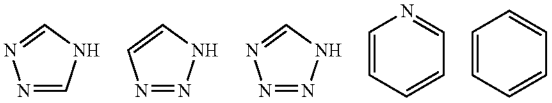
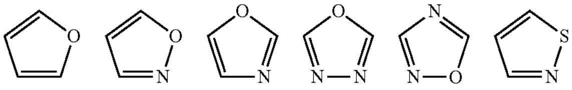
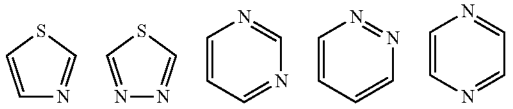
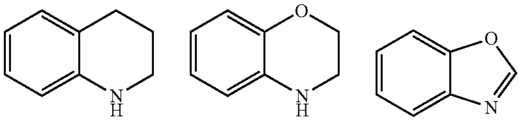
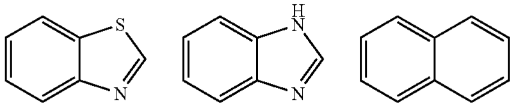
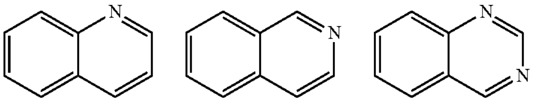
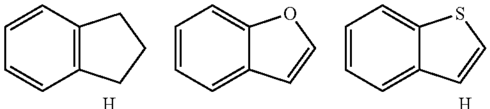
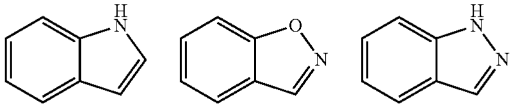

-continued

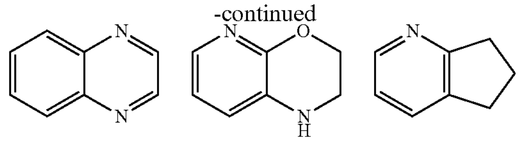
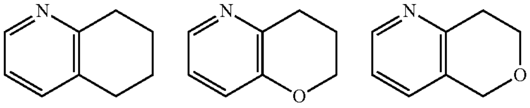
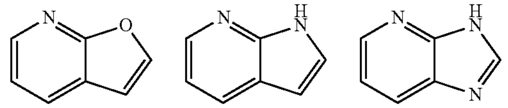
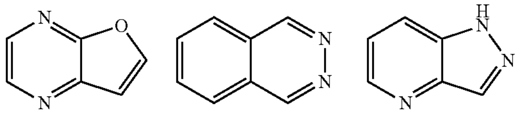
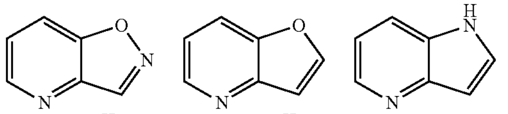
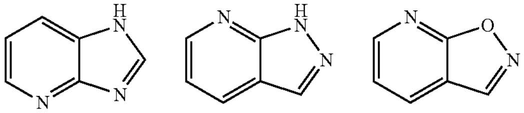
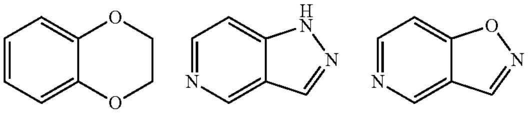
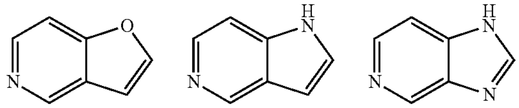
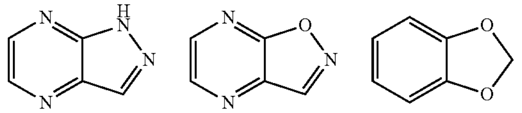
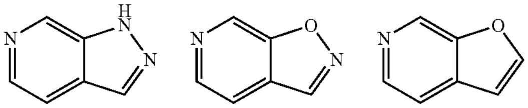
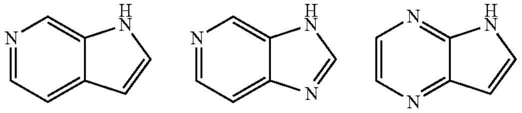
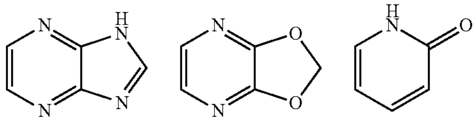
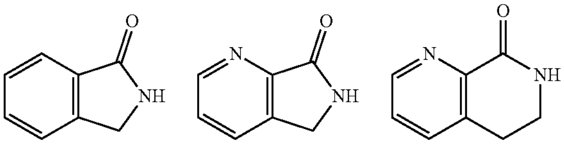
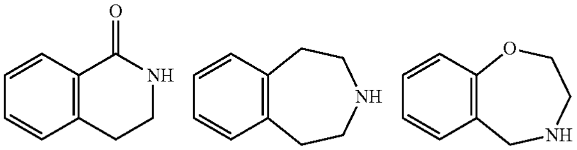
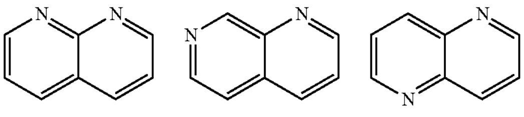

-continued

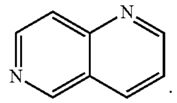

.

In certain embodiments of the compounds of Formula (I), $R_{24}$ is —C(O)$R_{25}$; C(O)O$R_{25}$; or —S(O)$_2R_{25}$; and $R_{25}$ is selected from the following groups, and $R_{25}$ is optionally substituted;

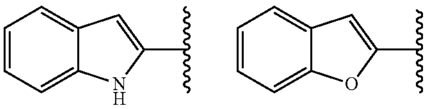
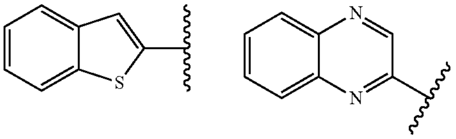
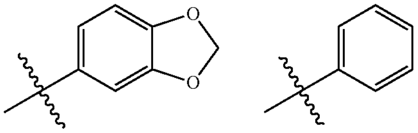
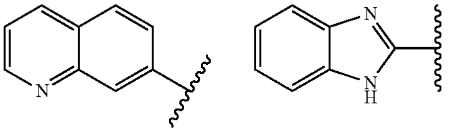
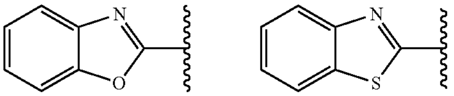
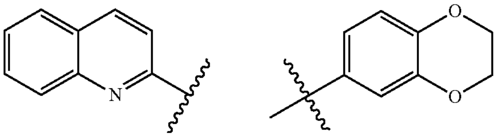
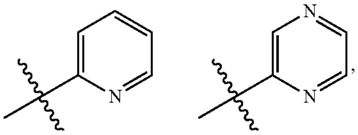

,

Preferably the substituents are independently selected from halogen, CN, $NH_2$, optionally substituted —$C_1$-$C_3$ alkoxy, optionally substituted —$C_1$-$C_3$ alkyl, optionally substituted —$C_3$-$C_6$ cycloalkyl, optionally substituted aryl, and optionally substituted heteroaryl. Preferably the number of substituents is 0 to 3.

In certain embodiments of the compounds of Formula (I), $R_{24}$ is optionally substituted —$C_1$-$C_8$ alkyl, optionally substituted —$C_3$-$C_{12}$ cycloalkyl, —C(O)$R_{25}$, C(O)O$R_{25}$, or —S(O)$_2R_{25}$; and $R_{25}$ is optionally substituted —$C_1$-$C_8$ alkyl or optionally substituted —$C_3$-$C_{12}$ cycloalkyl; preferably, $R_{25}$ is optionally substituted —$C_1$-$C_8$ alkyl.

In certain embodiments of the compounds of Formula (I), B is selected from the following groups, and B is optionally substituted:

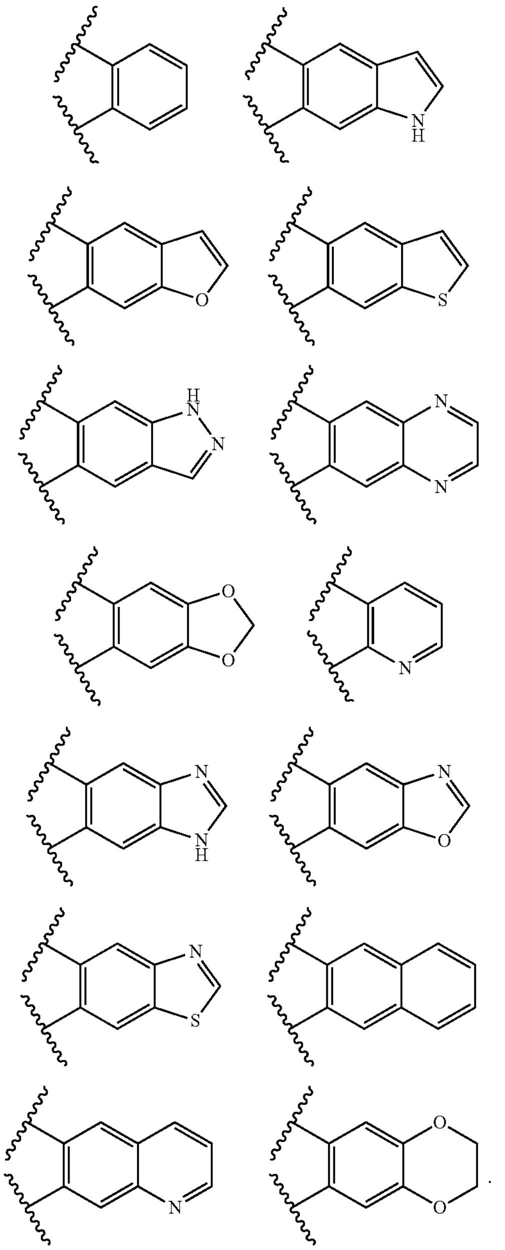

In certain embodiments of the present invention, the compound of Formula (I) is represented by one of Formulae (III-1)~(III-4), or a pharmaceutically acceptable salt, ester or prodrug thereof:

(III-1)

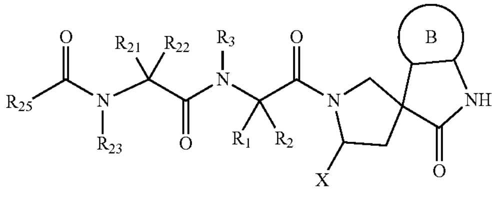

-continued (III-2)

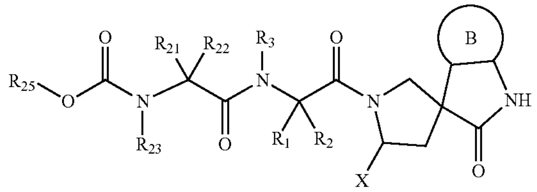

(III-3)

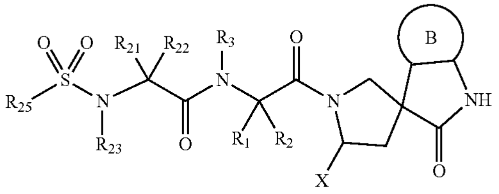

(III-4)

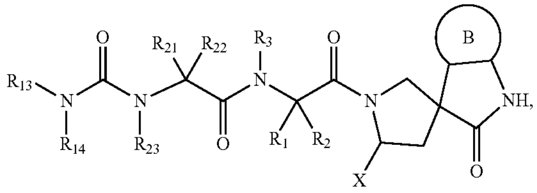

wherein B, X, $R_1$, $R_2$, $R_3$, $R_{13}$, $R_{14}$, $R_{21}$, $R_{22}$, $R_{23}$, and $R_{25}$ are as previously defined.

In certain embodiments of the present invention, the compound of Formula (I) is represented by Formula (III-5), or a pharmaceutically acceptable salt, ester or prodrug thereof:

(III-5)

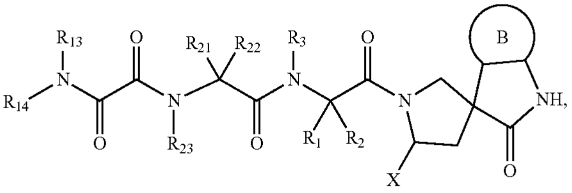

wherein B, X, $R_1$, $R_2$, $R_3$, $R_{13}$, $R_{14}$, $R_{21}$, $R_{22}$, and $R_{23}$ are as previously defined.

In certain embodiments of the present invention, the compound of Formula (I) is represented by one of Formulae (III-1A)~(III-4A), or a pharmaceutically acceptable salt, ester or prodrug thereof:

(III-1A)

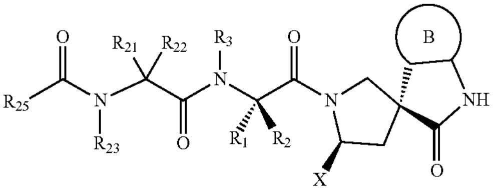

-continued (III-2A)

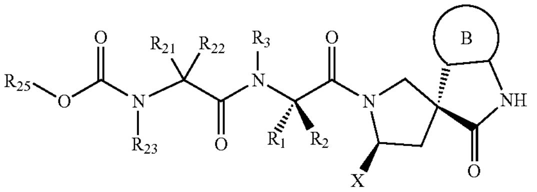

(III-3A)

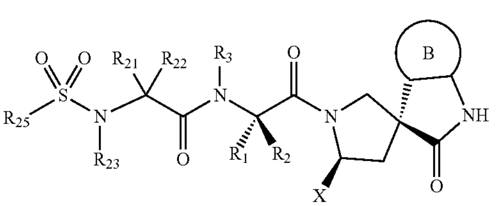

(III-4A)

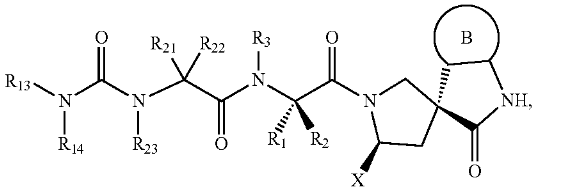

wherein B, X, $R_1$, $R_2$, $R_3$, $R_1$, $R_{14}$, $R_{21}$, $R_{22}$, $R_{23}$, and $R_{25}$ are as previously defined.

In certain embodiments of the present invention, the compound of Formula (I) is represented by Formula (III-5A), or a pharmaceutically acceptable salt, ester or prodrug thereof:

(III-5A)

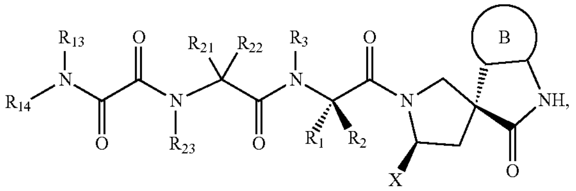

wherein B, X, $R_1$, $R_2$, $R_3$, $R_{13}$, $R_{14}$, $R_{21}$, $R_{22}$, and $R_{23}$ are as previously defined.

In certain embodiments of the present invention, the compound of Formula (I) is represented by one of Formulae (IV-1)~(V-4), or a pharmaceutically acceptable salt, ester or prodrug thereof:

(IV-1)

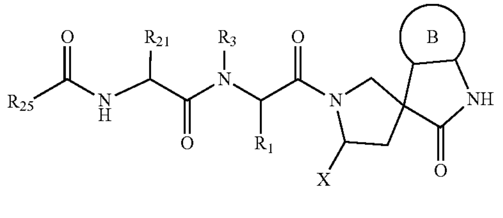

-continued (IV-2)

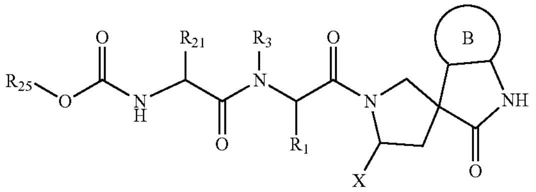

(IV-3)

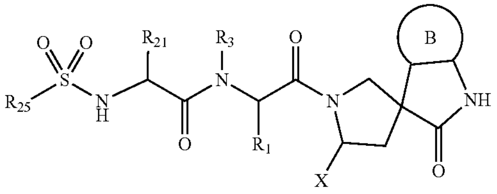

(IV-4)

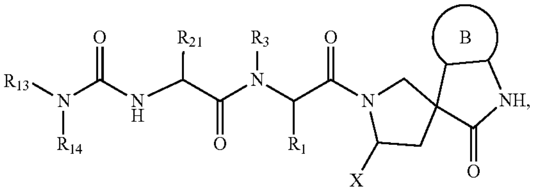

wherein B, X, $R_1$, $R_3$, $R_{13}$, $R_{14}$, $R_{21}$, and $R_{25}$ are as previously defined.

In certain embodiments of the present invention, the compound of Formula (I) is represented by Formula (IV-5), or a pharmaceutically acceptable salt, ester or prodrug thereof:

(IV-5)

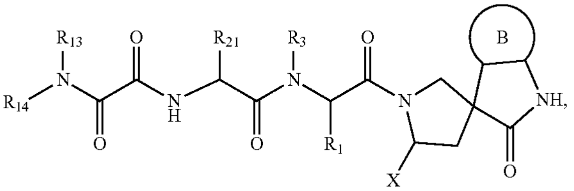

wherein B, X, $R_1$, $R_3$, $R_{13}$, $R_{14}$, and $R_{21}$ are as previously defined.

In certain embodiments of the present invention, the compound of Formula (I) is represented by one of Formulae (IV-1A) (IV-4A), or a pharmaceutically acceptable salt, ester or prodrug thereof:

(IV-1A)

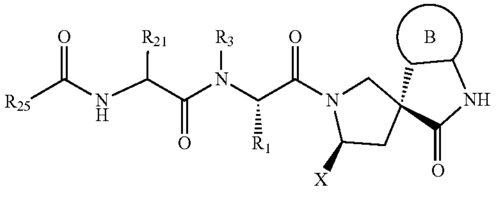

-continued (IV-2A)

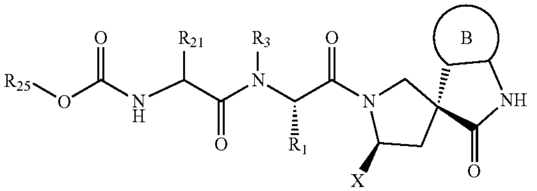

(IV-3A)

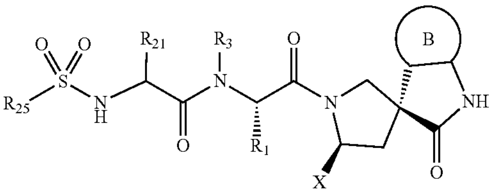

(IV-4A)

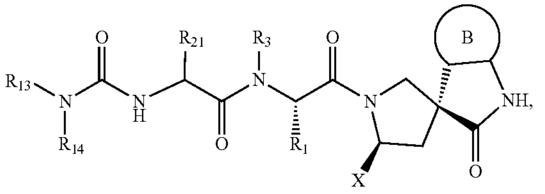

wherein B, X, $R_1$, $R_3$, $R_{13}$, $R_{14}$, $R_{21}$, and $R_{25}$ are as previously defined.

In certain embodiments of the present invention, the compound of Formula (I) is represented by Formula (IV-5A), or a pharmaceutically acceptable salt, ester or prodrug thereof:

(IV-5A)

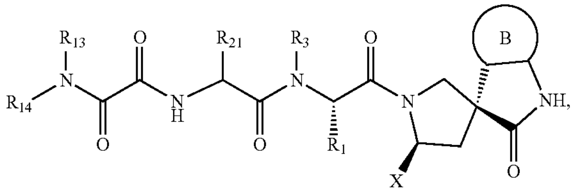

wherein B, X, $R_1$, $R_3$, $R_{13}$, $R_{14}$, and $R_{21}$ are as previously defined.

In certain embodiments, the compound of Formula (I) is represented by Formula (V):

(V)

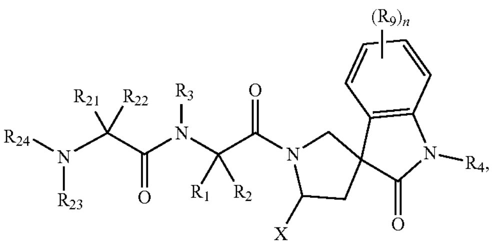

wherein $R_1$, $R_2$, $R_3$, $R_4$, $R_{21}$, $R_{22}$, $R_{23}$, $R_{24}$ and X are as previously defined, preferably, $R_4$ is hydrogen; each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl; and
11) Optionally substituted heteroaryl;

and n is 0, 1, 2, 3, or 4.

In certain embodiments, the compound of Formula (I) is represented by Formula (V):

(V)

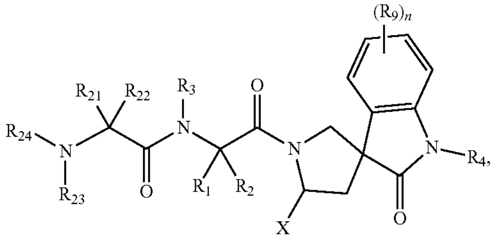

wherein n, $R_1$, $R_2$, $R_3$, $R_4$, $R_{21}$, $R_{22}$, $R_{23}$, $R_{24}$ and X are as previously defined, preferably, $R_4$ is hydrogen; each $R_9$ is independently selected from:

1) —$OC(O)R_{25}$;
2) —$C(O)NR_{13}R_{14}$;
3) —$S(O)R_{25}$;
4) —$S(O)_2R_{25}$;
5) —$S(O)(NH)R_{25}$;
6) —$S(O)_2$—$NR_{13}R_{14}$;
7) —$NR_{13}(C{=}O)R_{25}$;
8) —$NR_{13}(C{=}O)OR_{25}$;
9) —$NR_{13}(C{=}O)NR_{13}R_{14}$;
10) —$NR_{13}$—$S(O)_2$—$R_{25}$; and
11) —$NR_{13}$—$S(O)_2$—$NR_{13}R_{14}$;

and $R_{13}$, $R_{14}$, $R_{25}$ are as previously defined.

In certain embodiments, the compound of Formula (I) is represented by Formula (VT):

(VI)

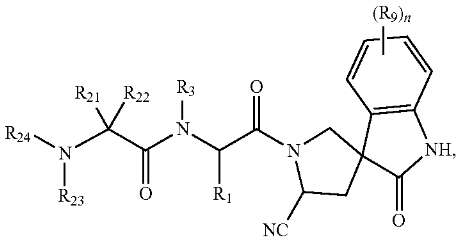

wherein $R_1$, $R_3$, $R_9$, $R_{21}$, $R_{22}$, $R_{23}$, $R_{24}$ and n are as previously defined. Preferably, n is 0 or 1, In certain embodiments, the compound of Formula (I) is represented by Formula (VI-A) or Formula (VI-B):

(VI-A)

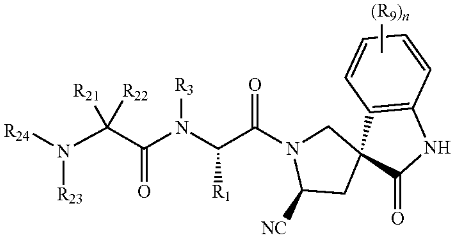

(VI-B)

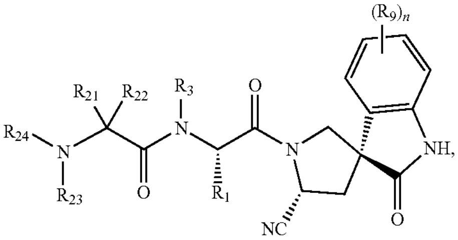

wherein $R_1$, $R_3$, $R_9$, $R_{21}$, $R_{22}$, $R_{23}$, $R_{24}$ and n are as previously defined. Preferably, n is 0 or 1.

In certain embodiments, the compound of Formula (I) is represented by one of Formulae (VII-1) to (VII-4):

(VII-1)

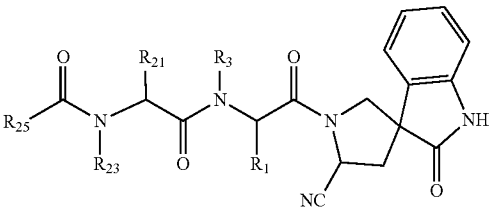

(VII-2)

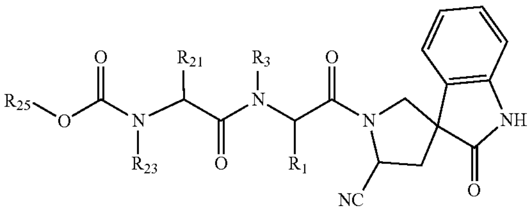

(VII-3)

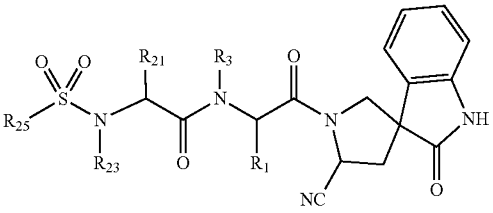

-continued (VII-4)

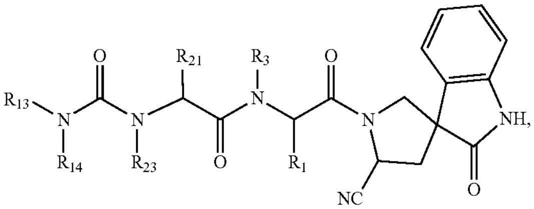

wherein $R_1$, $R_3$, $R_{21}$, $R_{23}$, $R_{25}$, $R_{13}$, and $R_{14}$ are as previously defined. Preferably, $R_3$ is hydrogen, Me.

In certain embodiments, the compound of Formula (I) is represented by one of Formulae (VII-1) to (VII-4), wherein $R_1$, $R_{21}$, $R_{23}$, $R_{25}$, $R_{13}$, and $R_{14}$ are as previously defined, and $R_3$ is $CD_3$.

In certain embodiments of the present invention, the compound of Formula (I) is represented by Formula (VII-5), or a pharmaceutically acceptable salt, ester or prodrug thereof:

(VII-5)

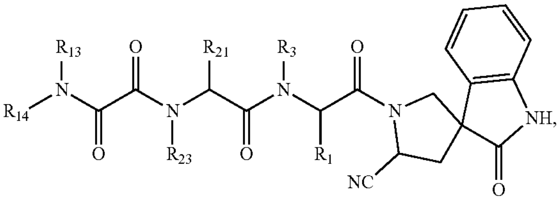

wherein $R_1$, $R_3$, $R_{21}$, $R_{23}$, $R_{25}$, $R_{13}$, and $R_{14}$ are as previously defined. Preferably, $R_3$ is hydrogen, Me or $CD_3$.

In certain embodiments, the compound of Formula (I) is represented by one of Formulae (VII-1A) to (VII-4A):

(VII-1A)

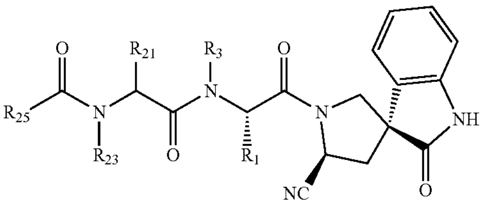

(VII-2A)

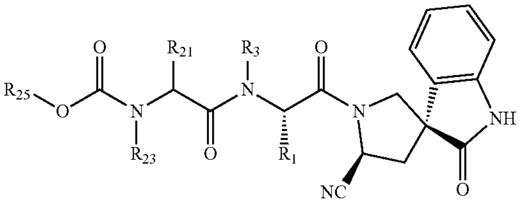

-continued (VII-3A)

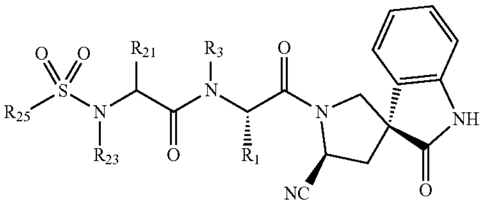

(VII-4A)

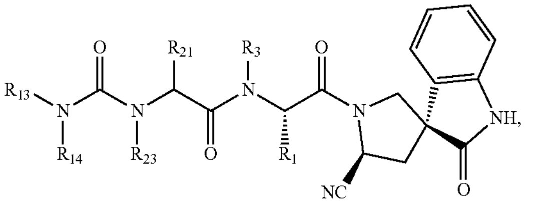

wherein $R_1$, $R_3$, $R_{21}$, $R_{23}$, $R_{25}$, $R_{13}$, and $R_{14}$ are as previously defined. Preferably, $R_3$ is hydrogen, Me.

In certain embodiments, the compound of Formula (I) is represented by one of Formulae (VII-1A) to (VII-4A), wherein $R_1$, $R_{21}$, $R_{23}$, $R_{25}$, $R_{13}$, and $R_{14}$ are as previously defined, and $R_3$ is $CD_3$.

In certain embodiments of the present invention, the compound of Formula (I) is represented by Formula (VII-5A), or a pharmaceutically acceptable salt, ester or prodrug thereof:

(VII-5A)

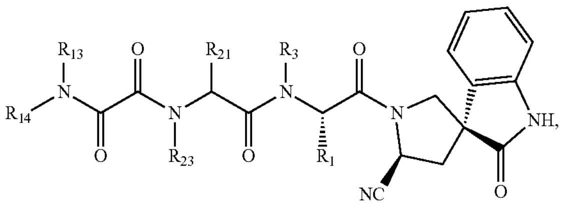

wherein $R_1$, $R_3$, $R_{21}$, $R_{23}$, $R_{25}$, $R_{13}$, and $R_{14}$ are as previously defined. Preferably, $R_3$ is hydrogen, Me or $CD_3$.

In certain embodiments of the present invention, the compound of Formula (I) is represented by one of Formulae (VIII-1) (VIII-3), or a pharmaceutically acceptable salt, ester or prodrug thereof:

(VIII-1)

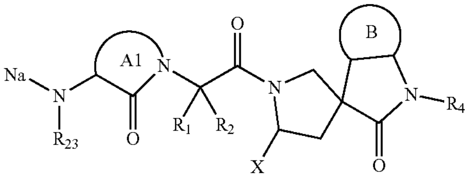

-continued (VIII-2)

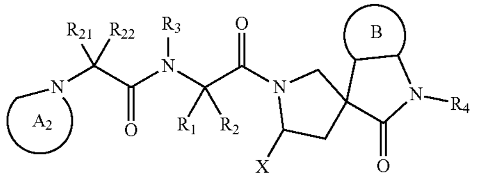

(VIII-3)

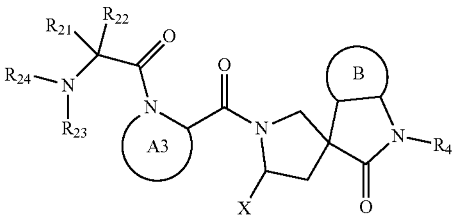

wherein A1 is an optionally substituted 4- to 8-membered lactam; A2 is an optionally substituted 3- to 12-membered heterocyclic ring, or an optionally substituted 5- to 12-membered heteroaryl ring; A3 is an optionally substituted 3- to 8-membered heterocyclic ring; and B, X, $R_1$, $R_2$, $R_3$, $R_4$, $R_{21}$, $R_{22}$, $R_{23}$, and $R_{24}$ are as previously defined.

In certain embodiments of the present invention, the compound of Formula (I) is represented by one of Formulae (VIII-1) (VIII-3), or a pharmaceutically acceptable salt, ester or prodrug thereof, wherein A1 is 2-pyridone; A2 is an optionally substituted 3- to 12-membered heterocyclic ring, or an optionally substituted 5- to 12-membered heteroaryl ring; A3 is an optionally substituted 3- to 8-membered heterocyclic ring; and B, X, $R_1$, $R_2$, $R_3$, $R_4$, $R_{21}$, $R_{22}$, $R_{23}$, and $R_{24}$ are as previously defined.

In certain embodiments of the present invention, the compound of Formula (I) is represented by one of Formulae (IX-1) (IX-3), or a pharmaceutically acceptable salt, ester or prodrug thereof:

(IX-1)

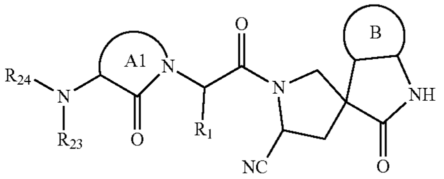

(IX-2)

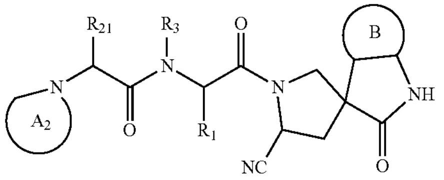

(IX-3)

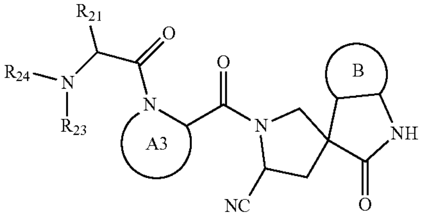

wherein A1, A2, A3, B, $R_1$, $R_3$, $R_{21}$, $R_{23}$, and $R_{24}$ are as previously defined.

In certain embodiments of the present invention, the compound of Formula (I) is represented by one of Formulae (X-1) (X-3), or a pharmaceutically acceptable salt, ester or prodrug thereof:

(X-1)

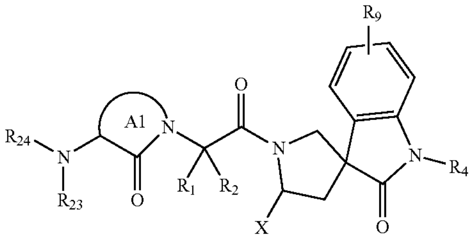

(X-2)

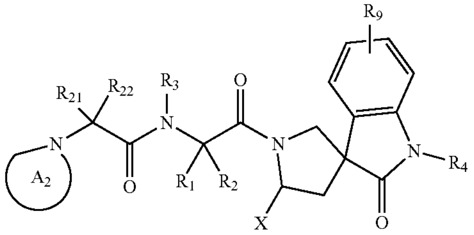

(X-3)

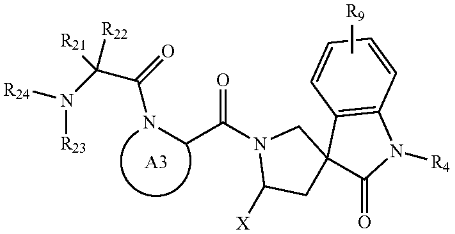

wherein A1, A2, A3, X, $R_1$, $R_2$, $R_3$, $R_4$, $R_9$, $R_{21}$, $R_{22}$, $R_{23}$, and $R_{24}$ are as previously defined.

In certain embodiments of the present invention, the compound of Formula (I) is represented by one of Formulae (XI-1) (XI-3), or a pharmaceutically acceptable salt, ester or prodrug thereof:

(XI-1)

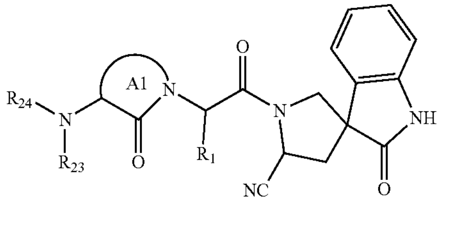

(XI-2)

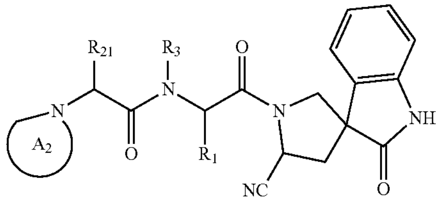

-continued (XI-3)

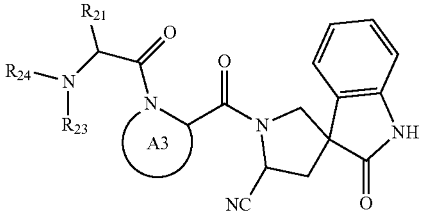

wherein A1, A2, A3, $R_1$, $R_3$, $R_{21}$, $R_{23}$, and $R_{24}$ are as previously defined.

In certain embodiments of the present invention, the compound of Formula (I) is represented by one of Formulae (XII-1)~(XII-10), or a pharmaceutically acceptable salt, ester or prodrug thereof:

(XII-1)

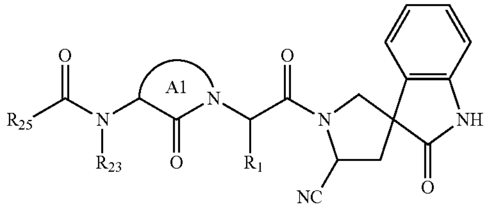

(XII-2)

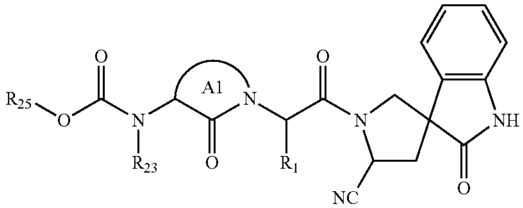

(XII-3)

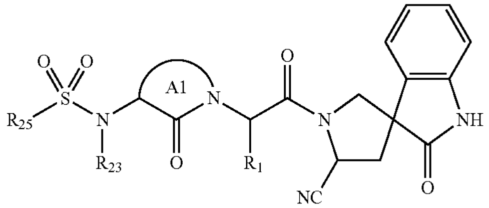

(XII-4)

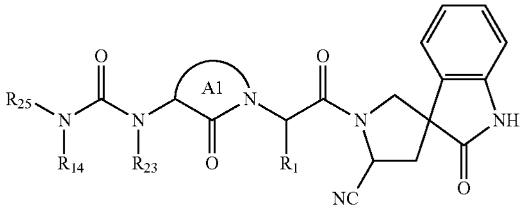

(XII-5)

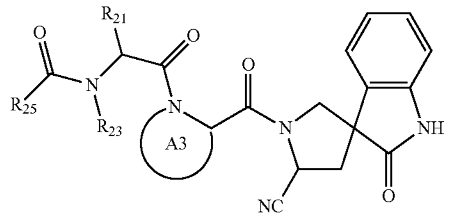

-continued (XII-6)

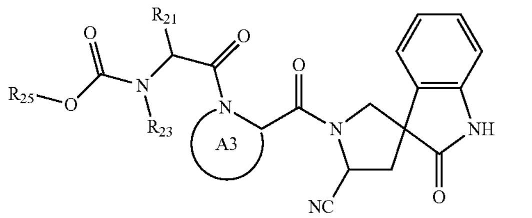

(XII-7)

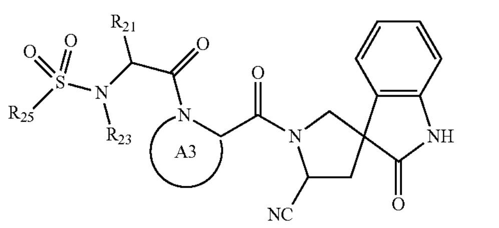

(XII-8)

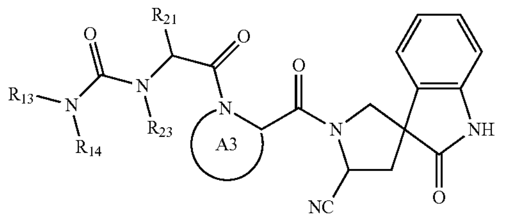

(XII-9)

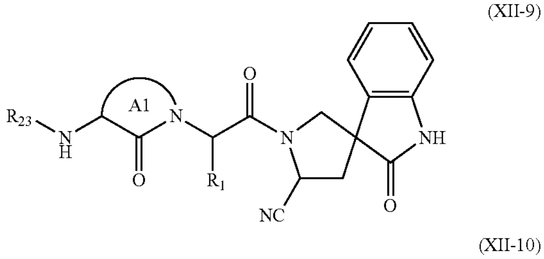

(XII-10)

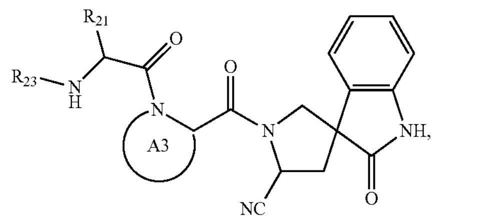

wherein A1, A3, $R_1$, $R_{13}$, $R_{14}$, $R_{21}$, $R_{23}$, and $R_{25}$ are as previously defined.

In certain embodiments of the present invention, the compound of Formula (I) is represented by one of Formulae (XII-11) (XII-12), or a pharmaceutically acceptable salt, ester or prodrug thereof:

(XII-11)

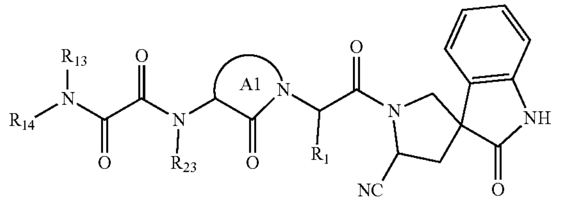

(XII-12)

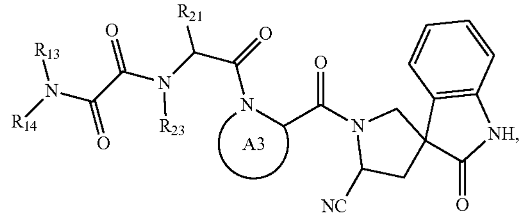

wherein A1, A3, $R_1$, $R_{13}$, $R_{14}$, $R_{21}$, and $R_{23}$ are as previously defined.

In certain embodiments of the present invention, the compound of Formula (I) is represented by Formula (XIII), (XIII)

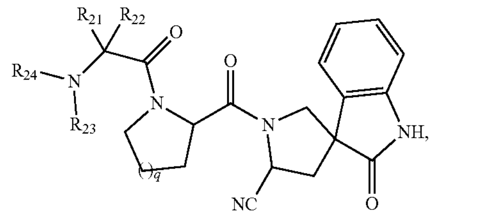

wherein q is 1 or 2, and $R_{21}$, $R_{22}$, $R_{23}$, and $R_{24}$ are as previously defined.

In certain embodiments of the present invention, the compound of Formula (I) is represented by one of Formulae (XIV-1)~(XIV-5), (XIV-1)

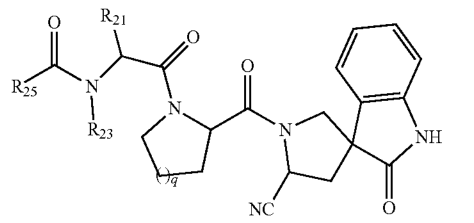

(XIV-2)

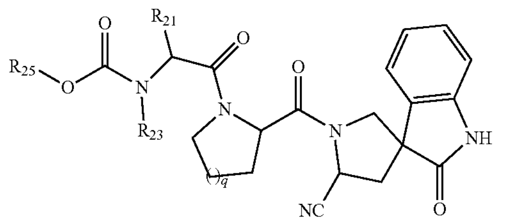

(XIV-3)

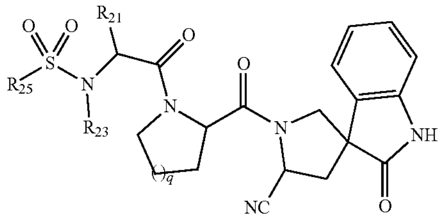

(XIV-4)

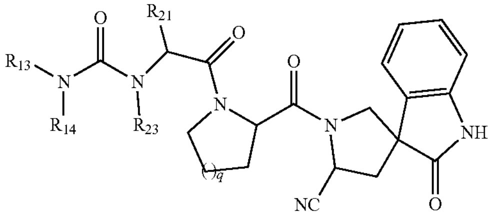

(XIV-5)

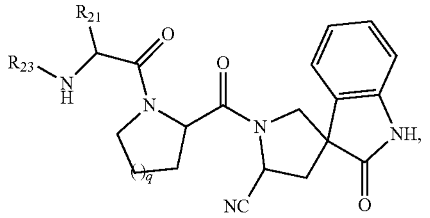

wherein q, $R_{13}$, $R_{14}$, $R_{21}$, $R_{23}$, and $R_{25}$ are as previously defined.

In certain embodiments of the present invention, the compound of Formula (I) is represented by Formula (XIV-6), (XIV-6)

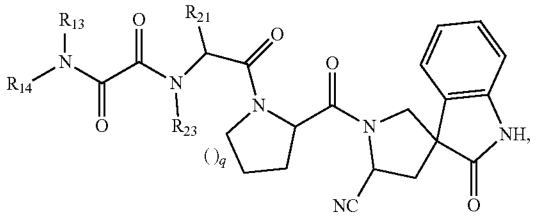

wherein q, $R_{13}$, $R_{14}$, $R_{21}$, and $R_{23}$ are as previously defined.

In certain embodiments of the present invention, the compound of Formula (I) is represented by one of Formulae (XV-1)~(XV-4), (XV-1)

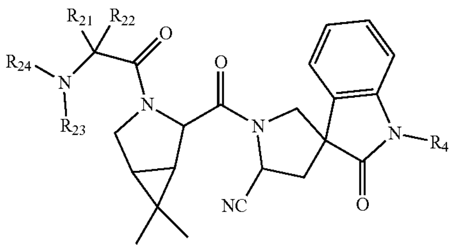

(XV-2)

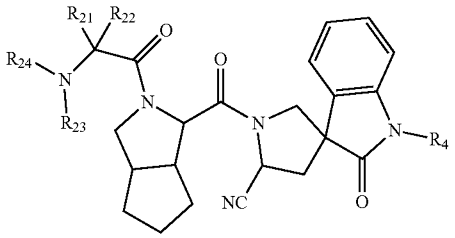

(XV-3)

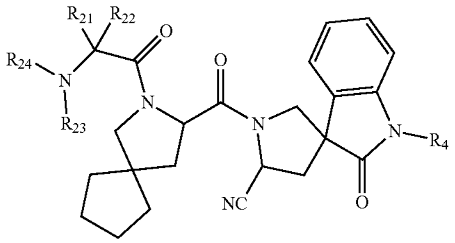

(XV-4)

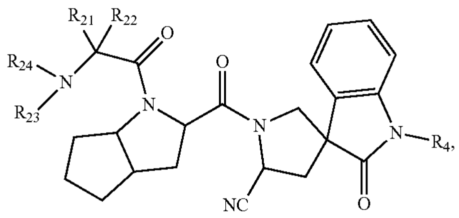

wherein $R_{21}$, $R_{22}$, $R_{23}$, $R_{24}$, and $R_4$ are as previously defined; preferably $R_4$ is hydrogen or a prodrug moiety.

In certain embodiments of the present invention, the compound of Formula (I) is represented by one of Formulas (XVI-1)~(XVI-6), (XVI-1)

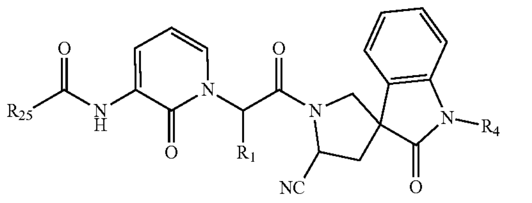

(XVI-2)

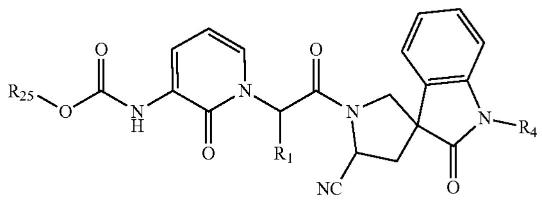

-continued (XVI-3)

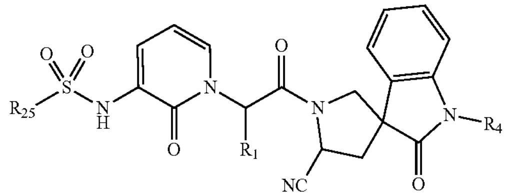

(XVI-4)

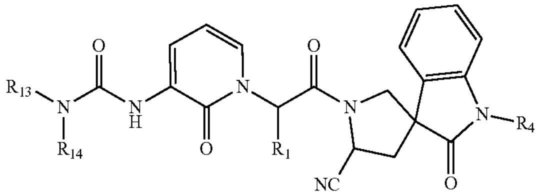

(XVI-5)

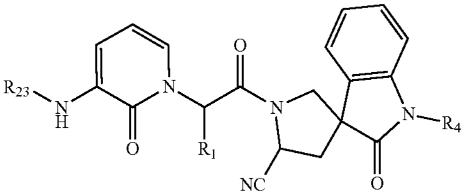

(XVI-6)

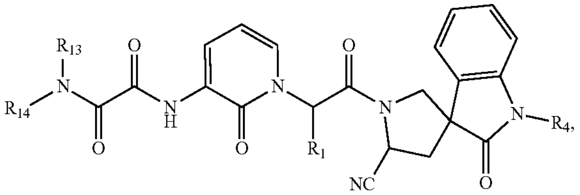

wherein $R_1$, $R_4$, $R_{13}$, $R_{14}$, $R_{23}$, and $R_{25}$ are as previously defined; preferably $R_4$ is hydrogen or a prodrug moiety.

In certain embodiments of the present invention, the compound of Formula (I) is represented by one of Formulas (XVII-1)~(XVII-2), (XVII-1)

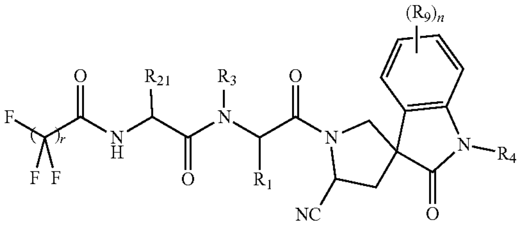

(XVII-2)

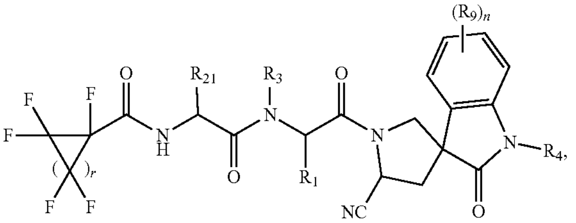

wherein r is 1, 2, 3, or 4, and n, $R_1$, $R_3$, $R_4$, $R_9$, and $R_{21}$, are as previously defined; preferably $R_4$ is hydrogen or a prodrug moiety.

In certain embodiments of the present invention, the compound of Formula (I) is represented by one of Formulas (XVIII-1)~(XVIII-4), (XVIII-1)

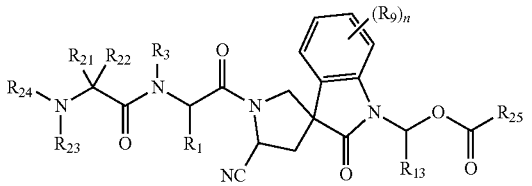

(XVIII-2)

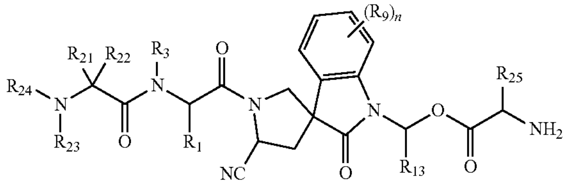

(XVIII-3)

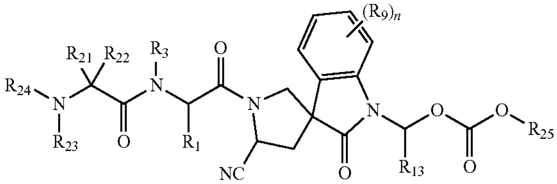

(XVIII-4)

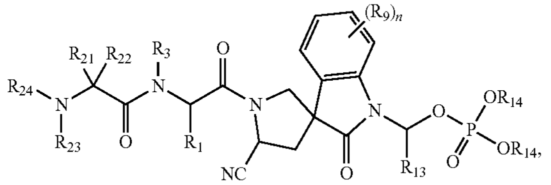

wherein n, $R_1$, $R_3$, $R_9$, $R_{13}$, $R_{14}$, $R_{21}$, $R_{22}$, $R_{23}$, $R_{24}$ and $R_{25}$ are as previously defined.

In certain embodiments of the present invention, the compound of Formula (I) is represented by one of Formulas (XVIII-1a)~(XVIII-4a), (XVIII-1a)

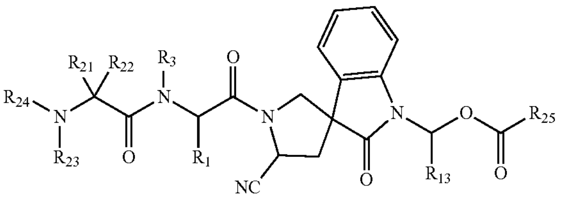

-continued (XVIII-2a)

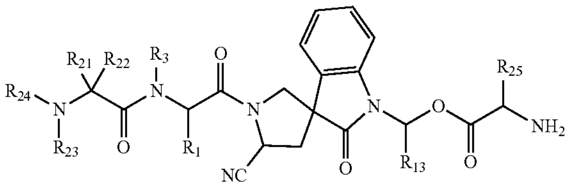

(XVIII-3a)

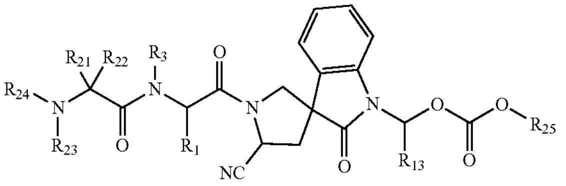

(XVIII-4a)

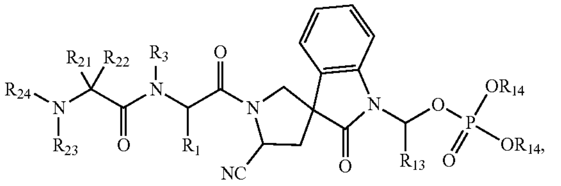

wherein $R_1$, $R_3$, $R_{13}$, $R_{14}$, $R_{21}$, $R_{22}$, $R_{23}$, $R_{24}$ and $R_{25}$ are as previously defined.

In certain embodiments, the compound of Formula (I) is represented by Formula (XIX):

(XIX)

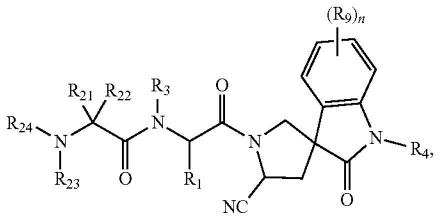

wherein $R_1$, $R_3$, $R_4$, $R_9$, $R_{21}$, $R_{22}$, $R_{23}$, $R_{24}$ and n are as previously defined. Preferably, n is 0 or 1, and $R_4$ is hydrogen or a prodrug moiety.

In certain embodiments, the compound of Formula (I) is represented by Formula (XIX-A) or Formula (XIX-B):

(XIX-A)

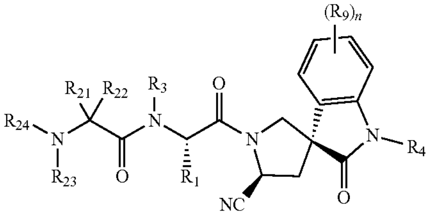

-continued (XIX-B)

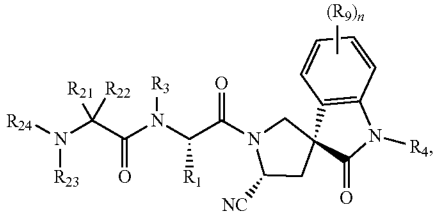

wherein $R_1$, $R_3$, $R_4$, $R_9$, $R_{21}$, $R_{22}$, $R_{23}$, $R_{24}$ and n are as previously defined. Preferably, n is 0 or 1, and $R_4$ is hydrogen or a prodrug moiety.

In certain embodiments, the compound of Formula (I) is represented by one of Formulas (XX-1) to (XX-5):

(XX-1)

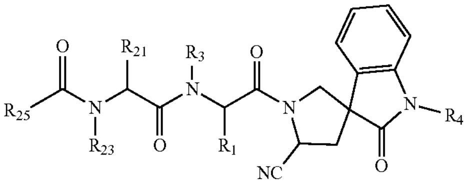

(XX-2)

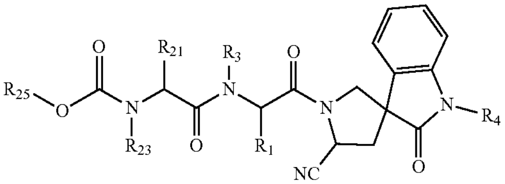

(XX-3)

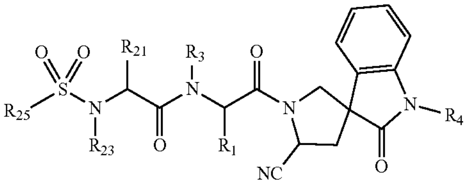

(XX-4)

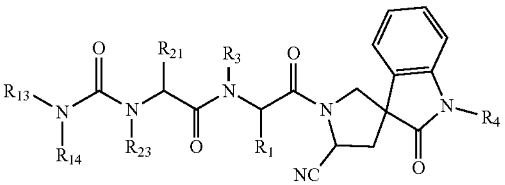

(XX-5)

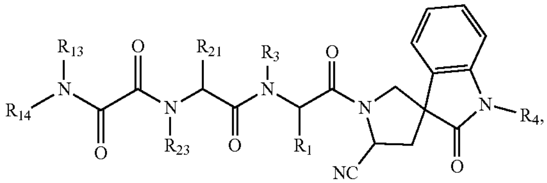

wherein $R_1$, $R_3$, $R_4$, $R_{21}$, $R_{23}$, $R_{25}$, $R_{13}$, and $R_{14}$ are as previously defined. Preferably, $R_3$ is hydrogen or Me or $CD_3$, and $R_4$ is hydrogen or a prodrug moiety.

In certain embodiments, the compound of Formula (I) is represented by one of Formulas (XX-1A) to (XX-5A):

(XX-1A)

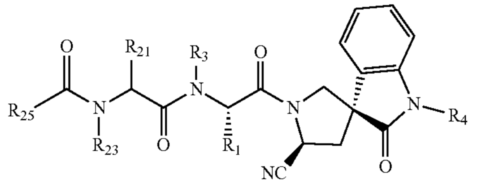

(XX-2A)

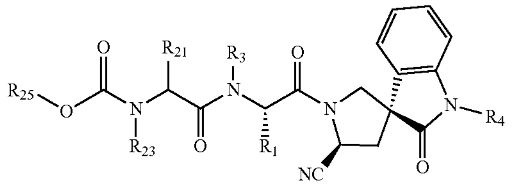

(XX-3A)

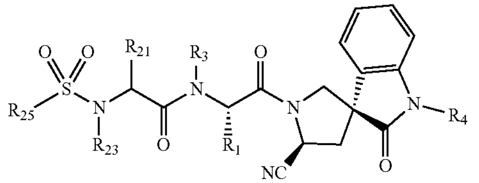

(XX-4A)

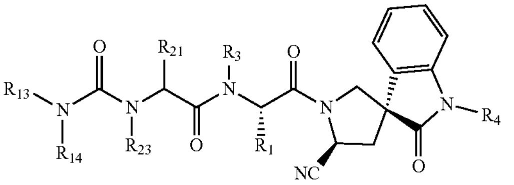

(XX-5A)

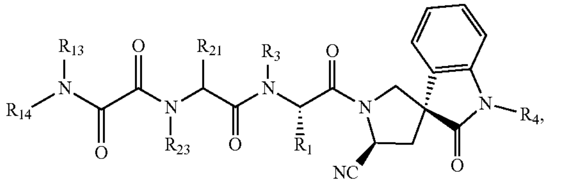

wherein $R_1$, $R_3$, $R_{21}$, $R_{23}$, $R_{25}$, $R_{13}$, and $R_{14}$ are as previously defined. Preferably, $R_3$ is hydrogen, Me or $CD_3$, and $R_4$ is hydrogen or a prodrug moiety.

In certain embodiments of the present invention, the compound of Formula (I) is represented by Formula (XXI), (XXI)

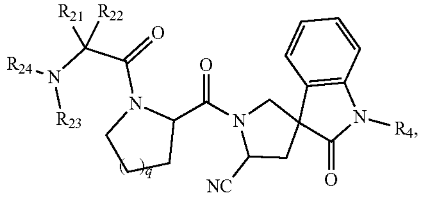

wherein q is 1 or 2, and $R_4$, $R_{21}$, $R_{22}$, $R_{23}$, and $R_{24}$ are as previously defined. Preferably, $R_4$ is hydrogen or a prodrug moiety.

In certain embodiments of the present invention, the compound of Formula (I) is represented by Formula (XXII), (XXII)

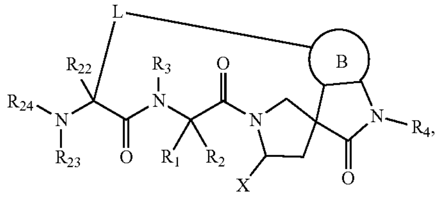

wherein B, X, $R_1$, $R_2$, $R_3$, $R_4$, $R_{22}$, $R_{23}$, and $R_{24}$ are as previously defined, and L is —$R_a$-Q-$R_b$—, wherein when $R_a$ is not absent, $R_a$ is connected to B, and when $R_a$ is absent, Q is connected to B;

$R_a$ is selected from the group consisting of absent, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_a$ is absent;

$R_b$ is selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl;

Q is selected from the group consisting of —$CR_{31}$=$CR_{32}$—, —$CR_{31}R_{33}$—$CR_{32}R_{34}$—, —$CR_{31}R_{33}$C(O)—, —$CR_{31}R_{33}$—O—, —$CR_{31}R_{33}$—S—, —$CR_{31}R_{33}$N($R_{17}$)—, —$NR_{13}$C(O)—, —$NR_{13}$C(O)O—, —$NR_{13}$C(O)$NR_{14}$—, —C(O)O—, —C(O)S—, —OC(O)O—, —C(O)—, O—, —S—, —S(O)—, —S(O)$_2$—, —S(O)(NH)—, —N($R_{17}$)—, optionally substituted aryl, optionally substituted heteroaryl, optionally substituted —$C_3$-$C_8$ cycloalkyl, and optionally substituted 3- to 8-membered heterocycloalkyl;

In certain embodiments, L is an optionally substituted $C_4$-$C_{10}$-alkylene or an optionally substituted $C_4$-$C_{10}$-alkenylene, wherein in said $C_4$-$C_{10}$-alkylene or $C_4$-$C_{10}$-alkenylene one $CH_2$ group is optionally replaced with an oxygen atom or NH group; preferably L is a $C_4$-$C_8$-alkylene or a $C_4$-$C_8$-alkenylene, wherein said $C_4$-$C_8$-alkylene or $C_4$-$C_8$-alkenylene is optionally substituted with oxo;

$R_{31}$ and $R_{32}$ at each occurrence are each independently selected from the group consisting of hydrogen, halogen, optionally substituted —$C_1$-$C_8$ s alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_{31}$ and $R_{32}$ are both hydrogen; and $R_{33}$ and $R_{34}$ at each occurrence are each independently selected from the group consisting of: hydrogen, halogen, —OH, —$OR_{12}$, —OC(O)$R_{11}$, —OC(O)$OR_{12}$, —OC(O)$NR_{13}R_{14}$, —$NR_{13}R_{17}$, —$N_3$, —CN, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; in certain embodiments, $R_{33}$ and $R_{34}$ are both hydrogen;

$R_{11}$ and $R_{12}$ are each independently selected from the group consisting of optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, or optionally substituted heteroarylalkyl;

$R_{13}$ and $R_{14}$ at each occurrence are independently selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, and optionally substituted heteroarylalkyl; alternatively $R_{13}$ and $R_{14}$ are taken together with the nitrogen atom to which they are attached to form an optionally substituted 3- to 8-membered heterocyclic ring; and $R_{17}$ is selected from the group consisting of hydrogen, optionally substituted —$C_1$-$C_8$ alkyl, optionally substituted —$C_2$-$C_8$ alkenyl, optionally substituted —$C_2$-$C_8$ alkynyl, optionally substituted —$C_3$-$C_8$ cycloalkyl, optionally substituted 3- to 8-membered heterocycloalkyl, optionally substituted aryl, optionally substituted arylalkyl, optionally substituted heteroaryl, optionally substituted heteroarylalkyl, —C(O)Rn, —C(O)O$R_{12}$, —C(O)N$R_{13}R_{14}$, —C(O)C(O)N$R_{13}R_{14}$, —S(O)$_2R_{11}$, and —S(O)$_2$N$R_{13}R_{14}$.

In certain embodiments of the present invention, the compound of Formula (I) is represented by Formula (XXIII), (XXIII)

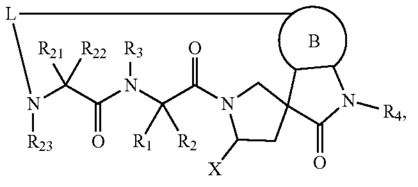

wherein B, X, $R_1$, $R_2$, $R_3$, $R_4$, $R_{21}$, $R_{22}$, $R_{23}$, and L are as previously defined.

In certain embodiments, the compound of Formula (I) is represented by one of Formulae (XXIV-1) to (XXIV-5):

(XXIV-1)

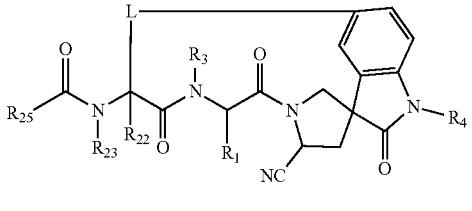

-continued (XXIV-2)

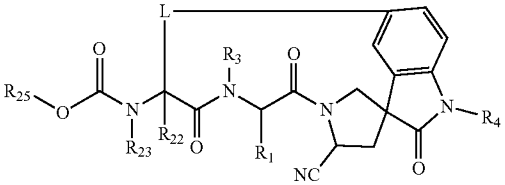

(XXIV-3)

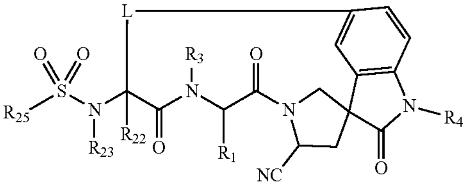

(XXIV-4)

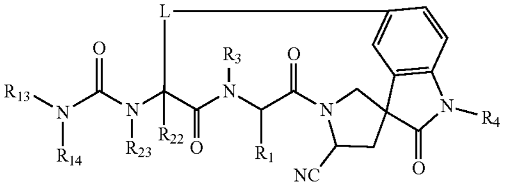

(XXIV-5)

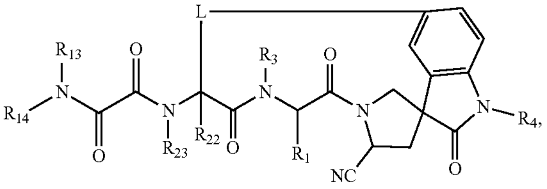

wherein $R_1$, $R_3$, $R_4$, $R_{22}$, $R_{23}$, $R_{25}$, $R_{13}$, and $R_{14}$ are as previously defined. Preferably, $R_3$ is hydrogen or Me or $CD_3$, and $R_4$ is hydrogen or a prodrug moiety.

In certain embodiments, the compound of Formula (I) is represented by one of Formulas (XXV-1) to (XXV-5):

(XXV-1)

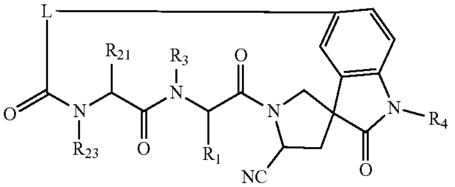

(XXV-2)

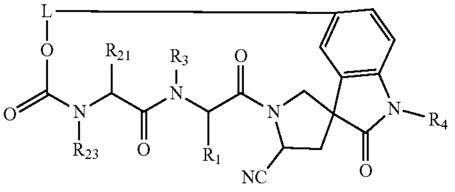

-continued (XXV-3)

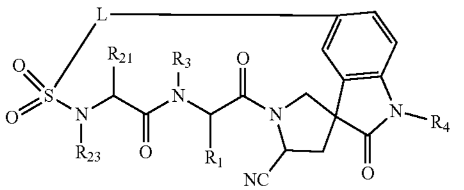

(XXV-4)

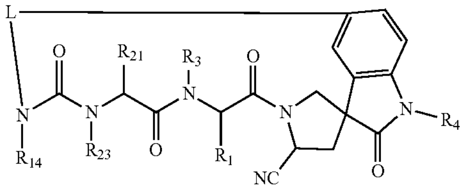

(XXV-5)

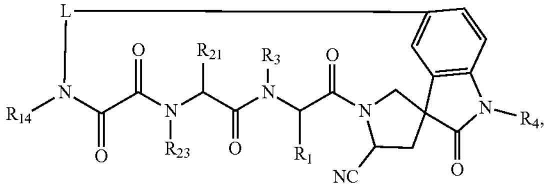

wherein $R_1$, $R_3$, $R_4$, $R_{21}$, $R_{23}$, and $R_{14}$ are as previously defined. Preferably, $R_3$ is hydrogen or Me or $CD_3$, and $R_4$ is hydrogen or a prodrug moiety.

It will be appreciated that the description of the present invention herein should be construed in congruity with the laws and principles of chemical bonding. In some instances, it may be necessary to remove a hydrogen atom in order to accommodate a substituent at any given location.

It is intended that the definition of any substituent or variable (e.g., $R_1$, $R_2$, etc.) at a particular location in a molecule be independent of its definitions elsewhere in that molecule. For example, in Formula (V) when n is 2, each of the two $R_9$ groups may be the same or different. It will be yet appreciated that the compounds of the present invention may contain one or more asymmetric carbon atoms and may exist in racemic, diastereoisomeric, and optically active forms. It will still be appreciated that certain compounds of the present invention may exist in different tautomeric forms. All tautomers are contemplated to be within the scope of the present invention.

Definitions

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, and indenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzoxazolyl, quinoxalinyl. A polycyclic heteroaryl can comprise fused rings, covalently attached rings or a combination thereof.

In accordance with the invention, aromatic groups can be substituted or unsubstituted.

The term "bicyclic aryl" or "bicyclic heteroaryl" refers to a ring system consisting of two rings wherein at least one ring is aromatic; and the two rings can be fused or covalently attached.

The term "alkyl" as used herein, refers to saturated, straight- or branched-chain hydrocarbon radicals. "$C_1$-$C_4$ alkyl," "$C_1$-$C_6$ alkyl," "$C_1$-$C_8$ alkyl," "$C_1$-$C_{12}$ alkyl," "$C_2$-$C_4$ alkyl," or "$C_3$-$C_6$ alkyl," refer to alkyl groups containing from one to four, one to six, one to eight, one to twelve, 2 to 4 and 3 to 6 carbon atoms respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The term "alkenyl" as used herein, refers to straight- or branched-chain hydrocarbon radicals having at least one carbon-carbon double bond by the removal of a single hydrogen atom. "$C_2$-$C_8$ alkenyl," "$C_2$-$C_{12}$ alkenyl," "$C_2$-$C_4$ alkenyl," "$C_3$-$C_4$ alkenyl," or "$C_3$-$C_6$ alkenyl," refer to alkenyl groups containing from two to eight, two to twelve, two to four, three to four or three to six carbon atoms respectively. Alkenyl groups include, but are not limited to, for example, ethenyl, propenyl, butenyl, 2-methyl-2-buten-2-yl, heptenyl, octenyl, and the like.

The term "alkynyl" as used herein, refers to straight- or branched-chain hydrocarbon radicals having at least one carbon-carbon double bond by the removal of a single hydrogen atom. "$C_2$-$C_8$ alkynyl," "$C_2$-$C_{12}$ alkynyl," "$C_2$-$C_4$ alkynyl," "$C_3$-$C_4$ alkynyl," or "$C_3$-$C_6$ alkynyl," refer to alkynyl groups containing from two to eight, two to twelve, two to four, three to four or three to six carbon atoms respectively. Representative alkynyl groups include, but are not limited to, for example, ethynyl, 2-propynyl, 2-butynyl, heptynyl, octynyl, and the like.

The term "cycloalkyl", as used herein, refers to a monocyclic or polycyclic saturated carbocyclic ring or a bi- or tri-cyclic group fused, bridged or spiro system, and the carbon atoms may be optionally oxo-substituted or optionally substituted with exocyclic olefinic double bond. Preferred cycloalkyl groups include $C_3$-$C_{12}$ cycloalkyl, $C_3$-$C_6$ cycloalkyl, $C_3$-$C_8$ cycloalkyl and $C_4$-$C_7$ cycloalkyl. Examples of $C_3$-$C_{12}$ cycloalkyl include, but not limited to, cyclopropyl, cyclobutyl, cyclopentyl, cyclohexyl, cyclopentyl, cyclooctyl, 4-methylene-cyclohexyl, bicyclo[2.2.1]heptyl, bicyclo[3.1.0]hexyl, spiro[2.5]octyl, 3-methylenebicyclo[3.2.1]octyl, spiro[4.4]nonanyl, and the like.

The term "cycloalkenyl", as used herein, refers to monocyclic or polycyclic carbocyclic ring or a bi- or tri-cyclic group fused, bridged or spiro system having at least one carbon-carbon double bond and the carbon atoms may be optionally oxo-substituted or optionally substituted with exocyclic olefinic double bond. Preferred cycloalkenyl groups include $C_3$-$C_{12}$ cycloalkenyl, $C_3$-$C_8$ cycloalkenyl or $C_5$-$C_7$ cycloalkenyl groups. Examples of $C_3$-$C_{12}$ cycloalkenyl include, but not limited to, cyclopropenyl, cyclobutenyl, cyclopentenyl, cyclohexenyl, cycloheptenyl, cyclooctenyl, bicyclo[2.2.1]hept-2-enyl, bicyclo[3.1.0]hex-2-enyl, spiro[2.5]oct-4-enyl, spiro[4.4]non-2-enyl, bicyclo[4.2.1]non-3-en-12-yl, and the like.

As used herein, the term "arylalkyl" means a functional group wherein an alkylene chain is attached to an aryl group, e.g., —$CH_2CH_2$-phenyl. The term "substituted arylalkyl" means an arylalkyl functional group in which the aryl group is substituted. Similarly, the term "heteroarylalkyl" means a functional group wherein an alkylene chain is attached to a heteroaryl group. The term "substituted heteroarylalkyl" means a heteroarylalkyl functional group in which the heteroaryl group is substituted. Preferably, as used herein, arylalkyl is aryl-$C_1$-$C_6$ alkyl, and heteroarylalkyl is heteroaryl-$C_1$-$C_6$ alkyl.

As used herein, the term "alkoxy" employed alone or in combination with other terms means, unless otherwise stated, an alkyl group having the designated number of carbon atoms connected to the rest of the molecule via an oxygen atom, such as, for example, methoxy, ethoxy, 2-propoxy, 2-propoxy (isopropoxy) and the higher homologs and isomers. Preferred alkoxy are ($C_2$-$C_3$) alkoxy.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds. Examples of aliphatic groups are functional groups, such as alkyl, alkenyl, alkynyl, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, $NHC(O)NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted.

The terms "heterocyclic" or "heterocycloalkyl" can be used interchangeably and referred to a non-aromatic ring or a bi- or tri-cyclic group fused, bridged or spiro system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted or optionally substituted with exocyclic olefinic double bond. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, 2-azabicyclo[2.2.1]-heptyl, 8-azabicyclo[3.2.1]octyl, 5-azaspiro[2.5]octyl, 2-oxa-7-azaspiro[4.4]nonanyl, 7-oxooxepan-4-yl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s). One of skill in the art can readily determine the valence of any such group from the context in which it occurs.

The term "substituted" refers to substitution by independent replacement of one, two, or three or more of the hydrogen atoms with substituents including, but not limited to, —F, —Cl, —Br, —I, —OH, $C_1$-$C_{12}$-alkyl; $C_2$-$C_{12}$-alkenyl, $C_2$-$C_{12}$-alkynyl, —$C_3$-$C_{12}$-cycloalkyl, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)— heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH— heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocyloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocyclo-alkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, $NHC(S)NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O) —$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthiomethyl. In certain embodiments, the substituents are independently selected from halo, preferably Cl and F; $C_1$-$C_4$-alkyl, preferably methyl and ethyl; halo-$C_1$-$C_4$-alkyl, such as fluoromethyl, difluoromethyl, and trifluoromethyl; $C_2$-$C_4$-alkenyl; halo-$C_2$-$C_4$-alkenyl; $C_3$-$C_6$-cycloalkyl, such as cyclopropyl; $C_1$-$C_4$-alkoxy, such as methoxy and ethoxy; halo-$C_1$-$C_4$-alkoxy, such as fluoromethoxy, difluoromethoxy, and trifluoromethoxy; acetyl; —CN; —OH; $NH_2$; $C_1$-$C_4$-alkylamino; di($C_1$-$C_4$-alkyl)amino; and $NO_2$. It is understood that the aryls, heteroaryls, alkyls, and the like can be further substituted. In some cases, each substituent in a substituted moiety is additionally optionally substituted with one or more groups, each group being independently selected from $C_1$-$C_4$-alkyl; —$CF_3$, —$OCH_3$, —$OCF_3$, —F, —Cl, —Br, —I, —OH, —$NO_2$, —CN, and —$NH_2$. Preferably, a substituted alkyl group is substituted with one or more halogen atoms, more preferably one or more fluorine or chlorine atoms.

The term "halo" or halogen" alone or as part of another substituent, as used herein, refers to a fluorine, chlorine, bromine, or iodine atom.

The term "optionally substituted", as used herein, means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

The term "hydrogen" includes hydrogen and deuterium. In addition, the recitation of an atom includes other isotopes of that atom so long as the resulting compound is pharmaceutically acceptable.

The term "hydroxy activating group," as used herein, refers to a labile chemical moiety which is known in the art to activate a hydroxyl group so that it will depart during synthetic procedures such as in a substitution or an elimination reaction. Examples of hydroxyl activating group include, but not limited to, mesylate, tosylate, triflate, p-nitrobenzoate, phosphonate and the like.

The term "activated hydroxyl," as used herein, refers to a hydroxy group activated with a hydroxyl activating group, as defined above, including mesylate, tosylate, triflate, p-nitrobenzoate, phosphonate groups, for example.

The term "hydroxy protecting group," as used herein, refers to a labile chemical moiety which is known in the art to protect a hydroxyl group against undesired reactions during synthetic procedures. After said synthetic procedure(s) the hydroxy protecting group as described herein may be selectively removed. Hydroxy protecting groups as known in the art are described generally in T. H. Greene and P. G. M. Wuts, *Protective Groups in Organic Synthesis,* 3rd edition, John Wiley & Sons, New York (1999). Examples of hydroxyl protecting groups include benzyloxycarbonyl, 4-methoxybenzyloxycarbonyl, tert-butoxy-carbonyl, isopropoxycarbonyl, diphenylmethoxycarbonyl, 2,2,2-trichloroethoxycarbonyl, allyloxycarbonyl, acetyl, formyl, chloroacetyl, trifluoroacetyl, methoxyacetyl, phenoxyacetyl, benzoyl, methyl, t-butyl, 2,2,2-trichloroethyl, 2-trimethylsilyl ethyl, allyl, benzyl, triphenyl-methyl (trityl), methoxymethyl, methylthiomethyl, benzyloxymethyl, 2-(trimethylsilyl)-ethoxymethyl, methanesulfonyl, trimethylsilyl, triisopropylsilyl, and the like.

The term "protected hydroxy," as used herein, refers to a hydroxy group protected with a hydroxy protecting group, as defined above, including benzoyl, acetyl, trimethylsilyl, triethylsilyl, methoxymethyl groups, for example.

The term "hydroxy prodrug group," as used herein, refers to a promoiety group which is known in the art to change the physicochemical, and hence the biological properties of a parent drug in a transient manner by covering or masking the hydroxy group. After said synthetic procedure(s), the hydroxy prodrug group as described herein must be capable of reverting back to hydroxy group in vivo. Hydroxy prodrug groups as known in the art are described generally in Kenneth B. Sloan, Prodrugs, *Topical and Ocular Drug Delivery*, (Drugs and the Pharmaceutical Sciences; Volume 53), Marcel Dekker, Inc., New York (1992). Preferably the hydroxy prodrug group is phosphate, sulfamate, or an acyl group derived from an amino acid, preferably an α-amino acid.

The term "amino protecting group," as used herein, refers to a labile chemical moiety which is known in the art to protect an amino group against undesired reactions during synthetic procedures. After said synthetic procedure(s) the amino protecting group as described herein may be selectively removed. Amino protecting groups as known in the art are described generally in T. H. Greene and P. G. M. Wuts, *Protective Groups in Organic Synthesis,* 3rd edition, John Wiley & Sons, New York (1999). Examples of amino protecting groups include, but are not limited to, methoxycarbonyl, t-butoxycarbonyl, 12-fluorenyl-methoxycarbonyl, benzyloxycarbonyl, and the like.

The term "protected amino," as used herein, refers to an amino group protected with an amino protecting group as defined above.

The term "leaving group" means a functional group or atom which can be displaced by another functional group or atom in a substitution reaction, such as a nucleophilic substitution reaction. By way of example, representative leaving groups include chloro, bromo and iodo groups; sulfonic ester groups, such as mesylate, tosylate, brosylate, nosylate and the like; and acyloxy groups, such as acetoxy, trifluoroacetoxy and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

The term "protic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification,* 4th ed., edited by John A. Riddick et al., Vol. II, in the *Techniques of Chemistry Series*, John Wiley & Sons, N Y, 1986.

Combinations of substituents and variables envisioned by this invention are only those that result in the formation of stable compounds. The term "stable," as used herein, refers to compounds which possess stability sufficient to allow manufacture and which maintains the integrity of the compound for a sufficient period of time to be useful for the purposes detailed herein (e.g., therapeutic or prophylactic administration to a subject).

The synthesized compounds can be separated from a reaction mixture and further purified by a method such as column chromatography, high pressure liquid chromatography, or recrystallization. As can be appreciated by the skilled artisan, further methods of synthesizing the compounds of the Formula herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations,* $2^{nd}$ Ed. Wiley-VCH (1999); T. W. Greene and P. G. M. Wuts, *Protective Groups in Organic Synthesis,* 3rd Ed., John Wiley and Sons (1999); L. Fieser and M. *Fieser, Fieser and Fieser's Reagents for Organic Synthesis*, John Wiley and Sons (1994); and L. Paquette, ed., *Encyclopedia of Reagents for Organic Synthesis*, John Wiley and Sons (1995), and subsequent editions thereof.

The term "subject," as used herein, refers to an animal. Preferably, the animal is a mammal. More preferably, the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. Tautomers may be in cyclic or acyclic. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Certain compounds of the present invention may also exist in different stable conformational forms which may be separable. Torsional asymmetry due to restricted rotation about an asymmetric single bond, for example because of steric hindrance or ring strain, may permit separation of different conformers. The present invention includes each conformational isomer of these compounds and mixtures thereof.

As used herein, the term "pharmaceutically acceptable salt," refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in J. Pharmaceutical Sciences, 66: 2-19 (1977). The salts can be prepared in situ during the final isolation and purification of the compounds of the invention, or separately by reacting the free base function with a suitable organic acid. Examples of pharmaceutically acceptable salts include, but are not limited to, nontoxic acid addition salts are salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentane-propionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl having from 1 to 6 carbon atoms, sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

The term "pharmaceutically acceptable prodrug" as used herein refers to a prodrug of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the present invention.

The term "prodrug" as used herein means a compound which is convertible in vivo by metabolic means (e.g., by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113-191 (1991); Bundgaard, et al., Journal of Drug Deliver Reviews, 8:1-38(1992); Bundgaard, J. of Pharmaceutical Sciences, 77:285 et seq. (1988); Higuchi and Stella (eds.) Prodrugs as Novel Drug Delivery Systems, American Chemical Society (1975); and Bernard Testa & Joachim Mayer, "Hydrolysis In Drug And Prodrug Metabolism: Chemistry, Biochemistry And Enzymology," John Wiley and Sons, Ltd. (2002). For example, compounds of formula (I) having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula (I). The amino acid residues include but are not limited to the 20 naturally occurring amino acids commonly designated by three letter symbols and also includes 4-hydroxyproline, hydroxyysine, demosine, isodemosine, 3-methylhistidine, norvalin, beta-alanine, gamma-aminobutyric acid, citrulline, homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, ethyl succinate, phosphate esters, dimethylaminoacetates, and phosphoryloxymethyloxycarbonyls, as outlined in Advanced Drug Delivery Reviews, 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in J. Med. Chem. 1996, 39, 10. Free amines can also be derivatized as amides, sulfonamides or phosphonamides. All of these prodrug moieties may incorporate groups including but not limited to ether, amine and carboxylic acid functionalities.

The term "amino acid" refers to naturally occurring and synthetic a, 3, y, or 6 amino acids, and includes but is not limited to, amino acids found in proteins or intermediates in metabolism of amino acids or proteins, i.e. glycine, alanine, valine, leucine, isoleucine, methionine, phenylalanine, tryptophan, proline, serine, threonine, cysteine, tyrosine, asparagine, glutamine, aspartate, glutamate, lysine, citrulline, arginine and histidine. In certain embodiments, the amino acid is in the L-configuration. In certain embodiments, the amino acid is in the D-configuration. In certain embodiments, the amino acid is provided as a substituent of a compound described herein, wherein the amino acid is a residue selected from the group consisting of alanyl, valinyl, leucinyl, isoleuccinyl, prolinyl, phenylalaninyl, tryptophanyl, methioninyl, glycinyl, serinyl, threoninyl, cysteinyl, tyrosinyl, asparaginyl, glutaminyl, aspartoyl, glutaroyl, lysinyl, argininyl, histidinyl, β-alanyl, β-valinyl, β-leucinyl, β-isoleuccinyl, β-prolinyl, β-phenylalaninyl, β-tryptophanyl, β-methioninyl, β-glycinyl, β-serinyl, β-threoninyl, β-cysteinyl, β-tyrosinyl, β-asparaginyl, β-glutaminyl, β-aspartoyl, β-glutaroyl, β-lysinyl, β-argininyl and β-histidinyl.

The term "amino acid derivative" refers to a group derivable from a naturally or non-naturally occurring amino acid, as described and exemplified herein. Amino acid derivatives are apparent to those of skill in the art and include, but are not limited to, ester, amino alcohol, amino aldehyde, amino lactone, and N-methyl derivatives of naturally and non-naturally occurring amino acids. In an embodiment, an amino acid derivative is provided as a substituent of a compound described herein, wherein the substituent is —$NR^u$-G($S_c$) —C(O)-$Q^1$, wherein $Q^1$ is —$SR^v$, —$NR^vR^v$ or alkoxyl, $R^v$ is hydrogen or alkyl, S, is a side-chain of a naturally occurring or non-naturally occurring amino acid, G is $C_1$-$C_2$ alkyl, and $R^u$ is hydrogen; or $R^u$ and S, are taken together with the atoms to which they are attached to form a five-membered heterocyclic ring. In an embodiment, an amino acid derivative is provided as a substituent of a compound described herein, wherein the substituent is —O—C(O)-G($S_c$)—NH-$Q^2$, wherein $Q^2$ is hydrogen or alkoxyl, S, is a side-chain of a naturally occurring or non-naturally occurring amino acid and G is $C_1$-$C_2$ alkyl. In certain embodiments, $Q^2$ and S, are taken together with the atoms to which they are attached to form a five-membered heterocyclic ring. In certain embodiments, G is an optionally substituted methylene and S, is selected from the group consisting of hydrogen, alkyl, arylalkyl, heterocycloalkyl, carboxylalkyl, heteroarylalkyl, aminoalkyl, hydroxylalkyl, aminoiminoaminoalkyl, aminocarbonylalkyl, sulfanylalkyl, carbamoylalkyl, alkylsulfanylalkyl and hydroxylarylalkyl. In an embodiment, an amino acid derivative is provided as a substituent of a compound described herein, wherein the amino acid derivative is in the D-configuration. In an embodiment, an amino acid derivative is provided as a substituent of a compound described herein, wherein the amino acid derivative is in the L-configuration.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semisolid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intra-arterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectable.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference).

Antiviral Activity

In certain embodiments, the present invention provides a method of treating or preventing a viral infection in a subject in need thereof, comprising administering to the subject a therapeutically effective amount of a compound of Formula (I) or a pharmaceutically acceptable salt thereof. The viral infection is preferably a coronavirus infection. In certain embodiments, the coronavirus is SARS-CoV-1, SARS-CoV-2, or MERS-CoV. Preferably the coronavirus is SARS-CoV-2.

A viral inhibitory amount or dose of the compounds of the present invention may range from about 0.01 mg/Kg to about 500 mg/Kg, alternatively from about 1 to about 50 mg/Kg. Inhibitory amounts or doses will also vary depending on route of administration, as well as the possibility of co-usage with other agents.

According to the methods of treatment of the present invention, viral infections are treated or prevented in a patient such as a human or another animal by administering to the patient a therapeutically effective amount of a compound of the invention, in such amounts and for such time as is necessary to achieve the desired result.

By a "therapeutically effective amount" of a compound of the invention is meant an amount of the compound which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). A therapeutically effective amount of the compound described above may range, for example, from about 0.1 mg/Kg to about 500 mg/Kg, preferably from about 1 to about 50 mg/Kg. Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

The compounds of the present invention described herein can, for example, be administered by injection, intravenously, intra-arterial, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

Combination and Alternation Therapy

The compounds of the present invention may be used in combination with one or more antiviral therapeutic agents or anti-inflammatory agents useful in the prevention or treatment of viral diseases or associated pathophysiology. Thus, the compounds of the present invention and their salts, solvates, or other pharmaceutically acceptable derivatives thereof, may be employed alone or in combination with other antiviral or anti-inflammatory therapeutic agents. The compounds herein and pharmaceutically acceptable salts thereof may be used in combination with one or more other agents which may be useful in the prevention or treatment of respiratory disease, inflammatory disease, autoimmune disease, for example; anti-histamines, corticosteroids, (e.g., fluticasone propionate, fluticasone furoate, beclomethasone dipropionate, budesonide, ciclesonide, mometasone furoate, triamcinolone, flunisolide), NSAIDs, Ieukotriene modulators (e.g., montelukast, zafirlukast.pranlukast), tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (Iysophosphatidic) inhibitors or FLAP (5-lipoxygenase activating protein) inhibitors (e.g., sodium 3-(3-(tert-butylthio)-1-(4-(6-ethoxypyridin-3-yl)benzyl)-5-((5-ethylpyridin-2-yl)methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen non-specific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents), suitable anti-infective agents including antibiotic agents, antifungal agents, antheimintic agents, antimalarial agents, antiprotozoal agents, antitubercuiosis agents, and antiviral agents, including those listed at https://www.drugs.com/drug-class/anti-infectives.html. In general, combination therapy is typically preferred over alternation therapy because it induces multiple simultaneous stresses on the virus.

When the compositions of this invention comprise a combination of a compound of the Formula described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, combined with a compound of this invention in a single composition.

The "additional therapeutic or prophylactic agents" include but are not limited to, immune therapies (e.g. interferon), therapeutic vaccines, antifibrotic agents, anti-inflammatory agents such as corticosteroids or NSAIDs, bronchodilators such as beta-2 adrenergic agonists and xanthines (e.g. theophylline), mucolytic agents, anti-muscarinics, anti-leukotrienes, inhibitors of cell adhesion (e.g. ICAM antagonists), anti-oxidants (e.g. N-acetylcysteine), cytokine agonists, cytokine antagonists, lung surfactants and/or antimicrobial and anti-viral agents (e.g. ribavirin and amantidine). The compositions according to the invention may also be used in combination with gene replacement therapy.

Abbreviations

Abbreviations which may be used in the descriptions of the scheme and the examples that follow are: Ac for acetyl; AcOH for acetic acid; $Boc_2O$ for di-tert-butyl-dicarbonate; Boc for t-butoxycarbonyl; Bz for benzoyl; Bn for benzyl; t-BuOK for potassium tert-butoxide; Brine for sodium chloride solution in water; CDI for carbonyldiimidazole; DCM or $CH_2Cl_2$ for dichloromethane; $CH_3$ for methyl; $CH_3CN$ for acetonitrile; $Cs_2CO_3$ for cesium carbonate; CuCl for copper (I) chloride; CuI for copper (I) iodide; dba for dibenzylidene acetone; DBU for 1,8-diazabicyclo[5.4.0]-undec-7-ene; DEAD for diethylazodicarboxylate; DIAD for diisopropyl azodicarboxylate; DIPEA or $(i\text{-}Pr)_2EtN$ for N,N,-diisopropylethyl amine; DMP or Dess-Martin periodinane for 1,1,2-tris(acetyloxy)-1,2-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EtOAc for ethyl acetate; EtOH for ethanol; $Et_2O$ for diethyl ether; HATU for O-(7-azabenzotriazol-2-yl)-N,N,N',N',-tetramethyluronium Hexafluorophosphate; HCl for hydrogen chloride; $K_2CO_3$ for potassium carbonate; n-BuLi for n-butyl lithium; DDQ for 2,3-dichloro-5,6-dicyano-1,4-benzoquinone; LDA for lithium diisopropylamide; LiTMP for lithium 2,2,6,6-tetramethylpiperidinate; MeOH for methanol; Mg for magnesium; MOM for methoxymethyl; Ms for mesyl or $—SO_2—CH_3$; NaHMDS for sodium bis(trimethylsilyl)amide; NaCl for sodium chloride; NaH for sodium hydride; $NaHCO_3$ for sodium bicarbonate or sodium hydrogen carbonate; $Na_2CO_3$ sodium carbonate; NaOH for sodium hydroxide; $Na_2SO_4$ for sodium sulfate; $NaHSO_3$ for sodium bisulfite or sodium hydrogen sulfite; $Na_2S_2O_3$ for sodium thiosulfate; $NH_2NH_2$ for hydrazine; $NH_4C_1$ for ammonium chloride; Ni for nickel; OH for hydroxyl; $OsO_4$ for osmium tetroxide; OTf for triflate; PPA for polyphosphoric acid; PTSA for p-toluenesulfonic acid; PPTS for pyridinium p-toluenesulfonate; TBAF for tetrabutylammonium fluoride; TEA or $Et_3N$ for triethylamine; TES for triethylsilyl; TESCl for triethylsilyl chloride; TESOTf for triethylsilyl trifluoromethanesulfonate; TFA for trifluoroacetic acid; THE for tetrahydrofuran; TMEDA for N,N,N',N'-tetramethylethylene-diamine; TPP or $PPh_3$ for triphenyl-phosphine; Tos or Ts for tosyl or $—SO_2—C_6H_4CH_3$; $Ts_2O$ for tolylsulfonic anhydride or tosyl-anhydride; TsOH for p-tolylsulfonic acid; Pd for palladium; Ph for phenyl; $Pd_2(dba)_3$ for tris(diben-zylideneacetone) dipalladium (0); $Pd(PPh_3)_4$ for tetrakis(triphenylphosphine)-palladium (0); $PdCl_2(PPh_3)_2$ for trans-dichlorobis-(triphenylphosphine)palladium (II); Pt for platinum; Rh for rhodium; rt for room temperature; Ru for ruthenium; TBS for tert-butyl dimethylsilyl; TMS for trimethylsilyl; and TMSCl for trimethylsilyl chloride.

Synthetic Methods

The compounds and processes of the present invention will be better understood in connection with the following synthetic schemes that illustrate the methods by which the compounds of the invention may be prepared, which are intended as an illustration only and not to limit the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

Scheme 1 illustrates a general method to prepare the compound of Formula (VI)

(VI)

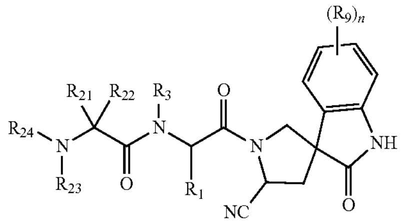

wherein $R_1$, $R_3$, n, $R_9$, $R_{21}$, $R_{22}$, $R_{23}$, and $R_{24}$ are as previously defined. Amide coupling of compound 1 with compound 2 under standard peptide coupling conditions provides compound 3. The standard peptide coupling conditions are summarized in *Chem. Rev.* 2011, 111, 11, 6557-6602 by Ayman El-Faham and Fernando Albericio. The $PG_1$ and $PG_2$ are normal protecting group such as, but not limited to Cbz, Boc or Fmoc. The $PG_1$ and $PG_2$ can be removed in standard deprotection conditions which are summarized in Greene's Protective Groups in Organic Synthesis, 5th Edition, Peter G. M. Wuts, Wiley 2014. After removal of $PG_1$ protecting group of compound 3, compound 4 is obtained and subjected to amide coupling reaction again with compound 5 using standard peptide coupling chemistry, to afford compound 6. Upon removal of $PG_2$ protecting group, functionalization of the nitrogen group of compound 7 affords compound 8 with various $R_{24}$ substitutions. Final conversion of the primary amide group in compound 8 to CN group under dehydration conditions, such as, but not limited to TFAA/$NEt_3$, Burgess reagent, and $Pd(OCOCF_3)_2$/$Cl_2CHCN$, provides compound 9 with Formula (VI).

Scheme 1

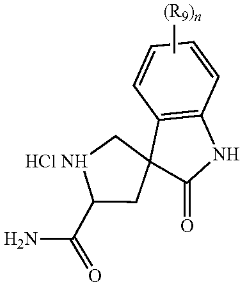

1

+

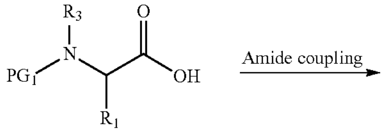

2

-continued

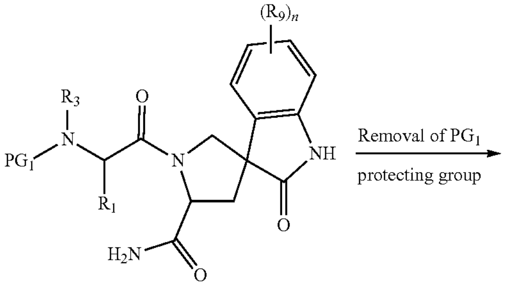

3

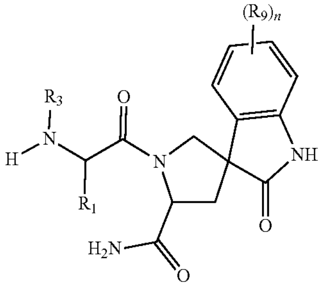

4

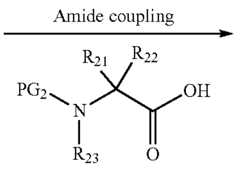

5

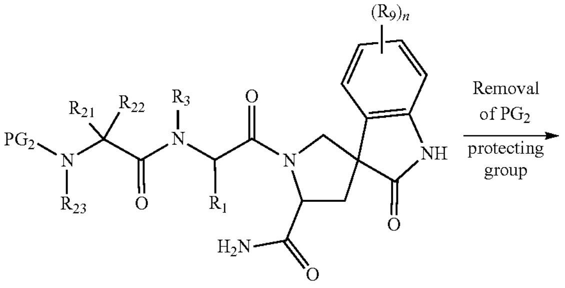

6

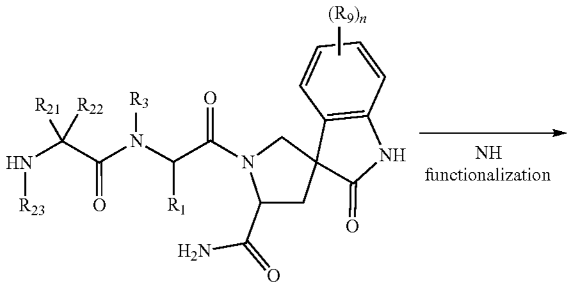

7

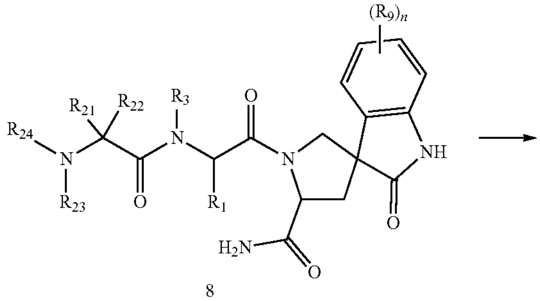

8

-continued

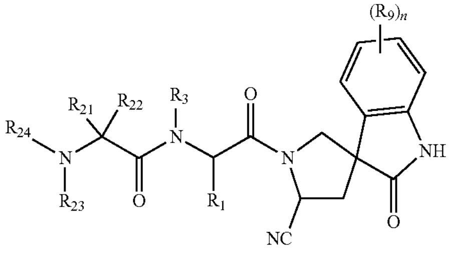

9
(VI)

Alternatively, as shown in Scheme 2, compound 7 can be converted to nitrile compound 10 first under standard dehydration conditions such as, but not limited to TFAA/$NEt_3$, Burgess reagent, and $Pd(OCOCF_3)_2/Cl_2CHCN$. Subsequent removal of $PG_2$ protecting group and introduction $R_{24}$ on NH forms compound 9 with Formula (VI).

Scheme 2

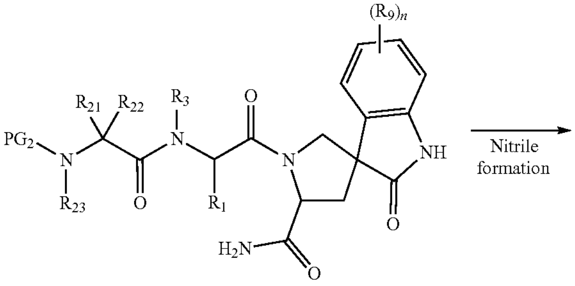

7

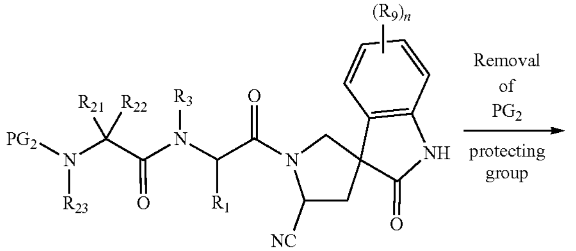

10

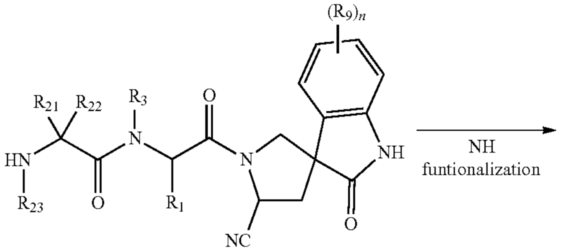

11

-continued

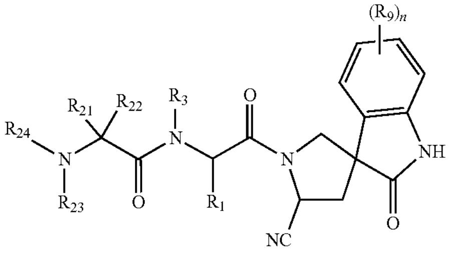

(VI)

Scheme 3 illustrates a general method to prepare the compound of Formula (V'), (V')

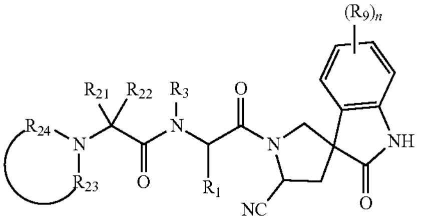

where $R_{23}$ and $R_{24}$, together with the N atom they are attaching to, forms an optionally substituted 3- to 8-membered heterocyclic or heteroaryl ring. Compound 14 can be synthesized from compound 4 and compound 12 through an amide coupling reaction followed by removal of $PG_2$ protecting group. The primary amine group of compound 14 can then be converted to various optionally substituted 3- to 8-membered heterocyclic or heteroaryl ring following literature procedures to form compound 15 which is subsequently converted to compound 16 with Formula (V') Selected literature procedures can be found in the following references: Huang, P.-Q.; Fan, T., *European Journal of Organic Chemistry* 2017, 43, 6369-6374; Dhingra, S. K.; Arora, S. K.; Singh, K.; Prasad, M.; Kumar, Y., WO 2006090265; Mochizuki, A.; Kishida, M.; Kanno, H., WO 2008111300; Chen, K. X.; Njoroge, F.; George; S.; Mousumi; N; Latha G.; et al, WO 2005085242; Sugiyama, S.; Morishita, K.; Chiba, M.; Ishii, K., Heterocycles 2002, 57, 637-648; Meng, G., Guo, T., Ma, T. et al., *Nature* 2019, 574, 86-89.

Scheme 3

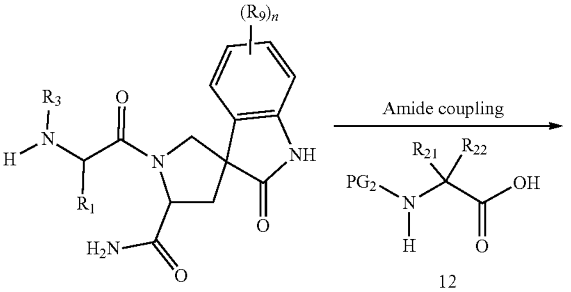

4

12

-continued

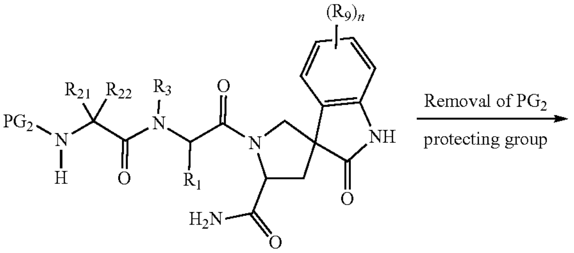

13

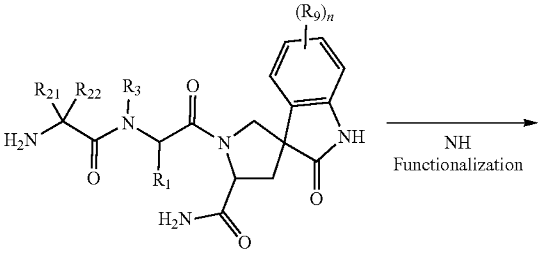

14

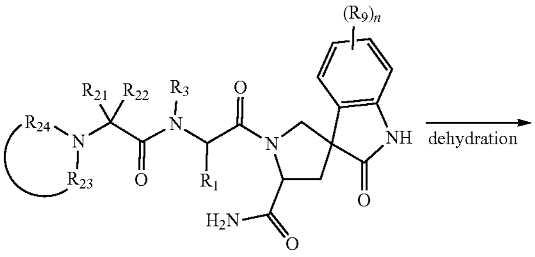

15

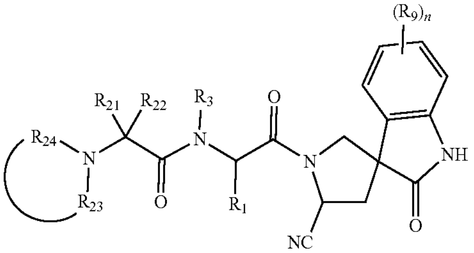

16
(V')

A compound with Formula (VI')

(VI')

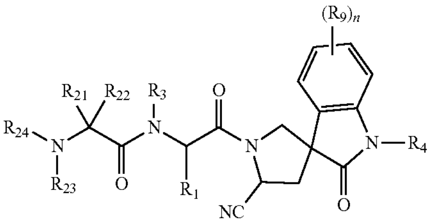

can be prepared from a compound with Formula (VI') by reacting with appropriate alkylating agents, such as, but not limited to $Me_2SO_4$, MeI, alkyl iodide, alkyl bromide, allyl bromide in the presence of a suitable base, such as but not limited to $K_2CO_3$, NaH, or KOt-Bu, as shown in Scheme 4.

Scheme 4

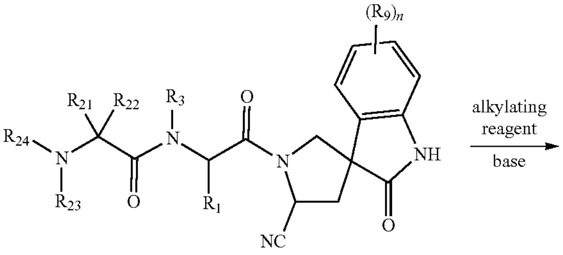

(VI)

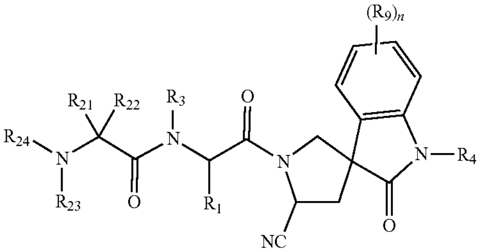

(VI')

Alternatively, a compound with Formula (VI') can be prepared from compound 21 following similar chemistry described previously for compound 9. Compound 21 can be obtained from compound 18 through alkylation, subsequent functional group transformation and removal of $PG_3$ protecting group as shown in Scheme 5.

Scheme 5

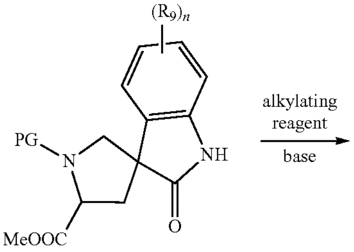

18

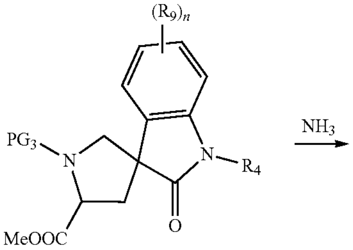

19

-continued

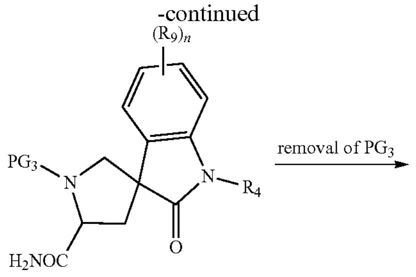

20

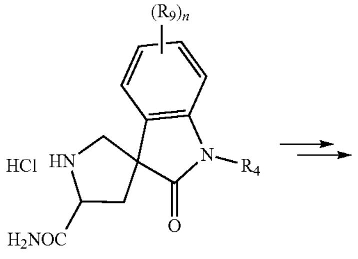

21

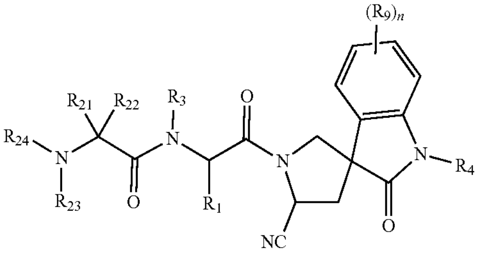

(VI')

Compound with Formula (VI")

(VI")

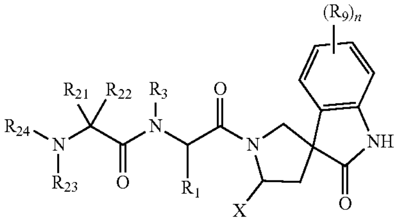

whereas X is as described previously, can be prepared from aldehyde intermediate 25 using standard functional group transformations. Compound 18 is converted to alcohol compound 22 via reduction of ester. The reducing agent can be, but not limited to, $LiBH_4$, DIBAL, $NaBH_4$. Removal of the PG group of compound 22 affords intermediate 23, which is then converted to compound 24 using similar chemistry described previously. Aldehyde 25 is prepared from alcohol intermediate 24 via oxidation of the OH group using conditions such as, but not limited to IBX oxidation, Swern oxidation, Dess-Martin oxidation, or Albright-Goldman oxidation. Compound 26 with Formula (VI") can then be synthesized from aldehyde intermediate 25 using appropriate chemistry depending on the nature of X. Selected chemistry and procedures have been described in the following references: *J. Med. Chem.* 2020, 63, 4562-4578, WO 2020/030143, and *J. Med. Chem.* 2015, 58, 3144-3155.

Scheme 6

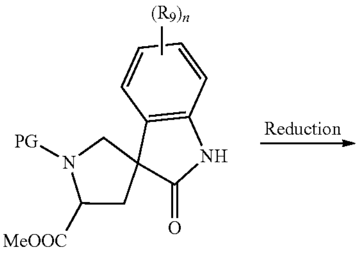

18

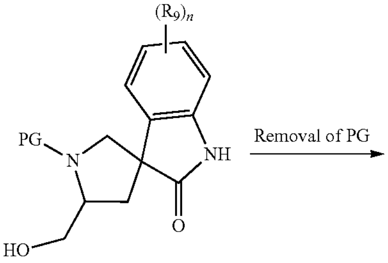

22

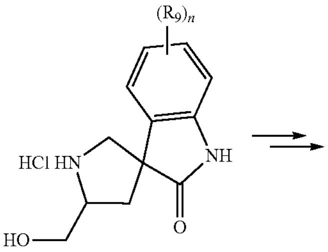

23

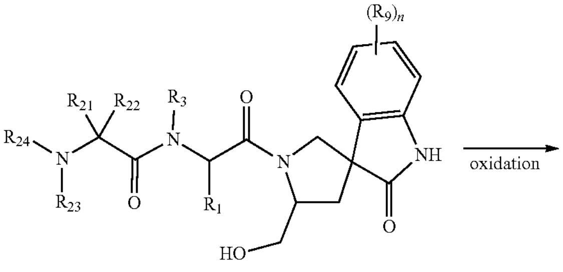

24

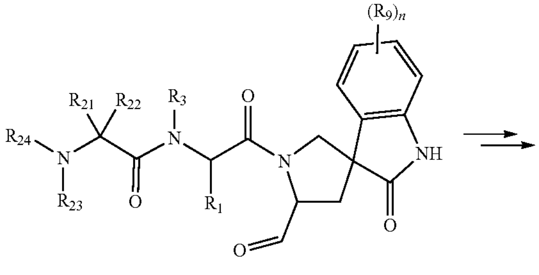

25

-continued

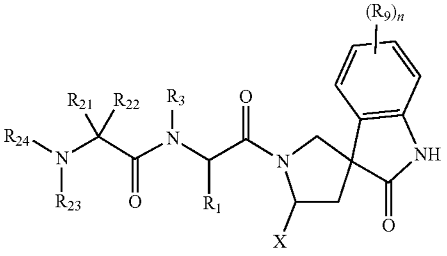

(VI'')

EXAMPLES

The compounds and processes of the present invention will be better understood in connection with the following examples, which are intended as an illustration only and not limiting of the scope of the invention. Starting materials were either available from a commercial vendor or produced by methods well known to those skilled in the art.

General Conditions:

Mass spectra were run on LC-MS systems using electrospray ionization. These were Agilent 1290 Infinity II systems with an Agilent 6120 Quadrupole detector. Spectra were obtained using a ZORBAX Eclipse XDB-C18 column (4.6x30 mm, 1.8 micron). Spectra were obtained at 298K using a mobile phase of 0.1% formic acid in water (A) and 0.1% formic acid in acetonitrile (B). Spectra were obtained with the following solvent gradient: 5% (B) from 0-1.5 min, 5-95% (B) from 1.5-4.5 min, and 95% (B) from 4.5-6 min. The solvent flowrate was 1.2 mL/min. Compounds were detected at 210 nm and 254 nm wavelengths. $[M+H]^+$ refers to mono-isotopic molecular weights.

NMR spectra were run on a Bruker 400 MHz spectrometer. Spectra were measured at 298K and referenced using the solvent peak. Chemical shifts for $^1H$ NMR are reported in parts per million (ppm).

Compounds were purified via reverse-phase high-performance liquid chromatography (RPHPLC) using a Gilson GX-281 automated liquid handling system. Compounds were purified on a Phenomenex Kinetex EVO C18 column (250x21.2 mm, 5 micron), unless otherwise specified. Compounds were purified at 298K using a mobile phase of water (A) and acetonitrile (B) using gradient elution between 0% and 100% (B), unless otherwise specified. The solvent flowrate was 20 mL/min and compounds were detected at 254 nm wavelength.

Alternatively, compounds were purified via normal-phase liquid chromatography (NPLC) using a Teledyne ISCO Combiflash purification system. Compounds were purified on a REDISEP silica gel cartridge. Compounds were purified at 298K and detected at 254 nm wavelength.

Example 1

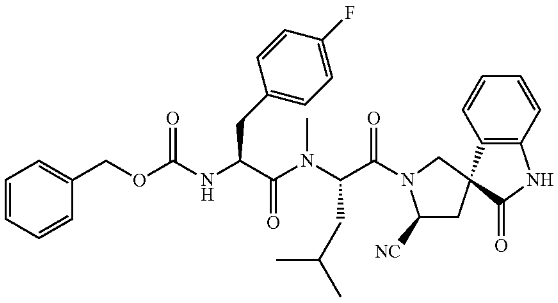 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)OCc1ccccc1]

Steps 1-3: Synthesis of (3R,5'S)-2-oxospiro[indoline-3,3'-pyrrolidine]-5'-carboxamide hydrochloride

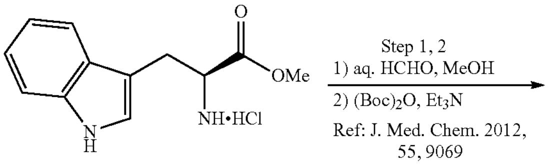

L-Trp-OMe HCl
1-1

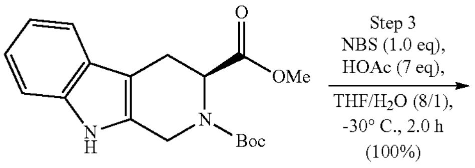

1-2

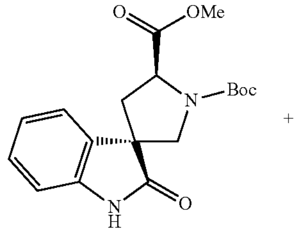

major
1-3a
dr 10/1

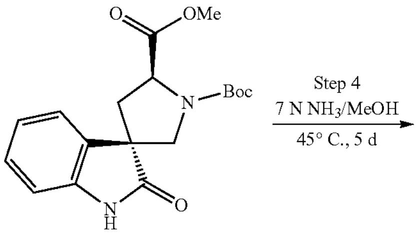

minor
1-3b

-continued

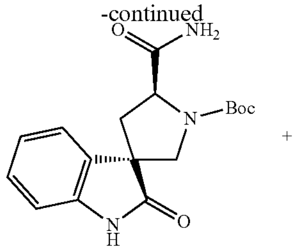

major
1-4a

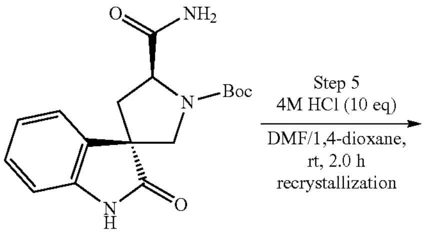

minor
1-4b

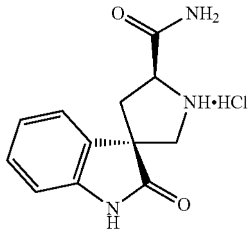

1-5

Steps 1 and 2: Compound 1-2 was prepared following literature reported procedures, such as described in *J. Med. Chem.* 2012, 55, 9069.

Step 3: To a clear solution of the compound 1-2 (45.0 g, 136 mmol) in THE (720 mL) in a three neck 2000 mL flask at 0° C. was added water (90 mL) in one portion. Acetic acid (54.6 mL, 953 mmol) was added at 0° C. The cloudy mixture was cooled to −30° C. A solution of NBS (24.24 g, 136 mmol) in THF/$H_2O$ (8/1, 207 mL) was added dropwise over 30 min while maintaining the internal temperature below −30° C. The milky mixture became a yellow cloudy solution and was stirred at −30° C. (internal temperature) for 1.0 h. The cloudy yellow solution was allowed to warm up to −20° C. and poured portionwise into a mixture of potassium carbonate (65.9 g, 477 mmol) in cold water (~300 mL), saturated $NaHCO_3$ solution (~400 mL) and EtOAc (300 mL) with stirring. The mixture was further diluted with EtOAc (500 mL). The aqueous layer was extracted with EtOAc (1×). The combined organic layers were washed with brine (1×), dried over $Na_2SO_4$, filtered and concentrated to afford crude product as a light yellow sticky oil (56.0 g). The crude product was dissolved in DCM (60 mL) and filtered through a 330 g silica gel column (MTBE/Cyclohexane) to afford the desired product 1-3 as an off-white foam (48.20 g, 102%). $^1$H NMR (400 MHz, DMSO-$d_6$) showed dr 10/1 (1-3a/1-3b).

Step 4: A clear colorless solution of compound 1-3 (48.20 g, 139 mmol, dr 10/1) in 7 N ammonia in MeOH (400 mL) was stirred at 45° C. in a sealed tube for 4 days. The mixture was allowed to cool down and concentrated. The solid was dried under vacuum to afford the desired compound 1-4 as a yellow solid (42.80 g, 93%). $^1$H NMR (400 MHz, DMSO-$d_6$) showed dr 10/1 (1-4a/1-4b).

Step 5: To a clear solution of compound 1-4 (42.80 g, 129 mmol, dr 10/1) in DMF (85 mL) at rt was added 4 M HCl in 1,4-dioxane (323 mL, 1292 mmol). The resulting clear light yellow solution was stirred at rt for 2.5 h, and concentrated by rotavapor. The resulting clear solution was poured into DCM (1700 mL) with stirring to form a slurry. The precipitated solid was collected by filtration, and rinsed with DCM (×2). The solid was dried under vacuum to afford crude 1-5 as a light yellow solid (35.20 g, 102%).

Recrystallization: 3 g of the above crude compound 1-5 was mixed with DMF (9 mL) and heated to form a near clear solution. Solid started to appear while heating. The mixture was allowed to cool down to rt. The precipitated solid was collected by filtration and rinsed with DMF (1 mL) and DCM (2×). The solid was dried under vacuum to afford the desired product compound 1-5 as a white solid (2.14 g). $^1$H NMR (400 MHz, DMSO-$d_6$) showed clean product with ~0.9 eq DMF, but no minor diastereomer. $^1$H NMR (400 MHz, DMSO-$d_6$) δ 11.14 (brs, 1H), 10.81 (s, 1H), 9.08 (brs, 1H), 8.07 (s, 1H), 7.78 (s, 1H), 7.66 (d, J=7.4 Hz, 1H), 7.27 (td, J=7.7, 1.2 Hz, 1H), 7.04 (td, J=7.6, 1.1 Hz, 1H), 6.92 (d, J=7.7 Hz, 1H), 4.65 (dd, J=11.2, 7.1 Hz, 1H), 3.59 (d, J=12.3 Hz, 1H), 3.45 (d, J=12.3 Hz, 1H), 2.50 (dd, J=12.9, 11.2 Hz, 1H), 2.22 (dd, J=12.9, 11.2 Hz, 1H).

Steps 6-9: Synthesis of Example 1

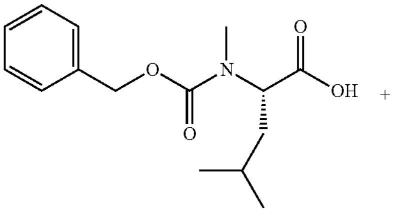

1.05 eq

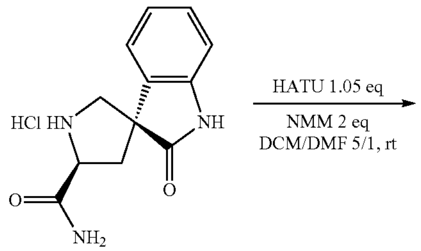

1-5

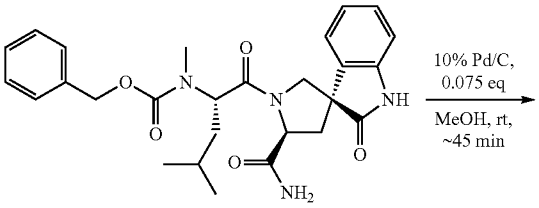

1-6

-continued

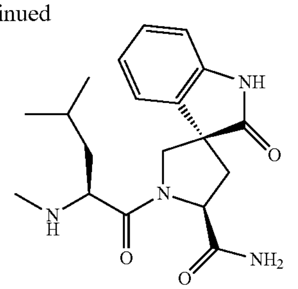

1-7

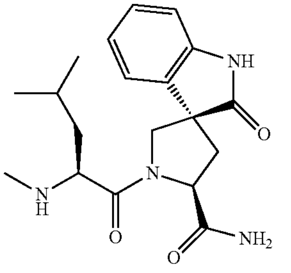

1-7

+

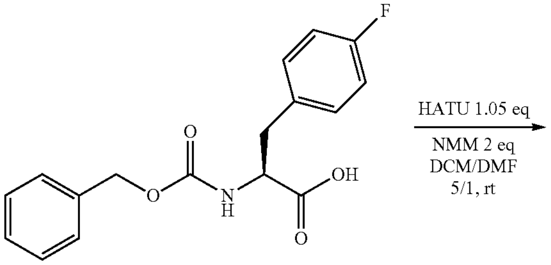

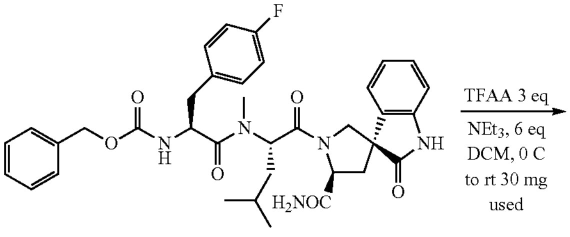

1-8

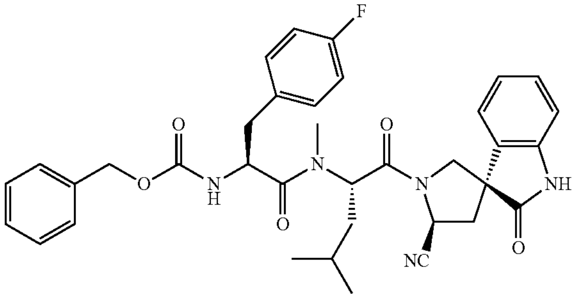

Example 1

Step 6: To a mixture of compound 1-5 (5 g, 14.90 mmol) and N-((benzyloxy)carbonyl)-N-methyl-L-leucine (4.29 g, 15.35 mmol) in dry $CH_2Cl_2$ (60 mL) and DMF (10 mL) at 0° C. were added 4-methylmorpholine (4.92 mL, 44.7 mmol) and HATU (5.84 g, 15.35 mmol). The resulting mixture was stirred at 0° C. for 30 min and then at rt for 1 h. The reaction mixture was diluted with DCM (100 mL), and washed sequentially with 5% $NaHCO_3$ (100 mL), water (100 mL) and brine (100 mL). The collected organic layer was dried over $Na_2SO_4$, and concentrated in vacuo. The residue was purified by silica gel chromatography (0 to 10% MeOH/DCM) to afford the desired compound 1-6 (5.33 g, 10.82 mmol, 72.6% yield) as a white solid. LC-MS, ES+: 493.14 [M+1].

Step 7: To a solution of compound 1-6 (4.0 g, 7.63 mmol) in MeOH (76 mL) was added 10% Pd—C (0.406 g, 0.382 mmol). The mixture was stirred under $H_2$ balloon for 60 min. The mixture was then filtered through celite, and concentrated in vacuo to provide compound 1-7 (2.7 g, 7.53 mmol, 99% yield), which was used in the next step without further purification.

Step 8: To a mixture of compound 1-7 (300 mg, 0.837 mmol) and (S)-2-(((benzyloxy)carbonyl)amino)-3-(4-fluorophenyl)propanoic acid (279 mg, 0.879 mmol) in dry $CH_2Cl_2$ (7 mL) and DMF (1.4 mL) at 0° C. were added 4-methylmorpholine (184 μl, 1.674 mmol) and HATU (350 mg, 0.921 mmol). The resulting mixture was stirred at 0° C. for 30 min and then at rt for several hours until LC-MS indicated the reaction was completed. The reaction mixture was diluted with DCM, and washed with 5% $NaHCO_3$, water, and brine. The collected organic layer was dried over $Na_2SO_4$, and concentrated in vacuo. The residue was purified by silica gel chromatography (0 to 10% MeOH/DCM) to afford the desired compound 1-8 (400 mg, 0.61 mmol, 73% yield) as a white solid. LC-MS, ES+: 658.26 [M+1].

Step 9: To a solution of compound 1-8 (28 mg, 0.043 mmol) and triethylamine (35.6 μL, 0.255 mmol) in dry $CH_2Cl_2$ (1 mL) at 0° C. was added TFAA (17.75 μL, 0.128 mmol) dropwise. The mixture was then stirred at 0° C. for 30-60 min until LC-MS indicated the reaction was complete. The reaction mixture was diluted with DCM, washed with 10% aq. $NaHCO_3$, brine, dried over $Na_2SO_4$, and concentrated. The residue was purified by silica gel chromatography (0 to 40% acetone/cyclohexane) to afford Example 1 (18 mg, 0.028 mmol, 66.1% yield). LC-MS, $ES^-$: 638.1 [M−H]. $^1H$ NMR (400 MHz, Acetone-$d_6$) δ 9.73 (s, 1H), 7.35-7.28 (m, 2H), 7.25-7.18 (m, 2H), 7.17 (dt, J=7.9, 4.5 Hz, 1H), 7.10-6.92 (m, 3H), 6.40 (d, J=9.0 Hz, 1H), 5.45 (dd, J=9.3, 5.8 Hz, 1H), 5.21 (t, J=8.5 Hz, 1H), 4.95 (d, J=2.2 Hz, 2H), 4.63 (td, J=9.7, 4.0 Hz, 1H), 4.04 (d, J=10.7 Hz, 1H), 3.96 (d, J=10.6 Hz, 1H), 3.15 (s, 3H), 2.82-2.63 (m, 2H), 2.44 (dd, J=14.2, 10.3 Hz, 1H), 2.31 (dd, J=14.3, 4.1 Hz, 1H), 1.78 (ddd, J=14.2, 9.3, 5.0 Hz, 1H), 1.66 (ddd, J=14.1, 8.8, 5.8 Hz, 1H), 1.53 (dd, J=13.3, 6.9 Hz, 1H), 0.95 (d, J=6.6 Hz, 3H), 0.88 (d, J=6.5 Hz, 3H).

Example 2

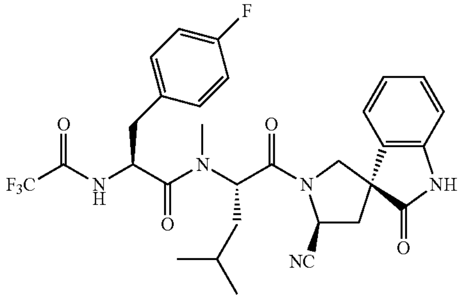

-continued

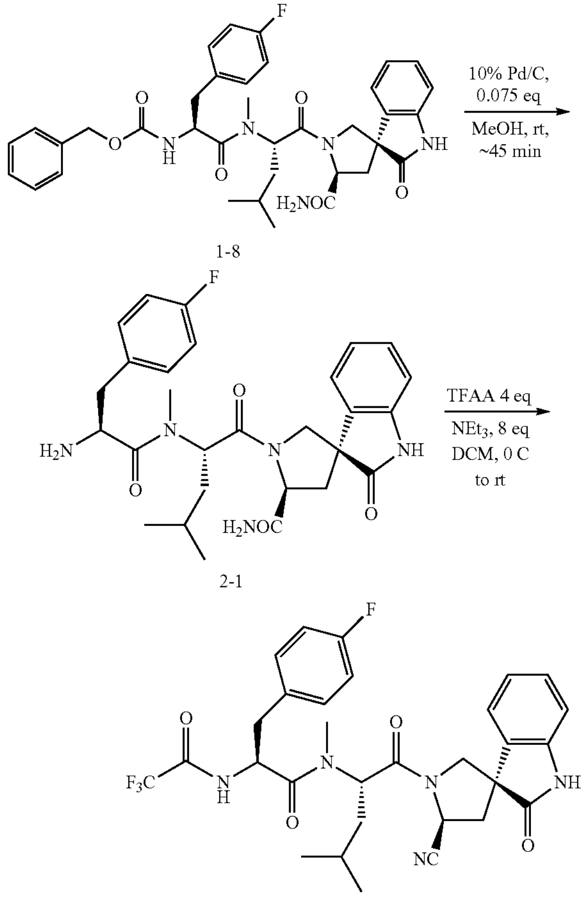

1-8

2-1

Example 2

Step 1: A mixture of compound 1-8 (370 mg, 0.563 mmol) and 10% Pd—C(29.9 mg, 0.028 mmol) in MeOH (5.63 mL) was stirred under $H_2$ balloon for 60 min. The mixture was filtered through celite, and concentrated in vacuo to provide compound 2-1 (290 mg, 98% yield), which was used directly without further purification. LC-MS, $ES^+$: 524.13 [M+1].

Step 2: To a solution of compound 2-1 (30 mg, 0.057 mmol) and triethylamine (63.9 μL, 0.458 mmol) in $CH_2Cl_2$ (1.146 mL) at 0° C. was added TFAA (31.9 μL, 0.229 mmol) dropwise. The mixture was stirred at 0° C. for ~30 min and then stirred at rt for ~60 min.

The reaction mixture was then diluted with DCM, washed with 10% aq. $NaHCO_3$, brine, dried over $Na_2SO_4$, and concentrated. The residue was purified by silica gel chromatography (0 to 50% acetone/cyclohexane) to afford Example 2 (22 mg, 0.037 mmol, 63.8% yield). LC-MS, $ES^-$: 600.0 [M−H]. 1H NMR (400 MHz, Acetone-$d_6$) δ 9.77 (s, 1H), 8.41 (d, J=8.4 Hz, 1H), 7.31-7.23 (m, 2H), 7.19 (ddd, J=7.7, 6.9, 2.0 Hz, 1H), 7.12-7.02 (m, 4H), 6.97 (dt, J=7.8, 0.9 Hz, 1H), 5.45 (dd, J=9.3, 5.9 Hz, 1H), 5.22 (t, J=8.5 Hz, 1H), 4.96 (td, J=9.0, 4.8 Hz, 1H), 4.05 (d, J=10.6 Hz, 1H), 3.99 (d, J=10.5 Hz, 1H), 3.20 (s, 3H), 2.80-2.64 (m, 2H), 2.64-2.47 (m, 2H), 1.80 (ddd, J=14.4, 9.3, 5.2 Hz, 1H), 1.70 (ddd, J=14.2, 8.6, 5.9 Hz, 1H), 1.58-1.43 (m, 1H), 0.92 (dd, J=26.3, 6.6 Hz, 6H).

Example 3

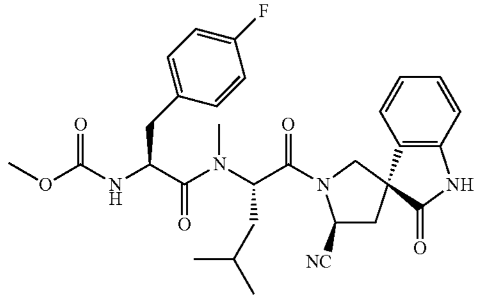

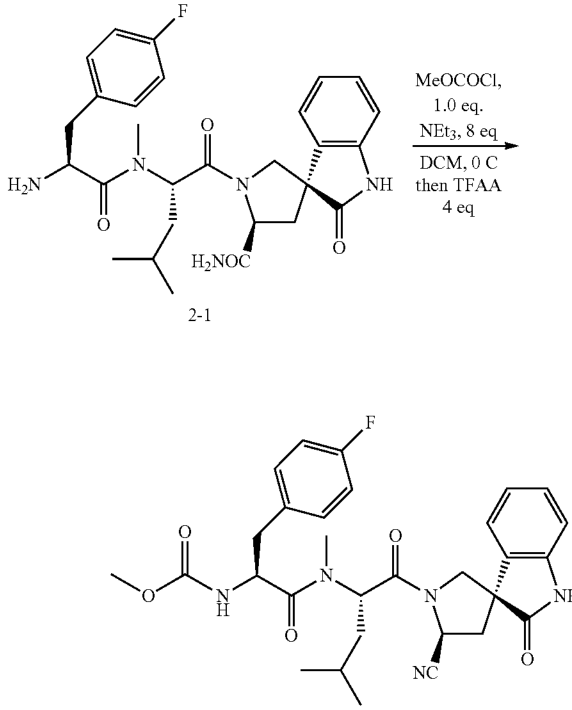

2-1

Example 3

To a solution of compound 2-1 (30 mg, 0.057 mmol) and triethylamine (63.9 μL, 0.458 mmol) in $CH_2Cl_{12}$ (1.146 mL) at 0° C. was added methyl chloroformate (4.43 μL, 0.057 mmol). After stirring at 0° C. for 45 min, TFAA (31.9 μL, 0.229 mmol) was added dropwise. After stirring at 0° C. for 30 min, the reaction was stirred at rt for ~60 min.

Work-up: the reaction mixture was diluted with DCM, washed with 10% aq. $NaHCO_3$, brine, dried over $Na_2SO_4$, and concentrated. The residue was purified by silica gel chromatography (0 to 50% acetone/cyclohexane) to afford Example 3 (5 mg, 15% yield). LC-MS, $ES^-$: 562.0 [M−H]. $^1H$ NMR (400 MHz, Acetone-$d_6$) δ 9.60 (s, 1H), 7.08 (dt, J=12.9, 4.8 Hz, 2H), 7.01 (td, J=5.2, 2.6 Hz, 1H), 6.93-6.85 (m, 4H), 6.80 (d, J=7.7 Hz, 1H), 6.11 (d, J=8.9 Hz, 1H), 5.29 (dd, J=9.2, 6.0 Hz, 1H), 5.06 (t, J=8.5 Hz, 1H), 4.45 (td, J=9.6, 4.1 Hz, 1H), 3.88 (d, J=10.7 Hz, 1H), 3.81 (d, J=10.6 Hz, 1H), 3.31 (s, 3H), 3.00 (s, 3H), 2.63-2.45 (m, 2H), 2.27 (dd, J=14.3, 10.1 Hz, 1H), 2.16 (dd, J=14.2, 4.2 Hz, 1H), 1.61 (dt, J=8.8, 5.1 Hz, 1H), 1.57-1.47 (m, 1H), 1.43-1.36 (m, 1H), 0.78 (dd, J=24.7, 6.5 Hz, 6H).

Example 4

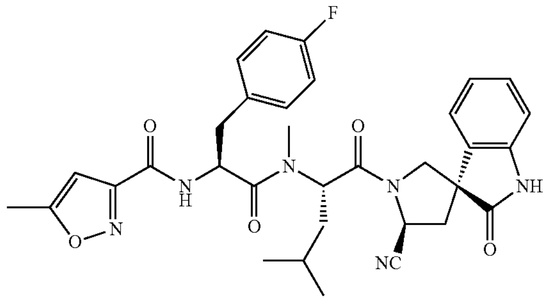

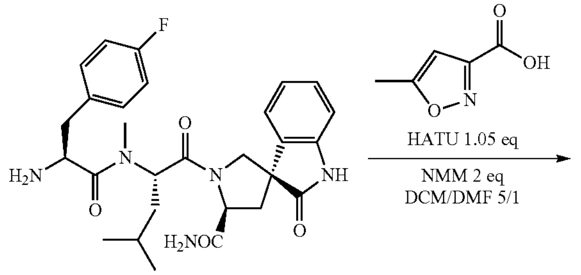

2-1

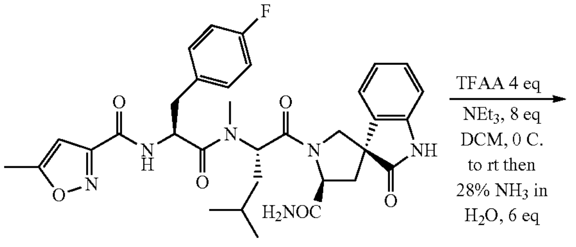

4-1

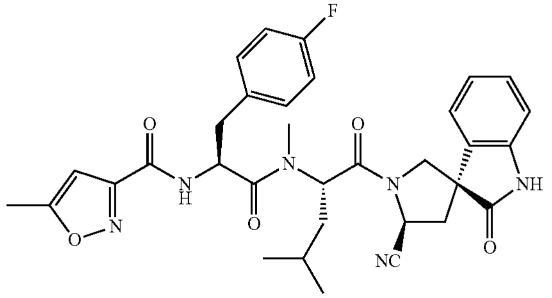

Example 4

Step 1: Compound 2-1 (25 mg, 0.048 mmol) and 5-methylisoxazole-3-carboxylic acid (6.37 mg, 0.050 mmol) were dissolved in $CH_2Cl_2$ (0.40 mL) and DMF (0.10 mL). 4-Methylmorpholine (10.50 μL, 0.095 mmol) and HATU (19.97 mg, 0.053 mmol) were added at 0° C. After stirring at 0° C. for 1 h, the reaction mixture was diluted with DCM, washed with 5% $NaHCO_3$, brine, dried over $Na_2SO_4$, and concentrated in vacuo. The crude compound 4-1 was directly used in the next step without purification. LC-MS, $ES^+$: 633.20 [M+H].

Step 2: Compound 4-1 (0.030 g, 0.048 mmol) was dissolved in $CH_2Cl_2$ (0.96 mL). At 0° C. triethylamine (0.040 mL, 0.288 mmol) and TFAA (0.020 mL, 0.144 mmol) were added. The mixture was stirred at 0° C. for ~30 min and then stirred at rt for ~60 min. 28% ammonia in water (19 uL, 0.29 mmol) was added. After stirring for another 1 h at rt, the reaction mixture was diluted with $CH_2Cl_2$, washed with water, brine, dried over $Na_2SO_4$, and concentrated. The residue was purified by silica gel chromatography (0 to 50% acetone/cyclohexane) to afford Example 4 (22 mg, 75% yield for 2 steps). LC-MS, $ES^+$: 615.2 [M+H]. 1H NMR (400 MHz, Acetone-$d_6$) δ 9.76 (s, 1H), 7.67 (d, J=8.5 Hz, 1H), 7.30-7.22 (m, 2H), 7.18 (td, J=7.3, 2.0 Hz, 1H), 7.11-6.91 (m, 5H), 6.35 (s, 1H), 5.45 (dd, J=9.2, 6.0 Hz, 1H), 5.24 (t, J=8.5 Hz, 1H), 5.10 (td, J=8.9, 4.3 Hz, 1H), 4.07 (d, J=10.7 Hz, 1H), 4.00 (d, J=10.6 Hz, 1H), 3.23 (s, 3H), 2.83-2.65 (m, 3H), 2.57 (dd, J=14.2, 4.3 Hz, 1H), 2.44 (s, 3H), 1.87-1.63 (m, 2H), 1.63-1.48 (m, 1H), 0.91 (dd, J=25.8, 6.6 Hz, 6H).

Example 5

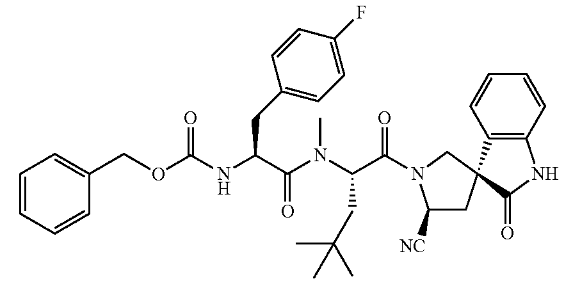

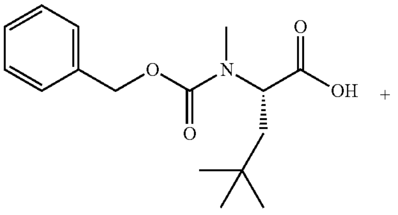

1.05 eq

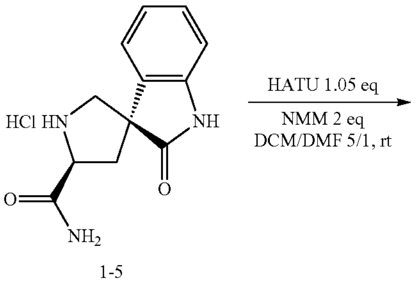

1-5

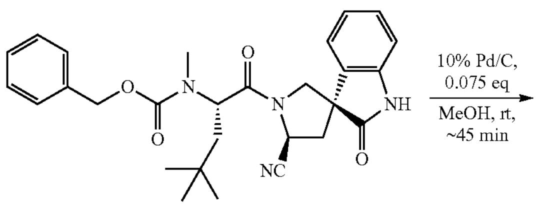

5-1

-continued

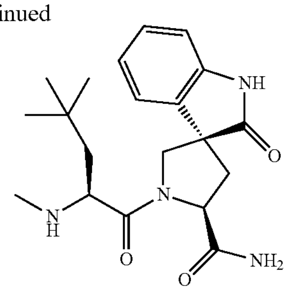

5-2

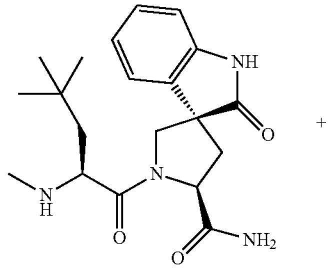

5-2

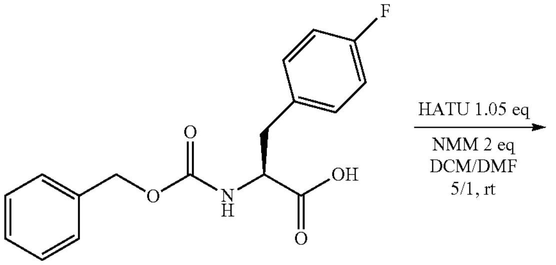

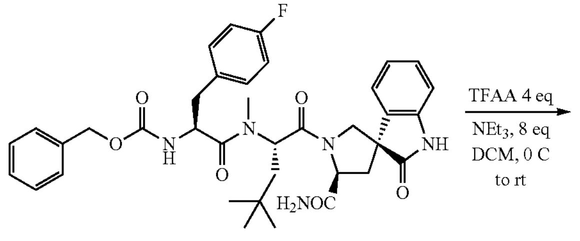

5-3

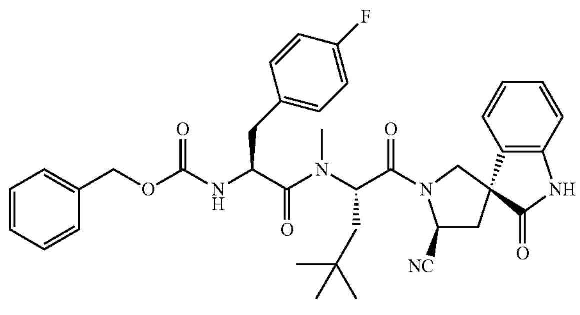

Example 5

Step 1-4: Example 5 was prepared following similar procedures as described in Example 1. $ES^-$: 651.99 [M−H].

Example 6

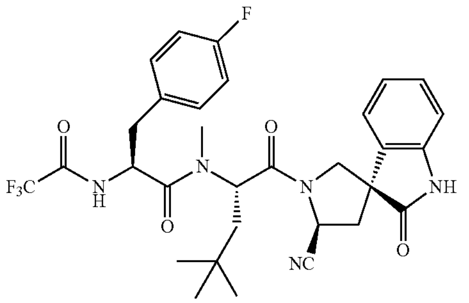

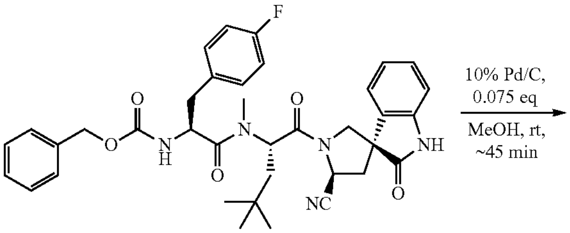

5-4

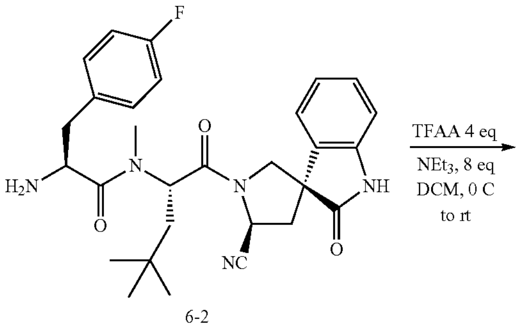

6-2

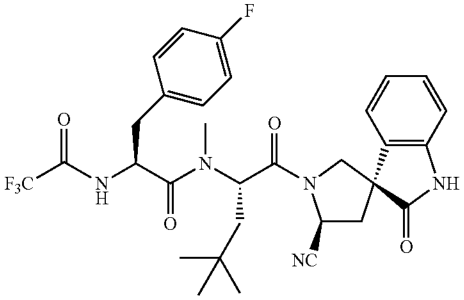

Example 6

Step 1: Compound 5-4 (237 mg, 0.363 mmol) was dissolved in MeOH (4.53 mL). 10% Pd—C (19.29 mg, 0.018 mmol) was added. The mixture was stirred under $H_2$ (balloon) for 60 min. The mixture was filtered through celite and concentrated in vacuo to provide compound 6-2 (187 mg, 0.360 mmol, 99% yield), which was used in the next step without further purification. LC-MS, $ES^+$: 520.24 [M+H].

Step 2: Compound 6-2 (20 mg, 0.038 mmol) was dissolved in $CH_2Cl_{12}$ (0.77 mL). At 0° C. triethylamine (16.09 μL, 0.115 mmol) and TFAA (8.03 μL, 0.058 mmol) were added. The mixture was stirred at 0° C. for ~45 min. The reaction mixture was diluted with DCM, washed with 10% aq. $NaHCO_3$, brine, dried over $Na_2SO_4$, and concentrated. The residue was purified by silica gel chromatography (0 to 50% acetone/cyclohexane) to afford Example 6. LC-MS, ES⁻: 614.06 [M−H]. 1H NMR (400 MHz, Acetone-$d_6$) δ 9.78 (s, 1H), 8.41 (d, J=8.9 Hz, 1H), 7.25 (ddd, J=8.4, 5.3, 2.5 Hz, 2H), 7.18 (ddd, J=7.7, 5.1, 3.8 Hz, 1H), 7.11-7.01 (m, 4H), 6.98 (dt, J=7.7, 0.9 Hz, 1H), 5.50 (dd, J=6.8, 5.7 Hz, 1H), 5.22 (t, J=8.6 Hz, 1H), 4.94 (td, J=9.0, 5.6 Hz, 1H), 4.07 (d, J=10.5 Hz, 1H), 4.00 (d, J=10.5 Hz, 1H), 3.21 (s, 3H), 2.80-2.67 (m, 2H), 2.49-2.42 (m, 2H), 2.17-2.11 (m, 1H), 1.56 (dd, J=14.2, 5.7 Hz, 1H), 0.94 (s, 9H).

Example 7

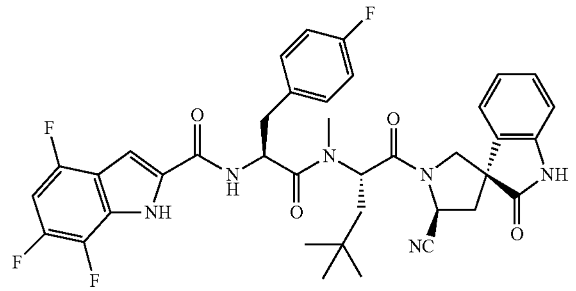

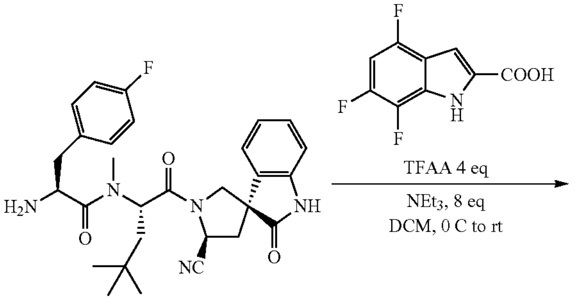

6-2

Example 7

Compound 6-2 (20 mg, 0.038 mmol) and 4,6,7-trifluoro-1H-indole-2-carboxylic acid (9.11 mg, 0.042 mmol) were dissolved in $CH_2Cl_2$ (0.321 mL) and DMF (0.064 mL). 4-Methylmorpholine (8.46 μl, 0.077 mmol) and HATU (16.83 mg, 0.044 mmol) were added at 0° C. The mixture was stirred at 0° C. to rt for 1 h. The reaction mixture was diluted with DCM, and washed with brine. The organic layer was dried over $Na_2SO_4$ and concentrated in vacuo. The residue was purified by silica gel chromatography (0 to 50% acetone/cyclohexane) to afford Example 7 (20 mg, 0.028 mmol, 72.5% yield). LC-MS, ES⁻: 715.09 [M−H]. 1H NMR (400 MHz, Acetone-$d_6$) δ 11.41 (s, 1H), 9.79 (s, 1H), 7.88 (d, J=9.0 Hz, 1H), 7.28 (td, J=5.6, 2.5 Hz, 3H), 7.20 (ddd, J=7.7, 5.9, 3.1 Hz, 1H), 7.13-7.08 (m, 2H), 7.03-6.96 (m, 3H), 6.90 (ddd, J=11.3, 9.6, 5.2 Hz, 1H), 5.53 (dd, J=7.0, 5.5 Hz, 1H), 5.23 (t, J=8.6 Hz, 1H), 5.12 (ddd, J=10.8, 9.0, 3.8 Hz, 1H), 4.11 (d, J=10.6 Hz, 1H), 4.01 (d, J=10.5 Hz, 1H), 3.24 (s, 3H), 2.79-2.66 (m, 2H), 2.50 (dd, J=14.2, 10.9 Hz, 1H), 2.39 (dd, J=14.2, 3.9 Hz, 1H), 2.15 (dd, J=14.2, 7.0 Hz, 1H), 1.52 (dd, J=14.1, 5.5 Hz, 1H), 0.92 (s, 9H).

Example 8

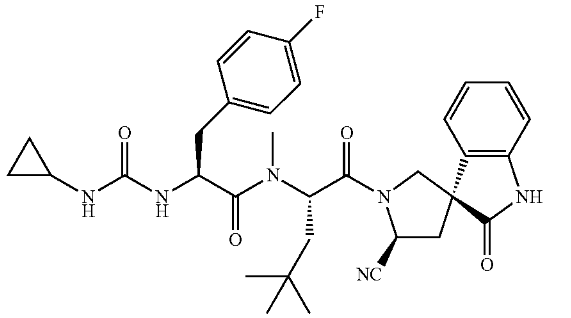

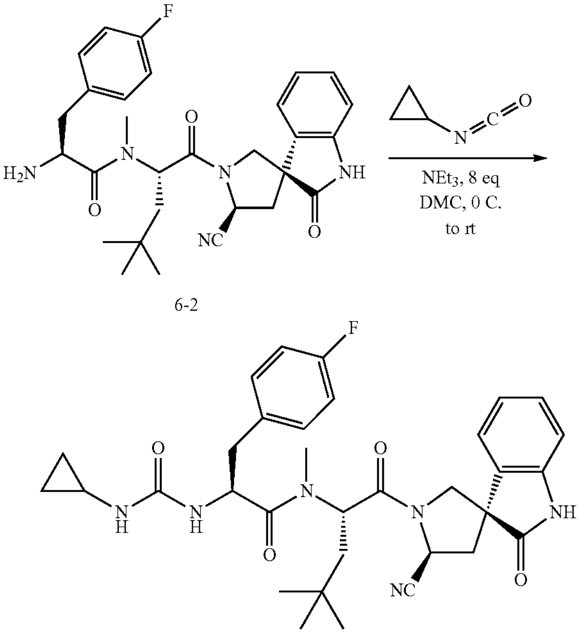

6-2

Example 8

To a solution of compound 6-2 (20 mg, 0.038 mmol) in dry $CH_2Cl_{12}$ (0.77 mL) at 0° C. was added triethylamine (21.46 μL, 0.154 mmol), followed by addition of isocyanatocyclopropane (3.49 μL, 0.050 mmol). The mixture was stirred at 0° C. for 1 h.

The reaction mixture was diluted with DCM and washed with 5% $NaHCO_3$. The organic layer was washed with brine, dried over $Na_2SO_4$, and concentrated in vacuo. The residue was purified by silica gel chromatography (0 to 50% acetone/cyclohexane) to afford Example 8 (16 mg, 0.027 mmol, 69.0% yield). LC-MS, ES⁻: 601.13 [M−H]. 1H NMR (400 MHz, Acetone-$d_6$) δ 9.79 (s, 1H), 7.20-7.12 (m, 3H), 7.08-6.92 (m, 5H), 5.63 (s, 1H), 5.56 (d, J=9.1 Hz, 1H), 5.48 (dd, J=7.0, 5.5 Hz, 1H), 5.21 (t, J=8.6 Hz, 1H), 4.78 (td, J=9.1, 4.9 Hz, 1H), 4.06 (dd, J=10.5, 1.2 Hz, 1H), 3.98 (d, J=10.4 Hz, 1H), 3.17 (s, 3H), 2.79-2.63 (m, 2H), 2.39-2.24 (m, 3H), 2.18-2.11 (m, 1H), 1.51 (dd, J=14.2, 5.5 Hz, 1H), 0.94 (s, 9H), 0.64-0.46 (m, 2H), 0.29 (ddt, J=5.9, 3.8, 2.2 Hz, 2H).

Example 9

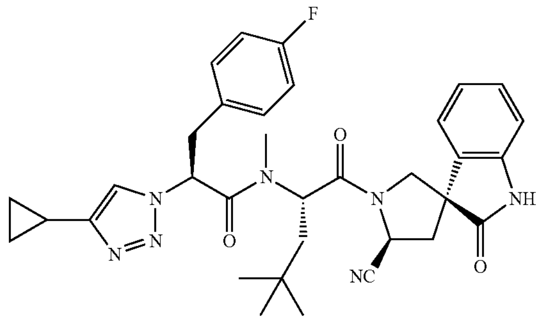

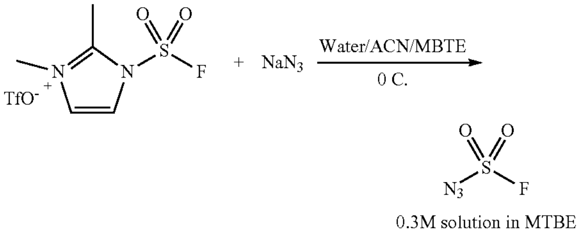

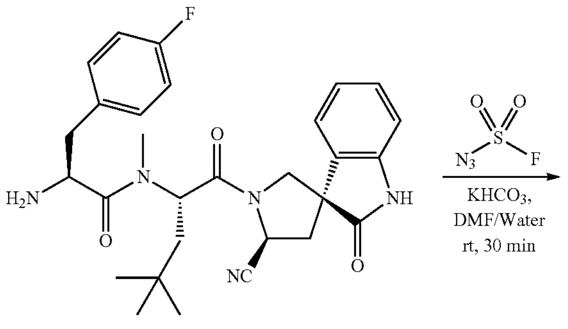

6-2

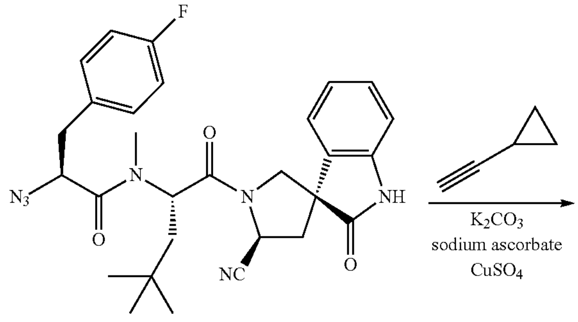

9-1

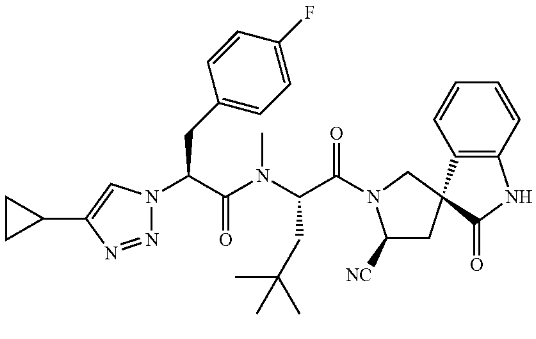

Example 9

Step 1: The $N_3SO_2F$ solution was prepared following the procedures reported by Meng, G., Guo, T., Ma, T. et al. *Nature* 574, 86-89 (2019).

In a plastic tube, to a solution of sodium azide (100 mg, 1.538 mmol) in $H_2O$ (4.05 mL) and MTBE (4.05 mL) at 0° C. was added ACN (0.4 mL, 1/10 of water amount), followed by addition of solid 1-(fluorosulfonyl)-2,3-dimethyl-1H-imidazol-3-ium trifluoromethanesulfonate (606 mg, 1.846 mmol). The mixture was stirred vigorously at 0° C. for 10-15 min. After standing at rt for 30 min, the organic phase was separated and kept in a loosely sealed plastical bottle at rt for at least 12 hrs. After standing for >12 hrs, the reddish aqueous layer on the bottom was removed. The desired product was diluted to total volume of 5.1 mL with MTBE to make a 0.3 M $N_3SO_2F$ solution and store at 4° C. away from light.

Step 2: The amine was converted to the azide following the procedures reported by Meng, G., Guo, T., Ma, T. et al. *Nature* 574, 86-89 (2019).

To a solution of compound 6-2 (85 mg, 0.164 mmol) in DMF (0.61 mL) at rt was added the above formed 0.3 M solution of sulfurazidic fluoridein MTBE (1063 µL, 0.213 mmol), followed by addition of $KHCO_3$ (3.0 M in water, 218 µL, 0.654 mmol). The resulting suspension was stirred at rt for ~30 min. The mixture was diluted with EtOAc, washed with sat $NaHCO_3$, water, brine, dried and concentrated to provide the crude azide compound 9-1 (82 mg, 0.150 mmol, 92% yield), which was directly used in the next step. LC-MS, $ES^-$ (m z): 544.1 [M-H].

Step 3: To a mixture of potassium carbonate (15.18 mg, 0.110 mmol) and sodium ascorbate (6.10 mg, 0.031 mmol), $CuSO_4 \cdot 5H_2O$ (3.84 mg, 0.015 mmol) and cyclopropylacetylene (14.89 µl, 0.176 mmol) in water (0.34 mL)/DMF (0.34 mL) was added compound 9-1 (24 mg, 0.044 mmol). The reaction mixture was heated at 55° C. for 60 min and then cooled to rt.

The reaction mixture was diluted with EtOAc, washed with sat $NaHCO_3$, water, brine, dried and concentrated. The residue was purified by silica gel chromatography (0 to 70% EtoAc/cyclohexane) to afford Example 9 (12 mg, 0.02 mmol, 45% yield). LC-MS, $ES^-$: 610.19 [M−H]. 1H NMR (400 MHz, Acetone-$d_6$) δ 9.79 (s, 1H), 7.63 (s, 1H), 7.23 (dtd, J=24.0, 7.6, 1.2 Hz, 2H), 7.13-6.87 (m, 6H), 5.73 (dd, J=11.1, 4.4 Hz, 1H), 5.47 (t, J=6.3 Hz, 1H), 5.22 (t, J=8.6 Hz, 1H), 4.21 (d, J=10.6 Hz, 1H), 4.00 (d, J=10.5 Hz, 1H), 3.16 (s, 3H), 3.12-3.00 (m, 1H), 2.79-2.66 (m, 2H), 2.64-2.53 (m, 1H), 2.05-1.98 (m, 1H), 1.87 (ddd, J=8.4, 6.8, 4.3 Hz, 1H), 1.48 (dd, J=14.3, 6.2 Hz, 1H), 0.87-0.83 (m, 2H), 0.83 (s, 9H), 0.70-0.60 (m, 2H).

Example 10

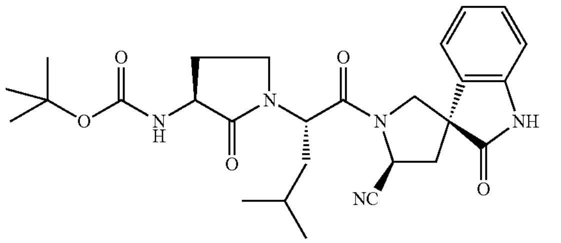

-continued

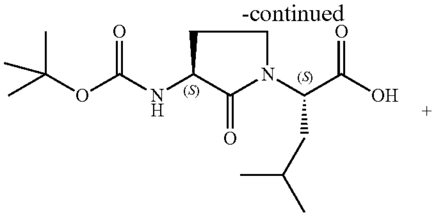

1.05 eq
Boc-Freidinger's lactam

-continued

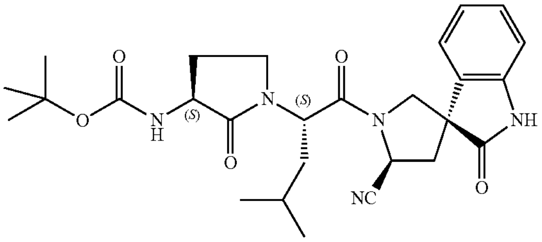

Example 10

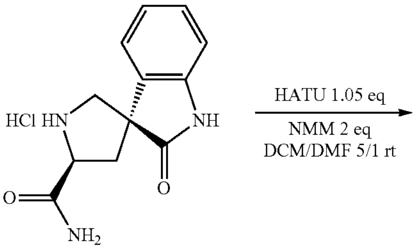

1-5

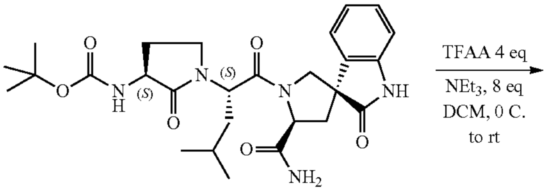

10-1

Step 1. Compound 1-5 (400 mg, 1.192 mmol) and Boc-Freidinger's lactam (394 mg, 1.252 mmol) was taken up in $CH_2Cl_2$ (4.97 mL) and DMF (0.994 mL) at 0° C. At 0° C., 4-methylmorpholine (393 μL, 3.58 mmol) and HATU (499 mg, 1.312 mmol) were added. The reaction was stirred at 0° C. for ~30 min and then warmed to rt and stirred for 90 min.

The mixture was diluted with DCM, washed with water and brine. The collected organic layer was dried over $MgSO_4$, and concentrated in vacuo. The residue was purified by silica gel chromotography (0 to 10% MeOH in DCM) to afford the desired compound 10-1 (600 mg, 1.137 mmol, 95% yield) as a white solid. LC-MS, $ES^+$: 528.15 [M+H].

Step 2: To a solution of 2 compound 10-1 (188 mg, 0.356 mmol) in $CH_2Cl_2$ (3.56 mL) at 0° C. was added triethylamine (298 μL, 2.138 mmol), followed by addition of TFAA (149 μL, 1.069 mmol). The mixture was stirred at 0° C. for ~45 min.

The reaction mixture was diluted with DCM, washed with 100 aq. $NaHCO_3$, brine, dried over $Na_2SO_4$, and concentrated. The residue was purified by silica gel chromatography (0-40% acetone/cyclohexane) to afford the desired compound Example 10 (82 mg, 4500 yield). LC-MS, $ES^+$: 510.12 [M+H].

TABLE 1

The following compounds were made following similar chemistry and procedures described as above.

| Example | Structure | MS | NMR |
|---|---|---|---|
| 11 | 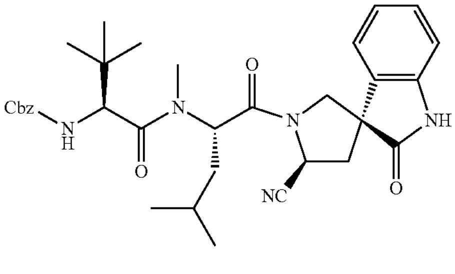 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C(C)(C)C] | 586.0 [M − H] | $^1$H NMR (400 MHz, Acetone-$d_6$) δ 9.71 (s, 1H), 7.30-7 40 (m, 5H), 7.28 (td, J = 7.5, 2.1 Hz, 1H), 7.06-6.97 (m, 3H), 6.24 (d, J = 9.8 Hz, 1H), 5.45 (dd, J = 9.2, 6.0 Hz, 1H), 5.20-5.00 (m, 3H), 4.48 (d, J = 9.7 Hz, 1H), 4.08 (d, J = 10.3 Hz, 1H), 4.02 (d, J = 10.4 Hz, 1H), 3.18 (s, 3H), 2.80-2.77 (m, 1H), 2.77-2.60 (m, 2H), 1.77-1.61 (m, 1H), 1.54-1.46 (m, 1H), 0.94 (d, J = 6.6 Hz, 3H), 0.87 (d, J = 6.5 Hz, 3H), 0.85 (s, 9H). |

TABLE 1-continued

| The following compounds were made following similar chemistry and procedures described as above. | | | |
|---|---|---|---|
| Example | Structure | MS | NMR |
| 12 | 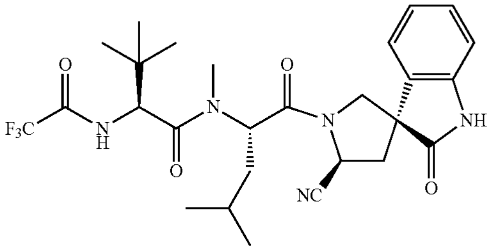 [SMILES: CC(C)C[C@@H](C(=O)N1C[C@]2(C[C@H]1C#N)C(=O)Nc1ccccc12)N(C)C(=O)[C@@H](NC(=O)C(F)(F)F)C(C)(C)C] | 548.05 [M − H] | 1H NMR (400 MHz, Acetone-d6) δ 9.73 (s, 1H), 8 08-7.90 (m, 1H), 7.35-7.19 (m, 1H), 7.12-6.96 (m, 3H), 5.45 (dd.J = 9.5, 5.9 Hz, 1H), 5.17 (t, J = 8.5 Hz, 1H), 4.91-4.84 (m, 1H), 4.09 (d, J = 10 4 Hz, 1H), 4.05 (d, J = 10.4 Hz, 1H), 3.21 (s, 3H), 2.79-2.60 (m, 2H), 1.79 (ddd, J = 14.6, 9.5, 5.3 Hz, 1H), 1.70 (ddd, J = 14.2, 8.6, 5.8 Hz, 1H), 1.56-1.45 (m, 1H), 0.96 (d, J = 6.7 Hz, 3H), 0.91 (s, 8H), 0.88 (d, J = 6.5 Hz, 3H). |
| 13 | 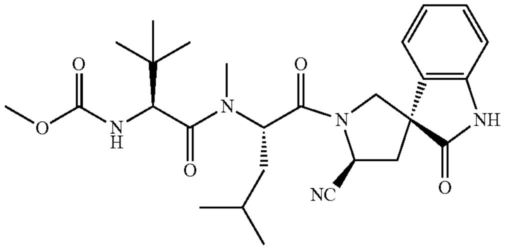 [SMILES: COC(=O)N[C@H](C(=O)N(C)[C@@H](CC(C)C)C(=O)N1C[C@]2(C[C@H]1C#N)C(=O)Nc1ccccc12)C(C)(C)C] | 510.0 [M − H] | 1H NMR (400 MHz, Acetone-d6) δ 9.72 (s, 1H), 7.33-7.22 (m, 1H), 7.03 (dt, J = 8.5, 6.6 Hz, 3H), 6.02 (d, J = 9 8 Hz, 1H), 5.45 (dd, J = 9.1, 62 Hz, 1H), 5 16 (t, J = 8 5 Hz, 1H), 4 46 (d, J = 9.8 Hz, 1H), 4.09 (d, J = 10.5 Hz, 1H), 4.02 (d, J = 10.3 Hz, 1H), 3.57 (s, 3H), 3.18 (s, 3H), 2.78-2.62 (m, 2H), 181-1.62 (m, 2H), 1.59-1.46 (m, 1H), 0.96 (d, J = 6.6 Hz, 3H), 0 88 (d, J = 6.6 Hz, 3H), 0.84 (s, 9H). |
| 14 | 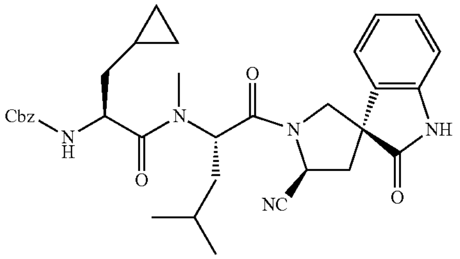 [SMILES: CC(C)C[C@@H](C(=O)N1C[C@]2(C[C@H]1C#N)C(=O)Nc1ccccc12)N(C)C(=O)[C@H](CC1CC1)NC(=O)OCc1ccccc1] | 684.1 [M − H] | $^{1}$H NMR (400 MHz, Acetone-$d_6$) δ 9.75 (s, 1H), 7.41-7.30 (m, 6H), 7.14-7.03 (m, 3H), 6.38 (d, J = 8.7 Hz, 1H), 5.47 (dd, J = 8.9, 6.1 Hz, 1H), 5.22-5.09 (m, 1H), 5.07 (d, J = 12.6 Hz, 2H), 4, 57 (td, J = 8 8, 4, 9 Hz, 1H), 3 99 (s, 2H), 3 13 (s, 3H), 2 83 (d, J = 2.2 Hz, 1H), 2.72 (qd, J = 13.1, 8.4 Hz, 2H), 1.74 (qdd, J = 14.1, 8.5, 5.7 Hz, 2H), 1.57 (dt, J = 13.7, 6.6 Hz, 1H), 1.24 (ddd, J = 14.9, 9.0, 6 6 Hz, 1H), 1.01 (dd, J = 23.8, 7.1 Hz, 1H), 0.96 (d, J = 6 5 Hz, 3H), 0.92 (d, J = 6.5 Hz, 3H), 0.61 (s, 1H), 0.43-0.32 (m, 2H), 0.11 (dd, J = 9.0, 4.3 Hz, 1H), 0.00 (m, 1H). |
| 15 | 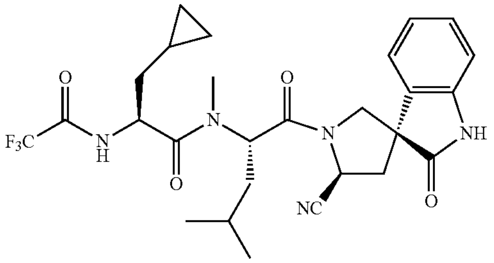 [SMILES: CC(C)C[C@@H](C(=O)N1C[C@]2(C[C@H]1C#N)C(=O)Nc1ccccc12)N(C)C(=O)[C@H](CC1CC1)NC(=O)C(F)(F)F] | 546.1 [M − H] | $^{1}$H NMR (400 MHz, Acetone-$d_6$) δ 9.58 (s, 1H), 8.21 (s, 1H), 7.17 (ddd, J = 7.8, 6.8, 2.0 Hz, 1H), 6.96-6.86 (m, 3H), 5.28 (dd, J = 8.9, 6.3 Hz, 1H), 5.00 (t, J = 8 4 Hz, 1H), 4.70 (td, J = 8.4, 5.1 Hz, 1H), 3.82 (s, 2H), 2.98 (s, 3H), 2.63-2.46 (m, 2H), 1.67-1 49 (m, 2H), 1.37 (dq, J = 13.8, 6 8 Hz, 1H), 1.18-1.00 (m, 2H), 0.80 (d, J = 6.6 Hz, 3H), 0.74 (d, J = 6.5 Hz, 3H), 0.46 (m, 1H), 0.32-0.21 (m, 2H), 0.00 (m, 1H), −0.15 (dd, J = 8.8, 4.3 Hz, 1H). |
| 16 | 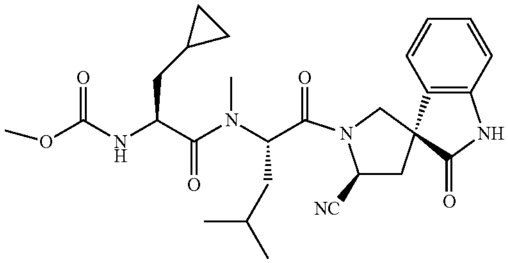 [SMILES: COC(=O)N[C@@H](CC1CC1)C(=O)N(C)[C@@H](CC(C)C)C(=O)N1C[C@]2(C[C@H]1C#N)C(=O)Nc1ccccc12] | 508.1 [M − H] | $^{1}$H NMR (400 MHz, Acetone-$d_6$) δ 9.75 (s, 1H), 7.38-7.26 (m, 1H), 7.13-7.03 (m, 3H), 6.21 (d, J = 8.7 Hz, 1H), 5.50-5.42 (m, 1H), 5.17 (t, J = 8 4 Hz, 1H), 4.59-174 49 (m, 1H), 4.00 (d, J = 14 4 Hz, 2H), 3.60 (s, 3H), 3.12 (s, 3H), 2.72 (qd, J = 13.2, 8.5 Hz, 2H), 1.72 (dq, J = 14.0, 7.0 Hz, 2H), 1.57 (dt, J = 13.4, 6.8 Hz, 1H), 1.27-1.16 (m, 1H), 1.07-0.96 (m, 4H), 0.93 (d, J = 6.5 Hz, 3H), 0.60 (s, 1H), 0.39 (d, J = 7.6 Hz, 2H), 0.09 (s, 1H), 0.00 (m, 1H). |

TABLE 1-continued

| The following compounds were made following similar chemistry and procedures described as above. | | | |
|---|---|---|---|
| Example | Structure | MS | NMR |
| 17 | 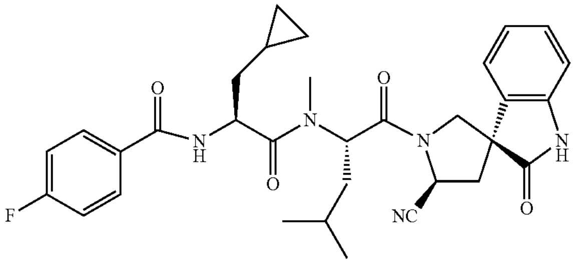 [SMILES: CC(C)C[C@@H](C(=O)N1C[C@]2(C[C@H]1C#N)C(=O)Nc1ccccc12)N(C)C(=O)[C@H](CC1CC1)NC(=O)c1ccc(F)cc1] | 572.2 [M − H] | $^1$H NMR (400 MHz, Acetone-$d_6$) δ 9.62 (s, 1H), 7 89-7.75 (m, 2H), 7.52 (d, J = 8 3 Hz, 1H), 7.25-7.17 (m, 1H), 7.14-7.04 (m, 2H), 7.01-6.90 (m, 3H), 5.34 (dd, J = 8.8, 6.3 Hz, 1H), 5.04 (t, J = 8 4 Hz, 1H), 4 85 (td, J = 8.7, 5.0 Hz, 1H), 3.92-3.80 (m, 2H), 3.04 (s, 3H), 2.71-2.48 (m, 2H), 1.68-1.51 (m, 2H), 1.44 (dp, J = 13.3, 6.5 Hz, 1H), 1.18 (ddd, J = 15.3, 9.0, 6.7 Hz, 1H), 1.05-0.89 (m, 1H), 0.82 (d, J = 6.7 Hz, 3H), 0.74 (d, J = 6.5 Hz, 3H), 0.50 (dq, J = 12.5, 7.3, 6.2 Hz, 1H), 0.30-0.21 (m, 1H), 0.25 (s, 1H), 0.00 (m, 1H), −0.08-−0.18 (m, 1H). |
| 18 | 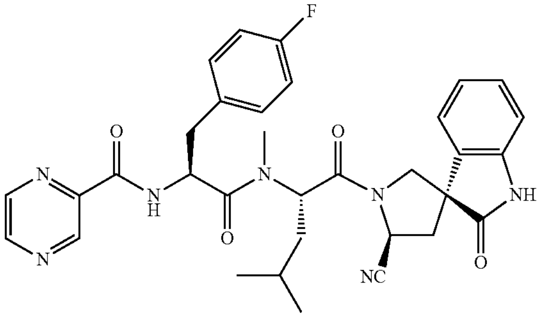 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)c1cnccn1] | 612.08 [M + H] | 1H NMR (400 MHz, Acetone-d6) δ 9.76 (s, 1H), 9.12 (d, J = 1.5 Hz, 1H), 8.81 (d, J = 2.5 Hz, 1H), 8.61 (dd, J = 2.5, 1.5 Hz, 1H), 8.36 (d, J = 8.5 Hz, 1H), 7.25-7.15 (m, 3H), 7.11-6.91 (m, 5H), 5.45 (dd, J = 9.1, 6.2 Hz, 1H), 5.26 (t, J = 8.5 Hz, 1H), 5.23-5.14 (m, 1H), 4.09 (d, J = 10.6 Hz, 1H), 4.02 (d, J = 10.5 Hz, 1H), 3.27 (s, 3H), 2.81-2.66 (m, 4H), 1.85-1.68 (m, 2H), 1.61-1.48 (m, 1H), 0.90 (dd, J = 27.0, 6.6 Hz, 6H). |
| 19 | 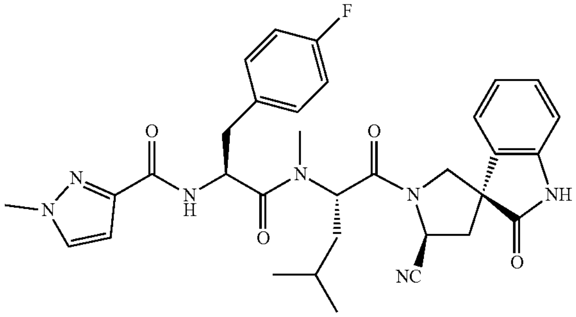 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)c1ccn(C)n1] | 612.04 [M − H] | 1H NMR (400 MHz, Acetone-d6) δ 9.74 (s, 1H), 7.61 (d, J = 2.3 Hz, 1H), 7.38 (d, J = 8.7 Hz, 1H), 7.20 (ddd, J = 10.1, 6.2, 3.5 Hz, 3H), 7.10-6.92 (m, 5H), 6.54 (d, J = 2.3 Hz, 1H), 5.44 (dd, J = 8.9, 6 3 Hz, 1H), 5.24 (t, J = 8.5 Hz, 1H), 5.14 (td, J = 8.6, 4.8 Hz, 1H), 4.08 (d, J = 10.6 Hz, 1H), 4.00 (d, J = 10.6 Hz, 1H), 3.89 (s, 3H), 3.22 (s, 3H), 2.78-2.67 (m, 2H), 2.67-2.55 (m, 2H), 1.82-1.67 (m, 2H), 1.54 (dp, J = 13.4, 6.6 Hz, 1H), 0.91 (dd, J = 24.5, 6.6 Hz, 6H). |
| 20 | 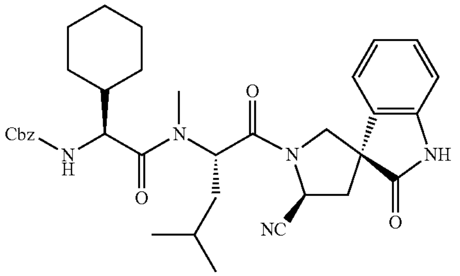 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C1CCCCC1] | 612.15 [M − 1] | 1H NMR (400 MHz, Acetone-d6) δ 9.72 (s, 1H), 7.45-7.24 (m, 6H), 7.11-6.97 (m, 3H), 6.33 (d, J = 9.4 Hz, 1H), 5.40 (t, J = 7.5 Hz, 1H), 5.19-4.97 (m, 3H), 4.28 (dd, J = 9.4, 7.8 Hz, 1H), 4.00 (d, J = 10.5 Hz, 1H), 3.93 (d, J = 10.5 Hz, 1H), 3.10 (s, 3H), 2.75-2.62 (m, 2H), 1.72-1.60 (m, 4H), 1.60-1.46 (m, 4H), 1.30-1.18 (m, 1H), 1.11-0.97 (m, 3H), 0.93 (d, J = 6.7 Hz, 3H), 0.88 (d, J = 6.5 Hz, 3H), 0.69-0.62 (m, 1H). |

TABLE 1-continued

The following compounds were made following similar chemistry and procedures described as above.

| Example | Structure | MS | NMR |
| --- | --- | --- | --- |
| 21 | 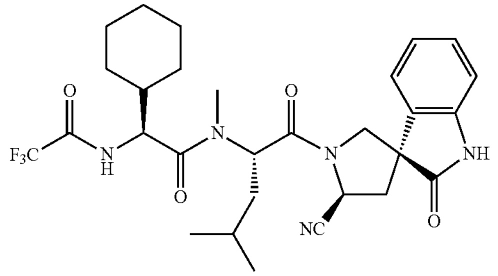 [SMILES: CC(C)C[C@@H](C(=O)N1C[C@]2(C[C@H]1C#N)C(=O)Nc1ccccc12)N(C)C(=O)[C@@H](NC(=O)C(F)(F)F)C1CCCCC1] | 574.14 [M − H] | 1H NMR (400 MHz, Acetone-d6) δ 9.74 (s, 1H), 8.40 (d, J = 8.7 Hz, 1H), 7.32 (ddd, J = 7.8, 5.6, 3.3 Hz, 1H), 7.12-7.00 (m, 3H), 5.41 (dd, J = 8.9, 6.3 Hz, 1H), 5.14 (t, J = 8.4 Hz, 1H), 4 62 (t, J = 8.5 Hz, 1H), 4.03 (d, J = 10.4 Hz, 1H), 3.97 (d, J = 10 4 Hz, 1H), 3.15 (s, 3H), 2.78-2.60 (m, 2H), 1.80-1.63 (m, 5H), 1.63-1.52 (m, 2H), 1.52-1.45 (m, 1H), 1.30 (d, J = 12.6 Hz, 1H), 1.14-1.00 (m, 3H), 0.94 (d, J = 6.7 Hz, 3H), 0.88 (d, J = 6.5 Hz, 3H), 0.70 (qd, J = 12.1, 3.9 Hz, 1H). |
| 22 | 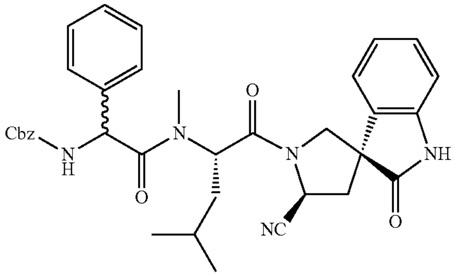 [SMILES: CC(C)C[C@@H](C(=O)N1C[C@]2(C[C@H]1C#N)C(=O)Nc1ccccc12)N(C)C(=O)C(NC(=O)OCc1ccccc1)c1ccccc1] | 606.10 [M − H] | |
| 23 | 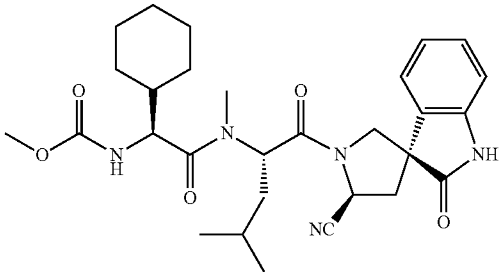 [SMILES: COC(=O)N[C@H](C(=O)N(C)[C@@H](CC(C)C)C(=O)N1C[C@]2(C[C@H]1C#N)C(=O)Nc1ccccc12)C1CCCCC1] | 538.19 [M + 1] | 1H NMR (400 MHz, Acetone-d6) δ 9.73 (s, 1H), 7.34-7.28 (m, 1H), 7.15-6.92 (m, 3H), 6.14 (d, J = 9.5 Hz, 1H), 5.40 (dd, J = 8.6, 6.4 Hz, 1H), 5.13 (t, J = 8.4 Hz, 1H), 4.25 (dd, J = 9.4, 7.7 Hz, 1H), 4.00 (d, J = 10.5 Hz, 1H), 3.93 (d, J = 10.5 Hz, 1H), 3.57 (s, 3H), 3.10 (s, 3H), 2.78-2.59 (m, 2H), 1.76-1.59 (m, 4H), 1.58-1.50 (m, 4H), 1.25-1.22 (m 1H), 1.14-0.87 (m, 4H), 0.92 (dd, J = 21.1, 6.6 Hz, 6H), 0 68-0.59 (m, 1H). |
| 24 | 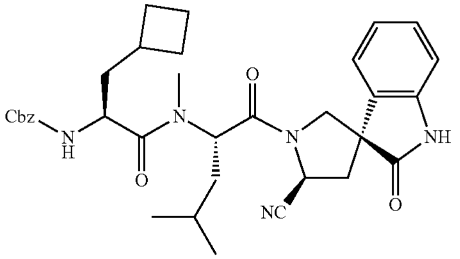 [SMILES: CC(C)C[C@@H](C(=O)N1C[C@]2(C[C@H]1C#N)C(=O)Nc1ccccc12)N(C)C(=O)[C@H](CC1CCC1)NC(=O)OCc1ccccc1] | 598.1 [M − H] | $^1$H NMR (400 MHz, Acetone-$d_6$) δ 9.72 (s, 1H), 7.35 (d, J = 4.3 Hz, 6H), 7.08 (dt, J = 22.1, 7.7 Hz, 3H), 6.24 (d, J = 8.8 Hz, 1H), 5.47-5.39 (m, 1H), 5.15 (1, J = 8.4 Hz, 1H), 5.11-4.98 (m, 2H), 4.35 (td, J = 9.6, 3.8 Hz, 1H), 3.96 (s, 2H), 3.07 (s, 3H), 2.77-2.61 (m, 2H), 2.30 (dt, J = 15.6, 7.8 Hz, 1H), 1.99-1.46 (m, 9H), 1.32 (ddd, J = 15.8, 10.1, 6.1 Hz, 1H), 1.16 (ddd, J = 13.5, 8.7, 3.9 Hz, 1H), 0.94 (d, J = 6.6 Hz, 3H), 0.88 (d, J = 6.5 Hz, 3H). |
| 25 | 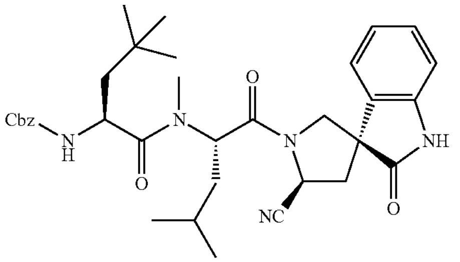 [SMILES: CC(C)C[C@@H](C(=O)N1C[C@]2(C[C@H]1C#N)C(=O)Nc1ccccc12)N(C)C(=O)[C@H](CC(C)(C)C)NC(=O)OCc1ccccc1] | 600.1 [M − H] | $^1$H NMR (400 MHz, Acetone-$d_6$) δ 9.71 (s, 1H), 7.34-7.26 (m, 6H), 7.05 (dd, J = 17.4, 6.1 Hz, 3H), 6.34 (s, 1H), 5.42 (dd, J = 9.2, 6.0 Hz, 1H), 5.15-5.06 (m, 2H), 5.03 (d, J = 12.8 Hz, 1H), 4.62 (t, J = 9.7 Hz, 1H), 4.05-3.93 (m, 2H), 3.09 (s, 3H), 2.75-2.60 (m, 2H), 1.76-1.59 (m, 2H), 1.52 (dt, J = 14.0, 6.6 Hz, 1H), 1.33 (dd, J = 14.5, 10.1 Hz, 1H), 1.16 (dd, J = 14.6, 2.7 Hz, 1H), 0.94 (d, J = 6.6 Hz, 3H), 0.91 (s, 9H), 0.88 (d, J = 6.6 Hz, 3H). |

TABLE 1-continued

| The following compounds were made following similar chemistry and procedures described as above. | | | |
|---|---|---|---|
| Example | Structure | MS | NMR |
| 26 | 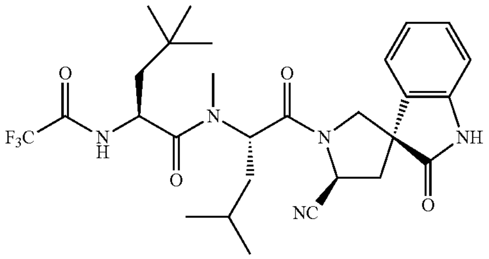 [SMILES: CC(C)C[C@@H](C(=O)N1C[C@]2(C[C@H]1C#N)C(=O)Nc1ccccc12)N(C)C(=O)[C@H](CC(C)(C)C)NC(=O)C(F)(F)F] | 562.2 [M − H] | $^1$H NMR (400 MHz, Acetone-$d_6$) δ 9.72 (s, 1H), 8.49 (d, J = 8.5 Hz, 1H), 7.32 (ddd, J = 7.7, 6.3, 2.6 Hz, 1H), 7.12-7.01 (m, 3H), 5.42 (dd, J = 9.5, 5.8 Hz, 1H), 5.11 (t, J = 8.3Hz, 1H), 4.89 (dd, J = 10.6, 8.3 Hz, 1H), 4.06-3.95 (m, 2H), 3.13 (s, 3H), 2.77-2.68 (m, 2H), 1.78 (ddd, J = 14.4, 9.5, 5.1 Hz, 1H), 1.66 (ddd, J = 14.3, 8.8, 5 8 Hz, 1H), 1.57-1.49 (m, 2H), 1.30 (dd, J = 14.9, 2.3 Hz, 1H), 0.96 (d, J = 6.5 Hz, 3H), 0.94 (s, 9H), 0.86 (d, J = 6.5 Hz, 3H). |
| 27 | 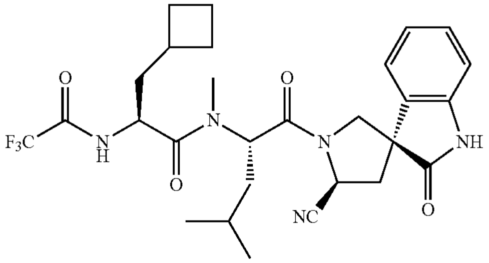 [SMILES: CC(C)C[C@@H](C(=O)N1C[C@]2(C[C@H]1C#N)C(=O)Nc1ccccc12)N(C)C(=O)[C@H](CC1CCC1)NC(=O)C(F)(F)F] | 560.1 [M − H] | $^1$H NMR (400 MHz, Acetone-$d_6$) δ 9.75 (s, 1H), 8.30 (d, J = 8.1 Hz, 1H), 7.35 (td, J = 7.4, 2.0 Hz, 1H), 7.15-7.03 (m, 3H), 5.43 (dd, J = 8.9, 6.3 Hz, 1H), 5.15 (t, , J = 8.4 Hz, 1H), 4.65 (d, J = 10.2 Hz, 1H), 3.97 (s, 2H), 3.10 (s, 3H), 2.78-2.62 (m, 2H), 2.31 (dt, J = 15.6, 7.9 Hz, 1H), 2.04-1.28 (m, 12H), 0.94 (d, J = 6.1 Hz, 3H), 0.88 (d, J = 6.5 Hz, 3H) |
| 28 | 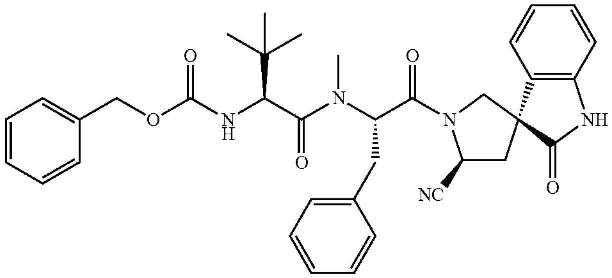 [SMILES: CN(C(=O)[C@@H](NC(=O)OCc1ccccc1)C(C)(C)C)[C@@H](Cc1ccccc1)C(=O)N1C[C@]2(C[C@H]1C#N)C(=O)Nc1ccccc12] | 644.3 [M + $Na^+$] | |
| 29 | 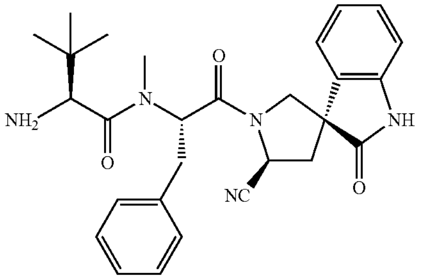 [SMILES: CN(C(=O)[C@@H](N)C(C)(C)C)[C@@H](Cc1ccccc1)C(=O)N1C[C@]2(C[C@H]1C#N)C(=O)Nc1ccccc12] | 488.3 [M + H] | |
| 30 | 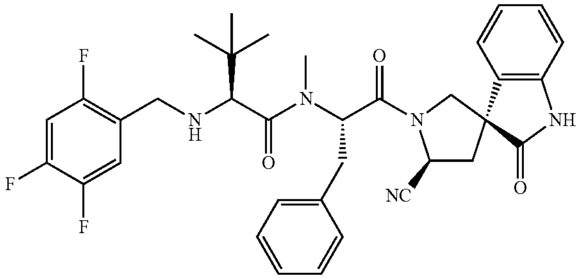 [SMILES: CN(C(=O)[C@@H](NCc1cc(F)c(F)cc1F)C(C)(C)C)[C@@H](Cc1ccccc1)C(=O)N1C[C@]2(C[C@H]1C#N)C(=O)Nc1ccccc12] | 632.3 [M + H] | — |

TABLE 1-continued

The following compounds were made following similar chemistry and procedures described as above.

| Example | Structure | MS | NMR |
| --- | --- | --- | --- |
| 31 | 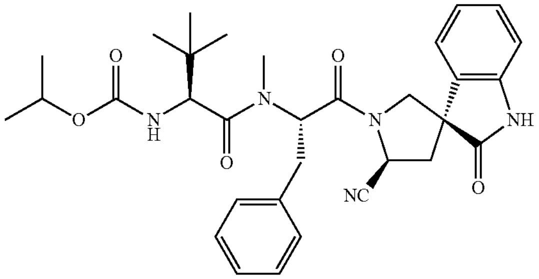 [SMILES: CC(C)OC(=O)N[C@H](C(=O)N(C)[C@@H](Cc1ccccc1)C(=O)N1C[C@]2(C[C@H]1C#N)C(=O)Nc1ccccc12)C(C)(C)C] | 596.3 [M + H] | — |
| 32 | 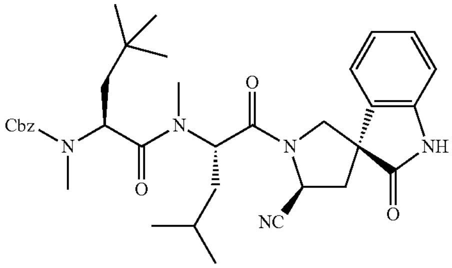 [SMILES: CC(C)C[C@@H](C(=O)N1C[C@]2(C[C@H]1C#N)C(=O)Nc1ccccc12)N(C)C(=O)[C@H](CC(C)(C)C)N(C)C(=O)OCc1ccccc1] | 614.2 [M − H] | — |
| 33 | 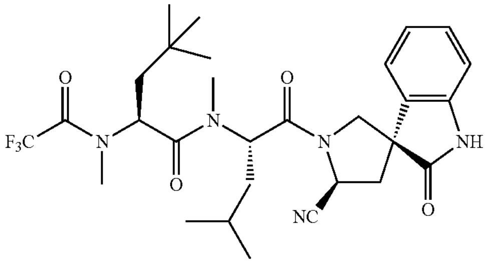 [SMILES: CC(C)C[C@@H](C(=O)N1C[C@]2(C[C@H]1C#N)C(=O)Nc1ccccc12)N(C)C(=O)[C@H](CC(C)(C)C)N(C)C(=O)C(F)(F)F] | 575.5 [M − H] | — |
| 34 | 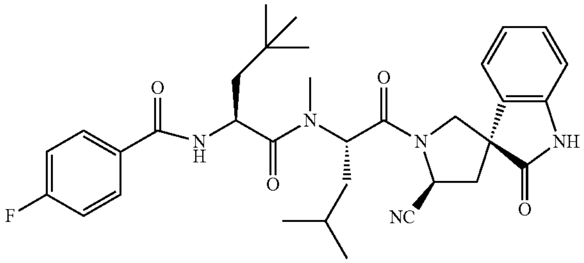 [SMILES: CC(C)C[C@@H](C(=O)N1C[C@]2(C[C@H]1C#N)C(=O)Nc1ccccc12)N(C)C(=O)[C@H](CC(C)(C)C)NC(=O)c1ccc(F)cc1] | 587.9 [M − H] | $^1$H NMR (400 MHz, Acetone-$d_6$) δ 9.73 (s, 1H), 8.06-7.90 (m, 2H), 7.63 (d, J = 8.7 Hz, 1H), 7.33 (ddd, J = 7.8, 5.9, 2.9 Hz, 1H), 7.27-7.15 (m, 2H), 7.14-7.01 (m, 3H), 5.43 (dd, J = 9.1, 5.9 Hz, 1H), 5.17-5.03 (m, 2H), 4.04 (dd, J = 10.5, 1.1 Hz, 1H), 3.98 (d, J = 10.5 Hz, 1H), 3.16 (s, 3H), 2.82-2.60 (m, 2H), 1.81-1.43 (m, 6H), 1.28-1.19 (m, 1H), 0.98-0.90 (m, 11H), 0.84 (d, J = 6.5 Hz, 3H). |
| 35 | 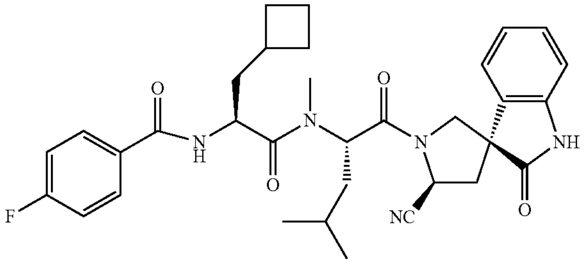 [SMILES: CC(C)C[C@@H](C(=O)N1C[C@]2(C[C@H]1C#N)C(=O)Nc1ccccc12)N(C)C(=O)[C@H](CC1CCC1)NC(=O)c1ccc(F)cc1] | 586.2 [M − H] | $^1$H NMR (400 MHz, Acetone-$d_6$) δ 9.75 (s, 1H), 8.06-7.91 (m, 2H), 7.54 (d, J = 8.5 Hz, 1H), 7.36 (td, J = 7.5, 1.7 Hz, 1H), 7.27-7.04 (m, 5H), 5.45 (dd, J = 8.5, 6.5 Hz, 1H), 5.16 (t, J = 8.4 Hz, 1H), 4.80 (ddd, J = 10.2, 8.4, 3.8 Hz, 1H), 4.04-3.92 (m, 2H), 3.12 (s, 3H), 2.78-2.60 (m, 2H), 2.34 (dt, J = 15.2, 7.8 Hz, 1H), 2.06-1.90 (m, 1H), 1.90-1.37 (m, 9H), 1.33-1.19 (m, 1H), 0.93 (d, J = 6.6 Hz, 3H), 0.85 (d, J = 6.5 Hz, 3H). |

TABLE 1-continued

The following compounds were made following similar chemistry and procedures described as above.

| Example | Structure | MS | NMR |
|---|---|---|---|
| 36 | 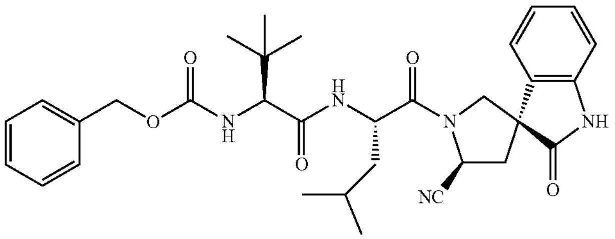 [SMILES: CC(C)C[C@H](NC(=O)[C@@H](NC(=O)OCc1ccccc1)C(C)(C)C)C(=O)N1C[C@]2(C[C@H]1C#N)C(=O)Nc1ccccc12] | 596.3 [M + Na+] | — |
| 37 | 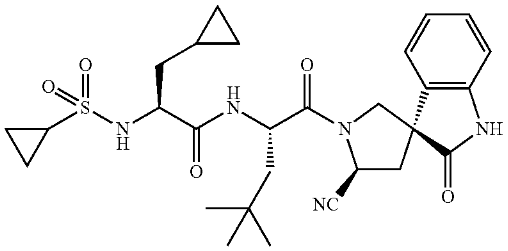 [SMILES: CC(C)(C)C[C@H](NC(=O)[C@H](CC1CC1)NS(=O)(=O)C1CC1)C(=O)N1C[C@]2(C[C@H]1C#N)C(=O)Nc1ccccc12] | 554.28 [M − 1] | $^1$H NMR (400 MHz, Acetone-$d_6$) δ 9.69 (s. 1H), 7.64 (d, J = 8.3 Hz, 1H), 7.30-7.20 (in. 1H), 7.03-6.96 (m, 2H), 6.19 (d, J = 9.0 Hz, 1H), 5.11 (t, J = 8.3 Hz, 1H), 4.74 (td, J = 8.0, 4.9 Hz, 1H), 4.27 (d, J = 10.2 Hz, 1H), 4.01 (d, J = 10.2 Hz, 1H), 3.31 (q, J = 7.1 Hz, 1H), 2.73-2.64 (m, 2H), 2.56-2.47 (m, 1H), 1.95-1.86 (m, 2H), 1.60 (dd, J = 14.4, 7.4 Hz, 2H), 1.53-1.43 (m, 2H), 1.18 (d, J = 7.1 Hz, 1H), 0.98 (d, J = 5.0 Hz, 9H), 0.51-0.44 (m, 1H), 0.16 (dt, J = 8.0.4.3 Hz, 1H). |
| 38 | 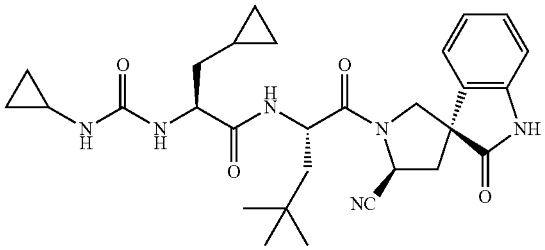 | 533.41 [M − H] | $^1$H NMR (400 MHz, Acetone-$d_6$) δ 9.68 (s, 1H), 7.61 (d, J = 8.7 Hz, 1H), 7.26 (td, J = 7.7-1.3 Hz, 1H), 7.10 (d, J = 7.4 Hz, 1H), 7.04-6.95 (in, 2H), 5.79-5.70 (m, 2H), 5.10 (t, J = 8.4 Hz, 1H), 4.73 (td, J = 8.0, 4.7 Hz, 1H), 4.29 (t, J = 7.8 Hz, 2H), 3.98 (d, J = 10.2 Hz, 1H), 2.66 (td, J = 12.9, 8.4 Hz, 2H), 2.50 (dd, J = 5.6, 3.3 Hz, 1H), 1.56 (dd, J = 14.3, 7.8 Hz, 1H), 1.47 (td, J = 6.9, 3.6 Hz, 2H), 0.96 (s, 9H), 0.64 (dt, J = 6.7, 3.3 Hz, 2H), 0.47-0.42 (m, 2H), 0.42-0.36 (m, 1H), 0.07 (dd, J = 9.9, 5.1 Hz, 2H). |
| 39 | 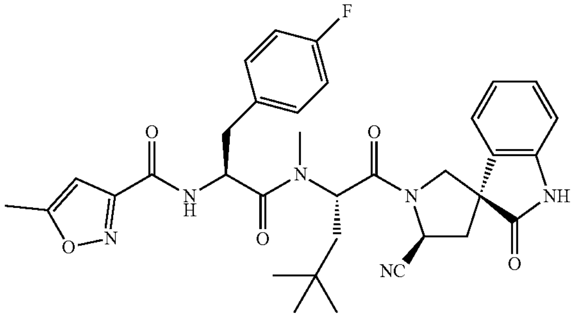 [SMILES: Cc1cc(C(=O)N[C@@H](Cc2ccc(F)cc2)C(=O)N(C)[C@@H](CC(C)(C)C)C(=O)N2C[C@]3(C[C@H]2C#N)C(=O)Nc2ccccc23)no1] | 627.00 [M − l] | 1H NMR (400 MHz, Acetone-d6) δ 9.79 (s, 1H), 7.98 (s, 1H), 7.65 (d, J = 8.8 Hz, 1H), 7.27-7.14 (m, 3H), 7.08 (d, J = 4.4 Hz, 2H), 7.04-6.94 (m, 3H), 6.31 (d, J = 1.0 Hz, 1H), 5.51 (dd, J = 7.1, 5.5 Hz, 1H), 5.23 (t, J = 8.6 Hz, 1H), 5.07 (ddd, J = 10.0, 8.8, 4.1 Hz, 1H), 4.09 (d, J = 10.5 Hz, 1H), 4.01 (d, y = 10.4 Hz, 1H), 3.24 (s, 3H), 2.96 (s, 3H), 2.78-2.68 (m, 2H), 2.63-2.55 (m, 1H), 2.49-2.44 (m, 1H), 2.19-2.12 (m, 1H), 1.54 (dd, J = 14.2, 5.5 Hz, 1H), 0.93 (s, 9H). |
| 40 | 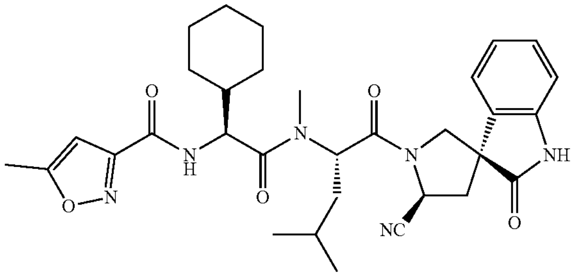 [SMILES: Cc1cc(C(=O)N[C@H](C(=O)N(C)[C@@H](CC(C)C)C(=O)N2C[C@]3(C[C@H]2C#N)C(=O)Nc2ccccc23)C2CCCCC2)no1] | 587.10 [M − H] | — |

TABLE 1-continued

The following compounds were made following similar chemistry and procedures described as above.

| Example | Structure | MS | NMR |
|---|---|---|---|
| 41 | 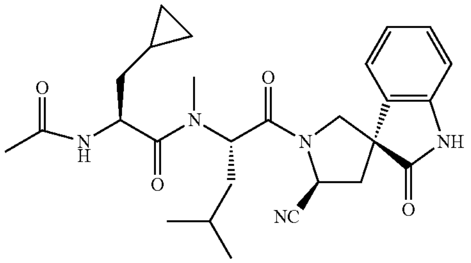 [SMILES: CC(=O)N[C@@H](CC1CC1)C(=O)N(C)[C@@H](CC(C)C)C(=O)N1C[C@]2(C[C@H]1C#N)C(=O)Nc1ccccc12] | 492.1 [M − H] | $^1$H NMR (400 MHz, Acetone-$d_6$) δ 9.70 (s, 1H), 7.28 (td, J = 7.6, 1.7 Hz, 1H), 7.09-6.99 (m, 3H), 7.00 (s, 1H), 5.40 (t, J = 7.6 Hz, 1H), 5.12 (t, J = 8.4 Hz, 1H), 4.75 (td, J = 8 5, 5.5 Hz, 1H), 4.00-3.88 (m, 2H), 3.06 (s, 3H), 2.75-2.58 (m, 2H), 1.84 (s, 3H), 1.67 (t, J = 7.2 Hz, 2H), 1.50 (dp, J = 13.3, 6.6 Hz, 1H), 1.16-0.95 (m, 2H), 0.92 (d, J = 6.6 Hz, 3H), 0.87 (d, J = 6.5 Hz, 3H), 0.46 (m, 1H), 0.38-0.22 (m, 2H), 0.00 (m, 1H), −0.08 (dq, J = 9.5, 4.6 Hz, 1H). |
| 42 | 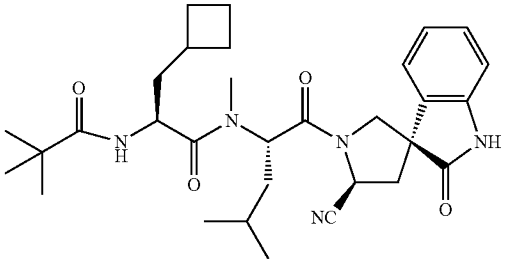 [SMILES: CC(C)C[C@@H](C(=O)N1C[C@]2(C[C@H]1C#N)C(=O)Nc1ccccc12)N(C)C(=O)[C@H](CC1CCC1)NC(=O)C(C)(C)C] | 548.2 [M − H] | $^1$H NMR (400 MHz, Acetone-$d_6$) δ 9.75 (s, 1H), 7.35 (td, J = 7.6, 1.4 Hz, 1H), 7.12 (td, J = 7.5, 1.0 Hz, 1H), 7.10-7.02 (m, 2H), 6.56 (d, J = 8.5 Hz, 1H), 5.43 (dd, J = 9.7, 5.4 Hz, 1H), 5.15 (t, J = 8.4 Hz, 1H), 4.59 (ddd, J = 10.0, 8.5, 4.0 Hz, 1H), 3.98 (dd, J = 10.6, 1.2 Hz, 1H), 3.93 (d, J = 10.7 Hz, 1H), 3.03 (s, 3H), 2.82-2.60 (m, 2H), 2.21 (dq, J = 15.7, 7.8 Hz, 1H), 2.02-1.69 (m, 4H), 1.65-1.40 (m, 4H), 1.30 (ddd, J = 13.8, 10.1, 7.2 Hz, 1H), 1.13 (s, 9H), 1.14-1.03 (m, 2H), 0.93 (d, J = 6.6 Hz, 3H), 0.86 (d, J = 6.4 Hz, 3H) |
| 43 | 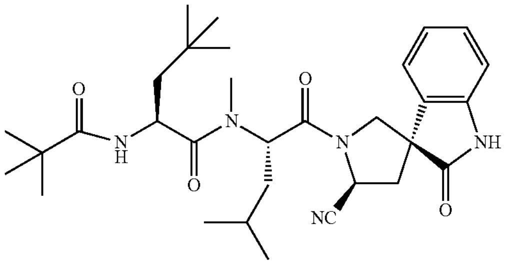 [SMILES: CC(C)C[C@@H](C(=O)N1C[C@]2(C[C@H]1C#N)C(=O)Nc1ccccc12)N(C)C(=O)[C@H](CC(C)(C)C)NC(=O)C(C)(C)C] | 550.1 [M − H] | $^1$H NMR (400 MHz, Acetone-$d_6$) δ 9.73 (s, 1H), 7.31 (dt, J = 7.8, 4.4 Hz, 1H), 7.10-7.00 (m, 3H), 6.59 (d, J = 8.9 Hz, 1H), 5.42 (dd, J = 10.1, 5.0 Hz, 1H), 5.11 (t, J = 8.3 Hz, 1H), 4.87 (ddd, J = 10.2, 8.8, 2.6 Hz, 1H), 4.04-3.93 (m, 2H), 3.06 (s, 3H), 2.82-2.68 (m, 1H), 2.65 (dd, J = 13.2, 8.2 Hz, 1H), 1.81 (ddd, J = 13.9, 10.1, 4.0 Hz, 1H), 1.60-1.40 (m, 2H), 1.32 (dd, J = 14.6, 10.2 Hz, 1H), 1.12 (s, 9H), 1.12-1.01 (m, 1H), 0.93 (d, J = 6.5 Hz, 3H), 0.87 (s, 9H), 0.85 (d, J = 6.3 Hz, 3H). |
| 44 | 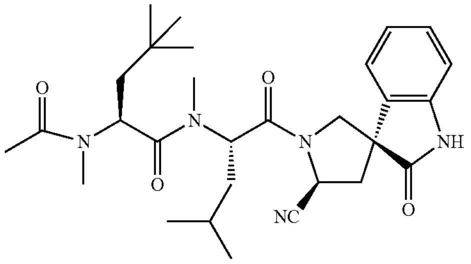 [SMILES: CC(=O)N(C)[C@@H](CC(C)(C)C)C(=O)N(C)[C@@H](CC(C)C)C(=O)N1C[C@]2(C[C@H]1C#N)C(=O)Nc1ccccc12] | 522.1 [M − H] | $^1$H NMR (400 MHz, Acetone-$d_6$) δ 9.71 (s, 1H), 7.31 (td, J = 7.7, 14 Hz, 1H), 7.11-6.96 (m, 3H), 5.44 (ddd, J = 10.9, 7.5, 6.4 Hz, 2H), 5.14 (t, J = 8.4 Hz, 1H), 4.03 (dd, J = 10.5, 1.2 Hz, 1H), 3.94 (d, J = 10.5 Hz, 1H), 2.99 (s, 3H), 2.78-2.61 (m, 2H), 2.01 (s, 3H), 1.69 (ddd, J = 8.4, 6.3, 1.8 Hz, 2H), 1.57-1.38 (m, 2H), 1.33-1.19 (m, 1H), 1.08-0.84 (m, 8H), 0.73 (s, 9H). |
| 45 | 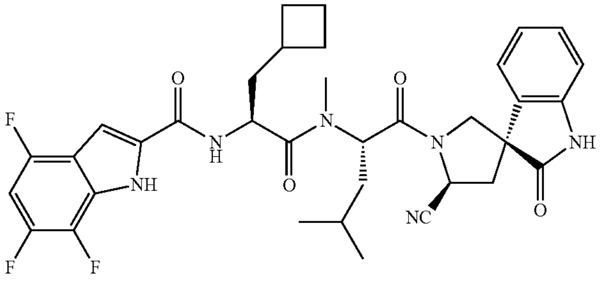 [SMILES: CC(C)C[C@@H](C(=O)N1C[C@]2(C[C@H]1C#N)C(=O)Nc1ccccc12)N(C)C(=O)[C@H](CC1CCC1)NC(=O)c1cc2c(F)cc(F)c(F)c2[nH]1] | 661.1 [M − H] | $^1$H NMR (400 MHz, Acetone-$d_6$) δ 11.54 (s, 1H), 9.76 (s, 1H), 7.73 (d, J = 8.8 Hz, 1H), 7.41-7.32 (m, 2H), 7.18-7.04 (m, 3H), 6.91 (ddd, J = 115, 9.6, 5.2 Hz, 1H), 5.46 (d, J = 7.5 Hz, 1H), 5.17 (t, J = 8.4 Hz, 1H), 4.84 (s, 1H), 4.05-3.92 (m, 2H), 3.13 (s, 3H), 2.75 (s, 1H), 2.68 (dd, J = 13.1, 8.5 Hz, 1H), 2.36 (dt, J = 15.9, 7.9 Hz, 1H), 2.05-1.38 (m, 10H), 1.36-1.24 (m, 1H), 0.92 (d, J = 6.7 Hz, 3H), 0.86 (d, J = 6.5 Hz, 3H). |

TABLE 1-continued
| The following compounds were made following similar chemistry and procedures described as above. | | | |
|---|---|---|---|
| Example | Structure | MS | NMR |
| 46 | 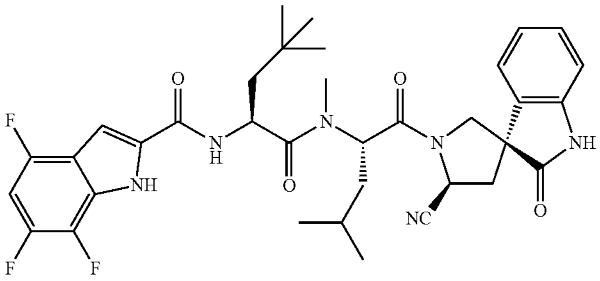 [SMILES: CC(C)C[C@@H](C(=O)N1C[C@]2(C[C@H]1C#N)C(=O)Nc1ccccc12)N(C)C(=O)[C@H](CC(C)(C)C)NC(=O)c1cc2c(F)cc(F)c(F)c2[nH]1] | 677.3 [M − H] | $^1$H NMR (400 MHz, Acetone-$d_6$) δ 11.49 (s, 1H), 9.74 (s, 1H), 7.33 (td, J = 7.6, 1.6 Hz, 1H), 7.09 (t, J = 7.5 Hz, 1H), 7.05 (dd, J = 7.6, 2.2 Hz, 3H), 6.94 (ddd, J = 11.3, 9.5, 5.1 Hz, 1H), 5.61 (t, J = 6.3 Hz, 1H), 5.47 (dd, J = 8.3, 6.9 Hz, 1H), 5.15 (t, J = 8.5 Hz, 1H), 4.07 (dd, J = 10.5, 1.2 Hz, 1H), 3.99 (d, J = 10.5 Hz, 1H), 3.27 (s, 3H), 3.10 (s, 3H), 2.77-2.62 (m, 2H), 1.73 (s, 2H), 1.77-1.66 (m, 1H), 1.50 (dd, J = 14.0, 7.6 Hz, 2H), 0.93 (t, J = 6.4 Hz, 6H), 0.81 (s, 9H). |
| 47 | 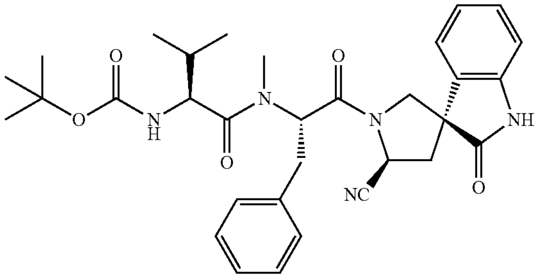 [SMILES: CC(C)[C@H](NC(=O)OC(C)(C)C)C(=O)N(C)[C@@H](Cc1ccccc1)C(=O)N1C[C@]2(C[C@H]1C#N)C(=O)Nc1ccccc12] | 596.3 [M + $Na^+$] | — |
| 48 | 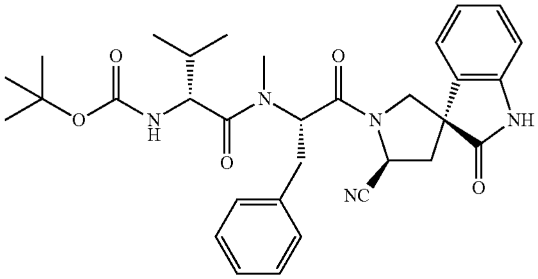 [SMILES: CC(C)[C@@H](NC(=O)OC(C)(C)C)C(=O)N(C)[C@@H](Cc1ccccc1)C(=O)N1C[C@]2(C[C@H]1C#N)C(=O)Nc1ccccc12] | 596.3 $[M + Na]^+$ | — |
| 49 | 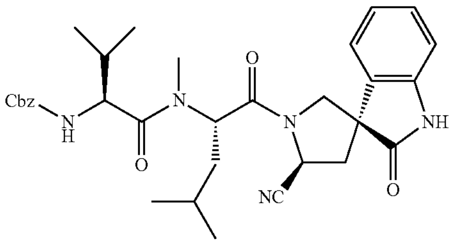 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C(C)C] | 572.3 [M − 1] | |
| 50 | 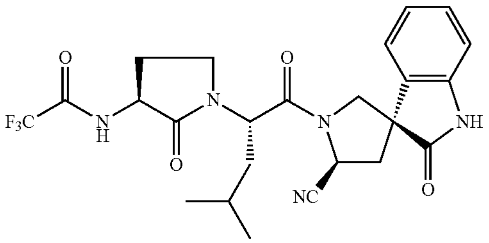 [SMILES: CC(C)C[C@@H](C(=O)N1C[C@]2(C[C@H]1C#N)C(=O)Nc1ccccc12)N1CC[C@H](NC(=O)C(F)(F)F)C1=O] | 504.19 [M − 1] | — |

TABLE 1-continued

| The following compounds were made following similar chemistry and procedures described as above. | | | |
|---|---|---|---|
| Example | Structure | MS | NMR |
| 51 | 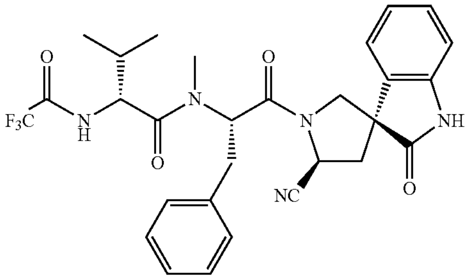 [SMILES: CC(C)[C@@H](NC(=O)C(F)(F)F)C(=O)N(C)[C@@H](Cc1ccccc1)C(=O)N1C[C@]2(C[C@H]1C#N)C(=O)Nc1ccccc12] | [M + Na+] 592.2 | — |
| 52 | 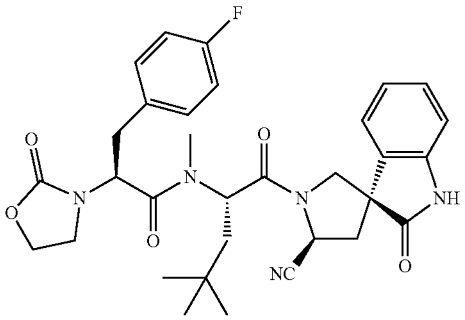 [SMILES: CN(C(=O)[C@H](Cc1ccc(F)cc1)N1CCOC1=O)[C@@H](CC(C)(C)C)C(=O)N1C[C@]2(C[C@H]1C#N)C(=O)Nc1ccccc12] | 588.28 [M − H] | — |
| 53 | 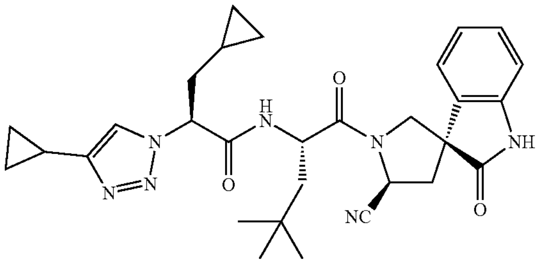 [SMILES: CC(C)(C)C[C@H](NC(=O)[C@H](CC1CC1)n1cc(C2CC2)nn1)C(=O)N1C[C@]2(C[C@H]1C#N)C(=O)Nc1ccccc12] | 542.4 [M − H] | $^1$H NMR (400 MHz, Acetone-$d_6$) δ 9.71 (s, 1H), 7.96 (d, J = 8.0 Hz, 1H), 7.68 (s, 1H), 7.29 (td, J = 7.6, 1.4 Hz, 1H), 7.11-7.06 (m, 1H), 7.06-6.98 (m, 2H), 5.35 (dd, J = 8.9, 6.3 Hz, 1H), 5.13 (t, J = 8.5 Hz, 1H), 4.68 (td, J = 8.1, 4.4 Hz, 1H), 4.27-4.21 (m, 1H), 4.00 (d, J = 10.2 Hz, 1H), 2.75-2.61 (m, 2H), 1.97-1.89 (m, 2H), 1.89-1.85 (m, 1H), 1.84-1.77 (m, 1H), 1.58 (dd, J = 14.4, 8.1 Hz, 1H), 0.90 (s, 9H), 0.74 (ddd, J = 6.4, 4.9, 3.3 Hz, 2H), 0.53-0.45 (m, 1H), 0.40-0.34 (m, 2H), 0.13-0.07 (m, 1H). |
| 54 | 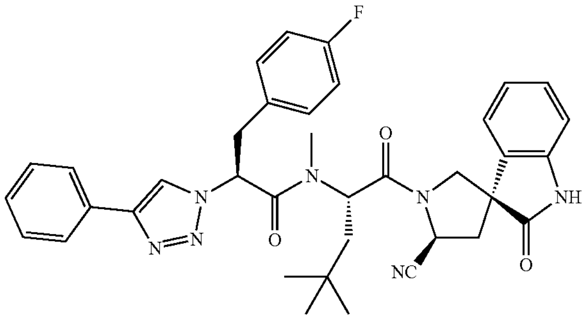 [SMILES: CN(C(=O)[C@H](Cc1ccc(F)cc1)n1cc(-c2ccccc2)nn1)[C@@H](CC(C)(C)C)C(=O)N1C[C@]2(C[C@H]1C#N)C(=O)Nc1ccccc12] | 646.23 [M − H] | 1H NMR (400 MHz, Acetone-d6) δ 9.82 (s, 1H), 8.39 (s, 1H), 7.91-7.79 (m, 2H), 7.43-7.37 (m, 2H), 7.34-7.19 (m, 3H), 7.18-7.10 (m, 3H), 7.03 (dd, J = 7.8, 1.2 Hz, 1H), 6.99-6.91 (m, 2H), 5.90 (dd, J = 11.3, 4.2 Hz, 1H), 5.51 (t, J = 6.3 Hz, 1H), 5.25 (t, J = 8.6 Hz, 1H), 4.22 (dd, J = 10.6, 1.3 Hz, 1H), 4.03 (d, J = 10.5 Hz, 1H), 3.25 (s, 3H), 3.15 (dd, J = 14.7, 11.3 Hz, 1H), 2.79-2.64 (m, 3H), 2.06 (dd, J = 14.3, 6.6 Hz, 1H), 1.52 (dd, J = 14.3, 6.1 Hz, 1H), 0.83 (s, 9H). |

Example 55

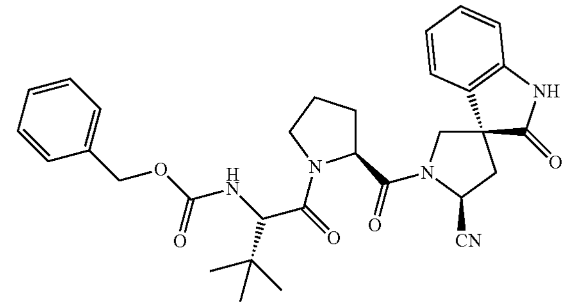

-continued

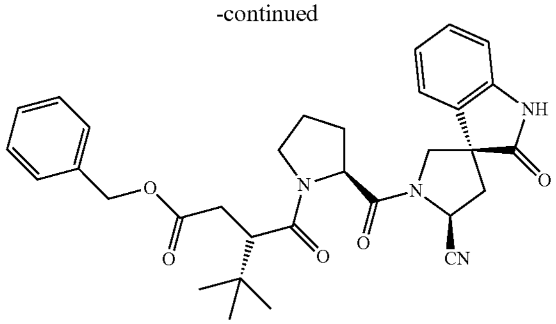

Example 55

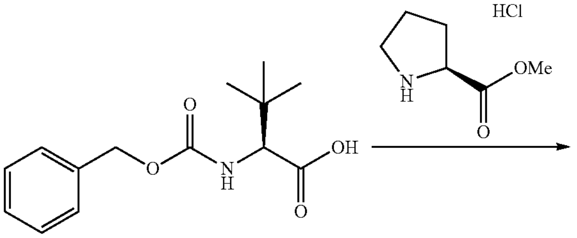

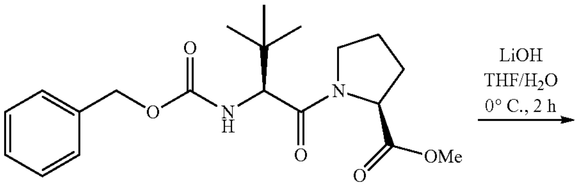

55-1

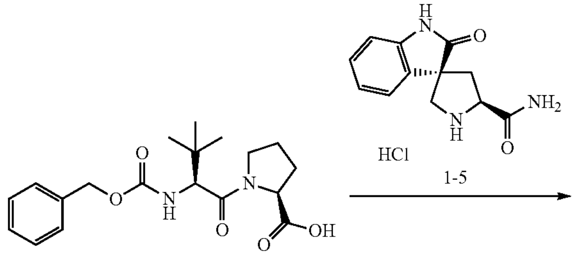

1-5

55-2

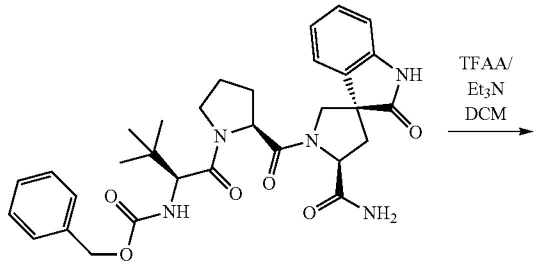

55-3

Step 1: (S)-2-(((benzyloxy)carbonyl)amino)-3,3-dimethylbutanoic acid (305 mg, 1.150 mmol) and methyl L-prolinate hydrochloride (209 mg, 1.265 mmol) were dissolved in $CH_2Cl_{12}$ (5.75 mL). DIPEA (531 μL, 2.87 mmol) and HATU (481 mg, 1.265 mmol) were added and the mixture was stirred at rt for 2 hrs. The reaction mixture was diluted with DCM, and washed sequentially with 1 M HCl, 5% $NaHCO_3$, and brine. The organic layer was dried over $MgSO_4$ and concentrated in vacuo. Purification of the residue on silica gel chromatography with 0-100% EtOAc/cyclohexane provided Compound 55-1 (316 mg, 0.839 mmol, 73.0% yield).

Step 2: Compound 55-1 (316 mg, 0.839 mmol) was dissolved in THE (5.60 mL) and water (2.80 mL). At 0° C. lithium hydroxide hydrate (88 mg, 2.099 mmol) was added. The mixture was stirred at 0° C. for 2 hrs, and at rt for 30 min. The reaction was quenched with 1 M HCl (2 mL), and extracted with MTBE. The organic layer was dried over $Na_2SO_4$ and concentrated in vacuo to afford Compound 55-2 (308 mg, 0.850 mmol, quant. yield).

Step 3: Compound 55-2 (250 mg, 0.690 mmol) and compound 1-5 (231 mg, 0.690 mmol) was dissolved in DCM (5 mL) and DMF (2 mL). 4-Methylmorpholine (283 μL, 2.069 mmol) and HATU (262 mg, 0.690 mmol) were added and the mixture was stirred at rt for 90 min. The reaction mixture was diluted with DCM, and washed sequentially with 1 M HCl, 5% $NaHCO_3$, and brine. The collected organic layer was dried over $MgSO_4$ and concentrated in vacuo. Purification of the residue on silica gel chromatography with 0-100% acetone/cyclohexane provided Compound 55-3 (308 mg, 0.535 mmol, 78% yield). LC-MS, $ES^+$: 576.3 [M+H].

Step 4: Compound 55-3 (308 mg, 0.535 mmol) was dissolved in DCM (3 mL). At 0° C. triethylamine (447 μL, 3.21 mmol) and TFAA (227 μl, 1.605 mmol) were added. The mixture was stirred at 0° C. for 20 min, and quenched with 5% $NaHCO_3$. The organic layer was loaded on silica gel and eluted with 0-50% acetone/cyclohexane to afford Example 55 (282 mg, 0.506 mmol, 95% yield). LC-MS, ES+: 580.26 [$M+Na^+$]; $^1H$ NMR (400 MHz, Acetone-$d_6$) δ 9.67 (s, 1H), 7.51-7.34 (m, 2H), 7.34 (t, J=0.9 Hz, 2H), 7.34-7.27 (m, 1H), 7.31-7.22 (m, 2H), 7.08-6.96 (m, 2H), 6.17 (d, J=9.4 Hz, 1H), 5.09 (td, J=9.7, 3.0 Hz, 2H), 5.03-4.93 (m, 1H), 4.63 (t, J=6.9 Hz, 1H), 4.39 (d, J=9.4 Hz, 1H), 4.29 (d, J=10.2 Hz, 1H), 4.02 (m, 1H), 3.91 (s, 1H), 3.82-3.74 (m, 1H), 2.78-2.58 (m, 2H), 2.32 (s, 1H), 2.19 (s, 1H), 2.01 (m, 2H), 1.11 (s, 9H).

Example 56

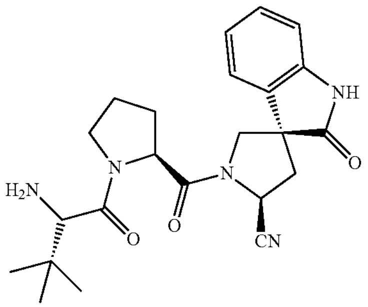

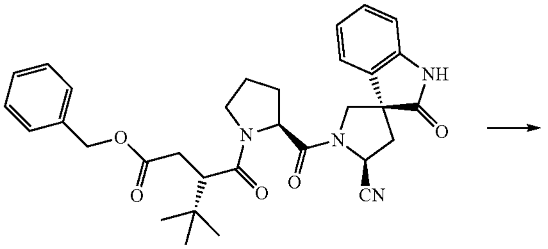

Example 55

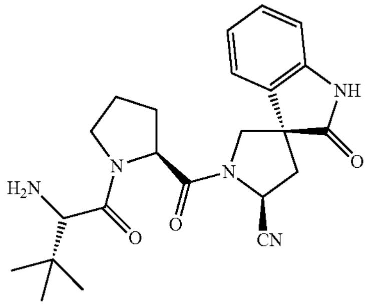

Example 56

Example 55 (282 mg, 0.506 mmol) was dissolved in MeOH (5 mL). 10% Pd—C(26.9 mg, 0.025 mmol) was added. The mixture was stirred under hydrogen (balloon) for 1 h. The mixture was filtered through Celite and concentrated in vacuo to afford Example 56 (199 mg, 0.470 mmol, 93% yield) as a white solid. LC-MS, $ES^+$: 424.29 [M+H]; $^1H$ NMR (400 MHz, DMSO-$d_6$) δ 10.68 (s, 1H), 7.30-7.17 (m, 2H), 7.01-6.86 (m, 2H), 5.07 (dd, J=8.5, 6.9 Hz, 1H), 4.53 (dd, J=8.3, 5.2 Hz, 1H), 4.09 (d, J=10.4 Hz, 1H), 3.89 (d, J=10.4 Hz, 1H), 3.83-3.66 (m, 1H), 3.56 (dt, J=9.8, 6.9 Hz, 1H), 3.17 (m, 1H), 2.67-2.57 (m, 1H), 2.47 (dd, J=13.1, 6.9 Hz, 1H), 2.26-2.11 (m, 1H), 2.00 (dt, J=12.7, 6.7 Hz, 1H), 1.81 (dtd, J=33.8, 12.2, 6.7 Hz, 2H), 0.95 (s, 9H).

Example 57

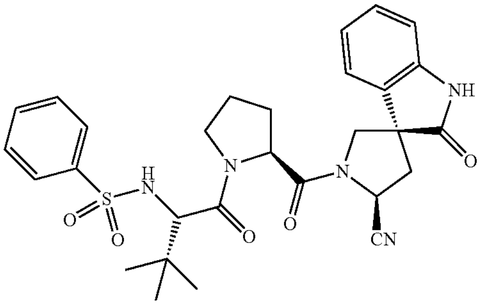

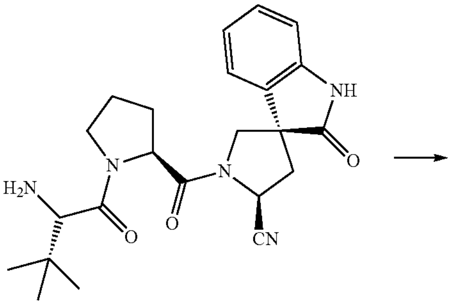

Example 56

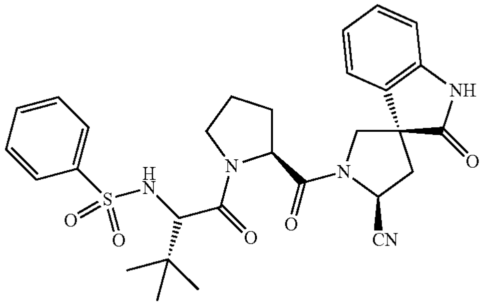

Example 57

Example 56 (20 mg, 0.047 mmol) was dissolved in DCM (0.472 mL). Hunig's base (24.74 μL, 0.142 mmol) and benzenesulfonyl chloride (7.25 μL, 0.057 mmol) were added. The mixture was stirred at rt for 10 min, quenched with 500 $NaHCO_3$, and extracted with DCM. The organic layer was loaded on silica gel and eluted with 0-50% acetone/cyclohexane to afford Example 57 (24 mg, 0.043 mmol, 90 yield). LC-MS, $ES^+$: 586.23 [M+$Na^+$].

Example 58

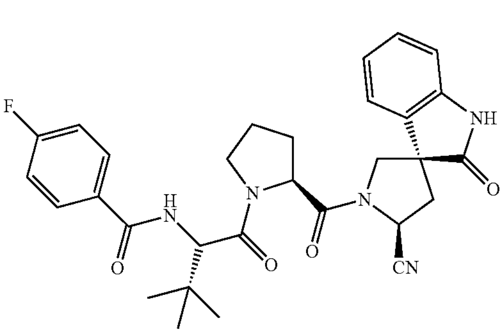

-continued

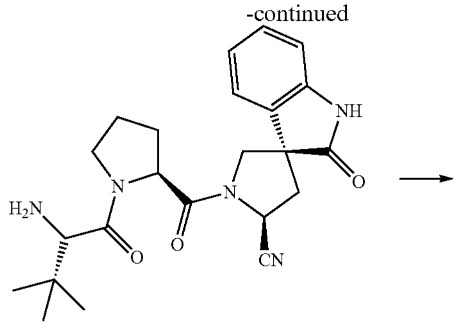

Example 56

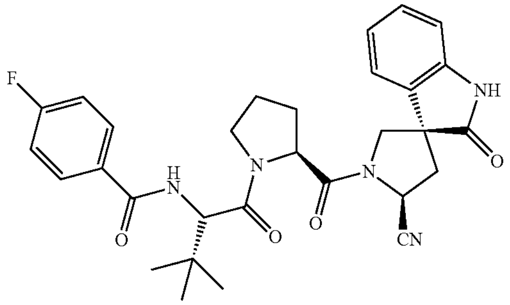

Example 58

Example 56 (20 mg, 0.047 mmol) was dissolved in DCM (0.472 mL). Hunig's base (24.74 μL, 0.142 mmol) and 4-fluorobenzoyl chloride (6.70 μL, 0.057 mmol) were added. The mixture was stirred at rt for 10 min, quenched with 5% $NaHCO_3$, and extracted with DCM. The organic layer was loaded on silica gel and eluted with 0-50% acetone/cyclohexane to afford Example 58 (22 mg, 0.040 mmol, 85% yield). LC-MS, $ES^+$: 568.24 [M+Na].

Example 59

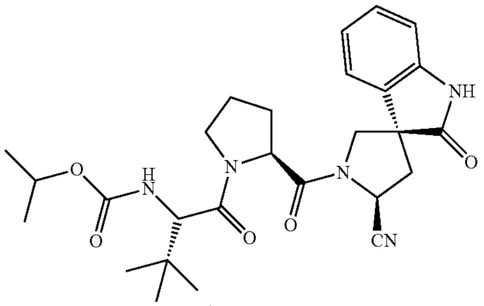

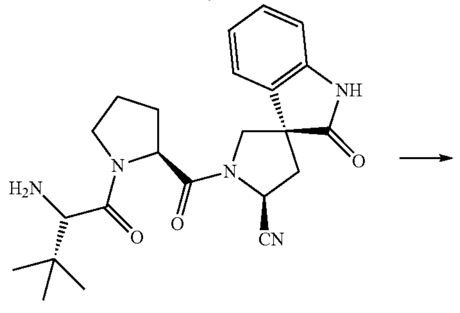

Example 56

-continued

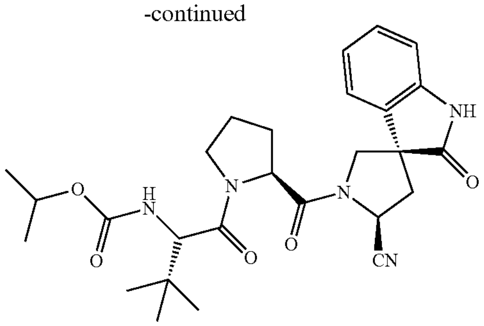

Example 59

Example 56 (20 mg, 0.047 mmol) was dissolved in DCM (0.472 mL). Hunig's base (24.74 μL, 0.142 mmol) and a 1.0 M solution of isopropyl carbonochloridate in toluene (56.7 μL, 0.057 mmol) were added. The mixture was stirred at rt for 10 min, quenched with 5% $NaHCO_3$, and extracted with DCM. The organic layer was loaded on silica gel and eluted with 0-50% acetone/cyclohexane to afford Example 59 (22 mg, 0.043 mmol, 91% yield). LC-MS, $ES^+$: 532.25 [M+Na].

Example 60

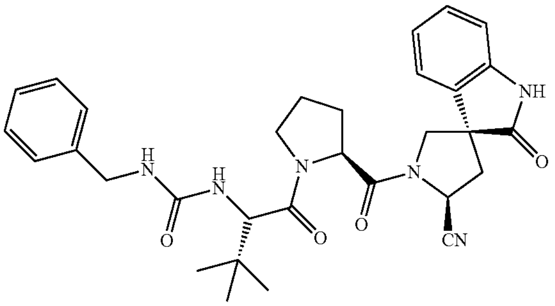

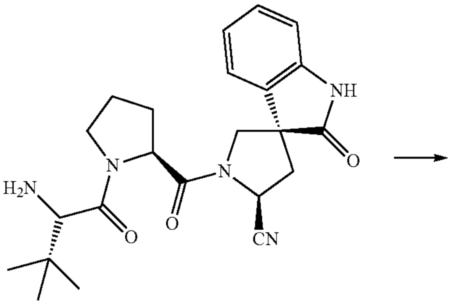

Example 56

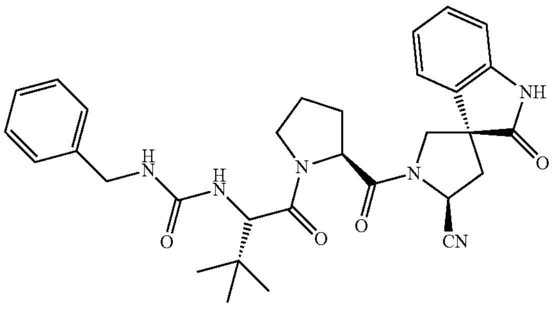

Example 60

Example 56 (22 mg, 0.052 mmol) was dissolved in DCM (0.519 mL). (Isocyanatomethyl)benzene (7.70 µL, 0.062 mmol) was added. The mixture was stirred at rt for 20 min, loaded on silica gel, and eluted with 0-50% acetone/cyclohexane to afford Example 60 (28 mg, 0.050 mmol, 97% yield). LC-MS, $ES^+$: 579.27 $[M+Na^+]$.

Example 61

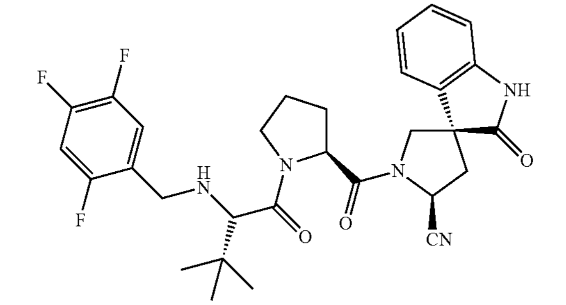

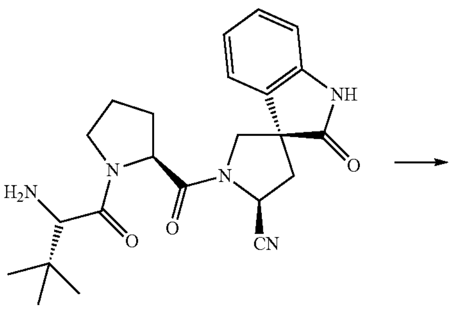

Example 56

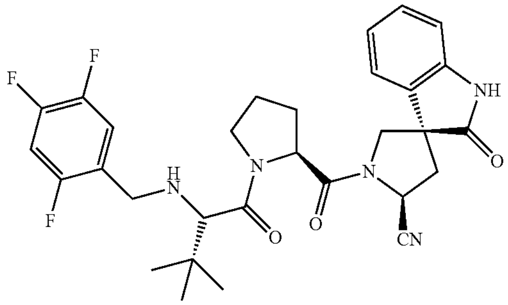

Example 61

Example 56 (22 mg, 0.052 mmol) was dissolved in DCM (0.519 mL). 2,4,5-Trifluorobenzaldehyde (8.91 µL, 0.078 mmol) was added. The mixture was stirred at rt for 1 h. Sodium cyanoborohydride (1 M in THF) (51.9 µL, 0.052 mmol) was added. The mixture was stirred at rt for 30 min, quenched with 5% $NaHCO_3$, and extracted with DCM. The organic layer was loaded on silica gel and eluted with 0-50% acetone/cyclohexane to afford Example 61 (8.6 mg, 0.015 mmol, 29.2% yield). LC-MS, $ES^+$: 568.25 [M+H].

Example 62

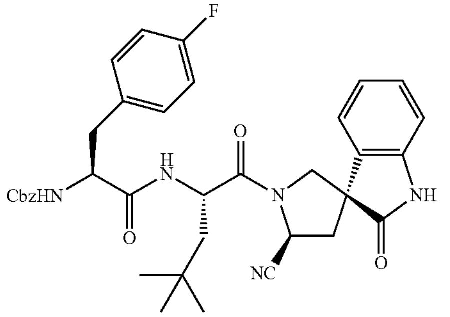

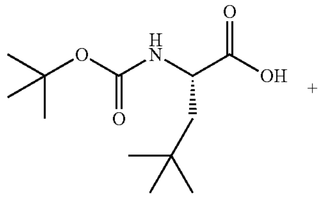

1.05 eq

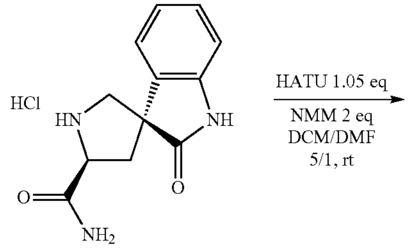

1-5

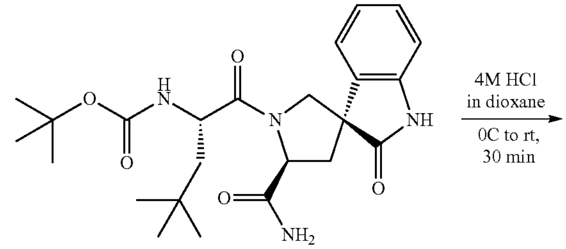

62-1

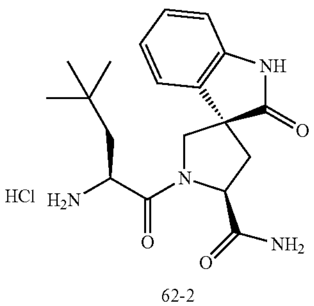

62-2

-continued

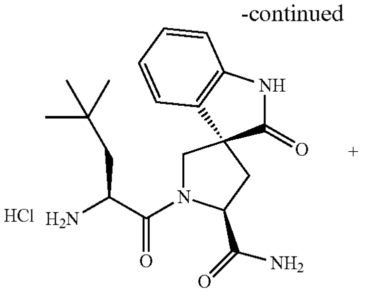

62-2

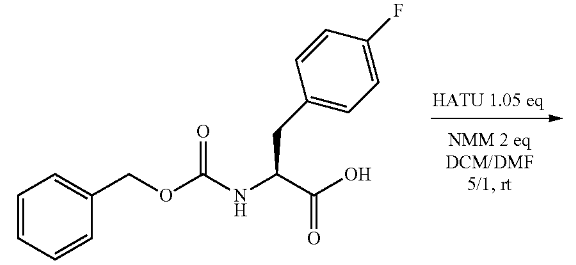

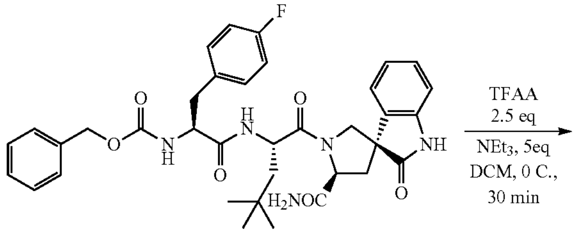

62-3

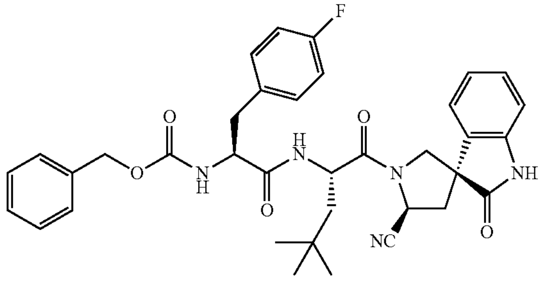

Example 62

Step 1: To a mixture of compound 1-5 (1.7 g, 5.07 mmol) and (S)-2-((tert-butoxycarbonyl)amino)-4,4-dimethylpentanoic acid (1.367 g, 5.57 mmol) in dry $CH_2Cl_2$ (17 mL) and DMF (3 mL) at 0° C. were added 4-methylmorpholine (1.67 mL, 15.2 mmol) and HATU (2.119 g, 5.57 mmol). The resulting mixture was stirred at 0° C. for ~30 min and then at rt for several hours until LC-MS indicated the reaction was completed. The reaction mixture was diluted with DCM, washed with 5% $NaHCO_3$, water, brine, dried over $Na_2SO_4$, and concentrated in vacuo. The residue was purified by silica gel chromatography (0 to 10% MeOH/DCM) to afford the desired compound 62-1 (1.7 g, 3.71 mmol, 73.2% yield) as a white solid. LC-MS, ES+: 456.3 [M+1].

Step 2: compound 62-1 (1.0 g, 2.181 mmol) was added to 4M HCl (10.90 ml, 43.6 mmol) at 0° C. After stirring for 15 min, removed ice bath and stirred at rt for 15 min.

MTBE (60 mL) was added to the reaction mixture. The resulting white precipitate was collected via filtration under $N_2$ and rinsed with MTBE (3×). The collected solid was further dried under high vacuum to provide the desired compound 62-2 (860 mg, 2.15 mmol, 100% yield) as nice solid. LC-MS, ES+: 359.49 [M+H].

Step 3: To a solution of (S)-2-(((benzyloxy)carbonyl)amino)-3-(4-fluorophenyl)propanoic acid (0.726 g, 2.289 mmol) and 4-methylmorpholine (0.959 ml, 8.72 mmol) in DCM (18.17 ml) and DMF (3.63 ml) at rt was added HATU (0.912 g, 2.398 mmol). The reaction mixture was stirred at rt for ~20 min and then cooled to 0° C. Compound 62-2 (0.86 g, 2.18 mmol) was added and the resulting mixture was stirred at 0° C. for ~1 h and then at rt for several hours until LC-MS indicated the reaction was completed. The reaction mixture was diluted with DCM, washed with 5% $NaHCO_3$, water, brine, dried over $Na_2SO_4$, and concentrated in vacuo. The residue was purified by silica gel chromatography (0 to 10% MeOH/DCM) to afford the desired compound 62-3 (958 mg, 1.456 mmol, 66.8% yield) as a white solid. LC-MS, $ES^+$: 658.26 [M+1].

Step 4: Compound 62-3 (473 mg, 0.719 mmol) was dissolved in DCM (7.2 mL). At 0° C., triethylamine (501 μL, 3.60 mmol) and TFAA (225 μL, 1.618 mmol) were added. The mixture was stirred at 0° C. for ~30 min. The reaction mixture was diluted with DCM, washed with sat aq. $NaHCO_3$, brine, dried over $Na_2SO_4$, and concentrated. The residue was purified by silica gel chromatography (0 to 40% acetone/cyclohexane) to afford Example 62 (400 mg, 0.719 mmol, 87% yield). LC-MS, ES−: 638.44 [M−H].

Example 63

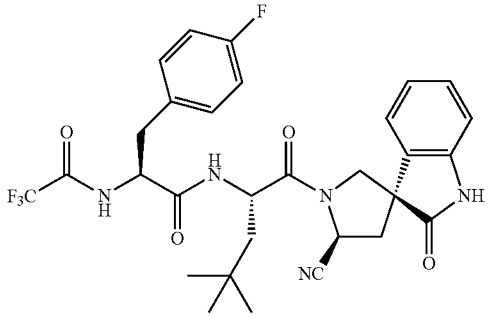

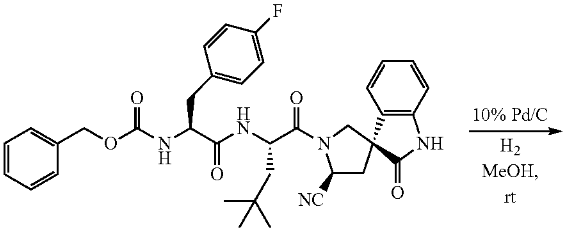

Example 62

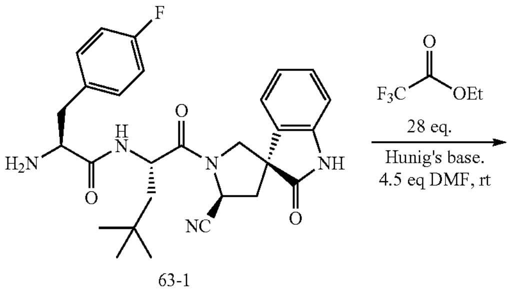

63-1

-continued

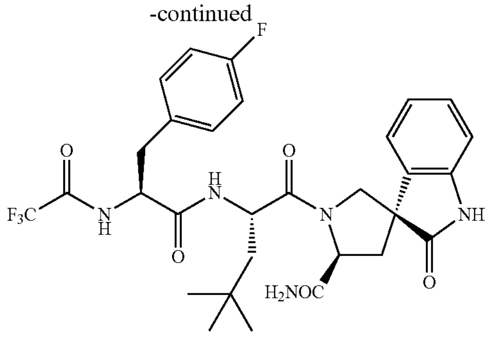

Example 63

Step 1: Example 62 (372 mg, 0.581 mmol) was dissolved in MeOH (7.27 ml). 10% Pd—C(30.9 mg, 0.029 mmol) was added. The mixture was stirred under $H_2$ (balloon) for 90 min. The mixture was filtered through celite, and concentrated in vacuo to provide compound 63-1 (280 mg, 0.554 mmol, 95% yield) as a solid. LC-MS, ES−: 504.5 [M−H].

Step 2: compound 63-1 (30 mg, 0.059 mmol) was dissolved in DMF (0.2 mL) and ethyl 2,2,2-trifluoroacetate (0.2 mL, 1.661 mmol) at rt. Hunig's base (46.6 μL, 0.267 mmol) was added. The reaction mixture was stirred at rt for 2 hrs, and concentrated to dryness. The residue was purified by silica gel chromatography (0 to 40% acetone/cyclohexane) to afford Example 63 (22 mg, 0.059 mmol, 62% yield). LC-MS, ES−: 600.4 [M−H]. 1H NMR (400 MHz, Acetone-$d_6$) δ 9.78 (s, 1H), 8.34 (d, J=8.3 Hz, 1H), 8.04 (s, 1H), 7.35-7.31 (m, 2H), 7.25 (td, J=7.7, 1.2 Hz, 1H), 7.11-7.03 (m, 3H), 7.02-6.94 (m, 2H), 5.18 (t, J=8.4 Hz, 1H), 4.80 (dtd, J=12.7, 8.7, 8.2, 4.4 Hz, 2H), 4.26 (d, J=10.2 Hz, 1H), 4.04 (d, J=10.2 Hz, 1H), 3.16 (dd, J=14.2, 4.4 Hz, 1H), 2.91-2.88 (m, 1H), 2.75-2.69 (m, 2H), 1.96-1.88 (m, 1H), 1.64 (dd, J=14.4, 8.3 Hz, 1H), 0.99 (s, 9H).

TABLE 2

The following examples were prepared employing similar protocol as described above.

| Example | Structure | MS | NMR |
|---|---|---|---|
| 64 | 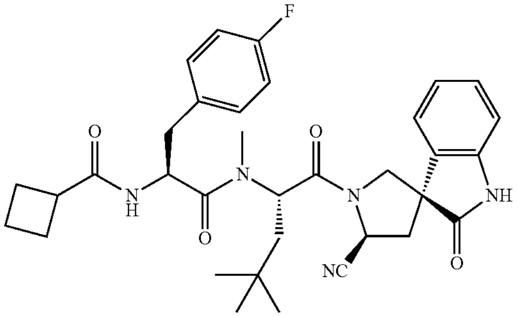 [SMILES: CN(C(=O)[C@H](Cc1ccc(F)cc1)NC(=O)C1CCC1)[C@@H](CC(C)(C)C)C(=O)N1C[C@]2(C[C@H]1C#N)C(=O)Nc1ccccc12] | 600.50 [M − H] | 1H NMR (400 MHz, Acetone-d6) δ 9.77 (s, 1H), 7.24-7.08 (m, 4H), 7.05 (dd, J = 7.4, 1.4 Hz, 1H), 7.03-6.94 (m, 3H), 6.88 (d, J = 9.1 Hz, 1H), 5.52-5.44 (m, 1H), 5.21 (t, J = 8.6 Hz, 1H), 4.89 (ddd, J = 10.5, 9.1, 4.2 Hz, 1H), 4.10 (dd, J = 10.6, 1.3 Hz, 1H), 3.96 (d, J = 10.5 Hz, 1H), 3.14 (s, 3H), 2.93 (td, J = 8.6, 7.4 Hz, 1H), 2.81 (q, J = 1.2 Hz, 1H), 2.78-2.65 (m, 2H), 2.36 (dd, J = 14.2, 10.5 Hz, 1H), 2.21 (dd, J = 14.2, 4.2 Hz, 1H), 2.14-2.08 (m, 1H), 1.99-1.77 (m, 4H), 1.74-1.64 (m, 1H), 1.51 (dd, J = 14.2, 5.8 Hz, 1H), 0.93 (s, 9H). |
| 65 | 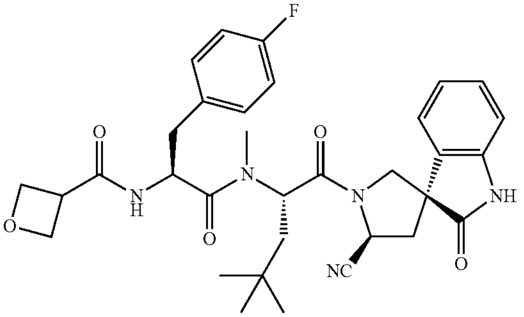 [SMILES: CN(C(=O)[C@H](Cc1ccc(F)cc1)NC(=O)C1COC1)[C@@H](CC(C)(C)C)C(=O)N1C[C@]2(C[C@H]1C#N)C(=O)Nc1ccccc12] | 602.3 [M − H] | 1H NMR (400 MHz, Acetone-d6) δ 9.77 (s, 1H), 7.23-7.12 (m, 4H), 7.11-6.95 (m, 5H), 5.49 (dd, J = 6.9, 5.7 Hz, 1H), 5.21 (t, J = 8.6 Hz, 1H), 4.96 (ddd, J = 10.2, 9.1, 4.5 Hz, 1H), 4.60-4.46 (m, 3H), 4.31 (dd, J = 6.6, 5.6 Hz, 1H), 4.09 (d, J = 10.6 Hz, 1H), 3.97 (d, J = 10.5 Hz, 1H), 3.70 (tt, J = 8.5, 6.7 Hz, 1H), 3.17 (s, 3H), 2.77-2.66 (m, 2H), 2.38-2.21 (m, 2H), 2.12 (dd, J = 14.2, 6.9 Hz, 1H), 1.51 (dd, J = 14.2, 5.6 Hz, 1H), 0.93 (s, 9H). |
| 66 | 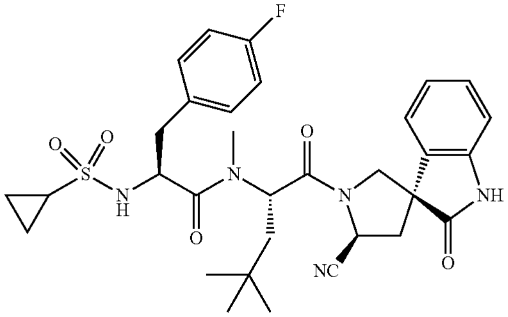 [SMILES: CN(C(=O)[C@H](Cc1ccc(F)cc1)NS(=O)(=O)C1CC1)[C@@H](CC(C)(C)C)C(=O)N1C[C@]2(C[C@H]1C#N)C(=O)Nc1ccccc12] | 622.3 [M − H] | 1H NMR (400 MHz, Acetone-d6) δ 9.76 (s, 1H), 7.31-7.24 (m, 2H), 7.15-6.99 (m, 6H), 6.97-6.91 (m, 1H), 6.09 (d, J = 9.8 Hz, 1H), 5.49 (dd, J = 8.1, 4.2 Hz, 1H), 5.21 (t, J = 8.6 Hz, 1H), 4.35 (td, J = 10.3, 3.7 Hz, 1H), 3.20 (s, 3H), 2.82-2.66 (m, 3H), 2.38-2.20 (m, 3H), 1.97 (tt, J = 7.9, 4.9 Hz, 1H), 1.47-1.40 (m, 1H), 0.80-0.65 (m, 4H). |

TABLE 2-continued

The following examples were prepared employing similar protocol as described above.

| Example | Structure | MS | NMR |
|---|---|---|---|
| 67 | 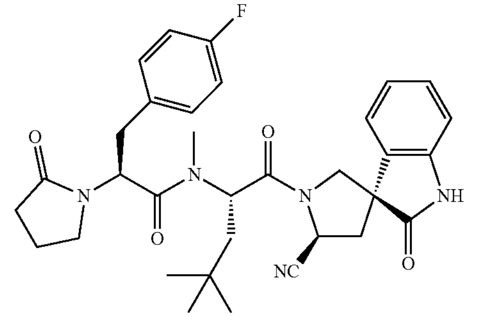 [SMILES: CN(C(=O)[C@H](Cc1ccc(F)cc1)N1CCCC1=O)[C@@H](CC(C)(C)C)C(=O)N1C[C@]2(C[C@H]1C#N)C(=O)Nc1ccccc12] | 586.34 [M − H] | |
| 68 | 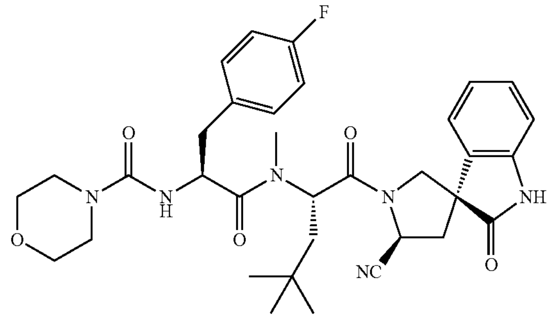 [SMILES: CN(C(=O)[C@H](Cc1ccc(F)cc1)NC(=O)N1CCOCC1)[C@@H](CC(C)(C)C)C(=O)N1C[C@]2(C[C@H]1C#N)C(=O)Nc1ccccc12] | 631.4 [M − H] | 1H NMR (400 MHz, Acetone-d6) δ 9.80 (s, 1H), 7.24-7.13 (m, 3H), 7.10-6.98 (m, 4H), 6.95 (dt, J = 7.8, 0.9 Hz, 1H), 5.76 (d, J = 9.0 Hz, 1H), 5.49 (dd, J = 7.2, 5.2 Hz, 1H), 5.21 (t, J = 8.6 Hz, 1H), 4.74 (ddd, J = 10.5, 9.0, 4.1 Hz, 1H), 4.05 (dd, J = 10.5, 1.2 Hz, 1H), 3.98 (d, J = 10.5 Hz, 1H), 3.47 (ddd, J = 5.5, 4.1, 1.6 Hz, 4H), 3.28-3.18 (m, 4H), 3.17 (s, 3H), 2.80-2.64 (m, 2H), 2.32 (dd, J = 14.1, 10.5 Hz, 1H), 2.25-2.12 (m, 2H), 1.51-1.45 (m, 1H), 0.94 (s, 9H). |
| 69 | 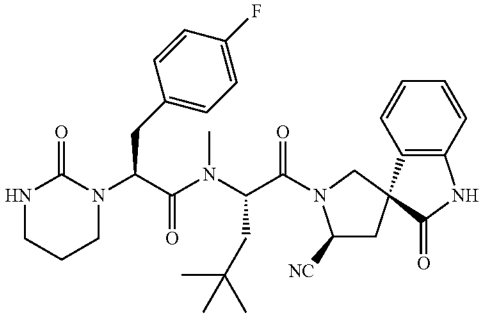 [SMILES: CN(C(=O)[C@H](Cc1ccc(F)cc1)N1CCCNC1=O)[C@@H](CC(C)(C)C)C(=O)N1C[C@]2(C[C@H]1C#N)C(=O)Nc1ccccc12] | 601.3 [M − H] | 1H NMR (400 MHz, Acetone-d6) δ 9.69 (s, 1H), 7.10 (t, J = 7.7 Hz, 1H), 7.01 (dq, J = 14.1, 7.6, 6.5 Hz, 3H), 6.82 (p, J = 8.8 Hz, 4H), 5.44-5.32 (m, 2H), 5.27 (dd, J = 10.2, 5.5 Hz, 1H), 5.05 (t, J = 8.6 Hz, 1H), 4.03 (d, J = 10.7 Hz, 1H), 3.76 (d, J = 10.6 Hz, 1H), 3.03-2.92 (m, 3H), 2.92 (s, 3H), 2.66-2.47 (m, 3H), 2.15-1.96 (m, 2H), 1.67-1.43 (m, 2H), 1.25 (dd, J = 14.1, 4.8 Hz, 1H), 0.81 (s, 9H). |
| 70 | 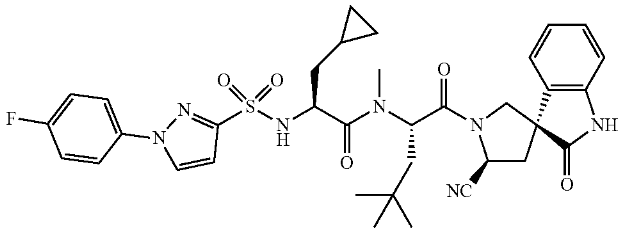 [SMILES: CN(C(=O)[C@H](CC1CC1)NS(=O)(=O)c1ccn(-c2ccc(F)cc2)n1)[C@@H](CC(C)(C)C)C(=O)N1C[C@]2(C[C@H]1C#N)C(=O)Nc1ccccc12] | 688.3 [M − H] | 1H NMR (400 MHz, Acetone-d6) δ 9.76 (s, 1H), 8.80 (s, 1H), 8.04-7.96 (m, 2H), 7.93 (s, 1H), 7.43-7.28 (m, 3H), 7.08-6.94 (m, 3H), 6.44 (d, J = 9.5 Hz, 1H), 5.24 (dd, J = 9.3, 3.1 Hz, 1H), 5.11 (t, J = 8.5 Hz, 1H), 4.25 (td, J = 9.5, 3.9 Hz, 1H), 3.96 (d, J = 10.4 Hz, 1H), 3.85 (dd, J = 10.4, 1.1 Hz, 1H), 3.02 (s, 3H), 2.76-2.61 (m, 2H), 2.15 (dd, J = 13.3, 9.2 Hz, 1H), 1.20 (ddd, J = 14.4, 9.4, 5.2 Hz, 1H), 0.90-0.80 (m, 2H), 0.77 (s, 9H), 0.75-0.70 (m, 1H), 0.49-0.32 (m, 2H), 0.15-0.06 (m, 1H), 0.01 (dq, J = 9.4, 4.7 Hz, 1H). |

TABLE 2-continued

The following examples were prepared employing similar protocol as described above.

| Example | Structure | MS | NMR |
|---|---|---|---|
| 71 | 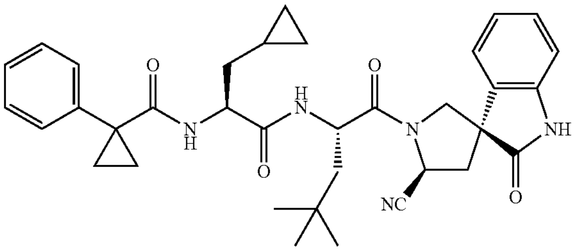 [SMILES: CC(C)(C)C[C@H](NC(=O)[C@H](CC1CC1)NC(=O)C1(c2ccccc2)CC1)C(=O)N1C[C@]2(C[C@H]1C#N)C(=O)Nc1ccccc12] | 594.75 [M − H] | $^1$H NMR (400 MHz, Acetone-$d_6$) δ 9.78 (s, 1H), 7.61-7.42 (m, 6H), 7.38 (td, J = 7.7, 1.3 Hz, 1H), 7.15-7.01 (m, 3H), 6.25 (d, J = 7.8 Hz, 1H), 5.19 (t, J = 8.4 Hz, 1H), 4.77 (td, J = 8.3, 4.2 Hz, 1H), 4.57-4.51 (m, 1H), 4.30 (d, J = 10.2 Hz, 1H), 4.07 (d, J = 10.3 Hz, 1H), 2.81-2.73 (m, 2H), 1.93 (dd, J = 14.4, 4.2 Hz, 1H), 1.68 (dd, J = 14.4, 8.3 Hz, 1H), 1.63-1.47 (m, 4H), 1.07 (s, 9H), 0.68-0.57 (m, 1H), 0.46-0.38 (m, 1H), 0.38-0.30 (m, 1H), 0.05 (s, 2H). |
| 72 | 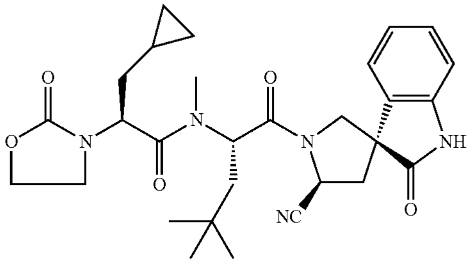 [SMILES: CN(C(=O)[C@H](CC1CC1)N1CCOC1=O)[C@@H](CC(C)(C)C)C(=O)N1C[C@]2(C[C@H]1C#N)C(=O)Nc1ccccc12] | 534.5 [M − H] | 1H NMR (400 MHz, Acetone-d6) δ 9.75 (s, 1H), 7.30 (t, J = 7.7 Hz, 1H), 7.12-6.95 (m, 3H), 5.47 (dd, J = 7.2, 5.2 Hz, 1H), 5.16 (t, J = 8.5 Hz, 1H), 4.60 (dd, J = 9.4, 5.5 Hz, 1H), 4.27 (ddd, J = 8.8, 7.3, 4.1 Hz, 2H), 4.10-4.02 (m, 1H), 3.93 (d, J = 10.5 Hz, 1H), 3.59-3.49 (m, 2H), 3.09 (s, 3H), 2.74-2.63 (m, 2H), 2.15 (dd, J = 14.1, 7.1 Hz, 1H), 1.44 (ddd, J = 20.7, 14.6, 5.4 Hz, 2H), 0.93 (s, 9H), 0.90-0.79 (m, 1H), 0.36 (q, J = 7.9, 6.2 Hz, 2H), 0.32-0.24 (m, 1H), −0.01 (q, J = 5.2, 3.8 Hz, 2H). |
| 73 | 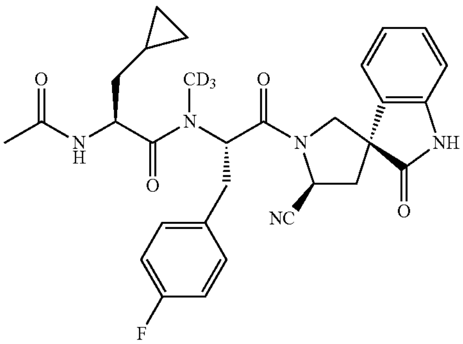 [SMILES: [2H]C([2H])([2H])N(C(=O)[C@H](CC1CC1)NC(C)=O)[C@@H](Cc1ccc(F)cc1)C(=O)N1C[C@]2(C[C@H]1C#N)C(=O)Nc1ccccc12] | 547.2 [M − H] | |
| 74 | 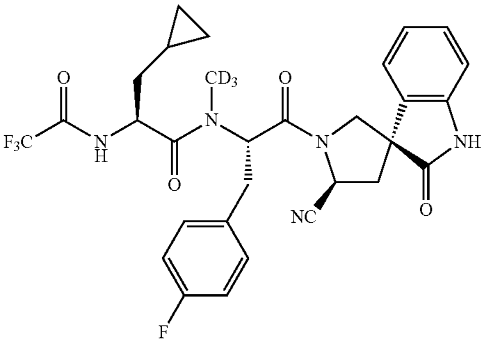 [SMILES: [2H]C([2H])([2H])N(C(=O)[C@H](CC1CC1)NC(=O)C(F)(F)F)[C@@H](Cc1ccc(F)cc1)C(=O)N1C[C@]2(C[C@H]1C#N)C(=O)Nc1ccccc12] | 601.3 [M − H] | |

TABLE 2-continued

The following examples were prepared employing similar protocol as described above.

| Example | Structure | MS | NMR |
| --- | --- | --- | --- |
| 75 | 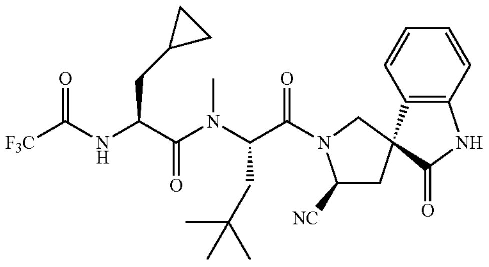 [SMILES: CN(C(=O)[C@H](CC1CC1)NC(=O)C(F)(F)F)[C@@H](CC(C)(C)C)C(=O)N1C[C@]2(C[C@H]1C#N)C(=O)Nc1ccccc12] | 560.2 [M − H] | $^1$H NMR (500 MHz, Acetone-$d_6$) δ 9.62 (s, 1H), 8.19 (d, J = 8.4 Hz, 1H), 7.19 (td, J = 7.7, 1.4 Hz, 1H), 6.97-6.86 (m, 3H), 5.33 (dd, J = 12, 5.2 Hz, 1H), 5.02 (t, J = 8.5 Hz, 1H), 4.70 (td, J = 8.6, 5.0 Hz, 1H), 3.84 (s, 2H), 3.01 (s, 3H), 2.67 (d, J = 5.5 Hz, 1H), 2.59 (dd, J = 13.2, 8.3 Hz, 1H), 2.53 (dd, J = 13.1, 8.8 Hz, 1H), 2.02 (dd, J = 14.1, 7.2 Hz, 1H), 1.37 (dd, J = 14.1, 5.3 Hz, 1H), 1.11-0.97 (m, 2H), 0.80 (s, 9H), 0.44 (pd, J = 7.5, 3.7 Hz, 1H), 0.31-0.20 (m, 2H), −0.01 (m, 1H), −0.16 (dtd, J = 9.9, 5.0, 4.0, 2.6 Hz, 1H). |
| 76 | 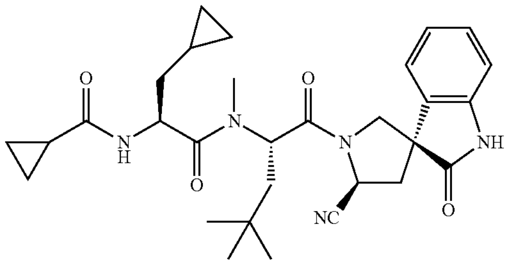 [SMILES: CN(C(=O)[C@H](CC1CC1)NC(=O)C1CC1)[C@@H](CC(C)(C)C)C(=O)N1C[C@]2(C[C@H]1C#N)C(=O)Nc1ccccc12] | 532.4 [M − H] | |
| 77 | 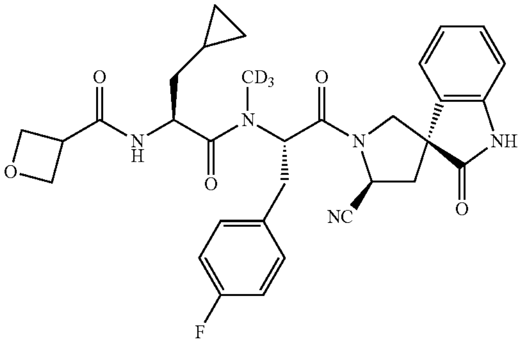 [SMILES: [2H]C([2H])([2H])N(C(=O)[C@H](CC1CC1)NC(=O)C1COC1)[C@@H](Cc1ccc(F)cc1)C(=O)N1C[C@]2(C[C@H]1C#N)C(=O)Nc1ccccc12] | 589.4 [M − H] | |
| 78 | 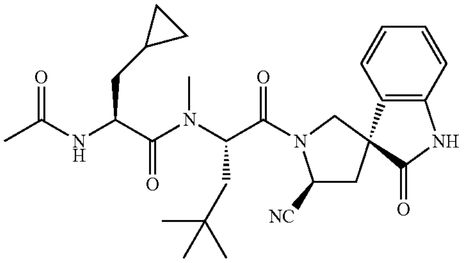 | 506.3 [M − H] | |
| 79 | 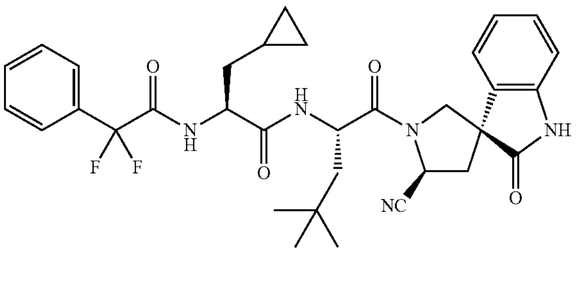 [SMILES: CC(C)(C)C[C@H](NC(=O)[C@H](CC1CC1)NC(=O)C(F)(F)c1ccccc1)C(=O)N1C[C@]2(C[C@H]1C#N)C(=O)Nc1ccccc12] | 604.30 [M − H] | $^1$H NMR (400 MHz, Acetone-$d_6$) δ 9.70 (s, 1H), 7.93 (d, J = 8.2 Hz, 1H), 7.67-7.61 (m, 2H), 7.56-7.46 (m, 2H), 7.27 (td, J = 7.6, 1.4 Hz, 1H), 7.08-6.94 (m, 3H), 5.10 (t, J = 8.5 Hz, 1H), 4.73 (td, J = 8.1, 4.6 Hz, 1H), 4.58-4.51 (m, 1H), 4.22 (d, J = 10.2 Hz, 1H), 4.00 (d, J = 10.2 Hz, 1H), 2.71-2.62 (m, 2H), 1.85 (dd, J = 14.4, 4.6 Hz, 1H), 1.61-1.51 (m, 3H), 0.94 (s, 9H), 0.71-0.59 (m, 1H), 0.37-0.29 (m, 2H), 0.12-0.06 (m, 1H). |

TABLE 2-continued

The following examples were prepared employing similar protocol as described above.

| Example | Structure | MS | NMR |
|---|---|---|---|
| 80 | 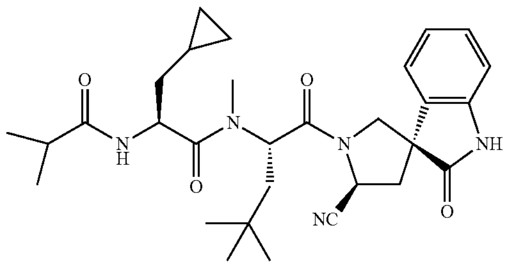 [SMILES: CC(C)C(=O)N[C@@H](CC1CC1)C(=O)N(C)[C@@H](CC(C)(C)C)C(=O)N1C[C@]2(C[C@H]1C#N)C(=O)Nc1ccccc12] | 534.3 [M − H] | $^1$H NMR (500 MHz, Acetone-$d_6$) δ 9.73 (s, 1H), 7.29 (td, J = 7.7, 1.3 Hz, 1H), 7.08-7.00 (m, 2H), 6.98 (dd, J = 7.5, 1.3 Hz, 1H), 6.92 (d, J = 8.7 Hz, 1H), 5.45 (dd, J = 6.9, 5.5 Hz, 1H), 5.13 (t, J = 8.5 Hz, 1H), 4.74 (td, J = 8.7, 5.2 Hz, 1H), 4.00 (dd, J = 10.5, 1.3 Hz, 1H), 3.93 (d, J = 10.5 Hz, 1H), 3.09 (s, 3H), 2.71 (ddd, J = 13.1, 8.3, 1.2 Hz, 1H), 2.65 (dd, J = 13.1, 8.7 Hz, 1H), 2.43 (hept, J = 6.8 Hz, 1H), 2.16-2.06 (m, 1H), 1.46 (dd, J = 14.2, 5.5 Hz, 1H), 1.12-1.02 (m, 4H), 1.00 (d, J = 6.9 Hz, 3H), 0.98-0.92 (m, 1H), 0.91 (s, 9H), 0.48-0.39 (m, 1H), 0.29 (ddddd, J = 18.1, 9.1, 7.9, 5.3, 3.9 Hz, 2H), 0.00 (m, 1H), −0.06-−0.14 (m, 1H). |
| 81 | 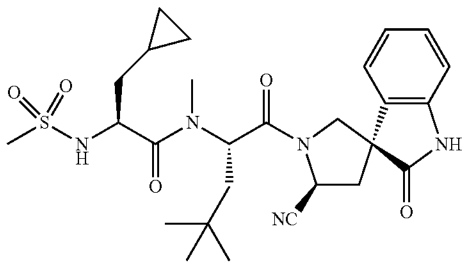 [SMILES: CN(C(=O)[C@H](CC1CC1)NS(C)(=O)=O)[C@@H](CC(C)(C)C)C(=O)N1C[C@]2(C[C@H]1C#N)C(=O)Nc1ccccc12] | 542.2 [M − H] | $^1$H NMR (500 MHz, Acetone-$d_6$) δ 9.71 (s, 1H), 7.28 (td, J = 7.6, 1.4 Hz, 1H), 7.04-6.97 (m, 2H), 6.96 (dd, J = 7.8, 1.4 Hz, 1H), 6.01 (d, J = 9.5 Hz, 1H), 5.43 (dd, J = 8.0, 4.1 Hz, 1H), 5.11 (t, J = 8.5 Hz, 1H), 4.27 (td, J = 9.4, 4.3 Hz, 1H), 3.96 (d, J = 10.4 Hz, 1H), 3.92 (dd, J = 10.4, 1.2 Hz, 1H), 3.06 (s, 3H), 2.80 (s, 3H), 2.72-2.56 (m, 2H), 2.26 (dd, J = 13.9, 8.1 Hz, 1H), 1.42-1.35 (m, 1H), 1.17 (ddd, J = 14.7, 9.8, 5.8 Hz, 1H), 0.93 (s, 9H), 0.91-0.83 (m, 2H), 0.69 (dtt, J = 10.6, 8.0, 5.2 Hz, 1H), 0.45-0.32 (m, 2H), 0.14-0.06 (m, 1H), 0.02 0.0 (m, 1H). |
| 82 | 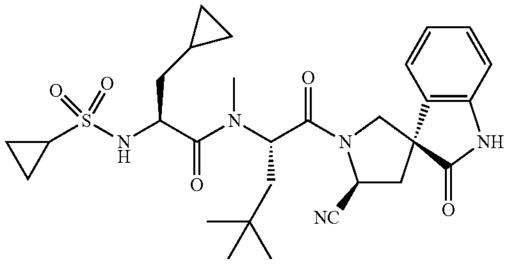 [SMILES: CN(C(=O)[C@H](CC1CC1)NS(=O)(=O)C1CC1)[C@@H](CC(C)(C)C)C(=O)N1C[C@]2(C[C@H]1C#N)C(=O)Nc1ccccc12] | 568.3 [M − H] | $^1$H NMR (500 MHz, Acetone-$d_6$) δ 9.62 (s, 1H), 7.19 (td, J = 7.6, 1.5 Hz, 1H), 6.99-6.88 (m, 2H), 6.88 (dd, J = 7.7, 1.5 Hz, 1H), 5.88 (d, J = 9.6 Hz, 1H), 5.34 (dd, J = 8.4, 3.8 Hz, 1H), 5.02 (t, J = 8.5 Hz, 1H), 4.19-4.11 (m, 1H), 3.91-3.81 (m, 2H), 2.98 (s, 3H), 2.63-2.55 (m, 1H), 2.54 (dd, J = 13.1, 8.8 Hz, 1H), 2.29 (tt, J = 7.9, 5.0 Hz, 1H), 2.19 (dd, J = 13.8, 8.4 Hz, 1H), 1.34-1.15 (m, 2H), 1.15-1.06 (m, 1H), 0.84 (s, 9H), 0.87-0.75 (m, 3H), 0.67-0.56 (m, 1H), 0.36-0.23 (m, 2H), 0.05-0.00 (m, 1H), −0.05-−0.15 (m, 1H). |
| 83 | 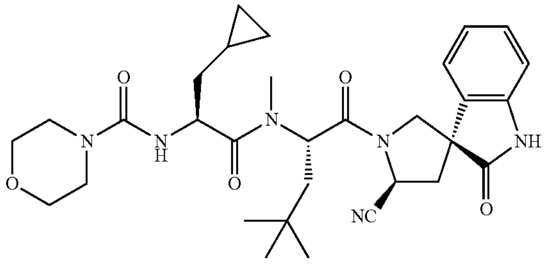 [SMILES: CN(C(=O)[C@H](CC1CC1)NC(=O)N1CCOCC1)[C@@H](CC(C)(C)C)C(=O)N1C[C@]2(C[C@H]1C#N)C(=O)Nc1ccccc12] | 577.4 [M − H] | $^1$H NMR (500 MHz, Acetone-$d_6$) δ 9.70 (s, 1H), 7.28 (td, J = 7.6, 1.3 Hz, 1H), 7.06-6.99 (m, 2H), 6.97 (d, J = 7.1 Hz, 1H), 5.62 (d, J = 8.7 Hz, 1H), 5.42 (dd, J = 7.5, 4.8 Hz, 1H), 5.11 (t, J = 8.5 Hz, 1H), 4.60 (td, J = 8.8, 5.0 Hz, 1H), 3.98-3.89 (m, 2H), 3.52 (dd, J = 5.5, 4.3 Hz, 4H), 3.29 (td, J = 4.5, 2.5 Hz, 4H), 3.07 (s, 3H), 2.72-2.57 (m, 2H), 2.18-2.10 (m, 1H), 1.45-1.38 (m, 1H), 1.10-1.02 (m, 1H), 0.90 (s, 9H), 0.49 (p, J = 5.3 Hz, 1H), 0.34-0.24 (m, 2H), −0.06-−0.14 (m, 1H). |

TABLE 2-continued

The following examples were prepared employing similar protocol as described above.

| Example | Structure | MS | NMR |
|---|---|---|---|
| 84 | 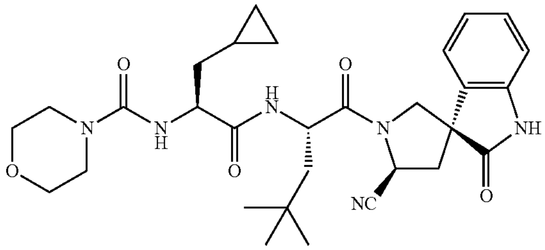 [SMILES: CC(C)(C)C[C@H](NC(=O)[C@H](CC1CC1)NC(=O)N1CCOCC1)C(=O)N1C[C@]2(C[C@H]1C#N)C(=O)Nc1ccccc12] | 563.45 [M − H] | $^1$H NMR (400 MHz, Acetone-$d_6$) δ 9.68 (s, 1H), 7.58 (d, J = 8.6 Hz, 1H), 7.26 (td, J = 7.7, 1.3 Hz, 1H), 7.08 (d, J = 7.5 Hz, 1H), 7.04-6.94 (m, 2H), 5.88 (d, J = 7.8 Hz, 1H), 5.10 (t, J = 8.4 Hz, 1H), 4.72 (td, J = 8.2, 4.7 Hz, 1H), 4.32-4.23 (m, 2H), 4.01-3.91 (m, 1H), 3.58 (dd, J = 5.6, 4.1 Hz, 4H), 3.39-3.31 (m, 3H), 2.74-2.54 (m, 2H), 1.85 (dd, J = 14.4, 4.7 Hz, 1H), 1.55 (dd, J = 14.3, 7.9 Hz, 2H), 1.46 (t, J = 7.0 Hz, 2H), 0.95 (s, 9H), 0.76-0.62 (m, 1H), 0.46-0.28 (m, 2H), 0.12-0.05 (m, 1H). |
| 85 | 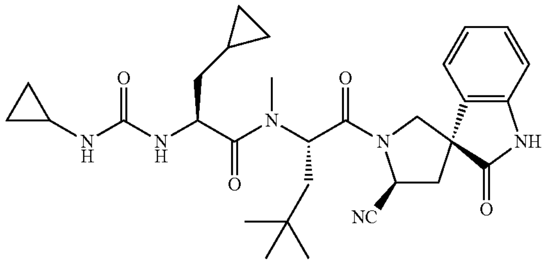 [SMILES: CN(C(=O)[C@H](CC1CC1)NC(=O)NC1CC1)[C@@H](CC(C)(C)C)C(=O)N1C[C@]2(C[C@H]1C#N)C(=O)Nc1ccccc12] | 547.4 [M − H] | $^1$H NMR (500 MHz, Acetone-$d_6$) δ 9.78 (s, 1H), 7.37-7.24 (m, 1H), 7.12-7.01 (m, 3H), 5.73 (s, 1H), 5.56 (d, J = 8.8 Hz, 1H), 5.49 (dd, J = 7.4, 5.0 Hz, 1H), 5.18 (t, J = 8.5 Hz, 1H), 4.68 (td, J = 8.5, 5.2 Hz, 1H), 4.05-3.96 (m, 2H), 3.13 (s, 3H), 2.79-2.63 (m, 2H), 2.53-2.46 (m, 1H), 2.24-2.16 (m, 1H), 1.52-1.44 (m, 1H), 1.24 (d, J = 1.2 Hz, 1H), 1.14-1.05 (m, 1H), 0.97 (s, 9H), 0.99-0.91 (m, 1H), 0.68-0.61 (m, 2H), 0.50 (s, 1H), 0.46-0.38 (m, 2H), 0.38-0.31 (m, 2H), 0.04-0.00 (m, 2H). |
| 86 | 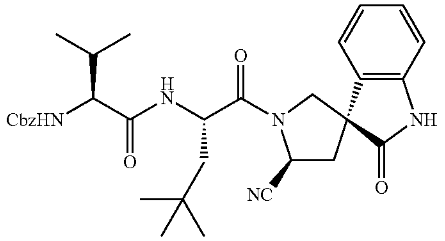 [SMILES: CC(C)[C@H](NC(=O)OCc1ccccc1)C(=O)N[C@@H](CC(C)(C)C)C(=O)N1C[C@]2(C[C@H]1C#N)C(=O)Nc1ccccc12] | 572.43 [M − H] | $^1$H NMR (400 MHz, Acetone-$d_6$) δ 9.74 (s, 1H), 7.63 (d, J = 8.1 Hz, 1H), 7.43-7.14 (m, 7H), 7.06 (d, J = 7.4 Hz, 1H), 6.99 (dd, J = 11.1, 7.5 Hz, 2H), 6.26 (d, J = 9.2 Hz, 1H), 5.08 (d, J = 15.3 Hz, 3H), 4.74 (td, J = 7.9, 4.7 Hz, 1H), 4.25 (d, J = 10.2 Hz, 1H), 4.08 (dd, J = 9.1, 6.2 Hz, 1H), 4.01 (d, J = 10.2 Hz, 1H), 2.67 (dt, J = 8.5, 4.1 Hz, 2H), 1.87 (dd, J = 14.2, 4.7 Hz, 1H), 1.60 (dd, J = 14.3, 7.7 Hz, 2H), 1.42 (s, 3H), 0.96 (s, 9H), 0.90 (d, J = 6.8 Hz, 3H), 0.84 (d, J = 6.8 Hz, 3H). |
| 87 | 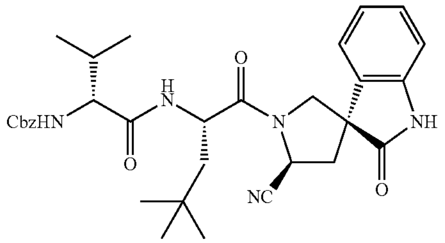 [SMILES: CC(C)[C@@H](NC(=O)OCc1ccccc1)C(=O)N[C@@H](CC(C)(C)C)C(=O)N1C[C@]2(C[C@H]1C#N)C(=O)Nc1ccccc12] | 573.4 [M − H] | $^1$H NMR (400 MHz, Acetone-$d_6$) δ 9.71 (s, 1H), 7.58 (d, J = 8.0 Hz, 1H), 7.42-7.29 (m, 4H), 7.26-7.15 (m, 1H), 7.05 (d, J = 7.3 Hz, 1H), 6.96 (d, J = 7.9 Hz, 2H), 5.08 (d, J = 7.8 Hz, 2H), 4.72-4.60 (m, 1H), 4.32 (d, J = 10.2 Hz, 1H), 4.07 (dt, J = 10.4, 6.8 Hz, 1H), 3.99 (d, J = 10.1 Hz, 1H), 2.85 (s, 4H), 2.74-2.57 (m, 2H), 1.85 (dd, J = 14.4, 4.4 Hz, 1H), 1.60 (dd, J = 14.4, 8.2 Hz, 1H), 1.42 (s, 3H), 0.97 (s, 9H), 0.92 (d, J = 6.8 Hz, 3H), 0.87 (d, J = 6.7 Hz, 3H). |
| 88 | 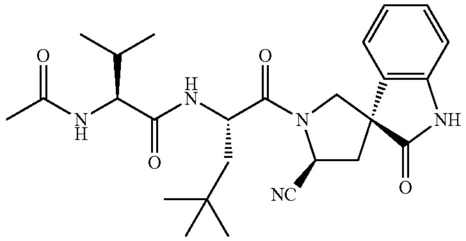 [SMILES: CC(=O)N[C@H](C(=O)N[C@@H](CC(C)(C)C)C(=O)N1C[C@]2(C[C@H]1C#N)C(=O)Nc1ccccc12)C(C)C] | 480.08 [M − H] | $^1$H NMR (400 MHz, Acetone-$d_6$) δ 9.72 (s, 1H), 7.53 (d, J = 8.1 Hz, 1H), 7.27 (td, J = 7.6, 1.4 Hz, 3H), 7.10-6.92 (m, 6H), 5.10 (t, J = 8.4 Hz, 2H), 4.70 (td, J = 8.0, 4.9 Hz, 2H), 4.32-4.19 (m, 3H), 4.00 (d, J = 10.2 Hz, 2H), 3.88-3.75 (m, 1H), 2.70-2.62 (m, 2H), 1.89-1.80 (m, 3H), 1.59 (dd, J = 14.3, 7.8 Hz, 2H), 0.95 (d, J = 1.4 Hz, 9H), 0.85 (d, J = 6.9 Hz, 3H), 0.81 (d, J = 6.9 Hz, 3H). |

TABLE 2-continued

The following examples were prepared employing similar protocol as described above.

| Example | Structure | MS | NMR |
|---|---|---|---|
| 89 | 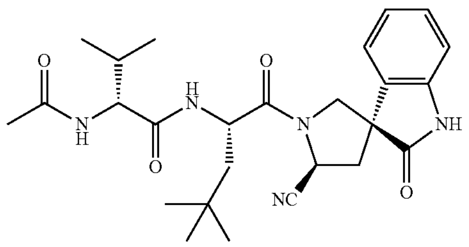 [SMILES: CC(=O)N[C@@H](C(=O)N[C@@H](CC(C)(C)C)C(=O)N1C[C@]2(C[C@H]1C#N)C(=O)Nc1ccccc12)C(C)C] | 480.3 [M − H] | $^1$H NMR (400 MHz, Acetone-$d_6$) δ 9.69 (s, 1H), 7.53 (d, J = 8.0 Hz, 1H), 7.25 (td, J = 7.7, 1.4 Hz, 1H), 7.06 (dd, J = 8.0, 1.4 Hz, 1H), 7.02-6.89 (m, 3H), 5.08 (t, J = 8.3 Hz, 1H), 4.66 (td, J = 8.0, 4.5 Hz, 1H), 4.33-4.24 (m, 2H), 3.98 (d, J = 10.2 Hz, 1H), 2.83 (d, J = 1.8 Hz, 3H), 2.71-2.63 (m, 2H), 1.93 (d, J = 2.0 Hz, 3H), 1.88-1.80 (m, 1H), 1.58 (dd, J = 14.4, 8.1 Hz, 1H), 0.97 (d, J = 1.9 Hz, 9H), 0.89 (dd, J = 6.9, 1.9 Hz, 3H), 0.84 (dd, J = 6.8, 2.0 Hz, 3H). |
| 90 | 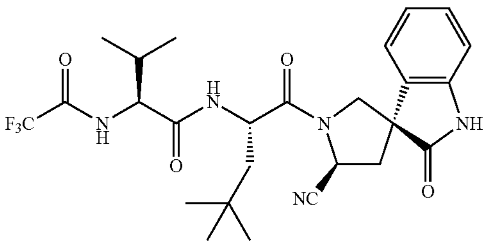 [SMILES: CC(C)[C@H](NC(=O)C(F)(F)F)C(=O)N[C@@H](CC(C)(C)C)C(=O)N1C[C@]2(C[C@H]1C#N)C(=O)Nc1ccccc12] | 534.4 [M − H] | $^1$H NMR (400 MHz, Acetone-$d_6$) δ 9.70 (d, J = 25.7 Hz, 1H), 7.07-6.94 (m, 4H), 5.12 (t, J = 8.5 Hz, 1H), 4.79-4.62 (m, 2H), 4.38 (t, J = 6.6 Hz, 1H), 4.23 (d, J = 10.2 Hz, 1H), 4.02 (d, J = 10.2 Hz, 1H), 2.75-2.63 (m, 2H), 2.35-2.28 (m, 1H), 0.96 (s, 9H), 0.88 (dd, J = 6.8, 1.6 Hz, 3H). |
| 91 | 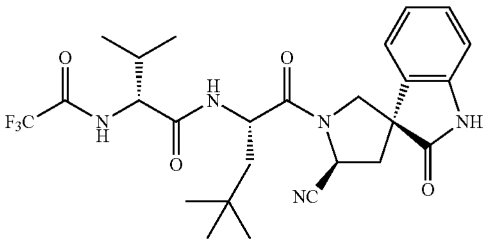 [SMILES: CC(C)[C@@H](NC(=O)C(F)(F)F)C(=O)N[C@@H](CC(C)(C)C)C(=O)N1C[C@]2(C[C@H]1C#N)C(=O)Nc1ccccc12] | 534.2 [M − H] | $^1$H NMR (400 MHz, Acetone-$d_6$) δ 9.65 (d, J = 46.1 Hz, 1H), 7.23 (td, J = 7.7, 1.3 Hz, 1H), 7.08-6.90 (m, 3H), 5.10 (t, J = 8.4 Hz, 1H), 4.69 (dt, J = 8.0, 5.1 Hz, 1H), 4.43 (t, J = 6.2 Hz, 1H), 4.31 (d, J = 10.2 Hz, 1H), 3.99 (d, J = 10.2 Hz, 1H), 2.74-2.60 (m, 3H), 2.23 (dt, J = 13.3, 6.6 Hz, 2H), 1.89 (dd, J = 14.4, 4.6 Hz, 2H), 1.61 (dd, J = 14.5, 8.1 Hz, 1H), 0.98 (s, 9H), 0.94 (d, J = 6.8 Hz, 3H), 0.89 (d, J = 6.8 Hz, 3H). |
| 92 | 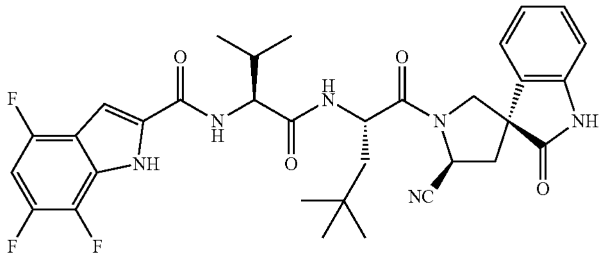 [SMILES: CC(C)[C@H](NC(=O)c1cc2c(F)cc(F)c(F)c2[nH]1)C(=O)N[C@@H](CC(C)(C)C)C(=O)N1C[C@]2(C[C@H]1C#N)C(=O)Nc1ccccc12] | 635.6 [M − H] | $^1$H NMR (400 MHz, Acetone-$d_6$) δ 11.56 (s, 1H), 7.28 (d, J = 2.8 Hz, 1H), 7.14 (td, J = 7.7, 1.3 Hz, 1H), 7.02-6.92 (m, 1H), 6.87 (t, J = 7.6 Hz, 2H), 6.79-6.72 (m, 1H), 5.02 (t, J = 8.4 Hz, 1H), 4.67 (td, J = 7.9, 4.9 Hz, 1H), 4.48 (t, J = 7.3 Hz, 1H), 4.17 (d, J = 10.1 Hz, 1H), 3.92 (d, J = 10.2 Hz, 1H), 2.63-2.51 (m, 2H), 1.81-1.68 (m, 1H), 1.60-1.40 (m, 1H), 0.84 (d, J = 2.3 Hz, 3H), 0.81 (d, J = 1.6 Hz, 9H), 0.80 (s, 3H). |
| 93 | 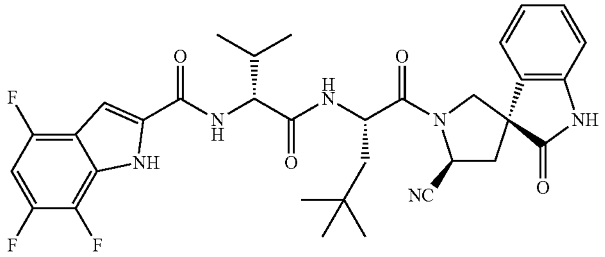 [SMILES: CC(C)[C@@H](NC(=O)c1cc2c(F)cc(F)c(F)c2[nH]1)C(=O)N[C@@H](CC(C)(C)C)C(=O)N1C[C@]2(C[C@H]1C#N)C(=O)Nc1ccccc12] | 635.3 [M − H] | $^1$H NMR (400 MHz, Acetone-$d_6$) δ 11.69 (s, 1H), 7.76 (dd, J = 123.4, 8.6 Hz, 1H), 7.36 (d, J = 2.8 Hz, 1H), 6.94 (tdd, J = 7.9, 5.9, 4.5 Hz, 3H), 6.89-6.80 (m, 1H), 6.76 (td, J = 7.5, 1.1 Hz, 1H), 5.08 (t, J = 8.4 Hz, 1H), 4.76 (dt, J = 7.6, 5.4 Hz, 1H), 4.63-4.55 (m, 1H), 4.39 (d, J = 10.2 Hz, 1H), 4.01 (d, J = 10.2 Hz, 1H), 2.69-2.59 (m, 2H), 2.22 (h, J = 6.8 Hz, 1H), 2.09 (s, 2H), 1.94 (dd, J = 14.3, 5.0 Hz, 1H), 1.63 (dd, J = 14.3, 7.6 Hz, 1H), 0.99 (s, 3H), 0.98 (d, J = 2.2 Hz, 9H), 0.96 (d, J = 6.8 Hz, 3H). |

TABLE 2-continued

The following examples were prepared employing similar protocol as described above.

| Example | Structure | MS | NMR |
|---|---|---|---|
| 94 | 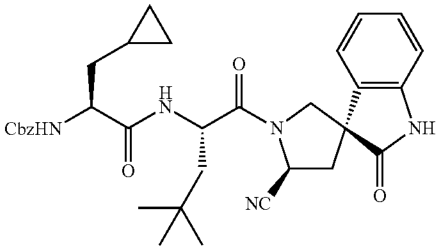 [SMILES: CC(C)(C)C[C@H](NC(=O)[C@H](CC1CC1)NC(=O)OCc1ccccc1)C(=O)N1C[C@]2(C[C@H]1C#N)C(=O)Nc1ccccc12] | 584.2 [M − H] | $^{1}$H NMR (400 MHz, Acetone-$d_6$) δ 9.68 (s, 1H), 7.51 (d, J = 8.5 Hz, 1H), 7.41-7.20 (m, 4H), 7.09-6.94 (m, 2H), 6.39 (d, J = 8.4 Hz, 1H), 5.08 (d, J = 7.4 Hz, 2H), 4.79-4.61 (m, 1H), 4.24 (dd, J = 15.1, 9.0 Hz, 2H), 3.99 (d, J = 10.3 Hz, 1H), 2.73-2.59 (m, 2H), 1.91-1.78 (m, 1H), 1.60-1.47 (m, 2H), 0.95 (s, 9H), 0.75 (s, 1H), 0.43-0.32 (m, 1H), 0.12 (d, J = 8.8 Hz, 1H). |
| 95 | 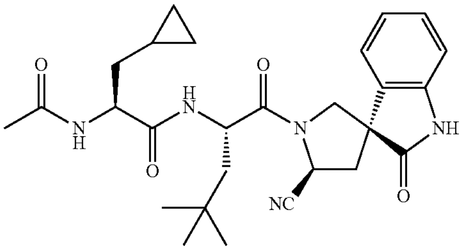 [SMILES: CC(=O)N[C@@H](CC1CC1)C(=O)N[C@@H](CC(C)(C)C)C(=O)N1C[C@]2(C[C@H]1C#N)C(=O)Nc1ccccc12] | 492.23 [M − H] | $^{1}$H NMR (400 MHz, Acetone-$d_6$) δ 9.69 (s, 1H), 7.51 (d, J = 8.5 Hz, 1H), 7.26 (td, J = 7.7, 1.4 Hz, 1H), 7.15 (d, J = 7.9 Hz, 1H), 7.09-6.94 (m, 3H), 4.73 (td, J = 8.1, 4.8 Hz, 1H), 4.41 (td, J = 8.0, 5.8 Hz, 1H), 4.27 (d, J = 10.1 Hz, 1H), 3.98 (d, J = 10.2 Hz, 1H), 2.79-2.77 (m, 3H), 2.75-2.61 (m, 2H), 1.90 (s, 3H), 1.84 (d, J = 4.7 Hz, 1H), 1.56 (dd, J = 14.3, 7.8 Hz, 1H), 1.52-1.35 (m, 2H), 0.95 (s, 9H), 0.76-0.62 (m, 1H), 0.46-0.30 (m, 2H), 0.09 (td, J = 8.9, 8.1, 4.8 Hz, 1H). |
| 96 | 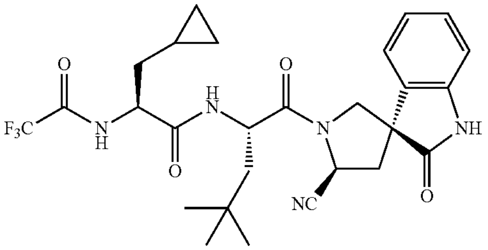 [SMILES: CC(C)(C)C[C@H](NC(=O)[C@H](CC1CC1)NC(=O)C(F)(F)F)C(=O)N1C[C@]2(C[C@H]1C#N)C(=O)Nc1ccccc12] | 546.51 [M − H] | $^{1}$H NMR (400 MHz, Acetone-$d_6$) δ 9.70 (s, 1H), 8.30 (s, 1H), 7.77 (d, J = 8.2 Hz, 1H), 7.28 (td, J = 7.6, 1.4 Hz, 1H), 7.09-6.94 (m, 3H), 5.11 (t, J = 8.4 Hz, 1H), 4.74 (ddd, J = 8.0, 6.3, 3.6 Hz, 1H), 4.63-4.52 (m, 1H), 4.22 (d, J = 10.1 Hz, 1H), 4.00 (d, J = 10.2 Hz, 1H), 2.80-2.76 (m, 3H), 2.75-2.58 (m, 2H), 1.90-1.82 (m, 1H), 1.60 (dtd, J = 20.7, 14.3, 7.7 Hz, 3H), 0.96 (s, 9H), 0.81-0.68 (m, 1H), 0.51-0.33 (m, 2H), 0.21-0.12 (m, 1H), 0.08 (ddd, J = 9.7, 4.8, 3.3 Hz, 1H). |
| 97 | 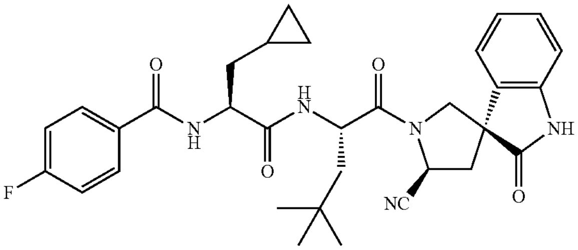 [SMILES: CC(C)(C)C[C@H](NC(=O)[C@H](CC1CC1)NC(=O)c1ccc(F)cc1)C(=O)N1C[C@]2(C[C@H]1C#N)C(=O)Nc1ccccc12] | 572.48 [M − H] | $^{1}$H NMR (400 MHz, Acetone-$d_6$) δ 9.69 (s, 1H), 8.02-7.90 (m, 2H), 7.67 (dd, J = 20.8, 8.2 Hz, 2H), 7.31-7.15 (m, 3H), 7.10 (d, J = 7.2 Hz, 1H), 7.06-6.94 (m, 2H), 5.11 (t, J = 8.4 Hz, 1H), 4.76 (td, J = 8.1, 4.7 Hz, 1H), 4.66 (q, J = 7.2 Hz, 1H), 4.27 (d, J = 10.1 Hz, 1H), 3.99 (d, J = 10.2 Hz, 1H), 2.78 (t, J = 1.1 Hz, 3H), 2.72-2.59 (m, 2H), 1.90-1.82 (m, 1H), 1.65-1.52 (m, 3H), 0.94 (s, 9H), 0.83-0.74 (m, 1H), 0.42 (hd, J = 9.1, 4.3 Hz, 2H), 0.17 (dd, J = 9.6, 4.5 Hz, 1H), 0.11-0.02 (m, 1H). |
| 98 | 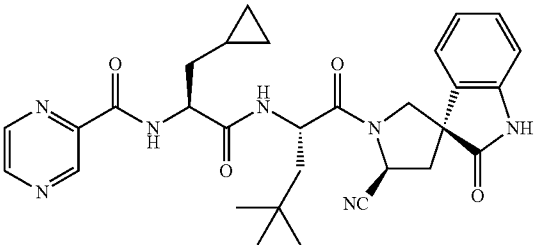 [SMILES: CC(C)(C)C[C@H](NC(=O)[C@H](CC1CC1)NC(=O)c1cnccn1)C(=O)N1C[C@]2(C[C@H]1C#N)C(=O)Nc1ccccc12] | 556.35 [M − H] | $^{1}$H NMR (400 MHz, Acetone-$d_6$) δ 9.70 (s, 1H), 9.23 (d, J = 1.5 Hz, 1H), 8.84 (d, J = 2.4 Hz, 1H), 8.67 (dd, J = 2.5, 1.5 Hz, 1H), 8.44 (d, J = 8.3 Hz, 1H), 7.79 (d, J = 8.3 Hz, 1H), 7.28 (td, J = 7.8, 1.4 Hz, 1H), 7.10 (d, J = 7.2 Hz, 1H), 7.06-6.96 (m, 2H), 5.13 (t, J = 8.4 Hz, 1H), 4.83-4.71 (m, 2H), 4.29 (d, J = 10.2 Hz, 1H), 4.02 (d, J = 10.2 Hz, 1H), 2.76-2.61 (m, 2H), 1.85 (d, J = 4.6 Hz, 1H), 1.75-1.66 (m, 2H), 1.61 (dd, J = 14.3, 8.0 Hz, 1H), 0.95 (s, 9H), 0.82-0.69 (m, 1H), 0.46-0.38 (m, 2H), 0.18-0.03 (m, 2H). |

TABLE 2-continued

The following examples were prepared employing similar protocol as described above.

| Example | Structure | MS | NMR |
|---|---|---|---|
| 99 | 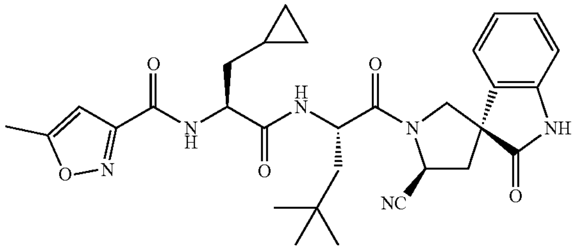 [SMILES: Cc1cc(C(=O)N[C@@H](CC2CC2)C(=O)N[C@@H](CC(C)(C)C)C(=O)N2C[C@]3(C[C@H]2C#N)C(=O)Nc2ccccc23)no1] | 559.56 [M − H] | $^1$H NMR (400 MHz, Acetone-$d_6$) δ 9.69 (s, 1H), 7.74-7.62 (m, 2H), 7.27 (td, J = 7.7, 1.3 Hz, 1H), 7.08 (d, J = 7.3 Hz, 1H), 7.05-6.97 (m, 2H), 6.46 (d, J = 1.1 Hz, 1H), 5.11 (t, J = 8.4 Hz, 1H), 4.80-4.74 (m, 1H), 4.72-4.61 (m, 1H), 4.27 (d, J = 10.3 Hz, 1H), 4.00 (d, J = 10.3 Hz, 1H), 2.69 (qd, J = 13.2, 8.4 Hz, 3H), 2.48 (d, J = 0.9 Hz, 2H), 1.85 (d, J = 4.5 Hz, 2H), 1.69-1.55 (m, 3H), 0.96 (s, 9H), 0.78 (d, J = 14.9 Hz, 2H), 0.45-0.38 (m, 2H), 0.12 (d, J = 4.0 Hz, 1H), 0.08 (d, J = 5.0 Hz, 1H). |
| 100 | 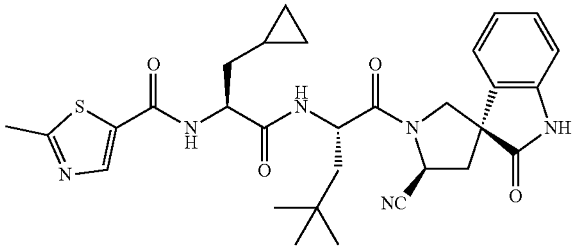 [SMILES: Cc1ncc(C(=O)N[C@@H](CC2CC2)C(=O)N[C@@H](CC(C)(C)C)C(=O)N2C[C@]3(C[C@H]2C#N)C(=O)Nc2ccccc23)s1] | 575.21 [M − H] | $^1$H NMR (400 MHz, Acetone-$d_6$) δ 9.69 (s, 1H), 8.18 (s, 1H), 7.67 (dd, J = 24.6, 8.2 Hz, 2H), 7.28 (td, J = 7.7, 1.4 Hz, 1H), 7.14-6.93 (m, 3H), 5.10 (t, J = 8.4 Hz, 1H), 4.75 (td, J = 8.2, 4.8 Hz, 1H), 4.61 (td, J = 8.2, 5.9 Hz, 1H), 4.26 (d, J = 10.1 Hz, 1H), 3.99 (d, J = 10.2 Hz, 1H), 2.68 (s, 3H), 1.86 (dd, J = 14.3, 4.7 Hz, 1H), 1.56 (dq, J = 13.7, 7.4, 6.9 Hz, 3H), 0.94 (s, 9H), 0.83-0.66 (m, 1H), 0.49-0.34 (m, 2H), 0.14 (dt, J = 10.8, 4.2 Hz, 1H), 0.07 (dd, J = 8.0, 4.0 Hz, 1H). |
| 101 | 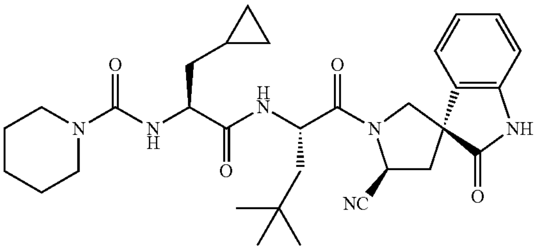 [SMILES: CC(C)(C)C[C@H](NC(=O)[C@H](CC1CC1)NC(=O)N1CCCCC1)C(=O)N1C[C@]2(C[C@H]1C#N)C(=O)Nc1ccccc12] | 561.68 [M − H] | $^1$H NMR (400 MHz, Acetone-$d_6$) δ 9.68 (s, 1H), 7.63 (d, J = 8.6 Hz, 1H), 7.26 (td, J = 7.7, 1.3 Hz, 1H), 7.09 (d, J = 7.6 Hz, 1H), 7.05-6.97 (m, 2H), 5.80 (d, J = 7.8 Hz, 1H), 5.10 (t, J = 8.4 Hz, 1H), 4.72 (td, J = 8.1, 4.8 Hz, 1H), 4.32-4.22 (m, 2H), 3.97 (d, J = 10.3 Hz, 1H), 3.44-3.31 (m, 4H), 2.68 (qd, J = 13.1, 8.3 Hz, 2H), 1.92-1.78 (m, 2H), 1.57 (dd, J = 13.6, 6.4 Hz, 2H), 1.53-1.40 (m, 5H), 0.95 (s, 9H), 0.69 (d, J = 7.7 Hz, 1H), 0.45-0.31 (m, 2H), 0.08 (dt, J = 8.2, 4.4 Hz, 1H). |
| 102 | 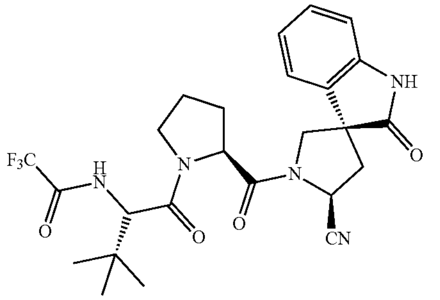 | 520.25 [M + H] | |
| 103 | 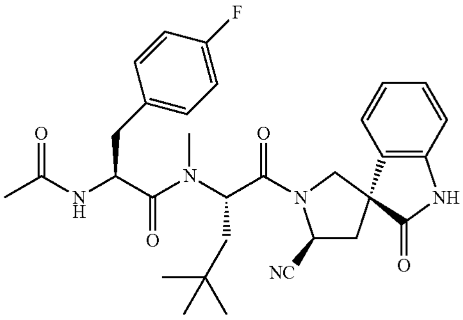 [SMILES: CC(=O)N[C@@H](Cc1ccc(F)cc1)C(=O)N(C)[C@@H](CC(C)(C)C)C(=O)N1C[C@]2(C[C@H]1C#N)C(=O)Nc1ccccc12] | 560.35 [M − H] | $^1$H NMR (400 MHz, Acetone-d6) δ 9.77 (s, 1H), 7.21-7.13 (m, 4H), 7.11-6.93 (m, 5H), 5.49 (dd, J = 7.0, 5.5 Hz, 1H), 5.20 (t, J = 8.6 Hz, 1H), 4.88 (ddd, J = 10.4, 9.0, 4.2 Hz, 1H), 4.08 (dd, J = 10.6, 1.3 Hz, 1H), 3.97 (d, J = 10.5 Hz, 1H), 3.14 (s, 3H), 2.77-2.66 (m, 2H), 2.35 (dd, J = 14.2, 10.4 Hz, 1H), 2.23 (dd, J = 14.2, 4.1 Hz, 1H), 2.17-2.09 (m, 1H), 1.72 (s, 3H), 1.49 (dd, J = 14.2, 5.5 Hz, 1H), 0.94 (s, 9H). |

TABLE 2-continued

The following examples were prepared employing similar protocol as described above.

| Example | Structure | MS | NMR |
| --- | --- | --- | --- |
| 104 | 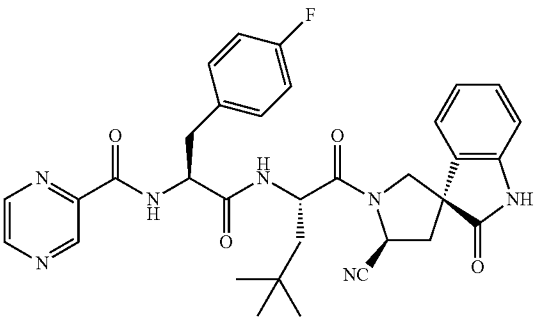 [SMILES: CC(C)(C)C[C@H](NC(=O)[C@H](Cc1ccc(F)cc1)NC(=O)c1cnccn1)C(=O)N1C[C@]2(C[C@H]1C#N)C(=O)Nc1ccccc12] | 610.6 [M − H] | 1H NMR (400 MHz, Acetone-d6) δ 9.75 (s, 1H), 9.20 (d, J = 1.5 Hz, 1H), 8.83 (d, J = 2.5 Hz, 1H), 8.62 (dd, J = 2.5, 1.5 Hz, 1H), 8.40 (d, J = 8.3 Hz, 1H), 8.01 (d, J = 8.0 Hz, 1H), 7.29 (ddd, J = 8.0, 5.1, 2.3 Hz, 2H), 7.25 (dd, J = 7.7, 1.3 Hz, 1H), 7.06-6.98 (m, 4H), 6.95 (td, J = 7.5, 1.0 Hz, 1H), 5.22 (t, J = 8.4 Hz, 1H), 5.00 (ddd, J = 8.3, 7.3, 4.8 Hz, 1H), 4.80 (td, J = 8.1, 4.4 Hz, 1H), 4.32 (d, J = 10.2 Hz, 1H), 4.05 (d, J = 10.2 Hz, 1H), 3.25 (dd, J = 14.1, 4.8 Hz, 1H), 3.11 (dd, J = 14.1, 7.3 Hz, 1H), 2.77-2.70 (m, 2H), 1.91 (dd, J = 14.4, 4.5 Hz, 1H), 1.66 (dd, J = 14.4, 8.2 Hz, 1H), 0.97 (s, 9H). |
| 105 | 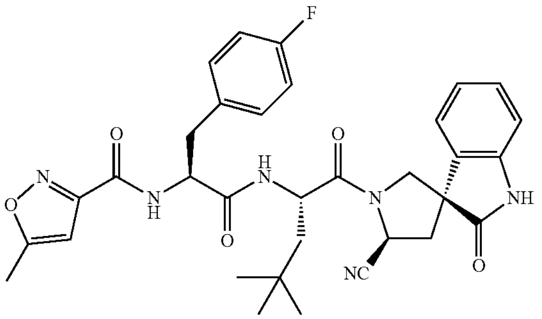 [SMILES: Cc1cc(C(=O)N[C@@H](Cc2ccc(F)cc2)C(=O)N[C@@H](CC(C)(C)C)C(=O)N2C[C@]3(C[C@H]2C#N)C(=O)Nc2ccccc23)no1] | 613.4 [M − H] | 1H NMR (400 MHz, Acetone-d6) δ 9.77 (s, 1H), 8.00 (d, J = 8.1 Hz, 1H), 7.67 (d, J = 8.3 Hz, 1H), 7.32 (ddd, J = 8.5, 5.4, 2.6 Hz, 2H), 7.24 (td, J = 7.7, 1.3 Hz, 1H), 7.09-6.87 (m, 5H), 6.41 (d, J = 1.1 Hz, 1H), 5.21 (t, J = 8.4 Hz, 1H), 4.93 (td, J = 8.3, 4.6 Hz, 1H), 4.80 (td, J = 8.1, 4.5 Hz, 1H), 4.31 (d, J = 10.3 Hz, 1H), 4.05 (d, J = 10.2 Hz, 1H), 3.19 (dd, J = 14.2, 4.5 Hz, 1H), 3.06 (dd, J = 14.3, 8.0 Hz, 1H), 2.77-2.66 (m, 2H), 2.46 (m, 3H), 1.91 (dd, J = 14.4, 4.6 Hz, 1H), 1.65 (dd, J = 14.4, 8.2 Hz, 1H), 0.98 (s, 9H). |
| 106 | 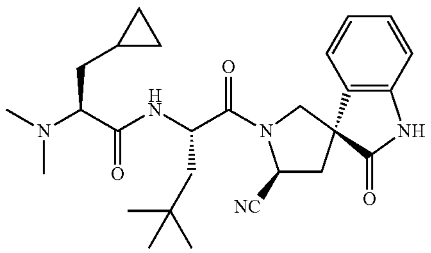 [SMILES: CN(C)[C@@H](CC1CC1)C(=O)N[C@@H](CC(C)(C)C)C(=O)N1C[C@]2(C[C@H]1C#N)C(=O)Nc1ccccc12] | 478.50 [M − H] | $^1$H NMR (400 MHz, Acetone-$d_6$) δ 9.69 (s, 1H), 7.52 (d, J = 8.4 Hz, 1H), 7.26 (td, J = 7.6, 1.3 Hz, 1H), 7.10-7.00 (m, 1H), 6.98 (ddd, J = 7.6, 2.5, 1.2 Hz, 2H), 5.11 (t, J = 8.5 Hz, 1H), 4.69 (td, J = 7.9, 4.0 Hz, 1H), 4.31 (d, J = 10.1 Hz, 1H), 3.98 (d, J = 10.2 Hz, 1H), 2.91-2.85 (m, 1H), 2.73-2.62 (m, 2H), 2.26 (s, 6H), 1.91 (dd, J = 14.3, 5.0 Hz, 1H), 1.64-1.55 (m, 2H), 1.25 (ddd, J = 19.1, 9.2, 5.3 Hz, 2H), 0.99 (s, 9H), 0.75-0.60 (m, 1H), 0.42-0.28 (m, 2H), −0.06 (s, 1H). |
| 107 | 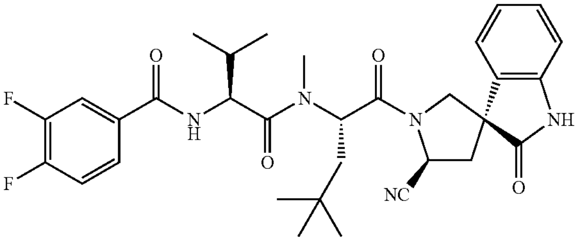 [SMILES: CC(C)[C@H](NC(=O)c1ccc(F)c(F)c1)C(=O)N(C)[C@@H](CC(C)(C)C)C(=O)N1C[C@]2(C[C@H]1C#N)C(=O)Nc1ccccc12] | 616.3 [M + $Na^+$] | |
| 108 | 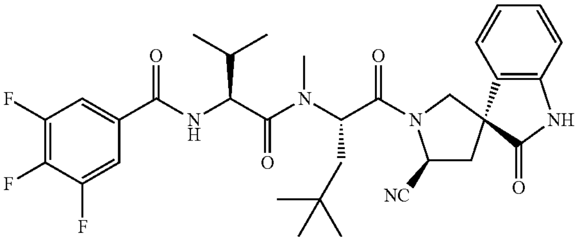 [SMILES: CC(C)[C@H](NC(=O)c1cc(F)c(F)c(F)c1)C(=O)N(C)[C@@H](CC(C)(C)C)C(=O)N1C[C@]2(C[C@H]1C#N)C(=O)Nc1ccccc12] | 634.3 [M + $Na^+$] | |

TABLE 2-continued
| Example | Structure | MS | NMR |
|---|---|---|---|
| The following examples were prepared employing similar protocol as described above. | | | |
| 109 | 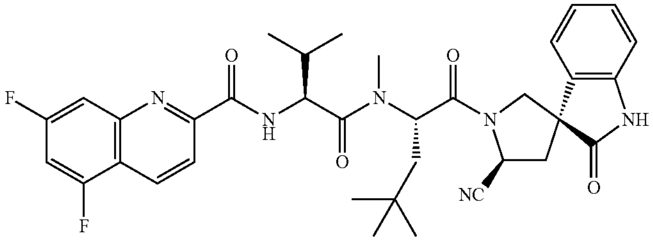 [SMILES: CC(C)[C@H](NC(=O)c1ccc2c(F)cc(F)cc2n1)C(=O)N(C)[C@@H](CC(C)(C)C)C(=O)N1C[C@]2(C[C@H]1C#N)C(=O)Nc1ccccc12] | 667.3 [M + Na+] | |
| 110 | 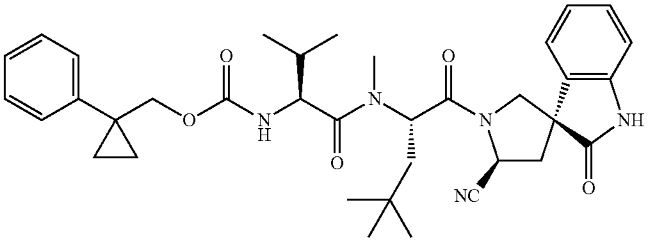 [SMILES: CC(C)[C@H](NC(=O)OCC1(c2ccccc2)CC1)C(=O)N(C)[C@@H](CC(C)(C)C)C(=O)N1C[C@]2(C[C@H]1C#N)C(=O)Nc1ccccc12] | 650.3 [M + Na+] | |
| 111 | 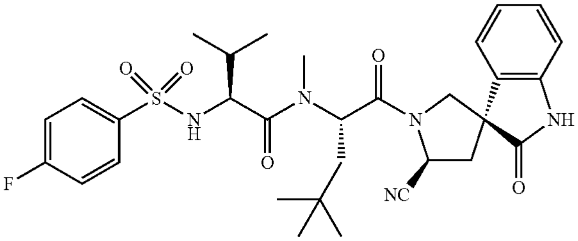 [SMILES: CC(C)[C@H](NS(=O)(=O)c1ccc(F)cc1)C(=O)N(C)[C@@H](CC(C)(C)C)C(=O)N1C[C@]2(C[C@H]1C#N)C(=O)Nc1ccccc12] | 634.2 [M + Na+] | |
| 112 | 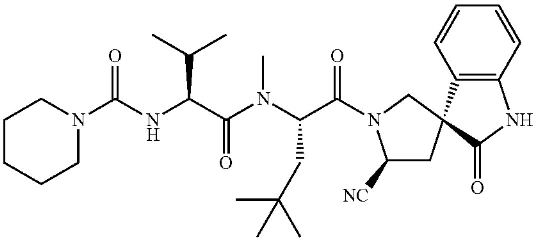 [SMILES: CC(C)[C@H](NC(=O)N1CCCCC1)C(=O)N(C)[C@@H](CC(C)(C)C)C(=O)N1C[C@]2(C[C@H]1C#N)C(=O)Nc1ccccc12] | 587.3 [M + Na+] | |
| 113 | 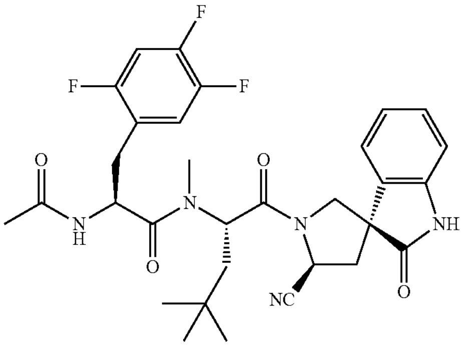 [SMILES: CC(=O)N[C@@H](Cc1cc(F)c(F)cc1F)C(=O)N(C)[C@@H](CC(C)(C)C)C(=O)N1C[C@]2(C[C@H]1C#N)C(=O)Nc1ccccc12] | 620.2 [M + Na+] | |

TABLE 2-continued
| The following examples were prepared employing similar protocol as described above. | | | |
|---|---|---|---|
| Example | Structure | MS | NMR |
| 114 | 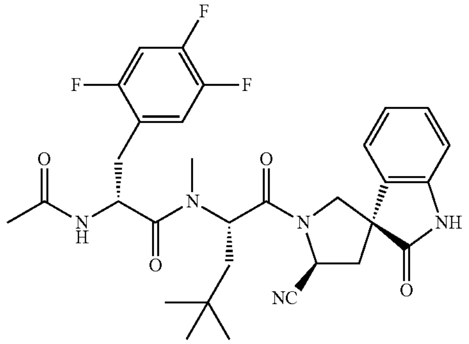 [SMILES: CC(=O)N[C@H](Cc1cc(F)c(F)cc1F)C(=O)N(C)[C@@H](CC(C)(C)C)C(=O)N1C[C@]2(C[C@H]1C#N)C(=O)Nc1ccccc12] | 620.2 [M + Na+] | |
| 115 | 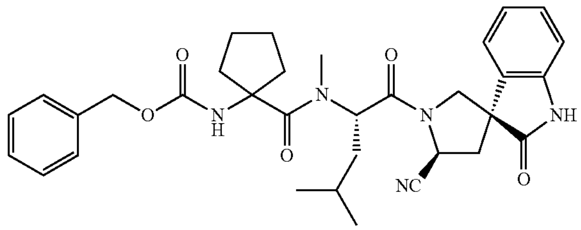 [SMILES: CC(C)C[C@@H](C(=O)N1C[C@]2(C[C@H]1C#N)C(=O)Nc1ccccc12)N(C)C(=O)C1(NC(=O)OCc2ccccc2)CCCC1] | 608.3 [M + Na+] | |
| 116 | 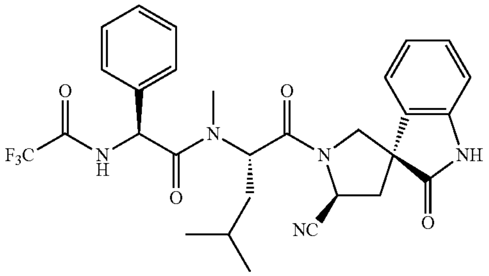 [SMILES: CC(C)C[C@@H](C(=O)N1C[C@]2(C[C@H]1C#N)C(=O)Nc1ccccc12)N(C)C(=O)[C@@H](NC(=O)C(F)(F)F)c1ccccc1] | 592.2 [M + Na+] | |
| 117 | 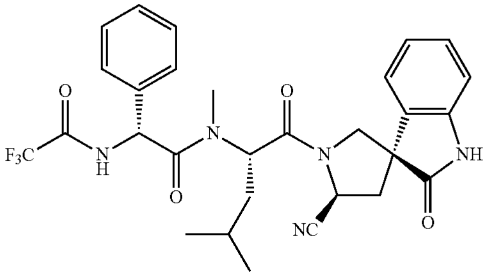 [SMILES: CC(C)C[C@@H](C(=O)N1C[C@]2(C[C@H]1C#N)C(=O)Nc1ccccc12)N(C)C(=O)[C@H](NC(=O)C(F)(F)F)c1ccccc1] | 592.2 [M + Na+] | |
| 118 | 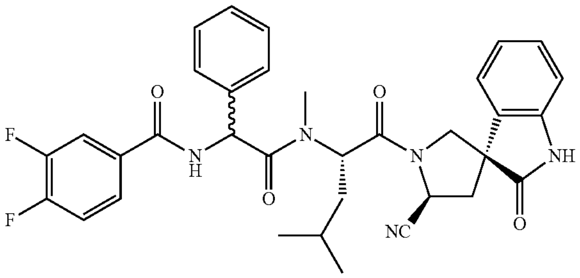 [SMILES: CC(C)C[C@@H](C(=O)N1C[C@]2(C[C@H]1C#N)C(=O)Nc1ccccc12)N(C)C(=O)C(NC(=O)c1ccc(F)c(F)c1)c1ccccc1] | 636.3 [M + Na+] | |

TABLE 2-continued
| The following examples were prepared employing similar protocol as described above. | | | |
|---|---|---|---|
| Example | Structure | MS | NMR |
| 119 | 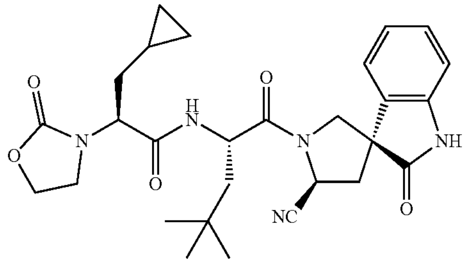 [SMILES: CC(C)(C)C[C@H](NC(=O)[C@H](CC1CC1)N1CCOC1=O)C(=O)N1C[C@]2(C[C@H]1C#N)C(=O)Nc1ccccc12] | 544.2 [M + Na+] | |
| 120 | 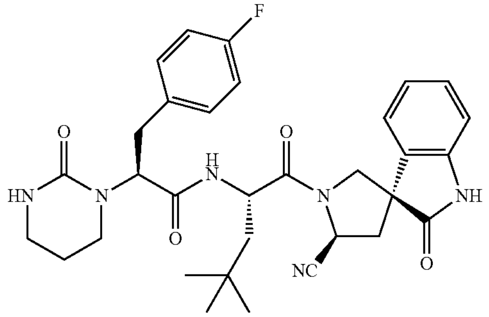 [SMILES: CC(C)(C)C[C@H](NC(=O)[C@H](Cc1ccc(F)cc1)N1CCCNC1=O)C(=O)N1C[C@]2(C[C@H]1C#N)C(=O)Nc1ccccc12] | 544.2 [M + Na+] | |
| 121 | 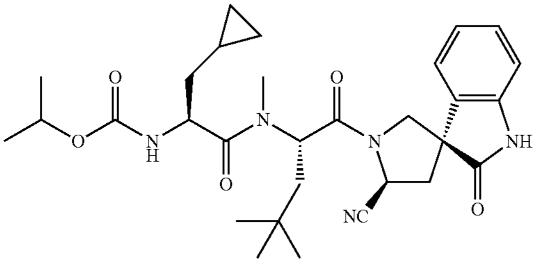 [SMILES: CC(C)OC(=O)N[C@@H](CC1CC1)C(=O)N(C)[C@@H](CC(C)(C)C)C(=O)N1C[C@]2(C[C@H]1C#N)C(=O)Nc1ccccc12] | 550.5 [M − H] | |
| 122 | 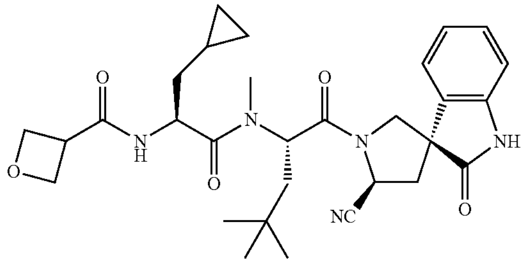 [SMILES: CN(C(=O)[C@H](CC1CC1)NC(=O)C1COC1)[C@@H](CC(C)(C)C)C(=O)N1C[C@]2(C[C@H]1C#N)C(=O)Nc1ccccc12] | 548.4 [M − H] | |
| 123 | 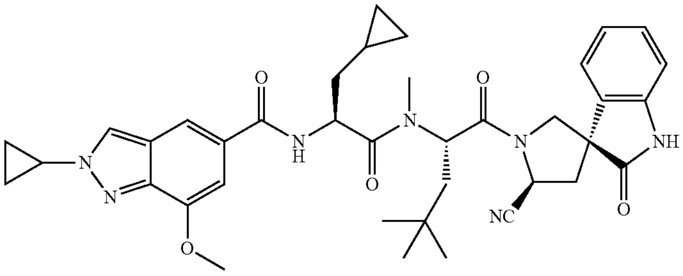 [SMILES: COc1cc(C(=O)N[C@@H](CC2CC2)C(=O)N(C)[C@@H](CC(C)(C)C)C(=O)N2C[C@]3(C[C@H]2C#N)C(=O)Nc2ccccc23)cc2cn(C3CC3)nc12] | 678.4 [M − H] | |

TABLE 2-continued
| Example | Structure | MS | NMR |
|---|---|---|---|
| The following examples were prepared employing similar protocol as described above. | | | |
| 124 | 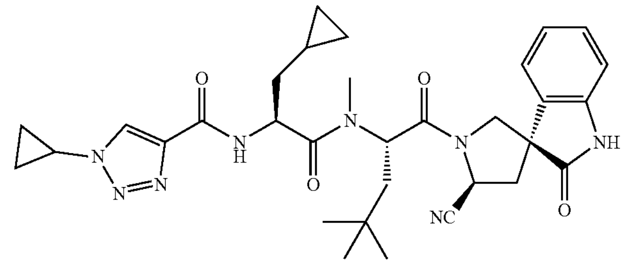 [SMILES: CN(C(=O)[C@H](CC1CC1)NC(=O)c1cn(C2CC2)nn1)[C@@H](CC(C)(C)C)C(=O)N1C[C@]2(C[C@H]1C#N)C(=O)Nc1ccccc12] | 599.6 [M − H] | |
| 125 | 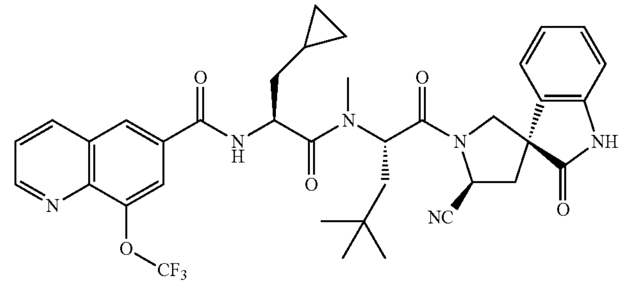 [SMILES: CN(C(=O)[C@H](CC1CC1)NC(=O)c1cc(OC(F)(F)F)c2ncccc2c1)[C@@H](CC(C)(C)C)C(=O)N1C[C@]2(C[C@H]1C#N)C(=O)Nc1ccccc12] | 703.5 [M − H] | |
| 126 | 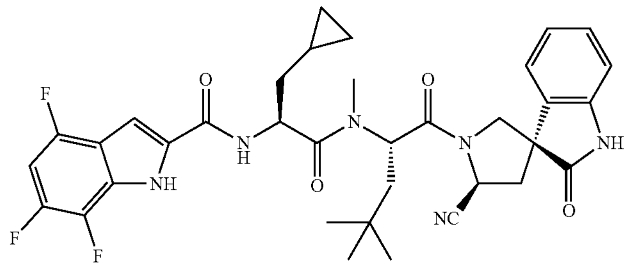 [SMILES: CN(C(=O)[C@H](CC1CC1)NC(=O)c1cc2c(F)cc(F)c(F)c2[nH]1)[C@@H](CC(C)(C)C)C(=O)N1C[C@]2(C[C@H]1C#N)C(=O)Nc1ccccc12] | 661.5 [M − H] | |
| 127 | 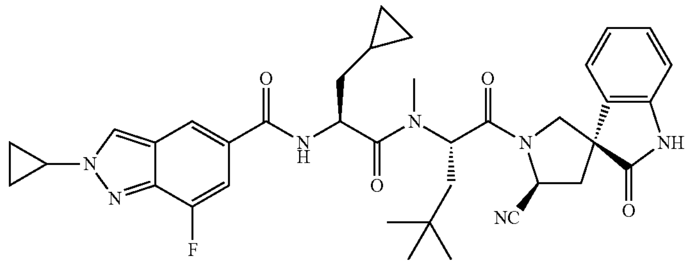 [SMILES: CN(C(=O)[C@H](CC1CC1)NC(=O)c1cc(F)c2nn(C3CC3)cc2c1)[C@@H](CC(C)(C)C)C(=O)N1C[C@]2(C[C@H]1C#N)C(=O)Nc1ccccc12] | 666.5 [M − H] | |
| 128 | 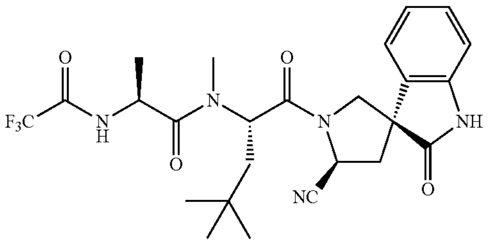 | 520.3 [M − H] | |

TABLE 2-continued
The following examples were prepared employing similar protocol as described above.
| Example | Structure | MS | NMR |
|---|---|---|---|
| 129 | 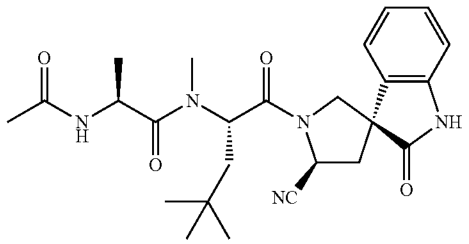 [SMILES: CC(=O)N[C@@H](C)C(=O)N(C)[C@@H](CC(C)(C)C)C(=O)N1C[C@]2(C[C@H]1C#N)C(=O)Nc1ccccc12] | 466.3 [M − H] | |
| 130 | 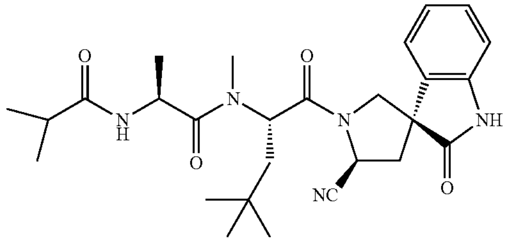 [SMILES: CC(C)C(=O)N[C@@H](C)C(=O)N(C)[C@@H](CC(C)(C)C)C(=O)N1C[C@]2(C[C@H]1C#N)C(=O)Nc1ccccc12] | 494.4 [M − H] | |
| 131 | 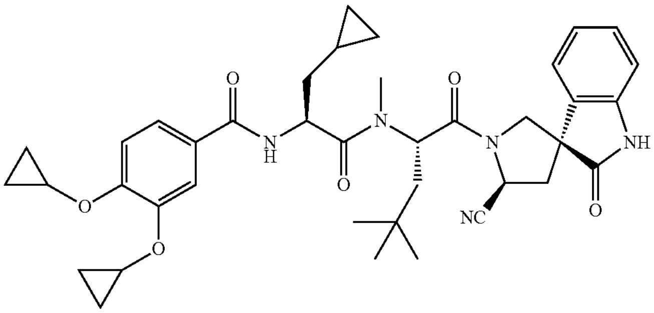 [SMILES: CN(C(=O)[C@H](CC1CC1)NC(=O)c1ccc(OC2CC2)c(OC2CC2)c1)[C@@H](CC(C)(C)C)C(=O)N1C[C@]2(C[C@H]1C#N)C(=O)Nc1ccccc12] | 680.5 [M − H] | |
| 132 | 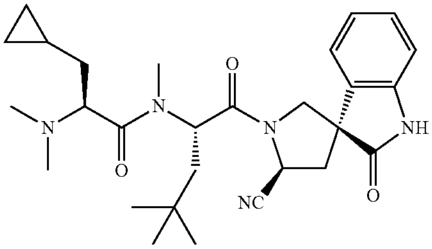 [SMILES: CN(C)[C@@H](CC1CC1)C(=O)N(C)[C@@H](CC(C)(C)C)C(=O)N1C[C@]2(C[C@H]1C#N)C(=O)Nc1ccccc12] | 492.3 [M − H] | |
| 133 | 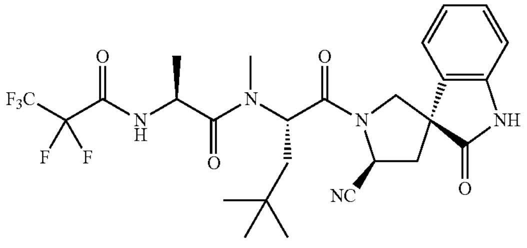 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccccc12] | 570.3 [M − H] | 1H NMR (400 MHz, Acetone-d6) δ 9.77 (s, 1H), 8.42 (d, J = 6.5 Hz, 1H), 7.29 (td, J = 7.5, 1.8 Hz, 1H), 7.12-6.95 (m, 3H), 5.46 (dd, J = 7.5, 4.8 Hz, 1H), 5.18 (t, J = 8.5 Hz, 1H), 4.75 (p, J = 7.0 Hz, 1H), 4.00-3.94 (m, 2H), 3.11 (s, 3H), 2.80-2.62 (m, 2H), 2.20 (dd, J = 14.0, 7.5 Hz, 1H), 1.52-1.42 (m, 1H), 0.94 (s, 9H), 0.90 (d, J = 6.9 Hz, 3H). |

TABLE 2-continued

The following examples were prepared employing similar protocol as described above.

| Example | Structure | MS | NMR |
|---|---|---|---|
| 134 | 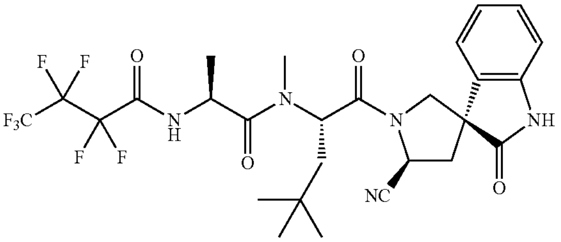 [SMILES: C[C@H](NC(=O)C(F)(F)C(F)(F)C(F)(F)F)C(=O)N(C)[C@@H](CC(C)(C)C)C(=O)N1C[C@]2(C[C@H]1C#N)C(=O)Nc1ccccc12] | 620.5 [M − H] | 1H NMR (400 MHz, Acetone-d6) δ 9.75 (s, 1H), 8.40 (s, 1H), 7.30 (td, J = 7.5, 1.8 Hz, 1H), 7.11-6.97 (m, 3H), 5.49-5.42 (m, 1H), 5.18 (t, J = 8.5 Hz, 1H), 4.77 (q, J = 7.0 Hz, 1H), 3.98-3.94 (m, 2H), 3.11 (s, J = 1.8 Hz, 3H), 2.76-2.65 (m, 2H), 2.21 (dd, J = 14.0, 7.6 Hz, 1H), 1.46 (dd, J = 14.0, 4.8 Hz, 1H), 0.94 (s, 9H), 0.89 (d, J = 6.9 Hz, 3H). |
| 135 | 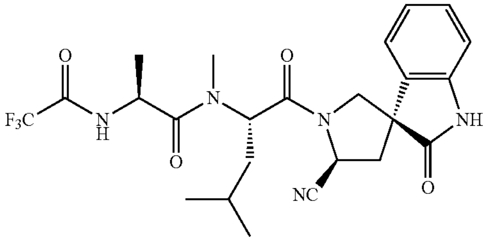 [SMILES: CC(C)C[C@@H](C(=O)N1C[C@]2(C[C@H]1C#N)C(=O)Nc1ccccc12)N(C)C(=O)[C@H](C)NC(=O)C(F)(F)F] | 506.4 [M − H] | 1H NMR (400 MHz, Acetone-d6) δ 9.73 (s, 1H), 8.31 (s, 1H), 7.28 (ddd, J = 7.8, 5.4, 3.5 Hz, 1H), 7.11-6.90 (m, 3H), 5.41 (dd, J = 8.6, 6.5 Hz, 1H), 5.15 (t, J = 8.4 Hz, 1H), 4.71 (p, J = 6.9 Hz, 1H), 4.00-3.87 (m, 2H), 3.07 (s, 3H), 2.74-2.59 (m, 2H), 1.79-1.62 (m, 2H), 1.51 (dp, J = 13.4, 6.7 Hz, 1H), 0.92 (dd, J = 9.1, 6.8 Hz, 6H), 0.87 (d, J = 6.5 Hz, 3H). |
| 136 | 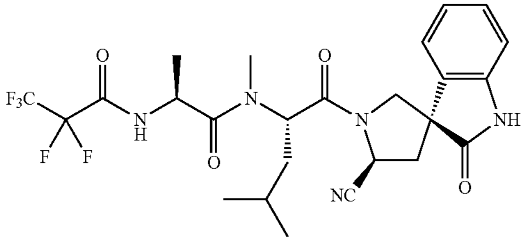 | 556.3 [M − H] | 1H NMR (400 MHz, Acetone-d6) δ 9.71 (d, J = 25.8 Hz, 1H), 8.45 (s, 1H), 7.37-7.22 (m, 1H), 7.12-6.92 (m, 3H), 5.43 (dd, J = 92, 5.9 Hz, 1H), 5.17 (t, J = 8.4 Hz, 1H), 4.76 (dd, J = 8.1, 5.7 Hz, 1H), 3.99-3.88 (m, 2H), 3.09 (s, 3H), 2.79-2.63 (m, 2H), 1.77 (ddd, J = 14.3, 9.3, 5.2 Hz, 1H), 1.72-1.61 (m, 1H), 1.58-1.46 (m, 1H), 0.94 (dd, J = 8.4, 6.8 Hz, 6H), 0.88 (d, J = 6.5 Hz, 3H). |
| 137 | 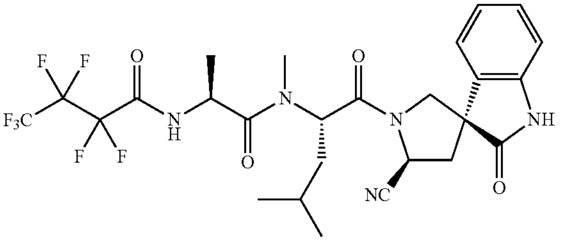 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(F)(F)C(F)(F)F] | 606.4 [M − H] | 1H NMR (400 MHz, Acetone-d6) δ 9.74 (s, 1H), 8.44 (d, J = 7.0 Hz, 1H), 7.35-7.22 (m, 1H), 7.11-6.96 (m, 3H), 5.43 (dd, J = 92, 5.9 Hz, 1H), 5.17 (t, J = 8.4 Hz, 1H), 4.78 (p, J = 7.0 Hz, 1H), 4.02-3.87 (m, 2H), 3.09 (s, 3H), 2.79-2.62 (m, 2H), 1.77 (ddd, J = 14.2, 9.1, 5.2 Hz, 1H), 1.67 (ddd, J = 14.2, 8.6, 5.9 Hz, 1H), 1.57-1.45 (m, 1H), 0.94 (dd, J = 7.9, 6.8 Hz, 6H), 0.89 (d, J = 6.5 Hz, 3H). |
| 138 | 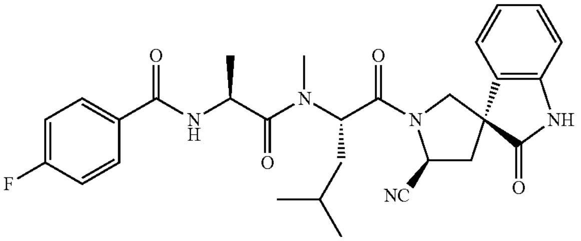 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1] | 532.4 [M − H] | 1H NMR (400 MHz, Acetone-d6) δ 9.77 (s, 1H), 7.96-7.88 (m, 2H), 7.67 (d, J = 7.6 Hz, 1H), 7.30 (ddd, J = 7.8, 6.7, 2.1 Hz, 1H), 7.23-7.16 (m, 2H), 7.12-7.00 (m, 3H), 5.45 (dd, J = 8.4, 6.6 Hz, 1H), 5.18 (t, J = 8.4 Hz, 1H), 4.89-4.78 (m, 1H), 4.02-3.91 (m, 2H), 3.11 (s, 3H), 2.81-2.63 (m, 2H), 1.77-1.64 (m, 2H), 1.64-1.50 (m, 1H), 0.94 (d, J = 6.6 Hz, 3H), 0.88 (d, J = 62 Hz, 6H). |
| 139 | 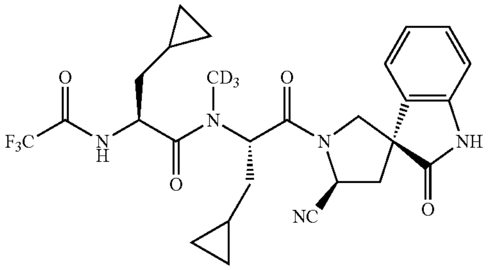 [SMILES: [2H]C([2H])([2H])N(C(=O)[C@H](CC1CC1)NC(=O)C(F)(F)F)[C@@H](CC1CC1)C(=O)N1C[C@]2(C[C@H]1C#N)C(=O)Nc1ccccc12] | 547.3 [M − H] | 1H NMR (400 MHz, Acetone-d6) δ 9.73 (s, 1H), 8.31 (d, J = 8.3 Hz, 1H), 7.30 (dt, J = 7.8, 4.5 Hz, 1H), 7.12-6.94 (m, 3H), 5.39 (t, J = 7.5 Hz, 1H), 5.13 (t, J = 8.4 Hz, 1H), 4.85 (td, J = 8.5, 5.1 Hz, 1H), 4.02-3.89 (m, 2H), 2.75-2.61 (m, 2H), 1.73 (dq, J = 25.6, 7.0 Hz, 2H), 1.32-1.13 (m, 2H), 0.72-0.53 (m, 2H), 0.39 (dddd, J = 10.1, 6.7, 4.9, 3.3 Hz, 4H), 0.12 (dddd, J = 8.0, 6.5, 4.9, 2.9 Hz, 3H), 0.04--0.11 (m, 1H). |

TABLE 2-continued

| The following examples were prepared employing similar protocol as described above. | | | |
|---|---|---|---|
| Example | Structure | MS | NMR |
| 140 | 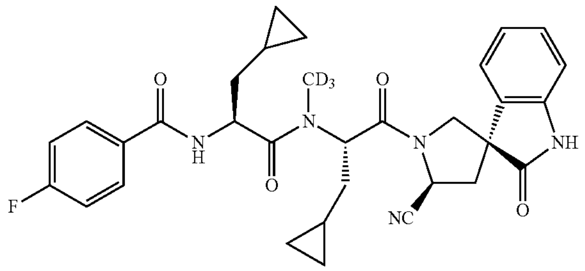 [SMILES: [2H]C([2H])([2H])N(C(=O)[C@H](CC1CC1)NC(=O)c1ccc(F)cc1)[C@@H](CC1CC1)C(=O)N1C[C@]2(C[C@H]1C#N)C(=O)Nc1ccccc12] | 573.7 [M − H] | |
| 141 | 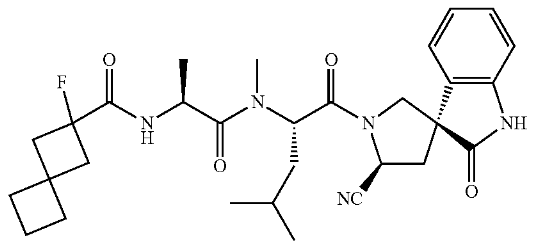 [SMILES: CC(C)C[C@@H](C(=O)N1C[C@]2(C[C@H]1C#N)C(=O)Nc1ccccc12)N(C)C(=O)[C@H](C)NC(=O)C1(F)CC2(CCC2)C1] | 550.3 [M − H] | |
| 142 | 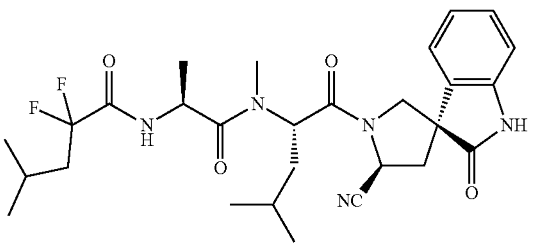 [SMILES: CC(C)C[C@@H](C(=O)N1C[C@]2(C[C@H]1C#N)C(=O)Nc1ccccc12)N(C)C(=O)[C@H](C)NC(=O)C(F)(F)CC(C)C] | 544.4 [M − H] | |
| 143 | 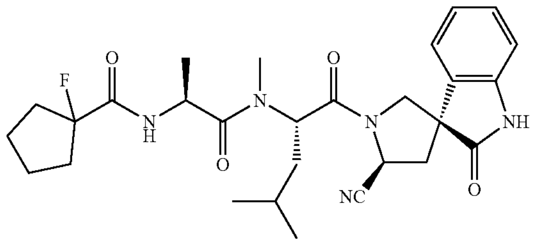 [SMILES: CC(C)C[C@@H](C(=O)N1C[C@]2(C[C@H]1C#N)C(=O)Nc1ccccc12)N(C)C(=O)[C@H](C)NC(=O)C1(F)CCCC1] | 524.3 [M − H] | 1H NMR (400 MHz, Acetone-d6) δ 9.72 (s, 1H), 7.34 (s, 1H), 7.29 (ddd, J = 7.8, 6.3, 2.6 Hz, 1H), 7.10-6.98 (m, 3H), 5.43 (dd, J = 8.9, 6.2 Hz, 1H), 5.17 (t, J = 8.4 Hz, 1H), 4.65 (p, J = 6.8 Hz, 1H), 3.95 (s, 2H), 3.07 (s, 3H), 2.69 (dq, J = 13.1, 8.4, 7.0 Hz, 2H), 2.02-1.63 (m, 10H), 1.52 (dt, J = 13.6, 6.8 Hz, 1H), 0.95 (d, J = 6.6 Hz, 3H), 0.90 (d, J = 6.5 Hz, 3H), 0.84 (d, J = 6.8 Hz, 3H). |
| 144 | 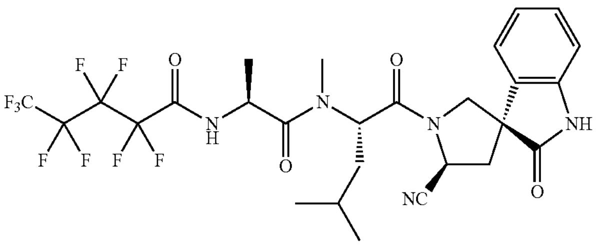 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(F)(F)C(F)(F)C(F)(F)F] | 656.4 [M − H] | 1H NMR (400 MHz, Acetone-d6) δ 9.74 (s, 1H), 8.44 (d, J = 7.1 Hz, 1H), 7.30 (ddd, J = 8.0, 5.4, 3.7 Hz, 1H), 7.12-6.92 (m, 3H), 5.44 (dd, J = 9.2, 5.8 Hz, 1H), 5.17 (t, J = 8.4 Hz, 1H), 4.78 (p, J = 7.0 Hz, 1H), 4.04-3.84 (m, 2H), 3.09 (s, 3H), 2.80-2.62 (m, 2H), 1.77 (ddd, J = 14.3, 9.2, 5.1 Hz, 1H), 1.66 (ddd, J = 14.3, 8.7, 5.8 Hz, 1H), 1.59-1.44 (m, 1H), 0.95 (d, J = 6.7 Hz, 3H), 0.92 (d, J = 6.7 Hz, 3H), 0.88 (d, J = 6.5 Hz, 3H). |

TABLE 2-continued

The following examples were prepared employing similar protocol as described above.

| Example | Structure | MS | NMR |
|---|---|---|---|
| 145 | 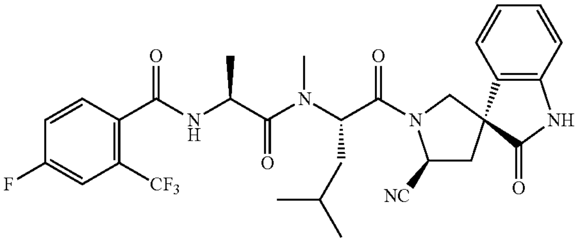 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1C(F)(F)F] | 600.3 [M − H] | 1H NMR (400 MHz, Acetone-d6) δ 9.78 (s, 1H), 7.69 (d, J = 7.8 Hz, 1H), 7.63-7.52 (m, 2H), 7.48 (td, J = 8.4, 2.6 Hz, 1H), 7.30 (ddd, J = 8.0, 7.0, 2.0 Hz, 1H), 7.15-7.05 (m, 2H), 7.05-6.96 (m, 1H), 5.47 (dd, J = 9.1, 5.9 Hz, 1H), 5.19 (t, J = 8.4 Hz, 1H), 4.93-4.66 (m, 1H), 4.06-3.80 (m, 2H), 3.12 (s, 3H), 2.69 (d, J = 8.4 Hz, 2H), 1.78 (ddd, J = 14.1, 9.1, 5.1 Hz, 1H), 1.67 (ddd, J = 14.1, 8.6, 5.9 Hz, 1H), 1.56 (dq, J = 13.8, 6.7 Hz, 1H), 0.95 (d, J = 6.6 Hz, 3H), 0.90 (d, J = 6.5 Hz, 3H), 0.87 (d, J = 6.8 Hz, 3H). |
| 146 | 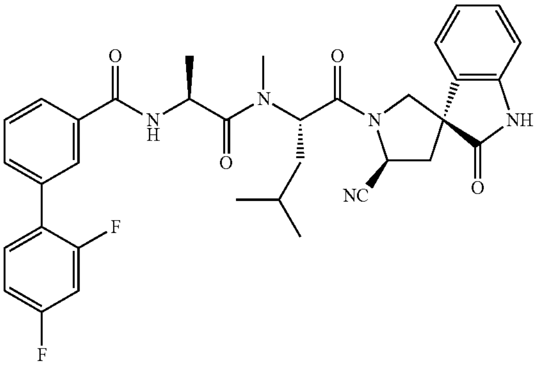 [SMILES: CC(C)C[C@@H](C(=O)N1C[C@]2(C[C@H]1C#N)C(=O)Nc1ccccc12)N(C)C(=O)[C@H](C)NC(=O)c1cccc(-c2ccc(F)cc2F)c1] | 626.6 [M − H] | 1H NMR (400 MHz, Acetone-d6) δ 9.80 (s, 1H), 8.01 (s, 1H), 7.90 (d, J = 7.7 Hz, 1H), 7.81 (d, J = 7.6 Hz, 1H), 7.69 (d, J = 7.7 Hz, 1H), 7.65-7.52 (m, 2H), 7.30 (dddd, J = 7.6, 6.6, 2.2, 0.8 Hz, 1H), 7.22-7.04 (m, 4H), 7.02 (dd, J = 7.8, 0.9 Hz, 1H), 5.46 (dd, J = 8.6, 6.4 Hz, 1H), 5.19 (t, J = 8.4 Hz, 1H), 4.88 (p, J = 7.0 Hz, 1H), 4.06-3.85 (m, 2H), 3.12 (s, 3H), 2.74-2.64 (m, 2H), 1.81-1.64 (m, 2H), 1.58 (dp, J = 13.3, 6.6 Hz, 1H), 0.94 (dd, J = 6.6, 0.8 Hz, 3H), 0.89 (t, J = 6.4 Hz, 6H). |
| 147 | 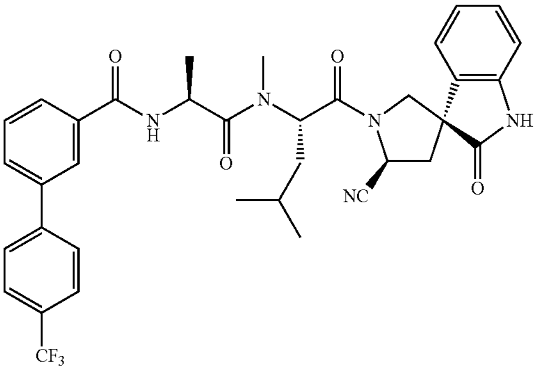 [SMILES: CC(C)C[C@@H](C(=O)N1C[C@]2(C[C@H]1C#N)C(=O)Nc1ccccc12)N(C)C(=O)[C@H](C)NC(=O)c1cccc(-c2ccc(C(F)(F)F)cc2)c1] | 658.5 [M − H] | 1H NMR (400 MHz, Acetone-d6) δ 9.79 (s, 1H), 8.19 (s, 1H), 8.04-7.78 (m, 7H), 7.59 (t, J = 7.7 Hz, 1H), 7.36-7.23 (m, 1H), 7.16-7.05 (m, 2H), 7.03 (d, J = 7.8 Hz, 1H), 5.46 (dd, J = 8.6, 6.4 Hz, 1H), 5.19 (t, J = 8.4 Hz, 1H), 4.90 (p, J = 7.0 Hz, 1H), 3.98 (q, J = 10.6 Hz, 2H), 3.13 (s, 3H), 2.79-2.62 (m, 2H), 1.79-1.65 (m, 2H), 1.57 (dh, J = 13.3, 6.5 Hz, 1H), 0.94 (d, J = 6.6 Hz, 3H), 0.91 (d, J = 6.9 Hz, 3H), 0.88 (d, J = 6.4 Hz, 3H). |
| 148 | 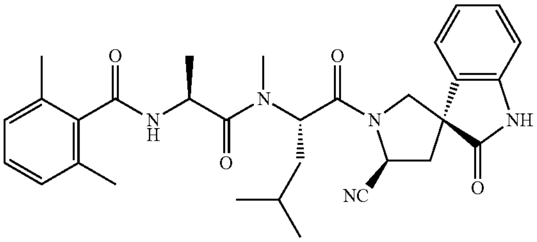 [SMILES: Cc1cccc(C)c1C(=O)N[C@@H](C)C(=O)N(C)[C@@H](CC(C)C)C(=O)N1C[C@]2(C[C@H]1C#N)C(=O)Nc1ccccc12] | 542.4 [M − H] | 1H NMR (400 MHz, Acetone-d6) δ 9.77 (s, 1H), 7.41 (d, J = 7.5 Hz, 1H), 7.35-7.26 (m, 1H), 7.15-7.05 (m, 3H), 6.99 (dd, J = 15.3, 7.6 Hz, 3H), 5.50 (dd, J = 9.7, 4.6 Hz, 1H), 5.18 (t, J = 8.5 Hz, 1H), 4.86 (p, J = 7.0 Hz, 1H), 3.94 (s, 2H), 3.15 (s, 3H), 2.74-2.63 (m, 2H), 2.21 (s, 6H), 1.83 (q, J = 9.3 Hz, 1H), 1.66-1.52 (m, 2H), 0.95 (d, J = 6.1 Hz, 3H), 0.91 (d, J = 5.9 Hz, 3H), 0.83 (d, J = 7.0 Hz, 3H). |

TABLE 2-continued

The following examples were prepared employing similar protocol as described above.

| Example | Structure | MS | NMR |
| --- | --- | --- | --- |
| 149 | 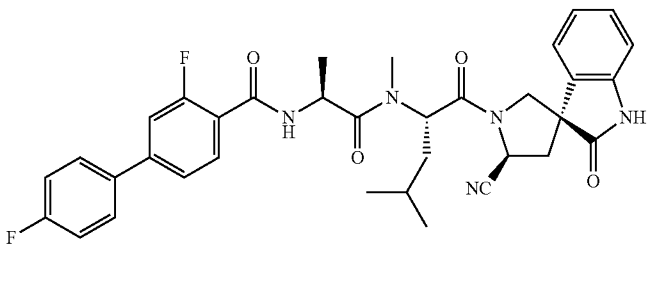 [SMILES: CC(C)C[C@@H](C(=O)N1C[C@]2(C[C@H]1C#N)C(=O)Nc1ccccc12)N(C)C(=O)[C@H](C)NC(=O)c1ccc(-c2ccc(F)cc2)cc1F] | 626.4 [M − H] | 1H NMR (400 MHz, Acetone-d6) δ 9.77 (s, 1H), 7.95 (t, J = 8.1 Hz, 1H), 7.84-7.76 (m, 2H), 7.69 (t, J = 7.8 Hz, 1H), 7.60 (dd, J = 8.1, 1.8 Hz, 1H), 7.52 (dd, J = 13.0, 1.8 Hz, 1H), 7.34-7.23 (m, 3H), 7.09 (d, J = 4.1 Hz, 2H), 7.01 (s, 1H), 5.48 (dd, J = 8.3, 6.8 Hz, 1H), 5.20 (t, J = 8.4 Hz, 1H), 4.91 (pd, J = 6.8, 1.5 Hz, 1H), 3.99 (s, 2H), 3.14 (s, 3H), 2.79-2.63 (m, 2H), 1.75 (ddd, J = 7.3, 6.4, 3.0 Hz, 2H), 1.58 (dp, J = 13.5, 6.6 Hz, 1H), 0.96 (d, J = 4.0 Hz, 3H), 0.94 (d, J = 4.3 Hz, 3H), 0.91 (d, J = 6.5 Hz, 3H). |
| 150 | 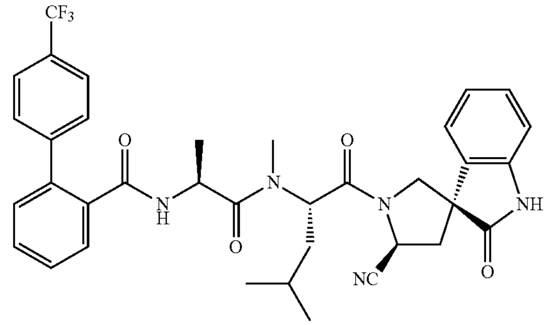 [SMILES: CC(C)C[C@@H](C(=O)N1C[C@]2(C[C@H]1C#N)C(=O)Nc1ccccc12)N(C)C(=O)[C@H](C)NC(=O)c1ccccc1-c1ccc(C(F)(F)F)cc1] | 658.48 [M − H] | 1H NMR (400 MHz, Acetone-d6) δ 9.76 (s, 1H), 7.73-7.66 (m, 2H), 7.66-7.60 (m, 2H), 7.58-7.41 (m, 4H), 7.38 (d, J = 7.8 Hz, 1H), 7.28 (ddd, J = 7.7, 6.9, 1.9 Hz, 1H), 7.11-6.93 (m, 3H), 5.40 (dd, J = 8.5, 6.5 Hz, 1H), 5.16 (t, J = 8.4 Hz, 1H), 4.72-4.60 (m, 1H), 4.00-3.84 (m, 2H), 3.02 (s, 3H), 2.66 (dd, J = 13.2, 8.5 Hz, 2H), 1.75-1.60 (m, 2H), 1.58-1.47 (m, 1H), 0.94 (d, J = 6.7 Hz, 3H), 0.88 (d, J = 6.2 Hz, 3H), 0.72 (d, J = 6.9 Hz, 3H). |
| 151 | 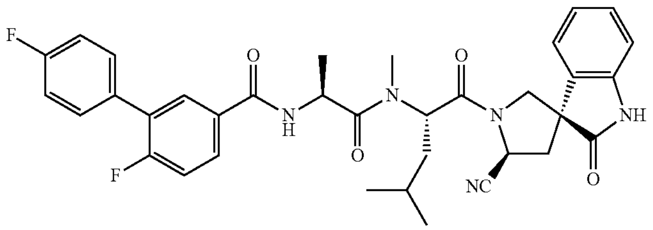 [SMILES: CC(C)C[C@@H](C(=O)N1C[C@]2(C[C@H]1C#N)C(=O)Nc1ccccc12)N(C)C(=O)[C@H](C)NC(=O)c1ccc(F)c(-c2ccc(F)cc2)c1] | 628.4 [M + H] | 1H NMR (400 MHz, Acetone-d6) δ 9.78 (s, 1H), 8.01 (dd, J = 7.6, 2.3 Hz, 1H), 7.92 (ddd, J = 8.6, 4.8, 2.4 Hz, 1H), 7.83 (d, J = 7.7 Hz, 1H), 7.64 (ddt, J = 6.9, 5.3, 1.7 Hz, 2H), 131-7.21 (m, 4H), 7.13-7.04 (m, 2H), 7.02 (d, J = 7.8 Hz, 1H), 5.45 (dd, J = 8.6, 6.5 Hz, 1H), 5.18 (t, J = 8.4 Hz, 1H), 4.87 (p, J = 7.1 Hz, 1H), 3.99 (d, J = 10.6 Hz, 1H), 3.94 (d, J = 10.6 Hz, 1H), 3.12 (s, 3H), 2.75-2.64 (m, 2H), 1.77-1.65 (m, 2H), 1.57 (dt, J = 13.4, 6.6 Hz, 1H), 0.93 (d, J = 6.6 Hz, 3H), 0.89 (d, J = 4.4 Hz, 3H), 0.87 (d, J = 3.8 Hz, 3H). |
| 152 | 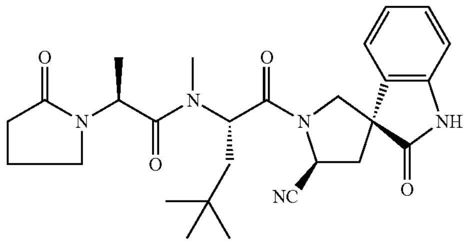 [SMILES: C[C@@H](C(=O)N(C)[C@@H](CC(C)(C)C)C(=O)N1C[C@]2(C[C@H]1C#N)C(=O)Nc1ccccc12)N1CCCC1=O] | 492.4 [M − H] | — |
| 153 | 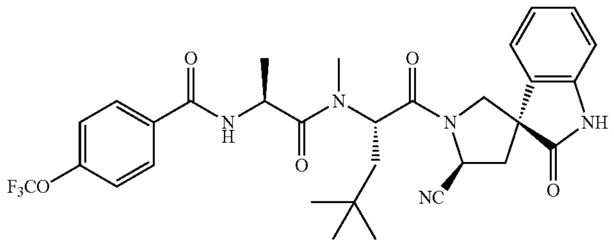 [SMILES: C[C@H](NC(=O)c1ccc(OC(F)(F)F)cc1)C(=O)N(C)[C@@H](CC(C)(C)C)C(=O)N1C[C@]2(C[C@H]1C#N)C(=O)Nc1ccccc12] | 612.4 [M − H] | 1H NMR (400 MHz, Acetone-d6) δ 9.80 (s, 1H), 7.98 (d, J = 8.8 Hz, 2H), 7.79 (d, J = 7.7 Hz, 1H), 7.41-7.35 (m, 2H), 7.31 (td, J = 7.6, 1.5 Hz, 1H), 7.13-7.07 (m, 1H), 7.04 (t, J = 7.5 Hz, 2H), 5.50 (dd, J = 7.6, 4.8 Hz, 1H), 5.20 (t, J = 8.5 Hz, 1H), 4.86 (p, J = 7.0 Hz, 1H), 4.06-3.92 (m, 2H), 3.14 (s, 3H), 2.83-2.65 (m, 2H), 2.21 (dd, J = 14.0, 7.6 Hz, 1H), 1.49 (dd, J = 14.0, 4.8 Hz, 1H), 0.94 (s, 9H), 0.86 (d, J = 6.9 Hz, 3H). |

TABLE 2-continued

The following examples were prepared employing similar protocol as described above.

| Example | Structure | MS | NMR |
|---|---|---|---|
| 154 | 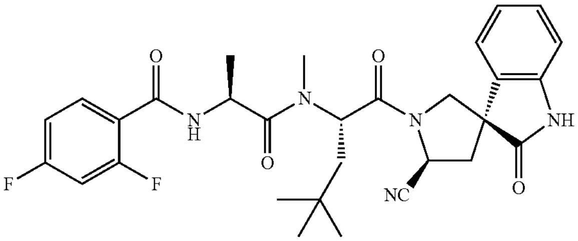 [SMILES: C[C@H](NC(=O)c1ccc(F)cc1F)C(=O)N(C)[C@@H](CC(C)(C)C)C(=O)N1C[C@]2(C[C@H]1C#N)C(=O)Nc1ccccc12] | 564.4 [M − H] | 1H NMR (400 MHz, Acetone-d6) δ 9.76 (s, 1H), 8.00-7.86 (m, 1H), 7.61 (t, J = 7.7 Hz, 1H), 7.35-7.20 (m, 1H), 7.16-6.99 (m, 5H), 5.49 (dd, J = 7.7, 4.6 Hz, 1H), 5.20 (t, J = 8.5 Hz, 1H), 4.85 (pd, J = 6.8, 1.5 Hz, 1H), 3.99 (s, 2H), 3.13 (s, 3H), 2.73 (qd, J = 13.2, 8.6 Hz, 2H), 2.24 (dd, J = 14.0, 7.7 Hz, 1H), 1.48 (dd, J = 14.0, 4.6 Hz, 1H), 0.95 (s, 9H), 0.89 (d, J = 6.8 Hz, 3H). |
| 155 | 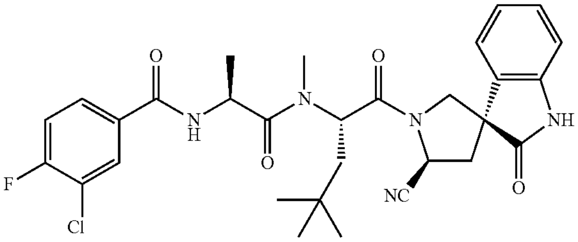 | 581.5 [M − H] | 1H NMR (400 MHz, Acetone-d6) δ 9.78 (s, 1H), 8.01 (dd, J = 7.2, 2.2 Hz, 1H), 7.88 (ddd, J = 9.0, 4.6, 2.1 Hz, 1H), 7.78 (d, J = 7.8 Hz, 1H), 7.38 (t, J = 8.8 Hz, 1H), 7.34-7.23 (m, 1H), 7.19-6.83 (m, 3H), 5.48 (dd, J = 7.6, 4.9 Hz, 1H), 5.19 (t, J = 8.5 Hz, 1H), 4.84 (p, J = 7.0 Hz, 1H), 3.99 (q, J = 10.6 Hz, 2H), 3.13 (s, 3H), 2.79-2.66 (m, 2H), 2.20 (dd, J = 14.0, 7.5 Hz, 1H), 1.48 (dd, J = 14.0, 4.6 Hz, 1H), 0.93 (s, 9H), 0.85 (d, J = 6.9 Hz, 3H). |
| 156 | 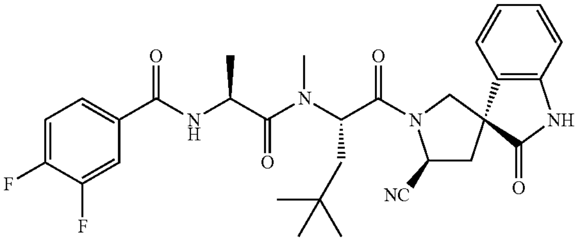 [SMILES: C[C@H](NC(=O)c1ccc(F)c(F)c1)C(=O)N(C)[C@@H](CC(C)(C)C)C(=O)N1C[C@]2(C[C@H]1C#N)C(=O)Nc1ccccc12] | 564.5 [M − H] | 1H NMR (400 MHz, Acetone-d6) δ 9.78 (s, 1H), 7.82 (ddd, J = 11.5, 7.7, 2.2 Hz, 1H), 7.74 (ddt, J = 7.6, 5.8, 1.7 Hz, 2H), 7.40 (dt, J = 10.4, 8.3 Hz, 1H), 7.31 (td, J = 7.6, 1.5 Hz, 1H), 7.13-7.07 (m, 1H), 7.07-6.99 (m, 2H), 5.49 (dd, J = 7.6, 4.8 Hz, 1H), 5.20 (t, J = 8.5 Hz, 1H), 4.84 (p, J = 7.0 Hz, 1H), 3.99 (q, J = 10.5 Hz, 2H), 3.13 (s, 3H), 2.79-2.65 (m, 2H), 2.21 (dd, J = 14.0, 7.6 Hz, 1H), 1.47 (dd, J = 14.0, 4.8 Hz, 1H), 0.93 (s, 9H), 0.85 (d, J = 6.9 Hz, 3H). |
| 157 | 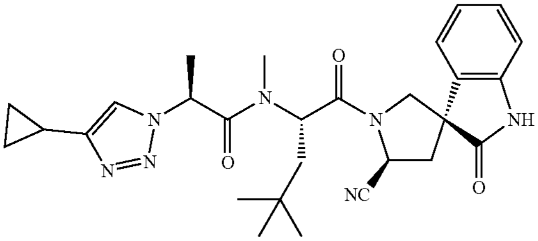 [SMILES: C[C@@H](C(=O)N(C)[C@@H](CC(C)(C)C)C(=O)N1C[C@]2(C[C@H]1C#N)C(=O)Nc1ccccc12)n1cc(C2CC2)nn1] | 516.4 [M − H] | 1H NMR (400 MHz, Acetone-d6) δ 9.80 (s, 1H), 7.56 (s, 1H), 7.34 (td, J = 7.7, 1.3 Hz, 1H), 7.15 (td, J = 7.6, 1.1 Hz, 1H), 7.05 (t, J = 7.9, Hz, 2H), 5.60 (q, J = 6.9 Hz, 1H), 5.45 (dd, J = 6.9, 5.7 Hz, 1H), 5.21 (t, J = 8.5 Hz, 1H), 4.14 (d, J = 10.6 Hz, 1H), 3.96 (d, J = 10.6 Hz, 1H), 3.13 (s, 3H), 2.78-2.67 (m, 2H), 1.95-1.88 (m, 1H), 1.49-1.44 (m, 1H), 1.15 (d, J = 7.0 Hz, 3H), 0.91-0.81 (m, 3H), 0.85 (s, 9H), 0.73 (ddt, J = 5.3, 4.4, 2.7 Hz, 2H). |
| 158 | 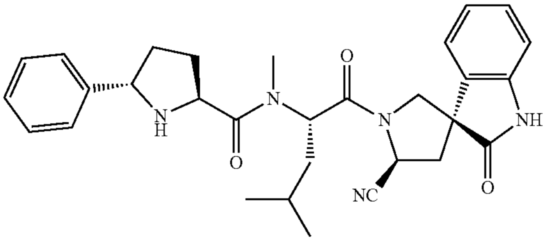 [SMILES: CC(C)C[C@@H](C(=O)N1C[C@]2(C[C@H]1C#N)C(=O)Nc1ccccc12)N(C)C(=O)[C@@H]1CC[C@@H](c2ccccc2)N1] | 514.5 [M + H] | 1H NMR (400 MHz, Acetone-d6) δ 9.86 (s, 1H), 7.37-7.30 (m, 2H), 7.30-7.22 (m, 3H), 7.21-7.14 (m, 1H), 7.10-6.97 (m, 3H), 5.48 (t, J = 7.5 Hz, 1H), 5.18 (t, J = 8.5 Hz, lH), 4.14 (dd, J = 8.0, 6.5 Hz, 1H), 4.11-4.02 (m, 2H), 3.98 (d, J = 10.5 Hz, 1H), 3.03 (s, 3H), 2.88 (br s, 1H), 2.77-2.64 (m, 2H), 2.00 (dp, J = 12.5, 4.5, 4.1 Hz, 1H), 1.81 (dddd, J = 12.0, 7.6, 6.3, 4.4 Hz, 1H), 1.74 (dd, J = 8.0, 6.5 Hz, 2H), 1.59-1.41 (m, 2H), 1.15 (dtd, J = 12.5, 8.1, 6.3 Hz, 1H), 0.97 (d, J = 6.6 Hz, 3H), 0.94 (d, J = 6.6 Hz, 3H). |

TABLE 2-continued

| The following examples were prepared employing similar protocol as described above. | | | |
|---|---|---|---|
| Example | Structure | MS | NMR |
| 159 | 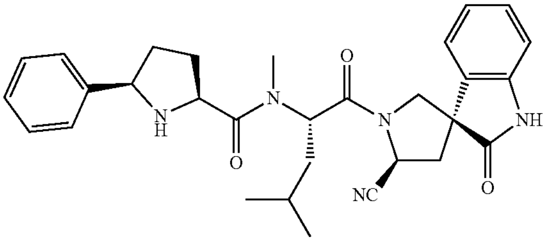 [SMILES: CC(C)C[C@@H](C(=O)N1C[C@]2(C[C@H]1C#N)C(=O)Nc1ccccc12)N(C)C(=O)[C@@H]1CC[C@H](c2ccccc2)N1] | 514.5 [M + H] | 1H NMR (400 MHz, Acetone-d6) δ 7.36-7.17 (m, 6H), 7.03 (d, J = 4.2 Hz, 2H), 6.95 (s, 1H), 5.48 (dd, J = 9.1, 6.0 Hz, 1H), 5.19 (t, J = 8.5 Hz, 1H), 4.10 (d, J = 10.6 Hz, 1H), 4.03-3.91 (m, 3H), 3.06 (s, 3H), 2.79-2.62 (m, 2H), 2.00-1.84 (m, 2H), 1.79 (ddd, J = 14.4, 9.1, 5.3 Hz, 1H), 1.70 (ddd, J = 14.2, 8.5, 6.0 Hz, 1H), 1.61-1.48 (m, 1H), 1.35 (dddd, J = 12.0, 7.0, 4.5, 2.4 Hz, 1H), 1.31-1.18 (m, 1H), 0.97 (d, J = 6.7 Hz, 3H), 0.94 (d, J = 6.5 Hz, 3H). |
| 160 | 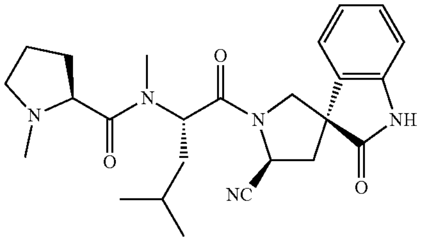 [SMILES: CC(C)C[C@@H](C(=O)N1C[C@]2(C[C@H]1C#N)C(=O)Nc1ccccc12)N(C)C(=O)[C@@H]1CCCN1C] | 452.4 [M + H] | |
| 161 | 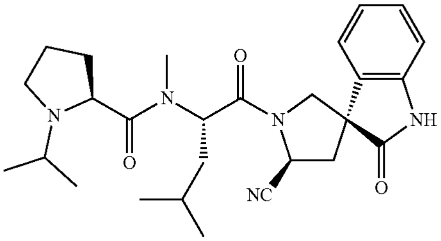 [SMILES: CC(C)C[C@@H](C(=O)N1C[C@]2(C[C@H]1C#N)C(=O)Nc1ccccc12)N(C)C(=O)[C@@H]1CCCN1C(C)C] | 478.4 [M − H] | 1H NMR (400 MHz, Acetone-d6) δ 9.84 (s, 1H), 7.28 (td, J = 7.2, 2.2 Hz, 1H), 7.15-6.90 (m, 3H), 5.45 (dd, J = 9.5, 5.7 Hz, 1H), 5.15 (t, J = 8.6 Hz, 1H), 4.04 (d, J = 10.7 Hz, 1H), 3.94 (d, J = 10.6 Hz, 1H), 3.79 (d, J = 8.7 Hz, 1H), 3.03 (s, 3H), 2.94-2.86 (m, 2H), 2.76-2.62 (m, 3H), 1.77 (ddd, J = 14.3, 9.6, 5.0 Hz, 2H), 1.63 (ddd, J = 14.2, 8.9, 5.8 Hz, 1H), 1.51 (dddd, J = 13.4, 11.6, 6.5, 2.2 Hz, 2H), 1.39 (dq, J = 12.3, 8.6 Hz, 1H), 1.03 (tt, J = 8.8, 3.3 Hz, 1H), 0.94 (dd, J = 19.1, 6.5 Hz, 12H). |
| 162 | 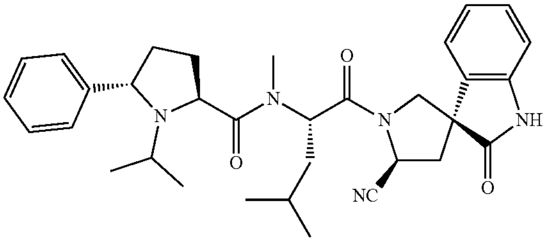 [SMILES: CC(C)C[C@@H](C(=O)N1C[C@]2(C[C@H]1C#N)C(=O)Nc1ccccc12)N(C)C(=O)[C@@H]1CC[C@@H](c2ccccc2)N1C(C)C] | 556.6 [M + H] | 1H NMR (400 MHz, Acetone-d6) δ 9.75 (s, 1H), 7.33-7.27 (m, 2H), 7.27-7.20 (m, 3H), 7.18-7.10 (m, 1H), 7.06-7.01 (m, 2H), 6.97 (d, J = 7.8 Hz, 1H), 5.51 (dd, J = 9.6, 5.6 Hz, 1H), 5.17 (t, J = 8.6 Hz, 1H), 4.38 (d, J = 6.8 Hz, 1H), 4.27-4.13 (m, 1H), 4.07 (dd, J = 10.7, 1.3 Hz, 1H), 3.97 (d, J = 10.7 Hz, 1H), 3.14 (p, J = 6.4 Hz, 1H), 3.02 (s, 3H), 2.78-2.63 (m, 2H), 1.94-1.76 (m, 3H), 1.64 (ddd, J = 14.1, 9.1, 5.6 Hz, 1H), 1.53 (dtd, J = 9.1, 6.6, 4.7 Hz, 1H), 1.08-1.01 (m, 1H), 0.99 (d, J = 6.6 Hz, 3H), 0.95 (d, J = 6.4 Hz, 3H), 0.92 (d, J = 6.3 Hz, 3H), 0.85 (q, J = 5.8, 5.1 Hz, 1H), 0.64 (d, J = 6.5 Hz, 3H). |
| 163 | 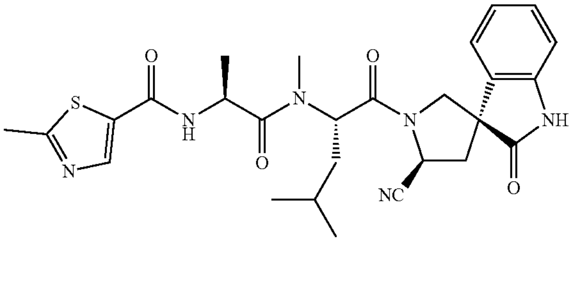 [SMILES: Cc1ncc(C(=O)N[C@@H](C)C(=O)N(C)[C@@H](CC(C)C)C(=O)N2C[C@]3(C[C@H]2C#N)C(=O)Nc2ccccc23)s1] | 535.4 [M − H] | 1H NMR (400 MHz, Acetone-d6) δ 9.75 (s, 1H), 8.13 (s, 1H), 7.70 (d, J = 7.7 Hz, 1H), 7.29 (ddd, J = 7.8, 6.6, 2.4 Hz, 1H), 7.10-6.98 (m, 3H), 5.41 (dd, J = 8.1, 6.9 Hz, 1H), 5.16 (t, J = 8.4 Hz, 1H), 4.78 (p, J = 7.0 Hz, 1H), 4.00-3.87 (m, 2H), 3.07 (s, 3H), 2.79-2.67 (m, 2H), 2.65 (s, 3H), 1.69 (td, J = 6.7, 1.7 Hz, 2H), 1.53 (dt, J = 13.4, 6.6 Hz, 1H), 0.92 (d, J = 6.6 Hz, 3H), 0.85 (dd, J = 10.9, 6.7 Hz, 6H). |

TABLE 2-continued
The following examples were prepared employing similar protocol as described above.
| Example | Structure | MS | NMR |
|---|---|---|---|
| 164 | 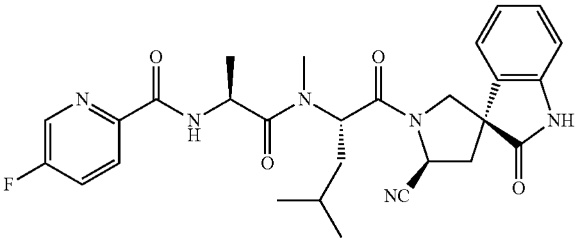 | 533.4 [M − H] | — |
| 165 | 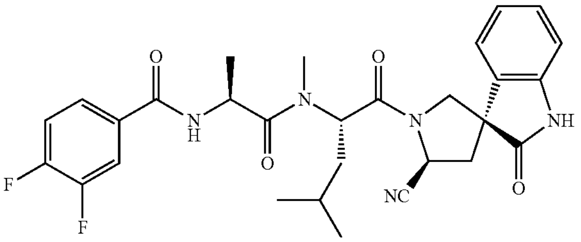 [SMILES: CC(C)C[C@@H](C(=O)N1C[C@]2(C[C@H]1C#N)C(=O)Nc1ccccc12)N(C)C(=O)[C@H](C)NC(=O)c1ccc(F)c(F)c1] | 550.4 [M − H] | 1H NMR (400 MHz, Acetone-d6) δ 9.78 (s, 1H), 7.85-7.71 (m, 3H), 7.40 (dt, J = 10.4, 8.2 Hz, 1H), 7.30 (ddd, J = 7.8, 6.6, 2.3 Hz, 1H), 7.12-7.00 (m, 3H), 5.45 (dd, J = 8.4, 6.6 Hz, 1H), 5.18 (t, J = 8.4 Hz, 1H), 4.83 (p, J = 7.0 Hz, 1H), 3.96 (d, J = 2.5 Hz, 2H), 3.11 (s, 3H), 2.83-2.61 (m, 2H), 1.79-1.65 (m, 2H), 1.56 (dq, J = 13.5, 6.7 Hz, 1H), 0.94 (d, J = 6.7 Hz, 3H), 0.88 (dd, J = 6.7, 1.7 Hz, 6H). |
| 166 | 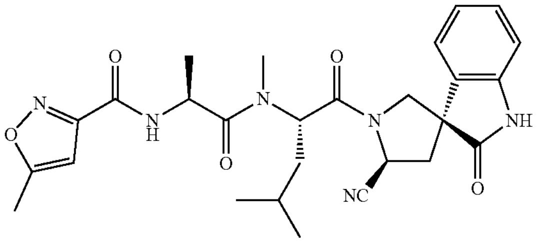 [SMILES: Cc1cc(C(=O)N[C@@H](C)C(=O)N(C)[C@@H](CC(C)C)C(=O)N2C[C@]3(C[C@H]2C#N)C(=O)Nc2ccccc23)no1] | 519.6 [M − H] | |
| 167 | 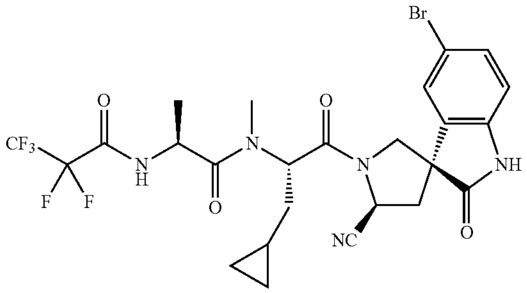 | 632.1 [M − H] | |
| 168 | 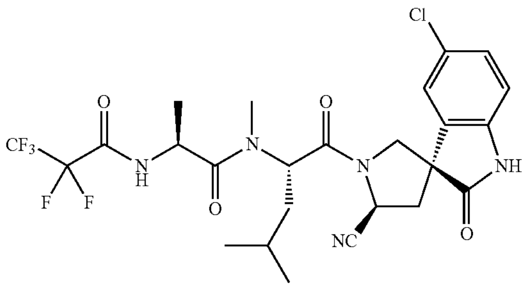 [SMILES: CC(C)C[C@@H](C(=O)N1C[C@]2(C[C@H]1C#N)C(=O)Nc1ccc(Cl)cc12)N(C)C(=O)[C@H](C)NC(=O)C(F)(F)C(F)(F)F] | 590.2 [M − H] | |

TABLE 2-continued
| The following examples were prepared employing similar protocol as described above. | | | |
|---|---|---|---|
| Example | Structure | MS | NMR |
| 169 | 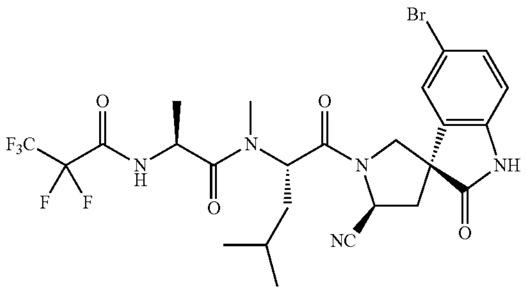 [SMILES: CC(C)C[C@@H](C(=O)N1C[C@]2(C[C@H]1C#N)C(=O)Nc1ccc(Br)cc12)N(C)C(=O)[C@H](C)NC(=O)C(F)(F)C(F)(F)F] | 634.2 [M − H] | |
| 170 | 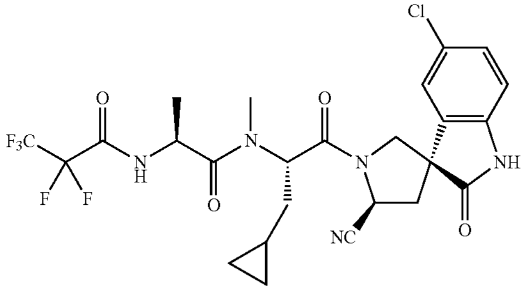 [SMILES: C[C@H](NC(=O)C(F)(F)C(F)(F)F)C(=O)N(C)[C@@H](CC1CC1)C(=O)N1C[C@]2(C[C@H]1C#N)C(=O)Nc1ccc(Cl)cc12] | 588.3 [M − H] | |
| 171 | 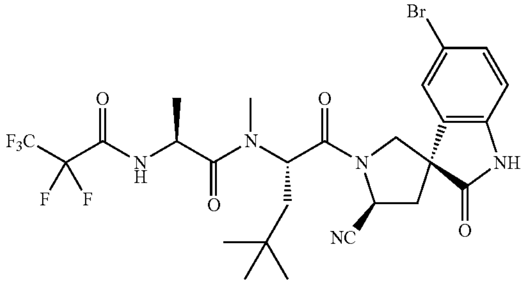 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccc(Br)cc12] | 648.1 [M − H] | |
| 172 | 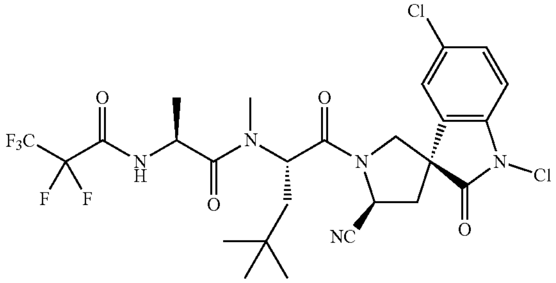 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)N(Cl)c1ccc(Cl)cc12] | 638.2 [M − H] | |
| 173 | 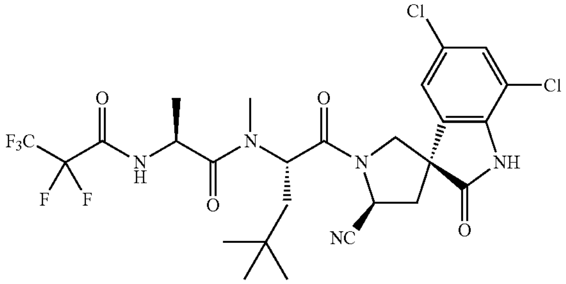 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1c(Cl)cc(Cl)cc12] | 638.2 [M − H] | |

TABLE 2-continued
| The following examples were prepared employing similar protocol as described above. | | | |
|---|---|---|---|
| Ex-am-ple | Structure | MS | NMR |
| 174 | 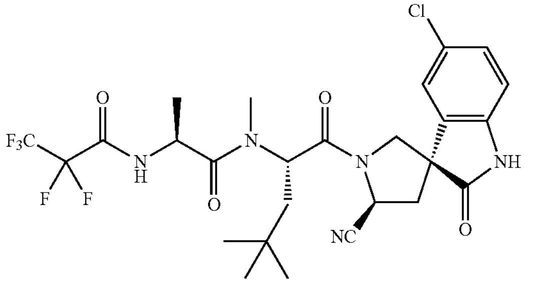 | 604.1 [M − H] | |
| 175 | 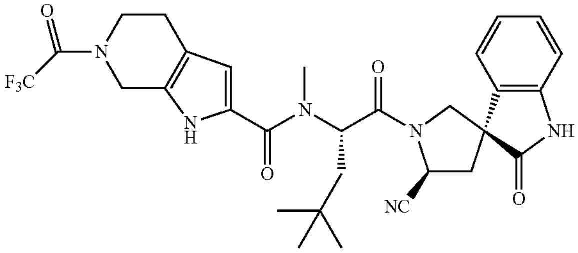 [SMILES: CN(C(=O)c1cc2c([nH]1)CN(C(=O)C(F)(F)F)CC2)[C@@H](CC(C)(C)C)C(=O)N1C[C@]2(C[C@H]1C#N)C(=O)Nc1ccccc12] | 597.1 [M − H] | |
| 176 | 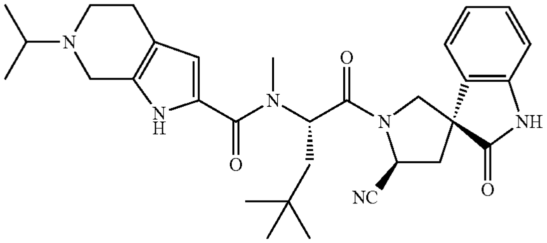 [SMILES: CC(C)N1CCc2cc(C(=O)N(C)[C@@H](CC(C)(C)C)C(=O)N3C[C@]4(C[C@H]3C#N)C(=O)Nc3ccccc34)[nH]c2C1] | 543.2 [M − H] | |
| 177 | 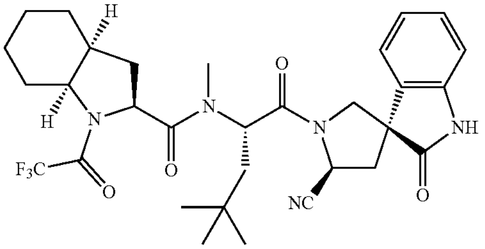 [SMILES: CN(C(=O)[C@@H]1C[C@@H]2CCCC[C@@H]2N1C(=O)C(F)(F)F)[C@@H](CC(C)(C)C)C(=O)N1C[C@]2(C[C@H]1C#N)C(=O)Nc1ccccc12] | 600.2 [M − H] | |
| 178 | 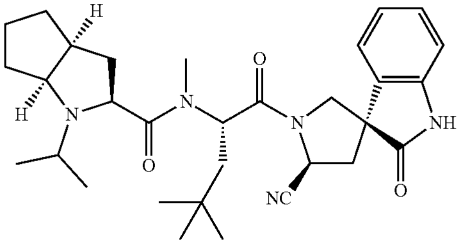 [SMILES: CC(C)N1[C@H](C(=O)N(C)[C@@H](CC(C)(C)C)C(=O)N2C[C@]3(C[C@H]2C#N)C(=O)Nc2ccccc23)C[C@@H]2CCC[C@@H]21] | 532.3 [M − H] | |

TABLE 2-continued
The following examples were prepared employing similar protocol as described above.
| Example | Structure | MS | NMR |
|---|---|---|---|
| 179 | 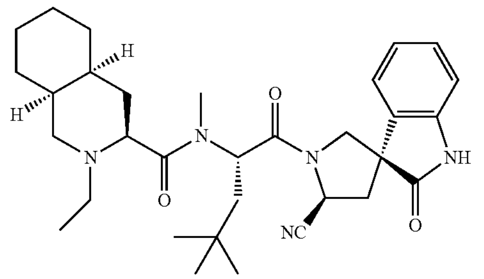 [SMILES: CCN1C[C@H]2CCCC[C@H]2C[C@H]1C(=O)N(C)[C@@H](CC(C)(C)C)C(=O)N1C[C@]2(C[C@H]1C#N)C(=O)Nc1ccccc12] | 546.4 [M − H] | |
| 180 | 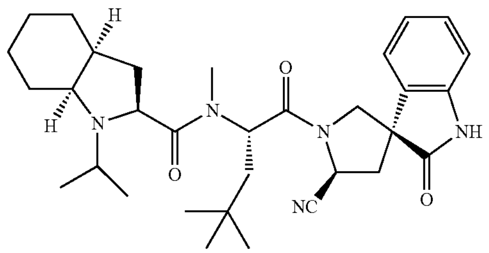 [SMILES: CC(C)N1[C@H](C(=O)N(C)[C@@H](CC(C)(C)C)C(=O)N2C[C@]3(C[C@H]2C#N)C(=O)Nc2ccccc23)C[C@@H]2CCCC[C@@H]21] | 546.4 [M − H] | |
| 181 | 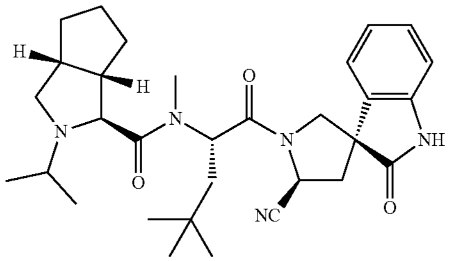 [SMILES: CC(C)N1C[C@@H]2CCC[C@@H]2[C@H]1C(=O)N(C)[C@@H](CC(C)(C)C)C(=O)N1C[C@]2(C[C@H]1C#N)C(=O)Nc1ccccc12] | 532.4 [M − H] | |
| 182 | 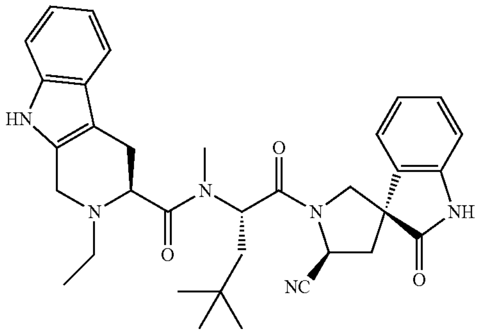 [SMILES: CCN1Cc2[nH]c3ccccc3c2C[C@H]1C(=O)N(C)[C@@H](CC(C)(C)C)C(=O)N1C[C@]2(C[C@H]1C#N)C(=O)Nc1ccccc12] | 679.3 [M − H] | |
| 183 | 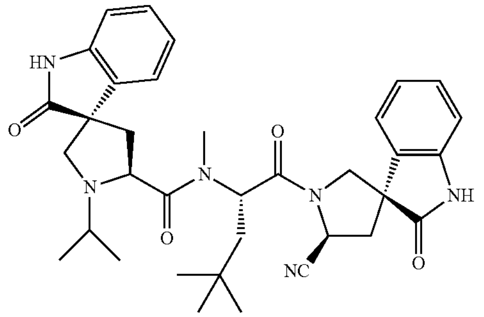 [SMILES: CC(C)N1C[C@]2(C[C@H]1C(=O)N(C)[C@@H](CC(C)(C)C)C(=O)N1C[C@]3(C[C@H]1C#N)C(=O)Nc1ccccc13)C(=O)Nc1ccccc12] | 609.3 [M − H] | |

TABLE 2-continued
The following examples were prepared employing similar protocol as described above.
| Example | Structure | MS | NMR |
|---|---|---|---|
| 184 | 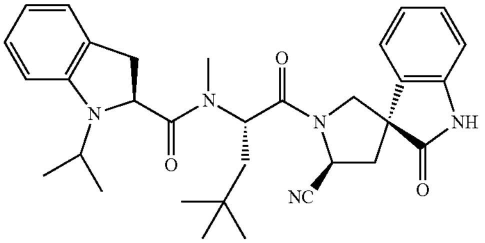 [SMILES: CC(C)N1c2ccccc2C[C@H]1C(=O)N(C)[C@@H](CC(C)(C)C)C(=O)N1C[C@]2(C[C@H]1C#N)C(=O)Nc1ccccc12] | 540.5 [M − H] | |
| 185 | 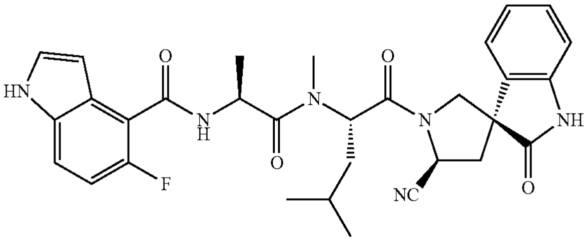 [SMILES: CC(C)C[C@@H](C(=O)N1C[C@]2(C[C@H]1C#N)C(=O)Nc1ccccc12)N(C)C(=O)[C@H](C)NC(=O)c1c(F)ccc2[nH]ccc12] | 571.2 [M − H] | |
| 186 | 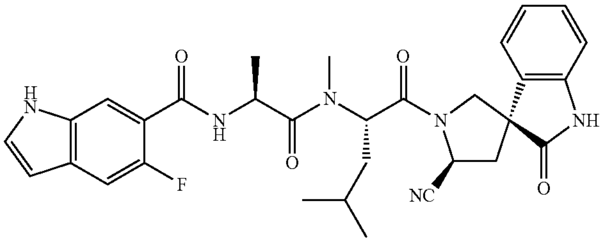 [SMILES: CC(C)C[C@@H](C(=O)N1C[C@]2(C[C@H]1C#N)C(=O)Nc1ccccc12)N(C)C(=O)[C@H](C)NC(=O)c1cc2[nH]ccc2cc1F] | 571.2 [M − H] | |
| 187 | 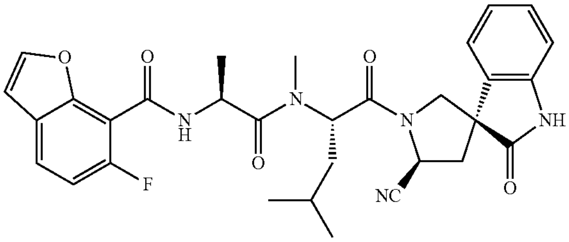 [SMILES: CC(C)C[C@@H](C(=O)N1C[C@]2(C[C@H]1C#N)C(=O)Nc1ccccc12)N(C)C(=O)[C@H](C)NC(=O)c1c(F)ccc2ccoc12] | 572.4 [M − H] | |
| 188 | 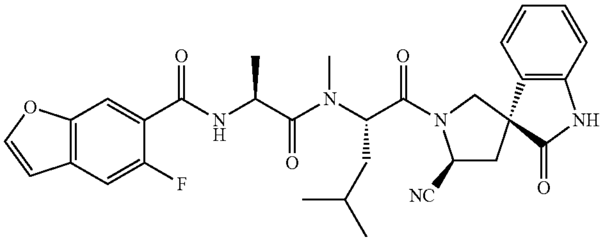 [SMILES: CC(C)C[C@@H](C(=O)N1C[C@]2(C[C@H]1C#N)C(=O)Nc1ccccc12)N(C)C(=O)[C@H](C)NC(=O)c1cc2occc2cc1F] | 572.3 [M − H] | |
| 189 | 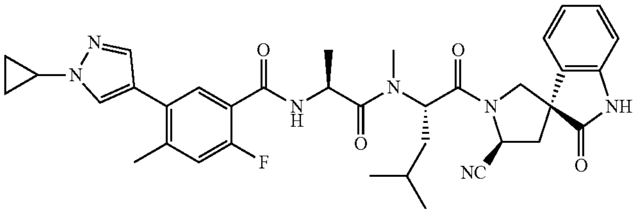 [SMILES: Cc1cc(F)c(C(=O)N[C@@H](C)C(=O)N(C)[C@@H](CC(C)C)C(=O)N2C[C@]3(C[C@H]2C#N)C(=O)Nc2ccccc23)cc1-c1cnn(C2CC2)c1] | 552.6 [M − H] | |

TABLE 2-continued
The following examples were prepared employing similar protocol as described above.
| Example | Structure | MS | NMR |
|---|---|---|---|
| 190 | 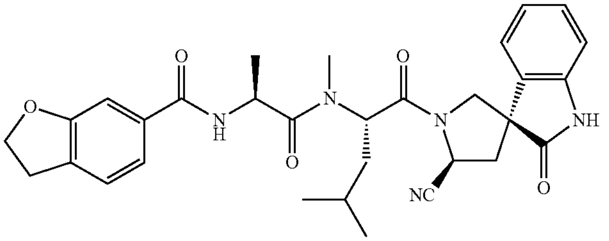 [SMILES: CC(C)C[C@@H](C(=O)N1C[C@]2(C[C@H]1C#N)C(=O)Nc1ccccc12)N(C)C(=O)[C@H](C)NC(=O)c1ccc2c(c1)OCC2] | 556.2 [M − H] | |
| 191 | 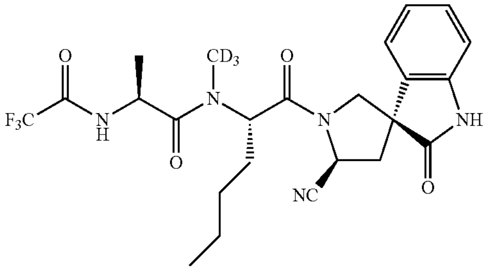 [SMILES: [2H]C([2H])([2H])N(C(=O)[C@H](C)NC(=O)C(F)(F)F)[C@@H](CCCC)C(=O)N1C[C@]2(C[C@H]1C#N)C(=O)Nc1ccccc12] | 509.2 [M − H] | |
| 192 | 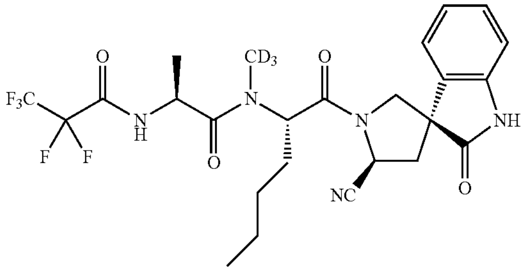 [SMILES: [2H]C([2H])([2H])N(C(=O)[C@H](C)NC(=O)C(F)(F)C(F)(F)F)[C@@H](CCCC)C(=O)N1C[C@]2(C[C@H]1C#N)C(=O)Nc1ccccc12] | 559.4 [M − H] | |
| 193 | 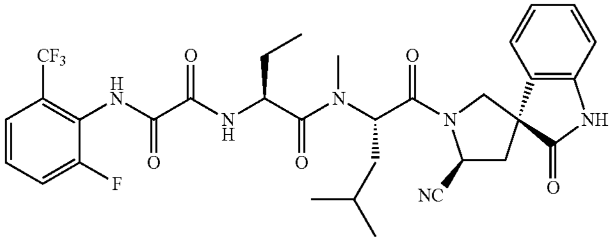 [SMILES: CC[C@H](NC(=O)C(=O)Nc1c(F)cccc1C(F)(F)F)C(=O)N(C)[C@@H](CC(C)C)C(=O)N1C[C@]2(C[C@H]1C#N)C(=O)Nc1ccccc12] | 657.3 [M − H] | |
| 194 | 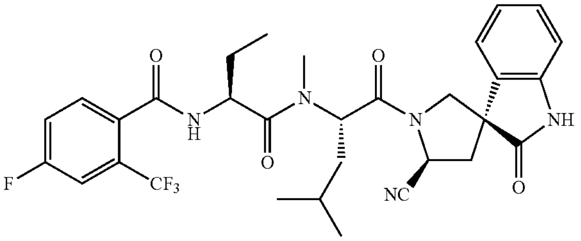 [SMILES: CC[C@H](NC(=O)c1ccc(F)cc1C(F)(F)F)C(=O)N(C)[C@@H](CC(C)C)C(=O)N1C[C@]2(C[C@H]1C#N)C(=O)Nc1ccccc12] | 614.3 [M − H] | |

TABLE 2-continued
The following examples were prepared employing similar protocol as described above.
| Example | Structure | MS | NMR |
|---|---|---|---|
| 195 | 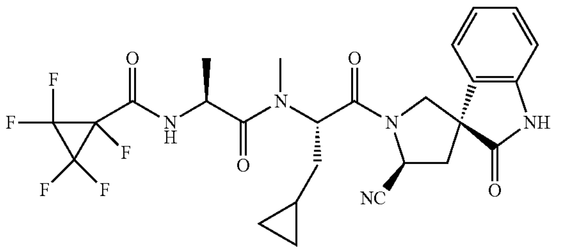 [SMILES: C[C@H](NC(=O)C1(F)C(F)(F)C1(F)F)C(=O)N(C)[C@@H](CC1CC1)C(=O)N1C[C@]2(C[C@H]1C#N)C(=O)Nc1ccccc12] | 566.5 [M − H] | |
| 196 | 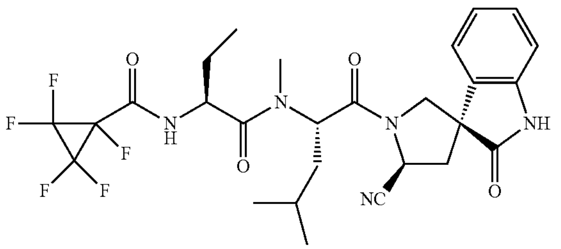 [SMILES: CC[C@H](NC(=O)C1(F)C(F)(F)C1(F)F)C(=O)N(C)[C@@H](CC(C)C)C(=O)N1C[C@]2(C[C@H]1C#N)C(=O)Nc1ccccc12] | 582.3 [M − H] | |
| 197 | 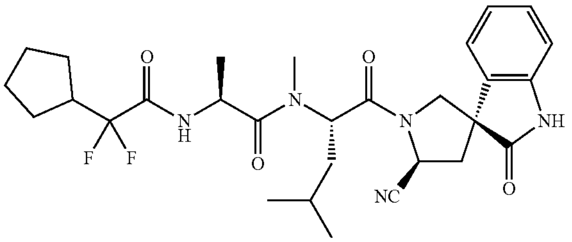 [SMILES: CC(C)C[C@@H](C(=O)N1C[C@]2(C[C@H]1C#N)C(=O)Nc1ccccc12)N(C)C(=O)[C@H](C)NC(=O)C(F)(F)C1CCCC1] | 556.4 [M − H] | |
| 198 | 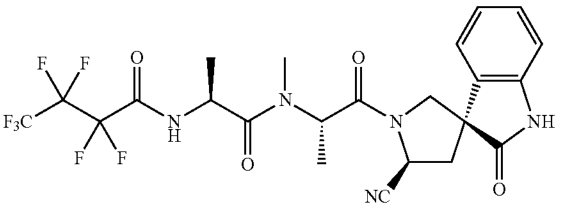 [SMILES: C[C@H](NC(=O)C(F)(F)C(F)(F)C(F)(F)F)C(=O)N(C)[C@@H](C)C(=O)N1C[C@]2(C[C@H]1C#N)C(=O)Nc1ccccc12] | 564.4 [M − H] | |
| 199 | 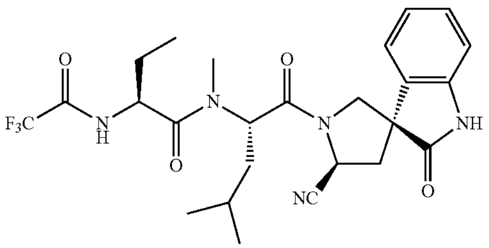 [SMILES: CC[C@H](NC(=O)C(F)(F)F)C(=O)N(C)[C@@H](CC(C)C)C(=O)N1C[C@]2(C[C@H]1C#N)C(=O)Nc1ccccc12] | 520.3 [M − H] | |
| 200 | 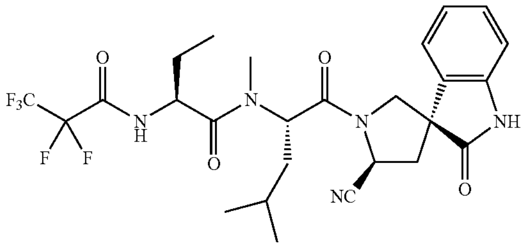 [SMILES: CC[C@H](NC(=O)C(F)(F)C(F)(F)F)C(=O)N(C)[C@@H](CC(C)C)C(=O)N1C[C@]2(C[C@H]1C#N)C(=O)Nc1ccccc12] | 570.4 [M − H] | |

TABLE 2-continued
The following examples were prepared employing similar protocol as described above.
| Example | Structure | MS | NMR |
|---|---|---|---|
| 201 | 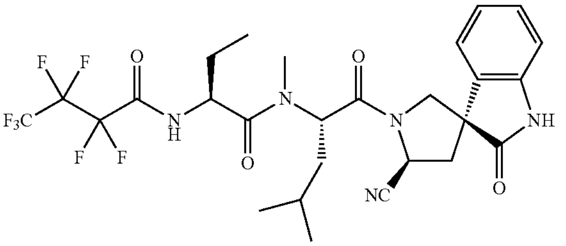 [SMILES: CC[C@H](NC(=O)C(F)(F)C(F)(F)C(F)(F)F)C(=O)N(C)[C@@H](CC(C)C)C(=O)N1C[C@]2(C[C@H]1C#N)C(=O)Nc1ccccc12] | 620.3 [M − H] | |
| 202 | 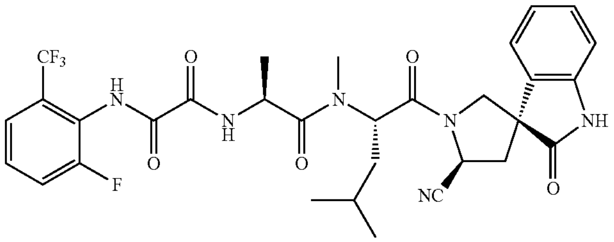 [SMILES: CC(C)C[C@@H](C(=O)N1C[C@]2(C[C@H]1C#N)C(=O)Nc1ccccc12)N(C)C(=O)[C@H](C)NC(=O)C(=O)Nc1c(F)cccc1C(F)(F)F] | 643.4 [M − H] | |
| 203 | 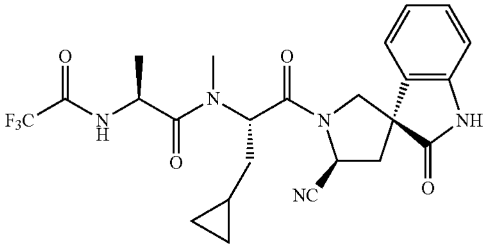 [SMILES: C[C@H](NC(=O)C(F)(F)F)C(=O)N(C)[C@@H](CC1CC1)C(=O)N1C[C@]2(C[C@H]1C#N)C(=O)Nc1ccccc12] | 504.2 [M − H] | |
| 204 | 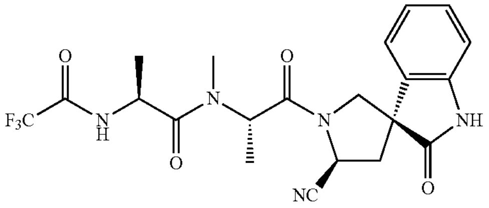 [SMILES: C[C@H](NC(=O)C(F)(F)F)C(=O)N(C)[C@@H](C)C(=O)N1C[C@]2(C[C@H]1C#N)C(=O)Nc1ccccc12] | 464.2 [M − H] | |
| 205 | 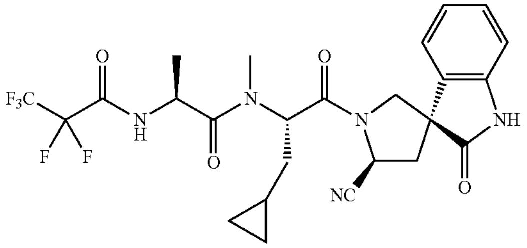 [SMILES: C[C@H](NC(=O)C(F)(F)C(F)(F)F)C(=O)N(C)[C@@H](CC1CC1)C(=O)N1C[C@]2(C[C@H]1C#N)C(=O)Nc1ccccc12] | 554.3 [M − H] | $^1$H NMR (500 MHz, Chloroform-d) δ 7.73 (s, 1H), 7.36 (d, J = 7.1 Hz, 1H), 7.34-7.28 (m, 1H), 7.07-6.92 (m, 2H), 6.83 (d, J = 7.4 Hz, 1H), 5.22 (dd, J = 8.6, 6.7 Hz, 1H), 4.98 (dd, J = 9.3, 8.1 Hz, 1H), 4.77 (p, J = 6.8 Hz, 1H), 4.15 (dd, J = 10.3, 1.3 Hz, 1H), 4.03 (d, J = 10.4 Hz, 1H), 3.13 (s, 3H), 2.87 (dd, J = 13.2, 9.3 Hz, 1H), 2.54 (ddd, J = 13.2, 8.1, 1.3 Hz, 1H), 1.87 (dt, J = 13.7, 7.9 Hz, 1H), 1.72 (dt, J = 13.5, 6.6 Hz, 1H), 1.55 (s, 2H), 1.36-1.22 (m, 1H), 1.11 (d, J = 6.7 Hz, 2H), 0.93-0.82 (m, 1H), 0.71-0.61 (m, 1H), 0.53 (ttd, J = 12.9, 7.7, 6.5, 3.0 Hz, 2H), 0.26-0.09 (m, 2H). |

TABLE 2-continued
The following examples were prepared employing similar protocol as described above.
| Example | Structure | MS | NMR |
|---|---|---|---|
| 206 | 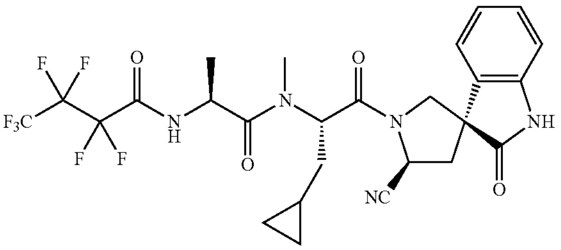 [SMILES: C[C@H](NC(=O)C(F)(F)C(F)(F)C(F)(F)F)C(=O)N(C)[C@@H](CC1CC1)C(=O)N1C[C@]2(C[C@H]1C#N)C(=O)Nc1ccccc12] | 604.5 [M − H] | |
| 207 | 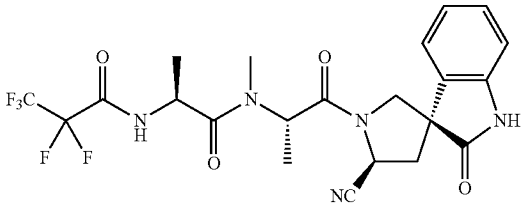 [SMILES: C[C@H](NC(=O)C(F)(F)C(F)(F)F)C(=O)N(C)[C@@H](C)C(=O)N1C[C@]2(C[C@H]1C#N)C(=O)Nc1ccccc12] | 514.3 [M − H] | |
| 208 | 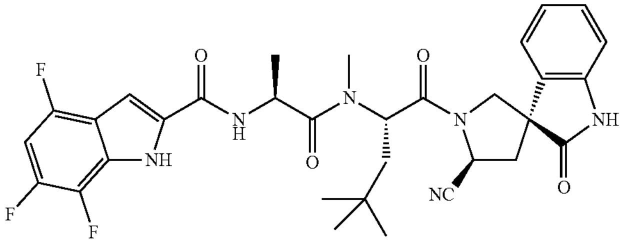 [SMILES: C[C@H](NC(=O)c1cc2c(F)cc(F)c(F)c2[nH]1)C(=O)N(C)[C@@H](CC(C)(C)C)C(=O)N1C[C@]2(C[C@H]1C#N)C(=O)Nc1ccccc12] | 621.3 [M − H] | |
| 209 | 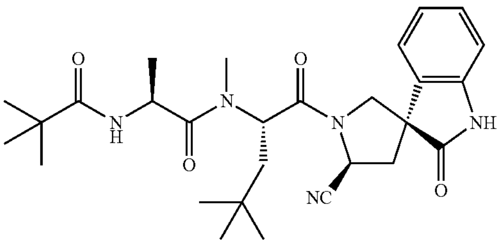 [SMILES: C[C@H](NC(=O)C(C)(C)C)C(=O)N(C)[C@@H](CC(C)(C)C)C(=O)N1C[C@]2(C[C@H]1C#N)C(=O)Nc1ccccc12] | 508.4 [M − H] | |
| 210 | 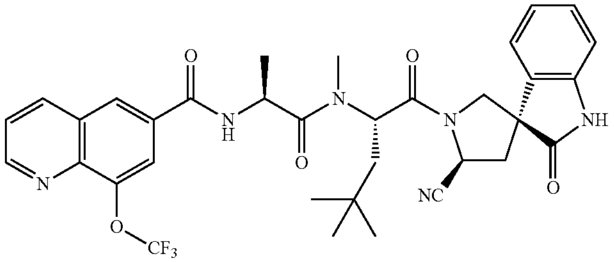 [SMILES: C[C@H](NC(=O)c1cc(OC(F)(F)F)c2ncccc2c1)C(=O)N(C)[C@@H](CC(C)(C)C)C(=O)N1C[C@]2(C[C@H]1C#N)C(=O)Nc1ccccc12] | 663.3 [M − H] | |
| 211 | 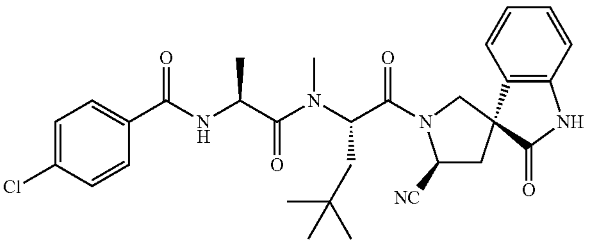 [SMILES: C[C@H](NC(=O)c1ccc(Cl)cc1)C(=O)N(C)[C@@H](CC(C)(C)C)C(=O)N1C[C@]2(C[C@H]1C#N)C(=O)Nc1ccccc12] | 562.6 [M − H] | |

TABLE 2-continued
The following examples were prepared employing similar protocol as described above.
| Example | Structure | MS | NMR |
|---|---|---|---|
| 212 | 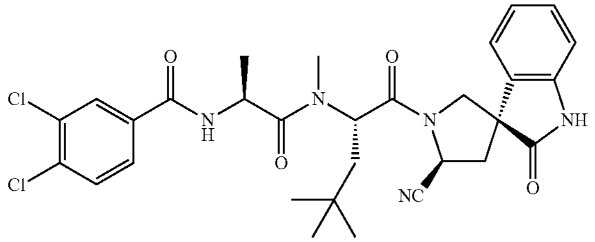 [SMILES: C[C@H](NC(=O)c1ccc(Cl)c(Cl)c1)C(=O)N(C)[C@@H](CC(C)(C)C)C(=O)N1C[C@]2(C[C@H]1C#N)C(=O)Nc1ccccc12] | 596.2 [M − H] | |
| 213 | 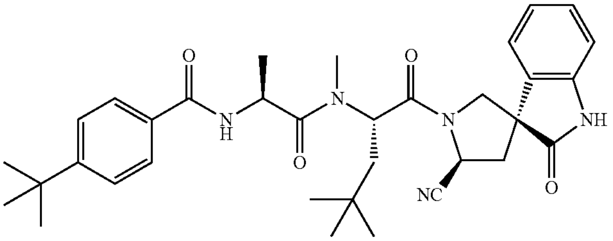 [SMILES: C[C@H](NC(=O)c1ccc(C(C)(C)C)cc1)C(=O)N(C)[C@@H](CC(C)(C)C)C(=O)N1C[C@]2(C[C@H]1C#N)C(=O)Nc1ccccc12] | 584.5 [M − H] | |
| 214 | 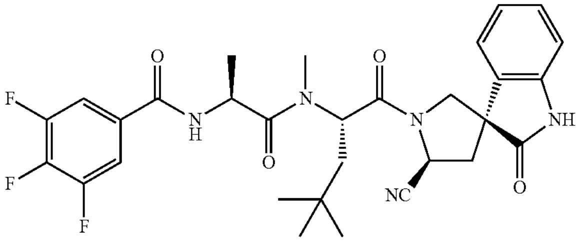 [SMILES: C[C@H](NC(=O)c1cc(F)c(F)c(F)c1)C(=O)N(C)[C@@H](CC(C)(C)C)C(=O)N1C[C@]2(C[C@H]1C#N)C(=O)Nc1ccccc12] | 582.4 [M − H] | |
| 215 | 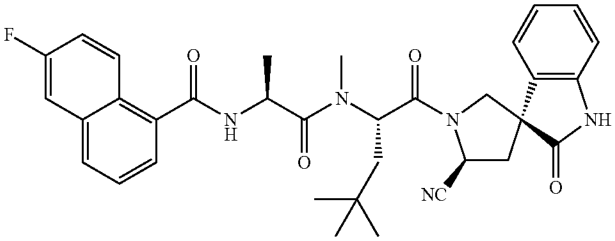 [SMILES: C[C@H](NC(=O)c1cccc2cc(F)ccc12)C(=O)N(C)[C@@H](CC(C)(C)C)C(=O)N1C[C@]2(C[C@H]1C#N)C(=O)Nc1ccccc12] | 596.3 [M − H] | |
| 216 | 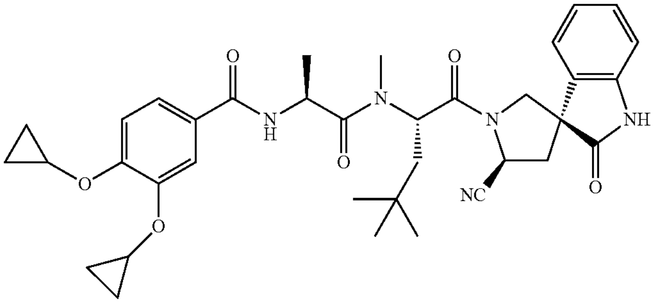 [SMILES: C[C@H](NC(=O)c1ccc(OC2CC2)c(OC2CC2)c1)C(=O)N(C)[C@@H](CC(C)(C)C)C(=O)N1C[C@]2(C[C@H]1C#N)C(=O)Nc1ccccc12] | 640.4 [M − H] | |

TABLE 2-continued
The following examples were prepared employing similar protocol as described above.
| Example | Structure | MS | NMR |
|---|---|---|---|
| 217 | 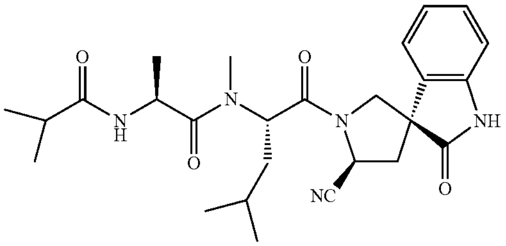 [SMILES: CC(C)C[C@@H](C(=O)N1C[C@]2(C[C@H]1C#N)C(=O)Nc1ccccc12)N(C)C(=O)[C@H](C)NC(=O)C(C)C] | 480.4 [M − H] | |
| 218 | 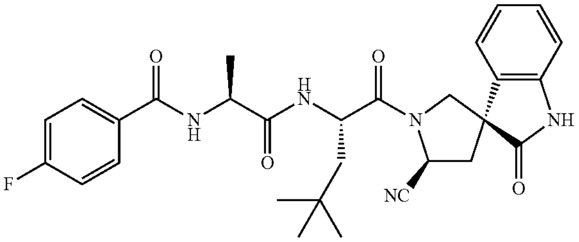 | 532.3 [M − H] | |
| 219 | 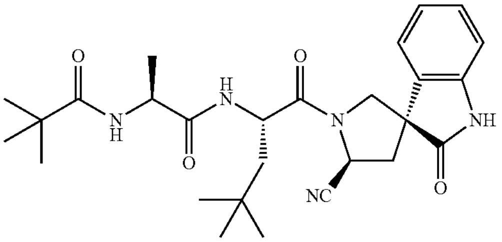 [SMILES: C[C@H](NC(=O)C(C)(C)C)C(=O)N[C@@H](CC(C)(C)C)C(=O)N1C[C@]2(C[C@H]1C#N)C(=O)Nc1ccccc12] | 494.3 [M − H] | |
| 220 | 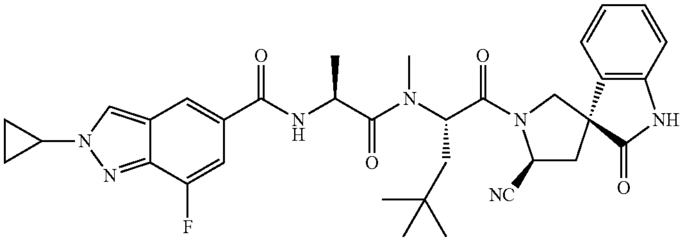 [SMILES: C[C@H](NC(=O)c1cc(F)c2nn(C3CC3)cc2c1)C(=O)N(C)[C@@H](CC(C)(C)C)C(=O)N1C[C@]2(C[C@H]1C#N)C(=O)Nc1ccccc12] | 626.3 [M − H] | |
| 221 | 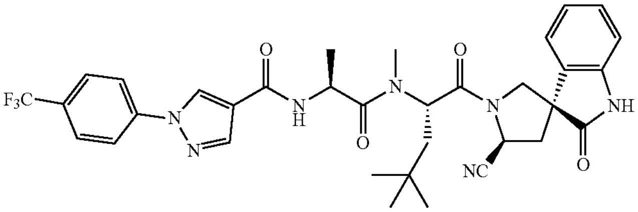 [SMILES: C[C@H](NC(=O)c1cnn(-c2ccc(C(F)(F)F)cc2)c1)C(=O)N(C)[C@@H](CC(C)(C)C)C(=O)N1C[C@]2(C[C@H]1C#N)C(=O)Nc1ccccc12] | 662.4 [M − H] | |
| 222 | 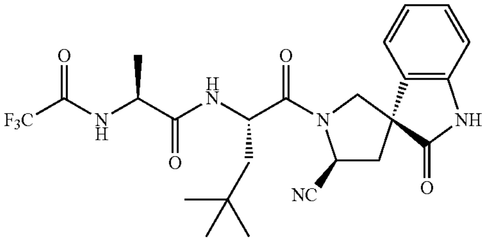 [SMILES: C[C@H](NC(=O)C(F)(F)F)C(=O)N[C@@H](CC(C)(C)C)C(=O)N1C[C@]2(C[C@H]1C#N)C(=O)Nc1ccccc12] | 506.2 [M − H] | |

TABLE 2-continued
The following examples were prepared employing similar protocol as described above.
| Example | Structure | MS | NMR |
|---|---|---|---|
| 223 | 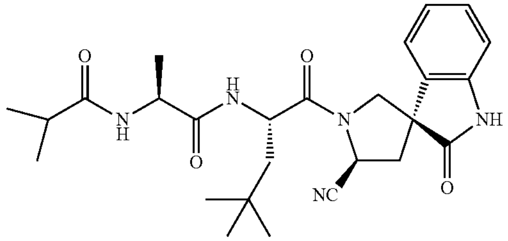 [SMILES: CC(C)C(=O)N[C@@H](C)C(=O)N[C@@H](CC(C)(C)C)C(=O)N1C[C@]2(C[C@H]1C#N)C(=O)Nc1ccccc12] | 480.2 [M − H] | |
| 224 | 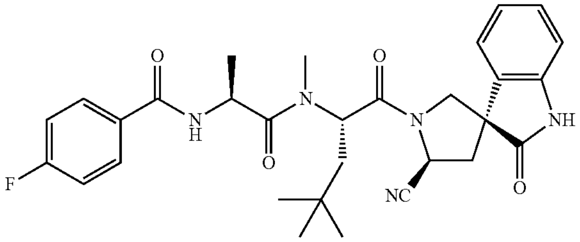 | 546.6 [M − H] | |
| 225 | 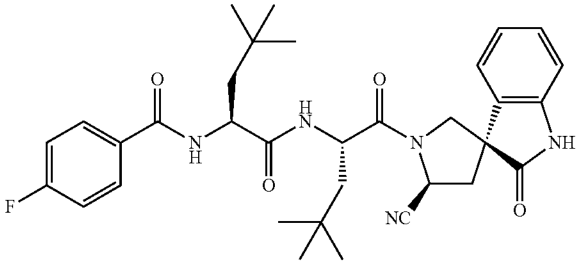 [SMILES: CC(C)(C)C[C@H](NC(=O)c1ccc(F)cc1)C(=O)N[C@@H](CC(C)(C)C)C(=O)N1C[C@]2(C[C@H]1C#N)C(=O)Nc1ccccc12] | 588.3 [M − H] | |
| 226 | 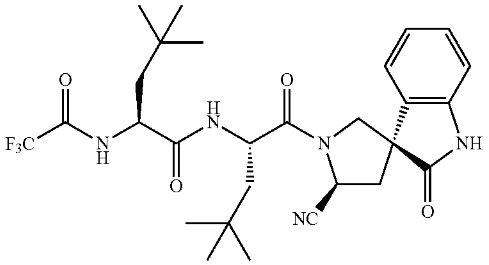 [SMILES: CC(C)(C)C[C@H](NC(=O)C(F)(F)F)C(=O)N[C@@H](CC(C)(C)C)C(=O)N1C[C@]2(C[C@H]1C#N)C(=O)Nc1ccccc12] | 562.4 [M − H] | |
| 227 | 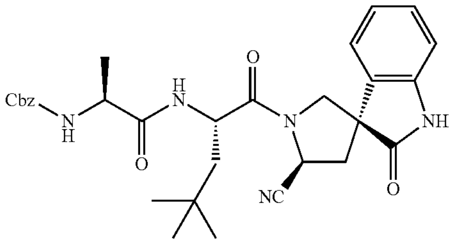 [SMILES: C[C@H](NC(=O)OCc1ccccc1)C(=O)N[C@@H](CC(C)(C)C)C(=O)N1C[C@]2(C[C@H]1C#N)C(=O)Nc1ccccc12] | 544.4 [M − H] | |

TABLE 2-continued

| The following examples were prepared employing similar protocol as described above. | | | |
|---|---|---|---|
| Example | Structure | MS | NMR |
| 228 | 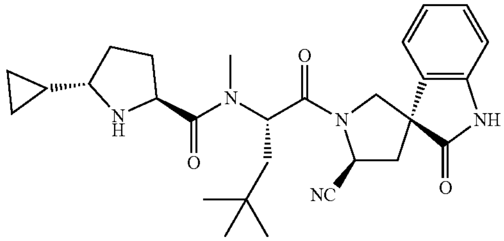 [SMILES: CN(C(=O)[C@@H]1CC[C@@H](C2CC2)N1)[C@@H](CC(C)(C)C)C(=O)N1C[C@]2(C[C@H]1C#N)C(=O)Nc1ccccc12] | [M + H+] 492.3 | $^1H$ NMR (400 MHz, Methanol-$d_4$) δ 7.32 (t, J = 7.7 Hz, 1H), 7.02 (dt, J = 26.2, 7.1 Hz, 3H), 5.41 (dd, J = 8.3, 4.2 Hz, 1H), 5.20 (t, J = 8.6 Hz, 1H), 4.54 (t, J = 8.0 Hz, 1H), 3.95 (s, 2H), 3.06 (s, 3H), 2.84-2.54 (m, 3H), 2.32 (ddd, J = 22.1, 13.3, 8.1 Hz, 2H), 1.78 (tt, J = 13.1, 7.4 Hz, 1H), 1.49 (dd, J = 13.9, 4.2 Hz, 1H), 1.29-1.11 (m, 1H), 0.98 (s, 9H), 0.68 (d, J = 8.0 Hz, 2H), 0.51-0.20 (m, 2H). |
| 229 | 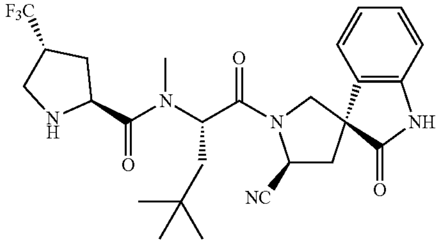 [SMILES: CN(C(=O)[C@@H]1C[C@@H](C(F)(F)F)CN1)[C@@H](CC(C)(C)C)C(=O)N1C[C@]2(C[C@H]1C#N)C(=O)Nc1ccccc12] | [M + Na+] 542.2 | $^1H$ NMR (400 MHz, Acetone-$d_6$) δ 9.77 (s, 1H), 7.29 (td, J = 7.7, 1.3 Hz, 1H), 7.14-6.82 (m, 4H), 5.49 (dd, J = 7.2, 5.3 Hz, 1H), 5.18 (td, J = 8.6, 6.4 Hz, 1H), 4.13 (dd, J = 10.6, 1.3 Hz, 1H), 3.92 (d, J = 10.6 Hz, 1H), 3.81 (dd, J = 7.9, 6.0 Hz, 1H), 3.18 (dd, J = 11.8, 8.0 Hz, 1H), 3.07 (s, 3H), 2.84-2.58 (m, 4H), 2.13 (dd, J = 14.5, 7.6 Hz, 1H), 1.67 (ddd, J = 13.8, 7.9, 6.3 Hz, 1H), 1.50 (dd, J = 14.1, 5.3 Hz, 1H), 1.42-1.26 (m, 1H), 0.95 (m, 10H). |
| 230 | 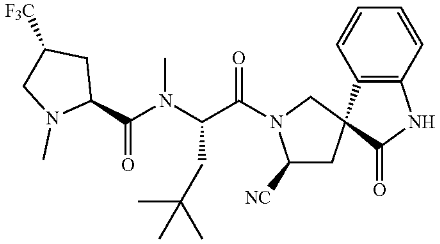 [SMILES: CN1C[C@H](C(F)(F)F)C[C@H]1C(=O)N(C)[C@@H](CC(C)(C)C)C(=O)N1C[C@]2(C[C@H]1C#N)C(=O)Nc1ccccc12] | [M + H+] 534.2 | $^1H$ NMR (400 MHz, Acetone-$d_6$) δ 9.77 (s, 1H), 7.28 (td, J = 7.7, 1.3 Hz, 1H), 7.12-6.87 (m, 3H), 5.61-5.43 (m, 1H), 5.18 (td, J = 8.6, 3.0 Hz, 1H), 4.24-4.04 (m, 1H), 4.01-3.86 (m, 1H), 3.50 (dd, J = 7.9, 5.2 Hz, 1H), 3.09 (s, 3H), 2.81-2.61 (m, 3H), 2.57-2.43 (m, 1H), 2.23 (s, 3H), 2.23-2.14 (m, 1H), 1.75 (dt, J = 13.1, 7.4 Hz, 1H), 1.48 (d, J = 5.1 Hz, 1H), 1.34-1.18 (m, 1H), 0.96 (s, 9H). |
| 231 | 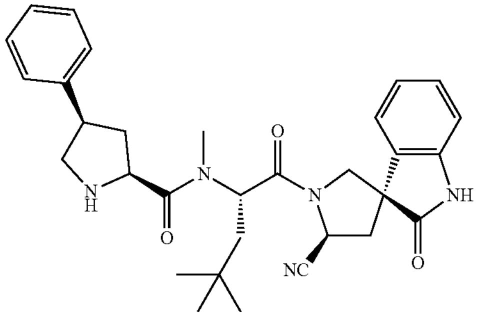 [SMILES: CN(C(=O)[C@@H]1C[C@H](c2ccccc2)CN1)[C@@H](CC(C)(C)C)C(=O)N1C[C@]2(C[C@H]1C#N)C(=O)Nc1ccccc12] | [M + H+] 528.3 | $^1H$ NMR (400 MHz, Methanol-$d_4$) δ 7.37-7.28 (m, 2H), 7.31-7.23 (m, 1H), 7.11-7.03 (m, 2H), 6.92-6.75 (m, 3H), 6.55 (dd, J = 7.7, 1.0 Hz, 1H), 5.48 (dd, J = 8.2, 4.1 Hz, 1H), 5.16 (t, J = 8.6 Hz, 1H), 3.99 (dd, J = 9.8, 6.9 Hz, 1H), 3.94 (d, J = 10.6 Hz, 1H), 3.89 (dd, J = 10.6, 1.2 Hz, 1H), 3.33-3.13 (m, 2H), 3.04 (s, 3H), 2.94 (dd, J = 10.6, 8.8 Hz, 1H), 2.69 (dd, J = 13.1, 8.9 Hz, 1H), 2.58 (ddd, J = 12.9, 8.3, 1.2 Hz, 1H), 2.30 (dd, J = 13.9, 8.2 Hz, 1H), 2.15 (dt, J = 12.5, 7.1 Hz, 1H), 1.44 (dd, J = 13.9, 4.1 Hz, 1H), 0.98 (s, 9H), 0.92-0.82 (m, 1H). |
| 232 | 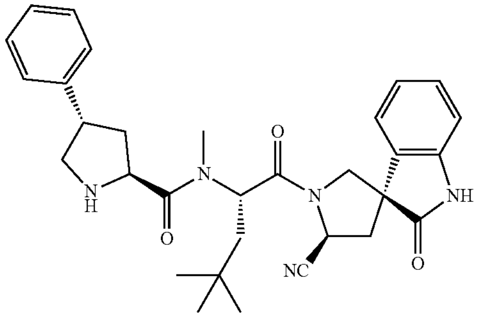 [SMILES: CN(C(=O)[C@@H]1C[C@@H](c2ccccc2)CN1)[C@@H](CC(C)(C)C)C(=O)N1C[C@]2(C[C@H]1C#N)C(=O)Nc1ccccc12] | [M + H+] 528.3 | $^1H$ NMR (400 MHz, Methanol-$d_4$) δ 7.35 (dd, J = 8.3, 6.9 Hz, 2H), 7.31-7.21 (m, 1H), 7.16 (dd, J = 7.0, 1.7 Hz, 2H), 6.99-6.80 (m, 3H), 6.78-6.69 (m, 1H), 5.53-5.43 (m, 1H), 5.18 (t, J = 8.6 Hz, 1H), 4.03 (dd, J = 9.8, 4.6 Hz, 1H), 3.97-3.89 (m, 3H), 3.40-3.30 (m, 1H), 3.03 (s, 3H), 2.80-2.55 (m, 4H), 2.27 (dd, J = 13.9, 8.0 Hz, 1H), 2.01 (dt, J = 12.9, 9.9 Hz, 1H), 1.50-1.41 (m, 1H), 1.32 (ddd, J = 13.1, 8.3, 4.6 Hz, 1H), 0.98 (s, 9H). |

TABLE 2-continued

| The following examples were prepared employing similar protocol as described above. | | | |
|---|---|---|---|
| Example | Structure | MS | NMR |
| 233 | 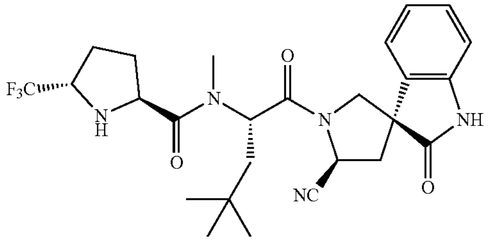 [SMILES: CN(C(=O)[C@@H]1CC[C@@H](C(F)(F)F)N1)[C@@H](CC(C)(C)C)C(=O)N1C[C@]2(C[C@H]1C#N)C(=O)Nc1ccccc12] | [M + H+] 520.2 | $^1$H NMR (400 MHz, Acetone-$d_6$) δ 9.76 (s, 1H), 7.33 (t, J = 7.7 Hz, 1H), 7.06 (dt, J = 20.3, 7.6 Hz, 4H), 5.47 (dd, J = 7.8, 4.5 Hz, 1H), 5.19 (t, J = 8.8 Hz, 1H), 4.04-3.91 (m, 2H), 3.86 (t, J = 6.4 Hz, 1H), 3.79 (s, 1H), 3.01 (s, 3H), 2.71 (m, 2H), 2.23 (m, 1H), 2.11 (s, 1H), 1.91 (m, 1H), 1.61 (m, 1H), 1.51 (m, 1H), 0.95 (s, 9H). |
| 234 | 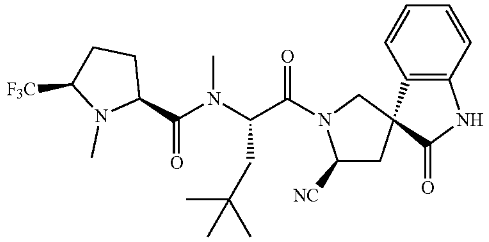 [SMILES: CN(C(=O)[C@@H]1CC[C@H](C(F)(F)F)N1C)[C@@H](CC(C)(C)C)C(=O)N1C[C@]2(C[C@H]1C#N)C(=O)Nc1ccccc12] | [M + H+] 534.3 | $^1$H NMR (400 MHz, Acetone-$d_6$) δ 9.73 (s, 1H), 7.29 (td, J = 7.7, 1.4 Hz, 1H), 7.09-6.94 (m, 3H), 5.53 (dd, J = 7.2, 5.1 Hz, 1H), 5.16 (t, J = 8.6 Hz, 1H), 4.08 (dd, J = 10.6, 1.3 Hz, 1H), 3.92 (d, J = 10.6 Hz, 1H), 3.48 (dd, J = 8.8, 6.0 Hz, 1H), 3.15 (ddd, J = 9.5, 7.6, 4.4 Hz, 1H), 3.09 (s, 3H), 2.78-2.62 (m, 2H), 2.36 (s, 3H), 2.16 (dd, J = 14.1, 7.3 Hz, 1H), 1.76 (ddt, J = 12.7, 8.2, 4.2 Hz, 1H), 1.69-1.54 (m, 1H), 1.26 (dq, J = 11.6, 8.5 Hz, 1H), 0.96 (s, 9H). |
| 235 | 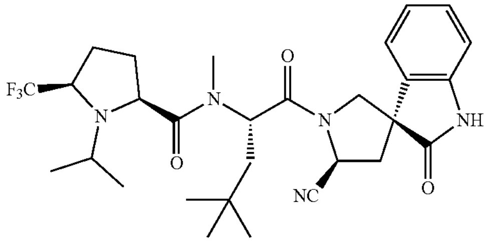 [SMILES: CC(C)N1[C@H](C(=O)N(C)[C@@H](CC(C)(C)C)C(=O)N2C[C@]3(C[C@H]2C#N)C(=O)Nc2ccccc23)CC[C@@H]1C(F)(F)F] | [M + H+] 562.3 | $^1$H NMR (400 MHz, Acetone-$d_6$) δ 9.72 (s, 1H), 7.29 (td, J = 7.7, 1.2 Hz, 1H), 7.09-6.99 (m, 2H), 6.96 (d, J = 7.4 Hz, 1H), 5.49 (dd, J = 7.9, 4.1 Hz, 1H), 5.17 (t, J = 8.6 Hz, 1H), 4.09 (d, J = 10.6 Hz, 1H), 3.91 (d, J = 10.6 Hz, 1H), 3.84 (t, J = 7.3 Hz, 1H), 3.52 (pd, J = 8.2, 3.4 Hz, 1H), 3.08 (s, 3H), 3.13-2.99 (m, 1H), 2.77-2.63 (m, 2H), 2.25 (dd, J = 13.9, 7.9 Hz, 1H), 1.84 (dq, J = 12.9, 8.8 Hz, 1H), 1.70 (ddt, J = 12.5, 7.5, 3.9 Hz, 1H), 1.60 (dt, J = 12.5, 6.1 Hz, 1H), 1.35 (dd, J = 13.9, 4.1 Hz, 1H), 1.18 (q, J = 10.5, 9.2 Hz, 1H), 0.99 (d, J = 6.6 Hz, 3H), 0.95 (s, 12H). |
| 236 | 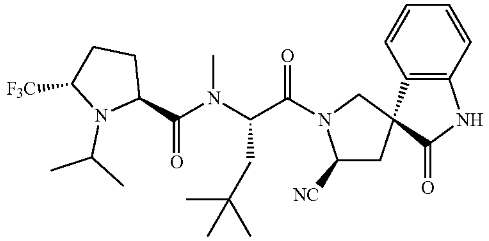 [SMILES: CC(C)N1[C@H](C(F)(F)F)CC[C@H]1C(=O)N(C)[C@@H](CC(C)(C)C)C(=O)N1C[C@]2(C[C@H]1C#N)C(=O)Nc1ccccc12] | [M + H+] 562.3 | $^1$H NMR (400 MHz, Acetone-$d_6$) δ 9.75 (s, 1H), 7.31 (td, J = 7.7, 1.3 Hz, 1H), 7.12-6.94 (m, 3H), 5.47 (dd, J = 7.9, 4.1 Hz, 1H), 5.19 (t, J = 8.7 Hz, 1H), 4.20-4.09 (m, 1H), 3.95 (d, J = 10.8 Hz, 1H), 3.73 (q, J = 7.6 Hz, 1H), 3.14-3.06 (m, 1H), 3.04 (s, 3H), 2.77-2.66 (m, 2H), 2.29 (dt, J = 13.9, 7.3 Hz, 1H), 1.06 (d, J = 6.8 Hz, 3H), 0.95 (d, J = 5.2 Hz, 12H). |
| 237 | 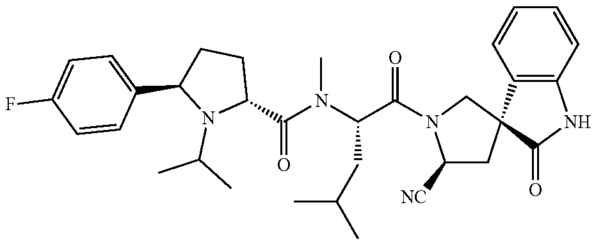 [SMILES: CC(C)C[C@@H](C(=O)N1C[C@]2(C[C@H]1C#N)C(=O)Nc1ccccc12)N(C)C(=O)[C@H]1CC[C@H](c2ccc(F)cc2)N1C(C)C] | [M + Na+] 596.3 | $^1$H NMR (400 MHz, Acetone-$d_6$) δ 9.72 (s, 1H), 7.40-7.32 (m, 2H), 7.29 (td, J = 7.4, 2.0 Hz, 1H), 7.11-6.96 (m, 5H), 5.50 (dd, J = 9.2, 5.9 Hz, 1H), 5.15 (t, J = 8.4 Hz, 1H), 4.42 (d, J = 7.5 Hz, 1H), 4.35 (dd, J = 10.1, 2.2 Hz, 1H), 4.04 (s, 2H), 3.08 (s, 3H), 2.89-2.79 (m, 1H), 2.71 (qd, J = 13.1, 8.4 Hz, 2H), 2.48-2.33 (m, 1H), 2.22 (tt, J = 12.4, 7.7 Hz, 1H), 1.82-1.59 (m, 2H), 1.49 (dq, J = 13.4, 6.5 Hz, 1H), 1.43-1.34 (m, 1H), 0.97 (dd, J = 14.0, 6.6 Hz, 6H), 0.58 (dd, J = 10.6, 6.4 Hz, 6H). |

TABLE 2-continued

The following examples were prepared employing similar protocol as described above.

| Example | Structure | MS | NMR |
|---|---|---|---|
| 238 | 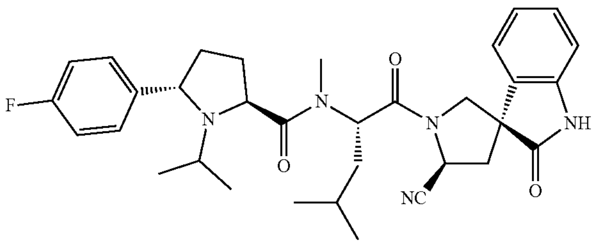 [SMILES: CC(C)C[C@@H](C(=O)N1C[C@]2(C[C@H]1C#N)C(=O)Nc1ccccc12)N(C)C(=O)[C@@H]1CC[C@@H](c2ccc(F)cc2)N1C(C)C] | [M + H+] 574.3 | $^1$H NMR (400 MHz, Acetone-d$_6$) δ 9.73 (s, 1H), 7.37-7.29 (m, 2H), 7.32-7.19 (m, 1H), 7.08-6.94 (m, 5H), 5.51 (dd, J = 9.6, 5.6 Hz, 1H), 5.17 (t, J = 8.6 Hz, 1H), 4.38 (d, J = 6.8 Hz, 1H), 4.26-4.18 (m, 1H), 4.06 (dd, J = 10.6, 1.3 Hz, 1H), 3.97 (d, J = 10.7 Hz, 1H), 3.11 (tt, J = 13.1, 6.8 Hz, 1H), 3.02 (s, 3H), 2.76-2.61 (m, 2H), 1.97-1.75 (m, 3H), 1.64 (ddd, J = 14.2, 9.1, 5.6 Hz, 1H), 1.53 (dtd, J = 9.2, 6.7, 4.8 Hz, 1H), 1.00-0.89 (m, 9H), 0.89-0.78 (m, 1H), 0.63 (d, J = 6.5 Hz, 3H). |
| 239 | 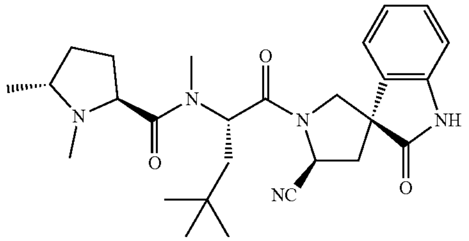 [SMILES: C[C@@H]1CC[C@@H](C(=O)N(C)[C@@H](CC(C)(C)C)C(=O)N2C[C@]3(C[C@H]2C#N)C(=O)Nc2ccccc23)N1C] | [M + H+] 480.3 | $^1$H NMR (400 MHz, Acetone-d$_6$) δ 9.76 (s, 1H), 7.31 (td, J = 7.6, 1.6 Hz, 1H), 7.05 (dt, J = 12.8, 7.4 Hz, 3H), 5.48 (dd, J = 7.5, 4.8 Hz, 1H), 5.18 (t, J = 8.6 Hz, 1H), 4.29 (s, 1H), 4.05 (d, J = 10.5 Hz, 1H), 3.98 (d, J = 10.5 Hz, 1H), 3.50 (s, 1H), 3.05 (s, 3H), 2.72 (qd, J = 13.2, 8.6 Hz, 2H), 2.57 (s, 3H), 2.21 (dd, J = 14.0, 7.5 Hz, 1H), 1.74-1.60 (m, 1H), 1.49 (dd, J = 14.0, 4.8 Hz, 1H), 1.41 (t, J = 7.3 Hz, 1H), 1.14 (m, 4H), 0.96 (s, 9H). |
| 240 | 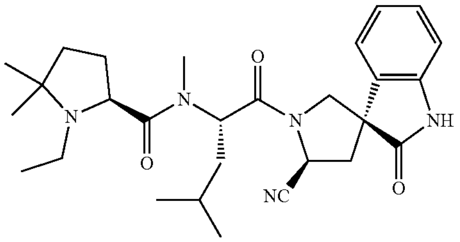 [SMILES: CCN1[C@H](C(=O)N(C)[C@@H](CC(C)C)C(=O)N2C[C@]3(C[C@H]2C#N)C(=O)Nc2ccccc23)CCC1(C)C] | [M + H+] 494.3 | $^1$H NMR (500 MHz, Acetone-d$_6$) δ 9.74 (s, 1H), 7.28 (ddd, J = 7.7, 6.6, 2.5 Hz, 1H), 7.02 (qd, J = 7.6, 4.0 Hz, 3H), 5.45 (dd, J = 9.5, 5.8 Hz, 1H), 5.15 (q, J = 9.4, 8.5 Hz, 1H), 4.12-4.03 (m, 1H), 3.94 (d, J = 10.7 Hz, 1H), 3.71 (dt, J = 9.8, 4.9 Hz, 1H), 3.06 (s, 3H), 2.76-2.60 (m, 3H), 2.34 (dq, J = 12.4, 7.2 Hz, 1H), 1.86 (ddd, J = 18.6, 9.2, 3.8 Hz, 1H), 1.76 (ddd, J = 14.4, 9.5, 5.0 Hz, 1H), 1.63 (ddd, J = 14.2, 8.9, 5.7 Hz, 1H), 1.56-1.47 (m, 1H), 1.43-1.26 (m, 3H), 1.07 (s, 3H), 1.01-0.95 (m, 3H), 0.95-0.89 (m, 6H), 0.86 (t, J = 7.2 Hz, 3H). |
| 241 | 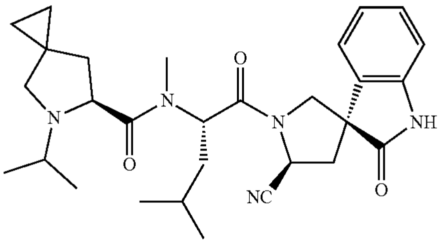 [SMILES: CC(C)C[C@@H](C(=O)N1C[C@]2(C[C@H]1C#N)C(=O)Nc1ccccc12)N(C)C(=O)[C@@H]1CC2(CC2)CN1C(C)C] | [M + H+] 506.3 | $^1$H NMR (400 MHz, Acetone-d$_6$) δ 10.05 (s, 1H), 7.33 (td, J = 7.5, 1.9 Hz, 1H), 7.14-7.02 (m, 3H), 5.55 (t, J = 7.5 Hz, 1H), 5.20 (t, J = 8.7 Hz, 1H), 4.10-3.98 (m, 2H), 3.91 (dd, J = 10.6, 1.2 Hz, 1H), 3.08 (s, 3H), 2.95 (d, J = 8.3 Hz, 1H), 2.82-2.66 (m, 2H), 1.92 (s, 1H), 1.76 (t, J = 7.2 Hz, 2H), 1.58 (dp, J = 13.4, 6.7 Hz, 1H), 1.08-0.92 (m, 12H), 0.75 (dd, J = 12.5, 4.4 Hz, 1H), 0.50 (ddd, J = 9.5, 5.7, 3.8 Hz, 1H), 0.43 (ddd, J = 9.5, 5.6, 3.8 Hz, 1H), 0.33 (ddd, J = 9.3, 5.7, 3.8 Hz, 1H), −0.00 (ddd, J = 9.7, 5.7, 3.8 Hz, 1H). |
| 242 | 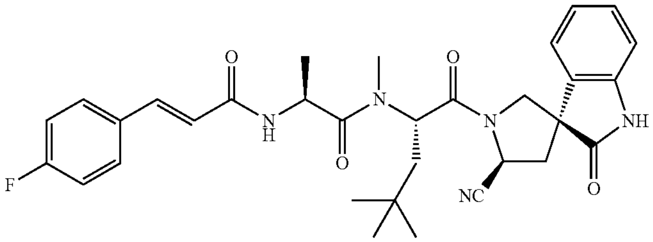 [SMILES: C[C@H](NC(=O)/C=C/c1ccc(F)cc1)C(=O)N(C)[C@@H](CC(C)(C)C)C(=O)N1C[C@]2(C[C@H]1C#N)C(=O)Nc1ccccc12] | [M − H]− 572.3 | $^1$H NMR (400 MHz, Acetone-d$_6$) δ 9.76 (s, 1H), 7.67-7.59 (m, 2H), 7.49 (d, J = 15.7 Hz, 1H), 7.35-7.24 (m, 2H), 7.22-7.00 (m, 5H), 6.71 (d, J = 15.7 Hz, 1H), 5.48 (dd, J = 7.7, 4.7 Hz, 1H), 5.19 (t, J = 8.5 Hz, 1H), 4.83-4.72 (m, 1H), 4.03 (dd, J = 10.5, 1.3 Hz, 1H), 3.96 (d, J = 10.5 Hz, 1H), 3.11 (s, 3H), 2.79-2.60 (m, 2H), 2.26-2.14 (m, 1H), 0.94 (s, 9H), 0.78 (d, J = 6.8 Hz, 3H). |

TABLE 2-continued

| The following examples were prepared employing similar protocol as described above. | | | |
|---|---|---|---|
| Example | Structure | MS | NMR |
| 243 | 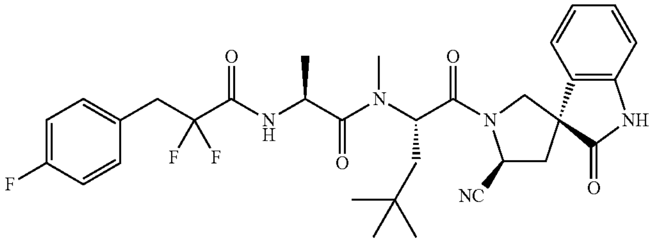 [SMILES: C[C@H](NC(=O)C(F)(F)Cc1ccc(F)cc1)C(=O)N(C)[C@@H](CC(C)(C)C)C(=O)N1C[C@]2(C[C@H]1C#N)C(=O)Nc1ccccc12] | [M − H]⁻ 610.3 | $^{1}$H NMR (400 MHz, Acetone-$d_6$) δ 9.75 (s, 1H), 7.58 (d, J = 7.4 Hz, 1H), 7.34-7.25 (m, 3H), 7.12-6.97 (m, 5H), 5.42 (dd, J = 7.8, 4.5 Hz, 1H), 5.17 (t, J = 8.5 Hz, 1H), 4.58 (p, J = 6.9 Hz, 1H), 4.01-3.89 (m, 2H), 3.38 (t, J = 16.9 Hz, 2H), 3.04 (s, 3H), 2.78-2.62 (m, 2H), 2.21 (dd, J = 13.9, 7.9 Hz, 1H), 1.46-1.37 (m, 1H), 0.93 (s, 9H), 0.73 (d, J = 6.8 Hz, 3H). |
| 244 | 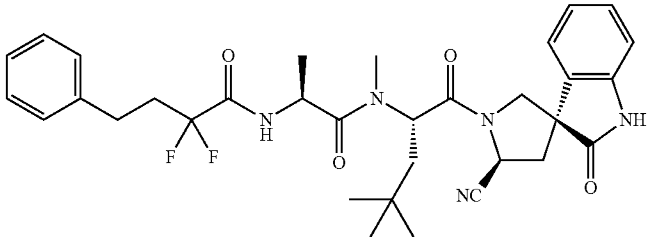 [SMILES: C[C@H](NC(=O)C(F)(F)CCc1ccccc1)C(=O)N(C)[C@@H](CC(C)(C)C)C(=O)N1C[C@]2(C[C@H]1C#N)C(=O)Nc1ccccc12] | [M − H]⁻ 606.3 | $^{1}$H NMR (400 MHz, Acetone-$d_6$) δ 9.75 (s, 1H), 7.82-7.76 (m, 1H), 7.33-7.16 (m, 6H), 7.11-6.99 (m, 3H), 5.47 (dd, J = 7.8, 4.5 Hz, 1H), 5.19 (t, J = 8.5 Hz, 1H), 4.72-4.60 (m, 1H), 3.97 (d, J = 2.5 Hz, 2H), 3.10 (s, 3H), 2.77-2.62 (m, 4H), 2.45-2.28 (m, 2H), 2.23 (dd, J = 13.9, 7.7 Hz, 1H), 0.94 (d, J = 0.8 Hz, 9H), 0.86 (d, J = 6.8 Hz, 3H). |
| 245 | 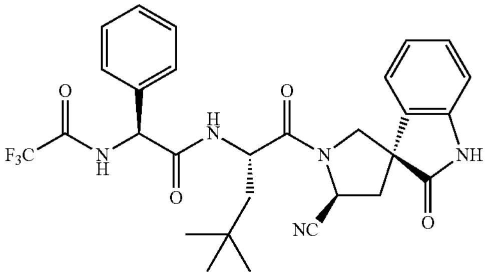 [SMILES: CC(C)(C)C[C@H](NC(=O)[C@@H](NC(=O)C(F)(F)F)c1ccccc1)C(=O)N1C[C@]2(C[C@H]1C#N)C(=O)Nc1ccccc12] | [M + $Na^+$] 592.2 | $^{1}$H NMR (400 MHz, Acetone-$d_6$) δ 9.70 (s, 1H), 8.74 (s, 1H), 8.01 (d, J = 7.9 Hz, 1H), 7.56-7.32 (m, 5H), 7.32-7.23 (m, 1H), 7.04-6.94 (m, 3H), 5.68 (d, J = 7.1 Hz, 1H), 5.06 (t, J = 8.3 Hz, 1H), 4.77 (td, J = 8.2, 4.1 Hz, 1H), 4.21 (d, J = 10.2 Hz, 1H), 3.99 (d, J = 10.2 Hz, 1H), 2.74-2.59 (m, 2H), 1.84 (dd, J = 14.5, 4.2 Hz, 1H), 1.65 (dd, J = 14.5, 8.4 Hz, 1H), 1.00 (s, 9H). |
| 246 | 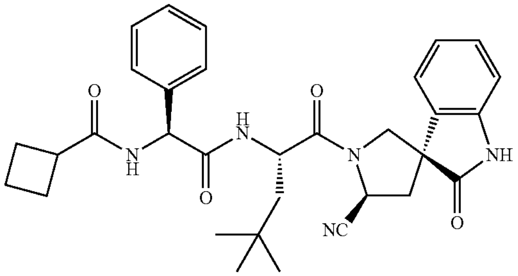 [SMILES: CC(C)(C)C[C@H](NC(=O)[C@@H](NC(=O)C1CCC1)c1ccccc1)C(=O)N1C[C@]2(C[C@H]1C#N)C(=O)Nc1ccccc12] | [M + $Na^+$] 578.3 | $^{1}$H NMR (400 MHz, Acetone-$d_6$) δ 9.67 (s, 1H), 7.83 (d, J = 8.2 Hz, 1H), 7.49-7.22 (m, 7H), 7.03-6.91 (m, 3H), 5.61 (d, J = 8.0 Hz, 1H), 5.04 (t, J = 8.2 Hz, 1H), 4.76 (td, J = 8.1, 4.6 Hz, 1H), 4.21 (d, J = 10.2 Hz, 1H), 3.98 (d, J = 10.1 Hz, 1H), 3.31-3.18 (m, 1H), 2.75-2.58 (m, 2H), 2.35-2.14 (m, 2H), 2.01-1.72 (m, 3H), 1.64 (dd, J = 14.4, 8.0 Hz, 1H), 0.98 (s, 9H). |
| 247 | 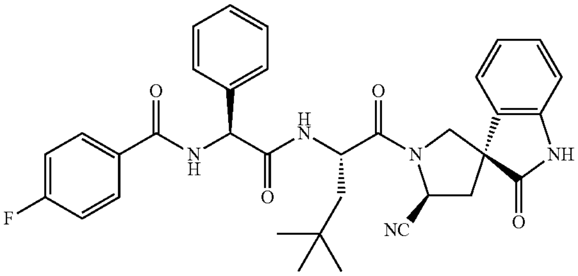 [SMILES: CC(C)(C)C[C@H](NC(=O)[C@@H](NC(=O)c1ccc(F)cc1)c1ccccc1)C(=O)N1C[C@]2(C[C@H]1C#N)C(=O)Nc1ccccc12] | [M + $Na^+$] 618.3 | $^{1}$H NMR (400 MHz, Acetone-$d_6$) δ 9.68 (s, 1H), 8.07-7.94 (m, 4H), 7.53-7.46 (m, 2H), 7.42-7.30 (m, 3H), 7.30-7.17 (m, 3H), 7.05-6.94 (m, 3H), 5.84 (d, J = 7.7 Hz, 1H), 5.06 (t, J = 8.3 Hz, 1H), 4.80 (td, J = 8.1, 4.4 Hz, 1H), 4.23 (d, J = 10.2 Hz, 1H), 4.00 (d, J = 10.2 Hz, 1H), 2.74-2.59 (m, 2H), 1.87 (dd, J = 14.4, 4.5 Hz, 1H), 1.66 (dd, J = 14.4, 8.1 Hz, 1H), 0.99 (s, 9H). |

TABLE 2-continued

| The following examples were prepared employing similar protocol as described above. | | | |
|---|---|---|---|
| Example | Structure | MS | NMR |
| 248 | 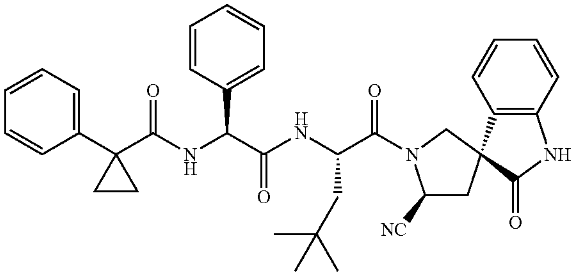 [SMILES: CC(C)(C)C[C@H](NC(=O)[C@@H](NC(=O)C1(c2ccccc2)CC1)c1ccccc1)C(=O)N1C[C@]2(C[C@H]1C#N)C(=O)Nc1ccccc12] | [M + H+] 618.3 | $^1$H NMR (400 MHz, Acetone-$d_6$) δ 9.65 (s, 1H), 7.84 (d, J = 8.0 Hz, 1H), 7.52-7.17 (m, 11H), 7.01-6.94 (m, 1H), 6.91-6.83 (m, 2H), 6.55 (d, J = 7.5 Hz, 1H), 5.56 (d, J = 7.6 Hz, 1H), 4.99 (t, J = 8.1 Hz, 1H), 4.67 (td, J = 8.2, 4.1 Hz, 1H), 4.09 (d, J = 10.3 Hz, 1H), 3.92 (d, J = 10.2 Hz, 1H), 2.73-2.52 (m, 2H), 1.80 (dd, J = 14.5, 4.1 Hz, 1H), 1.61 (dd, J = 14.5, 8.4 Hz, 1H), 1.11-0.99 (m, 2H), 0.98 (s, 9H). |
| 249 | 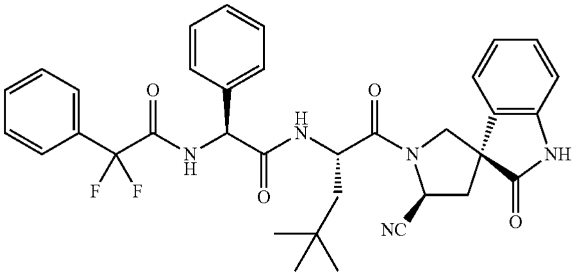 [SMILES: CC(C)(C)C[C@H](NC(=O)[C@@H](NC(=O)C(F)(F)c1ccccc1)c1ccccc1)C(=O)N1C[C@]2(C[C@H]1C#N)C(=O)Nc1ccccc12] | [M + Na+] 650.3 | $^1$H NMR (400 MHz, Acetone-$d_6$) δ 9.69 (s, 1H), 8.28 (d, J = 7.7 Hz, 1H), 7.96 (d, J = 9.1 Hz, 1H), 7.67-7.61 (m, 2H), 7.52 (ddd, J = 14.8, 8.2, 6.4 Hz, 3H), 7.46-7.32 (m, 5H), 7.32-7.23 (m, 1H), 7.04-6.98 (m, 1H), 7.02-6.91 (m, 2H), 5.68-5.62 (m, 1H), 5.05 (t, J = 8.2 Hz, 1H), 4.77 (td, J = 8.1, 4.2 Hz, 1H), 4.20 (d, J = 10.2 Hz, 1H), 3.99 (d, J = 10.2 Hz, 1H), 2.74-2.59 (m, 2H), 1.88-1.79 (m, 1H), 1.63 (dd, J = 14.5, 8.3 Hz, 1H), 0.98 (s, 9H). |
| 250 | 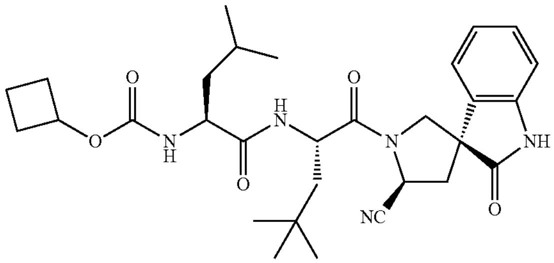 [SMILES: CC(C)C[C@H](NC(=O)OC1CCC1)C(=O)N[C@@H](CC(C)(C)C)C(=O)N1C[C@]2(C[C@H]1C#N)C(=O)Nc1ccccc12] | [M + Na+] 574.3 | $^1$H NMR (400 MHz, Acetone-$d_6$) δ 9.56 (s, 1H), 7.34 (d, J = 8.5 Hz, 1H), 7.13 (td, J = 7.5, 1.7 Hz, 1H), 6.98-6.79 (m, 3H), 6.10 (d, J = 8.6 Hz, 1H), 4.96 (t, J = 8.4 Hz, 1H), 4.81-4.68 (m, 1H), 4.61 (td, J = 8.2, 4.6 Hz, 1H), 4.13 (d, J = 10.2 Hz, 1H), 4.00 (q, J = 8.2 Hz, 1H), 3.85 (d, J = 10.2 Hz, 1H), 2.63-2.44 (m, 2H), 2.19-2.04 (m, 2H), 1.89-1.79 (m, 1H), 1.78-1.66 (m, 1H), 1.64-1.38 (m, 3H), 1.36-1.30 (m, 2H), 0.83 (s, 9H), 0.76 (dd, J = 8.1, 6.5 Hz, 6H). |
| 251 | 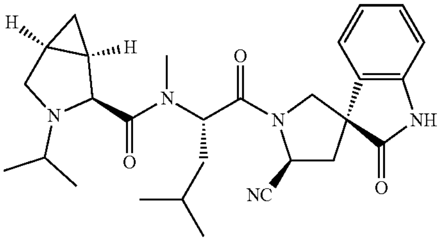 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C(C)C] | [M − H+] 490.3 | $^1$H NMR (400 MHz, Acetone-d6) δ 7.18 (s, 1H), 6.97-6.83 (m, 2H), 5.94 (s, 1H), 5.28 (d, J = 7.3 Hz, 1H), 5.06-4.90 (m, 1H), 4.27 (s, 1H), 2.97 (s, 1H), 2.62-2.50 (m, 2H), 1.90 (s, 25H), 1.22 (s, 3H), 1.19 (s, 3H), 0.88-0.75 (m, 3H). |
| 252 | 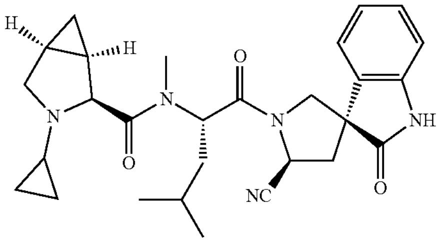 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C1CC1] | [M − H+] 488.2 | $^1$H NMR (400 MHz, Acetone-d6) δ 7.14 (d, J = 7.4 Hz, 2H), 6.94 (d, J = 8.1 Hz, 2H), 6.86 (d, J = 7.5 Hz, 2H), 5.62 (s, 1H), 5.30 (s, 1H), 3.94 (d, J = 6.7 Hz, 2H), 3.88 (s, 2H), 3.65 (s, 1H), 3.58 (s, 1H), 2.95 (d, J = 14.3 Hz, 3H), 2.68 (s, 3H), 1.57 (s, 2H), 1.16 (s, 3H), 1.09 (t, J = 7.0 Hz, 4H), 0.88-0.75 (m, 10H), 0.30 (s, 2H) |

TABLE 2-continued

The following examples were prepared employing similar protocol as described above.

| Ex-am-ple | Structure | MS | NMR |
|---|---|---|---|
| 253 | 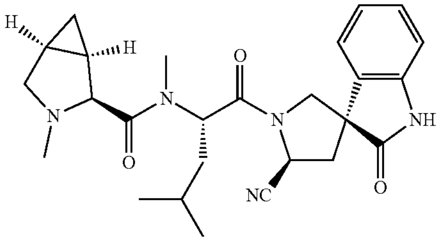 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C] | [M − H+] 462.1 | $^1$H NMR (400 MHz, Acetone-d6) δ 7.22 (t, J = 7.5 Hz, 1H), 7.09-6.81 (m, 3H), 5.30 (q, J = 7.4 Hz, 1H), 5.17-4.98 (m, 3H), 3.95-3.84 (m, 1H), 3.78 (d, J = 10.7 Hz, 1H), 3.43 (s, 1H), 2.66 (d, J = 13.6 Hz, 3H), 2.53 (td, J = 13.3, 8.5 Hz, 2H), 2.41 (s, 1H), 2.30 (d, J = 17.3 Hz, 1H), 1.53 (d, J = 5.0 Hz, 3H), 1.40-1.32 (m, 1H), 1.16 (s, 1H), 0.80 (ddd, J = 12.3, 6.6, 2.1 Hz, 5H), 0.42 (s, 1H), 0.32 (s, 1H). |
| 254 | 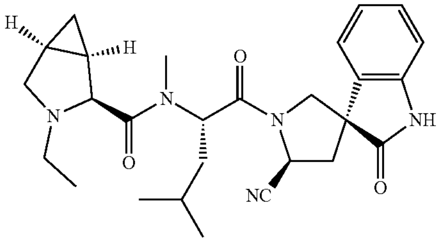 [SMILES: CCN1C[C@H]2C[C@H]2[C@H]1C(=O)N(C)[C@@H](CC(C)C)C(=O)N1C[C@]2(C[C@H]1C#N)C(=O)Nc1ccccc12] | [M − H+] 476.3 | $^1$H NMR (400 MHz, Acetone-d6) δ 9.58 (s, 1H), 7.14 (t, J = 7.6 Hz, 1H), 6.89 (dd, J = 18.7, 7.4 Hz, 3H), 5.61 (s, 1H), 5.30 (t, J = 7.6 Hz, 1H), 5.00 (t, J = 8.5 Hz, 1H), 3.86 (d, J = 10.6 Hz, 1H), 3.78 (d, J = 10.7 Hz, 1H), 3.53 (d, J = 1.2 Hz, 1H), 2.70-2.58 (m, 6H), 2.58 (s, 1H), 2.56-2.47 (m, 2H), 1.54 (d, J = 7.7 Hz, 2H), 1.46 (s, 1H), 1.41-1.33 (m, 2H), 1.20 (s, 1H), 0.80 (dd, J = 12.3, 6.5 Hz, 6H), 0.52 (t, J = 7.2 Hz, 3H), 0.44 (s, 1H), 0.31 (s, 1H). |
| 255 | 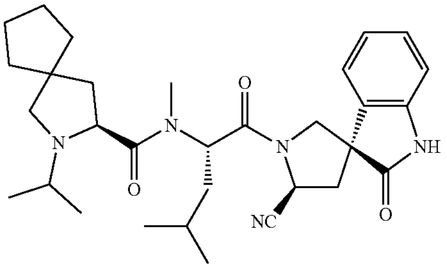 [SMILES: CC(C)C[C@@H](C(=O)N1C[C@]2(C[C@H]1C#N)C(=O)Nc1ccccc12)N(C)C(=O)[C@@H]1CC2(CCCC2)CN1C(C)C] | [M − H+] 532.2 | $^1$H NMR (400 MHz, Acetone-d6) δ 9.67 (s, 1H), 7.18 (s, 1H), 6.92 (t, J = 5.9 Hz, 3H), 5.31 (dd, J = 9.2, 6.0 Hz, 1H), 5.00 (t, J = 8.6 Hz, 1H), 4.81 (s, 1H), 3.94 (d, J = 10.5 Hz, 1H), 3.68 (s, 1H), 3.58 (d, J = 10.3 Hz, 1H), 3.24 (d, J = 11.7 Hz, 1H), 2.68-2.60 (m, 4H), 2.60-2.48 (m, 3H), 1.86 (s, 5H), 1.46 (s, 3H), 1.35 (s, 1H), 1.28 (d, J = 6.4 Hz, 3H), 1.21-1.13 (m, 3H), 0.79 (dd, J = 18.6, 6.6 Hz, 6H), 0.59 (s, 1H). |
| 256 | 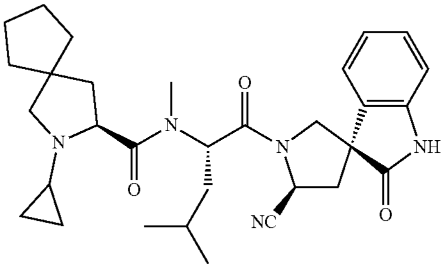 [SMILES: CC(C)C[C@@H](C(=O)N1C[C@]2(C[C@H]1C#N)C(=O)Nc1ccccc12)N(C)C(=O)[C@@H]1CC2(CCCC2)CN1C1CC1] | [M − H+] 530.1 | $^1$H NMR (400 MHz, Acetone-d6) δ 9.75 (s, 1H), 7.35-7.27 (m, 1H), 7.12-6.97 (m, 3H), 5.52 (dd, J = 9.7, 5.3 Hz, 1H), 5.14 (t, J = 8.6 Hz, 1H), 3.97-3.86 (m, 2H), 3.70 (dd, J = 9.1, 5.9 Hz, 1H), 2.89 (d, J = 8.3 Hz, 1H), 2.85-2.77 (m, 3H), 2.69 (qd, J = 13.2, 8.7 Hz, 3H), 2.41 (d, J = 8.4 Hz, 1H), 2.01 (s, 2H), 1.85 (s, 1H), 1.78 (ddd, J = 13.9, 9.7, 4.3 Hz, 2H), 1.65-1.48 (m, 6H), 1.47 (s, 2H), 1.44 (s, 1H), 1.32 (d, J = 11.6 Hz, 2H), 1.06 (d, J = 5.5 Hz, 1H), 0.96 (dd, J = 9.9, 6.4 Hz, 6H), 0.80 (dd, J = 12.5, 6.1 Hz, 2H), 0.37 (d, J = 9.1 Hz, 1H), 0.24 (d, J = 6.7 Hz, 2H). |
| 257 | 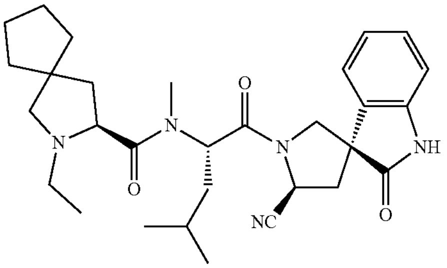 [SMILES: CCN1CC2(CCCC2)C[C@H]1C(=O)N(C)[C@@H](CC(C)C)C(=O)N1C[C@]2(C[C@H]1C#N)C(=O)Nc1ccccc12] | [M − H+] 518.2 | $^1$H NMR (400 MHz, Acetone-d6) δ 9.66 (s, 1H), 7.18 (s, 1H), 6.92 (d, J = 5.9 Hz, 2H), 5.31 (dd, J = 9.5, 5.7 Hz, 1H), 5.00 (t, J = 8.5 Hz, 1H), 3.92 (s, 1H), 3.71 (s, 1H), 3.62 (s, 1H), 3.28 (s, 1H), 2.64 (d, J = 13.5 Hz, 3H), 2.60-2.48 (m, 3H), 1.86 (s, 3H), 1.48 (s, 2H), 1.11 (s, 1H), 0.79 (dd, J = 16.8, 6.6 Hz, 5H). |

TABLE 2-continued

The following examples were prepared employing similar protocol as described above.

| Example | Structure | MS | NMR |
|---|---|---|---|
| 258 | 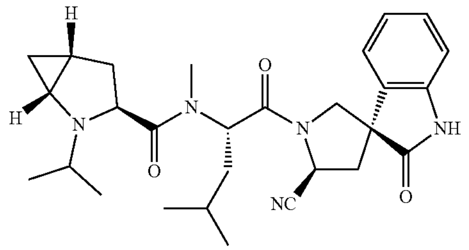 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C(C)C] | [M − H$^+$] 490.3 | $^1$H NMR (400 MHz, Acetone-d6) δ 7.17 (t, J = 7.9 Hz, 1H), 6.96-6.84 (m, 2H), 5.33-5.25 (m, 1H), 4.98 (t, J = 8.8 Hz, 1H), 3.81 (q, J = 10.3 Hz, 2H), 2.70-2.62 (m, 5H), 2.59-2.49 (m, 2H), 1.71 (d, J = 8.2 Hz, 2H), 1.53 (t, J = 6.9 Hz, 2H), 1.16 (s, 1H), 0.91 (d, J = 6.3 Hz, 2H), 0.84-0.70 (m, 6H), 0.33 (s, 1H). |
| 259 | 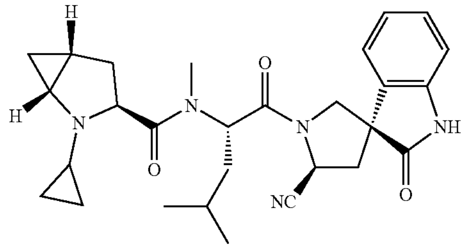 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C1CC1] | [M − H$^+$] 488.5 | $^1$H NMR (400 MHz, Acetone-d6) δ 9.57 (s, 1H), 7.17 (dd, J = 8.4, 7.1 Hz, 1H), 6.97-6.82 (m, 2H), 5.49 (d, J = 0.9 Hz, 1H), 5.37-5.22 (m, 1H), 4.99 (t, J = 8.6 Hz, 1H), 3.78 (q, J = 10.7 Hz, 2H), 3.13 (dd, J = 9.9, 7.5 Hz, 1H), 2.70-2.59 (m, 6H), 2.59-2.46 (m, 2H), 1.94-1.88 (m, 37H), 1.65-1.57 (m, 1H), 1.57-1.48 (m, 1H), 1.48-1.41 (m, 1H), 1.16 (s, 3H), 1.14-1.03 (m, 2H), 0.93-0.82 (m, 2H), 0.82-0.71 (m, 4H), 0.32-0.15 (m, 2H). |
| 260 | 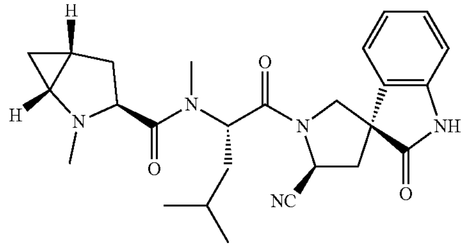 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C] | [M − H$^+$] 462.3 | $^1$H NMR (400 MHz, Acetone-d6) δ 7.13 (dd, J = 25.2, 7.7 Hz, 1H), 7.04-6.85 (m, 2H), 5.36-5.26 (m, 1H), 5.13 (q, J = 10.8 Hz, 1H), 4.99 (td, J = 8.4, 2.8 Hz, 1H), 3.77 (d, J = 3.1 Hz, 1H), 3.77-3.69 (m, 1H), 2.85 (d, J = 4.5 Hz, 2H), 2.66 (d, J = 13.5 Hz, 4H), 2.60-2.43 (m, 3H), 1.60 (ddd, J = 17.5, 8.5, 4.6 Hz, 2H), 1.55-1.46 (m, 1H), 1.30 (s, 1H), 1.16 (s, 1H), 1.04 (s, 1H), 0.79 (ddd, J = 13.8, 6.6, 1.9 Hz, 4H), 0.42 (s, 1H), −0.10-−0.19 (m, 1H). |
| 261 | 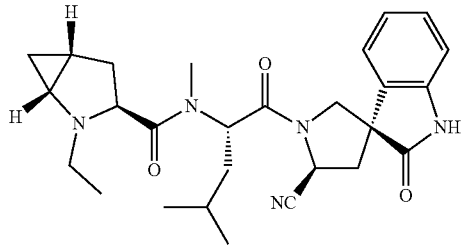 [SMILES: CCN1[C@@H]2C[C@@H]2C[C@H]1C(=O)N(C)[C@@H](CC(C)C)C(=O)N1C[C@]2(C[C@H]1C#N)C(=O)Nc1ccccc12] | [M − H$^+$] 476.5 | $^1$H NMR (400 MHz, Acetone-d6) δ 9.58 (s, 1H), 7.17 (t, J = 7.7 Hz, 1H), 6.92 (dd, J = 13.6, 6.1 Hz, 1H), 6.89-6.85 (m, 1H), 5.31 (dd, J = 8.9, 6.2 Hz, 1H), 4.98 (t, J = 8.5 Hz, 1H), 3.85-3.73 (m, 2H), 2.81 (dd, J = 10.0, 7.6 Hz, 1H), 2.66 (d, J = 13.6 Hz, 3H), 2.63-2.46 (m, 3H), 2.23 (dd, J = 11.3, 7.4 Hz, 1H), 1.64 (dd, J = 12.1, 7.7 Hz, 2H), 1.59-1.48 (m, 2H), 1.36-1.28 (m, 1H), 1.18-1.07 (m, 2H), 1.06 (s, 1H), 0.89 (s, 1H), 0.87-0.80 (m, 3H), 0.80-0.74 (m, 3H), 0.39 (s, 1H), −0.07-−0.17 (m, 1H). |
| 262 | 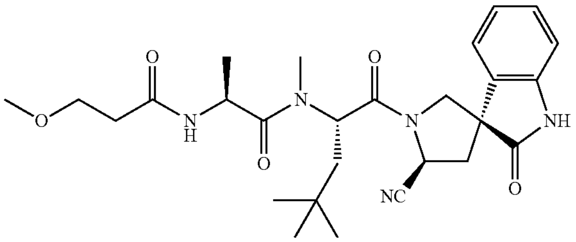 [SMILES: COCCC(=O)N[C@@H](C)C(=O)N(C)[C@@H](CC(C)(C)C)C(=O)N1C[C@]2(C[C@H]1C#N)C(=O)Nc1ccccc12] | [M − H$^+$] 510.2 | $^1$H NMR (400 MHz, Acetone-d6) 1H NMR (400 MHz, Acetone-d6) δ 9.59 (s, 1H), 7.15 (t, J = 7.7 Hz, 1H), 6.93 (q, J = 8.3, 7.5 Hz, 2H), 6.87 (t, J = 7.2 Hz, 2H), 5.31 (dd, J = 7.6, 4.8 Hz, 1H), 5.03 (t, J = 8.5 Hz, 1H), 4.48 (p, J = 7.0 Hz, 1H), 3.88 (d, J = 10.6 Hz, 1H), 3.79 (d, J = 10.5 Hz, 1H), 3.41 (dtt, J = 12.4, 9.3, 6.2 Hz, 3H), 3.15 (s, 1H), 3.09 (s, 3H), 2.66 (d, J = 12.8 Hz, 2H), 2.60 (d, J = 4.8 Hz, 1H), 2.58-2.48 (m, 2H), 2.21 (t, J = 6.3 Hz, 2H), 2.03 (dd, J = 14.0, 7.5 Hz, 1H), 1.89 (s, 6H), 1.29 (dd, J = 13.9, 4.7 Hz, 1H), 0.79 (s, 8H), 0.75 (s, 1H), 0.55 (d, J = 6.7 Hz, 3H). |

TABLE 2-continued

| The following examples were prepared employing similar protocol as described above. | | | |
|---|---|---|---|
| Example | Structure | MS | NMR |
| 263 | 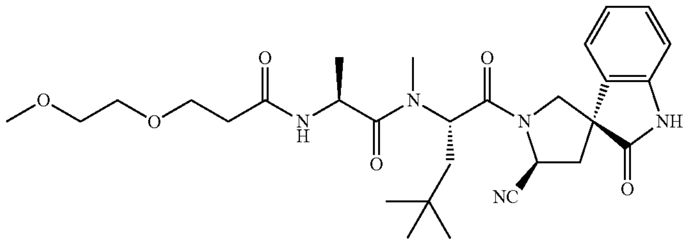 [SMILES: COCCOCCC(=O)N[C@@H](C)C(=O)N(C)[C@@H](CC(C)(C)C)C(=O)N1C[C@]2(C[C@H]1C#N)C(=O)Nc1ccccc12] | [M − H+] 554.3 | $^1$H NMR (400 MHz, Acetone-d6) δ 9.62 (s, 1H), 7.19-7.09 (m, 2H), 6.97-6.91 (m, 1H), 6.91-6.84 (m, 2H), 5.31 (dd, J = 7.6, 4.7 Hz, 1H), 5.04 (t, J = 8.4 Hz, 1H), 4.56-4.44 (m, 1H), 3.86 (t, J = 4.7 Hz, 7H), 3.80 (d, J = 10.5 Hz, 2H), 3.57 (t, J = 6.3 Hz, 1H), 3.50 (t, J = 6.1 Hz, 2H), 3.47-3.40 (m, 2H), 3.40-3.27 (m, 12H), 3.14 (d, J = 14.9 Hz, 5H), 2.96 (s, 1H), 2.91 (s, 3H), 2.68-2.48 (m, 2H), 2.40 (t, J = 6.3 Hz, 1H), 2.24 (td, J = 6.1, 1.6 Hz, 2H), 2.05 (dd, J = 14.0, 7.6 Hz, 1H), 1.29 (dd, J = 13.9, 4.7 Hz, 1H), 0.79 (s, 9H), 0.60 (d, J = 6.8 Hz, 3H). |
| 264 | 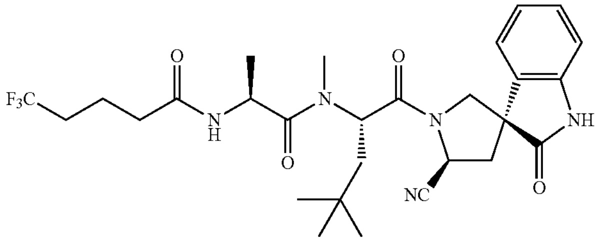 [SMILES: C[C@H](NC(=O)CCCC(F)(F)F)C(=O)N(C)[C@@H](CC(C)(C)C)C(=O)N1C[C@]2(C[C@H]1C#N)C(=O)Nc1ccccc12] | [M − H+] 562.7 | $^1$H NMR (400 MHz, Acetone-d6) 1H NMR (400 MHz, Acetone-d6) δ 9.60 (s, 1H), 7.15 (td, J = 7.6, 1.1 Hz, 1H), 6.99 (d, J = 7.7 Hz, 1H), 6.92 (dd, J = 8.0, 7.0 Hz, 1H), 6.87 (t, J = 6.4 Hz, 2H), 5.31 (dd, J = 7.5, 4.9 Hz, 1H), 5.03 (t, J = 8.5 Hz, 1H), 4.48 (p, J = 6.9 Hz, 1H), 3.85 (d, J = 10.6 Hz, 1H), 3.79 (d, J = 10.5 Hz, 1H), 2.70-2.48 (m, 4H), 2.12 (t, J = 7.1 Hz, 2H), 2.09-1.98 (m, 3H), 1.94-1.89 (m, 23H), 1.70-1.58 (m, 2H), 1.29 (dd, J = 14.0, 4.8 Hz, 1H), 0.78 (s, 7H), 0.56 (d, J = 6.8 Hz, 3H). |
| 265 | 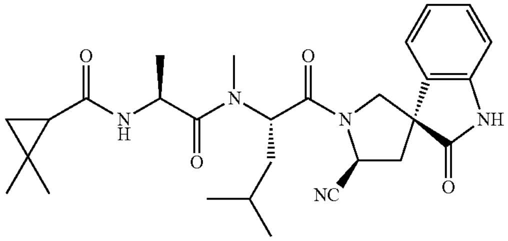 [SMILES: CC(C)C[C@@H](C(=O)N1C[C@]2(C[C@H]1C#N)C(=O)Nc1ccccc12)N(C)C(=O)[C@H](C)NC(=O)C1CC1(C)C] | [M − H+] 506.5 | $^1$H NMR (400 MHz, Acetone-d6) δ 9.64-9.60 (m, 1H), 7.19-7.00 (m, 2H), 6.98-6.78 (m, 3H), 5.33-5.24 (m, 1H), 5.02 (td, J = 8.4, 2.5 Hz, 1H), 4.51 (ddt, J = 13.3, 8.1, 6.7 Hz, 1H), 3.87-3.73 (m, 2H), 2.89 (dd, J = 2.4, 1.0 Hz, 3H), 2.70-2.47 (m, 4H), 1.67-1.49 (m, 2H), 1.49-1.34 (m, 2H), 1.32 (dd, J = 8.1, 5.4 Hz, 1H), 0.99-0.89 (m, 6H), 0.84-0.69 (m, 8H), 0.57 (ddd, J = 9.6, 6.8, 0.9 Hz, 3H), 0.47 (dd, J = 8.0, 3.8 Hz, 1H). |
| 266 | 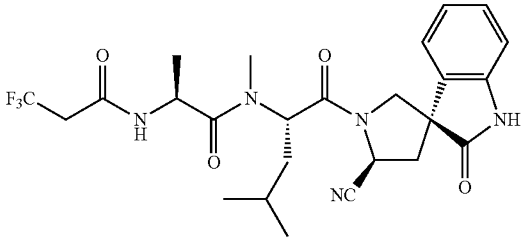 [SMILES: CC(C)C[C@@H](C(=O)N1C[C@]2(C[C@H]1C#N)C(=O)Nc1ccccc12)N(C)C(=O)[C@H](C)NC(=O)CC(F)(F)F] | [M − H+] 520.0 | $^1$H NMR (400 MHz, Acetone-d6) δ 9.61 (s, 1H), 7.45-7.33 (m, 1H), 7.15 (ddd, J = 7.9, 6.9, 2.0 Hz, 1H), 6.97-6.84 (m, 3H), 5.28 (dd, J = 8.6, 6.4 Hz, 1H), 5.03 (t, J = 8.4 Hz, 1H), 4.55 (p, J = 6.9 Hz, 1H), 3.32 (q, J = 10.8 Hz, 1H), 3.11 (qd, J = 10.9, 2.9 Hz, 2H), 2.91 (s, 3H), 2.65-2.48 (m, 2H), 1.64-1.47 (m, 2H), 1.43-1.28 (m, 1H), 0.79 (d, J = 6.6 Hz, 3H), 0.74 (d, J = 6.5 Hz, 3H), 0.64 (d, J = 6.8 Hz, 3H). |
| 267 | 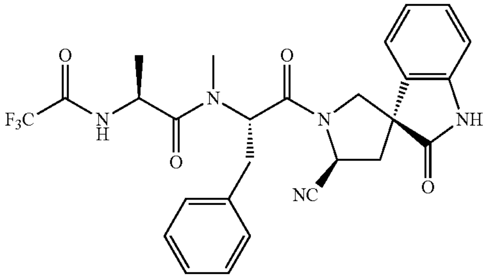 [SMILES: C[C@H](NC(=O)C(F)(F)F)C(=O)N(C)[C@@H](Cc1ccccc1)C(=O)N1C[C@]2(C[C@H]1C#N)C(=O)Nc1ccccc12] | [M − H+] 540.1 | $^1$H NMR (400 MHz, Acetone-d6) δ 9.55 (s, 1H), 7.14 (s, 1H), 7.13-7.01 (m, 3H), 6.92 (d, J = 6.0 Hz, 1H), 6.85 (d, J = 7.7 Hz, 1H), 5.41 (t, J = 7.6 Hz, 1H), 5.02 (t, J = 8.4 Hz, 1H), 3.71 (d, J = 10.6 Hz, 1H), 3.53 (d, J = 10.6 Hz, 1H), 3.17 (dd, J = 13.9, 7.3 Hz, 1H), 3.04 (s, 2H), 2.88 (dd, J = 13.8, 8.1 Hz, 1H), 2.46 (dd, J = 13.1, 8.6 Hz, 1H), 1.16 (s, 2H), 0.73 (d, J = 6.8 Hz, 2H). |

TABLE 2-continued

The following examples were prepared employing similar protocol as described above.

| Example | Structure | MS | NMR |
|---|---|---|---|
| 268 | 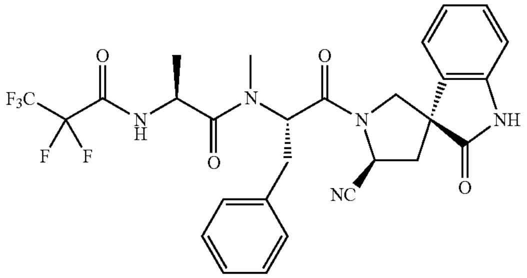 [SMILES: C[C@H](NC(=O)C(F)(F)C(F)(F)F)C(=O)N(C)[C@@H](Cc1ccccc1)C(=O)N1C[C@]2(C[C@H]1C#N)C(=O)Nc1ccccc12] | [M − H+] 590.3 | ¹H NMR (400 MHz, Acetone-d6) δ 9.55 (s, 1H), 7.14-7.01 (m, 3H), 6.91 (d, J = 7.0 Hz, 1H), 6.85 (d, J = 7.8 Hz, 1H), 5.41 (t, J = 7.7 Hz, 1H), 5.02 (t, J = 8.4 Hz, 1H), 3.71 (d, J = 10.7 Hz, 1H), 3.53 (d, J = 10.7 Hz, 1H), 3.03 (d, J = 2.6 Hz, 2H), 2.46 (dd, J = 13.1, 8.5 Hz, 1H), 1.16 (s, 1H), 0.74 (t, J = 7.5 Hz, 2H). |
| 269 | 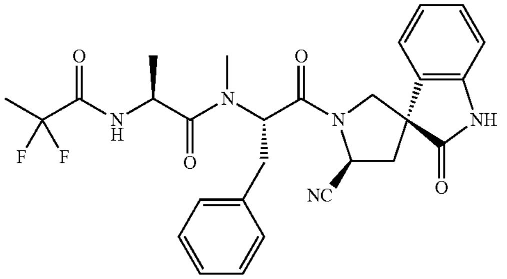 [SMILES: C[C@H](NC(=O)C(C)(F)F)C(=O)N(C)[C@@H](Cc1ccccc1)C(=O)N1C[C@]2(C[C@H]1C#N)C(=O)Nc1ccccc12] | [M − H+] 536.4 | ¹H NMR (400 MHz, Acetone-d6) δ 9.55 (s, 1H), 7.23 (s, 1H), 7.13 (t, J = 6.1 Hz, 3H), 7.10-7.02 (m, 2H), 6.91 (d, J = 6.3 Hz, 2H), 6.85 (d, J = 7.7 Hz, 1H), 5.41 (t, J = 7.6 Hz, 1H), 5.02 (t, J = 8.4 Hz, 1H), 4.46 (t, J = 7.0 Hz, 1H), 3.73 (d, J = 10.4 Hz, 1H), 3.52 (d, J = 10.6 Hz, 1H), 3.17 (dd, J = 13.8, 7.3 Hz, 1H), 3.01 (d, J = 3.0 Hz, 2H), 2.89 (dd, J = 13.7, 7.9 Hz, 1H), 2.60 (s, 4H), 2.46 (dd, J = 13.3, 8.6 Hz, 1H), 1.60 (s, 1H), 1.52 (d, J = 19.4 Hz, 2H), 1.16 (s, 1H), 0.70 (d, J = 6.8 Hz, 2H). |
| 270 | 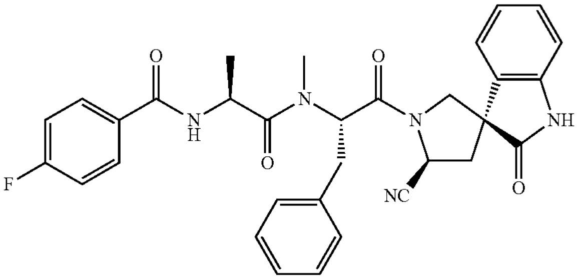 [SMILES: C[C@H](NC(=O)c1ccc(F)cc1)C(=O)N(C)[C@@H](Cc1ccccc1)C(=O)N1C[C@]2(C[C@H]1C#N)C(=O)Nc1ccccc12] | [M − H+] 566.4 | ¹H NMR (400 MHz, Acetone-d6) δ 9.56 (s, 1H), 7.76-7.68 (m, 1H), 7.15-6.99 (m, 5H), 6.95 (s, 2H), 6.86 (d, J = 7.7 Hz, 1H), 5.43 (t, J = 7.7 Hz, 1H), 5.03 (t, J = 8.3 Hz, 1H), 4.71-4.63 (m, 1H), 3.80 (d, J = 10.8 Hz, 1H), 3.54 (d, J = 10.5 Hz, 1H), 3.38 (d, J = 8.0 Hz, 1H), 3.16 (d, J = 6.5 Hz, 1H), 3.04 (s, 2H), 2.60 (d, J = 1.0 Hz, 3H), 2.56 (s, 2H), 2.52-2.44 (m, 2H), 1.31 (t, J = 7.2 Hz, 2H), 1.16 (s, 1H), 0.69 (d, J = 6.8 Hz, 2H). |
| 271 | 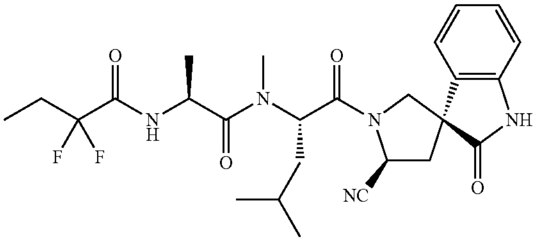 [SMILES: CCC(F)(F)C(=O)N[C@@H](C)C(=O)N(C)[C@@H](CC(C)C)C(=O)N1C[C@]2(C[C@H]1C#N)C(=O)Nc1ccccc12] | [M − H+] 516.5 | ¹H NMR (400 MHz, Acetone-d6) δ 9.58 (s, 1H), 7.19-7.10 (m, 1H), 6.97-6.81 (m, 3H), 5.29 (dd, J = 9.0, 6.0 Hz, 1H), 5.02 (t, J = 8.4 Hz, 1H), 4.53 (q, J = 6.9 Hz, 1H), 3.85-3.74 (m, 2H), 2.93 (s, 3H), 1.67-1.46 (m, 3H), 1.37 (dq, J = 13.7, 6.7 Hz, 1H), 0.82-0.78 (m, 4H), 0.73 (t, J = 7.1 Hz, 6H). |
| 272 | 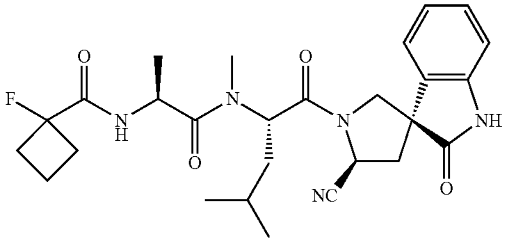 [SMILES: CC(C)C[C@@H](C(=O)N1C[C@]2(C[C@H]1C#N)C(=O)Nc1ccccc12)N(C)C(=O)[C@H](C)NC(=O)C1(F)CCC1] | [M − H+] 510.3 | ¹H NMR (400 MHz, Acetone-d6) δ 9.63 (s, 1H), 7.14 (ddd, J = 7.9, 6.0, 2.7 Hz, 1H), 7.07 (s, 1H), 6.97-6.90 (m, 2H), 6.87 (dd, J = 7.8, 2.3 Hz, 1H), 5.29 (ddd, J = 8.9, 6.1, 2.3 Hz, 1H), 5.03 (td, J = 8.4, 2.3 Hz, 1H), 4.57-4.46 (m, 1H), 3.80 (d, J = 2.3 Hz, 2H), 2.93 (d, J = 2.3 Hz, 3H), 2.59-2.49 (m, 2H), 2.40-2.25 (m, 3H), 2.25-2.07 (m, 3H), 1.99-1.92 (m, 2H), 1.82-1.47 (m, 6H), 1.46-1.33 (m, 1H), 1.16 (s, 1H), 0.84-0.66 (m, 10H). |

TABLE 2-continued

| Example | Structure | MS | NMR |
|---|---|---|---|
| The following examples were prepared employing similar protocol as described above. | | | |
| 273 | 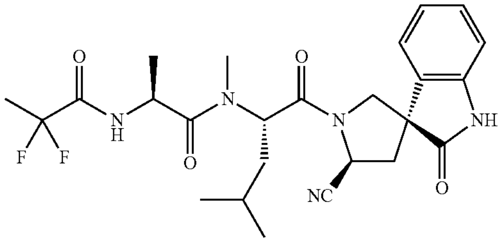 [SMILES: CC(C)C[C@@H](C(=O)N1C[C@]2(C[C@H]1C#N)C(=O)Nc1ccccc12)N(C)C(=O)[C@H](C)NC(=O)C(C)(F)F] | [M − H⁺] 502.3 | $^1$H NMR (400 MHz, Acetone-d6) δ 9.59 (s, 2H), 7.54 (s, 1H), 7.15 (ddd, J = 8.0, 5.9, 3.1 Hz, 2H), 6.97-6.90 (m, 3H), 6.87 (d, J = 7.8 Hz, 2H), 5.28 (dd, J = 8.5, 6.5 Hz, 2H), 5.03 (t, J = 8.5 Hz, 2H), 4.51 (t, J = 6.9 Hz, 2H), 3.86-3.75 (m, 4H), 2.93 (s, 5H), 2.68-2.63 (m, 15H), 2.60 (s, 7H), 2.53 (dd, J = 13.2, 8.5 Hz, 3H), 1.64-1.49 (m, 10H), 1.38 (dt, J = 13.7, 6.7 Hz, 3H), 1.16 (s, 2H), 0.80 (d, J = 6.6 Hz, 5H), 0.74 (t, J = 6.8 Hz, 10H). |
| 274 | 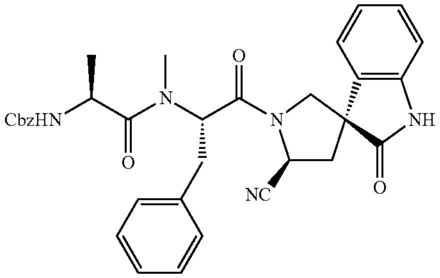 [SMILES: C[C@H](NC(=O)OCc1ccccc1)C(=O)N(C)[C@@H](Cc1ccccc1)C(=O)N1C[C@]2(C[C@H]1C#N)C(=O)Nc1ccccc12] | [M − H⁺] 578.4 | $^1$H NMR (400 MHz, Acetone-d6) δ 9.53 (s, 1H), 7.25-6.99 (m, 11H), 6.91 (s, 1H), 6.84 (d, J = 7.7 Hz, 1H), 5.36 (t, J = 7.5 Hz, 1H), 4.99 (t, J = 8.4 Hz, 1H), 4.90 (s, 2H), 4.26 (t, J = 7.2 Hz, 1H), 3.75 (d, J = 10.6 Hz, 1H), 3.50 (d, J = 10.6 Hz, 1H), 3.16 (dd, J = 13.8, 7.3 Hz, 1H), 2.98 (s, 3H), 2.86 (dd, J = 14.0, 7.6 Hz, 1H), 2.71-2.63 (m, 14H), 2.55 (dd, J = 13.3, 8.4 Hz, 2H), 2.44 (dd, J = 13.1, 8.4 Hz, 1H), 0.64 (d, J = 6.9 Hz, 2H). |
| 275 | 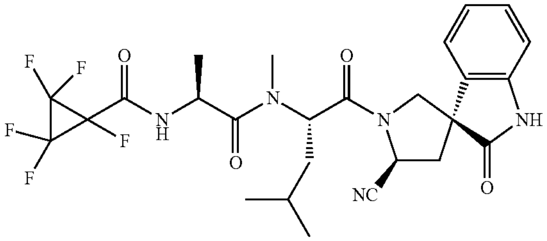 [SMILES: CC(C)C[C@@H](C(=O)N1C[C@]2(C[C@H]1C#N)C(=O)Nc1ccccc12)N(C)C(=O)[C@H](C)NC(=O)C1(F)C(F)(F)C1(F)F] | [M − H⁺] 568.3 | $^1$H NMR (400 MHz, Acetone-d6) δ 9.59 (s, 1H), 7.15 (s, 1H), 6.91 (s, 2H), 5.29 (s, 1H), 5.07-4.96 (m, 1H), 4.59 (s, 1H), 3.88-3.66 (m, 3H), 2.94 (s, 2H), 1.58 (s, 2H), 1.16 (s, 2H), 0.85-0.65 (m, 6H). |
| 276 | 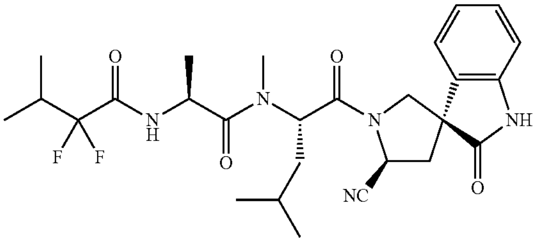 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(C)C] | [M − H⁺] 530.3 | $^1$H NMR (400 MHz, Acetone-d6) δ 9.73 (s, 1H), 7.34-7.25 (m, 1H), 7.10-6.99 (m, 2H), 5.44 (dd, J = 9.3, 5.8 Hz, 1H), 5.17 (t, J = 8.4 Hz, 1H), 4.68 (t, J = 6.9 Hz, 1H), 3.94 (q, J = 10.7 Hz, 2H), 3.08 (s, 2H), 1.75 (dd, J = 9.1, 5.0 Hz, 1H), 1.71-1.59 (m, 2H), 1.53 (s, 1H), 1.30 (s, 1H), 0.99-0.91 (m, 6H), 0.88 (dd, J = 9.3, 6.7 Hz, 4H). |
| 277 | 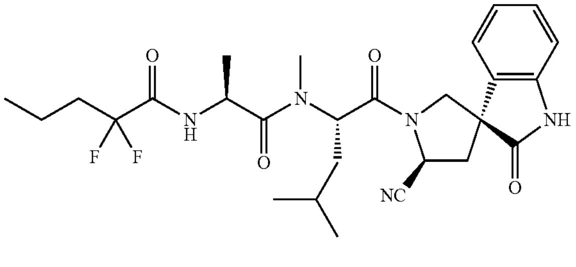 [SMILES: CCCC(F)(F)C(=O)N[C@@H](C)C(=O)N(C)[C@@H](CC(C)C)C(=O)N1C[C@]2(C[C@H]1C#N)C(=O)Nc1ccccc12] | [M − H⁺] 530.2 | $^1$H NMR (400 MHz, Acetone-d6) δ 9.73 (s, 1H), 7.34-7.23 (m, 1H), 7.12-6.94 (m, 4H), 5.43 (dd, J = 9.2, 5.9 Hz, 1H), 5.17 (t, J = 8.4 Hz, 1H), 4.71-4.63 (m, 1H), 4.00-3.82 (m, 3H), 3.06 (d, J = 9.2 Hz, 3H), 2.78-2.62 (m, 5H), 1.78-1.61 (m, 3H), 1.56-1.48 (m, 2H), 1.41 (q, J = 7.7 Hz, 3H), 1.30 (s, 1H), 1.05-0.83 (m, 13H), 0.68 (d, J = 6.9 Hz, 1H). |

TABLE 2-continued

The following examples were prepared employing similar protocol as described above.

| Example | Structure | MS | NMR |
|---|---|---|---|
| 278 | 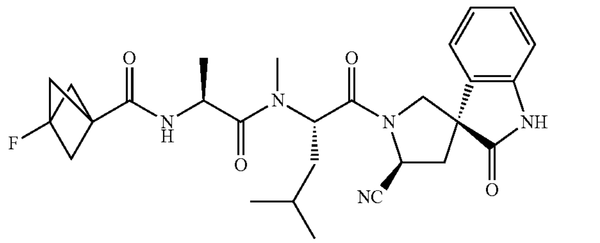 [SMILES: CC(C)C[C@@H](C(=O)N1C[C@]2(C[C@H]1C#N)C(=O)Nc1ccccc12)N(C)C(=O)[C@H](C)NC(=O)C12CC(F)(C1)C2] | [M − H+] 522.2 | ¹H NMR (400 MHz, Acetone-d6) δ 9.60 (s, 1H), 7.20-7.11 (m, 1H), 6.92 (dd, J = 13.3, 5.8 Hz, 3H), 6.88 (d, J = 7.7 Hz, 1H), 5.32-5.23 (m, 1H), 5.03 (t, J = 8.4 Hz, 1H), 4.53-4.45 (m, 1H), 3.81 (q, J = 10.7 Hz, 2H), 2.89 (s, 3H), 2.66-2.48 (m, 2H), 2.20 (d, J = 2.5 Hz, 4H), 2.11 (d, J = 2.6 Hz, 6H), 1.60-1.51 (m, 2H), 1.41-1.33 (m, 1H), 1.17 (s, 1H), 0.81 (d, J = 6.6 Hz, 3H), 0.75 (d, J = 6.5 Hz, 3H), 0.61 (d, J = 6.9 Hz, 3H). |
| 279 | 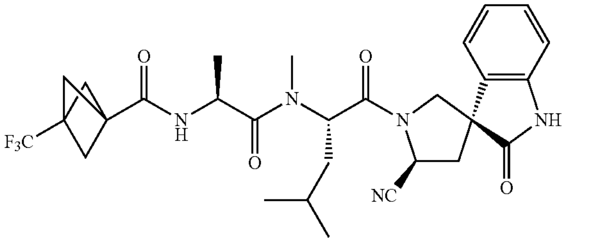 [SMILES: CC(C)C[C@@H](C(=O)N1C[C@]2(C[C@H]1C#N)C(=O)Nc1ccccc12)N(C)C(=O)[C@H](C)NC(=O)C12CC(C(F)(F)F)(C1)C2] | [M − H+] 572.5 | ¹H NMR (400 MHz, Acetone-d6) δ 9.74 (s, 1H), 7.34-7.25 (m, 1H), 7.11 (d, J = 13.4 Hz, 1H), 7.08-6.99 (m, 2H), 5.42 (t, J = 7.6 Hz, 1H), 5.17 (t, J = 8.4 Hz, 1H), 4.67-4.59 (m, 1H), 3.95 (q, J = 10.7 Hz, 2H), 3.03 (s, 2H), 2.27 (s, 1H), 2.19 (s, 3H), 1.69 (t, J = 7.3 Hz, 2H), 1.55-1.47 (m, 1H), 1.30 (s, 1H), 0.95 (d, J = 6.7 Hz, 2H), 0.89 (d, J = 6.5 Hz, 2H), 0.75 (d, J = 6.8 Hz, 2H). |
| 280 | 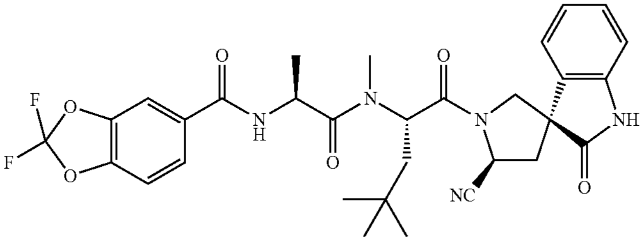 [SMILES: C[C@H](NC(=O)c1ccc2c(c1)OC(F)(F)O2)C(=O)N(C)[C@@H](CC(C)(C)C)C(=O)N1C[C@]2(C[C@H]1C#N)C(=O)Nc1ccccc12] | [M − H+] 608.1 | ¹H NMR (400 MHz, Acetone-d6) δ 9.63 (s, 1H), 7.66-7.59 (m, 2H), 7.54 (d, J = 7.7 Hz, 1H), 7.24-7.12 (m, 2H), 6.99-6.90 (m, 2H), 6.90-6.86 (m, 1H), 5.34 (dd, J = 7.6, 4.7 Hz, 1H), 5.05 (t, J = 8.5 Hz, 1H), 4.69 (p, J = 6.9 Hz, 1H), 3.87 (d, J = 10.5 Hz, 1H), 3.81 (d, J = 10.5 Hz, 1H), 2.98 (s, 3H), 2.67-2.51 (m, 6H), 2.06 (dd, J = 13.9, 7.6 Hz, 1H), 1.32 (dd, J = 14.0, 4.7 Hz, 1H), 0.79 (s, 9H), 0.70 (d, J = 6.8 Hz, 3H) |
| 281 | 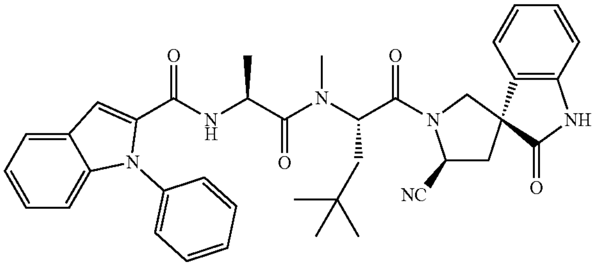 [SMILES: C[C@H](NC(=O)c1cc2ccccc2n1-c1ccccc1)C(=O)N(C)[C@@H](CC(C)(C)C)C(=O)N1C[C@]2(C[C@H]1C#N)C(=O)Nc1ccccc12] | [M − H+] 643.4 | ¹H NMR (400 MHz, Acetone-d6) δ 9.62 (s, 1H), 7.38 (t, J = 7.4 Hz, 2H), 7.34-7.26 (m, 2H), 7.20-7.11 (m, 2H), 7.05-6.96 (m, 3H), 6.96-6.83 (m, 3H), 5.31 (dd, J = 7.6, 4.7 Hz, 1H), 5.03 (t, J = 8.5 Hz, 1H), 4.52 (q, J = 7.1 Hz, 1H), 3.99-3.70 (m, 3H), 2.89 (s, 2H), 2.71-2.63 (m, 17H), 2.62-2.49 (m, 4H), 2.03 (dd, J = 13.9, 7.6 Hz, 1H), 1.92 (d, J = 2.2 Hz, 38H), 1.26 (dd, J = 14.0, 4.7 Hz, 1H), 0.79 (s, 9H), 0.63 (d, J = 6.7 Hz, 2H). |
| 282 | 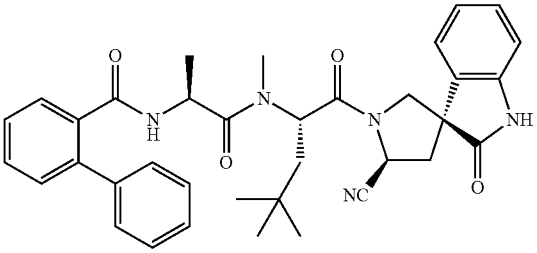 [SMILES: C[C@H](NC(=O)c1ccccc1-c1ccccc1)C(=O)N(C)[C@@H](CC(C)(C)C)C(=O)N1C[C@]2(C[C@H]1C#N)C(=O)Nc1ccccc12] | [M − H+] 604.5 | ¹H NMR (400 MHz, Acetone-d6) δ 9.60 (s, 1H), 7.39-7.29 (m, 2H), 7.29-7.23 (m, 2H), 7.23-7.19 (m, 4H), 7.19-7.11 (m, 1H), 6.95-6.86 (m, 2H), 6.83 (d, J = 7.4 Hz, 1H), 6.73 (d, J = 7.6 Hz, 1H), 5.24 (dd, J = 7.8, 4.6 Hz, 1H), 5.02 (t, J = 8.5 Hz, 1H), 4.46 (p, J = 6.9 Hz, 1H), 3.82-3.71 (m, 2H), 2.71-2.47 (m, 19H), 2.02 (dd, J = 13.9, 7.8 Hz, 1H), 1.26-1.14 (m, 2H), 0.78 (s, 9H), 0.43 (d, J = 6.8 Hz, 2H). |

TABLE 2-continued

The following examples were prepared employing similar protocol as described above.

| Example | Structure | MS | NMR |
|---|---|---|---|
| 283 | 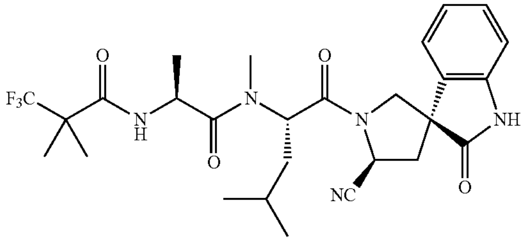 [SMILES: CC(C)C[C@@H](C(=O)N1C[C@]2(C[C@H]1C#N)C(=O)Nc1ccccc12)N(C)C(=O)[C@H](C)NC(=O)C(C)(C)C(F)(F)F] | [M − H+] 548.7 | $^1$H NMR (400 MHz, Acetone-d6) δ 9.58 (s, 2H), 7.19-7.11 (m, 1H), 6.97-6.84 (m, 3H), 5.28 (dd, J = 9.2, 5.9 Hz, 1H), 5.02 (t, J = 8.4 Hz, 1H), 4.50 (t, J = 7.0 Hz, 1H), 3.80 (s, 1H), 2.89 (s, 2H), 2.81 (s, 1H), 2.61 (d, J = 27.8 Hz, 18H), 2.52 (dd, J = 13.2, 8.4 Hz, 2H), 1.59 (dd, J = 9.1, 5.1 Hz, 1H), 1.55-1.44 (m, 2H), 1.37 (s, 1H), 1.28 (s, 1H), 1.22 (d, J = 5.0 Hz, 4H), 0.80 (d, J = 6.6 Hz, 2H), 0.74 (d, J = 6.4 Hz, 2H), 0.64 (d, J = 6.8 Hz, 2H). |
| 284 | 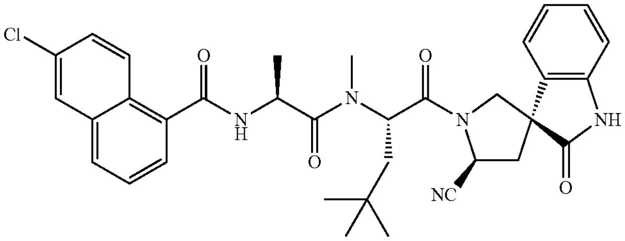 [SMILES: C[C@H](NC(=O)c1cccc2cc(Cl)ccc12)C(=O)N(C)[C@@H](CC(C)(C)C)C(=O)N1C[C@]2(C[C@H]1C#N)C(=O)Nc1ccccc12] | [M − H+] 613.8 | $^1$H NMR (400 MHz, Acetone-d6) δ 9.61 (s, 1H), 8.21 (d, J = 9.1 Hz, 1H), 7.88-7.79 (m, 2H), 7.56 (d, J = 7.5 Hz, 1H), 7.50 (dd, J = 7.1, 1.3 Hz, 1H), 7.41 (dd, J = 8.3, 7.1 Hz, 1H), 7.35 (dd, J = 9.1, 2.3 Hz, 1H), 7.16 (td, J = 7.6, 1.5 Hz, 1H), 7.01-6.85 (m, 3H), 5.39 (dd, J = 7.6, 4.8 Hz, 1H), 5.07 (t, J = 8.5 Hz, 1H), 4.76 (p, J = 7.0 Hz, 1H), 3.92-3.85 (m, 1H), 3.83 (d, J = 10.5 Hz, 1H), 3.06 (s, 3H), 2.81 (s, 1H), 2.67-2.50 (m, 9H), 2.15-2.07 (m, 1H), 1.39 (dd, J = 14.0, 4.8 Hz, 1H), 1.16 (s, 1H), 0.83 (s, 9H), 0.75 (d, J = 6.9 Hz, 3H). |
| 285 | 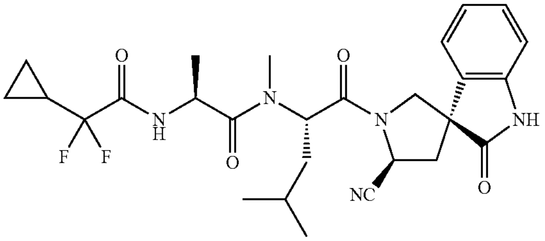 [SMILES: CC(C)C[C@@H](C(=O)N1C[C@]2(C[C@H]1C#N)C(=O)Nc1ccccc12)N(C)C(=O)[C@H](C)NC(=O)C(F)(F)C1CC1] | [M − H+] 528.3 | $^1$H NMR (400 MHz, Acetone-d6) δ 9.60 (s, 1H), 7.52 (d, J = 7.3 Hz, 1H), 7.19-7.08 (m, 1H), 6.97-6.79 (m, 3H), 5.37-5.24 (m, 1H), 5.03 (t, J = 8.4 Hz, 1H), 4.47 (dp, J = 37.1, 6.9 Hz, 1H), 3.85-3.78 (m, 2H), 3.00-2.88 (m, 3H), 2.61 (s, 4H), 2.59-2.48 (m, 1H), 1.98-1.92 (m, 5H), 1.67-1.31 (m, 6H), 1.16 (s, 2H), 0.80 (d, J = 6.6 Hz, 3H), 0.73 (dd, J = 13.0, 6.6 Hz, 6H), 0.60-0.56 (m, 2H), 0.56-0.45 (m, 6H). |
| 286 | 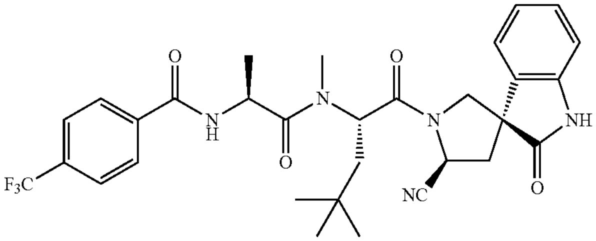 [SMILES: C[C@H](NC(=O)c1ccc(C(F)(F)F)cc1)C(=O)N(C)[C@@H](CC(C)(C)C)C(=O)N1C[C@]2(C[C@H]1C#N)C(=O)Nc1ccccc12] | [M − H+] 597.4 | $^1$H NMR (400 MHz, Acetone-d6) δ 9.62 (s, 1H), 7.91 (d, J = 8.1 Hz, 2H), 7.77-7.62 (m, 3H), 7.16 (td, J = 7.6, 1.5 Hz, 1H), 6.99-6.91 (m, 1H), 6.91-6.86 (m, 2H), 5.35 (dd, J = 7.6, 4.8 Hz, 1H), 5.05 (t, J = 8.6 Hz, 1H), 4.72 (p, J = 7.0 Hz, 1H), 3.88 (dd, J = 10.4, 1.2 Hz, 1H), 3.82 (d, J = 10.5 Hz, 1H), 2.99 (s, 3H), 2.67-2.49 (m, 9H), 2.11-2.01 (m, 1H), 1.33 (dd, J = 14.0, 4.8 Hz, 1H), 0.79 (s, 9H), 0.72 (d, J = 6.9 Hz, 3H). |
| 287 | 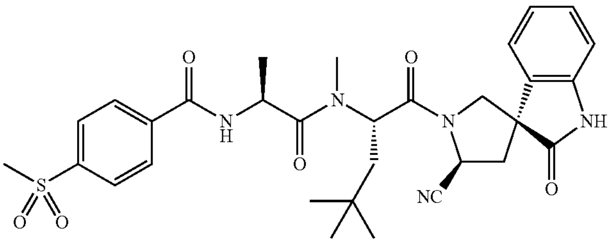 [SMILES: C[C@H](NC(=O)c1ccc(S(C)(=O)=O)cc1)C(=O)N(C)[C@@H](CC(C)(C)C)C(=O)N1C[C@]2(C[C@H]1C#N)C(=O)Nc1ccccc12] | [M − H+] 606.0 | $^1$H NMR (400 MHz, Acetone-d6) δ 9.62 (s, 1H), 7.94 (d, J = 8.5 Hz, 2H), 7.90-7.83 (m, 2H), 7.73 (d, J = 7.6 Hz, 1H), 7.17 (td, J = 7.6, 1.5 Hz, 1H), 7.00-6.86 (m, 3H), 5.35 (dd, J = 7.6, 4.8 Hz, 1H), 5.05 (t, J = 8.5 Hz, 1H), 4.78-4.67 (m, 1H), 3.88 (d, J = 10.7 Hz, 1H), 3.82 (d, J = 10.5 Hz, 1H), 3.00 (d, J = 6.4 Hz, 5H), 2.65 (t, J = 1.1 Hz, 4H), 2.65-2.49 (m, 3H), 2.11-2.01 (m, 1H), 1.34 (dd, J = 14.0, 4.8 Hz, 1H), 0.79 (s, 9H), 0.73 (d, J = 6.9 Hz, 3H). |

TABLE 2-continued

The following examples were prepared employing similar protocol as described above.

| Example | Structure | MS | NMR |
|---|---|---|---|
| 288 | 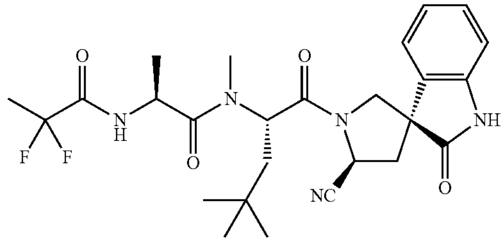 [SMILES: C[C@H](NC(=O)C(C)(F)F)C(=O)N(C)[C@@H](CC(C)(C)C)C(=O)N1C[C@]2(C[C@H]1C#N)C(=O)Nc1ccccc12] | [M − H+] 516.4 | $^1$H NMR (400 MHz, Acetone-d6) δ 9.60 (s, 1H), 7.15 (td, J = 7.6, 1.7 Hz, 1H), 6.96-6.84 (m, 3H), 5.31 (dd, J = 7.7, 4.6 Hz, 1H), 5.04 (t, J = 8.5 Hz, 1H), 4.49 (t, J = 7.0 Hz, 1H), 3.82 (s, 2H), 2.94 (s, 2H), 2.71-2.62 (m, 18H), 2.62-2.49 (m, 3H), 1.61 (s, 1H), 1.54 (d, J = 19.3 Hz, 2H), 1.31 (dd, J = 14.0, 4.6 Hz, 1H), 1.16 (s, 1H), 0.79 (s, 9H), 0.69 (d, J = 6.8 Hz, 2H). |
| 289 | 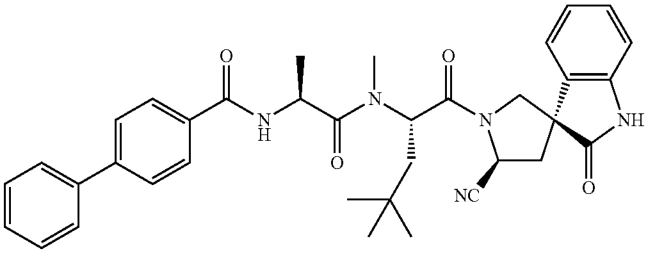 [SMILES: C[C@H](NC(=O)c1ccc(-c2ccccc2)cc1)C(=O)N(C)[C@@H](CC(C)(C)C)C(=O)N1C[C@]2(C[C@H]1C#N)C(=O)Nc1ccccc12] | [M − H+] 604.9 | $^1$H NMR (400 MHz, Acetone-d6) δ 9.62 (s, 1H), 7.84-7.77 (m, 2H), 7.63-7.53 (m, 4H), 7.51 (d, J = 7.7 Hz, 1H), 7.40-7.34 (m, 1H), 7.34-7.22 (m, 2H), 7.17 (td, J = 7.7, 1.4 Hz, 1H), 6.96 (td, J = 7.6, 1.0 Hz, 1H), 6.90 (dd, J = 7.3, 6.0 Hz, 2H), 5.36 (dd, J = 7.6, 4.7 Hz, 1H), 5.06 (t, J = 8.6 Hz, 1H), 4.73 (p, J = 7.0 Hz, 1H), 3.94-3.86 (m, 1H), 3.82 (d, J = 10.5 Hz, 1H), 2.81 (s, 1H), 2.71-2.60 (m, 12H), 2.60 (s, 2H), 2.55 (dd, J = 13.1, 8.7 Hz, 1H), 2.12-2.02 (m, 1H), 1.34 (dd, J = 14.0, 4.7 Hz, 1H), 1.16 (s, 1H), 0.80 (s, 9H), 0.72 (d, J = 6.8 Hz, 3H). |
| 290 | 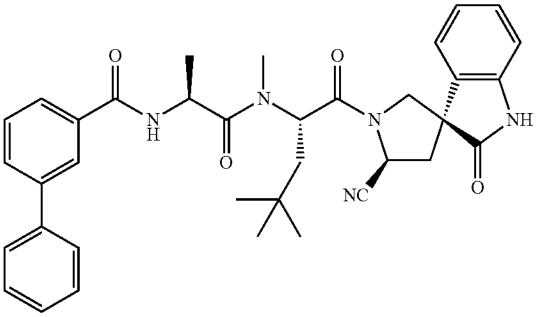 [SMILES: C[C@H](NC(=O)c1cccc(-c2ccccc2)c1)C(=O)N(C)[C@@H](CC(C)(C)C)C(=O)N1C[C@]2(C[C@H]1C#N)C(=O)Nc1ccccc12] | [M − H+] 604.3 | $^1$H NMR (400 MHz, Acetone-d6) δ 9.62 (s, 1H), 7.98 (t, J = 1.9 Hz, 1H), 7.71 (dt, J = 7.7, 1.5 Hz, 1H), 7.68-7.61 (m, 2H), 7.61-7.50 (m, 2H), 7.44-7.30 (m, 3H), 7.29-7.21 (m, 1H), 7.17 (td, J = 7.7, 1.4 Hz, 1H), 6.96 (td, J = 7.6, 1.0 Hz, 1H), 6.94-6.86 (m, 2H), 5.35 (dd, J = 7.6, 4.8 Hz, 1H), 5.05 (t, J = 8.5 Hz, 1H), 4.74 (p, J = 7.0 Hz, 1H), 3.90 (dd, J = 10.5, 1.3 Hz, 1H), 3.81 (d, J = 10.5 Hz, 1H), 3.00 (s, 3H), 2.81 (s, 1H), 2.67-2.50 (m, 8H), 2.05 (dd, J = 14.0, 7.5 Hz, 1H), 1.34 (dd, J = 14.0, 4.8 Hz, 1H), 0.79 (s, 9H), 0.72 (d, J = 6.9 Hz, 3H). |
| 291 | 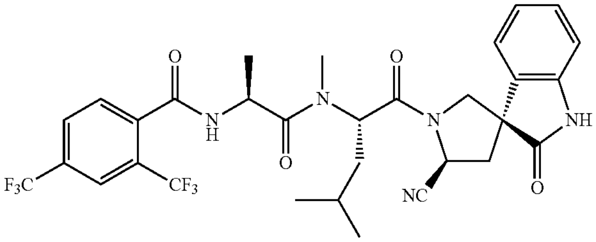 [SMILES: CC(C)C[C@@H](C(=O)N1C[C@]2(C[C@H]1C#N)C(=O)Nc1ccccc12)N(C)C(=O)[C@H](C)NC(=O)c1ccc(C(F)(F)F)cc1C(F)(F)F] | [M − H+] 650.3 | $^1$H NMR (400 MHz, Acetone-d6) δ 9.59 (s, 1H), 7.92 (d, J = 8.7 Hz, 2H), 7.68 (d, J = 7.9 Hz, 1H), 7.60 (d, J = 7.8 Hz, 1H), 7.20-7.12 (m, 1H), 6.99-6.90 (m, 2H), 6.88 (d, J = 7.8 Hz, 1H), 5.33 (dd, J = 9.1, 5.8 Hz, 1H), 5.04 (t, J = 8.5 Hz, 1H), 4.77-4.67 (m, 1H), 3.87-3.77 (m, 2H), 2.99 (s, 2H), 2.68-2.63 (m, 7H), 2.60 (s, 3H), 2.53 (dd, J = 13.2, 8.4 Hz, 1H), 1.64 (ddd, J = 14.2, 9.1, 5.1 Hz, 1H), 1.53 (ddd, J = 14.2, 8.6, 5.9 Hz, 1H), 1.41 (dt, J = 14.2, 6.6 Hz, 1H), 1.16 (s, 1H), 0.84-0.71 (m, 7H). |
| 292 | 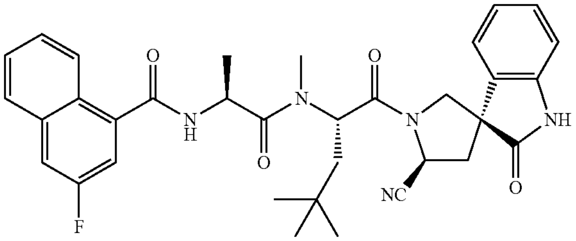 [SMILES: C[C@H](NC(=O)c1cc(F)cc2ccccc12)C(=O)N(C)[C@@H](CC(C)(C)C)C(=O)N1C[C@]2(C[C@H]1C#N)C(=O)Nc1ccccc12] | [M − H+] 596.6 | $^1$H NMR (400 MHz, Acetone-d6) δ 9.60 (s, 1H), 8.13 (d, J = 8.6 Hz, 1H), 7.85-7.75 (m, 1H), 7.64 (d, J = 7.3 Hz, 1H), 7.55 (dd, J = 9.7, 2.6 Hz, 1H), 7.43 (t, J = 7.6 Hz, 1H), 7.38-7.25 (m, 2H), 7.16 (td, J = 7.6, 1.5 Hz, 1H), 7.01-6.85 (m, 3H), 5.40 (dd, J = 7.5, 4.7 Hz, 1H), 5.07 (t, J = 8.6 Hz, 1H), 4.77 (p, J = 7.1 Hz, 1H), 3.89 (d, J = 10.4 Hz, 1H), 3.83 (d, J = 10.6 Hz, 1H), 2.81 (s, 1H), 2.71-2.50 (m, 13H), 2.10 (dd, J = 14.0, 7.5 Hz, 1H), 1.40 (dd, J = 14.0, 4.7 Hz, 1H), 1.17 (d, J = 13.2 Hz, 1H), 0.83 (s, 9H), 0.76 (d, J = 6.9 Hz, 3H). |

TABLE 2-continued

| The following examples were prepared employing similar protocol as described above. | | | |
|---|---|---|---|
| Example | Structure | MS | NMR |
| 293 | 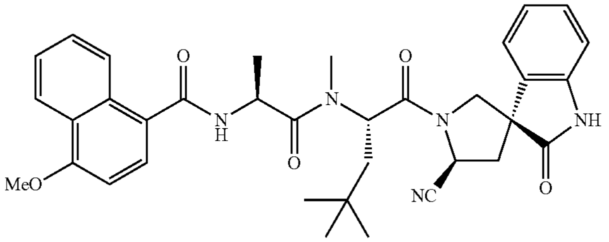 [SMILES: COc1ccc(C(=O)N[C@@H](C)C(=O)N(C)[C@@H](CC(C)(C)C)C(=O)N2C[C@]3(C[C@H]2C#N)C(=O)Nc2ccccc23)c2ccccc12] | [M − H+] 608.1 | $^1$H NMR (400 MHz, Acetone-d6) δ 9.75 (s, 1H), 8.44-8.37 (m, 1H), 8.25 (dt, J = 8.2, 2.5 Hz, 1H), 7.61 (d, J = 8.0 Hz, 1H), 7.57-7.44 (m, 3H), 7.35-7.27 (m, 1H), 7.11 (t, J = 7.4 Hz, 1H), 7.04 (dd, J = 12.1, 7.5 Hz, 2H), 6.92 (d, J = 8.0 Hz, 1H), 5.53 (dd, J = 7.5, 4.7 Hz, 1H), 5.21 (t, J = 8.6 Hz, 1H), 4.89 (p, J = 7.1 Hz, 1H), 4.04 (d, J = 5.6 Hz, 3H), 3.97 (d, J = 10.6 Hz, 1H), 3.20 (s, 2H), 2.96 (s, 1H), 2.82-2.76 (m, 5H), 2.75-2.65 (m, 3H), 2.24 (dd, J = 13.9, 7.6 Hz, 1H), 1.53 (dd, J = 13.9, 4.7 Hz, 1H), 0.97 (s, 9H), 0.88 (d, J = 6.9 Hz, 3H). |
| 294 | 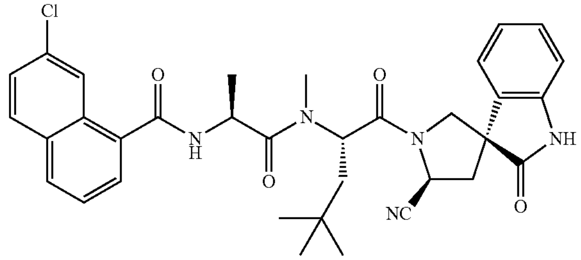 [SMILES: C[C@H](NC(=O)c1cccc2ccc(Cl)cc12)C(=O)N(C)[C@@H](CC(C)(C)C)C(=O)N1C[C@]2(C[C@H]1C#N)C(=O)Nc1ccccc12] | [M − H+] 612.1 | $^1$H NMR (400 MHz, Acetone-d6) δ 9.75 (s, 1H), 8.42 (d, J = 2.2 Hz, 1H), 8.06-7.95 (m, 2H), 7.76-7.67 (m, 2H), 7.53 (ddd, J = 8.0, 4.4, 2.2 Hz, 2H), 7.31 (td, J = 7.7, 1.5 Hz, 1H), 7.11 (t, J = 7.4 Hz, 1H), 7.04 (dd, J = 15.7, 7.5 Hz, 2H), 5.55 (dd, J = 7.5, 4.8 Hz, 1H), 5.21 (t, J = 8.5 Hz, 1H), 4.91 (p, J = 7.0 Hz, 1H), 4.03 (d, J = 10.3 Hz, 1H), 3.97 (d, J = 10.5 Hz, 1H), 3.21 (s, 3H), 2.96 (s, 1H), 2.82-2.79 (m, 4H), 2.79-2.65 (m, 6H), 2.24 (dd, J = 14.1, 7.6 Hz, 1H), 1.56 (dd, J = 14.0, 4.8 Hz, 1H), 0.99 (s, 9H), 0.91 (d, J = 7.0 Hz, 3H). |
| 295 | 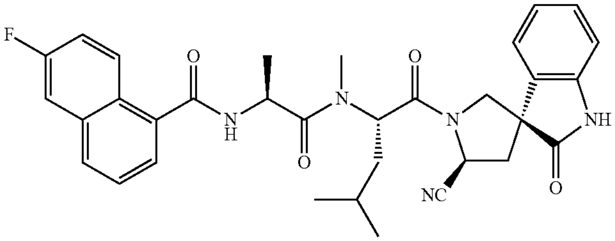 [SMILES: CC(C)C[C@@H](C(=O)N1C[C@]2(C[C@H]1C#N)C(=O)Nc1ccccc12)N(C)C(=O)[C@H](C)NC(=O)c1cccc2cc(F)ccc12] | [M − H+] 582.5 | $^1$H NMR (400 MHz, Acetone-d6) δ 9.74 (s, 1H), 8.41 (dd, J = 9.4, 5.8 Hz, 1H), 7.98 (d, J = 8.0 Hz, 1H), 7.72 (d, J = 7.5 Hz, 1H), 7.68-7.55 (m, 2H), 7.53 (d, J = 7.5 Hz, 1H), 7.41-7.26 (m, 2H), 7.15-7.07 (m, 2H), 7.02 (d, J = 7.8 Hz, 1H), 5.53 (dd, J = 9.5, 4.9 Hz, 1H), 5.20 (t, J = 8.4 Hz, 1H), 4.90 (p, J = 6.9 Hz, 1H), 4.03-3.92 (m, 2H), 3.18 (s, 2H), 2.96 (s, 1H), 2.75 (s, 5H), 2.68 (dd, J = 13.2, 8.4 Hz, 2H), 1.85 (q, J = 9.2 Hz, 1H), 1.66 (dd, J = 9.8, 4.8 Hz, 2H), 1.30 (s, 1H), 1.01-0.88 (m, 8H). |
| 296 | 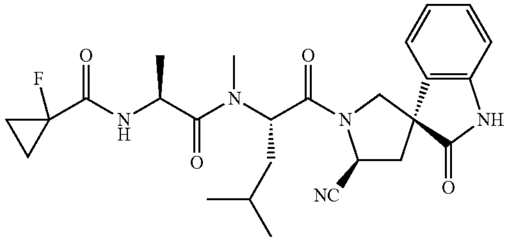 [SMILES: CC(C)C[C@@H](C(=O)N1C[C@]2(C[C@H]1C#N)C(=O)Nc1ccccc12)N(C)C(=O)[C@H](C)NC(=O)C1(F)CC1] | [M − H+] 496.3 | $^1$H NMR (400 MHz, Acetone-d6) δ 9.73 (s, 1H), 7.47 (s, 1H), 7.29 (d, J = 5.5 Hz, 1H), 7.10-6.99 (m, 2H), 5.48-5.40 (m, 1H), 5.17 (t, J = 8.4 Hz, 1H), 4.75-4.67 (m, 1H), 3.96 (s, 1H), 3.08 (s, 2H), 2.82-2.77 (m, 11H), 2.75-2.63 (m, 4H), 1.76-1.67 (m, 2H), 1.59-1.49 (m, 1H), 1.23-1.13 (m, 2H), 0.95 (d, J = 6.6 Hz, 2H), 0.89 (dd, J = 10.9, 6.7 Hz, 4H). |
| 297 | 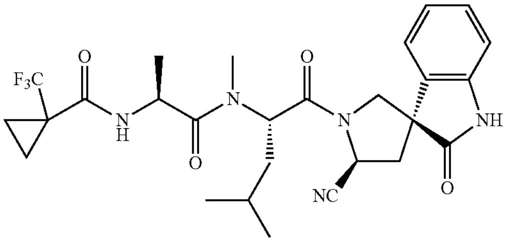 [SMILES: CC(C)C[C@@H](C(=O)N1C[C@]2(C[C@H]1C#N)C(=O)Nc1ccccc12)N(C)C(=O)[C@H](C)NC(=O)C1(C(F)(F)F)CC1] | [M − H+] 546.3 | $^1$H NMR (400 MHz, Acetone-d6) δ 9.72 (s, 1H), 7.32-7.22 (m, 1H), 7.18-6.92 (m, 4H), 5.47-5.37 (m, 1H), 5.17 (t, J = 8.5 Hz, 1H), 4.68 (t, J = 6.9 Hz, 1H), 4.01-3.89 (m, 2H), 2.82-2.77 (m, 11H), 2.77-2.62 (m, 5H), 1.76-1.66 (m, 2H), 0.93 (dd, J = 21.4, 6.6 Hz, 4H), 0.83 (d, J = 6.8 Hz, 2H). |

TABLE 2-continued

| The following examples were prepared employing similar protocol as described above. | | | |
|---|---|---|---|
| Example | Structure | MS | NMR |
| 298 | 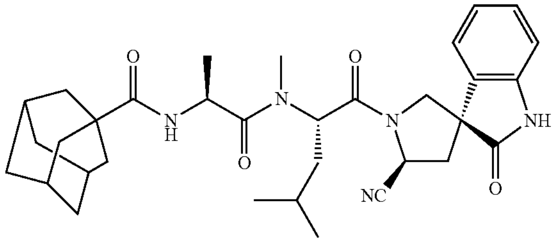 [SMILES: CC(C)C[C@@H](C(=O)N1C[C@]2(C[C@H]1C#N)C(=O)Nc1ccccc12)N(C)C(=O)[C@H](C)NC(=O)C12CC3CC(CC(C3)C1)C2] | [M − H+] 572.5 | $^1$H NMR (400 MHz, Acetone-d6) δ 9.73 (s, 1H), 7.29 (t, J = 7.6 Hz, 1H), 7.05 (dt, J = 16.6, 7.7 Hz, 2H), 6.62 (s, 1H), 5.42 (dd, J = 9.1, 5.9 Hz, 1H), 5.17 (t, J = 8.4 Hz, 1H), 4.67-4.37 (m, 2H), 4.01-3.89 (m, 2H), 3.02 (d, J = 1.0 Hz, 2H), 2.83 (s, 8H), 2.81-2.62 (m, 11H), 2.07 (p, J = 2.2 Hz, 38H), 1.97 (s, 2H), 1.83-1.78 (m, 3H), 1.73 (d, J = 9.3 Hz, 3H), 1.70 (s, 2H), 0.94 (d, J = 6.6 Hz, 2H), 0.89 (d, J = 6.4 Hz, 2H), 0.73 (d, J = 6.7 Hz, 2H). |
| 299 | 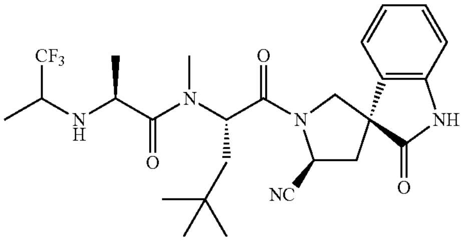 [SMILES: CC(N[C@@H](C)C(=O)N(C)[C@@H](CC(C)(C)C)C(=O)N1C[C@]2(C[C@H]1C#N)C(=O)Nc1ccccc12)C(F)(F)F] | [M − H+] 520.5 | $^1$H NMR (400 MHz, Acetone-d6) δ 9.59 (s, 1H), 7.13 (t, J = 7.6 Hz, 1H), 6.93-6.80 (m, 2H), 5.37 (ddd, J = 17.1, 7.6, 4.2 Hz, 1H), 5.02 (t, J = 8.5 Hz, 1H), 3.92-3.77 (m, 2H), 3.53 (s, 1H), 2.89 (s, 2H), 2.71 (s, 1H), 2.65 (s, 6H), 2.58 (d, J = 8.8 Hz, 1H), 2.53 (dd, J = 13.0, 8.8 Hz, 1H), 2.00 (s, 2H), 1.29 (ddd, J = 26.8, 13.9, 4.6 Hz, 2H), 1.16 (s, 1H), 0.98 (d, J = 6.8 Hz, 2H), 0.82 (d, J = 4.1 Hz, 8H), 0.53 (t, J = 6.3 Hz, 2H). |
| 300 | 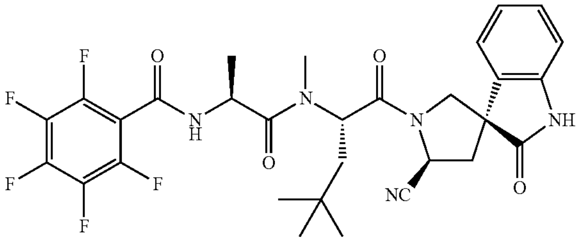 [SMILES: C[C@H](NC(=O)c1c(F)c(F)c(F)c(F)c1F)C(=O)N(C)[C@@H](CC(C)(C)C)C(=O)N1C[C@]2(C[C@H]1C#N)C(=O)Nc1ccccc12] | [M − H+] 618.5 | $^1$H NMR (400 MHz, Acetone-d6) δ 9.60 (s, 1H), 7.91-7.81 (m, 1H), 7.16 (td, J = 7.6, 1.4 Hz, 1H), 6.98-6.85 (m, 3H), 5.34 (dd, J = 7.4, 5.0 Hz, 1H), 5.05 (t, J = 8.6 Hz, 1H), 4.78-4.67 (m, 1H), 3.87 (d, J = 10.5 Hz, 1H), 3.81 (d, J = 10.5 Hz, 1H), 2.67 (d, J = 13.7 Hz, 7H), 2.60 (d, J = 2.7 Hz, 2H), 2.54 (dd, J = 13.2, 8.7 Hz, 1H), 2.05 (dd, J = 14.1, 7.4 Hz, 1H), 1.35 (dd, J = 14.0, 5.0 Hz, 1H), 0.80 (s, 9H), 0.73 (d, J = 6.8 Hz, 2H). |
| 301 | 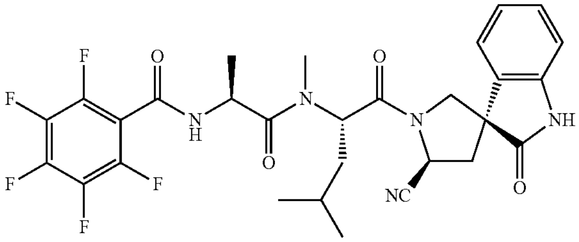 [SMILES: CC(C)C[C@@H](C(=O)N1C[C@]2(C[C@H]1C#N)C(=O)Nc1ccccc12)N(C)C(=O)[C@H](C)NC(=O)c1c(F)c(F)c(F)c(F)c1F] | [M − H+] 604.9 | $^1$H NMR (400 MHz, Acetone-d6) δ 9.58 (s, 1H), 7.16 (td, J = 7.5, 1.9 Hz, 1H), 6.99-6.82 (m, 3H), 5.32 (dd, J = 9.2, 5.8 Hz, 1H), 5.04 (t, J = 8.4 Hz, 1H), 4.78-4.70 (m, 1H), 3.88-3.76 (m, 2H), 2.98 (s, 3H), 2.67-2.58 (m, 6H), 2.53 (dd, J = 13.2, 8.4 Hz, 1H), 1.65 (ddd, J = 14.2, 9.4, 5.0 Hz, 2H), 1.52 (ddd, J = 14.2, 8.6, 5.8 Hz, 2H), 1.41 (dt, J = 13.8, 6.7 Hz, 1H), 1.16 (s, 1H), 0.81 (d, J = 6.6 Hz, 2H), 0.75 (dd, J = 6.7, 2.3 Hz, 4H). |
| 302 | 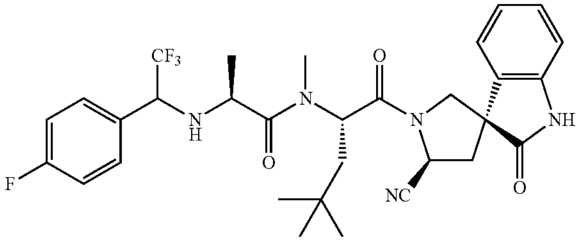 [SMILES: C[C@H](NC(c1ccc(F)cc1)C(F)(F)F)C(=O)N(C)[C@@H](CC(C)(C)C)C(=O)N1C[C@]2(C[C@H]1C#N)C(=O)Nc1ccccc12] | [M − H+] 600.8 | $^1$H NMR (400 MHz, Acetone-d6) δ 7.34-7.26 (m, 1H), 7.00 (t, J = 8.7 Hz, 1H), 6.88-6.77 (m, 2H), 5.21 (s, 1H), 4.98 (t, J = 8.7 Hz, 1H), 4.05 (s, 1H), 3.75 (d, J = 3.3 Hz, 1H), 3.53 (s, 1H), 2.78 (s, 1H), 2.71 (s, 3H), 2.65 (d, J = 2.2 Hz, 9H), 2.58-2.47 (m, 2H), 1.16 (s, 2H), 0.84 (s, 1H), 0.78 (s, 5H), 0.54 (t, J = 6.7 Hz, 2H). |

TABLE 2-continued

The following examples were prepared employing similar protocol as described above.

| Example | Structure | MS | NMR |
|---|---|---|---|
| 303 | 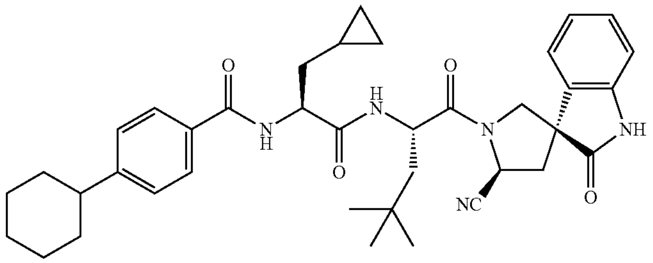 [SMILES: CC(C)(C)C[C@H](NC(=O)[C@H](CC1CC1)NC(=O)c1ccc(C2CCCCC2)cc1)C(=O)N1C[C@]2(C[C@H]1C#N)C(=O)Nc1ccccc12] | [M − H+] 636.4 | $^1$H NMR (400 MHz, Acetone-d6) δ 9.69 (s, 1H), 7.99-7.93 (m, 1H), 7.82 (dd, J = 7.4, 5.5 Hz, 2H), 7.62 (dd, J = 25.0, 8.3 Hz, 2H), 7.39-7.24 (m, 4H), 7.14-6.95 (m, 3H), 5.11 (t, J = 8.4 Hz, 1H), 4.76 (td, J = 8.0, 4.8 Hz, 1H), 4.64 (q, J = 7.6 Hz, 1H), 4.28 (d, J = 10.2 Hz, 1H), 3.99 (d, J = 10.2 Hz, 1H), 2.71-2.64 (m, 2H), 1.74 (d, J = 12.8 Hz, 2H), 1.66-1.54 (m, 3H), 0.94 (s, 9H), 0.47-0.33 (m, 2H), 0.14 (d, J = 12.0 Hz, 1H), 0.07 (dd, J = 8.3, 4.3 Hz, 1H). |
| 304 | 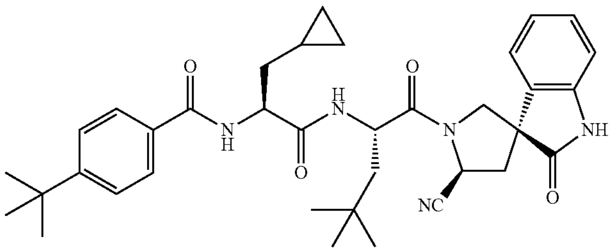 [SMILES: CC(C)(C)C[C@H](NC(=O)[C@H](CC1CC1)NC(=O)c1ccc(C(C)(C)C)cc1)C(=O)N1C[C@]2(C[C@H]1C#N)C(=O)Nc1ccccc12] | [M − H+] 610.7 | $^1$H NMR (400 MHz, Acetone-d6) δ 9.69 (s, 1H), 7.97 (d, J = 8.5 Hz, 1H), 7.83 (d, J = 8.4 Hz, 2H), 7.69-7.46 (m, 4H), 7.32-7.23 (m, 1H), 7.12-6.97 (m, 3H), 5.11 (t, J = 8.4 Hz, 1H), 4.81-4.72 (m, 1H), 4.65 (d, J = 7.0 Hz, 1H), 4.28 (d, J = 10.2 Hz, 1H), 3.99 (d, J = 10.3 Hz, 1H), 1.85 (d, J = 4.8 Hz, 2H), 1.66-1.52 (m, 3H), 1.34 (d, J = 7.4 Hz, 9H), 0.94 (s, 9H), 0.78 (s, 1H), 0.42 (tt, J = 8.1, 4.4 Hz, 2H), 0.20-0.14 (m, 1H), 0.09-0.00 (m, 1H). |
| 305 | 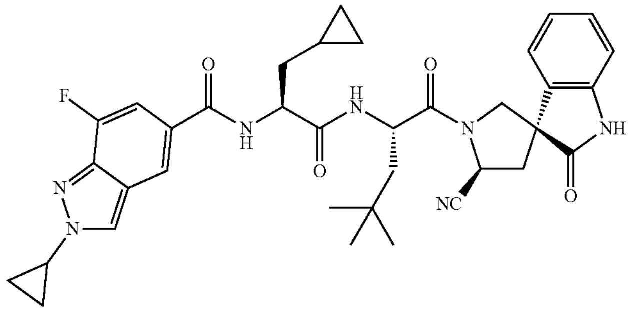 [SMILES: CC(C)(C)C[C@H](NC(=O)[C@H](CC1CC1)NC(=O)c1cc(F)c2nn(C3CC3)cc2c1)C(=O)N1C[C@]2(C[C@H]1C#N)C(=O)Nc1ccccc12] | [M − H+] 652.3 | $^1$H NMR (400 MHz, Acetone-d6) δ 9.69 (s, 1H), 8.62 (d, J = 2.7 Hz, 1H), 8.14 (d, J = 1.3 Hz, 1H), 7.68 (dd, J = 14.2, 8.2 Hz, 2H), 7.51-7.43 (m, 1H), 7.28 (td, J = 7.6, 1.3 Hz, 1H), 7.14-6.97 (m, 3H), 5.11 (t, J = 8.4 Hz, 1H), 4.76 (td, J = 8.1, 4.7 Hz, 1H), 4.67 (q, J = 7.4 Hz, 1H), 4.28 (d, J = 10.2 Hz, 1H), 4.20 (tt, J = 7.5, 4.0 Hz, 1H), 3.99 (d, J = 10.2 Hz, 1H), 2.75-2.61 (m, 2H), 1.85 (d, J = 4.7 Hz, 1H), 1.65-1.54 (m, 3H), 1.46-1.36 (m, 2H), 1.23-1.16 (m, 2H), 0.94 (s, 9H), 0.79 (d, J = 3.1 Hz, 1H), 0.50-0.35 (m, 2H), 0.17 (dq, J = 7.8, 4.4, 4.0 Hz, 1H), 0.08 (dq, J = 9.7, 4.9, 4.4 Hz, 1H). |
| 306 | 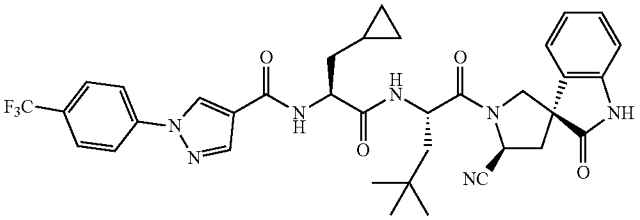 [SMILES: CC(C)(C)C[C@H](NC(=O)[C@H](CC1CC1)NC(=O)c1cnn(-c2ccc(C(F)(F)F)cc2)c1)C(=O)N1C[C@]2(C[C@H]1C#N)C(=O)Nc1ccccc12] | [M − H+] 688.4 | $^1$H NMR (400 MHz, Acetone-d6) δ 9.72 (s, 1H), 9.04 (s, 1H), 8.24-8.13 (m, 3H), 7.90 (d, J = 8.6 Hz, 3H), 7.53 (d, J = 8.4 Hz, 1H), 7.29 (td, J = 7.7, 1.4 Hz, 1H), 7.13-6.93 (m, 3H), 5.13 (t, J = 8.4 Hz, 1H), 4.83-4.69 (m, 2H), 4.31 (d, J = 10.3 Hz, 1H), 4.02 (d, J = 10.2 Hz, 1H), 2.73-2.61 (m, 2H), 1.89 (dd, J = 14.3, 5.0 Hz, 1H), 1.63-1.49 (m, 3H), 0.94 (s, 9H), 0.82-0.73 (m, 1H), 0.48-0.35 (m, 2H), 0.20-0.12 (m, 1H), 0.08 (dt, J = 9.3, 4.5 Hz, 1H). |
| 307 | 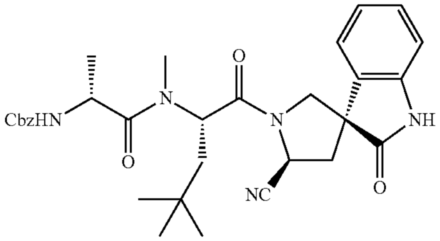 [SMILES: C[C@@H](NC(=O)OCc1ccccc1)C(=O)N(C)[C@@H](CC(C)(C)C)C(=O)N1C[C@]2(C[C@H]1C#N)C(=O)Nc1ccccc12] | [M − H+] 558.4 | $^1$H NMR (400 MHz, Acetone-d6) δ 9.62 (s, 1H), 7.37 (d, J = 5.6 Hz, 5H), 7.14-7.05 (m, 1H), 7.02-6.78 (m, 3H), 5.93 (d, J = 7.3 Hz, 1H), 5.45 (t, J = 6.2 Hz, 1H), 5.14 (t, J = 8.0 Hz, 1H), 5.07-4.89 (m, 2H), 4.40 (q, J = 7.0 Hz, 1H), 4.24 (d, J = 10.8 Hz, 1H), 3.90 (d, J = 10.7 Hz, 1H), 3.11 (s, 3H), 2.72 (dd, J = 13.4, 8.6 Hz, 1H), 2.63 (dd, J = 13.3, 7.4 Hz, lH), 2.12 (dd, J = 14.2, 6.7 Hz, 1H), 1.57-1.46 (m, 1H), 1.19 (d, J = 6.9 Hz, 2H), 0.93 (s, 9H). |

TABLE 2-continued

The following examples were prepared employing similar protocol as described above.

| Example | Structure | MS | NMR |
| --- | --- | --- | --- |
| 308 | 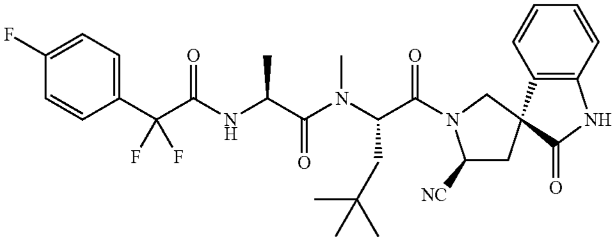 [SMILES: C[C@H](NC(=O)C(F)(F)c1ccc(F)cc1)C(=O)N(C)[C@@H](CC(C)(C)C)C(=O)N1C[C@]2(C[C@H]1C#N)C(=O)Nc1ccccc12] | [M − H[+]] 596.5 | $^1$H NMR (400 MHz, Acetone-d6) δ 9.73 (s, 1H), 7.66 (dd, J = 8.7, 5.3 Hz, 2H), 7.32-7.17 (m, 4H), 7.10-6.89 (m, 4H), 5.43 (dd, J = 7.6, 4.6 Hz, 1H), 5.16 (t, J = 8.5 Hz, 1H), 4.69-4.61 (m, 1H), 3.94 (s, 2H), 3.03 (d, J = 5.0 Hz, 3H), 2.72-2.58 (m, 2H), 2.23-2.12 (m, 2H), 1.40 (dd, J = 14.0, 4.7 Hz, 2H), 0.93-0.85 (m, 9H), 0.85-0.79 (m, 4H). |
| 309 | 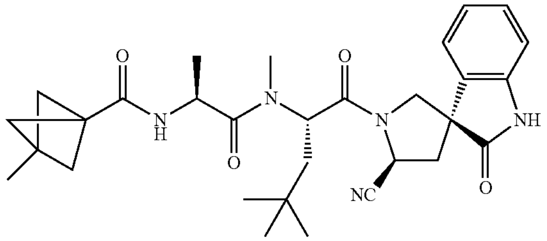 [SMILES: C[C@H](NC(=O)C12CC(C)(C1)C2)C(=O)N(C)[C@@H](CC(C)(C)C)C(=O)N1C[C@]2(C[C@H]1C#N)C(=O)Nc1ccccc12] | [M − H[+]] 532.3 | $^1$H NMR (400 MHz, Acetone-d6) δ 9.73 (s, 1H), 7.31-7.20 (m, 1H), 7.07-6.96 (m, 2H), 6.74 (d, J = 8.2 Hz, 1H), 5.44 (dd, J = 7.4, 5.2 Hz, 1H), 5.16 (t, J = 8.5 Hz, 1H), 4.60-4.53 (m, 1H), 4.00 (d, J = 10.5 Hz, 1H), 3.91 (d, J = 10.5 Hz, 1H), 2.98 (d, J = 31.5 Hz, 3H), 2.72-2.65 (m, 1H), 2.13 (dd, J = 14.0, 7.4 Hz, 1H), 1.78 (s, 3H), 1.45 (dd, J = 14.1, 5.1 Hz, 1H), 1.12 (s, 2H), 0.92 (s, 9H), 0.67 (d, J = 6.8 Hz, 2H). |
| 310 | 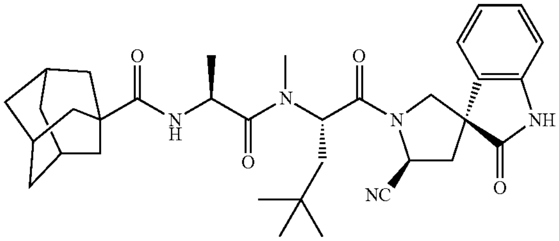 [SMILES: C[C@H](NC(=O)C12CC3CC(CC(C3)C1)C2)C(=O)N(C)[C@@H](CC(C)(C)C)C(=O)N1C[C@]2(C[C@H]1C#N)C(=O)Nc1ccccc12] | [M − H[+]] 586.6 | $^1$H NMR (400 MHz, Acetone-d6) δ 9.73 (s, 1H), 7.28 (td, J = 7.6, 1.4 Hz, 1H), 7.12-6.96 (m, 3H), 6.59 (d, J = 7.7 Hz, 1H), 5.45 (dd, J = 7.3, 5.1 Hz, 1H), 5.16 (t, J = 8.5 Hz, 1H), 4.58 (p, J = 6.9 Hz, 1H), 4.02-3.87 (m, 2H), 2.73 (s, 5H), 2.71-2.62 (m, 2H), 2.14 (dd, J = 14.1, 7.3 Hz, 1H), 1.75-1.63 (m, 7H), 1.45 (dd, J = 14.1, 5.1 Hz, 1H), 0.92 (s, 9H), 0.69 (d, J = 6.8 Hz, 3H). |
| 311 | 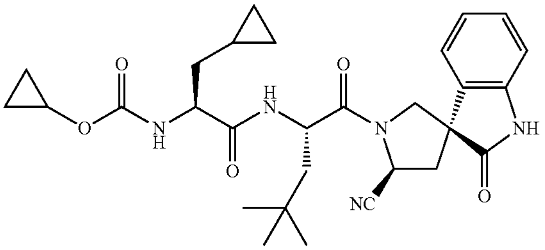 [SMILES: CC(C)(C)C[C@H](NC(=O)[C@H](CC1CC1)NC(=O)OC1CC1)C(=O)N1C[C@]2(C[C@H]1C#N)C(=O)Nc1ccccc12] | [M − H[+]] 534.1 | $^1$H NMR (400 MHz, Acetone-d6) δ 9.68 (s, 1H), 7.50 (d, J = 8.4 Hz, 1H), 7.26 (td, J = 7.6, 1.4 Hz, 1H), 7.07 (d, J = 7.5 Hz, 1H), 7.00 (dd, J = 12.5, 7.6 Hz, 2H), 6.22 (d, J = 8.5 Hz, 1H), 5.10 (t, J = 8.3 Hz, 1H), 4.74 (td, J = 8.1, 4.6 Hz, 1H), 4.26 (d, J = 10.2 Hz, 1H), 4.19 (q, J = 7.4 Hz, 1H), 4.04-3.95 (m, 2H), 2.80-2.69 (m, 4H), 2.69-2.60 (m, 2H), 1.86 (dd, J = 14.4, 4.7 Hz, 1H), 1.58 (dd, J = 14.4, 7.9 Hz, 1H), 1.50 (t, J = 6.9 Hz, 2H), 0.96 (s, 9H), 0.66-0.59 (m, 2H), 0.56 (d, J = 3.3 Hz, 2H), 0.41 (s, 1H), 0.41-0.33 (m, 1H), 0.16-0.03 (m, 2H). |
| 312 | 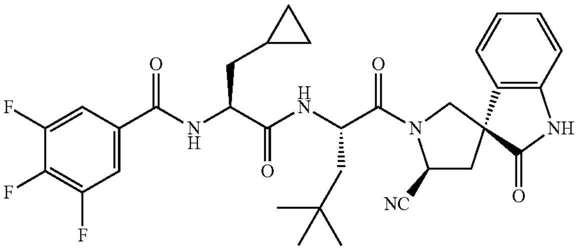 [SMILES: CC(C)(C)C[C@H](NC(=O)[C@H](CC1CC1)NC(=O)c1cc(F)c(F)c(F)c1)C(=O)N1C[C@]2(C[C@H]1C#N)C(=O)Nc1ccccc12] | [M − H[+]] 608.5 | $^1$H NMR (400 MHz, Acetone-d6) δ 9.70 (s, 1H), 7.85 (d, J = 7.8 Hz, 1H), 7.81-7.70 (m, 2H), 7.67 (d, J = 8.3 Hz, 1H), 7.28 (td, J = 7.7, 1.4 Hz, 1H), 7.08 (d, J = 7.4 Hz, 1H), 7.05-6.95 (m, 2H), 5.11 (t, J = 8.4 Hz, 1H), 4.75 (td, J = 8.1, 4.6 Hz, 1H), 4.66 (q, J = 7.5 Hz, 1H), 4.25 (d, J = 10.2 Hz, 1H), 4.00 (d, J = 10.2 Hz, 1H), 1.85 (d, J = 4.7 Hz, 1H), 1.62-1.58 (m, 2H), 0.95 (s, 9H), 0.49-0.35 (m, 2H), 0.21-0.12 (m, 1H), 0.08 (dt, J = 9.9, 4.8 Hz, 1H). |

TABLE 2-continued

The following examples were prepared employing similar protocol as described above.

| Example | Structure | MS | NMR |
|---|---|---|---|
| 313 | 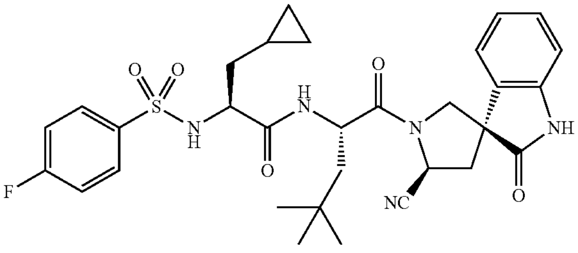 [SMILES: CC(C)(C)C[C@H](NC(=O)[C@H](CC1CC1)NS(=O)(=O)c1ccc(F)cc1)C(=O)N1C[C@]2(C[C@H]1C#N)C(=O)Nc1ccccc12] | [M − H+] 608.4 | $^1$H NMR (400 MHz, Acetone-d6) δ 9.69 (s, 1H), 7.94-7.85 (m, 2H), 7.57 (d, J = 8.2 Hz, 1H), 7.34-7.22 (m, 2H), 6.99 (dd, J = 6.8, 2.9 Hz, 2H), 6.64 (d, J = 8.5 Hz, 1H), 5.07 (t, J = 8.4 Hz, 1H), 4.52 (q, J = 7.2 Hz, 1H), 4.15 (d, J = 10.1 Hz, 1H), 3.95 (d, J = 10.3 Hz, 1H), 2.70-2.61 (m, 2H), 1.82 (dd, J = 14.2, 5.7 Hz, 1H), 1.46 (dt, J = 14.4, 7.5 Hz, 1H), 1.37-1.29 (m, 2H), 0.88 (s, 9H), 0.41-0.31 (m, 1H), 0.31-0.21 (m, 1H), 0.07 (d, J = 4.7 Hz, 1H). |
| 314 | 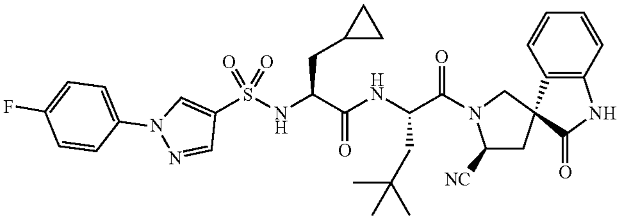 [SMILES: CC(C)(C)C[C@H](NC(=O)[C@H](CC1CC1)NS(=O)(=O)c1cnn(-c2ccc(F)cc2)c1)C(=O)N1C[C@]2(C[C@H]1C#N)C(=O)Nc1ccccc12] | [M − H+] 674.5 | $^1$H NMR (400 MHz, Acetone-d6) δ 9.69 (s, 1H), 8.69 (s, 1H), 7.95-7.88 (m, 2H), 7.57 (d, J = 8.1 Hz, 1H), 7.34-7.24 (m, 2H), 7.05-6.95 (m, 2H), 6.58 (d, J = 8.6 Hz, 1H), 5.06 (t, J = 8.3 Hz, 1H), 4.53 (q, J = 7.5 Hz, 1H), 4.14 (d, J = 10.2 Hz, 1H), 4.04-3.96 (m, 1H), 3.93 (d, J = 10.1 Hz, 1H), 2.69-2.60 (m, 2H), 1.78 (dd, J = 14.2, 5.3 Hz, 1H), 1.56 (dt, J = 14.4, 7.3 Hz, 1H), 1.46-1.32 (m, 2H), 0.80 (s, 9H), 0.40 (tt, J = 8.5, 4.3 Hz, 1H), 0.35-0.25 (m, 1H), 0.14--0.01 (m, 2H). |
| 315 | 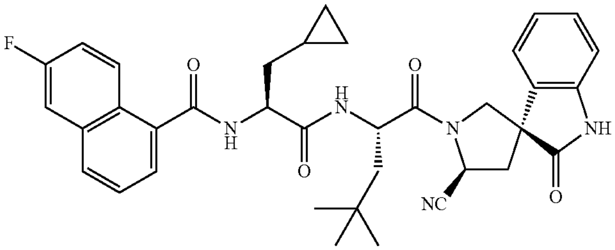 [SMILES: CC(C)(C)C[C@H](NC(=O)[C@H](CC1CC1)NC(=O)c1cccc2cc(F)ccc12)C(=O)N1C[C@]2(C[C@H]1C#N)C(=O)Nc1ccccc12] | [M − H+] 622.6 | $^1$H NMR (400 MHz, Acetone-d6) δ 9.70 (s, 1H), 8.49 (dd, J = 9.4, 5.7 Hz, 1H), 8.00 (d, J = 8.3 Hz, 1H), 7.78-7.62 (m, 4H), 7.60-7.53 (m, 1H), 7.47-7.32 (m, 1H), 7.26 (td, J = 7.7, 1.3 Hz, 1H), 7.12 (d, J = 7.4 Hz, 1H), 7.08-6.94 (m, 2H), 5.15 (t, J = 8.4 Hz, 1H), 4.83 (td, J = 8.2, 4.7 Hz, 1H), 4.76 (td, J = 8.0, 6.2 Hz, 1H), 4.32-4.25 (m, 1H), 4.02 (d, J = 10.2 Hz, 1H), 2.71-2.65 (m, 1H), 1.97-1.85 (m, 1H), 1.71-1.60 (m, 3H), 0.99 (s, 9H), 0.55-0.37 (m, 2H), 0.20 (dq, J = 7.7, 4.4 Hz, 1H), 0.16-0.07 (m, 1H). |
| 316 | 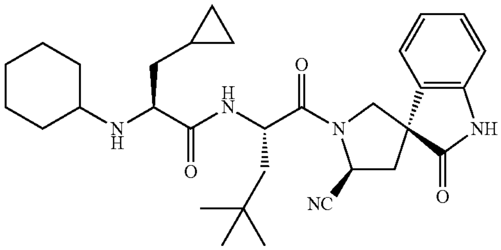 [SMILES: CC(C)(C)C[C@H](NC(=O)[C@H](CC1CC1)NC1CCCCC1)C(=O)N1C[C@]2(C[C@H]1C#N)C(=O)Nc1ccccc12] | [M − H+] 532.8 | $^1$H NMR (400 MHz, Acetone-d6) δ 9.69 (s, 1H), 7.92 (d, J = 8.8 Hz, 1H), 7.27 (td, J = 7.6, 1.4 Hz, 1H), 7.06-6.94 (m, 2H), 5.12 (t, J = 8.4 Hz, 1H), 4.77-4.68 (m, 1H), 4.30 (d, J = 10.2 Hz, 1H), 4.00 (d, J = 10.2 Hz, 1H), 3.21-3.13 (m, 1H), 2.76-2.61 (m, 3H), 2.44-2.35 (m, 1H), 1.97 (d, J = 6.0 Hz, 1H), 1.82 (dd, J = 14.4, 4.0 Hz, 2H), 1.73 (d, J = 12.6 Hz, 2H), 1.59 (dd, J = 14.3, 8.7 Hz, 2H), 1.45-1.33 (m, 2H), 1.33-1.16 (m, 3H), 1.16-1.09 (m, 1H), 1.06 (d, J = 10.0 Hz, 1H), 0.97 (s, 9H), 0.84-0.76 (m, 1H), 0.42 (ddd, J = 13.6, 8.0, 3.6 Hz, 2H), 0.15-0.03 (m, 2H). |
| 317 | 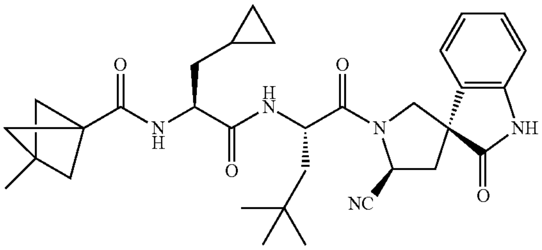 [SMILES: CC(C)(C)C[C@H](NC(=O)[C@H](CC1CC1)NC(=O)C12CC(C)(C1)C2)C(=O)N1C[C@]2(C[C@H]1C#N)C(=O)Nc1ccccc12] | [M − H+] 558.2 | $^1$H NMR (400 MHz, Acetone-d6) δ 9.69 (s, 1H), 7.48 (d, J = 8.4 Hz, 1H), 7.27 (td, J = 7.7, 1.4 Hz, 1H), 7.07 (d, J = 7.4 Hz, 1H), 7.05-6.96 (m, 2H), 6.86 (d, J = 8.1 Hz, 1H), 5.10 (t, J = 8.4 Hz, 1H), 4.70 (td, J = 8.2, 4.5 Hz, 1H), 4.40 (td, J = 8.1, 5.6 Hz, 1H), 4.29-4.22 (m, 1H), 3.98 (d, J = 10.2 Hz, 1H), 2.81-2.76 (m, 4H), 2.75-2.60 (m, 2H), 1.84 (s, 6H), 1.60-1.46 (m, 2H), 1.40 (dt, J = 14.3, 7.5 Hz, 1H), 1.15 (s, 2H), 0.95 (s, 9H), 0.66 (dq, J = 12.8, 6.8, 5.8 Hz, 1H), 0.45-0.30 (m, 2H), 0.15-0.04 (m, 1H). |

TABLE 2-continued

The following examples were prepared employing similar protocol as described above.

| Example | Structure | MS | NMR |
|---|---|---|---|
| 318 | 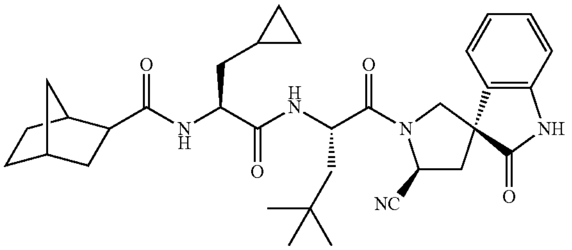 [SMILES: CC(C)(C)C[C@H](NC(=O)[C@H](CC1CC1)NC(=O)C1CC2CCC1C2)C(=O)N1C[C@]2(C[C@H]1C#N)C(=O)Nc1ccccc12] | [M − H+] 572.3 | $^1$H NMR (400 MHz, Acetone-d6) δ 9.69 (s, 1H), 7.27 (dd, J = 8.4, 6.9 Hz, 1H), 7.11-6.96 (m, 4H), 5.13-5.07 (m, 1H), 4.74 (d, J = 7.7 Hz, 1H), 4.48-4.33 (m, 1H), 4.31-4.22 (m, 1H), 3.98 (dd, J = 10.3, 5.3 Hz, 1H), 2.80-2.75 (m, 6H), 2.74-2.60 (m, 5H), 2.34 (d, J = 11.4 Hz, 1H), 1.96-1.81 (m, 2H), 1.69 (d, J = 10.4 Hz, 1H), 1.59-1.41 (m, 6H), 1.39 (s, 1H), 1.29 (t, J = 16.5 Hz, 3H), 1.07 (d, J = 10.1 Hz, 1H), 0.94 (d, J = 4.8 Hz, 9H), 0.69 (s, 1H), 0.36 (tt, J = 8.2, 3.9 Hz, 2H), 0.15-0.03 (m, 2H). |
| 319 | 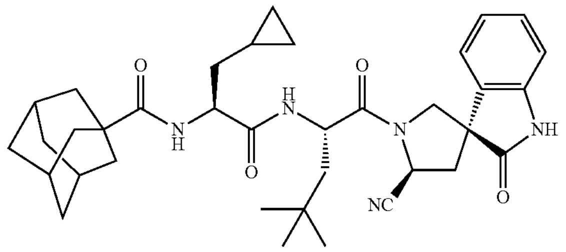 [SMILES: CC(C)(C)C[C@H](NC(=O)[C@H](CC1CC1)NC(=O)C12CC3CC(CC(C3)C1)C2)C(=O)N1C[C@]2(C[C@H]1C#N)C(=O)Nc1ccccc12] | [M − H+] 612.6 | $^1$H NMR (500 MHz, Acetone-d6) δ 9.67 (s, 1H), 7.43 (d, J = 8.4 Hz, 1H), 7.24 (td, J = 7.7, 1.3 Hz, 1H), 7.07 (d, J = 7.4 Hz, 1H), 7.03-6.94 (m, 2H), 6.69 (d, J = 7.7 Hz, 1H), 5.08 (t, J = 8.3 Hz, 1H), 4.70 (td, J = 8.1, 4.9 Hz, 1H), 4.39 (q, J = 7.0 Hz, 1H), 4.24 (d, J = 10.3 Hz, 1H), 3.96 (d, J = 10.2 Hz, 1H), 2.78-2.74 (m, 3H), 2.71 (s, 2H), 2.71-2.65 (m, 2H), 2.65-2.59 (m, 1H), 2.00-1.95 (m, 2H), 1.88-1.80 (m, 5H), 1.76-1.65 (m, 5H), 1.56-1.49 (m, 1H), 1.47 (d, J = 6.8 Hz, 1H), 0.93 (s, 9H), 0.70-0.60 (m, 1H), 0.42-0.31 (m, 2H), 0.12-0.03 (m, 1H). |
| 320 | 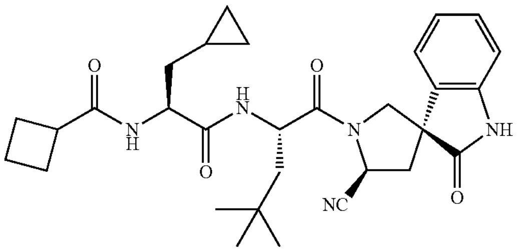 [SMILES: CC(C)(C)C[C@H](NC(=O)[C@H](CC1CC1)NC(=O)C1CCC1)C(=O)N1C[C@]2(C[C@H]1C#N)C(=O)Nc1ccccc12] | [M − H+] 532.4 | $^1$H NMR (500 MHz, Acetone-d6) δ 9.61 (s, 1H), 7.41 (d, J = 8.5 Hz, 1H), 7.19 (td, J = 7.7, 1.3 Hz, 1H), 7.00 (d, J = 7.3 Hz, 1H), 6.97-6.89 (m, 2H), 6.85 (d, J = 8.2 Hz, 1H), 5.02 (t, J = 8.4 Hz, 1H), 4.65 (td, J = 8.1, 4.8 Hz, 1H), 4.34 (td, J = 8.0, 5.7 Hz, 1H), 4.18 (d, J = 10.2 Hz, 1H), 3.90 (d, J = 10.2 Hz, 1H), 3.11-2.99 (m, 2H), 2.65 (s, 2H), 2.63-2.53 (m, 2H), 2.22-2.15 (m, 2H), 2.15-2.10 (m, 2H), 2.10-1.99 (m, 2H), 1.96-1.67 (m, 6H), 1.51-1.29 (m, 4H), 1.21 (s, 1H), 0.87 (s, 9H), 0.64-0.54 (m, 1H), 0.36-0.23 (m, 2H), −0.03-−0.11 (m, 1H). |
| 321 | 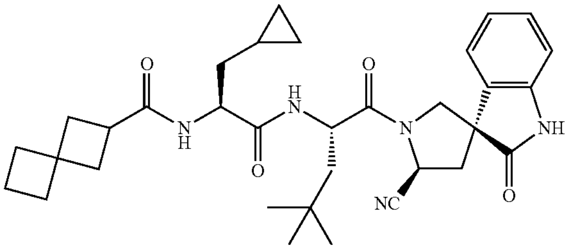 [SMILES: CC(C)(C)C[C@H](NC(=O)[C@H](CC1CC1)NC(=O)C1CC2(CCC2)C1)C(=O)N1C[C@]2(C[C@H]1C#N)C(=O)Nc1ccccc12] | [M − H+] 572.5 | $^1$H NMR (500 MHz, Acetone-d6) δ 9.67 (s, 1H), 7.46 (d, J = 8.5 Hz, 1H), 7.25 (td, J = 7.6, 1.4 Hz, 1H), 7.06 (d, J = 7.3 Hz, 1H), 7.04-6.96 (m, 2H), 6.92 (d, J = 8.1 Hz, 1H), 5.09 (t, J = 8.4 Hz, 1H), 4.71 (td, J = 8.1, 4.7 Hz, lH), 4.38 (td, J = 8.0, 5.7 Hz, 1H), 4.25 (d, J = 10.3 Hz, 1H), 3.97 (d, J = 10.2 Hz, 1H), 2.93 (p, J = 8.4 Hz, 1H), 2.77 (t, J = 1.1 Hz, 4H), 2.72 (s, 2H), 2.71-2.60 (m, 2H), 2.18 (q, J = 8.9 Hz, 2H), 2.13-2.06 (m, 2H), 2.03-1.97 (m, 7H), 1.86 (dt, J = 14.3, 5.8 Hz, 2H), 1.81-1.71 (m, 2H), 1.46 (dddd, J = 50.0, 21.7, 14.4, 7.6 Hz, 3H), 1.28 (s, 1H), 0.93 (s, 9H), 0.70-0.62 (m, 1H), 0.36 (dtt, J = 22.2, 8.8, 4.6 Hz, 2H), 0.14-0.04 (m, 2H). |

TABLE 2-continued

The following examples were prepared employing similar protocol as described above.

| Example | Structure | MS | NMR |
|---|---|---|---|
| 322 | 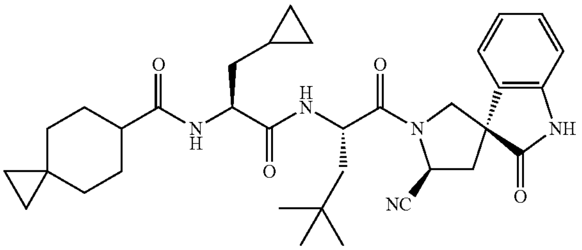 [SMILES: CC(C)(C)C[C@H](NC(=O)[C@H](CC1CC1)NC(=O)C1CCC2(CC1)CC2)C(=O)N1C[C@]2(C[C@H]1C#N)C(=O)Nc1ccccc12] | [M − H+] 586.5 | 1H NMR (500 MHz, Acetone-d6) δ 9.69 (s, 1H), 7.48 (d, J = 8.5 Hz, 1H), 7.26 (td, J = 7.7, 1.3 Hz, 1H), 7.11-6.96 (m, 3H), 5.10 (t, J = 8.3 Hz, 1H), 4.74 (td, J = 8.0, 4.9 Hz, 1H), 4.41 (q, J = 7.2 Hz, 1H), 4.26 (d, J = 10.3 Hz, 1H), 3.98 (d, J = 10.2 Hz, 1H), 2.80-2.76 (m, 3H), 2.75-2.61 (m, 4H), 2.25 (tt, J = 11.3, 3.5 Hz, 1H), 1.87 (dd, J = 14.3, 4.8 Hz, 1H), 1.82-1.49 (m, 7H), 1.47 (td, J = 7.0, 2.2 Hz, 2H), 1.29 (s, 1H), 0.95 (s, 9H), 0.75-0.64 (m, 1H), 0.45-0.32 (m, 2H), 0.15-0.06 (m, 1H), 0.06-−0.02 (m, 1H). |
| 323 | 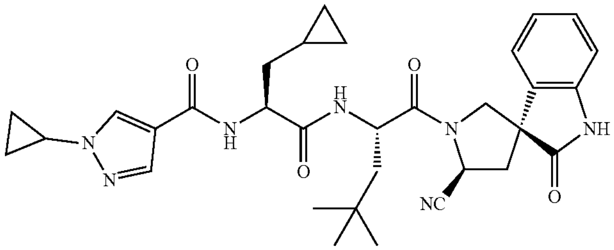 [SMILES: CC(C)(C)C[C@H](NC(=O)[C@H](CC1CC1)NC(=O)c1cnn(C2CC2)c1)C(=O)N1C[C@]2(C[C@H]1C#N)C(=O)Nc1ccccc12] | [M − H+] 584.3 | 1H NMR (400 MHz, Acetone-d6) δ 9.69 (s, 1H), 8.16 (s, 1H), 7.81 (d, J = 0.7 Hz, 1H), 7.62 (d, J = 8.5 Hz, 1H), 7.31-7.20 (m, 2H), 7.09 (d, J = 7.2 Hz, 1H), 7.05-6.95 (m, 2H), 5.10 (t, J = 8.4 Hz, 1H), 4.74 (td, J = 8.0, 4.9 Hz, 1H), 4.58 (q, J = 7.2 Hz, 1H), 4.27 (d, J = 10.2 Hz, 1H), 3.98 (d, J = 10.2 Hz, 1H), 3.73 (tt, J = 7.5, 3.9 Hz, 1H), 3.60-3.52 (m, 1H), 2.75-2.60 (m, 2H), 1.85 (d, J = 4.9 Hz, 1H), 1.54 (dt, J = 18.7, 7.4 Hz, 3H), 1.15-1.07 (m, 2H), 1.07-0.97 (m, 2H), 0.93 (s, 9H), 0.80-0.67 (m, 1H), 0.46-0.31 (m, 2H), 0.12 (d, J = 3.9 Hz, 2H), 0.09--0.02 (m, 1H). |
| 324 | 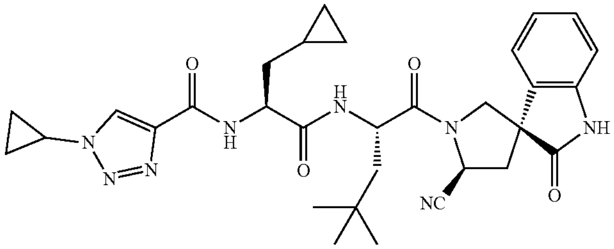 [SMILES: CC(C)(C)C[C@H](NC(=O)[C@H](CC1CC1)NC(=O)c1cn(C2CC2)nn1)C(=O)N1C[C@]2(C[C@H]1C#N)C(=O)Nc1ccccc12] | [M − H+] 585.5 | 1H NMR (400 MHz, Acetone-d6) δ 9.69 (s, 1H), 8.36 (s, 1H), 7.74 (dd, J = 15.5, 8.3 Hz, 2H), 7.27 (td, J = 7.7, 1.3 Hz, 1H), 7.13-7.06 (m, 1H), 7.06-6.90 (m, 2H), 5.12 (t, J = 8.4 Hz, 1H), 4.78 (td, J = 8.2, 4.6 Hz, 1H), 4.74-4.64 (m, 1H), 4.28 (d, J = 10.2 Hz, 1H), 4.05-3.96 (m, 2H), 2.77-2.60 (m, 2H), 1.86 (dd, J = 14.4, 4.7 Hz, 1H), 1.73-1.63 (m, 2H), 1.60 (dd, J = 14.3, 7.9 Hz, 1H), 1.35-1.25 (m, 3H), 1.25-1.14 (m, 2H), 0.95 (s, 9H), 0.76 (ddd, J = 12.8, 8.4, 4.8 Hz, 1H), 0.41 (dq, J = 7.9, 1.6 Hz, 2H), 0.16-0.10 (m, 1H), 0.09 (d, J = 4.8 Hz, 1H). |
| 325 | 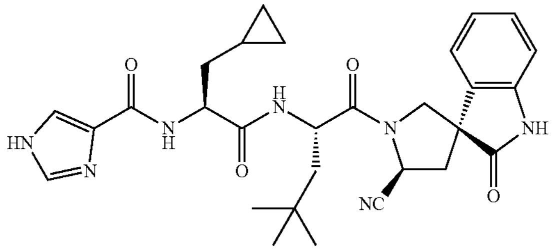 [SMILES: CC(C)(C)C[C@H](NC(=O)[C@H](CC1CC1)NC(=O)c1c[nH]cn1)C(=O)N1C[C@]2(C[C@H]1C#N)C(=O)Nc1ccccc12] | [M − H+] 544.3 | 1H NMR (400 MHz, Acetone-d6) δ 9.71 (d, J = 16.3 Hz, 1H), 8.01-7.93 (m, 1H), 7.66 (d, J = 20.5 Hz, 1H), 7.34-7.25 (m, 1H), 7.06-6.93 (m, 3H), 5.12 (td, J = 8.4, 3.5 Hz, 1H), 4.78 (tt, J = 8.2, 4.2 Hz, 1H), 4.41 (td, J = 8.2, 4.5 Hz, 1H), 4.19 (d, J = 10.2 Hz, 1H), 4.03 (d, J = 10.2 Hz, 1H), 2.72-2.62 (m, 2H), 1.90-1.79 (m, 2H), 1.70-1.53 (m, 3H), 0.96 (d, J = 9.5 Hz, 9H), 0.53 (dd, J = 7.5, 4.1 Hz, 1H), 0.41 (d, J = 8.2 Hz, 1H), 0.26-0.14 (m, 2H). |
| 326 | 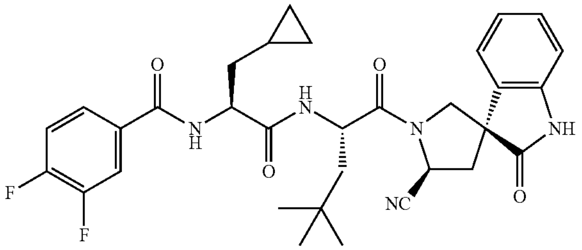 [SMILES: CC(C)(C)C[C@H](NC(=O)[C@H](CC1CC1)NC(=O)c1ccc(F)c(F)c1)C(=O)N1C[C@]2(C[C@H]1C#N)C(=O)Nc1ccccc12] | [M − H+] 590.8 | 1H NMR (400 MHz, Acetone-d6) δ 9.70 (s, 1H), 7.89-7.83 (m, 1H), 7.82-7.76 (m, 2H), 7.66 (d, J = 8.3 Hz, 1H), 7.42 (dt, J = 10.4, 8.3 Hz, 1H), 7.28 (td, J = 7.6, 1.3 Hz, 1H), 7.11-7.06 (m, 1H), 7.05-6.97 (m, 2H), 5.11 (t, J = 8.4 Hz, 1H), 4.75 (td, J = 8.1, 4.7 Hz, 1H), 4.66 (q, J = 7.2 Hz, 1H), 4.26 (d, J = 10.2 Hz, 1H), 3.99 (d, J = 10.2 Hz, 1H), 2.73 (s, 3H), 2.71-2.57 (m, 2H), 1.92-1.81 (m, 1H), 1.65-1.53 (m, 3H), 0.94 (s, 9H), 0.81-0.75 (m, 1H), 0.49-0.35 (m, 2H), 0.20-0.12 (m, 2H), 0.10-0.03 (m, 1H). |

TABLE 2-continued

The following examples were prepared employing similar protocol as described above.

| Example | Structure | MS | NMR |
|---|---|---|---|
| 327 | 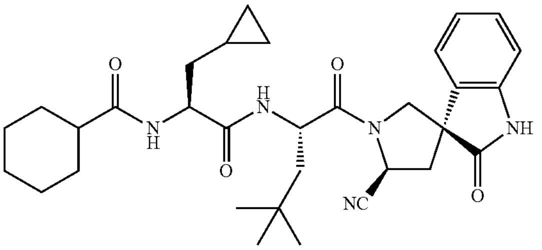 [SMILES: CC(C)(C)C[C@H](NC(=O)[C@H](CC1CC1)NC(=O)C1CCCCC1)C(=O)N1C[C@]2(C[C@H]1C#N)C(=O)Nc1ccccc12] | [M − H⁺] 560.4 | $^1$H NMR (400 MHz, Acetone-d6) δ 9.69 (s, 1H), 7.46 (d, J = 8.6 Hz, 1H), 7.26 (td, J = 7.6, 1.3 Hz, 1H), 7.08 (d, J = 7.1 Hz, 1H), 7.05-6.95 (m, 3H), 5.10 (t, J = 8.4 Hz, 1H), 4.73 (td, J = 8.1, 4.8 Hz, 1H), 4.39 (td, J = 7.8, 6.2 Hz, 1H), 4.26 (d, J = 10.2 Hz, 1H), 3.98 (d, J = 10.2 Hz, 1H), 2.73 (d, J = 1.3 Hz, 3H), 2.72-2.62 (m, 2H), 2.27-2.15 (m, 1H), 1.91-1.84 (m, 1H), 1.81-1.69 (m, 4H), 1.54 (dd, J = 14.3, 7.7 Hz, 1H), 1.48-1.36 (m, 4H), 0.95 (s, 9H), 0.76-0.63 (m, 1H), 0.49-0.29 (m, 2H), 0.10 (ddd, J = 12.7, 8.8, 4.5 Hz, 1H). |
| 328 | 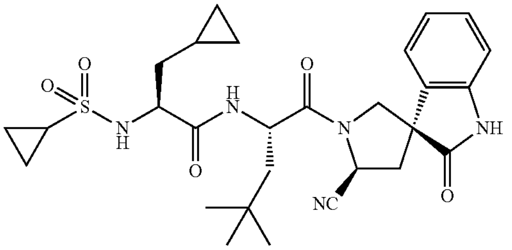 [SMILES: CC(C)(C)C[C@H](NC(=O)[C@H](CC1CC1)NS(=O)(=O)C1CC1)C(=O)N1C[C@]2(C[C@H]1C#N)C(=O)Nc1ccccc12] | [M − H⁺] 554.3 | $^1$H NMR (400 MHz, Acetone-d6) δ 9.69 (s, 1H), 7.64 (d, J = 8.3 Hz, 1H), 7.30-7.20 (m, 1H), 7.03-6.96 (m, 2H), 6.19 (d, J = 9.0 Hz, 1H), 5.11 (t, J = 8.3 Hz, 1H), 4.74 (td, J = 8.0, 4.9 Hz, 1H), 4.27 (d, J = 10.2 Hz, 1H), 4.01 (d, J = 10.2 Hz, 1H), 3.31 (q, J = 7.1 Hz, 1H), 2.73-2.64 (m, 2H), 2.56-2.47 (m, 1H), 1.95-1.86 (m, 2H), 1.60 (dd, J = 14.4, 7.4 Hz, 2H), 1.53-1.43 (m, 2H), 1.18 (t, J = 7.1 Hz, 1H), 0.98 (d, J = 5.0 Hz, 9H), 0.51-0.44 (m, 1H), 0.16 (dt, J = 8.0, 4.3 Hz, 1H). |
| 329 | 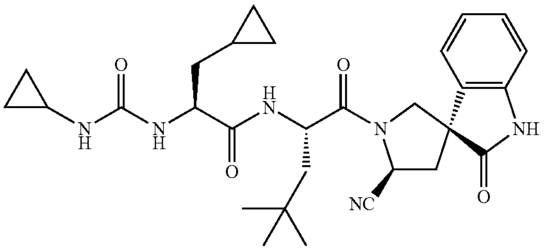 [SMILES: CC(C)(C)C[C@H](NC(=O)[C@H](CC1CC1)NC(=O)NC1CC1)C(=O)N1C[C@]2(C[C@H]1C#N)C(=O)Nc1ccccc12] | [M − H⁺] 533.4 | $^1$H NMR (400 MHz, Acetone-$d_6$) δ 9.68 (s, 1H), 7.61 (d, J = 8.7 Hz, 1H), 7.26 (td, J = 7.7, 1.3 Hz, 1H), 7.10 (d, J = 7.4 Hz, 1H), 7.04-6.95 (m, 2H), 5.79-5.70 (m, 2H), 5.10 (t, J = 8.4 Hz, 1H), 4.73 (td, J = 8.0, 4.7 Hz, 1H), 4.29 (t, J = 7.8 Hz, 2H), 3.98 (d, J = 10.2 Hz, 1H), 2.66 (td, J = 12.9, 8.4 Hz, 2H), 2.50 (dd, J = 5.6, 3.3 Hz, 1H), 1.56 (dd, J = 14.3, 7.8 Hz, 1H), 1.47 (td, J = 6.9, 3.6 Hz, 2H), 0.96 (s, 9H), 0.64 (dt, J = 6.7, 3.3 Hz, 2H), 0.47-0.42 (m, 2H), 0.42-0.36 (m, 1H), 0.07 (dd, J = 9.9, 5.1 Hz, 2H). |
| 330 | 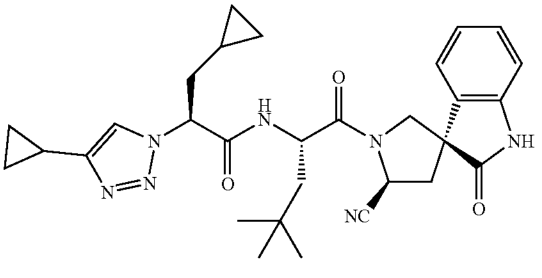 [SMILES: CC(C)(C)C[C@H](NC(=O)[C@H](CC1CC1)n1cc(C2CC2)nn1)C(=O)N1C[C@]2(C[C@H]1C#N)C(=O)Nc1ccccc12] | [M − H⁺] 542.4 | $^1$H NMR (400 MHz, Acetone-$d_6$) δ 9.71 (s, 1H), 7.96 (d, J = 8.0 Hz, 1H), 7.68 (s, 1H), 7.29 (td, J = 7.6, 1.4 Hz, 1H), 7.11-7.06 (m, 1H), 7.06-6.98 (m, 2H), 5.35 (dd, J = 8.9, 6.3 Hz, 1H), 5.13 (t, J = 8.5 Hz, 1H), 4.68 (td, J = 8.1, 4.4 Hz, 1H), 4.27-4.21 (m, 1H), 4.00 (d, J = 10.2 Hz, 1H), 2.75-2.61 (m, 2H), 1.97-1.89 (m, 2H), 1.89-1.85 (m, 1H), 1.84-1.77 (m, 1H), 1.58 (dd, J = 14.4, 8.1 Hz, 1H), 0.90 (s, 9H), 0.74 (ddd, J = 6.4, 4.9, 3.3 Hz, 2H), 0.53-0.45 (m, 1H), 0.40-0.34 (m, 2H), 0.13-0.07 (m, 1H). |
| 331 | 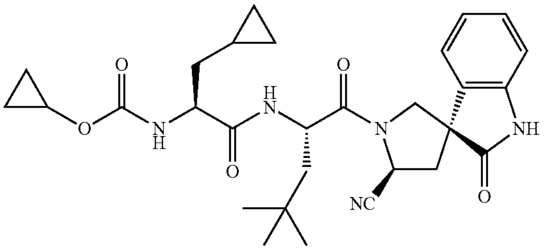 [SMILES: CC(C)(C)C[C@H](NC(=O)[C@H](CC1CC1)NC(=O)OC1CC1)C(=O)N1C[C@]2(C[C@H]1C#N)C(=O)Nc1ccccc12] | [M − H⁺] 534.1 | $^1$H NMR (400 MHz, Acetone-d6) δ 9.68 (s, 1H), 7.50 (d, J = 8.4 Hz, 1H), 7.26 (td, J = 7.6, 1.4 Hz, 1H), 7.07 (d, J = 7.5 Hz, 1H), 7.00 (dd, J = 12.5, 7.6 Hz, 2H), 6.22 (d, J = 8.5 Hz, 1H), 5.10 (t, J = 8.3 Hz, 1H), 4.74 (td, J = 8.1, 4.6 Hz, 1H), 4.26 (d, J = 10.2 Hz, 1H), 4.19 (q, J = 7.4 Hz, 1H), 4.04-3.95 (m, 2H), 2.80-2.69 (m, 4H), 2.69-2.60 (m, 2H), 1.86 (dd, J = 14.4, 4.7 Hz, 1H), 1.58 (dd, J = 14.4, 7.9 Hz, 1H), 1.50 (t, J = 6.9 Hz, 2H), 0.96 (s, 9H), 0.66-0.59 (m, 2H), 0.56 (d, J = 3.3 Hz, 2H), 0.41 (s, 1H), 0.41-0.33 (m, 1H), 0.16-0.03 (m, 2H). |

TABLE 2-continued

The following examples were prepared employing similar protocol as described above.

| Example | Structure | MS | NMR |
|---|---|---|---|
| 332 | 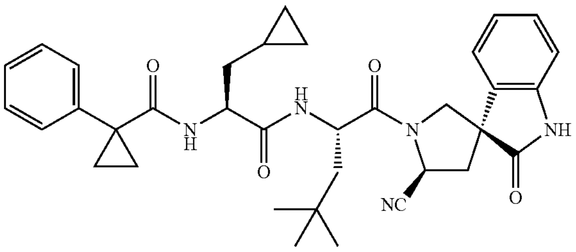 [SMILES: CC(C)(C)C[C@H](NC(=O)[C@H](CC1CC1)NC(=O)C1(c2ccccc2)CC1)C(=O)N1C[C@]2(C[C@H]1C#N)C(=O)Nc1ccccc12] | [M − H+] 594.8 | 1H NMR (400 MHz, Acetone-$d_6$) δ 9.78 (s, 1H), 7.61-7.42 (m, 6H), 7.38 (td, J = 7.7, 1.3 Hz, 1H), 7.15-7.01 (m, 3H), 6.25 (d, J = 7.8 Hz, 1H), 5.19 (t, J = 8.4 Hz, 1H), 4.77 (td, J = 8.3, 4.2 Hz, 1H), 4.57-4.51 (m, 1H), 4.30 (d, J = 10.2 Hz, 1H), 4.07 (d, J = 10.3 Hz, 1H), 2.81-2.73 (m, 2H), 1.93 (dd, J = 14.4, 4.2 Hz, 1H), 1.68 (dd, J = 14.4, 8.3 Hz, 1H), 1.63-1.47 (m, 4H), 1.07 (s, 9H), 0.68-0.57 (m, 1H), 0.46-0.38 (m, 1H), 0.38-0.30 (m, 1H), 0.05 (s, 2H). |
| 333 | 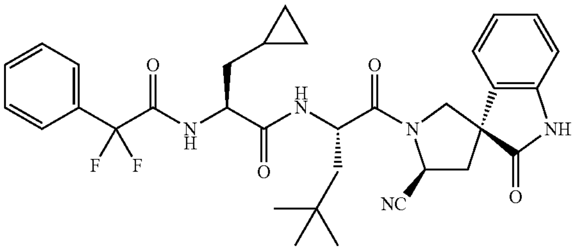 [SMILES: CC(C)(C)C[C@H](NC(=O)[C@H](CC1CC1)NC(=O)C(F)(F)c1ccccc1)C(=O)N1C[C@]2(C[C@H]1C#N)C(=O)Nc1ccccc12] | [M − H+] 604.3 | 1H NMR (400 MHz, Acetone-$d_6$) δ 9.70 (s, 1H), 7.93 (d, J = 8.2 Hz, 1H), 7.67-7.61 (m, 2H), 7.56-7.46 (m, 2H), 7.27 (td, J = 7.6, 1.4 Hz, 1H), 7.08-6.94 (m, 3H), 5.10 (t, J = 8.5 Hz, 1H), 4.73 (td, J = 8.1, 4.6 Hz, 1H), 4.58-4.51 (m, 1H), 4.22 (d, J = 10.2 Hz, 1H), 4.00 (d, J = 10.2 Hz, 1H), 2.71-2.62 (m, 2H), 1.85 (dd, J = 14.4, 4.6 Hz, 1H), 1.61-1.51 (m, 3H), 0.94 (s, 9H), 0.71-0.59 (m, 1H), 0.37-0.29 (m, 2H), 0.12-0.06 (m, 1H). |
| 334 | 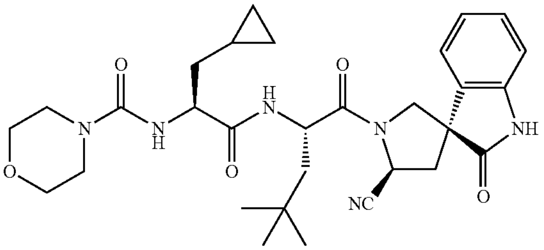 [SMILES: CC(C)(C)C[C@H](NC(=O)[C@H](CC1CC1)NC(=O)N1CCOCC1)C(=O)N1C[C@]2(C[C@H]1C#N)C(=O)Nc1ccccc12] | [M − H+] 563.5 | 1H NMR (400 MHz, Acetone-$d_6$) δ 9.68 (s, 1H), 7.58 (d, J = 8.6 Hz, 1H), 7.26 (td, J = 7.7, 1.3 Hz, 1H), 7.08 (d, J = 7.5 Hz, 1H), 7.04-6.94 (m, 2H), 5.88 (d, J = 7.8 Hz, 1H), 5.10 (t, J = 8.4 Hz, 1H), 4.72 (td, J = 8.2, 4.7 Hz, 1H), 4.32-4.23 (m, 2H), 4.01-3.91 (m, 1H), 3.58 (dd, J = 5.6, 4.1 Hz, 4H), 3.39-3.31 (m, 3H), 2.74-2.54 (m, 2H), 1.85 (dd, J = 14.4, 4.7 Hz, 1H), 1.55 (dd, J = 14.3, 7.9 Hz, 2H), 1.46 (t, J = 7.0 Hz, 2H), 0.95 (s, 9H), 0.76-0.62 (m, 1H), 0.46-0.28 (m, 2H), 0.12-0.05 (m, 1H). |
| 335 | 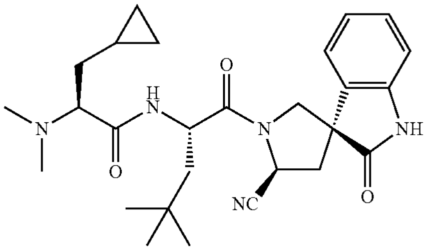 [SMILES: CN(C)[C@@H](CC1CC1)C(=O)N[C@@H](CC(C)(C)C)C(=O)N1C[C@]2(C[C@H]1C#N)C(=O)Nc1ccccc12] | [M − H+] 478.5 | 1H NMR (400 MHz, Acetone-$d_6$) δ 9.69 (s, 1H), 7.52 (d, J = 8.4 Hz, 1H), 7.26 (td, J = 7.6, 1.3 Hz, 1H), 7.10-7.00 (m, 1H), 6.98 (ddd, J = 7.6, 2.5, 1.2 Hz, 2H), 5.11 (t, J = 8.5 Hz, 1H), 4.69 (td, J = 7.9, 4.0 Hz, 1H), 4.31 (d, J = 10.1 Hz, 1H), 3.98 (d, J = 10.2 Hz, 1H), 2.91-2.85 (m, 1H), 2.73-2.62 (m, 2H), 2.26 (s, 6H), 1.91 (dd, J = 14.3, 5.0 Hz, 1H), 1.64-1.55 (m, 2H), 1.25 (ddd, J = 19.1, 9.2, 5.3 Hz, 2H), 0.99 (s, 9H), 0.75-0.60 (m, 1H), 0.42-0.28 (m, 2H), −0.06 (s, 1H). |
| 336 | 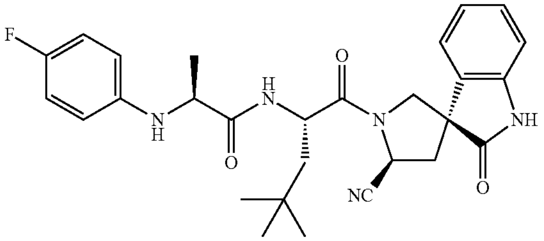 [SMILES: C[C@H](Nc1ccc(F)cc1)C(=O)N[C@@H](CC(C)(C)C)C(=O)N1C[C@]2(C[C@H]1C#N)C(=O)Nc1ccccc12] | [M + Na+] 528.2 | |

TABLE 2-continued
The following examples were prepared employing similar protocol as described above.
| Example | Structure | MS | NMR |
|---|---|---|---|
| 337 | 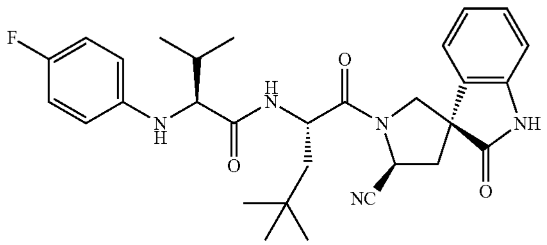 [SMILES: CC(C)[C@H](Nc1ccc(F)cc1)C(=O)N[C@@H](CC(C)(C)C)C(=O)N1C[C@]2(C[C@H]1C#N)C(=O)Nc1ccccc12] | [M + H] 534.3 | |
| 338 | 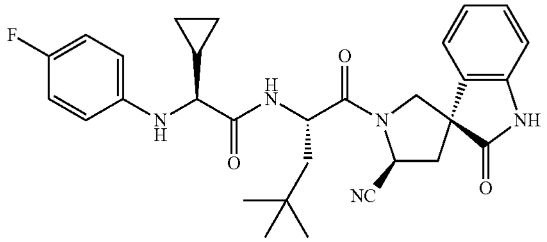 [SMILES: CC(C)(C)C[C@H](NC(=O)[C@@H](Nc1ccc(F)cc1)C1CC1)C(=O)N1C[C@]2(C[C@H]1C#N)C(=O)Nc1ccccc12] | [M + H] 532.3 | |
| 339 | 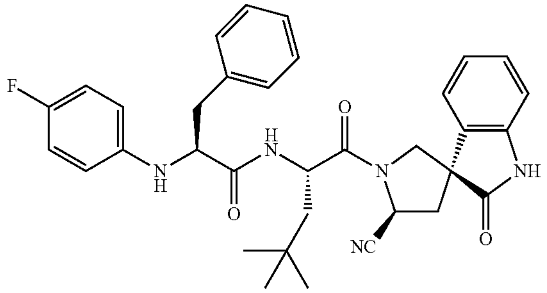 [SMILES: CC(C)(C)C[C@H](NC(=O)[C@H](Cc1ccccc1)Nc1ccc(F)cc1)C(=O)N1C[C@]2(C[C@H]1C#N)C(=O)Nc1ccccc12] | [M + H] 582.3 | |
| 340 | 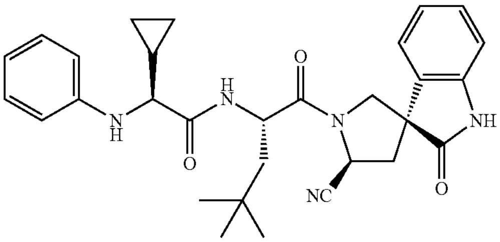 [SMILES: CC(C)(C)C[C@H](NC(=O)[C@@H](Nc1ccccc1)C1CC1)C(=O)N1C[C@]2(C[C@H]1C#N)C(=O)Nc1ccccc12] | [M + H] 514.3 | |
| 341 | 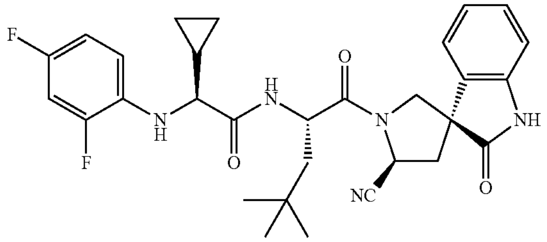 [SMILES: CC(C)(C)C[C@H](NC(=O)[C@@H](Nc1ccc(F)cc1F)C1CC1)C(=O)N1C[C@]2(C[C@H]1C#N)C(=O)Nc1ccccc12] | [M + H] 550.3 | |

TABLE 2-continued
The following examples were prepared employing similar protocol as described above.
| Example | Structure | MS | NMR |
|---|---|---|---|
| 342 | 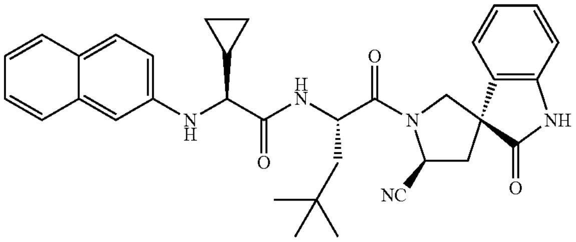 [SMILES: CC(C)(C)C[C@H](NC(=O)[C@@H](Nc1ccc2ccccc2c1)C1CC1)C(=O)N1C[C@]2(C[C@H]1C#N)C(=O)Nc1ccccc12] | [M + H] 564.4 | |
| 343 | 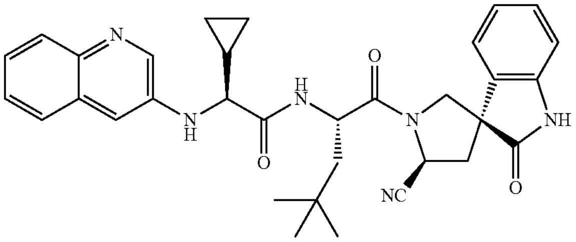 [SMILES: CC(C)(C)C[C@H](NC(=O)[C@@H](Nc1cnc2ccccc2c1)C1CC1)C(=O)N1C[C@]2(C[C@H]1C#N)C(=O)Nc1ccccc12] | [M + H] 565.3 | |
| 344 | 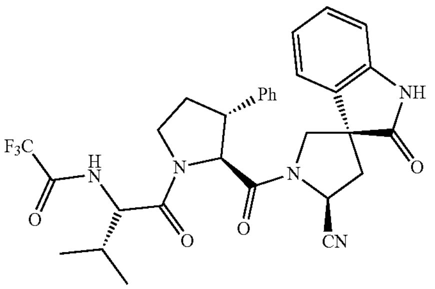 | 582.55 [M + H] | $^1$H NMR (400 MHz, Acetone-$d_6$) δ 9.59 (s, 1H), 8.36 (d, J = 8.2 Hz, 1H), 7.46-7.33 (m, 4H), 7.37-7.27 (m, 1H), 7.30-7.17 (m, 2H), 7.05-6.89 (m, 2H), 5.14-5.00 (m, 1H), 4.62 (t, J = 8.1 Hz, 1H), 4.53 (d, J = 8.4 Hz, 1H), 4.36-4.20 (m, 1H), 4.02-3.75 (m, 2H), 3.64-3.50 (m, 1H), 2.96 (d, J = 10.3 Hz, 1H), 2.82 (d, J = 1.4 Hz, 1H), 2.67-2.55 (m, 1H), 2.54-2.21 (m, 4H), 2.10 (s, 1H), 1.25-0.97 (dd, 6H). |
| 345 | 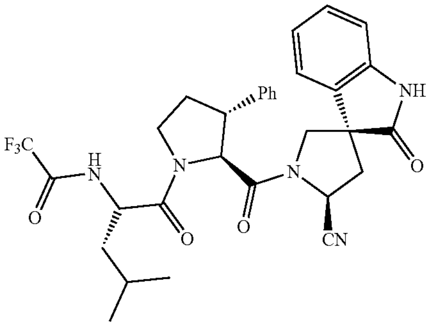 | 596.53 [M + H] | |

TABLE 2-continued

The following examples were prepared employing similar protocol as described above.

| Example | Structure | MS | NMR |
|---|---|---|---|
| 346 | 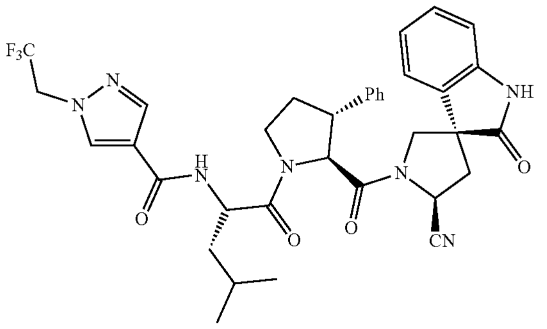 | 676.58 [M + H] | |
| 347 | 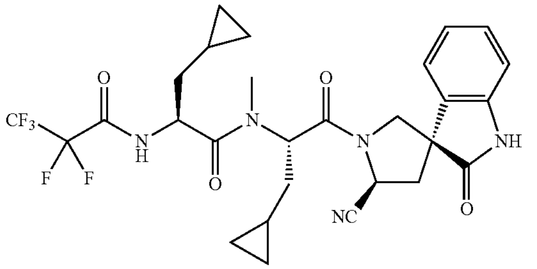 [SMILES: CN(C(=O)[C@H](CC1CC1)NC(=O)C(F)(F)C(F)(F)F)[C@@H](CC1CC1)C(=O)N1C[C@]2(C[C@H]1C#N)C(=O)Nc1ccccc12] | 594.25 [M − H] | $^1$H NMR (400 MHz, Chloroform-d) δ 8.78 (s, 1H), 7.42 (d, J = 8.1 Hz, 1H), 7.35-7.27 (m, 1H), 7.05-6.91 (m, 2H), 6.84 (d, J = 7.5 Hz, 1H), 5.22 (dd, J = 8.4, 6.8 Hz, 1H), 5.05-4.88 (m, 2H), 4.19-4.08 (m, 2H), 4.01 (d, J = 10.3 Hz, 1H), 3.17 (s, 3H), 2.84 (dd, J = 13.1, 9.1 Hz, 1H), 2.59-2.47 (m, 1H), 2.17 (d, J = 0.7 Hz, 3H), 1.86 (dt, J = 13.6, 7.9 Hz, 2H), 1.71 (dt, J = 13.6, 6.7 Hz, 1H), 1.44-1.32 (m, 1H), 1.32-1.18 (m, 2H), 0.73-0.60 (m, 1H), 0.60-0.40 (m, 5H), 0.16 (tq, J = 9.6, 4.8, 4.4 Hz, 2H), 0.06 (dt, J = 9.0, 4.9 Hz, 1H), −0.02 (dt, J = 7.3, 3.5 Hz, 1H). |

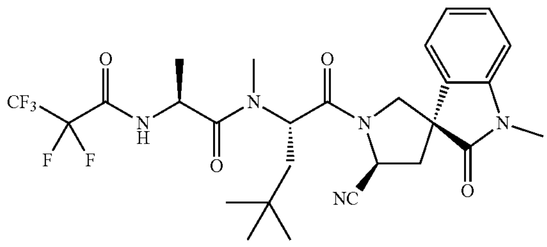

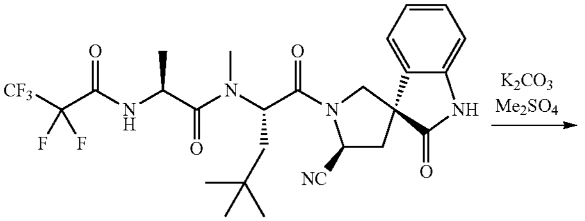

(1-1)

-continued

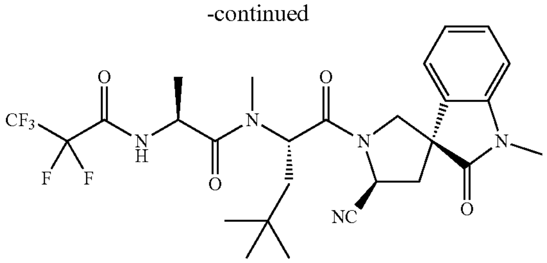

Example 1

To a solution of Compound 1-1 (15 mg, 0.026 mmol) in Acetone (0.131 ml) was added $K_2CO_3$ (5.44 mg, 0.039 mmol) and dimethyl sulfate (3.73 μl, 0.039 mmol) at rt. The reaction mixture was then heated under reflux for ~3 hrs and monitored by LC-MS. The mixture was concentrated to remove acetone, then diluted with EtOAc, washed with water, brine, dried and concentrated. The crude was purified by silica gel column by eluting 0 to 50% acetone/cyclohexane to give Example 348 (3.5 mg, 5.98 μmol) in 22.8% yield. LC-MS, ES−: 584.09 [M−1]. 1H NMR (400 MHz, Acetone-d6) 1H NMR (400 MHz, Acetone-d6) δ 8.22 (s, 1H), 7.24 (td, J=7.7, 1.4 Hz, 1H), 7.01-6.89 (m, 2H), 5.29 (dd, J=7.5, 4.8 Hz, 1H), 5.04 (t, J=8.5 Hz, 1H), 4.60 (t, J=7.0 Hz, 1H), 3.88-3.75 (m, 2H), 3.11 (s, 2H), 2.96 (s, 2H), 2.85 (s, 1H), 2.56 (dd, J=8.3, 6.1 Hz, 3H), 1.16 (s, 3H), 0.77 (d, J=14.3 Hz, 8H).

TABLE 3

The following examples were prepared employing similar protocol as described above.

| Example | Structure | MS | NMR |
|---|---|---|---|
| 349 | 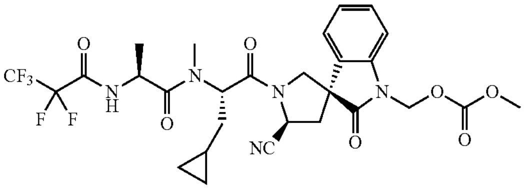 [SMILES: COC(=O)OCN1C(=O)[C@]2(C[C@@H](C#N)N(C(=O)[C@H](CC3CC3)N(C)C(=O)[C@H](C)NC(=O)C(F)(F)C(F)(F)F)C2)c2ccccc21] | 584.09 [M − H] | $^{1}$H NMR (400 MHz, Chloroform-d) δ 7.43-7.29 (m, 2H), 7.18 (d, J = 7.9 Hz, 1H), 7.08 (td, J = 7.6, 1.0 Hz, 1H), 6.87 (dd, J = 7.5, 1.2 Hz, 1H), 5.83 (s, 2H), 5.17 (dd, J = 8.7, 6.6 Hz, 1H), 4.98 (t, J = 8.7 Hz, 1H), 4.77 (p, J = 6.8 Hz, 1H), 4.19 (dd, J = 10.4, 1.2 Hz, 1H), 4.05 (d, J = 10.3 Hz, 1H), 3.84 (s, 3H), 3.14 (s, 3H), 2.88 (dd, J = 13.2, 9.2 Hz, 1H), 2.53 (ddd, J = 13.2, 8.1, 1.2 Hz, 1H), 1.85 (ddd, J = 13.6, 8.7, 7.4 Hz, 1H), 1.73 (dt, J = 13.4, 6.5 Hz, 1H), 1.60 (d, J = 19.0 Hz, 1H), 1.15 (d, J = 6.7 Hz, 3H), 0.72-0.60 (m, 1H), 0.54 (ddt, J = 12.8, 6.5, 2.6 Hz, 2H), 0.25-0.09 (m, 2H). |
| 350 | 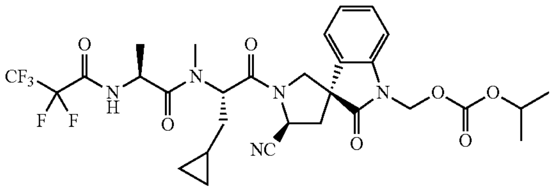 [SMILES: CC(C)OC(=O)OCN1C(=O)[C@]2(C[C@@H](C#N)N(C(=O)[C@H](CC3CC3)N(C)C(=O)[C@H](C)NC(=O)C(F)(F)C(F)(F)F)C2)c2ccccc21] | 670.12 [M − H] | $^{1}$H NMR (500 MHz, Chloroform-d) δ 7.48-7.32 (m, 2H), 7.19 (t, J = 5.1 Hz, 1H), 7.07 (td, J = 8.6, 7.5, 3.5 Hz, 1H), 6.87 (t, J = 6.3 Hz, 1H), 5.82 (d, J = 2.3 Hz, 2H), 5.34-5.13 (m, 1H), 5.13-4.89 (m, 2H), 4.88-4.75 (m, 1H), 4.20 (t, J = 11.3 Hz, 1H), 4.16-3.99 (m, 1H), 3.14 (s, 3H), 3.00-2.84 (m, 1H), 2.53 (dt, J = 13.0, 7.4 Hz, 1H), 2.17 (d, J = 2.8 Hz, 2H), 1.85 (dt, J = 15.8, 7.9 Hz, 1H), 1.73 (dt, J = 13.3, 6.6 Hz, 1H), 1.61 (s, 1H), 1.45-1.29 (m, 6H), 1.29-1.23 (m, 1H), 0.74-0.64 (m, 1H), 0.63-0.48 (m, 2H), 0.13-0.21 (m, 2H). |
| 351 | 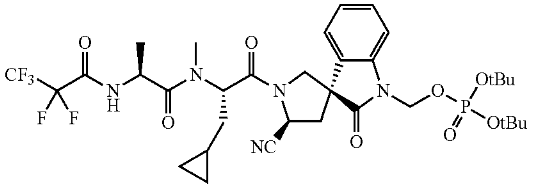 [SMILES: C[C@H](NC(=O)C(F)(F)C(F)(F)F)C(=O)N(C)[C@@H](CC1CC1)C(=O)N1C[C@]2(C[C@H]1C#N)C(=O)N(COP(=O)(OC(C)(C)C)OC(C)(C)C)c1ccccc12] | 776.04 [M − H] | |
| 352 | 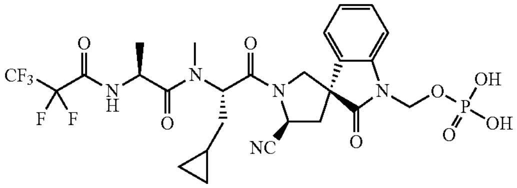 [SMILES: C[C@H](NC(=O)C(F)(F)C(F)(F)F)C(=O)N(C)[C@@H](CC1CC1)C(=O)N1C[C@]2(C[C@H]1C#N)C(=O)N(COP(=O)(O)O)c1ccccc12] | 664.08 [M − H] | |

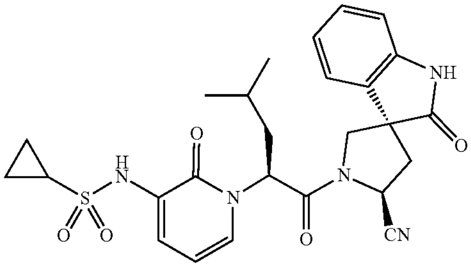

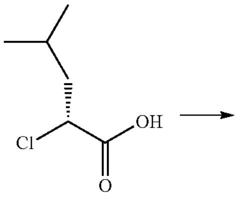

(1-1)

-continued

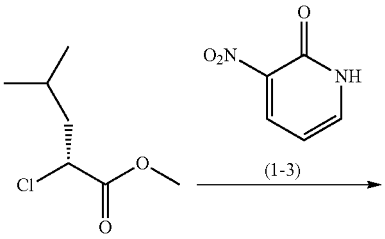

(1-2)

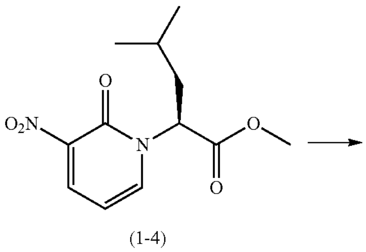

(1-4)

-continued

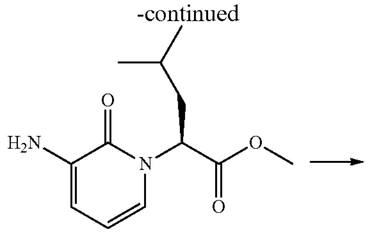

(1-5)

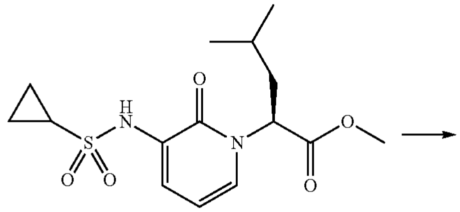

(1-6)

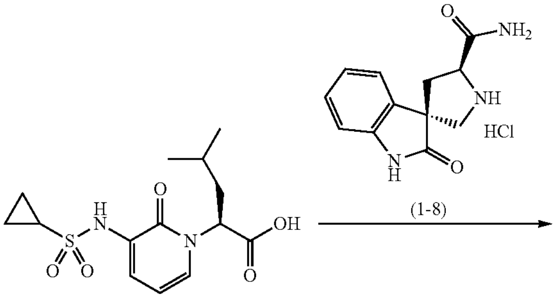

(1-8)

(1-7)

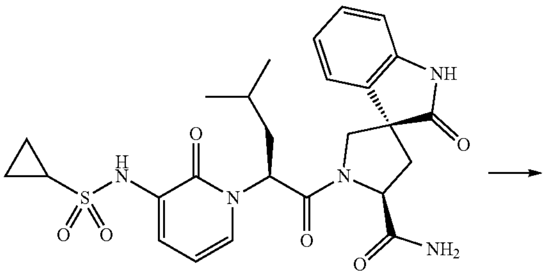

(1-9)

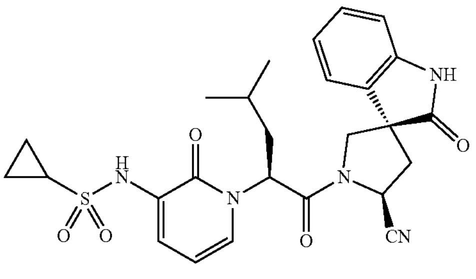

Example 353

Step 1-1

Compound (1-1) (6.2 g) was dissolved in methanol (250 ml). Thionyl chloride (10 ml) was added, and the mixture was stirred at rt overnight. Then, the volatiles were removed to produce compound (1-2) (6 g), which was used directly in the next step without further purification.

Step 1-2

Compound (1-3) (1.5 g) was dissolved in DMF (15 ml) at 0° C., then 90% NaH powder (500 mg) was added under an inert nitrogen atmosphere. After 1 h, a solution of compound (1-2) (2 g) in DMF (30 ml) was added at 0° C. The mixture was allowed to reach rt, then heated to 80° C. for 20 h. The volatiles were removed and the residue was purified on silica gel to provide the product, compound (1-4) (50 mg).

Step 1-3

Compound (1-4) (690 mg) was dissolved in MeOH (50 ml). 10% Pd/C (50 mg) was added, and the mixture was stirred at rt for 12 h under a hydrogen atmosphere. Then, the reaction was opened to air and filtered over celite. The filtrate was concentrated and purified on silica gel to provide compound (1-5) (300 mg).

Step 1-4

To a solution of compound (1-5) (190 mg) and $Et_3N$ (161 mg) in DCM (3 mL) was added cyclopropanesulfonyl chloride (125 mg) at 0° C. Then the mixture was stirred at rt for 2 h. The mixture was poured into water (20 mL), the aqueous layer was extracted with DCM (10 mL×2). The combined organic phases were dried over $Na_2SO_4$ and concentrated under reduced pressure. The residue was purified by silica column eluting with (0-40% EtOAc in Petroleum ether) to afford the compound (1-6) (50 mg) as a yellow oil.

Step 1-5

To the solution of compound (1-6) (110 mg) in THE (2 mL), MeOH (2 mL) and $H_2O$ (2 mL) was added LiOH·$H_2O$ (67 mg). Then the mixture was stirred at 50° C. for 3 h. The mixture was poured into water (20 mL), the aqueous was acidified to pH 2-3 with 2 N HCl. Extracted with EtOAc (10 mL×3). The combined organic phases were dried over $Na_2SO_4$ and concentrated to give compound (1-7) (130 mg) which was used directly without further purification.

Step 1-6

To a solution of compound (1-7) (130 mg) in DMF (3 mL) was added compound (1-8) (91 mg), EDCl (228 mg), HOBT (107 mg), DIEA (102 mg), then the reaction mixture was stirred at r.t for 4 h. The reaction mixture was diluted with water (20 mL) and extracted EtOAc (10 mL×3). The organic layers were dried over $Na_2SO_4$ and evaporated in vacuo. The residue was purified by silica column eluting with (0-5% MeOH in DCM) to afford the compound (1-9) (88 mg) as a yellow solid.

Step 1-7

To a solution of compound (1-9) (88 mg) in THE (2 mL) was added TEA (49 mg) and TFAA (51 mg). The reaction was stirred at r.t for 12 h, then it was poured into water and extracted with EtOAc (10 mL×2). The combined organic layers were dried over $Na_2SO_4$ and concentrated. The residue was purified by reverse-phase HPLC to give Example 353 (7.9 mg) as a white solid along with the corresponding epimer (7.5 mg).

$^1$H NMR (400 MHz, DMSO-$d_6$) δ 7.75-7.53 (m, 2H), 7.46-7.30 (m, 2H), 7.22-6.88 (m, 4H), 6.37 (td, J=7.2, 1.8 Hz, 1H), 6.08-4.98 (m, 2H), 4.02-3.68 (m, 2H), 3.00-2.47 (m, 3H), 2.23-1.97 (m, 2H), 1.65-1.43 (m, 2H), 1.22-1.09 (m, 1H), 1.04-0.86 (m, 8H). $[M-H]^-$ m/z 521.8.

TABLE 4

| The following examples were prepared employing a similar protocol as described above. | | | |
|---|---|---|---|
| Example | Structure | MS | NMR |
| 354 | 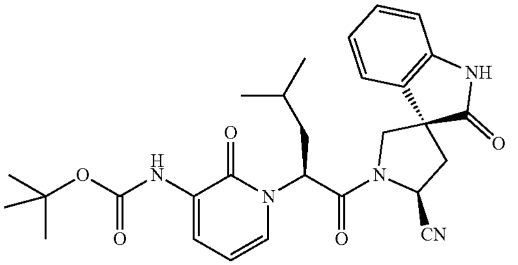 [SMILES: CC(C)C[C@@H](C(=O)N1C[C@]2(C[C@H]1C#N)C(=O)Nc1ccccc12)n1cccc(NC(=O)OC(C)(C)C)c1=O] | [M − H]− 518.2 | $^1$H NMR (300 MHz, chloroform-d): δ 8.07-7.53 (m, 3H), 7.34-7.18 (m, 1H), 7.09-6.79 (m, 4H), 6.36 (t, J = 7.2 Hz, 1H), 6.16-4.99 (m, 2H), 4.01-3.48 (m, 2H), 2.97-2.64 (m, 2H), 2.25-1.94 (m, 2H), 1.51 (d, J = 8.5 Hz, 9H), 1.02-0.84 (m, 7H) |
| 355 | 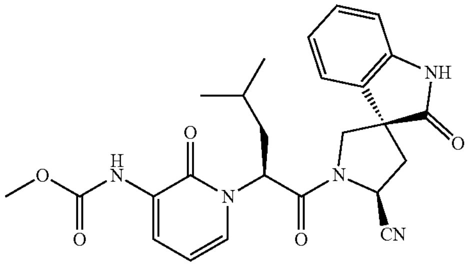 [SMILES: COC(=O)Nc1cccn([C@@H](CC(C)C)C(=O)N2C[C@]3(C[C@H]2C#N)C(=O)Nc2ccccc23)c1=O] | [M − H]+ 462.2 | (300 MHz, chloroform-d): δ 8.41-7.93 (m, 3H), 7.33-6.70 (m, 6H), 6.34 (t, J = 7.3 Hz, 1H), 6.10-4.89 (m, 2H), 3.93-3.51 (m, 2H), 2.90-2.42 (m, 2H), 2.15 (d, J = 16.6 Hz, 3H), 1.70-1.61 (m, 1H), 1.44-1.33 (m, 1H), 0.94 (dd, J = 6.6, 1.7 Hz, 3H), 0.82 (dd, J = 17.4, 6.5 Hz, 3H) ppm. |
| 356 | 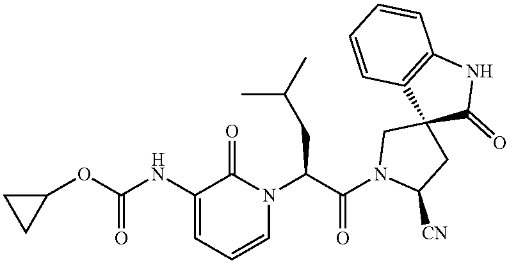 | [M + Na]+ m/z = 488.0 | $^1$H NMR (300 MHz, chloroform-d) δ 8.55 (d, J = 29.1 Hz, 1H), 8.45-8.37 (m, 1H), 8.02 (d, J = 17.6 Hz, 1H), 7.39-7.30 (m, 1H), 7.26-7.21 (m, 1H), 7.11-7.06 (m, 1H), 6.98-6.60 (m, 3H), 6.41 (t, J = 7.2 Hz, 1H), 6.19-5.92 (m, 1H), 5.90-5.00 (m, 1H), 4.01-3.58 (m, 2H), 2.98-2.67 (m, 2H), 2.21-1.97 (m, 2H), 1.78-1.40 (m, 1H), 1.14-1.07 (m, 2H), 1.02 (d, J = 6.7 Hz, 2H), 0.90 (dd, J = 18.3, 8.3 Hz, 6H) |
| 357 | 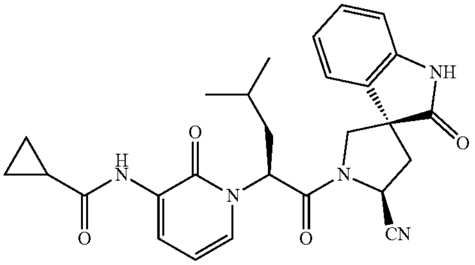 [SMILES: CC(C)C[C@@H](C(=O)N1C[C@]2(C[C@H]1C#N)C(=O)Nc1ccccc12)n1cccc(NC(=O)C2CC2)c1=O] | [M + Na]+ m/z = 488.0 | δ[1]H NMR (300 MHz, chloroform-d) δ 8.27 (dd, J = 7.4, 1.6 Hz, 1H), 8.10 (s, 1H), 7.74 (s, 1H), 7.36 (dd, J = 7.1, 1.7 Hz, 1H), 7.17 (d, J = 6.9 Hz, 1H), 6.89 (d, J = 8.3 Hz, 1H), 6.75 (t, J = 7.3 Hz, 1H), 6.45 (d, J = 7.5 Hz, 1H), 6.34 (t, J = 7.3 Hz, 1H), 5.91 (t, J = 7.7 Hz, 1H), 4.95 (t, J = 8.6 Hz, 1H), 4.53 (d, J = 10.4 Hz, 1H), 4.01 (d, J = 10.5 Hz, 1H), 2.88 (dd, J = 13.3, 8.7 Hz, 1H), 2.52 (dd, J = 13.4, 8.4 Hz, 1H), 2.05-1.90 (m, 2H), 1.44 (ddd, J = 12.5, 8.8, 6.0 Hz, 2H), 1.02 (dd, J = 8.2, 3.0 Hz, 2H), 0.95 (t, J = 6.3 Hz, 6H), 0.85 (dd, J = 7.8, 6.3 Hz, 2H) |
| 358 | 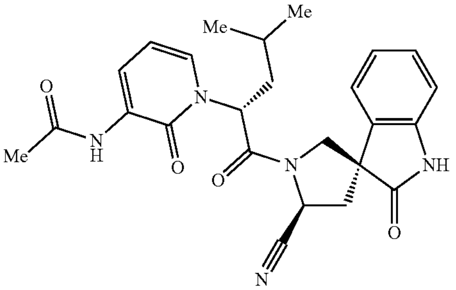 [SMILES: CC(=O)Nc1cccn([C@H](CC(C)C)C(=O)N2C[C@]3(C[C@H]2C#N)C(=O)Nc2ccccc23)c1=O] | [M + Na]+ m/z = 462.2 | $^1$H NMR (300 MHz, chloroform-d): δ 8.29 (d, J = 1.5 Hz, 1H), 7.88 (s, 1H), 7.62 (d, J = 5.7 Hz, 1H), 7.37 (dd, J = 7.2, 1.8 Hz, 1H), 7.21-7.11 (m, 1H), 6.92-6.85 (m, 1H), 6.75 (dd, J = 7.5, 6.8 Hz, 1H), 6.44 (d, J = 7.5 Hz, 1H), 6.35 (t, J = 7.2 Hz, 1H), 5.95-5.83 (m, 1H), 4.94 (t, J = 8.7 Hz, 1H), 4.51 (d, J = 9.6 Hz, 1H), 4.01 (d, J = 10.5 Hz, 1H), 2.87 (dd, J = 13.3, 8.7 Hz, 1H), 2.51 (dd, J = 13.4, 7.5 Hz, 1H), 2.08 (s, 3H), 2.05-1.91 (m, 2H), 1.51-1.41 (m, 1H), 0.95 (t, J = 6.6 Hz, 6H) |

TABLE 4-continued
The following examples were prepared employing a similar protocol as described above.
| Example | Structure | MS | NMR |
|---|---|---|---|
| 359 | 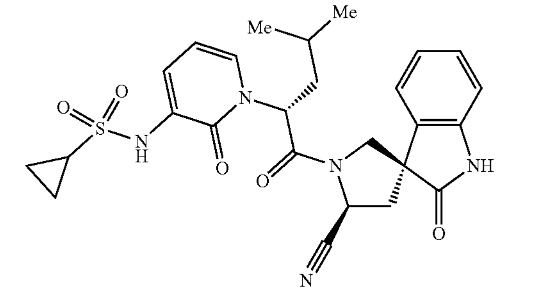 [SMILES: CC(C)C[C@H](C(=O)N1C[C@]2(C[C@H]1C#N)C(=O)Nc1ccccc12)n1cccc(NS(=O)(=O)C2CC2)c1=O] | [M − H]⁻ m/z = 521.8. | |
| 360 | 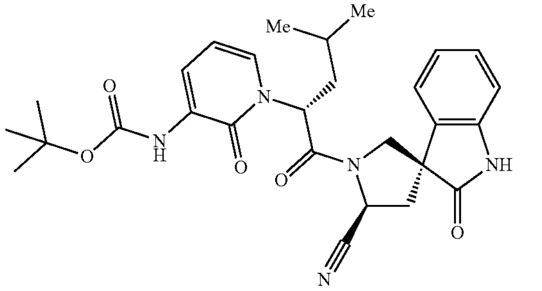 [SMILES: CC(C)C[C@H](C(=O)N1C[C@]2(C[C@H]1C#N)C(=O)Nc1ccccc12)n1cccc(NC(=O)OC(C)(C)C)c1=O] | [M − H]⁻ m/z = 518.1 | $^1$H NMR (300 MHz, chloroform-d): δ 7.95-7.84 (m, 2H), 7.30 (dd, J = 7.1, 1.7 Hz, 1H), 7.20-7.11 (m, 2H), 6.86 (d, J = 7.8 Hz, 1H), 6.75 (t, J = 7.6 Hz, 1H), 6.43 (d, J = 7.4 Hz, 1H), 6.32 (t, J = 7.3 Hz, 1H), 5.90 (t, J = 7.7 Hz, 1H), 4.94 (t, J = 8.6 Hz, 1H), 4.50 (d, J = 10.4 Hz, 1H), 3.99 (d, J = 10.6 Hz, 1H), 2.86 (dd, J = 13.3, 8.7 Hz, 1H), 2.50 (dd, J = 13.6, 8.1 Hz, 1H), 2.05-1.86 (m, 2H), 1.48 (s, 9H), 1.34 (t, J = 7.4 Hz, 1H), 0.98-0.90 (m, 6H) |
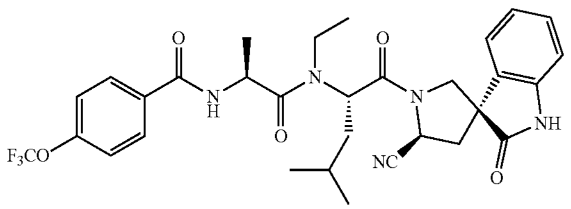
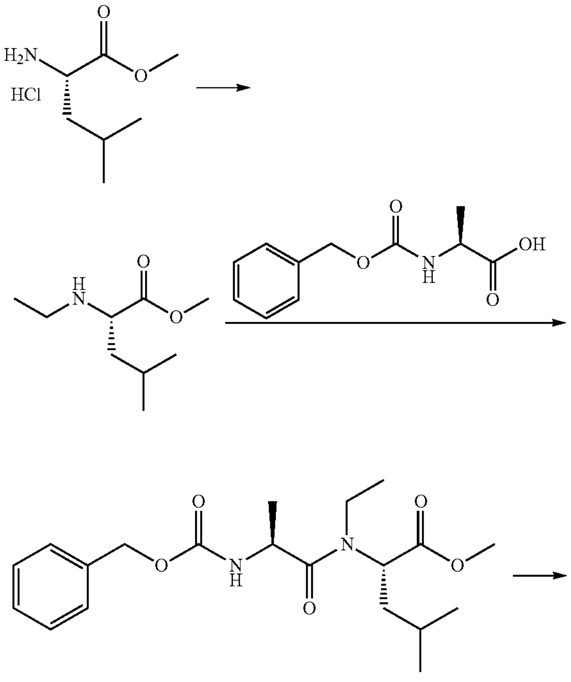
-continued
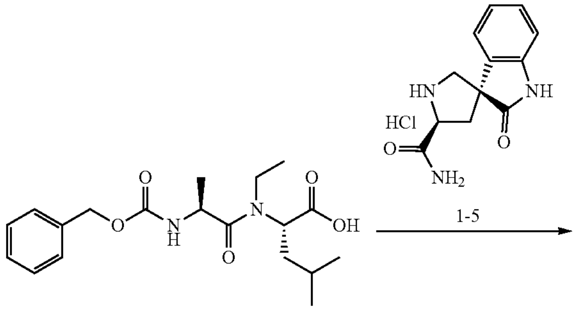
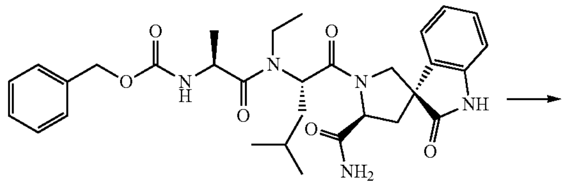
361-1
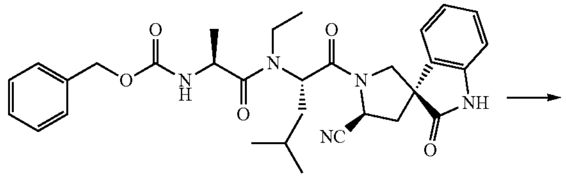
361-2

-continued

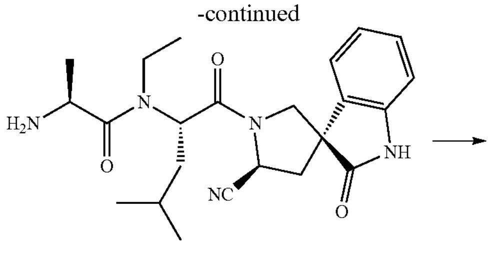

361-3

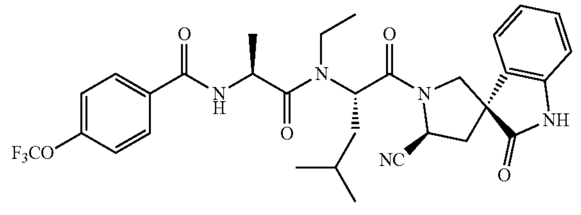

Example 361

Step 1

Methyl L-leucinate hydrochloride (1036 mg, 5.70 mmol) was dissolved in DCM (25 ml) and MeOH (5.00 ml). At 0° C., triethylamine (1590 μl, 11.41 mmol), sodium cyanotrihydroborate (287 mg, 4.56 mmol) and acetaldehyde (384 μl, 6.84 mmol) were added. The mixture was stirred at 0° C. for 2 h, warmed to rt, and stirred for 18 h. The reaction was quenched with 5% $NaHCO_3$, and extracted with DCM. The organic layer was washed with brine, dried over $Na_2SO_4$, and concentrated in vacuo. Purification of the residue on silica gel with 0-10% MeOH/DCM afforded methyl ethyl-L-leucinate (787 mg, 4.54 mmol, 80% yield) as an oil. $^1H$ NMR (400 MHz, Chloroform-d) δ 3.74 (s, 3H), 3.34 (td, J=7.3, 1.3 Hz, 1H), 2.73-2.48 (m, 2H), 1.80-1.59 (m, 1H), 1.59-1.42 (m, 2H), 1.13 (td, J=7.2, 1.3 Hz, 3H), 0.94 (ddd, J=10.0, 6.6, 1.0 Hz, 6H).

Step 2

Methyl ethyl-L-leucinate (582 mg, 3.36 mmol) was dissolved in DMF (7 ml). ((benzyloxy)carbonyl)-L-alanine (750 mg, 3.36 mmol), Hunig's base (587 μl, 3.36 mmol), and HATU (1277 mg, 3.36 mmol) were added. The mixture was stirred at rt for 5 min, heated to 80° C., and stirred at for 70 min. The reaction mixture was cooled to rt, diluted with MTBE, and quenched with 5% $NaHCO_3$. The organic layer was washed with brine, dried with $MgSO_4$, and concentrated in vacuo. Purification of the residue on silica gel with 0-50% EtOAc/cyclohexane provided methyl N-(((benzyloxy)carbonyl)-L-alanyl)-N-ethyl-L-leucinate (774 mg, 2.045 mmol, 60.9% yield). $^1H$ NMR (400 MHz, Chloroform-d) δ 7.43-7.28 (m, 5H), 5.68 (d, J=8.4 Hz, 1H), 5.18-5.07 (m, 2H), 4.85 (dd, J=9.7, 5.1 Hz, 1H), 4.67 (dt, J=8.2, 6.7 Hz, 1H), 3.70 (s, 3H), 3.51 (dq, J=14.5, 7.1 Hz, 1H), 3.35-3.21 (m, 1H), 1.88 (ddd, J=14.2, 9.2, 5.1 Hz, 1H), 1.71 (ddd, J=14.3, 9.8, 4.6 Hz, 1H), 1.42-1.24 (m, 6H), 1.05-0.91 (m, 6H).

Step 3

Methyl N-(((benzyloxy)carbonyl)-L-alanyl)-N-ethyl-L-leucinate (963 mg, 2.54 mmol) was dissolved in THE (13 ml) and water (13.00 ml). At 0° C., lithium hydroxide hydrate (214 mg, 5.09 mmol) was added. The mixture was stirred at 0° C. for 2 h and diluted with cyclohexane/water (10 mL each). The collected aqueous layer was quenched with 1 M HCl (6 mL), and extracted with DCM (2×) and EtOAc (2×). The combined organic layer was washed with brine, dried with $MgSO_4$, and concentrated in vacuo. N-(((benzyloxy)carbonyl)-L-alanyl)-N-ethyl-L-leucine (649 mg, 1.781 mmol, 70.0% yield) was obtained as a colorless oil. $^1H$ NMR (400 MHz, Chloroform-d) δ 7.42-7.28 (m, 5H), 5.81 (d, J=8.3 Hz, 1H), 5.18-5.06 (m, 2H), 4.77-4.60 (m, 2H), 3.54 (dq, J=14.4, 7.1 Hz, 1H), 3.30 (dq, J=14.8, 7.2 Hz, 1H), 1.92 (ddd, J=14.3, 8.9, 5.5 Hz, 1H), 1.75 (ddd, J=14.3, 9.4, 5.1 Hz, 1H), 1.62 (m, 1H), 1.42-1.24 (m, 6H), 1.04-0.92 (m, 6H).

Step 4

Compound 1-5 (496 mg, 1.482 mmol) and N-(((benzyloxy)carbonyl)-L-alanyl)-N-ethyl-L-leucine (540 mg, 1.482 mmol) were dissolved in DMF (5 ml). At 0° C., HOAt (0.6 M in DMF) (494 μl, 0.296 mmol), 2,4,6-trimethylpyridine (431 μl, 3.26 mmol), and HATU (620 mg, 1.630 mmol) were added. The mixture was stirred at 0° C. for 3.5 h, warmed to rt, and stirred for 1 h. The reaction was quenched at 0° C. with 5% $NaHCO_3$ and extracted with DCM (2×). The organic layer was washed with 1 M HCl, brine, dried over $MgSO_4$, and concentrated in vacuo. Purification of the residue on silica gel with 0-100% acetone/cyclohexane provided 361-1 (823 mg, 1.425 mmol, 96% yield). $^1H$ NMR (400 MHz, Acetone-$d_6$) δ 9.67 (s, 1H), 7.37-7.23 (m, 5H), 7.08 (m, 2H), 7.08-6.92 (m, 3H), 6.40 (s, 1H), 6.27 (d, J=8.2 Hz, 1H), 5.44 (t, J=7.2 Hz, 1H), 5.03 (s, 2H), 4.84-4.75 (m, 1H), 4.40 (p, J=7.1 Hz, 1H), 3.89 (d, J=10.1 Hz, 1H), 3.79 (d, J=10.2 Hz, 1H), 3.67 (dq, J=14.7, 7.4 Hz, 1H), 3.36 (dt, J=15.5, 7.2 Hz, 1H), 2.51 (dd, J=12.7, 9.9 Hz, 1H), 2.38 (m, 1H), 1.82-1.73 (m, 1H), 1.55 (dq, J=14.5, 6.5 Hz, 2H), 1.32 (t, J=7.1 Hz, 3H), 0.92 (dd, J=13.8, 6.3 Hz, 6H), 0.65 (d, J=6.8 Hz, 3H). [M+H$^+$] 578.3.

Step 5.

Compound 361-1 (823 mg, 1.425 mmol) was dissolved in $CH_2Cl_2$ (7.12 ml). At 0° C., triethylamine (993 μl, 7.12 mmol) and TFAA (443 μl, 3.13 mmol) were added dropwise. The mixture was stirred at 0° C. for 15 min, quenched with 5% $NaHCO_3$, and extracted with DCM. The organic layer was loaded on silica gel and eluted with 0-50% acetone/cyclohexane to provide 361-2 (530 mg, 0.947 mmol, 66.5% yield)$^1H$ NMR (400 MHz, Acetone-$d_6$) δ 9.72 (s, 1H), 7.37-7.24 (m, 6H), 7.12-6.93 (m, 3H), 6.33 (d, J=8.2 Hz, 1H), 5.46 (t, J=7.4 Hz, 1H), 5.16 (t, J=8.4 Hz, 1H), 5.04 (d, J=2.1 Hz, 2H), 4.46 (p, J=7.1 Hz, 1H), 3.96 (d, J=10.5 Hz, 1H), 3.85 (d, J=10.5 Hz, 1H), 3.66 (dq, J=14.5, 7.1 Hz, 1H), 3.40 (dq, J=14.7, 7.1 Hz, 1H), 2.82-2.63 (m, 2H), 1.80 (dt, J=14.2, 7.5 Hz, 1H), 1.61 (m, 2H), 1.33 (t, J=7.2 Hz, 3H), 0.94 (dd, J=10.7, 6.5 Hz, 6H), 0.79 (d, J=6.9 Hz, 3H). [M+Na$^+$] 582.2.

Step 6

Compound 361-2 (530 mg, 0.947 mmol) was dissolved in MeOH (9.47 ml). 10% Pd/C (50.4 mg, 0.047 mmol) was added. The mixture was stirred under hydrogen (balloon) at rt for 90 min, filtered through Celite, and concentrated in vacuo. 361-3 (430 mg, 1.010 mmol, quant. yield) was obtained as a white solid. $^1H$ NMR (400 MHz, DMSO-$d_6$) δ 10.72 (s, 1H), 7.23 (td, J=7.6, 1.4 Hz, 1H), 7.00 (dd, J=7.5, 1.4 Hz, 1H), 6.98-6.91 (m, 1H), 6.88 (d, J=7.7 Hz, 1H), 5.26 (t, J=7.2 Hz, 1H), 5.15 (t, J=8.0 Hz, 1H), 3.76 (d, J=10.6 Hz, 1H), 3.55 (d, J=10.5 Hz, 1H), 3.42 (m, 1H), 3.29-3.15 (m, 1H), 2.63 (m, 1H), 2.51-2.43 (m, 1H), 1.71 (dt, J=13.8, 7.3 Hz, 1H), 1.47 (m, 2H), 1.14 (t, J=7.1 Hz, 3H), 0.89 (dt, J=9.4, 4.7 Hz, 6H), 0.55 (d, J=6.5 Hz, 3H). [M+H$^+$] 426.3.

Step 7

Compound 361-3 (16 mg, 0.038 mmol) was dissolved in $CH_2Cl_{12}$ (0.313 ml) and DMF (0.063 ml). 4-(trifluoromethoxy)benzoic acid (7.75 mg, 0.038 mmol), 4-methylmorpholine (8.27 μl, 0.075 mmol) and HATU (14.30 mg, 0.038 mmol) were added. The mixture was stirred at rt for 1 h, quenched with 5% $NaHCO_3$, and extracted with DCM.

The organic layer was loaded on silica gel and eluted with 0-50% acetone to afford Example 361 (20 mg, 0.033 mmol, 87% yield). $^1$H NMR (400 MHz, Acetone-$d_6$) δ 9.74 (s, 1H), 8.05-7.97 (m, 2H), 7.71 (d, J=7.6 Hz, 1H), 7.40 (d, J=8.3 Hz, 2H), 7.31 (td, J=7.6, 1.6 Hz, 1H), 7.12 (d, J=7.2 Hz, 1H), 7.11-7.03 (m, 1H), 7.03 (d, J=7.8 Hz, 1H), 5.48 (t, J=7.4 Hz, 1H), 5.18 (t, J=8.4 Hz, 1H), 4.88 (p, J=7.1 Hz, 1H), 3.98 (d, J=10.5 Hz, 1H), 3.89 (d, J=10.5 Hz, 1H), 3.74 (dq, J=14.4, 7.1 Hz, 1H), 3.46 (dq, J=14.6, 7.1 Hz, 1H), 2.75 (d, J=8.5 Hz, 1H), 2.69 (dd, J=13.2, 8.4 Hz, 1H), 1.82 (dt, J=14.7, 7.5 Hz, 1H), 1.72-1.53 (m, 2H), 1.39 (t, J=7.2 Hz, 3H), 0.97-0.87 (m, 9H). [M+Na$^+$]636.2.

TABLE 5

The following compounds were made following similar chemistry and procedures described as above.

| Example | Structure | MS | NMR |
|---|---|---|---|
| 362 | 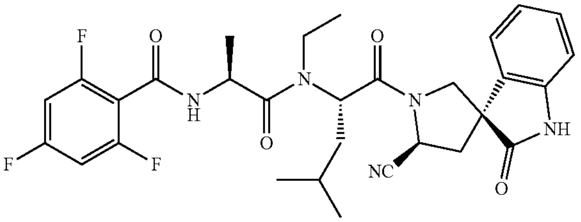 [SMILES: CCN(C(=O)[C@H](C)NC(=O)c1c(F)cc(F)cc1F)[C@@H](CC(C)C)C(=O)N1C[C@]2(C[C@H]1C#N)C(=O)Nc1ccccc12] | [M + Na$^+$] 606.2 | $^1$H NMR (400 MHz, Acetone-$d_6$) δ 9.74 (s, 1H), 7.90 (d, J = 8.0 Hz, 1H), 7.30 (td, J = 7.5, 1.7 Hz, 1H), 7.16-7.04 (m, 2H), 7.04-6.90 (m, 3H), 5.49 (t, J = 7.5 Hz, 1H), 5.18 (t, J = 8.4 Hz, 1H), 4.99-4.82 (m, 1H), 3.97 (d, J = 10.5 Hz, 1H), 3.90 (d, J = 10.5 Hz, 1H), 3.75 (dq, J = 14.4, 7.2 Hz, 1H), 3.48 (dq, J = 14.6, 7.1 Hz, 1H), 2.78-2.63 (m, 2H), 1.82-1.67 (m, 2H), 1.57 (dp, J = 13.2, 6.6 Hz, 1H), 1.36 (t, J = 7.1 Hz, 3H), 0.96-0.87 (m, 9H). |
| 363 | 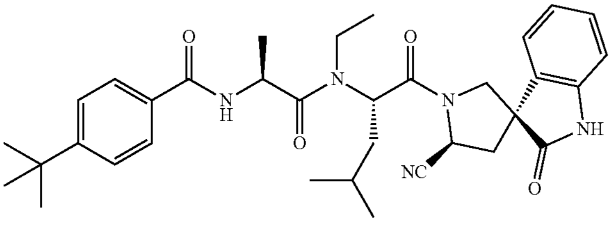 [SMILES: CCN(C(=O)[C@H](C)NC(=O)c1ccc(C(C)(C)C)cc1)[C@@H](CC(C)C)C(=O)N1C[C@]2(C[C@H]1C#N)C(=O)Nc1ccccc12] | [M + Na$^+$] 608.3 | $^1$H NMR (400 MHz, Acetone-$d_6$) δ 9.76 (s, 1H), 7.91-7.74 (m, 2H), 7.58-7.42 (m, 3H), 7.30 (td, J = 7.6, 1.5 Hz, 1H), 7.18-6.95 (m, 3H), 5.48 (t, J = 7.4 Hz, 1H), 5.18 (t, J = 8.4 Hz, 1H), 4.90 (h, J = 7.0, 6.6 Hz, 1H), 3.98 (d, J = 10.5 Hz, 1H), 3.90 (d, J = 10.5 Hz, 1H), 3.75 (dq, J = 14.5, 7.1 Hz, 1H), 3.46 (dq, J = 14.6, 7.1 Hz, 1H), 2.79-2.64 (m, 2H), 1.82 (dt, J = 13.5, 7.4 Hz, 1H), 1.71-1.50 (m, 2H), 1.38 (t, J = 7.1 Hz, 3H), 1.32 (s, 9H), 0.99-0.79 (m, 9H). |
| 364 | 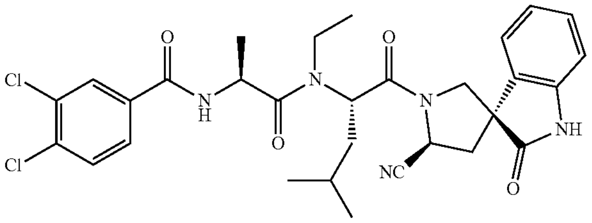 [SMILES: CCN(C(=O)[C@H](C)NC(=O)c1ccc(Cl)c(Cl)c1)[C@@H](CC(C)C)C(=O)N1C[C@]2(C[C@H]1C#N)C(=O)Nc1ccccc12] | [M + Na$^+$] 621.2 | $^1$H NMR (400 MHz, Acetone-$d_6$) δ 9.74 (s, 1H), 8.05 (d, J = 2.1 Hz, 1H), 7.84 (dd, J = 8.3, 2.1 Hz, 2H), 7.66 (d, J = 8.4 Hz, 1H), 7.30 (td, J = 7.6, 1.5 Hz, 1H), 7.19-6.96 (m, 3H), 5.47 (t, J = 7.4 Hz, 1H), 5.18 (t, J = 8.4 Hz, 1H), 4.86 (p, J = 7.0 Hz, 1H), 3.98 (d, J = 10.5 Hz, 1H), 3.89 (d, J = 10.5 Hz, 1H), 3.74 (dq, J = 14.5, 7.2 Hz, 1H), 3.46 (dq, J = 14.7, 7.1 Hz, 1H), 2.78-2.61 (m, 2H), 1.83 (dt, J = 13.6, 7.4 Hz, 1H), 1.72-1.51 (m, 2H), 1.39 (t, J = 7.1 Hz, 3H), 0.98-0.82 (m, 9H). |
| 365 | 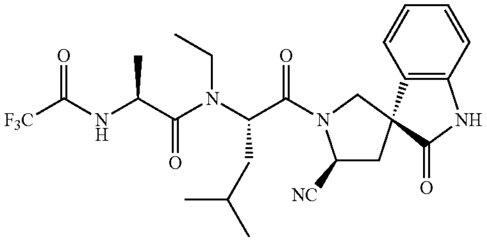 [SMILES: CCN(C(=O)[C@H](C)NC(=O)C(F)(F)F)[C@@H](CC(C)C)C(=O)N1C[C@]2(C[C@H]1C#N)C(=O)Nc1ccccc12] | [M − H$^+$] 520.3 | $^1$H NMR (400 MHz, Acetone-d6) δ 9.59 (s, 1H), 7.19-7.11 (m, 1H), 6.91 (dt, J = 23.0, 7.6 Hz, 3H), 5.31 (t, J = 7.4 Hz, 1H), 5.02 (t, J = 8.4 Hz, 1H), 4.58 (t, J = 6.9 Hz, 1H), 3.83 (d, J = 10.5 Hz, 1H), 3.71 (d, J = 10.5 Hz, 1H), 3.52 (dt, J = 14.3, 7.3 Hz, 1H), 3.31 (dt, J = 15.8, 7.3 Hz, 1H), 2.64-2.58 (m, 2H), 2.53 (dd, J = 13.1, 8.3 Hz, 1H), 1.69 (dt, J = 14.3, 7.5 Hz, 2H), 1.57-1.46 (m, 1H), 1.41 (dt, J = 13.4, 6.6 Hz, 1H), 1.20 (t, J = 7.1 Hz, 3H), 0.84-0.75 (m, 7H). |
| 366 | 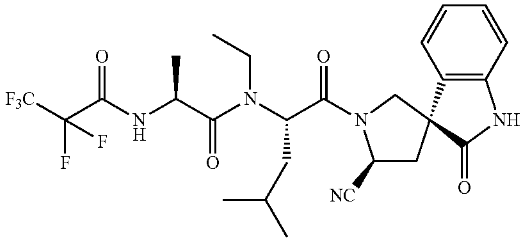 [SMILES: CCN(C(=O)[C@H](C)NC(=O)C(F)(F)C(F)(F)F)[C@@H](CC(C)C)C(=O)N1C[C@]2(C[C@H]1C#N)C(=O)Nc1ccccc12] | [M − H$^+$] 570.3 | $^1$H NMR (400 MHz, Acetone-d6) δ 9.59 (s, 1H), 7.15 (t, J = 7.6 Hz, 1H), 6.96 (d, J = 7.6 Hz, 1H), 6.90 (dd, J = 15.5, 7.7 Hz, 2H), 5.32 (t, J = 7.5 Hz, 1H), 5.02 (t, J = 8.4 Hz, 1H), 4.65-4.57 (m, 1H), 3.83 (d, J = 10.5 Hz, 1H), 3.70 (d, J = 10.5 Hz, 1H), 3.53 (dq, J = 14.7, 7.2 Hz, 1H), 3.30 (dq, J = 14.6, 7.2 Hz, 1H), 2.65 (d, J = 1.3 Hz, 4H), 2.63-2.58 (m, 1H), 2.53 (dd, J = 13.2, 8.3 Hz, 1H), 1.70-1.50 (m, 3H), 1.40 (dq, J = 13.6, 6.6 Hz, 1H), 1.20 (t, J = 7.2 Hz, 3H), 0.79 (q, J = 6.6 Hz, 8H). |

TABLE 5-continued

The following compounds were made following similar chemistry and procedures described as above.

| Example | Structure | MS | NMR |
|---|---|---|---|
| 367 | 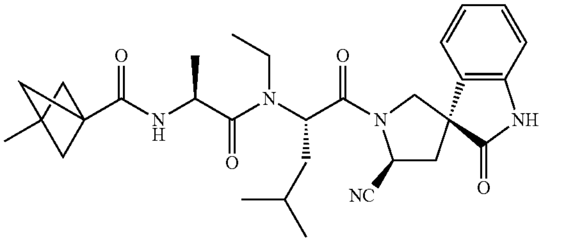 [SMILES: CCN(C(=O)[C@H](C)NC(=O)C12CCC(C)(C1)C2)[C@@H](CC(C)C)C(=O)N1C[C@]2(C[C@H]1C#N)C(=O)Nc1ccccc12] | [M − H+] 532.5 | $^1$H NMR (400 MHz, Acetone-d6) δ 9.58 (s, 1H), 7.14 (t, J = 7.5 Hz, 1H), 6.96-6.83 (m, 3H), 5.29 (t, J = 7.5 Hz, 1H), 5.01 (t, J = 8.3 Hz, 1H), 4.50 (p, J = 7.0 Hz, 1H), 3.75 (d, J = 10.5 Hz, 1H), 3.52 (dt, J = 14.0, 7.0 Hz, 1H), 3.22 (dq, J = 14.3, 7.0 Hz, 1H), 2.59 (d, J = 8.3 Hz, 2H), 2.53 (dd, J = 13.2, 8.5 Hz, 1H), 1.65 (s, 5H), 1.50 (td, J = 14.0, 7.6 Hz, 2H), 1.38 (dt, J = 13.0, 6.4 Hz, 1H), 1.14 (t, J = 7.1 Hz, 3H), 0.99 (s, 2H), 0.79 (dd, J = 12.6, 6.5 Hz, 5H), 0.61 (d, J = 6.8 Hz, 2H). |
| 368 | 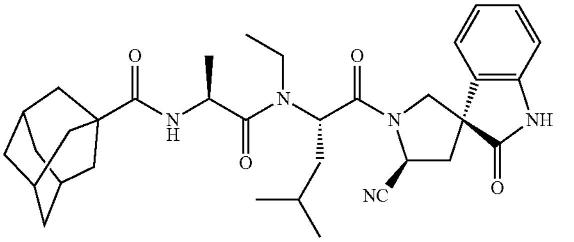 [SMILES: CCN(C(=O)[C@H](C)NC(=O)C12CC3CC(CC(C3)C1)C2)[C@@H](CC(C)C)C(=O)N1C[C@]2(C[C@H]1C#N)C(=O)Nc1ccccc12] | [M − H+] 586.3 | $^1$H NMR (400 MHz, Acetone-d6) δ 9.58 (s, 1H), 7.14 (t, J = 7.6 Hz, 1H), 6.98-6.84 (m, 3H), 6.35 (s, 1H), 5.31 (t, J = 7.5 Hz, 1H), 5.02 (t, J = 8.3 Hz, 1H), 4.54-4.46 (m, 1H), 3.81 (d, J = 10.5 Hz, 1H), 3.73 (d, J = 10.5 Hz, 1H), 3.53 (dd, J = 15.5, 7.3 Hz, 1H), 3.23 (dd, J = 15.4, 7.4 Hz, 1H), 2.53 (dd, J = 13.3, 8.4 Hz, 2H), 1.83 (s, 3H), 1.66 (d, J = 2.9 Hz, 5H), 1.55 (t, J = 10.9 Hz, 7H), 1.43-1.35 (m, 1H), 1.15 (t, J = 7.1 Hz, 3H), 0.89 (dd, J = 23.1, 7.2 Hz, 1H), 0.78 (dd, J = 13.0, 6.6 Hz, 5H), 0.61 (d, J = 6.8 Hz, 2H). |
| 369 | 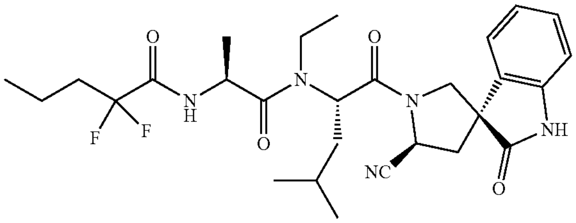 [SMILES: CCCC(F)(F)C(=O)N[C@@H](C)C(=O)N(CC)[C@@H](CC(C)C)C(=O)N1C[C@]2(C[C@H]1C#N)C(=O)Nc1ccccc12] | [M + Na+] 568.2 | |
| 370 | 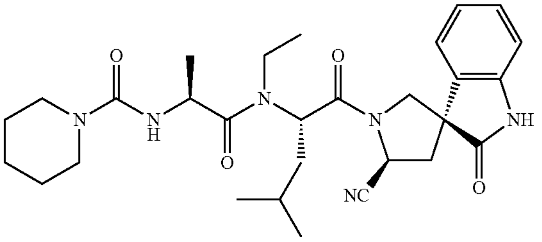 [SMILES: CCN(C(=O)[C@H](C)NC(=O)N1CCCCC1)[C@@H](CC(C)C)C(=O)N1C[C@]2(C[C@H]1C#N)C(=O)Nc1ccccc12] | [M + Na+] 559.3 | |
| 371 | 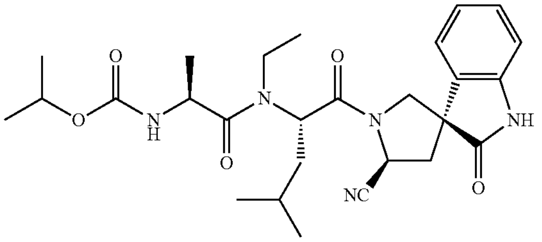 [SMILES: CCN(C(=O)[C@H](C)NC(=O)OC(C)C)[C@@H](CC(C)C)C(=O)N1C[C@]2(C[C@H]1C#N)C(=O)Nc1ccccc12] | [M + Na+] 534.2 | |
| 372 | 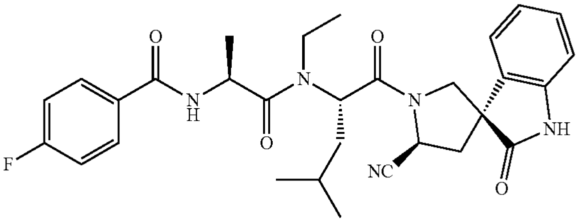 [SMILES: CCN(C(=O)[C@H](C)NC(=O)c1ccc(F)cc1)[C@@H](CC(C)C)C(=O)N1C[C@]2(C[C@H]1C#N)C(=O)Nc1ccccc12] | [M + Na+] 570.3 | $^1$H NMR (400 MHz, Acetone-$d_6$) δ 9.74 (s, 1H), 7.99-7.90 (m, 2H), 7.62 (d, J = 7.7 Hz, 1H), 7.30 (td, J = 7.6, 1.6 Hz, 1H), 7.25-7.14 (m, 2H), 7.14-6.99 (m, 3H), 5.48 (t, J = 7.4 7.0 Hz, 1H), 3.97 (d, J = 10.5 Hz, 1H), 3.89 (d, J = 10.5 Hz, 1H), 3.74 (dq, J = 14.4, 7.1 Hz, 1H), 3.46 (dq, J = 14.6, 7.1 Hz, 1H), 2.83-2.64 (m, 2H), 1.82 (dt, J = 13.5, 7.4 Hz, 1H), 1.71-1.51 (m, 2H), 1.39 (m, 3H), 0.96-0.87 (m, 9H). |

The following examples are prepared employing similar procedures as described above.
| Entry | Structure |
| --- | --- |
| 380 | 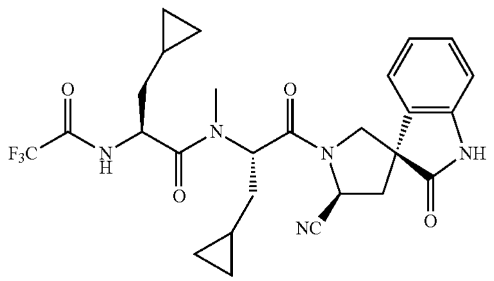 [SMILES: CN(C(=O)[C@H](CC1CC1)NC(=O)C(F)(F)F)[C@@H](CC1CC1)C(=O)N1C[C@]2(C[C@H]1C#N)C(=O)Nc1ccccc12] |
| 381 | 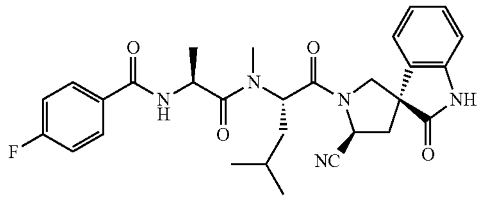 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1] |
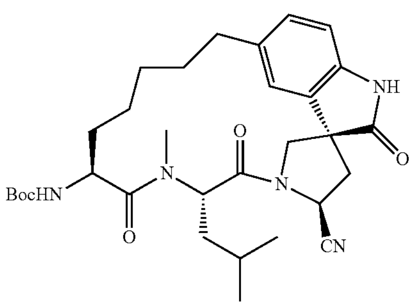
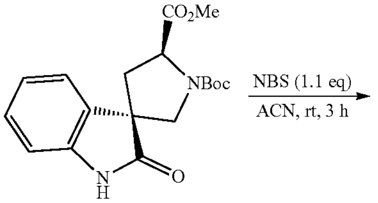
1-3a
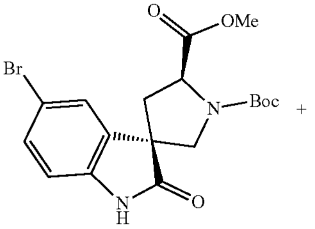
373-1
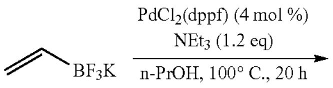
(1.2 eq)
-continued
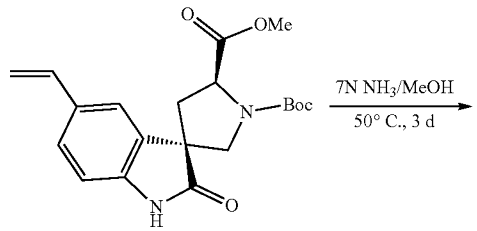
373-2
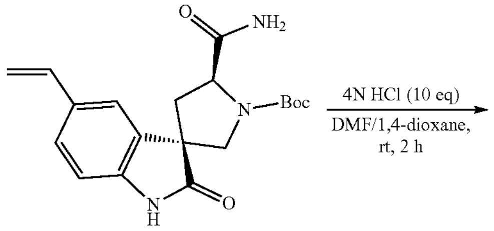
373-3
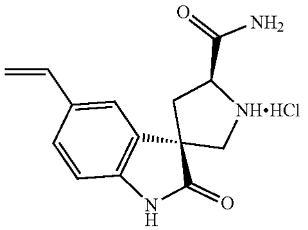
373-4
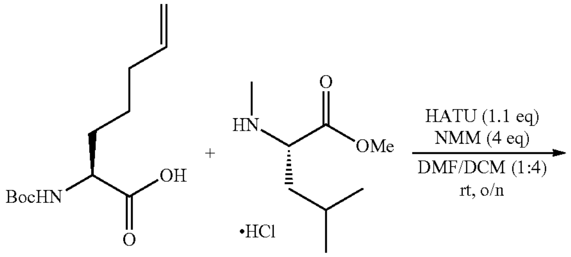
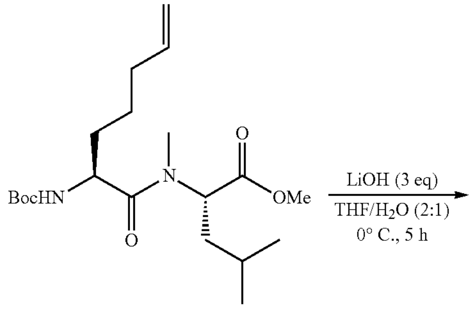
373-5

-continued

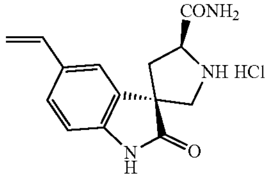

373-4

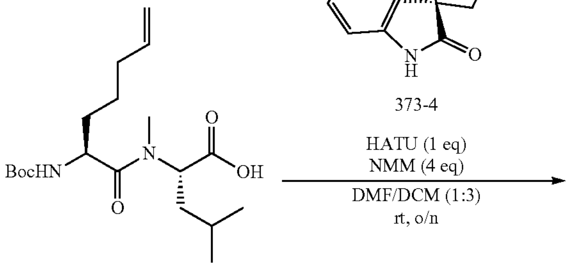

373-6

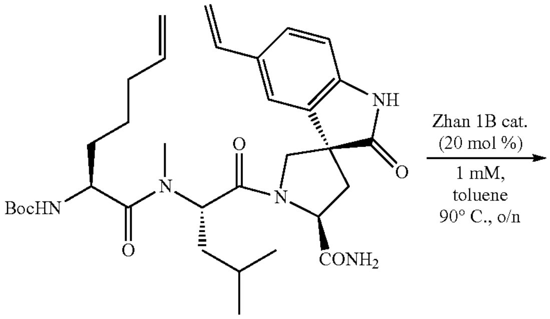

373-7

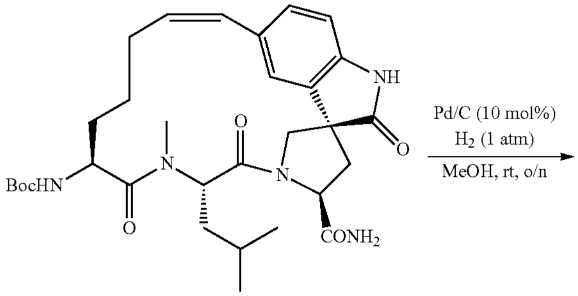

373-8

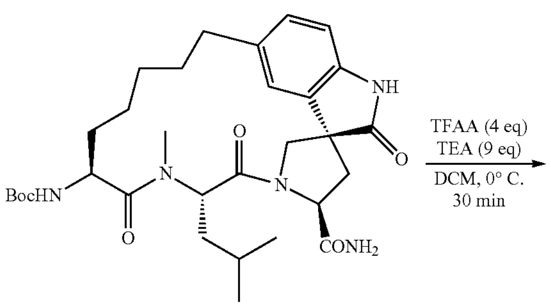

373-9

-continued

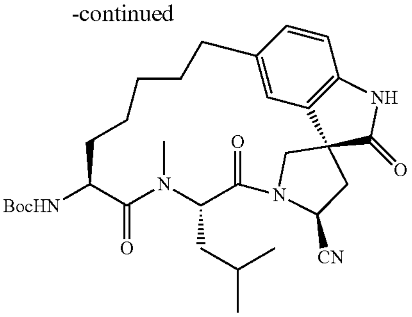

373-10

Step 373-1:

A clear colorless solution of the mixture of compounds from Step 1-3 (3.94 g, 11.4 mmol, dr 10/1) in acetonitrile (40 mL) was treated with NBS (2.23 g, 12.5 mmol) in three portions at room temperature. The reaction was stirred at room temperature for 3 h. It became a light yellow solution. LCMS showed no SM. The reaction was quenched with aqueous $Na_2S_2O_3$. The mixture was allowed to stir at room temperature for additional 30 min. The cloudy mixture was further diluted with EtOAc (80 mL). The aqueous layer was extracted with EtOAc twice. The combined organic layers were washed with brine, dried over $Na_2SO_4$, filtered and concentrated to afford crude product as an off-white solid. The crude was dissolved in DCM (10 mL) and filtered through an 80 g silica gel pad (MTBE) to afford the desired product (dr 10/1) as a white solid. The product was treated with MTBE/hexane (2:1) (30 mL). The mixture was sonicated over 10 min to form a milky suspension, which was filtered and washed with MTBE/hexane (2:1) to give the desired product as a white solid (4.23 g, 10.0 mmol, dr>100/1). ESI MS m/z=422.74, 424.64 $[M-H]^-$.

Step 373-2: A clear colorless solution of the compound from Step 373-1 (4.2 g, 9.9 mmol) in n-PrOH (35 mL) was treated with triethylamine (1.7 mL, 11.9 mmol), potassium vinyltrifluoroborate (1.6 g, 11.9 mmol) and $PdCl_2$(dppf) (290 mg, 0.4 mmol) under $N_2$. The mixture was degassed and backfilled with $N_2$ (*3). The resulting orange suspension was bubbled with $N_2$ for 10 min. The reaction was warmed to 100° C. and stirred for 20 h. It became dark red/brown mixture. TLC (CH/EtOAc 2:1) showed no SM. The reaction was diluted with ethyl acetate (100 mL) and quenched with aqueous $NaHCO_3$. The aqueous layer was extracted with ethyl acetate (*2). The combined organic layers were washed with water and brine, dried over $Na_2SO_4$, filtered and concentrated in vacuo. The crude was redissolved in ethyl acetate (20 mL) and treated with SiliaMetS DMT (8 g) as a metal scavenger. The mixture was stirred at room temperature for 16 h, then filtered, rinsed with MTBE/CH (2:1) (200 mL) and concentrated in vacuo. The brownish crude was redissolved in ethyl acetate (20 mL), treated with activated charcoal and warmed to 60° C. for 1 h. The mixture was filtered after cooling to give a light yellow solution, which was further concentrated in vacuo to give the desired product (3.3 g, 8.7 mmol, 90%) as an off-white foam. ESI MS m/z=370.79 $[M-H]^-$.

Step 373-3: A clear light yellow solution of the compound from Step 373-2 (3.3 g, 8.9 mmol) in 7 N ammonia in MeOH (80 ml, 560 mmol) was stirred at 50° C. in a sealed pressure vessel over the weekend (3 d). LCMS showed no SM. The mixture was allowed to cool down and concentrated in vacuo to give a yellow gel-like solid. The solid was redissolved in 30 mL MeOH/dioxane (1:10), co-evaporated in vacuo to give a light yellow solid. The crude was dried under high vacuum for 1 h, then mashed to small pieces and dried under high vacuum overnight to give a light yellow powder. The powder was washed with 10 mL DCM/MTBE (1:2), sonicated and filtered to give the desired product (3.05 g, 8.5 mmol, 96%) as an off-white solid. ESI MS m/z=355.79 $[M-H]^-$.

Step 373-4: To a clear solution of the compound from Step 373-3 (1.15 g, 3.22 mmol) in DMF (2 ml) at rt was added 4 M HCl in 1,4-dioxane (8 ml, 32 mmol). The resulting clear yellow solution was stirred at rt for 2 h. The mixture was concentrated by rotavapor. The residual clear DMF solution was poured into DCM (150 ml) with stirring to get a white slurry. The mixture was sonicated to form a cloudy suspension. The solid was collected by filtration, washing with DCM, and then MTBE. The solid was dried under vacuum to afford the desired product as an off-white powder (862 mg, 2.93 mmol, 91%). 1 g of the above product was mixed with DMF (2 ml) and heated with a heat gun to get an almost clear solution. Solid started to appear while heating. The mixture was allowed to cool down to rt. The solid was collected by filtration, washing with DMF (0.2 ml), DCM and MTBE. The solid was dried under vacuum to afford the desired product as a white solid (771 mg). ESI MS m/z=257.77 $[M-H]^-$.

Step 373-5:

A suspension of (S)-2-((tert-butoxycarbonyl)amino)hept-6-enoic acid (1 g, 4.11 mmol) and methyl methyl-L-leucinate hydrochloride (0.81 g, 4.14 mmol) in $CH_2Cl_2$ (12 ml) and DMF (3 ml) was treated with N-methylmorpholine (1.8 ml, 16.37 mmol) and HATU (1.71 g, 4.50 mmol) at room temperature. The reaction was stirred at room temperature overnight. The reaction was concentrated in vacuo and quenched with a saturated solution of sodium bicarbonate. The mixture was stirred at room temperature for additional 30 min and diluted with ethyl acetate. The organic layer was washed with water and brine over 3 times, dried over sodium sulfate, filtered and concentrated in vacuo. The crude was added to a 40 g silica gel column and eluted by ethyl acetate/cyclohexane from 0% to 25% to give the desired compound (1.12 g, 2.91 mmol, 71% yield) as a colorless syrup. ESI MS m/z=384.95 $[M+H]^+$.

Step 373-6:

A solution of the compound from Step 373-5 (1.1 g, 2.86 mmol) in THE (6 ml) and Water (3 ml) was treated with lithium hydroxide (200 mg, 8.35 mmol) at 0° C. The reaction was stirred at 0° C. for 5 h and neutralized with 6 N HCl to pH=2. The aqueous layer was extracted with ethyl acetate over 3 times. The combined organic layer was dried over sodium sulfate, filtered and concentrated in vacuo to give the desired compound (1.05 g, 2.83 mmol, 99% yield) as a white solid. ESI MS m/z=369.25 $[M-H]^-$.

Step 373-7:

A suspension of the compound from Step 373-6 (285 mg, 0.77 mmol) and the compound from Step 373-4 (221 mg, 0.75 mmol) in DMF (0.6 ml) and DCM (1.8 ml) was treated with N-methylmorpholine (330 μl, 3.00 mmol) and HATU (318 mg, 0.836 mmol). The reaction was stirred at room temperature for 1 h. The reaction was quenched with a saturated solution of sodium bicarbonate and diluted with ethyl acetate. The organic layer was washed with brine over 3 times, dried over sodium sulfate, filtered and concentrated in vacuo. The crude was added to a 24 g silica gel column and eluted by dichloromethane/methanol from 0% to 100% to give the desired product (77 mg, 0.126 mmol, 17% yield) as a white solid. ESI MS m/z=608.33 $[M-H]^-$.

Step 373-8:

A solution of the compound from Step 373-7 (77 mg, 0.126 mmol) in Toluene (125 ml) was treated with Zhan 1B cat. (17 mg, 0.023 mmol). The mixture was degassed and backfilled with $N_2$ by freeze-pump thaw at −78° C. The reaction was warmed to 90° C. and stirred overnight. The mixture was concentrated in vacuo. The crude was added to a 4 g silica gel column and eluted by dichloromethane/methanol from 0% to 100% to give the desired product (7 mg, 0.012 mmol, 10% yield) as a black foam. ESI MS m/z=580.19 $[M-H]^-$.

Step 373-9:

A solution of the compound from Step 373-8 (7 mg, 0.012 mmol) in MeOH (0.5 ml) was treated with Pd—C(2.7 mg, 2.54 μmol) under 1 atm $H_2$ (0.024 mg, 0.012 mmol). The reaction was stirred at room temperature overnight. The mixture was filtered through celite and rinsed with methanol. The filtrate was concentrated in vacuo to give the desired product (7 mg, 0.012 mmol, 100% yield) as a black foam. ESI MS m/z=582.33 $[M-H]^-$.

Step 373-10:

A solution of the compound from Step 373-9 (7 mg, 0.012 mmol) in $CH_2Cl_2$ (0.3 ml) was treated with TEA (15 μl, 0.108 mmol) and TFAA (6 μl, 0.042 mmol) dropwise at 0° C. The reaction was stirred at 0° C. for 30 min and then quenched with ammonium hydroxide. The aqueous layer was extracted with dichloromethane over 3 times. The combined organic layer was dried over sodium sulfate, filtered and concentrated in vacuo. The crude was added to a 4 g silica gel column and eluted by ethyl acetate/cyclohexane from 0% to 100% to give Example 373 (1.7 mg, 3.01 μmol, 25% yield) as a white solid. ESI MS m/z=564.22 $[M-H]^-$.

Example 374

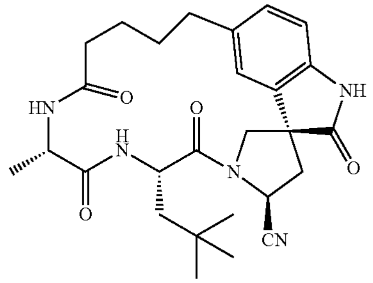

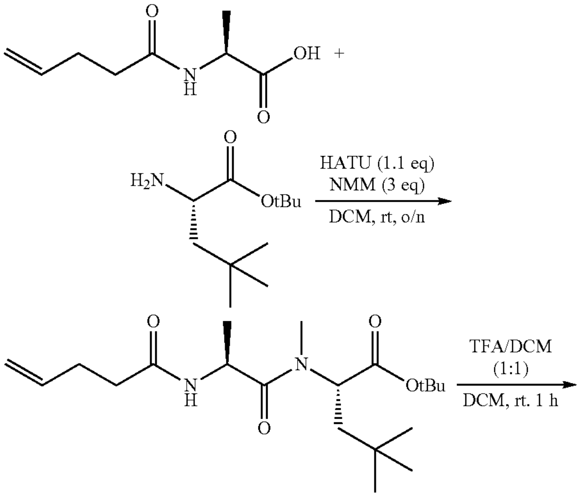

374-1

-continued

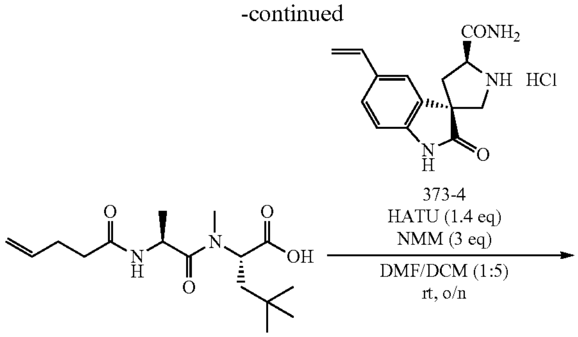

374-2

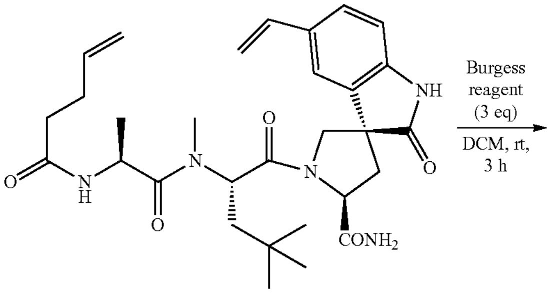

374-3

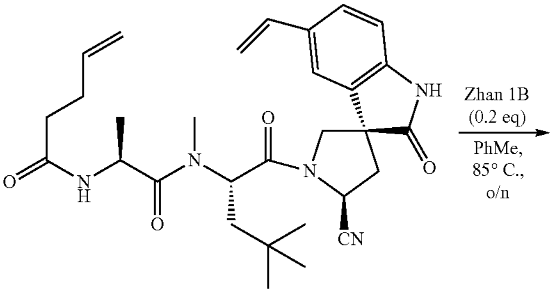

374-4

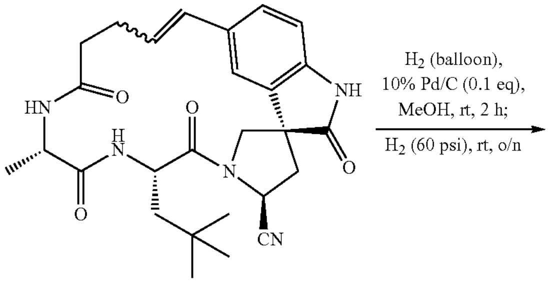

374-5

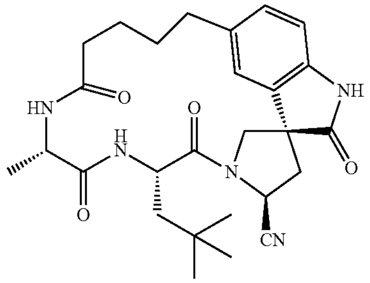

374-6

Step 374-1. To a solution of tert-butyl (2S)-2-amino-4,4-dimethylpentanoate (0.974 g, 4.84 mmol) and pent-4-enoyl-L-alanine (0.753 g, 4.40 mmol) in DCM (30 ml) at 0° C. was added 4-methylmorpholine (1.451 ml, 13.20 mmol), followed by HATU (1.840 g, 4.84 mmol). The resulting yellow milky solution was stirred at 0° C. for 5 min and then at rt for 2 h. The mixture was diluted with EtOAc and saturated $NaHCO_3$ solution. The organic layer was washed with brine (*1), dried over $Na_2SO_4$ (s), filtered and concentrated. The residue was purified by flash column chromatography (silica, cyclohexanes/EtOAc) to afford the desired compound as sticky colorless oil (1.280 g, 82%). ESI MS m/z=355.43 $[M+H]^+$.

Step 374-2. To a solution of the compound from step 374-1 (1.280 g, 3.61 mmol) in DCM (6 ml) at rt was added TFA (5.56 ml, 72.2 mmol). The solution was stirred at rt for 1 h before being concentrated. The residue was co-evaporated with toluene (*2), DCM (*1) and dried under vacuum to afford the desired compound as a sticky colorless oil (1.240 g, 100%), which was used directly for next step. ESI MS m/z=299.37 $[M+H]^+$.

Step 374-3. To a suspension of the compound from 373-4 (1.060 g, 3.61 mmol) and the compound from step 374-2 (1.077 g, 3.61 mmol) in DCM (10 ml) and DMF (2.000 ml) at 0° C. was added 4-methylmorpholine (1.191 ml, 10.83 mmol), followed by HATU (1.922 g, 5.05 mmol). The reaction mixture was stirred at 0° C. for 5 min and then at rt overnight. The mixture was diluted with saturated $NaHCO_3$ solution and EtOAc. The aqueous layer was extracted with DCM (*1). The combined organic layers were washed with brine (*1), dried over $Na_2SO_4$ (s), filtered and concentrated. The residue was purified by flash column chromatography (silica, cyclohexanes/acetone) to afford the desired compound as white solid (0.290 g, 15%). ESI MS m/z=538.31 $[M+H]^+$.

Step 374-4. To a solution of the compound from step 374-3 (0.120 g, 0.223 mmol) in $CH_2Cl_2$ (5 ml) and DMF (1.000 ml) at rt was added Burgess reagent (0.067 g, 0.268 mmol). The resulting clear solution was stirred at rt for 1.5 h. More Burgess reagent (0.067 g, 0.268 mmol) was added. The mixture was stirred at rt for 2 h. It was quenched with water, and extracted with DCM (*2). The combined organic layers were dried over $Na_2SO_4$ (s), filtered and concentrated. The residue was purified by flash column chromatography (silica, cyclohexanes/acetone) to afford the desired compound as yellow solid (40.0 mg, 35%). ESI MS m/z=520.29 $[M+H]^+$.

Step 374-5. To a solution of the compound from step 374-4 (0.0400 g, 0.077 mmol) in toluene (77 ml) was added Zhan 1B cat (0.011 g, 0.015 mmol). The mixture was purged with $N_2$ and then heated at 85° C. overnight. The mixture was allowed to cool down and concentrated. The residue was dissolved in DCM (10 ml) at rt. 2-mercaptonicotinic acid (0.024 g, 0.154 mmol) and $Et_3N$ (0.021 ml, 0.154 mmol) were added. The mixture was stirred at 40° C. for 30 min before most of DCM was evaporated. The residue was filtered through a 1 g silica column, washing with acetone. The filtrate was concentrated. The residue was purified by flash column chromatography (silica, cyclohexanes/acetone) to afford the desired compound as yellow solid (19.0 mg, 50%). ESI MS m/z=492.47 $[M+H]^+$.

Step 374-6. To a solution of the compound from step 374-5 (19.0 mg, 0.039 mmol) in MeOH (2.0 ml) at rt was added 10% Pd/C (4.11 mg, 3.86 μmol). The mixture was purged with $H_2$ and then stirred at rt for 2 h with a hydrogen balloon. LC-MS showed mostly SM, trace DP. The mixture was diluted with DCM (4 ml) and filtered through a short pad of celite, washing with DCM/MeOH (2/1). The filtrate was concentrated. The residue was re-subjected to above hydrogenation condition at 60 psi overnight. The mixture was diluted with DCM (4 ml) and filtered through a short pad of celite, washing with DCM/MeOH (2/1). The filtrate was concentrated. The residue was purified by flash column chromatography (silica, cyclohexanes/acetone) to afford Example 374 as white solid (6.0 mg, 31%). ESI MS m/z=494.28 $[M+H]^+$.

The following compounds were prepared following similar procedure as Example 374.

Example 375

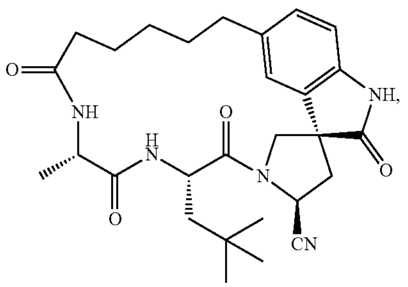 [SMILES: C[C@@H]1NC(=O)CCCCCc2ccc3c(c2)[C@@]2(C[C@@H](C#N)N(C2)C(=O)[C@H](CC(C)(C)C)NC1=O)C(=O)N3]

ESI MS m/z=508.43 $[M+H]^+$.

Example 376

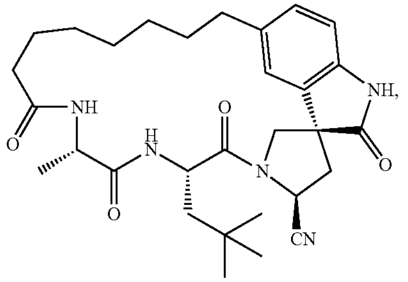 [SMILES: C[C@@H]1NC(=O)CCCCCCCc2ccc3c(c2)[C@@]2(C[C@@H](C#N)N(C2)C(=O)[C@H](CC(C)(C)C)NC1=O)C(=O)N3]

ESI MS m/z=536.44 $[M+H]^+$.

Example 377

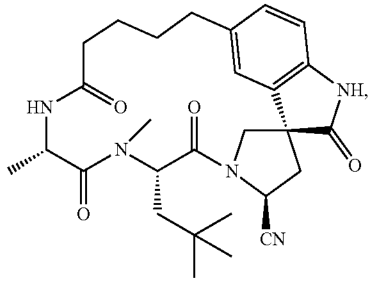 [SMILES: C[C@@H]1NC(=O)CCCCc2ccc3c(c2)[C@@]2(C[C@@H](C#N)N(C2)C(=O)[C@H](CC(C)(C)C)N(C)C1=O)C(=O)N3]

ESI MS m/z=508.37 $[M+H]^+$.

Example 378

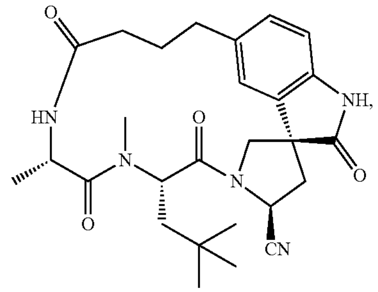 [SMILES: C[C@@H]1NC(=O)CCCc2ccc3c(c2)[C@@]2(C[C@@H](C#N)N(C2)C(=O)[C@H](CC(C)(C)C)N(C)C1=O)C(=O)N3]

ESI MS m/z=494.35 $[M+H]^+$.

Example 379

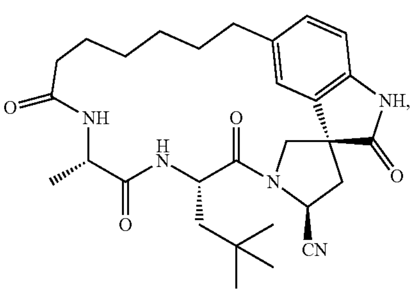 [SMILES: C[C@@H]1NC(=O)CCCCCCc2ccc3c(c2)[C@@]2(C[C@@H](C#N)N(C2)C(=O)[C@H](CC(C)(C)C)NC1=O)C(=O)N3]

ESI MS m/z=522.40 $[M+H]^+$.

Biological Activity

SARS-CoV-2 3C-like (3CL) protease fluorescence assay (FRET): Recombinant SARS-CoV-2 3CL-protease was expressed and purified. TAMRA-SITSAVLQSGFRKMK-Dabcyl-OH peptide 3CLpro substrate was synthesized. Black, low volume, round-bottom, 384 well microplates were used. In a typical assay, 0.85 μL of test compound was dissolved in DMSO then incubated with SARS-CoV-2 3CL-protease (10 nM) in 10 μL assay buffer (50 mM HEPES [pH 7.5], 1 mM DTT, 0.01% BSA, 0.01% Triton-X 100) for 30 min at RT. Next, 10 μL of 3CL-protease substrate (40 μM) in assay buffer was added and the assays were monitored continuously for 1 h in an Envision multimode plate reader operating in fluorescence kinetics mode with excitation at 540 nm and emission at 580 nm at RT. No compound (DMSO only) and no enzyme controls were routinely included in each plate. All experiments were run in duplicate. Data Analysis: SARS-CoV-2 3CL-protease enzyme activity was measured as initial velocity of the linear phase (RFU/s) and normalized to controlled samples DMSO (100% activity) and no enzyme (0% activity) to determine percent residual activity at various concentrations of test compounds (0-10 μM). Data were fitted to normalized activity (variable slope) versus concentration fit in GraphPad Prism 7 to determine $IC_{50}$. All experiments were run in duplicate, and $IC_{50}$ ranges are reported as follows: A<0.1 μM; B 0.1-1 μM; C>1 μM.

TABLE 6

| Summary of Activities | | | |
|---|---|---|---|
| Example | $IC_{50}$ | Example | $IC_{50}$ |
| 1 | A | 2 | A |
| 3 | A | 4 | A |
| 5 | A | 6 | A |
| 7 | A | 8 | A |
| 9 | A | 10 | B |
| 11 | A | 12 | A |
| 13 | A | 14 | A |
| 15 | A | 16 | A |
| 17 | A | 18 | A |
| 19 | A | 20 | A |
| 21 | A | 22 | A |
| 23 | A | 24 | A |
| 25 | A | 26 | A |
| 27 | A | 28 | A |
| 29 | A | 30 | A |
| 31 | A | 32 | A |
| 33 | A | 34 | A |
| 35 | A | 36 | A |
| 37 | A | 38 | A |
| 39 | A | 40 | A |
| 41 | A | 42 | A |
| 43 | A | 44 | A |
| 45 | A | 46 | A |
| 47 | A | 48 | A |
| 49 | A | 50 | B |
| 51 | A | 52 | A |
| 53 | A | 54 | A |
| 55 | B | 56 | C |
| 57 | C | 58 | C |
| 59 | C | 60 | C |
| 61 | C | 62 | A |
| 63 | A | 64 | A |
| 65 | A | 66 | A |
| 67 | A | 68 | A |
| 69 | A | 70 | A |
| 71 | A | 72 | A |
| 73 | A | 74 | A |
| 75 | A | 76 | A |
| 77 | A | 78 | A |
| 79 | A | 80 | A |
| 81 | A | 82 | A |
| 83 | A | 84 | A |
| 85 | A | 86 | A |
| 87 | A | 88 | B |
| 89 | B | 90 | A |
| 91 | B | 92 | A |
| 93 | C | 94 | A |
| 95 | A | 96 | A |
| 97 | A | 98 | A |
| 99 | A | 100 | A |
| 101 | A | 102 | C |
| 103 | A | 104 | A |
| 105 | A | 106 | C |
| 107 | A | 108 | A |
| 109 | A | 110 | A |
| 111 | A | 112 | A |
| 113 | A | 114 | A |
| 115 | A | 116 | A |
| 117 | A | 118 | A |
| 119 | A | 120 | A |
| 121 | A | 122 | A |
| 123 | A | 124 | A |
| 125 | A | 126 | A |
| 127 | A | 128 | A |
| 129 | A | 130 | A |
| 131 | A | 132 | B |
| 133 | A | 134 | A |
| 135 | A | 136 | A |
| 137 | A | 138 | A |
| 139 | A | 140 | A |
| 141 | A | 142 | A |
| 143 | A | 144 | A |
| 145 | A | 146 | A |
| 147 | A | 148 | A |
| 149 | A | 150 | A |
| 151 | A | 152 | B |

TABLE 6-continued

| Summary of Activities | | | |
|---|---|---|---|
| Example | $IC_{50}$ | Example | $IC_{50}$ |
| 153 | A | 154 | A |
| 155 | A | 156 | A |
| 157 | A | 158 | A |
| 159 | A | 160 | A |
| 161 | A | 162 | A |
| 163 | A | 164 | A |
| 165 | A | 166 | A |
| 167 | A | 168 | A |
| 169 | A | 170 | A |
| 171 | A | 172 | A |
| 173 | A | 174 | A |
| 175 | B | 176 | A |
| 177 | B | 178 | A |
| 179 | A | 180 | A |
| 181 | A | 182 | A |
| 183 | B | 184 | A |
| 185 | A | 186 | A |
| 187 | A | 188 | A |
| 189 | A | 190 | A |
| 191 | A | 192 | A |
| 193 | A | 194 | A |
| 195 | A | 196 | A |
| 197 | A | 198 | A |
| 199 | A | 200 | A |
| 201 | A | 202 | A |
| 203 | A | 204 | A |
| 205 | A | 206 | A |
| 207 | A | 208 | A |
| 209 | A | 210 | A |
| 211 | A | 212 | A |
| 213 | A | 214 | A |
| 215 | A | 216 | A |
| 217 | A | 218 | A |
| 219 | A | 220 | A |
| 221 | A | 222 | A |
| 223 | A | 224 | A |
| 225 | A | 226 | A |
| 227 | A | 228 | A |
| 229 | A | 230 | B |
| 231 | A | 232 | A |
| 233 | A | 234 | A |
| 235 | B | 236 | B |
| 237 | A | 238 | A |
| 239 | A | 240 | A |
| 241 | A | 242 | A |
| 243 | A | 244 | A |
| 245 | A | 246 | A |
| 247 | A | 248 | A |
| 249 | A | 250 | A |
| 251 | B | 252 | B |
| 253 | B | 254 | B |
| 255 | A | 256 | A |
| 257 | A | 258 | A |
| 259 | A | 260 | A |
| 261 | A | 262 | A |
| 263 | A | 264 | A |
| 265 | A | 266 | A |
| 267 | A | 268 | A |
| 269 | A | 270 | A |
| 271 | A | 272 | A |
| 273 | A | 274 | A |
| 275 | A | 276 | A |
| 277 | A | 278 | A |
| 279 | A | 280 | A |
| 281 | A | 282 | A |
| 283 | A | 284 | A |
| 285 | A | 286 | A |
| 287 | A | 288 | A |
| 289 | A | 290 | A |
| 291 | A | 292 | A |
| 293 | A | 294 | A |
| 295 | A | 296 | A |
| 297 | A | 298 | A |
| 299 | A | 300 | A |
| 301 | A | 302 | A |
| 303 | A | 304 | A |

TABLE 6-continued

| Summary of Activities | | | |
|---|---|---|---|
| Example | $IC_{50}$ | Example | $IC_{50}$ |
| 305 | A | 306 | A |
| 307 | A | 308 | A |
| 309 | A | 310 | A |
| 311 | A | 312 | A |
| 313 | A | 314 | B |
| 315 | A | 316 | B |
| 317 | A | 318 | A |
| 319 | A | 320 | A |
| 321 | A | 322 | A |
| 323 | A | 324 | A |
| 325 | B | 326 | A |
| 327 | A | 328 | A |
| 329 | A | 330 | A |
| 331 | B | 332 | A |
| 333 | A | 334 | A |
| 335 | C | 336 | B |
| 337 | B | 338 | A |
| 339 | A | 340 | A |
| 341 | A | 342 | A |
| 343 | A | 344 | A |
| 345 | A | 346 | A |
| 347 | A | 348 | A |
| 349 | B | 350 | B |
| 351 | A | 352 | A |
| 353 | A | 354 | B |
| 355 | C | 356 | C |
| 357 | A | 358 | A |
| 359 | B | 360 | A |
| 361 | A | 362 | A |
| 363 | A | 364 | A |
| 365 | A | 366 | A |
| 367 | A | 368 | A |
| 369 | A | 370 | A |
| 371 | A | 372 | A |
| 373 | A | 374 | B |
| 375 | C | 376 | C |
| 377 | A | 378 | A |
| 379 | C | | |

229E Assay Protocol

Viral stock preparation: MRC-5 cells, (a diploid cell culture line composed of fibroblasts, originally developed from the lung tissue of a 14-week-old aborted Caucasian male fetus), were used for the culturing of 229E human corona virus (hCoV). Flasks were inoculated with hCoV-229E and viral stocks were collected once cytopathic effect (CPE) was greater than 70%. Viral stocks in Growth Media (EMEM, 1% Penn/Strep, 1% nonessential amino acids, 10% heat-inactivated FBS) plus 5% glycerol were snap frozen using liquid nitrogen and stored at −80° C. Viral stock titers were quantified by a $TCID_{50}$ (50% median tissue culture infectious dose) assay, as described elsewhere.

229E live virus assay: 384-well black cell-culture-treated plastic clear-bottom plates are used in this assay. Using an ECHO liquid dispenser, 3-fold serial dilutions of control and test compounds suspended in DMSO are added to the plate wells in duplicate in a total volume of 125 nL per well. MRC-5 cells below passage 17 are seeded into the inner 240 wells of the 384-well plate at 1,500 cells per well in a volume of 12.5 μL using Growth Media. Viral stock is then added to the wells at a multiplicity of infection (MOI) of 0.05 in a volume of 12.5 μL per well, bringing the total volume of each well to ~25 μL. Each plate has a control row of 20 wells with cells plus DMSO and virus but no compound (positive control, max CPE, minimum ATPlite signal), and a row with cells plus DMSO but no compound or virus (negative control, minimum CPE, maximum ATPlite signal), and a row with no cells or virus or compound (background plate/reagent control). The control wells with cells but no virus are given an additional 12.5 μL of growth media containing an equal quantity of glycerol as those wells receiving the viral stock in order to keep consistent in media and volume conditions. The outer 2 rows/columns of wells are filled with 30 μL of moat media (DMEM, 1% Penn/Strep) to act as a thermal and evaporative barrier around the test wells. Following addition of all components, the sides of the plates are gently tapped by hand to promote even cell distribution across the wells. Upon confirmation of cell distribution, plates are incubated at 34° C. in a $CO_2$ humidity-controlled incubator for 6 days. Following the 6-day incubation period, the plates are read using ATPlite (12.5 μL added per well), which quantifies the amount of ATP (a measure of cell health) present in each well. Assay plates are read using an Envision luminometer. These data are used to calculate the percent cell health per well relative to the negative control wells and the $EC_{50}$ of each compound is calculated using ExcelFit software and 4-parameter logistical curve fitting analysis.

All experiments were run in duplicate, and $EC_{50}$ ranges are reported as follows: A<0.1 μM; B 0.1-1 μM; C>1 μM.

TABLE 7

| Summary of Activities | | | |
|---|---|---|---|
| Example | 229E $EC_{50}$ | Example | 229E $EC_{50}$ |
| 1 | A | 2 | A |
| 3 | A | 4 | A |
| 5 | A | 6 | A |
| 7 | A | 8 | A |
| 9 | A | 10 | B |
| 11 | B | 12 | B |
| 13 | B | 14 | A |
| 15 | A | 16 | A |
| 17 | A | 18 | A |
| 19 | A | 20 | A |
| 21 | A | 22 | A |
| 23 | B | 24 | A |
| 25 | A | 26 | A |
| 27 | A | 28 | B |
| 29 | B | 30 | B |
| 31 | A | 32 | A |
| 33 | B | 34 | A |
| 35 | A | 36 | B |
| 37 | — | 38 | — |
| 39 | A | 40 | B |
| 41 | A | 42 | A |
| 43 | A | 44 | B |
| 45 | B | 46 | B |
| 47 | A | 48 | A |
| 49 | A | 50 | C |
| 51 | B | 52 | A |
| 53 | — | 54 | A |
| 55 | C | 56 | C |
| 57 | C | 58 | C |
| 59 | C | 60 | C |
| 61 | C | 62 | C |
| 63 | A | 64 | A |
| 65 | A | 66 | A |
| 67 | A | 68 | A |
| 69 | B | 70 | A |
| 71 | — | 72 | A |
| 73 | A | 74 | A |
| 75 | A | 76 | A |
| 77 | B | 78 | A |
| 79 | — | 80 | A |
| 81 | A | 82 | A |
| 83 | A | 84 | — |
| 85 | A | 86 | B |
| 87 | C | 88 | B |
| 89 | B | 90 | B |
| 91 | B | 92 | B |
| 93 | C | 94 | A |

TABLE 7-continued

| Summary of Activities | | | |
|---|---|---|---|
| Example | 229E $EC_{50}$ | Example | 229E $EC_{50}$ |
| 95 | — | 96 | — |
| 97 | — | 98 | — |
| 99 | — | 100 | — |
| 101 | — | 102 | — |
| 103 | — | 104 | — |
| 105 | — | 106 | — |
| 107 | B | 108 | B |
| 109 | B | 110 | B |
| 111 | B | 112 | B |
| 113 | A | 114 | A |
| 115 | B | 116 | — |
| 117 | — | 118 | — |
| 119 | — | 120 | — |
| 121 | A | 122 | A |
| 123 | B | 124 | A |
| 125 | — | 126 | — |
| 127 | — | 128 | — |
| 129 | — | 130 | — |
| 131 | — | 132 | — |
| 133 | A | 134 | A |
| 135 | A | 136 | A |
| 137 | A | 138 | A |
| 139 | A | 140 | A |
| 141 | — | 142 | — |
| 143 | — | 144 | — |
| 145 | — | 146 | — |
| 147 | — | 148 | A |
| 149 | A | 150 | B |
| 151 | B | 152 | B |
| 153 | A | 154 | A |
| 155 | A | 156 | A |
| 157 | A | 158 | A |
| 159 | B | 160 | A |
| 161 | A | 162 | A |
| 163 | A | 164 | A |
| 165 | A | 166 | A |
| 373 | B | | |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound represented by Formula (I), or a pharmaceutically acceptable salt thereof, (I)

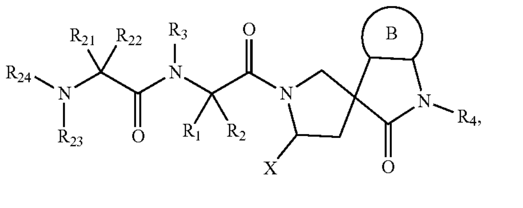

wherein:

$R_1$, $R_2$, $R_3$, $R_{21}$, $R_{22}$, and $R_{23}$ are each independently selected from:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;

6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_1$ and $R_2$ are taken together with the carbon atom to which they are attached to form an optionally substituted 3- to 8-membered carbocyclic ring or an optionally substituted 3- to 8-membered heterocyclic ring;

alternatively, $R_1$ and $R_3$ are taken together with the atoms to which they are attached to form an optionally substituted 3- to 8-membered heterocyclic ring;

alternatively, $R_{21}$ and $R_3$ are taken together with the intervening atoms to form an optionally substituted 4- to 8-membered heterocyclic ring;

alternatively, $R_{22}$ is absent and $R_{21}$ and $R_3$ are taken together with the intervening atoms to form an optionally substituted 4- to 8-membered partially unsaturated heterocyclic ring or an optionally substituted 5- to 6-membered heteroaryl ring;

alternatively, $R_{21}$ and $R_{22}$ are taken together with the carbon atom to which they are attached to form an optionally substituted 3- to 8-membered carbocyclic ring or an optionally substituted 3- to 8-membered heterocyclic ring;

$R_{24}$ is selected from:

1) —$C(O)R_{25}$;
2) —$C(O)OR_{25}$;
3) —$C(O)NR_{13}R_{14}$;
4) —$S(O)_2R_{25}$;
5) Hydrogen;
6) Optionally substituted —$C_1$-$C_8$ alkyl;
7) Optionally substituted —$C_2$-$C_8$ alkenyl;
8) Optionally substituted —$C_2$-$C_8$ alkynyl;
9) Optionally substituted —$C_3$-$C_{12}$ cycloalkyl;
10) Optionally substituted 3- to 12-membered heterocycloalkyl;
11) Optionally substituted aryl;
12) Optionally substituted arylalkyl;
13) Optionally substituted heteroaryl;
14) Optionally substituted heteroarylalkyl;
15) —$(CO)(CO)NR_{13}R_{14}$;
16) —$(CO)(CO)R_{25}$;
17) —$S(O)_2NR_{13}R_{14}$;
18) —$C(S)R_{25}$; and
19) —$C(S)NR_{13}R_{14}$;

alternatively, $R_{23}$ and $R_{24}$ are taken together with the nitrogen atom to which they are attached to form an optionally substituted 3- to 12-membered heterocyclic ring, or an optionally substituted 5- to 12-membered heteroaryl ring;

$R_{25}$ is selected from:

1) Optionally substituted —$C_1$-$C_8$ alkyl;
2) Optionally substituted —$C_2$-$C_8$ alkenyl;
3) Optionally substituted —$C_2$-$C_8$ alkynyl;
4) Optionally substituted —$C_3$-$C_{12}$ cycloalkyl;
5) Optionally substituted 3- to 12-membered heterocycloalkyl;
6) Optionally substituted aryl;
7) Optionally substituted arylalkyl;
8) Optionally substituted heteroaryl; and
9) Optionally substituted heteroarylalkyl;

$R_4$ is hydrogen, optionally substituted —$C_1$-$C_4$ alkyl, optionally substituted —$C_2$-$C_4$ alkenyl, optionally substituted —$C_3$-$C_6$ cycloalkyl, optionally substituted arylalkyl, optionally substituted heteroarylalkyl, halogen, —CN, —OH, or a prodrug moiety;

B is an optionally substituted aryl or optionally substituted heteroaryl;

alternatively, one of $R_{21}$ and $R_{24}$ is L-, wherein L is a saturated or unsaturated linker of 4 to 20 atoms in length which is attached to B X is selected from:

1) —CN;
2) —C(O)$R_{15}$;
3) —CH(OH)$SO_3R_{16}$;
4) —C(O)$NR_{13}R_{14}$,
5) —C(O)C(O)$NR_{13}R_{14}$,
6) —CH═CH—C(O)$OR_{25}$,
7) —CH═CH—C(O)$NR_{13}R_{14}$,
8) —CH═CH—$S(O)_2NR_{13}R_{14}$,
9) —$B(OR_{13})_2$;
10) —C≡$CR_{13}$;
11) —C≡C—C(O)$OR_{25}$;
12) —C≡C—C(O)$NR_{13}R_{14}$,
13) —C≡C—$S(O)_2NR_{13}R_{14}$;
14) —$(CR_{13}R_{14})_w$—CN; and
15) —$(CR_{13}R_{14})_w$—(C═O)—$R_{25}$;

w is 1, 2, 3, 4, or 5;

$R_{13}$ and $R_{14}$ are each independently selected from:

1) Hydrogen;
2) Optionally substituted —$C_1$-$C_8$ alkyl;
3) Optionally substituted —$C_2$-$C_8$ alkenyl;
4) Optionally substituted —$C_2$-$C_8$ alkynyl;
5) Optionally substituted —$C_3$-$C_8$ cycloalkyl;
6) Optionally substituted 3- to 8-membered heterocycloalkyl;
7) Optionally substituted aryl;
8) Optionally substituted arylalkyl;
9) Optionally substituted heteroaryl; and
10) Optionally substituted heteroarylalkyl;

alternatively, $R_{13}$ and $R_{14}$ are taken together with the nitrogen atom to which they are attached to form an optionally substituted 3- to 8-membered heterocyclic ring;

$R_{15}$ is hydrogen, hydroxy, optionally substituted —$C_1$-$C_8$ alkyl, optionally substituted aryl, optionally substituted heteroaryl, optionally substituted arylalkyl or heteroarylalkyl; and $R_{16}$ is hydrogen or $Na^+$.

2. The compound of claim 1, represented by one of Formulae (IV-1)~(IV-4), or a pharmaceutically acceptable salt thereof:

(IV-1)

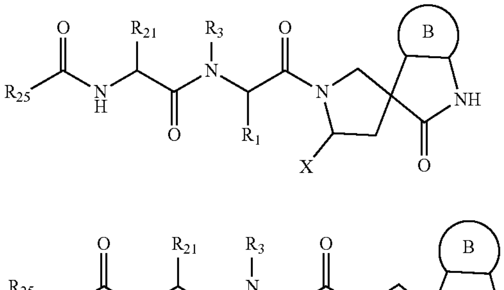

(IV-2)

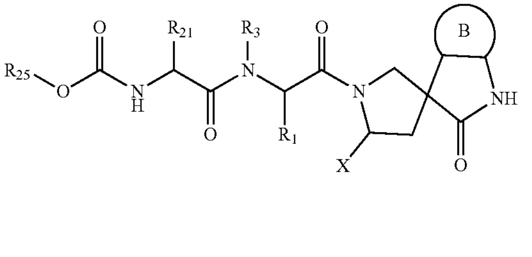

-continued (IV-3)

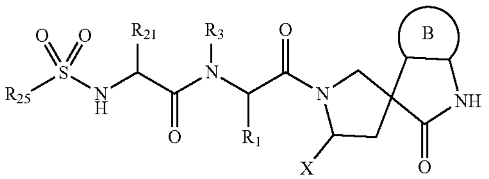

(IV-4)

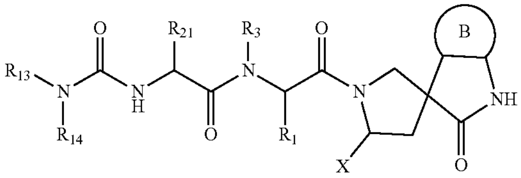

wherein B, X, $R_1$, $R_3$, $R_{13}$, $R_{14}$, $R_{21}$, and $R_{25}$ are as defined in claim 1.

3. The compound of claim 1, represented by one of Formula (V), or a pharmaceutically acceptable salt thereof:

(V)

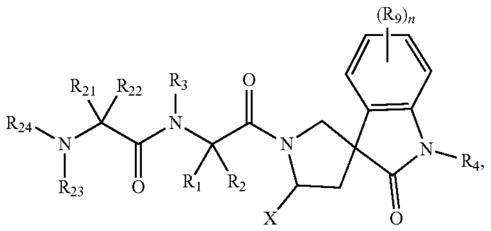

wherein each $R_9$ is independently selected from:

1) Halogen;
2) —CN;
3) —$OR_{13}$;
4) —$SR_{13}$;
5) —$NR_{13}R_{14}$;
6) —OC(O)$NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl;
11) Optionally substituted heteroaryl;
12) —OC(O)$R_{25}$;
13) —C(O)$NR_{13}R_{14}$;
14) —S(O)$R_{25}$;
15) —$S(O)_2$—$R_{25}$;
16) —S(O)(NH)$R_{25}$;
17) —$S(O)_2$—$NR_{13}R_{14}$;
18) —$NR_{13}$(C═O)$R_{25}$;
19) —$NR_{13}$(C═O)$OR_{25}$;
20) —$NR_{13}$(C═O)$NR_{13}R_{14}$;
21) —$NR_{13}$—$S(O)_2$-$R_{25}$; and
22) —$NR_{13}$—$S(O)_2$—$NR_{13}R_{14}$;

n is 0, 1, 2, 3, or 4; and $R_1$, $R_2$, $R_3$, $R_4$, $R_{13}$, $R_{14}$, $R_{21}$, $R_{22}$, $R_{23}$, $R_{24}$, $R_{25}$ and X are as defined in claim 1.

4. The compound of claim 1, represented by Formula (XIX), or a pharmaceutically acceptable salt thereof:

(XIX)

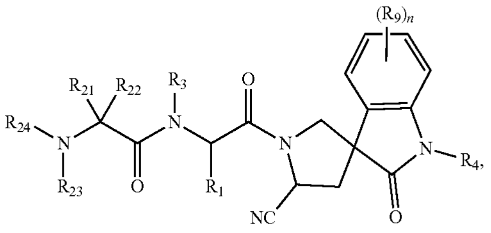

wherein each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl;
11) Optionally substituted heteroaryl;
12) —$OC(O)R_{25}$;
13) —$C(O)NR_{13}R_{14}$;
14) —$S(O)R_{25}$;
15) —$S(O)_2$—$R_{25}$;
16) —$S(O)(NH)R_{25}$;
17) —$S(O)_2$—$NR_{13}R_{14}$;
18) —$NR_{13}(C{=}O)R_{25}$;
19) —$NR_{13}(C{=}O)OR_{25}$;
20) —$NR_{13}(C{=}O)NR_{13}R_{14}$;
21) —$NR_{13}$—$S(O)_2R_{25}$; and
22) —$NR_{13}$—$S(O)_2NR_{13}R_{14}$;

n is 0, 1, 2, 3, or 4; and $R_1$, $R_3$, $R_4$, $R_{21}$, $R_{22}$, $R_{23}$, and $R_{24}$ are as defined in claim 1.

5. The compound of claim 1, represented by one of Formula (VII-1)~(VII-5), or a pharmaceutically acceptable salt thereof:

(VII-1)

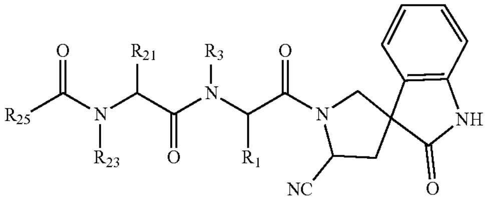

(VII-2)

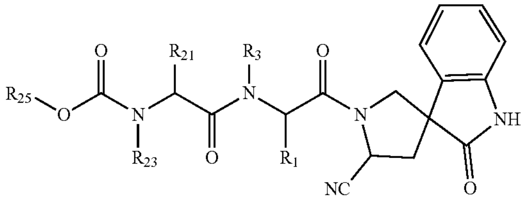

-continued (VII-3)

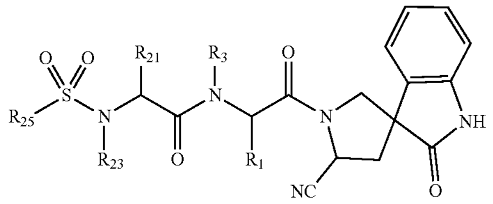

(VII-4)

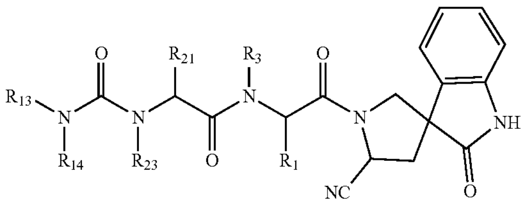

(VII-5)

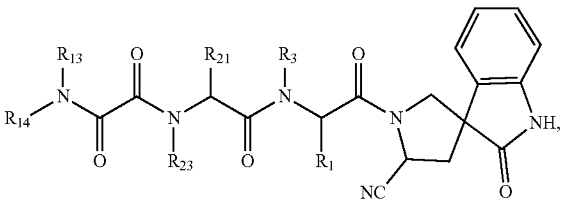

wherein $R_1$, $R_3$, $R_{21}$, $R_{23}$, $R_{25}$, $R_{13}$, and $R_{14}$ are as defined in claim 1.

6. The compound of claim 1, represented by one of Formula (XI-1)~(XI-3), or a pharmaceutically acceptable salt thereof:

(XI-1)

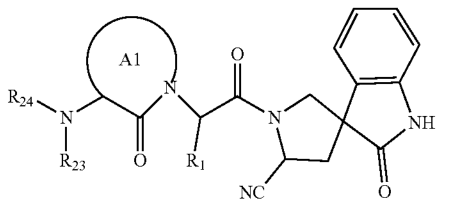

(XI-2)

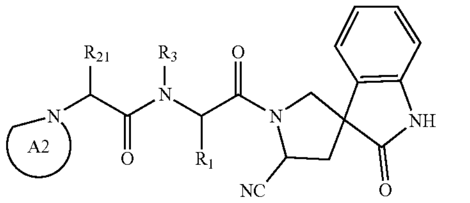

(XI-3)

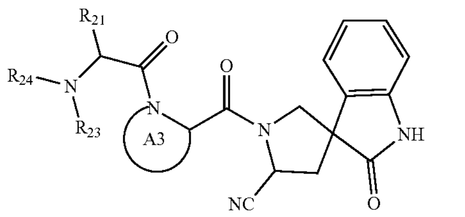

wherein A1 is an optionally substituted 4- to 8-membered lactam or optionally substituted 2-pyridone; A2 is an optionally substituted 3- to 12-membered heterocyclic ring, or an optionally substituted 5- to 12-membered heteroaryl ring; A3 is 3- to 8-membered heterocyclic ring; $R_1$, $R_3$, $R_{21}$, $R_{23}$, and $R_{24}$ are as defined in claim 1.

7. The compound of claim 1, represented by one of Formula (XVII-1)~(XVII-2), (XVII-1)

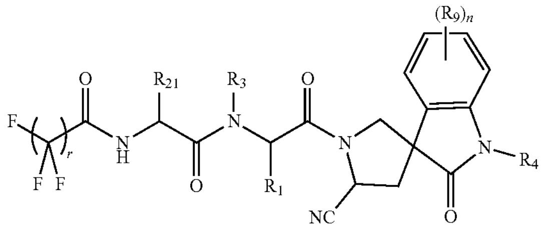

(XVII-2)

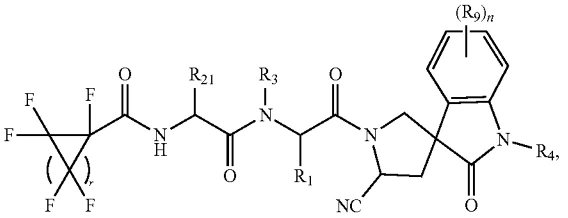

wherein each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl;
11) Optionally substituted heteroaryl;
12) —$OC(O)R_{25}$;
13) —$C(O)NR_{13}R_{14}$,
14) —$S(O)R_{25}$;
15) —$S(O)_2$—$R_{25}$;
16) —$S(O)(NH)R_{25}$;
17) —$S(O)_2$—$NR_{13}R_{14}$,
18) —$NR_{13}(C{=}O)R_{25}$;
19) —$NR_{13}(C{=}O)OR_{25}$;
20) —$NR_{13}(C{=}O)NR_{13}R_{14}$;
21) —$NR_{13}$—$S(O)_2R_{25}$; and
22) —$NR_{13}$—$S(O)_2NR_{13}R_{14}$;

n is 0, 1, 2, 3, or 4; r is 1, 2, 3, or 4, and $R_1$, $R_3$, $R_4$, and $R_{21}$, are as defined in claim 1.

8. The compound of claim 1, represented by one of Formulae (XVIII-1) (XVIII-4), (XVIII-1)

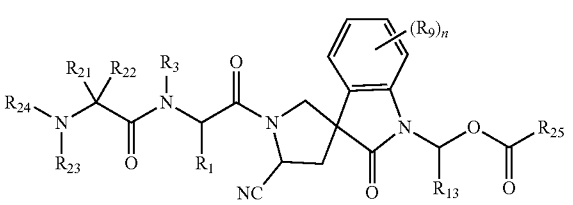

(XVIII-2)

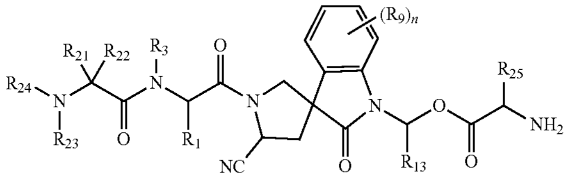

(XVIII-3)

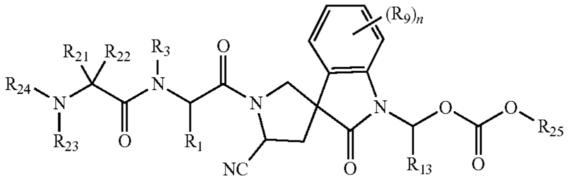

(XVIII-4)

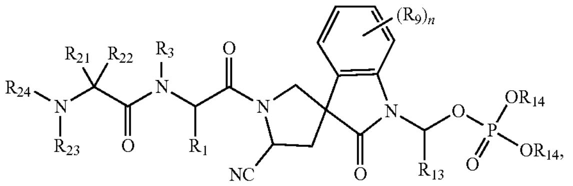

wherein each $R_9$ is independently selected from:

1) Halogen;
2) —CN;
3) —$OR_{13}$;
4) —$SR_{13}$;
5) —$NR_{13}R_{14}$;
6) —$OC(O)NR_{13}R_{14}$;
7) Optionally substituted —$C_1$-$C_6$ alkyl;
8) Optionally substituted —$C_3$-$C_8$ cycloalkyl;
9) Optionally substituted 3- to 8-membered heterocycloalkyl;
10) Optionally substituted aryl;
11) Optionally substituted heteroaryl;
12) —$OC(O)R_{25}$;
13) —$C(O)NR_{13}R_{14}$;
14) —$S(O)R_{25}$;
15) —$S(O)_2$—$R_{25}$;
16) —$S(O)(NH)R_{25}$;
17) —$S(O)_2$—$NR_{13}R_{14}$;
18) —$NR_{13}(C{=}O)R_{25}$;
19) —$NR_{13}(C{=}O)OR_{25}$;
20) —$NR_{13}(C{=}O)NR_{13}R_{14}$;
21) —$NR_{13}$—$S(O)_2R_{25}$; and
22) —$NR_{13}$—$S(O)_2NR_{13}R_{14}$;

n is 0, 1, 2, 3, or 4; and $R_1$, $R_3$, $R_{13}$, $R_{14}$, $R_{21}$, $R_{22}$, $R_{23}$, $R_{24}$ and $R_{25}$ are as defined in claim 1.

9. The compound of claim 1, selected from the compounds set forth below or a pharmaceutically acceptable salt thereof:

| Compound | Structure |
|---|---|
| 1 | 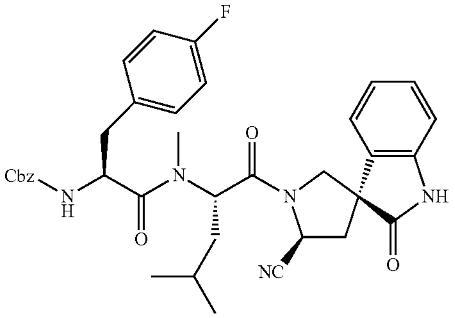 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)OCc1ccccc1] |
| 2 | 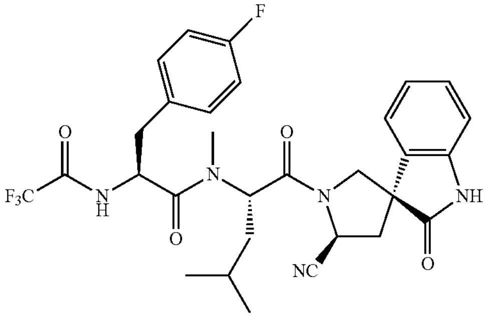 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)C(F)(F)F] |
| 3 | 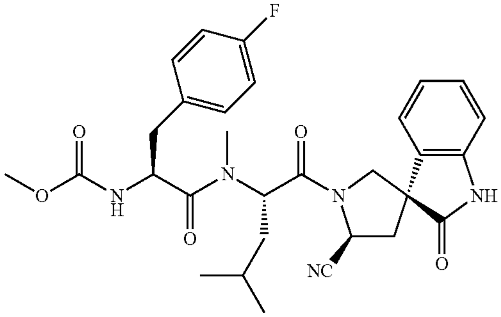 [SMILES: COC(=O)N[C@@H](Cc1ccc(F)cc1)C(=O)N(C)[C@@H](CC(C)C)C(=O)N1C[C@]2(C[C@H]1C#N)C(=O)Nc1ccccc12] |
| 4 | 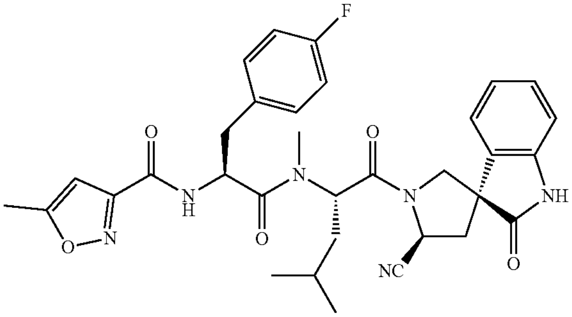 |
| 5 | 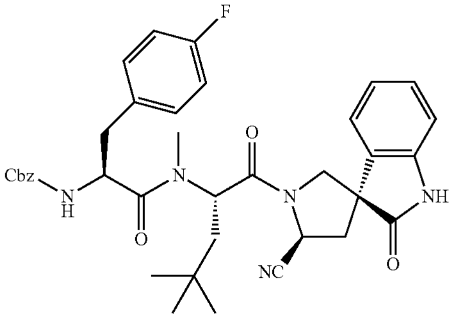 [SMILES: CN(C(=O)[C@H](Cc1ccc(F)cc1)NC(=O)OCc1ccccc1)[C@@H](CC(C)(C)C)C(=O)N1C[C@]2(C[C@H]1C#N)C(=O)Nc1ccccc12] |

-continued
| Compound | Structure |
|---|---|
| 6 | 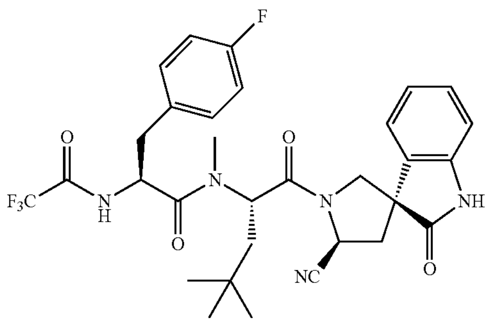 [SMILES: CN(C(=O)[C@H](Cc1ccc(F)cc1)NC(=O)C(F)(F)F)[C@@H](CC(C)(C)C)C(=O)N1C[C@]2(C[C@H]1C#N)C(=O)Nc1ccccc12] |
| 7 | 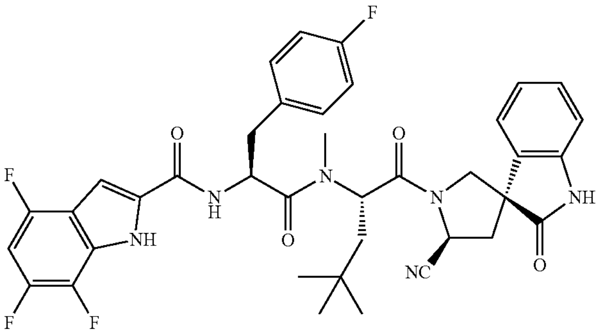 [SMILES: CN(C(=O)[C@H](Cc1ccc(F)cc1)NC(=O)c1cc2c(F)cc(F)c(F)c2[nH]1)[C@@H](CC(C)(C)C)C(=O)N1C[C@]2(C[C@H]1C#N)C(=O)Nc1ccccc12] |
| 8 | 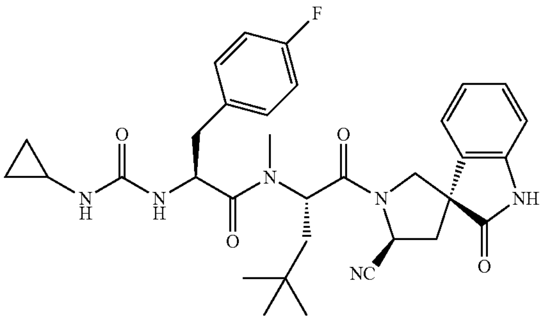 [SMILES: CN(C(=O)[C@H](Cc1ccc(F)cc1)NC(=O)NC1CC1)[C@@H](CC(C)(C)C)C(=O)N1C[C@]2(C[C@H]1C#N)C(=O)Nc1ccccc12] |
| 9 | 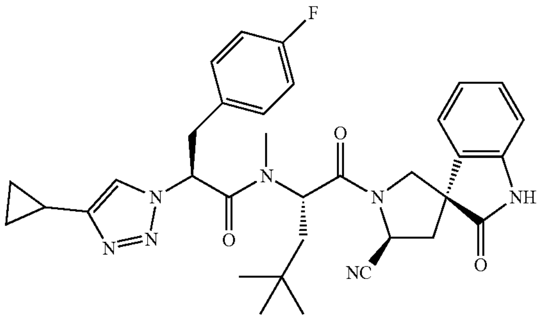 [SMILES: CN(C(=O)[C@H](Cc1ccc(F)cc1)n1cc(C2CC2)nn1)[C@@H](CC(C)(C)C)C(=O)N1C[C@]2(C[C@H]1C#N)C(=O)Nc1ccccc12] |
| 10 | 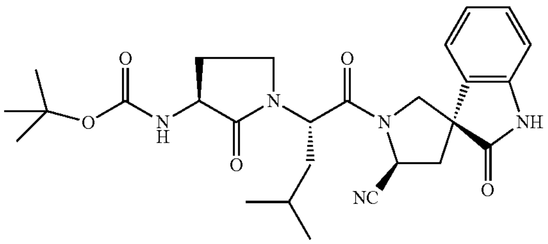 [SMILES: CC(C)C[C@@H](C(=O)N1C[C@]2(C[C@H]1C#N)C(=O)Nc1ccccc12)N1CC[C@H](NC(=O)OC(C)(C)C)C1=O] |

-continued
| Compound | Structure |
|---|---|
| 11 | 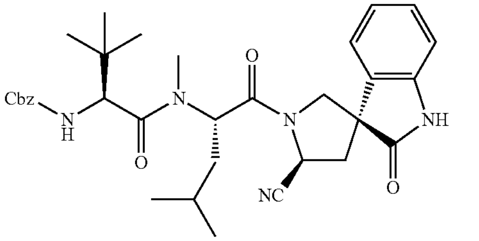 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C(C)(C)C] |
| 12 | 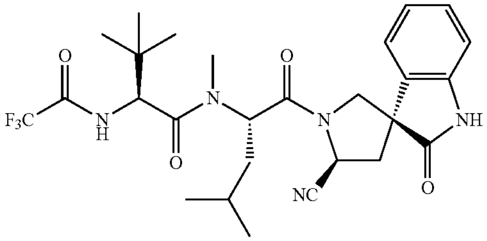 [SMILES: CC(C)C[C@@H](C(=O)N1C[C@]2(C[C@H]1C#N)C(=O)Nc1ccccc12)N(C)C(=O)[C@@H](NC(=O)C(F)(F)F)C(C)(C)C] |
| 13 | 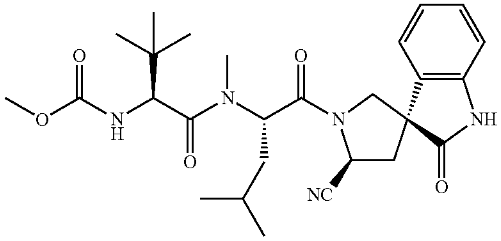 [SMILES: COC(=O)N[C@H](C(=O)N(C)[C@@H](CC(C)C)C(=O)N1C[C@]2(C[C@H]1C#N)C(=O)Nc1ccccc12)C(C)(C)C] |
| 14 | 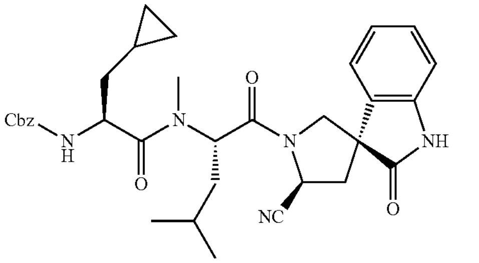 [SMILES: CC(C)C[C@@H](C(=O)N1C[C@]2(C[C@H]1C#N)C(=O)Nc1ccccc12)N(C)C(=O)[C@H](CC1CC1)NC(=O)OCc1ccccc1] |
| 15 | 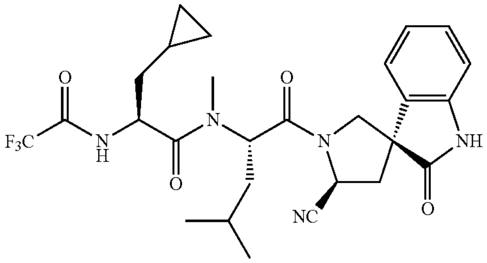 [SMILES: CC(C)C[C@@H](C(=O)N1C[C@]2(C[C@H]1C#N)C(=O)Nc1ccccc12)N(C)C(=O)[C@H](CC1CC1)NC(=O)C(F)(F)F] |
| 16 | 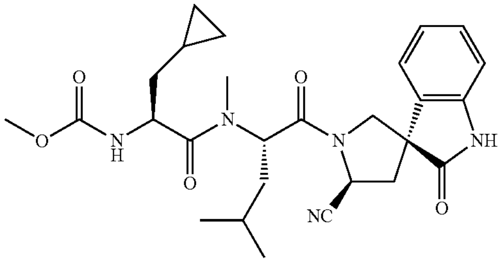 [SMILES: COC(=O)N[C@@H](CC1CC1)C(=O)N(C)[C@@H](CC(C)C)C(=O)N1C[C@]2(C[C@H]1C#N)C(=O)Nc1ccccc12] |

-continued
| Compound | Structure |
|---|---|
| 17 | 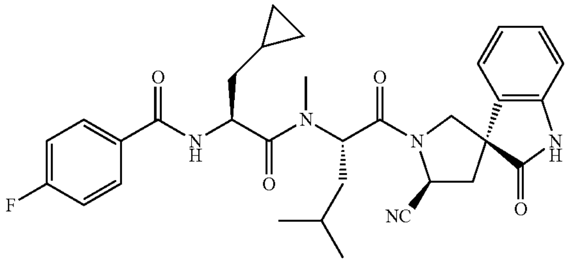 [SMILES: CC(C)C[C@@H](C(=O)N1C[C@]2(C[C@H]1C#N)C(=O)Nc1ccccc12)N(C)C(=O)[C@H](CC1CC1)NC(=O)c1ccc(F)cc1] |
| 18 | 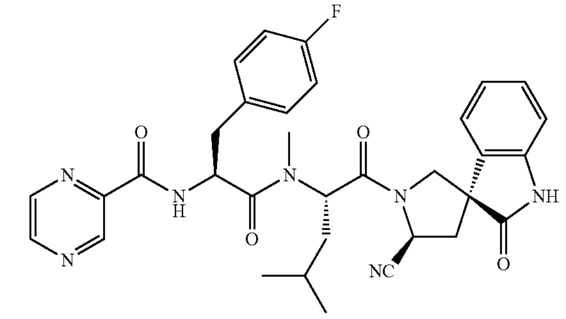 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)c1cnccn1] |
| 19 | 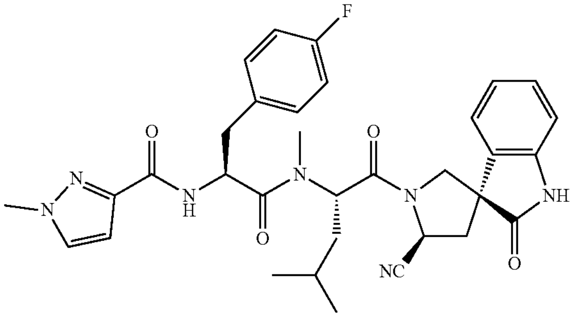 [SMILES: CC(C)C[C@@H](C(=O)N1C[C@]2(C[C@H]1C#N)C(=O)Nc1ccccc12)N(C)C(=O)[C@H](Cc1ccc(F)cc1)NC(=O)c1ccn(C)n1] |
| 20 | 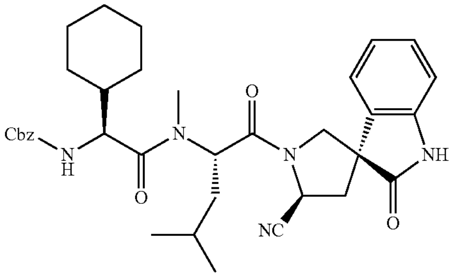 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C1CCCCC1] |
| 21 | 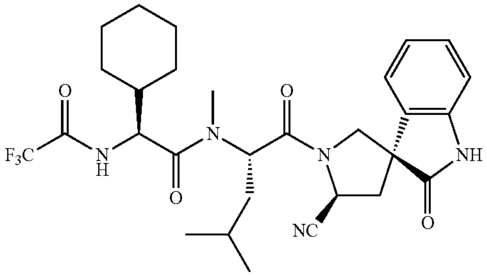 [SMILES: CC(C)C[C@@H](C(=O)N1C[C@]2(C[C@H]1C#N)C(=O)Nc1ccccc12)N(C)C(=O)[C@@H](NC(=O)C(F)(F)F)C1CCCCC1] |

-continued
| Compound | Structure |
| --- | --- |
| 22 | 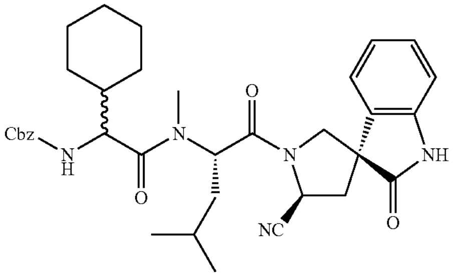 [SMILES: CC(C)C[C@@H](C(=O)N1C[C@]2(C[C@H]1C#N)C(=O)Nc1ccccc12)N(C)C(=O)C(NC(=O)OCc1ccccc1)C1CCCCC1] |
| 23 | 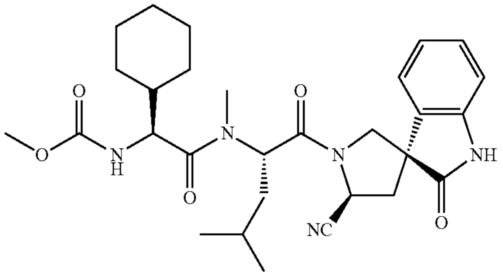 [SMILES: COC(=O)N[C@H](C(=O)N(C)[C@@H](CC(C)C)C(=O)N1C[C@]2(C[C@H]1C#N)C(=O)Nc1ccccc12)C1CCCCC1] |
| 24 | 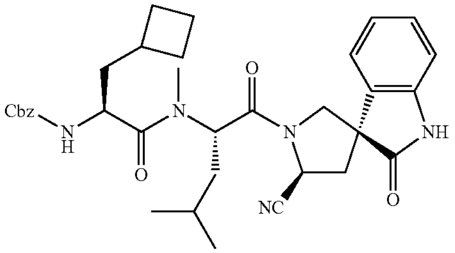 [SMILES: CC(C)C[C@@H](C(=O)N1C[C@]2(C[C@H]1C#N)C(=O)Nc1ccccc12)N(C)C(=O)[C@H](CC1CCC1)NC(=O)OCc1ccccc1] |
| 25 | 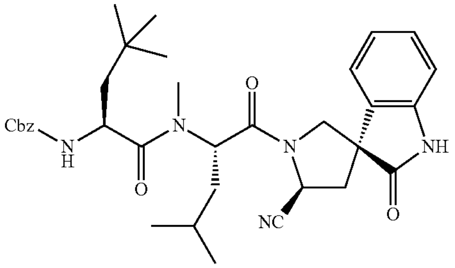 [SMILES: CC(C)C[C@@H](C(=O)N1C[C@]2(C[C@H]1C#N)C(=O)Nc1ccccc12)N(C)C(=O)[C@H](CC(C)(C)C)NC(=O)OCc1ccccc1] |
| 26 | 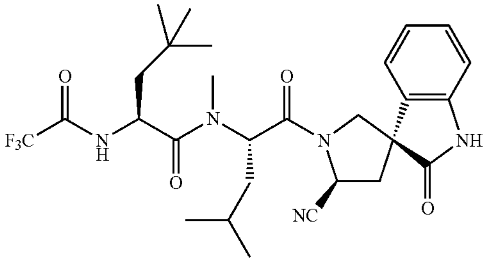 [SMILES: CC(C)C[C@@H](C(=O)N1C[C@]2(C[C@H]1C#N)C(=O)Nc1ccccc12)N(C)C(=O)[C@H](CC(C)(C)C)NC(=O)C(F)(F)F] |

-continued
| Compound | Structure |
| --- | --- |
| 27 | 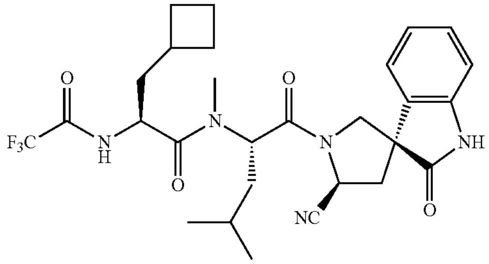 [SMILES: CC(C)C[C@@H](C(=O)N1C[C@]2(C[C@H]1C#N)C(=O)Nc1ccccc12)N(C)C(=O)[C@H](CC1CCC1)NC(=O)C(F)(F)F] |
| 28 | 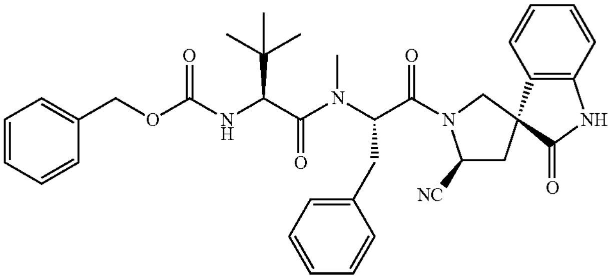 [SMILES: CN(C(=O)[C@@H](NC(=O)OCc1ccccc1)C(C)(C)C)[C@@H](Cc1ccccc1)C(=O)N1C[C@]2(C[C@H]1C#N)C(=O)Nc1ccccc12] |
| 29 | 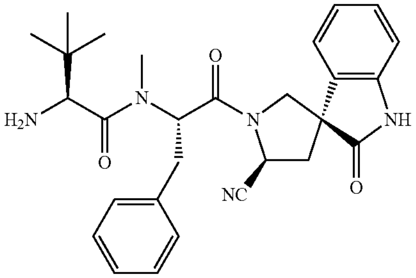 [SMILES: CN(C(=O)[C@@H](N)C(C)(C)C)[C@@H](Cc1ccccc1)C(=O)N1C[C@]2(C[C@H]1C#N)C(=O)Nc1ccccc12] |
| 30 | 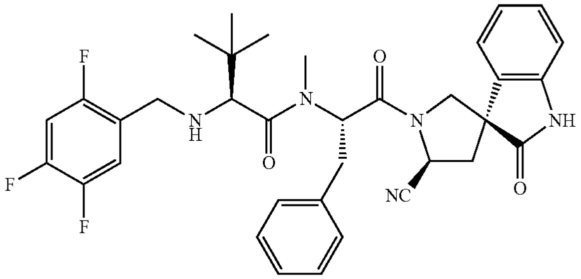 [SMILES: CN(C(=O)[C@@H](NCc1cc(F)c(F)cc1F)C(C)(C)C)[C@@H](Cc1ccccc1)C(=O)N1C[C@]2(C[C@H]1C#N)C(=O)Nc1ccccc12] |
| 31 | 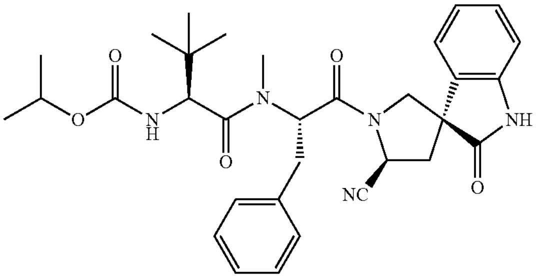 [SMILES: CC(C)OC(=O)N[C@H](C(=O)N(C)[C@@H](Cc1ccccc1)C(=O)N1C[C@]2(C[C@H]1C#N)C(=O)Nc1ccccc12)C(C)(C)C] |

-continued
| Compound | Structure |
|---|---|
| 32 | 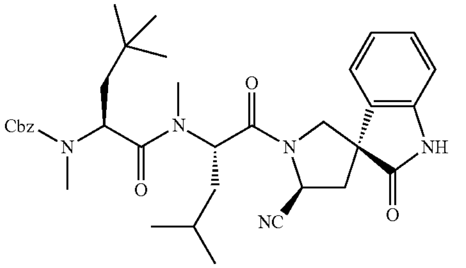 |
| 33 | 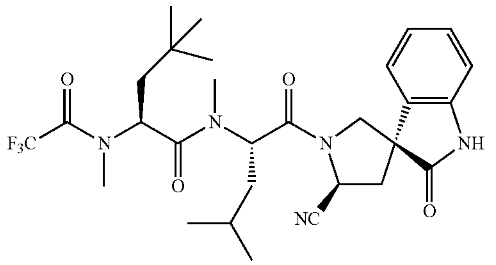 [SMILES: CC(C)C[C@@H](C(=O)N1C[C@]2(C[C@H]1C#N)C(=O)Nc1ccccc12)N(C)C(=O)[C@H](CC(C)(C)C)N(C)C(=O)C(F)(F)F] |
| 34 | 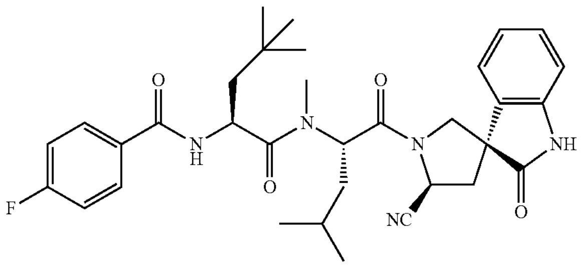 [SMILES: CC(C)C[C@@H](C(=O)N1C[C@]2(C[C@H]1C#N)C(=O)Nc1ccccc12)N(C)C(=O)[C@H](CC(C)(C)C)NC(=O)c1ccc(F)cc1] |
| 35 | 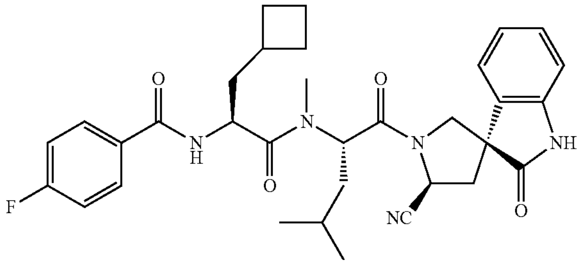 [SMILES: CC(C)C[C@@H](C(=O)N1C[C@]2(C[C@H]1C#N)C(=O)Nc1ccccc12)N(C)C(=O)[C@H](CC1CCC1)NC(=O)c1ccc(F)cc1] |
| 36 | 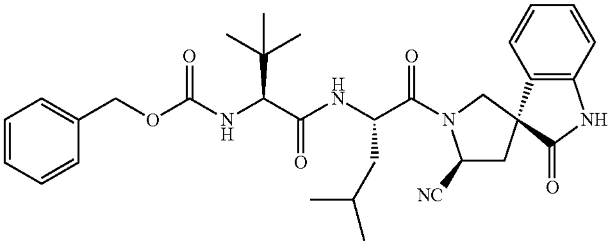 [SMILES: CC(C)C[C@H](NC(=O)[C@@H](NC(=O)OCc1ccccc1)C(C)(C)C)C(=O)N1C[C@]2(C[C@H]1C#N)C(=O)Nc1ccccc12] |
| 37 | 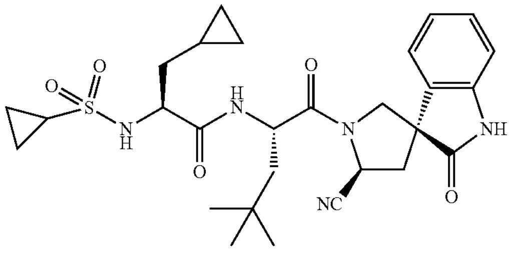 [SMILES: CC(C)(C)C[C@H](NC(=O)[C@H](CC1CC1)NS(=O)(=O)C1CC1)C(=O)N1C[C@]2(C[C@H]1C#N)C(=O)Nc1ccccc12] |

-continued
| Compound | Structure |
| --- | --- |
| 38 | 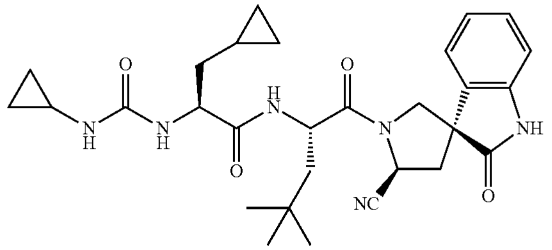 |
| 39 | 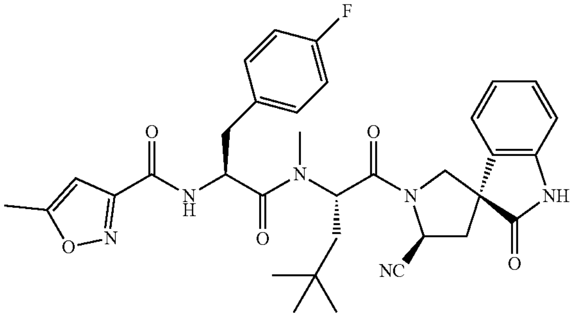 [SMILES: Cc1cc(C(=O)N[C@@H](Cc2ccc(F)cc2)C(=O)N(C)[C@@H](CC(C)(C)C)C(=O)N2C[C@]3(C[C@H]2C#N)C(=O)Nc2ccccc23)no1] |
| 40 | 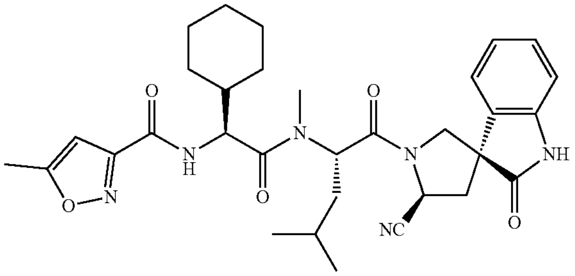 [SMILES: Cc1cc(C(=O)N[C@H](C(=O)N(C)[C@@H](CC(C)C)C(=O)N2C[C@]3(C[C@H]2C#N)C(=O)Nc2ccccc23)C2CCCCC2)no1] |
| 41 | 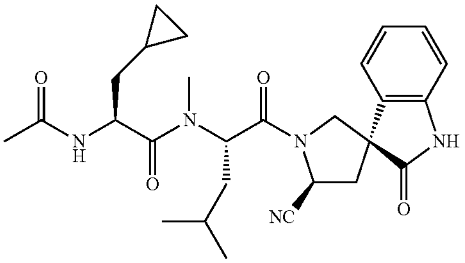 [SMILES: CC(=O)N[C@@H](CC1CC1)C(=O)N(C)[C@@H](CC(C)C)C(=O)N1C[C@]2(C[C@H]1C#N)C(=O)Nc1ccccc12] |
| 42 | 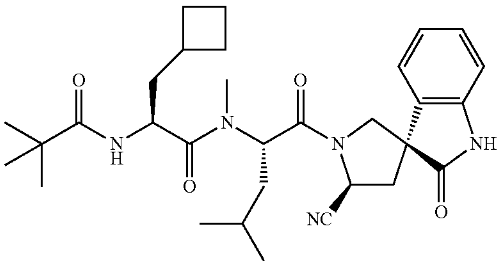 [SMILES: CC(C)C[C@@H](C(=O)N1C[C@]2(C[C@H]1C#N)C(=O)Nc1ccccc12)N(C)C(=O)[C@H](CC1CCC1)NC(=O)C(C)(C)C] |

-continued
| Compound | Structure |
| --- | --- |
| 43 | 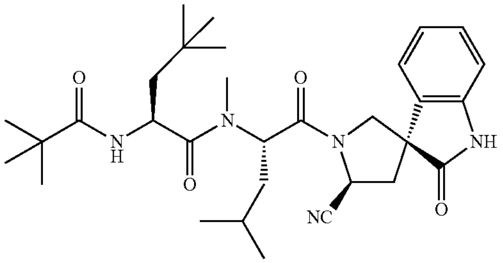 [SMILES: CC(C)C[C@@H](C(=O)N1C[C@]2(C[C@H]1C#N)C(=O)Nc1ccccc12)N(C)C(=O)[C@H](CC(C)(C)C)NC(=O)C(C)(C)C] |
| 44 | 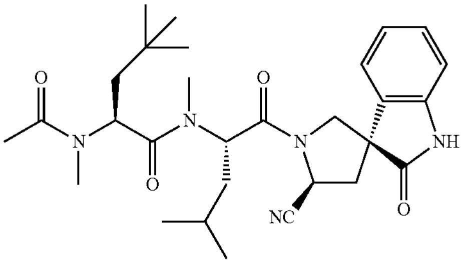 [SMILES: CC(=O)N(C)[C@@H](CC(C)(C)C)C(=O)N(C)[C@@H](CC(C)C)C(=O)N1C[C@]2(C[C@H]1C#N)C(=O)Nc1ccccc12] |
| 45 | 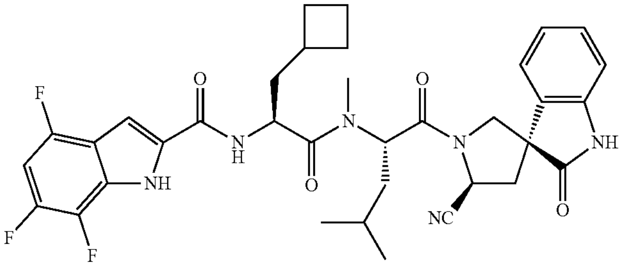 [SMILES: CC(C)C[C@@H](C(=O)N1C[C@]2(C[C@H]1C#N)C(=O)Nc1ccccc12)N(C)C(=O)[C@H](CC1CCC1)NC(=O)c1cc2c(F)cc(F)c(F)c2[nH]1] |
| 46 | 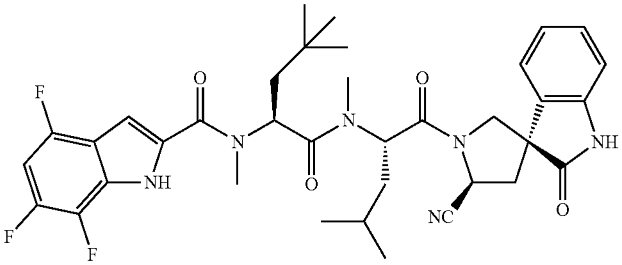 [SMILES: CC(C)C[C@@H](C(=O)N1C[C@]2(C[C@H]1C#N)C(=O)Nc1ccccc12)N(C)C(=O)[C@H](CC(C)(C)C)N(C)C(=O)c1cc2c(F)cc(F)c(F)c2[nH]1] |
| 47 | 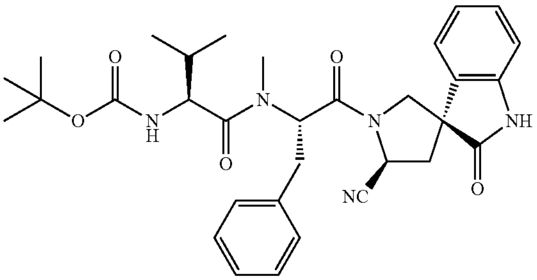 [SMILES: CC(C)[C@H](NC(=O)OC(C)(C)C)C(=O)N(C)[C@@H](Cc1ccccc1)C(=O)N1C[C@]2(C[C@H]1C#N)C(=O)Nc1ccccc12] |

-continued
| Compound | Structure |
|---|---|
| 48 | 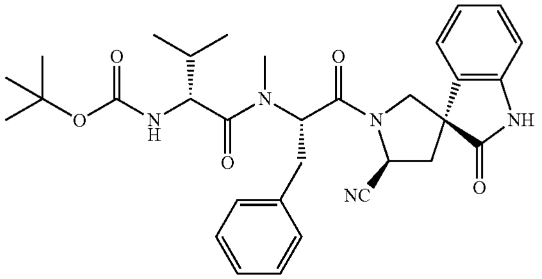 [SMILES: CC(C)[C@@H](NC(=O)OC(C)(C)C)C(=O)N(C)[C@@H](Cc1ccccc1)C(=O)N1C[C@]2(C[C@H]1C#N)C(=O)Nc1ccccc12] |
| 49 | 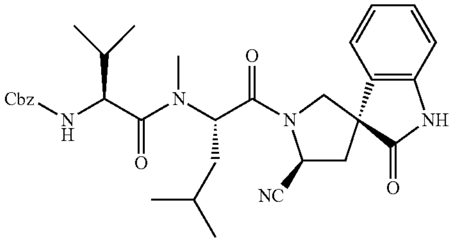 [SMILES: CC(C)C[C@@H](C(=O)N1C[C@]2(C[C@H]1C#N)C(=O)Nc1ccccc12)N(C)C(=O)[C@@H](NC(=O)OCc1ccccc1)C(C)C] |
| 50 | 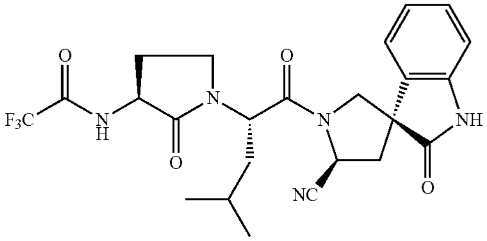 [SMILES: CC(C)C[C@@H](C(=O)N1C[C@]2(C[C@H]1C#N)C(=O)Nc1ccccc12)N1CC[C@H](NC(=O)C(F)(F)F)C1=O] |
| 51 | 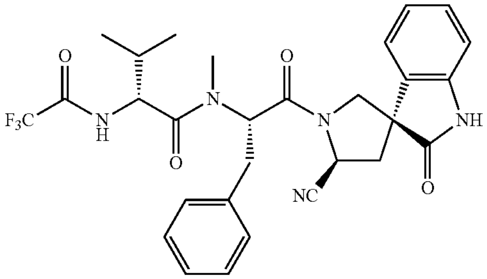 [SMILES: CC(C)[C@@H](NC(=O)C(F)(F)F)C(=O)N(C)[C@@H](Cc1ccccc1)C(=O)N1C[C@]2(C[C@H]1C#N)C(=O)Nc1ccccc12] |
| 52 | 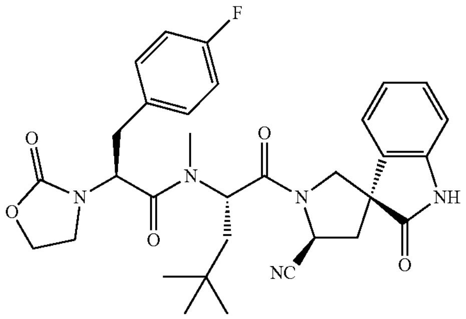 [SMILES: CN(C(=O)[C@H](Cc1ccc(F)cc1)N1CCOC1=O)[C@@H](CC(C)(C)C)C(=O)N1C[C@]2(C[C@H]1C#N)C(=O)Nc1ccccc12] |

-continued
| Compound | Structure |
|---|---|
| 53 | 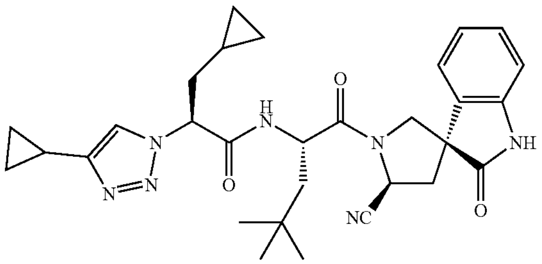 [SMILES: CC(C)(C)C[C@H](NC(=O)[C@H](CC1CC1)n1cc(C2CC2)nn1)C(=O)N1C[C@]2(C[C@H]1C#N)C(=O)Nc1ccccc12] |
| 54 | 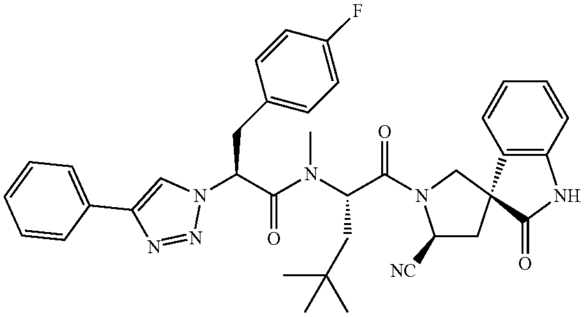 [SMILES: CN(C(=O)[C@H](Cc1ccc(F)cc1)n1cc(-c2ccccc2)nn1)[C@@H](CC(C)(C)C)C(=O)N1C[C@]2(C[C@H]1C#N)C(=O)Nc1ccccc12] |
| 55 | 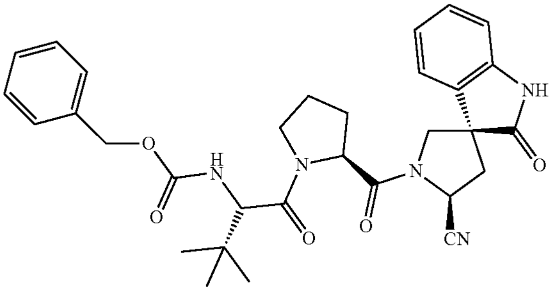 |
| 56 | 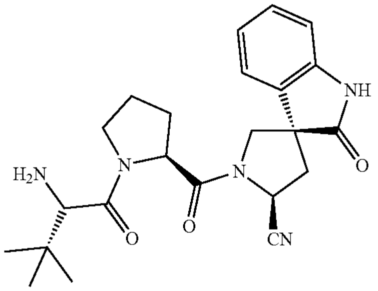 |
| 57 | 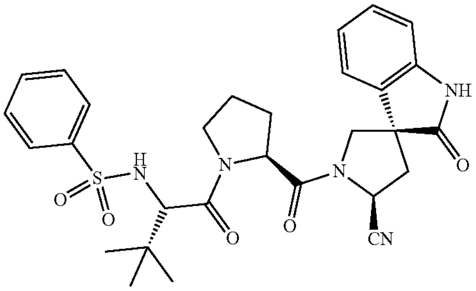 |

-continued
| Compound | Structure |
|---|---|
| 58 | 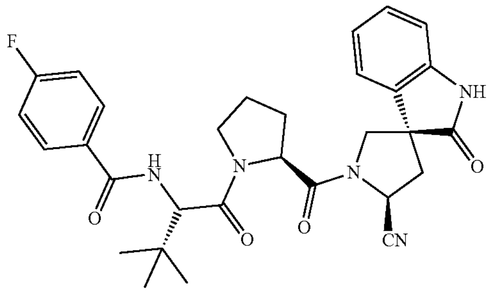 |
| 59 | 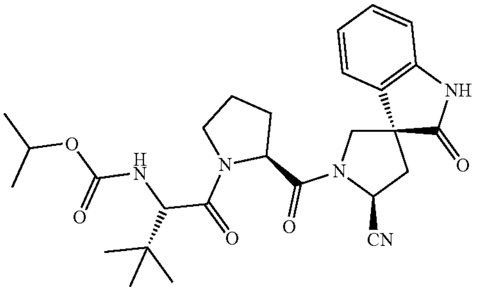 |
| 60 | 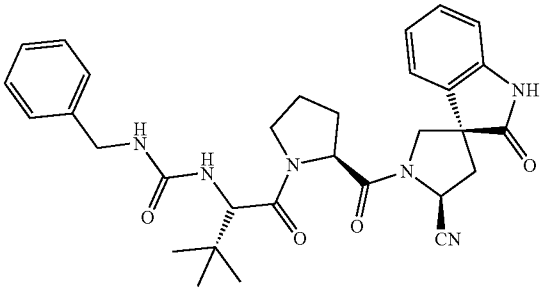 |
| 61 | 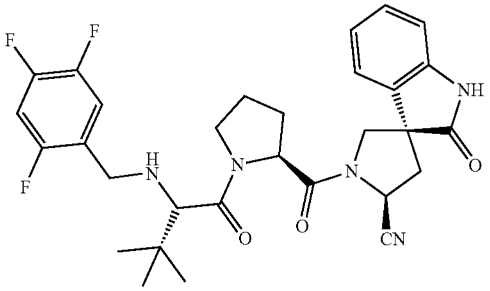 |
| 62 | 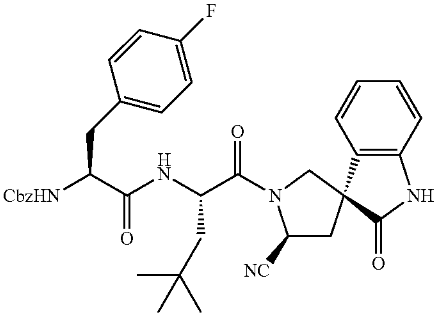 [SMILES: CC(C)(C)C[C@H](NC(=O)[C@H](Cc1ccc(F)cc1)NC(=O)OCc1ccccc1)C(=O)N1C[C@]2(C[C@H]1C#N)C(=O)Nc1ccccc12] |

-continued
| Compound | Structure |
| --- | --- |
| 63 | 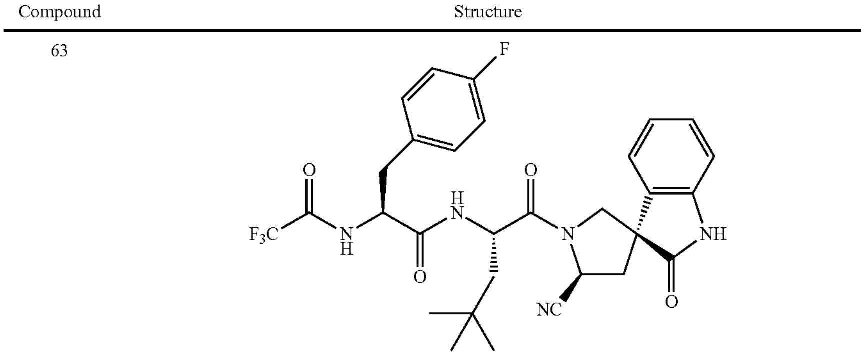 |
| 64 | 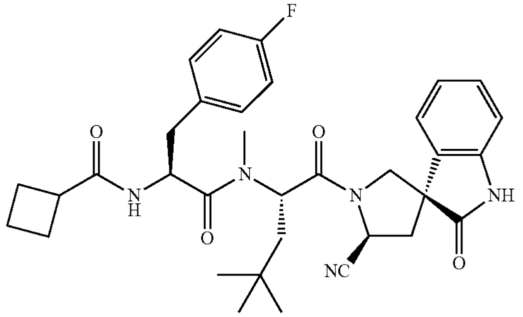 [SMILES: CN(C(=O)[C@H](Cc1ccc(F)cc1)NC(=O)C1CCC1)[C@@H](CC(C)(C)C)C(=O)N1C[C@]2(C[C@H]1C#N)C(=O)Nc1ccccc12] |
| 65 | 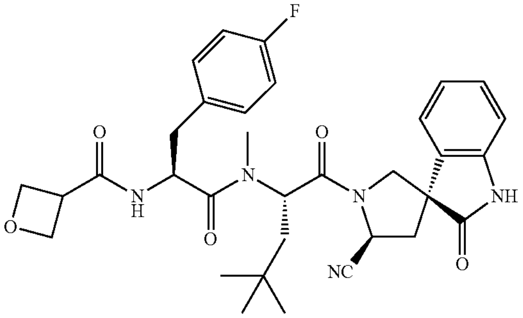 [SMILES: CN(C(=O)[C@H](Cc1ccc(F)cc1)NC(=O)C1COC1)[C@@H](CC(C)(C)C)C(=O)N1C[C@]2(C[C@H]1C#N)C(=O)Nc1ccccc12] |
| 66 | 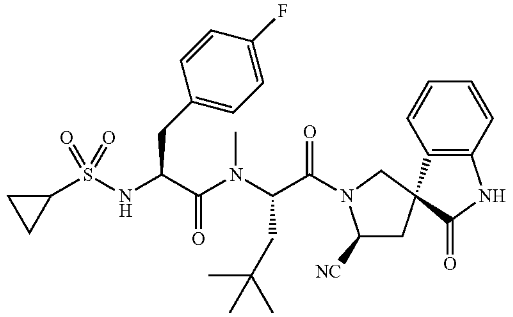 [SMILES: CN(C(=O)[C@H](Cc1ccc(F)cc1)NS(=O)(=O)C1CC1)[C@@H](CC(C)(C)C)C(=O)N1C[C@]2(C[C@H]1C#N)C(=O)Nc1ccccc12] |
| 67 | 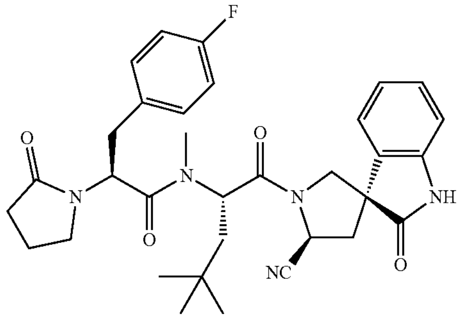 [SMILES: CN(C(=O)[C@H](Cc1ccc(F)cc1)N1CCCC1=O)[C@@H](CC(C)(C)C)C(=O)N1C[C@]2(C[C@H]1C#N)C(=O)Nc1ccccc12] |

-continued
| Compound | Structure |
| --- | --- |
| 68 | 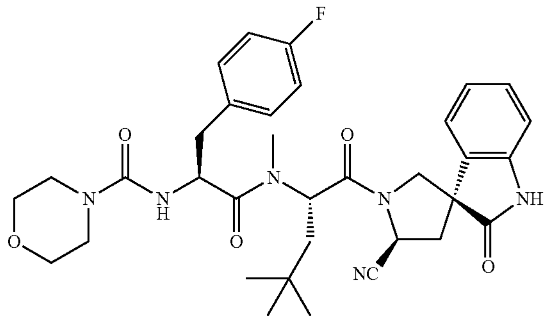 [SMILES: CN(C(=O)[C@H](Cc1ccc(F)cc1)NC(=O)N1CCOCC1)[C@@H](CC(C)(C)C)C(=O)N1C[C@]2(C[C@H]1C#N)C(=O)Nc1ccccc12] |
| 69 | 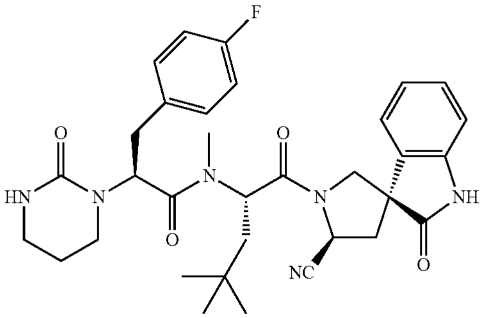 [SMILES: CN(C(=O)[C@H](Cc1ccc(F)cc1)N1CCCNC1=O)[C@@H](CC(C)(C)C)C(=O)N1C[C@]2(C[C@H]1C#N)C(=O)Nc1ccccc12] |
| 70 | 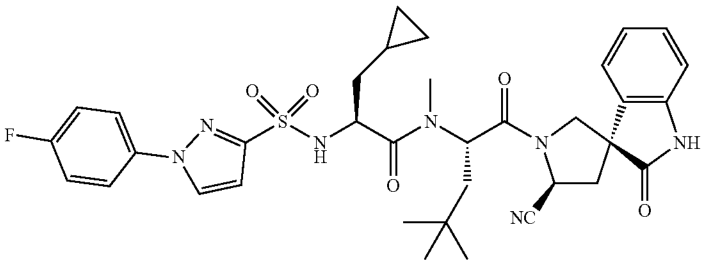 [SMILES: CN(C(=O)[C@H](CC1CC1)NS(=O)(=O)c1ccn(-c2ccc(F)cc2)n1)[C@@H](CC(C)(C)C)C(=O)N1C[C@]2(C[C@H]1C#N)C(=O)Nc1ccccc12] |
| 71 | 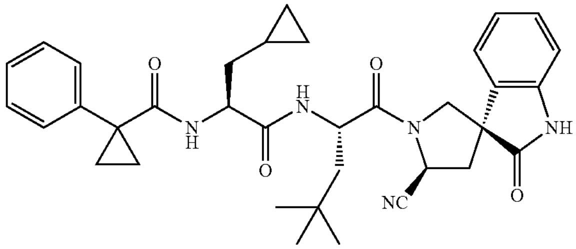 [SMILES: CC(C)(C)C[C@H](NC(=O)[C@H](CC1CC1)NC(=O)C1(c2ccccc2)CC1)C(=O)N1C[C@]2(C[C@H]1C#N)C(=O)Nc1ccccc12] |
| 72 | 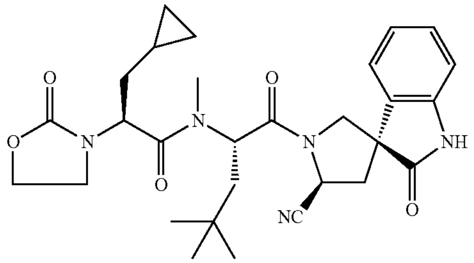 [SMILES: CN(C(=O)[C@H](CC1CC1)N1CCOC1=O)[C@@H](CC(C)(C)C)C(=O)N1C[C@]2(C[C@H]1C#N)C(=O)Nc1ccccc12] |

-continued
| Compound | Structure |
|---|---|
| 73 | 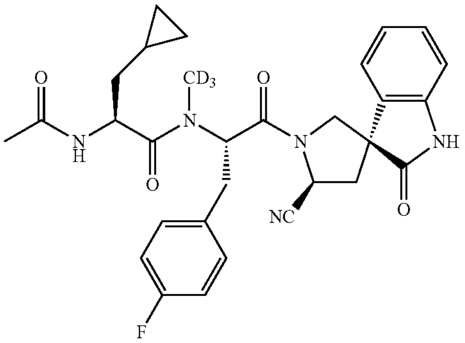 [SMILES: [2H]C([2H])([2H])N(C(=O)[C@H](CC1CC1)NC(C)=O)[C@@H](Cc1ccc(F)cc1)C(=O)N1C[C@]2(C[C@H]1C#N)C(=O)Nc1ccccc12] |
| 74 | 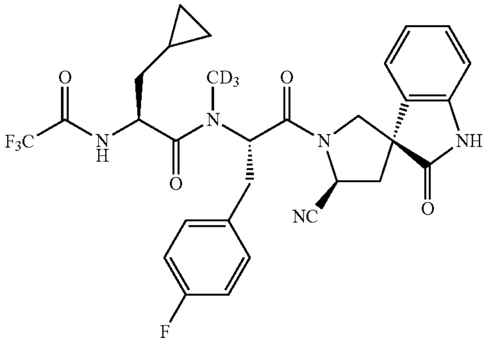 [SMILES: [2H]C([2H])([2H])N(C(=O)[C@H](CC1CC1)NC(=O)C(F)(F)F)[C@@H](Cc1ccc(F)cc1)C(=O)N1C[C@]2(C[C@H]1C#N)C(=O)Nc1ccccc12] |
| 75 | 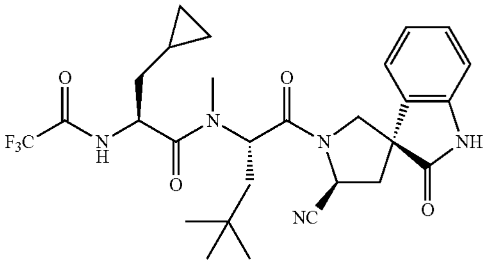 [SMILES: CN(C(=O)[C@H](CC1CC1)NC(=O)C(F)(F)F)[C@@H](CC(C)(C)C)C(=O)N1C[C@]2(C[C@H]1C#N)C(=O)Nc1ccccc12] |
| 76 | 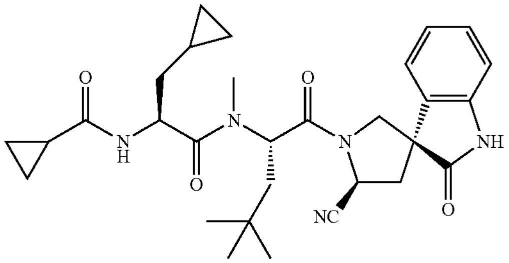 [SMILES: CN(C(=O)[C@H](CC1CC1)NC(=O)C1CC1)[C@@H](CC(C)(C)C)C(=O)N1C[C@]2(C[C@H]1C#N)C(=O)Nc1ccccc12] |
| 77 | 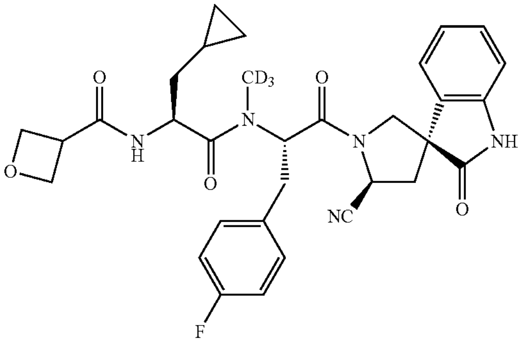 [SMILES: [2H]C([2H])([2H])N(C(=O)[C@H](CC1CC1)NC(=O)C1COC1)[C@@H](Cc1ccc(F)cc1)C(=O)N1C[C@]2(C[C@H]1C#N)C(=O)Nc1ccccc12] |

-continued
| Compound | Structure |
|---|---|
| 78 | 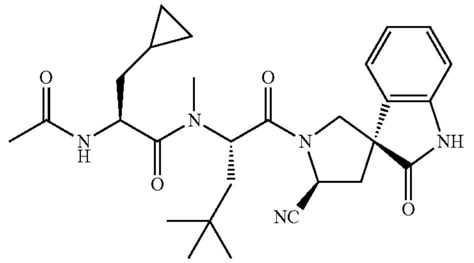 [SMILES: CC(=O)N[C@@H](CC1CC1)C(=O)N(C)[C@@H](CC(C)(C)C)C(=O)N1C[C@]2(C[C@H]1C#N)C(=O)Nc1ccccc12] |
| 79 | 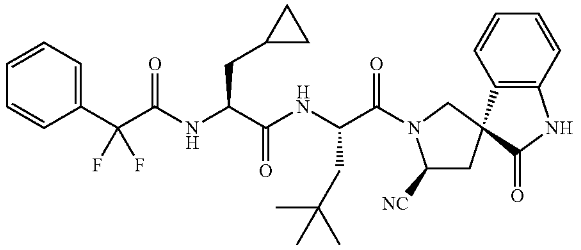 [SMILES: CC(C)(C)C[C@H](NC(=O)[C@H](CC1CC1)NC(=O)C(F)(F)c1ccccc1)C(=O)N1C[C@]2(C[C@H]1C#N)C(=O)Nc1ccccc12] |
| 80 | 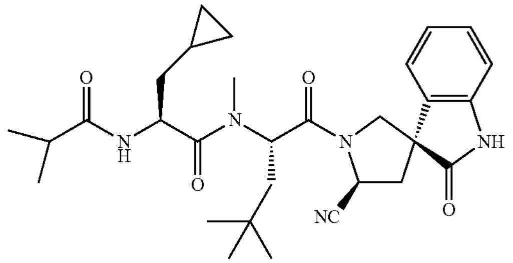 [SMILES: CC(C)C(=O)N[C@@H](CC1CC1)C(=O)N(C)[C@@H](CC(C)(C)C)C(=O)N1C[C@]2(C[C@H]1C#N)C(=O)Nc1ccccc12] |
| 81 | 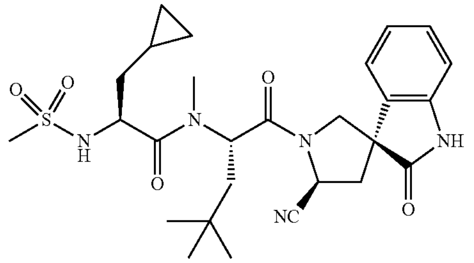 [SMILES: CN(C(=O)[C@H](CC1CC1)NS(C)(=O)=O)[C@@H](CC(C)(C)C)C(=O)N1C[C@]2(C[C@H]1C#N)C(=O)Nc1ccccc12] |
| 82 | 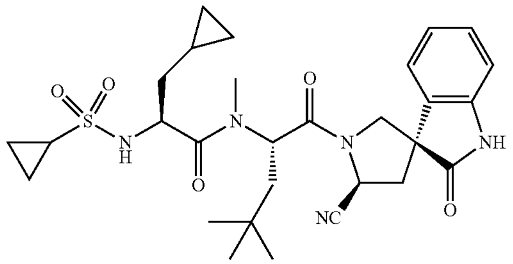 [SMILES: CN(C(=O)[C@H](CC1CC1)NS(=O)(=O)C1CC1)[C@@H](CC(C)(C)C)C(=O)N1C[C@]2(C[C@H]1C#N)C(=O)Nc1ccccc12] |
| 83 | 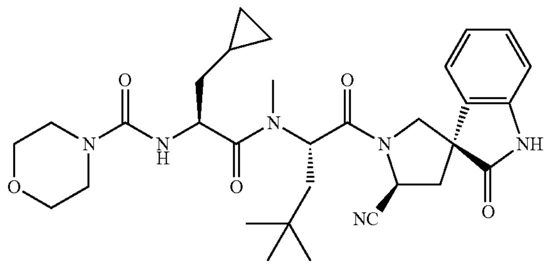 [SMILES: CN(C(=O)[C@H](CC1CC1)NC(=O)N1CCOCC1)[C@@H](CC(C)(C)C)C(=O)N1C[C@]2(C[C@H]1C#N)C(=O)Nc1ccccc12] |

-continued
| Compound | Structure |
| --- | --- |
| 84 | 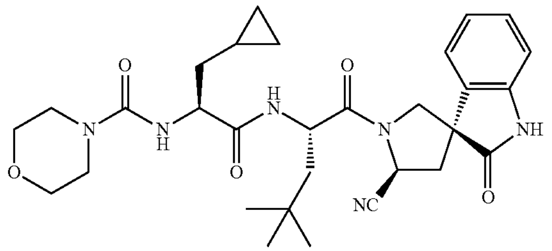 [SMILES: CC(C)(C)C[C@H](NC(=O)[C@H](CC1CC1)NC(=O)N1CCOCC1)C(=O)N1C[C@]2(C[C@H]1C#N)C(=O)Nc1ccccc12] |
| 85 | 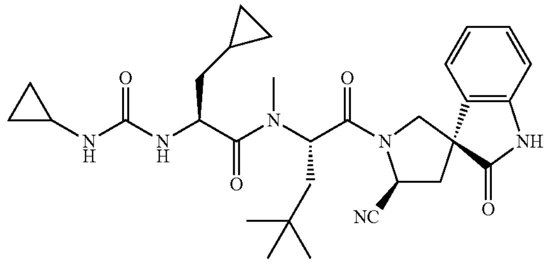 [SMILES: CN(C(=O)[C@H](CC1CC1)NC(=O)NC1CC1)[C@@H](CC(C)(C)C)C(=O)N1C[C@]2(C[C@H]1C#N)C(=O)Nc1ccccc12] |
| 86 | 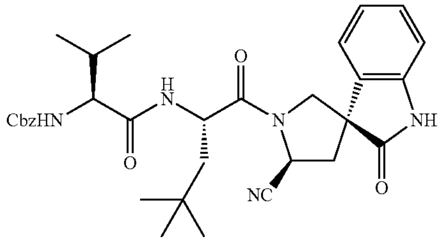 [SMILES: CC(C)[C@H](NC(=O)OCc1ccccc1)C(=O)N[C@@H](CC(C)(C)C)C(=O)N1C[C@]2(C[C@H]1C#N)C(=O)Nc1ccccc12] |
| 87 | 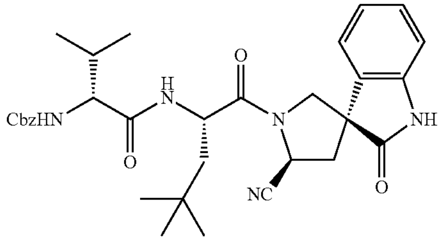 [SMILES: CC(C)[C@@H](NC(=O)OCc1ccccc1)C(=O)N[C@@H](CC(C)(C)C)C(=O)N1C[C@]2(C[C@H]1C#N)C(=O)Nc1ccccc12] |
| 88 | 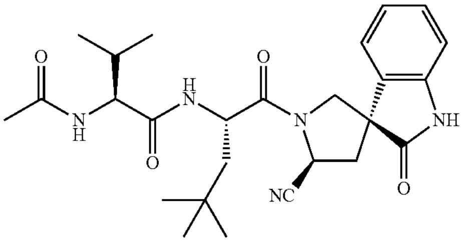 [SMILES: CC(=O)N[C@H](C(=O)N[C@@H](CC(C)(C)C)C(=O)N1C[C@]2(C[C@H]1C#N)C(=O)Nc1ccccc12)C(C)C] |
| 89 | 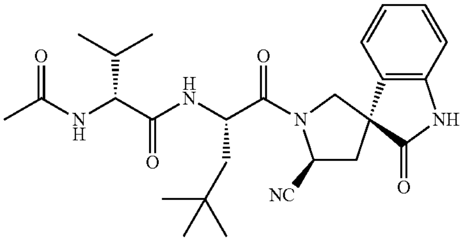 [SMILES: CC(=O)N[C@@H](C(=O)N[C@@H](CC(C)(C)C)C(=O)N1C[C@]2(C[C@H]1C#N)C(=O)Nc1ccccc12)C(C)C] |

-continued
| Compound | Structure |
| --- | --- |
| 90 | 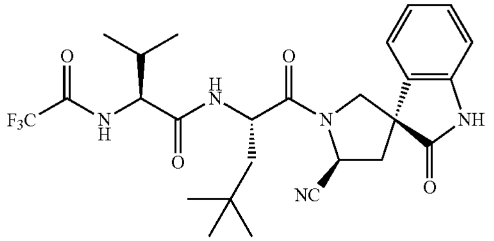 [SMILES: CC(C)[C@H](NC(=O)C(F)(F)F)C(=O)N[C@@H](CC(C)(C)C)C(=O)N1C[C@]2(C[C@H]1C#N)C(=O)Nc1ccccc12] |
| 91 | 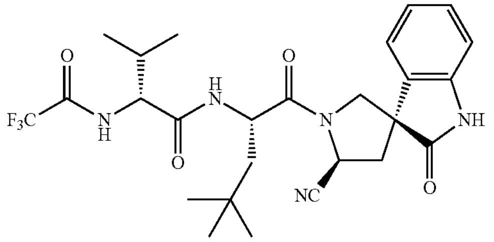 [SMILES: CC(C)[C@@H](NC(=O)C(F)(F)F)C(=O)N[C@@H](CC(C)(C)C)C(=O)N1C[C@]2(C[C@H]1C#N)C(=O)Nc1ccccc12] |
| 92 | 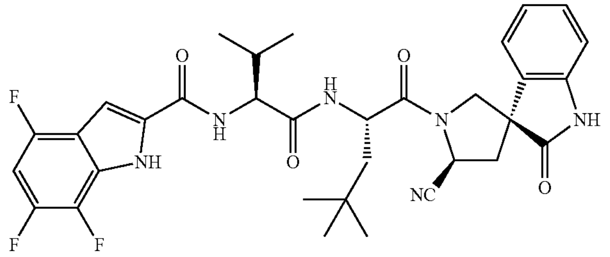 [SMILES: CC(C)[C@H](NC(=O)c1cc2c(F)cc(F)c(F)c2[nH]1)C(=O)N[C@@H](CC(C)(C)C)C(=O)N1C[C@]2(C[C@H]1C#N)C(=O)Nc1ccccc12] |
| 93 | 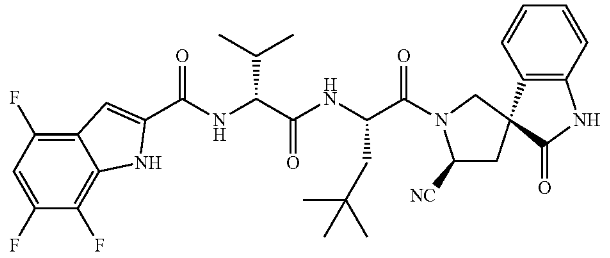 [SMILES: CC(C)[C@@H](NC(=O)c1cc2c(F)cc(F)c(F)c2[nH]1)C(=O)N[C@@H](CC(C)(C)C)C(=O)N1C[C@]2(C[C@H]1C#N)C(=O)Nc1ccccc12] |
| 94 | 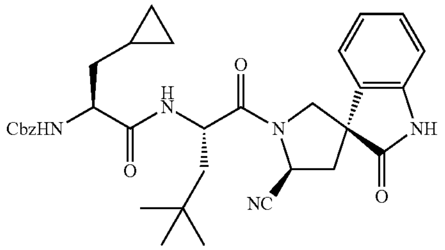 [SMILES: CC(C)(C)C[C@H](NC(=O)[C@H](CC1CC1)NC(=O)OCc1ccccc1)C(=O)N1C[C@]2(C[C@H]1C#N)C(=O)Nc1ccccc12] |
| 95 | 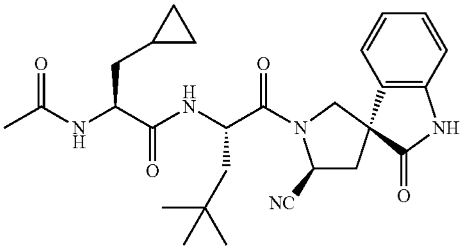 [SMILES: CC(=O)N[C@@H](CC1CC1)C(=O)N[C@@H](CC(C)(C)C)C(=O)N1C[C@]2(C[C@H]1C#N)C(=O)Nc1ccccc12] |

-continued
| Compound | Structure |
|---|---|
| 96 | 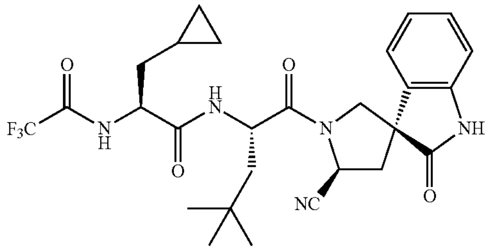 [SMILES: CC(C)(C)C[C@H](NC(=O)[C@H](CC1CC1)NC(=O)C(F)(F)F)C(=O)N1C[C@]2(C[C@H]1C#N)C(=O)Nc1ccccc12] |
| 97 | 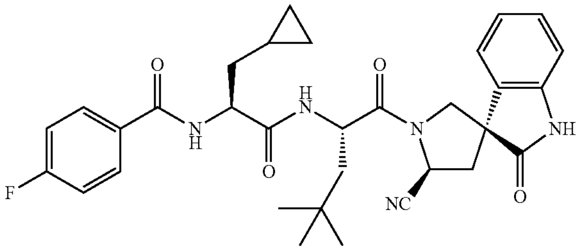 [SMILES: CC(C)(C)C[C@H](NC(=O)[C@H](CC1CC1)NC(=O)c1ccc(F)cc1)C(=O)N1C[C@]2(C[C@H]1C#N)C(=O)Nc1ccccc12] |
| 98 | 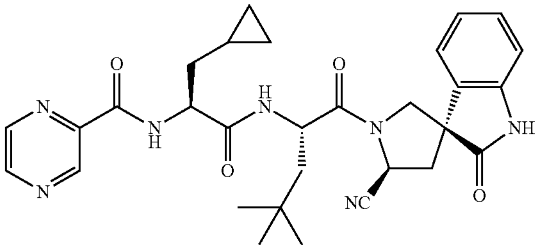 [SMILES: CC(C)(C)C[C@H](NC(=O)[C@H](CC1CC1)NC(=O)c1cnccn1)C(=O)N1C[C@]2(C[C@H]1C#N)C(=O)Nc1ccccc12] |
| 99 | 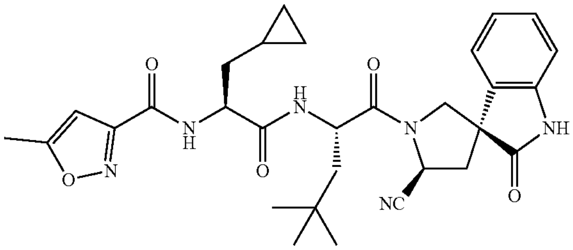 [SMILES: Cc1cc(C(=O)N[C@@H](CC2CC2)C(=O)N[C@@H](CC(C)(C)C)C(=O)N2C[C@]3(C[C@H]2C#N)C(=O)Nc2ccccc23)no1] |
| 100 | 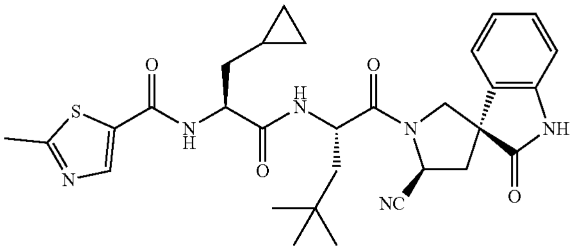 [SMILES: Cc1ncc(C(=O)N[C@@H](CC2CC2)C(=O)N[C@@H](CC(C)(C)C)C(=O)N2C[C@]3(C[C@H]2C#N)C(=O)Nc2ccccc23)s1] |
| 101 | 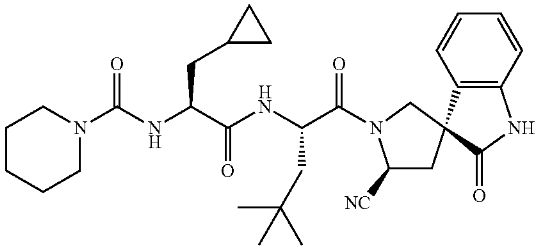 [SMILES: CC(C)(C)C[C@H](NC(=O)[C@H](CC1CC1)NC(=O)N1CCCCC1)C(=O)N1C[C@]2(C[C@H]1C#N)C(=O)Nc1ccccc12] |

-continued
| Compound | Structure |
| --- | --- |
| 102 | 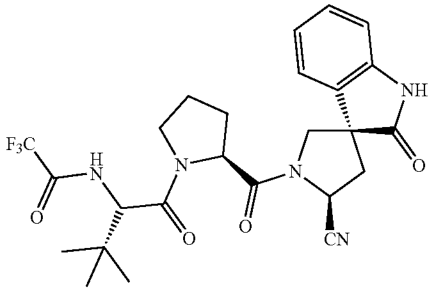 |
| 103 | 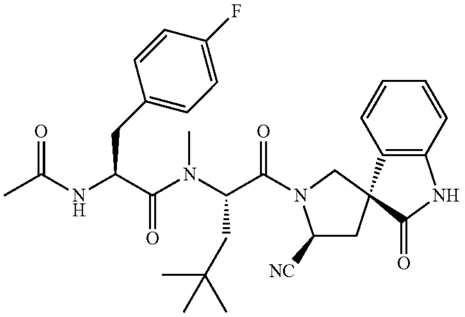 [SMILES: CC(=O)N[C@@H](Cc1ccc(F)cc1)C(=O)N(C)[C@@H](CC(C)(C)C)C(=O)N1C[C@]2(C[C@H]1C#N)C(=O)Nc1ccccc12] |
| 104 | 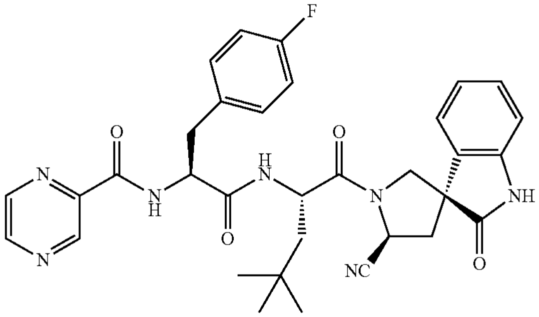 [SMILES: CC(C)(C)C[C@H](NC(=O)[C@H](Cc1ccc(F)cc1)NC(=O)c1cnccn1)C(=O)N1C[C@]2(C[C@H]1C#N)C(=O)Nc1ccccc12] |
| 105 | 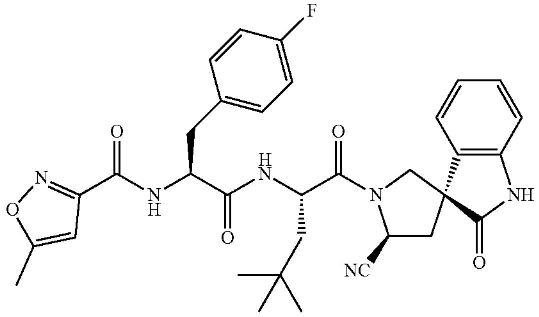 [SMILES: Cc1cc(C(=O)N[C@@H](Cc2ccc(F)cc2)C(=O)N[C@@H](CC(C)(C)C)C(=O)N2C[C@]3(C[C@H]2C#N)C(=O)Nc2ccccc23)no1] |
| 106 | 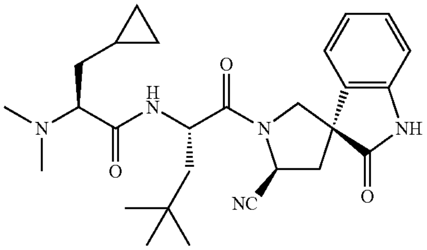 [SMILES: CN(C)[C@@H](CC1CC1)C(=O)N[C@@H](CC(C)(C)C)C(=O)N1C[C@]2(C[C@H]1C#N)C(=O)Nc1ccccc12] |

-continued
| Compound | Structure |
|---|---|
| 107 | 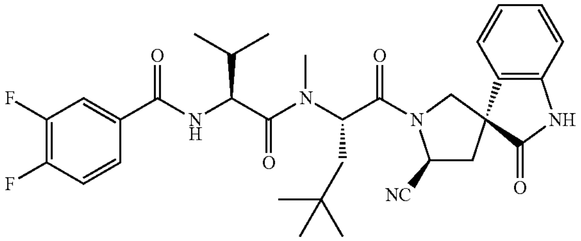 [SMILES: CC(C)[C@H](NC(=O)c1ccc(F)c(F)c1)C(=O)N(C)[C@@H](CC(C)(C)C)C(=O)N1C[C@]2(C[C@H]1C#N)C(=O)Nc1ccccc12] |
| 108 | 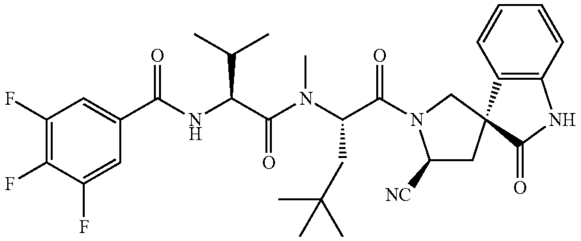 [SMILES: CC(C)[C@H](NC(=O)c1cc(F)c(F)c(F)c1)C(=O)N(C)[C@@H](CC(C)(C)C)C(=O)N1C[C@]2(C[C@H]1C#N)C(=O)Nc1ccccc12] |
| 109 | 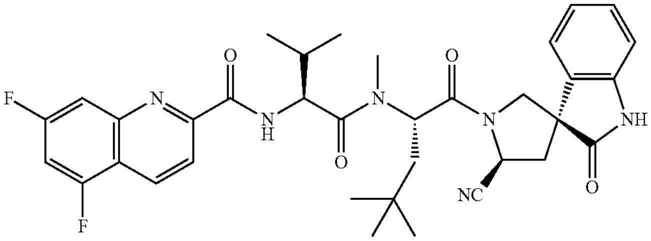 [SMILES: CC(C)[C@H](NC(=O)c1ccc2c(F)cc(F)cc2n1)C(=O)N(C)[C@@H](CC(C)(C)C)C(=O)N1C[C@]2(C[C@H]1C#N)C(=O)Nc1ccccc12] |
| 110 | 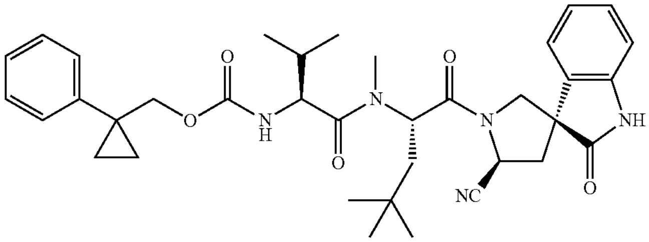 [SMILES: CC(C)[C@H](NC(=O)OCC1(c2ccccc2)CC1)C(=O)N(C)[C@@H](CC(C)(C)C)C(=O)N1C[C@]2(C[C@H]1C#N)C(=O)Nc1ccccc12] |
| 111 | 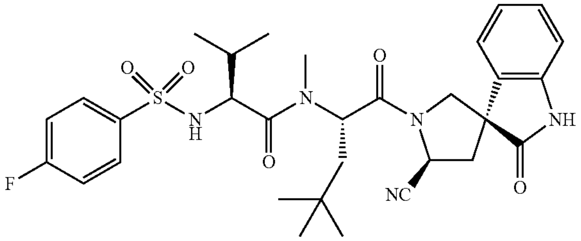 [SMILES: CC(C)[C@H](NS(=O)(=O)c1ccc(F)cc1)C(=O)N(C)[C@@H](CC(C)(C)C)C(=O)N1C[C@]2(C[C@H]1C#N)C(=O)Nc1ccccc12] |
| 112 | 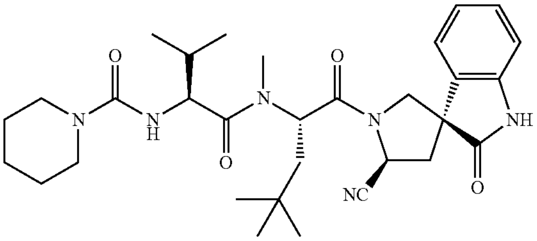 [SMILES: CC(C)[C@H](NC(=O)N1CCCCC1)C(=O)N(C)[C@@H](CC(C)(C)C)C(=O)N1C[C@]2(C[C@H]1C#N)C(=O)Nc1ccccc12] |

-continued
| Compound | Structure |
|---|---|
| 113 | 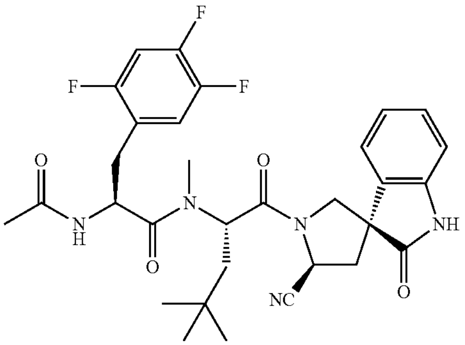 [SMILES: CC(=O)N[C@@H](Cc1cc(F)c(F)cc1F)C(=O)N(C)[C@@H](CC(C)(C)C)C(=O)N1C[C@]2(C[C@H]1C#N)C(=O)Nc1ccccc12] |
| 114 | 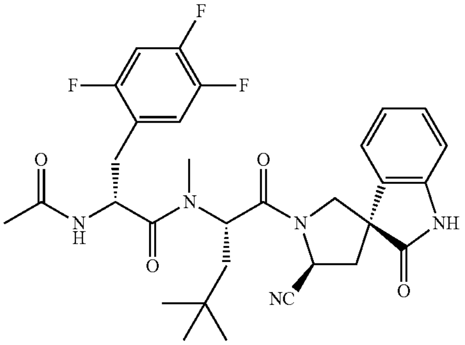 [SMILES: CC(=O)N[C@H](Cc1cc(F)c(F)cc1F)C(=O)N(C)[C@@H](CC(C)(C)C)C(=O)N1C[C@]2(C[C@H]1C#N)C(=O)Nc1ccccc12] |
| 115 | 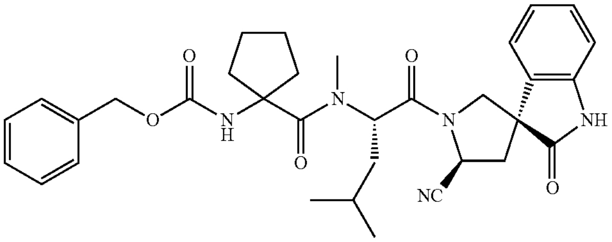 [SMILES: CC(C)C[C@@H](C(=O)N1C[C@]2(C[C@H]1C#N)C(=O)Nc1ccccc12)N(C)C(=O)C1(NC(=O)OCc2ccccc2)CCCC1] |
| 116 | 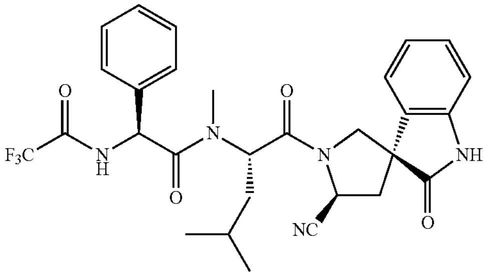 [SMILES: CC(C)C[C@@H](C(=O)N1C[C@]2(C[C@H]1C#N)C(=O)Nc1ccccc12)N(C)C(=O)[C@@H](NC(=O)C(F)(F)F)c1ccccc1] |
| 117 | 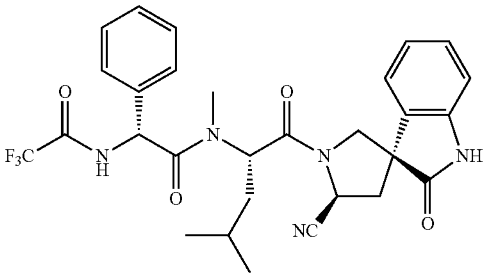 [SMILES: CC(C)C[C@@H](C(=O)N1C[C@]2(C[C@H]1C#N)C(=O)Nc1ccccc12)N(C)C(=O)[C@H](NC(=O)C(F)(F)F)c1ccccc1] |

-continued
| Compound | Structure |
|---|---|
| 118 | 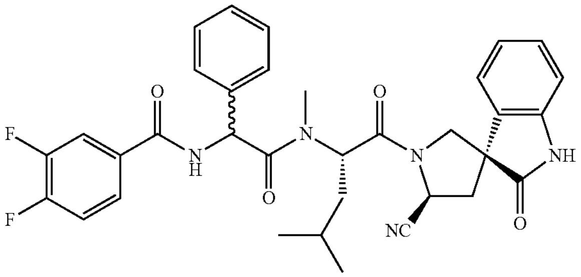 [SMILES: CC(C)C[C@@H](C(=O)N1C[C@]2(C[C@H]1C#N)C(=O)Nc1ccccc12)N(C)C(=O)C(NC(=O)c1ccc(F)c(F)c1)c1ccccc1] |
| 119 | 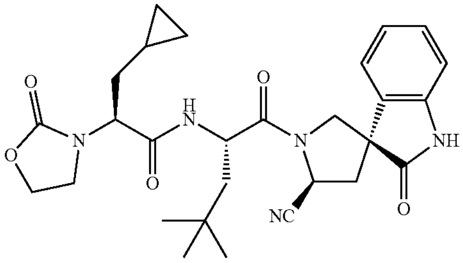 [SMILES: CC(C)(C)C[C@H](NC(=O)[C@H](CC1CC1)N1CCOC1=O)C(=O)N1C[C@]2(C[C@H]1C#N)C(=O)Nc1ccccc12] |
| 120 | 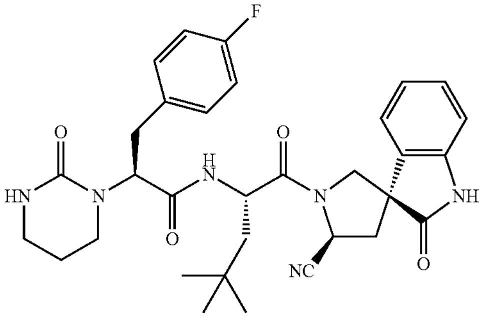 [SMILES: CC(C)(C)C[C@H](NC(=O)[C@H](Cc1ccc(F)cc1)N1CCCNC1=O)C(=O)N1C[C@]2(C[C@H]1C#N)C(=O)Nc1ccccc12] |
| 121 | 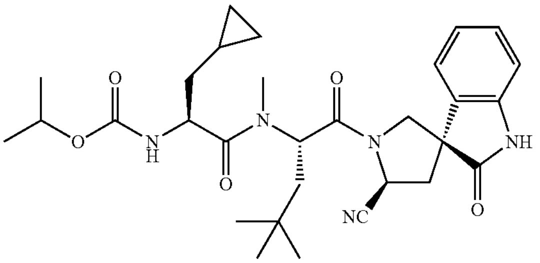 [SMILES: CC(C)OC(=O)N[C@@H](CC1CC1)C(=O)N(C)[C@@H](CC(C)(C)C)C(=O)N1C[C@]2(C[C@H]1C#N)C(=O)Nc1ccccc12] |
| 122 | 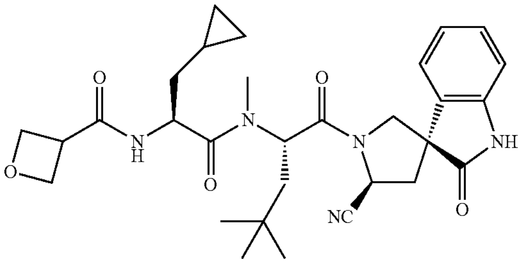 [SMILES: CN(C(=O)[C@H](CC1CC1)NC(=O)C1COC1)[C@@H](CC(C)(C)C)C(=O)N1C[C@]2(C[C@H]1C#N)C(=O)Nc1ccccc12] |

-continued
| Compound | Structure |
| --- | --- |
| 123 | 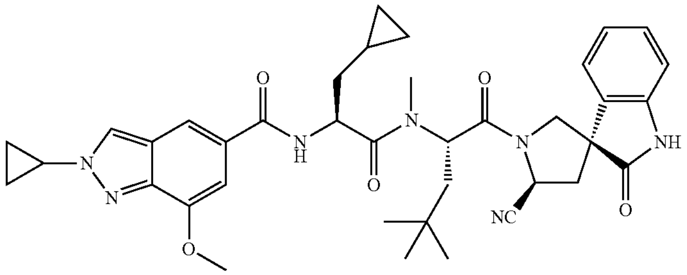 [SMILES: COc1cc(C(=O)N[C@@H](CC2CC2)C(=O)N(C)[C@@H](CC(C)(C)C)C(=O)N2C[C@]3(C[C@H]2C#N)C(=O)Nc2ccccc23)cc2cn(C3CC3)nc12] |
| 124 | 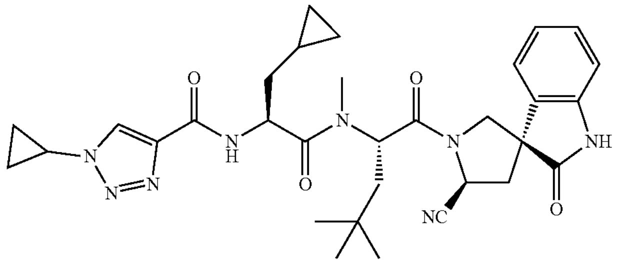 [SMILES: CN(C(=O)[C@H](CC1CC1)NC(=O)c1cn(C2CC2)nn1)[C@@H](CC(C)(C)C)C(=O)N1C[C@]2(C[C@H]1C#N)C(=O)Nc1ccccc12] |
| 125 | 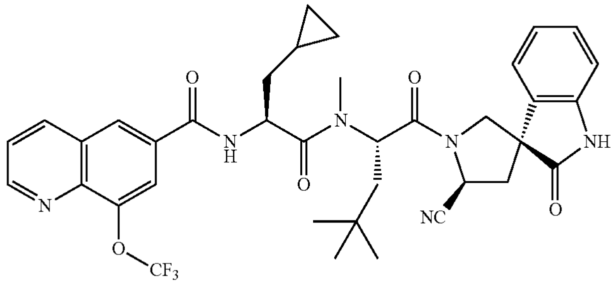 [SMILES: CN(C(=O)[C@H](CC1CC1)NC(=O)c1cc(OC(F)(F)F)c2ncccc2c1)[C@@H](CC(C)(C)C)C(=O)N1C[C@]2(C[C@H]1C#N)C(=O)Nc1ccccc12] |
| 126 | 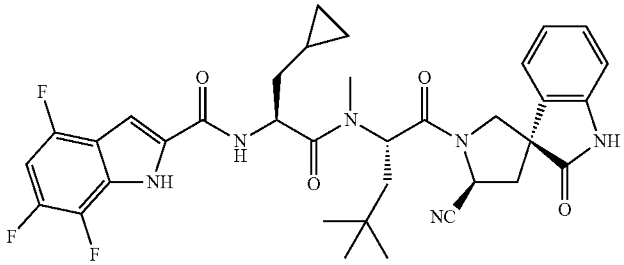 [SMILES: CN(C(=O)[C@H](CC1CC1)NC(=O)c1cc2c(F)cc(F)c(F)c2[nH]1)[C@@H](CC(C)(C)C)C(=O)N1C[C@]2(C[C@H]1C#N)C(=O)Nc1ccccc12] |
| 127 | 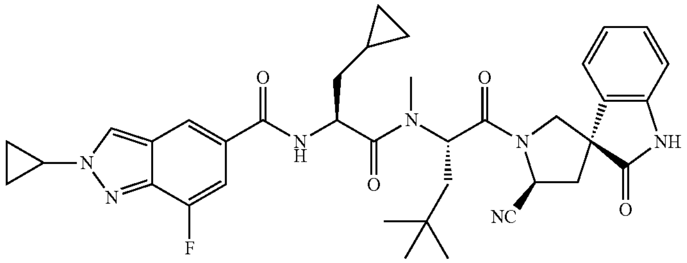 [SMILES: CN(C(=O)[C@H](CC1CC1)NC(=O)c1cc(F)c2nn(C3CC3)cc2c1)[C@@H](CC(C)(C)C)C(=O)N1C[C@]2(C[C@H]1C#N)C(=O)Nc1ccccc12] |

-continued
| Compound | Structure |
|---|---|
| 128 | 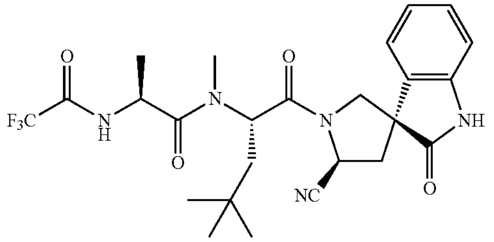 [SMILES: C[C@H](NC(=O)C(F)(F)F)C(=O)N(C)[C@@H](CC(C)(C)C)C(=O)N1C[C@]2(C[C@H]1C#N)C(=O)Nc1ccccc12] |
| 129 | 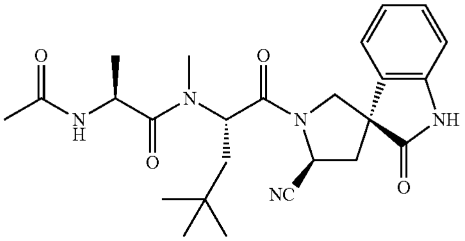 [SMILES: CC(=O)N[C@@H](C)C(=O)N(C)[C@@H](CC(C)(C)C)C(=O)N1C[C@]2(C[C@H]1C#N)C(=O)Nc1ccccc12] |
| 130 | 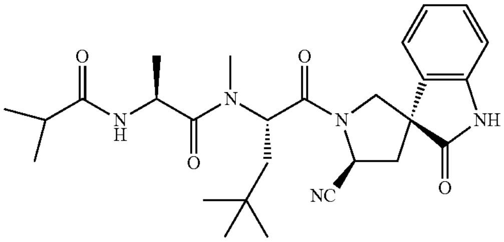 [SMILES: CC(C)C(=O)N[C@@H](C)C(=O)N(C)[C@@H](CC(C)(C)C)C(=O)N1C[C@]2(C[C@H]1C#N)C(=O)Nc1ccccc12] |
| 131 | 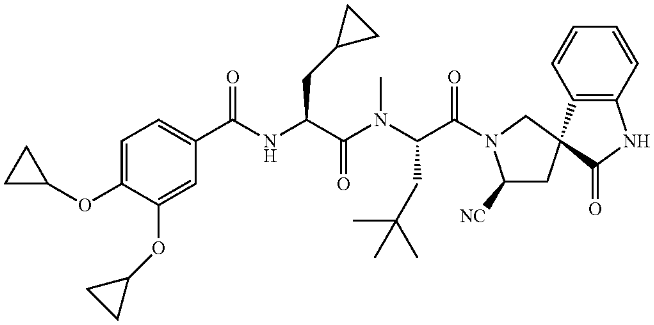 [SMILES: CN(C(=O)[C@H](CC1CC1)NC(=O)c1ccc(OC2CC2)c(OC2CC2)c1)[C@@H](CC(C)(C)C)C(=O)N1C[C@]2(C[C@H]1C#N)C(=O)Nc1ccccc12] |
| 132 | 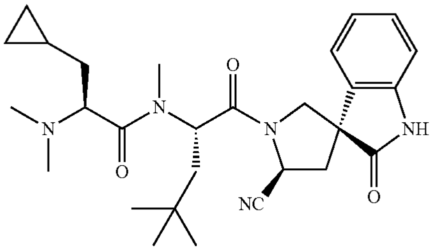 [SMILES: CN(C)[C@@H](CC1CC1)C(=O)N(C)[C@@H](CC(C)(C)C)C(=O)N1C[C@]2(C[C@H]1C#N)C(=O)Nc1ccccc12] |
| 133 | 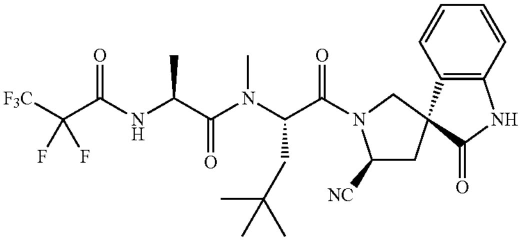 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccccc12] |

-continued
| Compound | Structure |
| --- | --- |
| 134 | 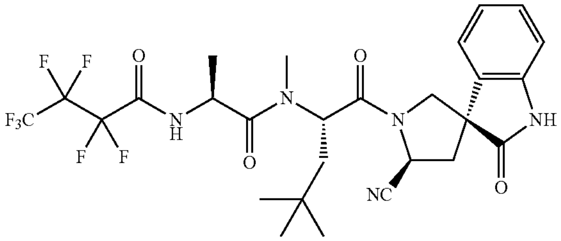 [SMILES: C[C@H](NC(=O)C(F)(F)C(F)(F)C(F)(F)F)C(=O)N(C)[C@@H](CC(C)(C)C)C(=O)N1C[C@]2(C[C@H]1C#N)C(=O)Nc1ccccc12] |
| 135 | 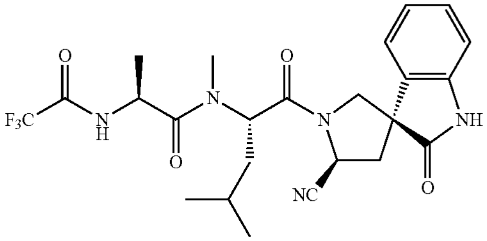 [SMILES: CC(C)C[C@@H](C(=O)N1C[C@]2(C[C@H]1C#N)C(=O)Nc1ccccc12)N(C)C(=O)[C@H](C)NC(=O)C(F)(F)F] |
| 136 | 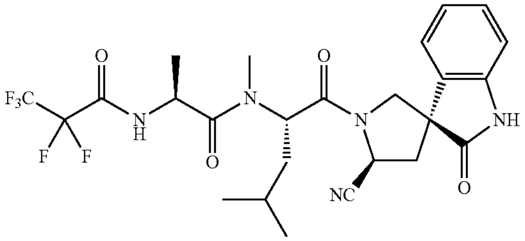 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(F)(F)F] |
| 137 | 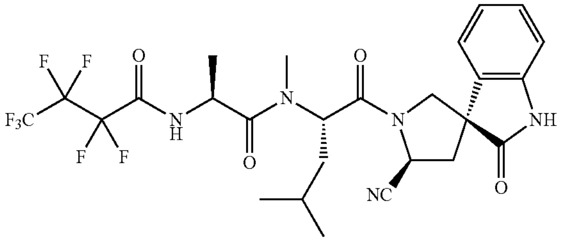 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(F)(F)C(F)(F)F] |
| 138 | 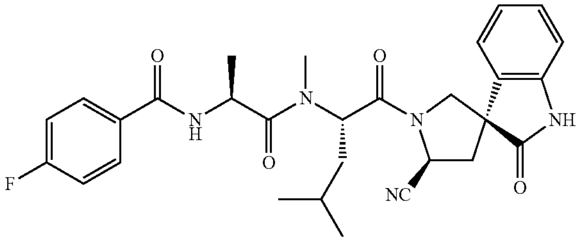 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1] |
| 139 | 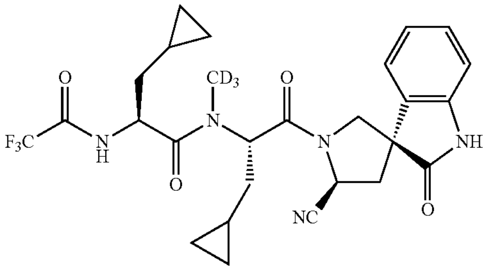 [SMILES: [2H]C([2H])([2H])N(C(=O)[C@H](CC1CC1)NC(=O)C(F)(F)F)[C@@H](CC1CC1)C(=O)N1C[C@]2(C[C@H]1C#N)C(=O)Nc1ccccc12] |

-continued
| Compound | Structure |
|---|---|
| 140 | 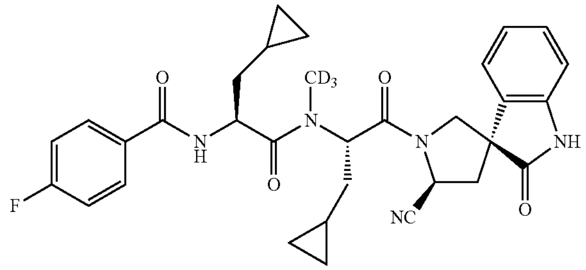 [SMILES: [2H]C([2H])([2H])N(C(=O)[C@H](CC1CC1)NC(=O)c1ccc(F)cc1)[C@@H](CC1CC1)C(=O)N1C[C@]2(C[C@H]1C#N)C(=O)Nc1ccccc12] |
| 141 | 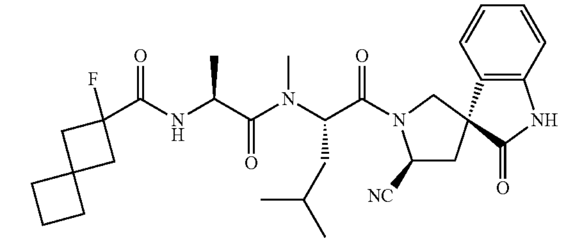 [SMILES: CC(C)C[C@@H](C(=O)N1C[C@]2(C[C@H]1C#N)C(=O)Nc1ccccc12)N(C)C(=O)[C@H](C)NC(=O)C1(F)CC2(CCC2)C1] |
| 142 | 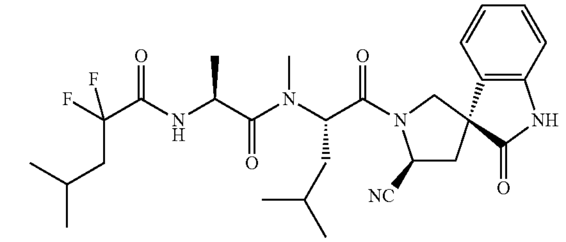 [SMILES: CC(C)C[C@@H](C(=O)N1C[C@]2(C[C@H]1C#N)C(=O)Nc1ccccc12)N(C)C(=O)[C@H](C)NC(=O)C(F)(F)CC(C)C] |
| 143 | 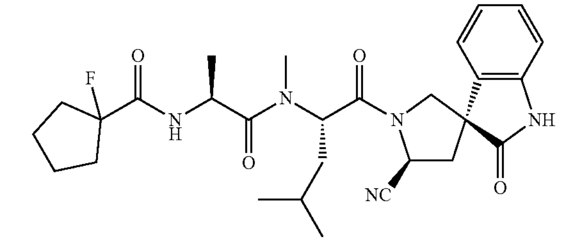 [SMILES: CC(C)C[C@@H](C(=O)N1C[C@]2(C[C@H]1C#N)C(=O)Nc1ccccc12)N(C)C(=O)[C@H](C)NC(=O)C1(F)CCCC1] |
| 144 | 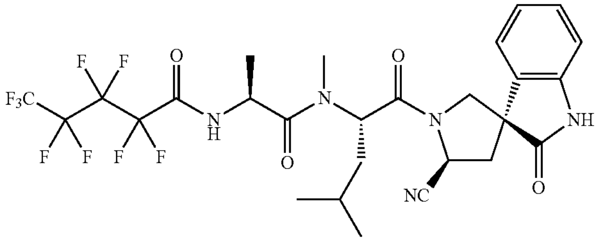 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(F)(F)C(F)(F)C(F)(F)F] |
| 145 | 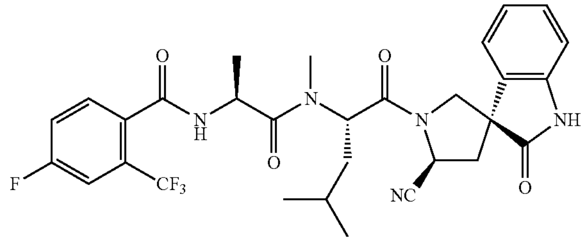 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1C(F)(F)F] |

-continued
| Compound | Structure |
| --- | --- |
| 146 | 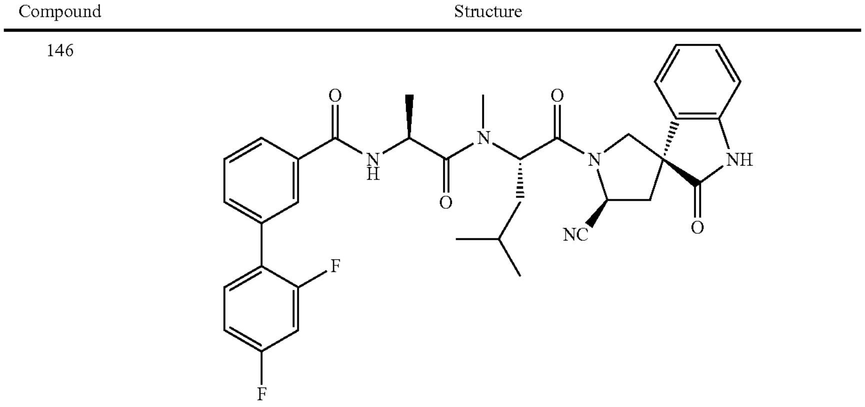 |
| 147 | 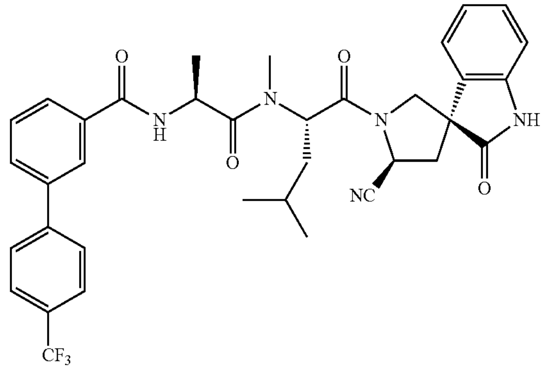 [SMILES: CC(C)C[C@@H](C(=O)N1C[C@]2(C[C@H]1C#N)C(=O)Nc1ccccc12)N(C)C(=O)[C@H](C)NC(=O)c1cccc(-c2ccc(C(F)(F)F)cc2)c1] |
| 148 | 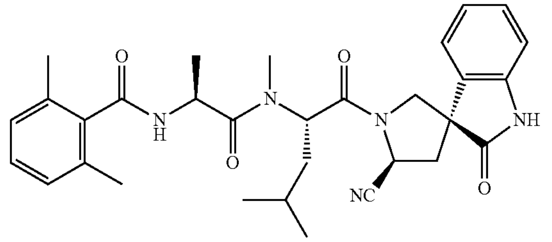 [SMILES: Cc1cccc(C)c1C(=O)N[C@@H](C)C(=O)N(C)[C@@H](CC(C)C)C(=O)N1C[C@]2(C[C@H]1C#N)C(=O)Nc1ccccc12] |
| 149 | 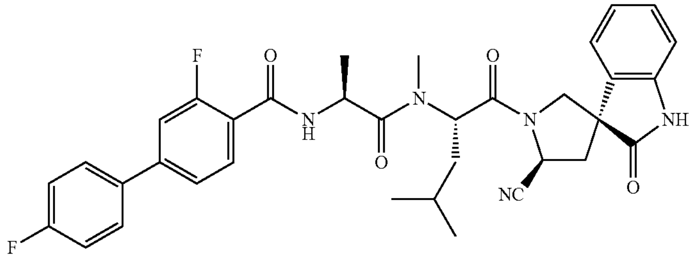 [SMILES: CC(C)C[C@@H](C(=O)N1C[C@]2(C[C@H]1C#N)C(=O)Nc1ccccc12)N(C)C(=O)[C@H](C)NC(=O)c1ccc(-c2ccc(F)cc2)cc1F] |
| 150 | 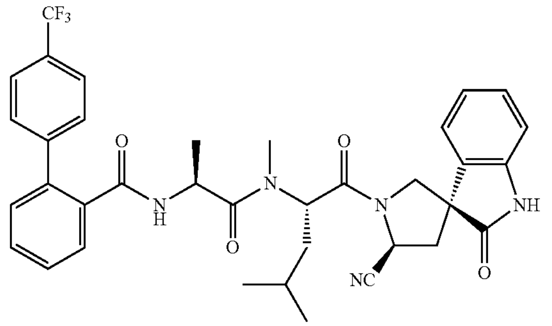 [SMILES: CC(C)C[C@@H](C(=O)N1C[C@]2(C[C@H]1C#N)C(=O)Nc1ccccc12)N(C)C(=O)[C@H](C)NC(=O)c1ccccc1-c1ccc(C(F)(F)F)cc1] |

-continued
| Compound | Structure |
| --- | --- |
| 151 | 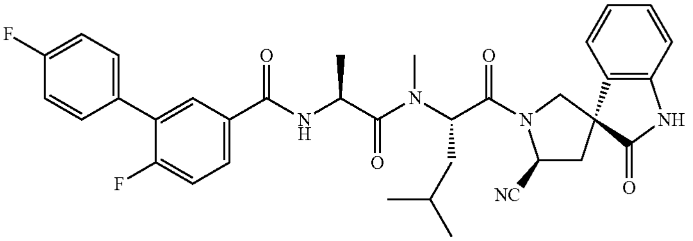 [SMILES: CC(C)C[C@@H](C(=O)N1C[C@]2(C[C@H]1C#N)C(=O)Nc1ccccc12)N(C)C(=O)[C@H](C)NC(=O)c1ccc(F)c(-c2ccc(F)cc2)c1] |
| 152 | 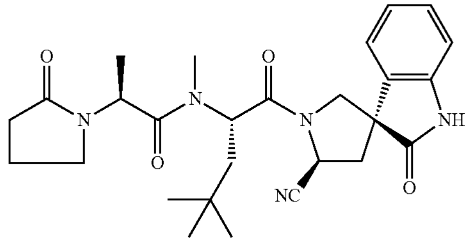 [SMILES: C[C@@H](C(=O)N(C)[C@@H](CC(C)(C)C)C(=O)N1C[C@]2(C[C@H]1C#N)C(=O)Nc1ccccc12)N1CCCC1=O] |
| 153 | 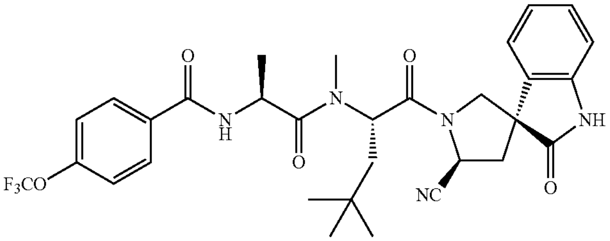 [SMILES: C[C@H](NC(=O)c1ccc(OC(F)(F)F)cc1)C(=O)N(C)[C@@H](CC(C)(C)C)C(=O)N1C[C@]2(C[C@H]1C#N)C(=O)Nc1ccccc12] |
| 154 | 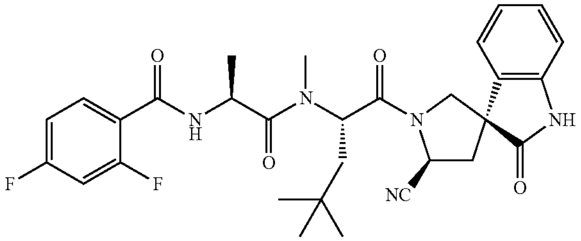 [SMILES: C[C@H](NC(=O)c1ccc(F)cc1F)C(=O)N(C)[C@@H](CC(C)(C)C)C(=O)N1C[C@]2(C[C@H]1C#N)C(=O)Nc1ccccc12] |
| 155 | 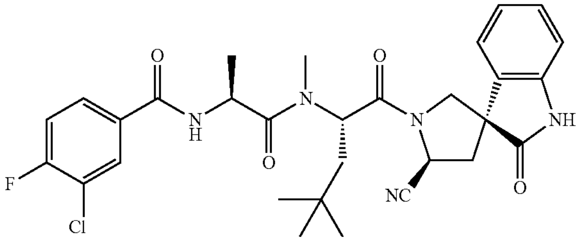 [SMILES: C[C@H](NC(=O)c1ccc(F)c(Cl)c1)C(=O)N(C)[C@@H](CC(C)(C)C)C(=O)N1C[C@]2(C[C@H]1C#N)C(=O)Nc1ccccc12] |
| 156 | 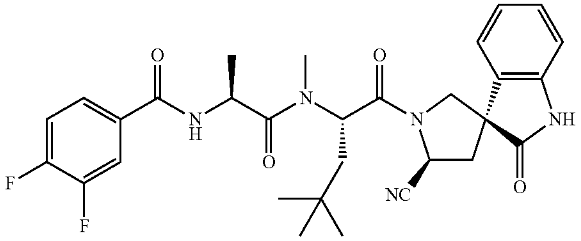 [SMILES: C[C@H](NC(=O)c1ccc(F)c(F)c1)C(=O)N(C)[C@@H](CC(C)(C)C)C(=O)N1C[C@]2(C[C@H]1C#N)C(=O)Nc1ccccc12] |

-continued
| Compound | Structure |
| --- | --- |
| 157 | 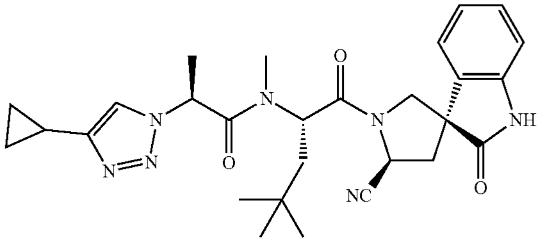 [SMILES: C[C@@H](C(=O)N(C)[C@@H](CC(C)(C)C)C(=O)N1C[C@]2(C[C@H]1C#N)C(=O)Nc1ccccc12)n1cc(C2CC2)nn1] |
| 158 | 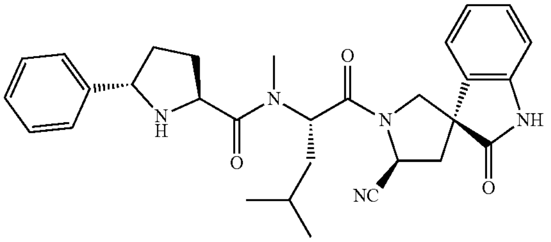 [SMILES: CC(C)C[C@@H](C(=O)N1C[C@]2(C[C@H]1C#N)C(=O)Nc1ccccc12)N(C)C(=O)[C@@H]1CC[C@@H](c2ccccc2)N1] |
| 159 | 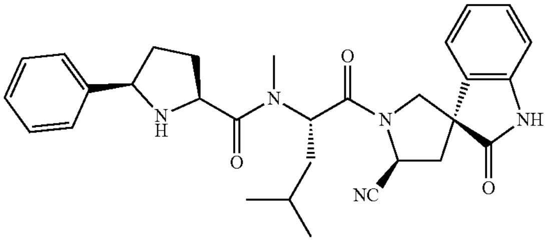 [SMILES: CC(C)C[C@@H](C(=O)N1C[C@]2(C[C@H]1C#N)C(=O)Nc1ccccc12)N(C)C(=O)[C@@H]1CC[C@H](c2ccccc2)N1] |
| 160 | 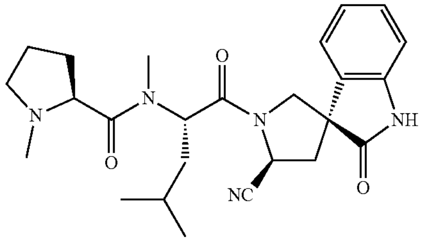 [SMILES: CC(C)C[C@@H](C(=O)N1C[C@]2(C[C@H]1C#N)C(=O)Nc1ccccc12)N(C)C(=O)[C@@H]1CCCN1C] |
| 161 | 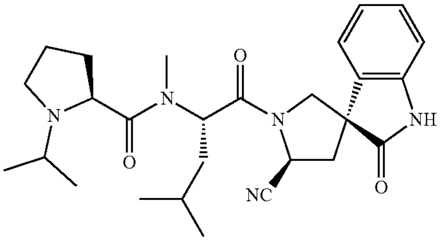 [SMILES: CC(C)C[C@@H](C(=O)N1C[C@]2(C[C@H]1C#N)C(=O)Nc1ccccc12)N(C)C(=O)[C@@H]1CCCN1C(C)C] |
| 162 | 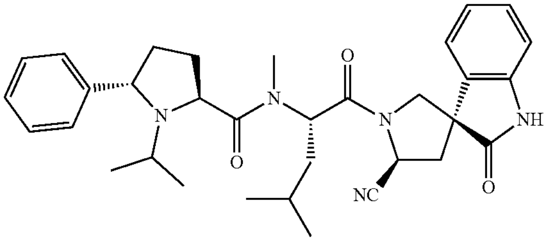 [SMILES: CC(C)C[C@@H](C(=O)N1C[C@]2(C[C@H]1C#N)C(=O)Nc1ccccc12)N(C)C(=O)[C@@H]1CC[C@@H](c2ccccc2)N1C(C)C] |

-continued
| Compound | Structure |
|---|---|
| 163 | 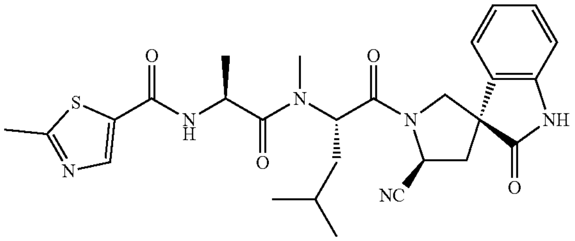 [SMILES: Cc1ncc(C(=O)N[C@@H](C)C(=O)N(C)[C@@H](CC(C)C)C(=O)N2C[C@]3(C[C@H]2C#N)C(=O)Nc2ccccc23)s1] |
| 164 | 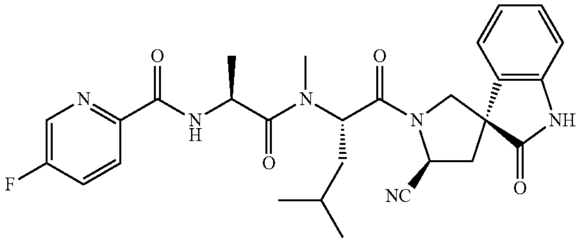 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cn1] |
| 165 | 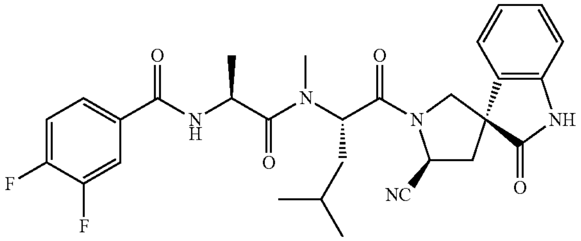 [SMILES: CC(C)C[C@@H](C(=O)N1C[C@]2(C[C@H]1C#N)C(=O)Nc1ccccc12)N(C)C(=O)[C@H](C)NC(=O)c1ccc(F)c(F)c1] |
| 166 | 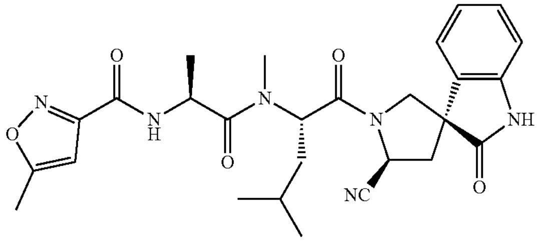 [SMILES: Cc1cc(C(=O)N[C@@H](C)C(=O)N(C)[C@@H](CC(C)C)C(=O)N2C[C@]3(C[C@H]2C#N)C(=O)Nc2ccccc23)no1] |
| 167 | 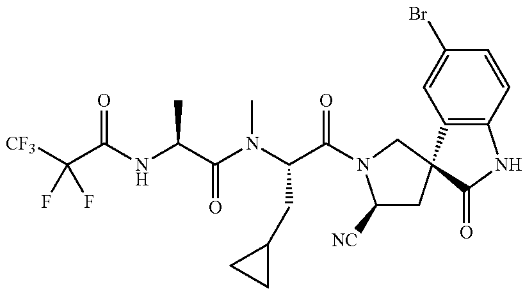 |
| 168 | 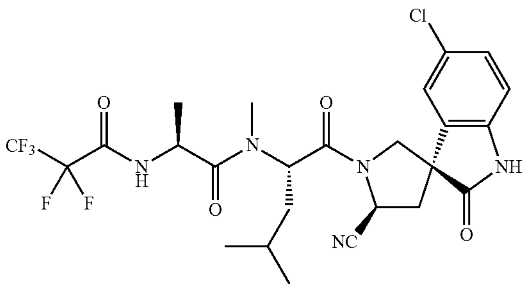 [SMILES: CC(C)C[C@@H](C(=O)N1C[C@]2(C[C@H]1C#N)C(=O)Nc1ccc(Cl)cc12)N(C)C(=O)[C@H](C)NC(=O)C(F)(F)C(F)(F)F] |

-continued
| Compound | Structure |
|---|---|
| 169 | 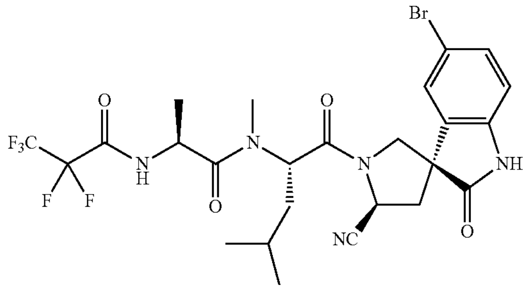 [SMILES: CC(C)C[C@@H](C(=O)N1C[C@]2(C[C@H]1C#N)C(=O)Nc1ccc(Br)cc12)N(C)C(=O)[C@H](C)NC(=O)C(F)(F)C(F)(F)F] |
| 170 | 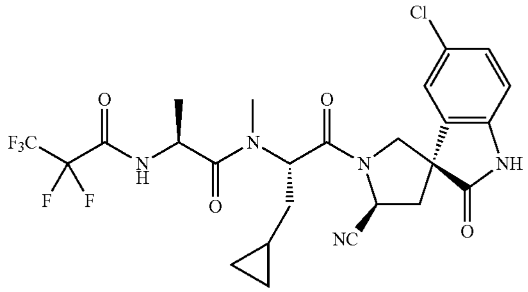 [SMILES: C[C@H](NC(=O)C(F)(F)C(F)(F)F)C(=O)N(C)[C@@H](CC1CC1)C(=O)N1C[C@]2(C[C@H]1C#N)C(=O)Nc1ccc(Cl)cc12] |
| 171 | 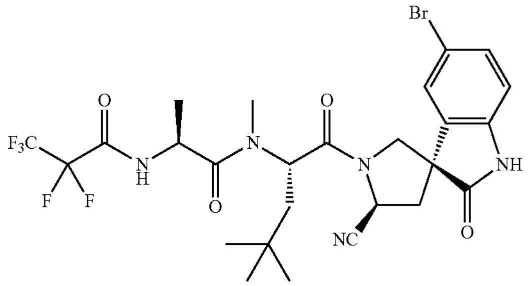 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccc(Br)cc12] |
| 172 | 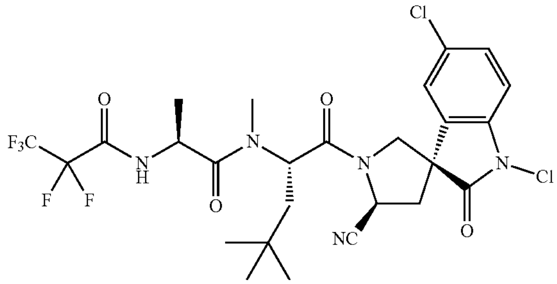 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)N(Cl)c1ccc(Cl)cc12] |
| 173 | 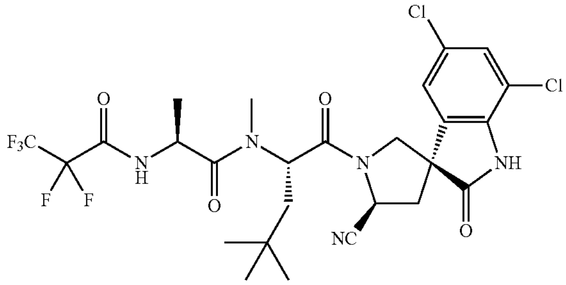 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1c(Cl)cc(Cl)cc12] |

-continued
| Compound | Structure |
| --- | --- |
| 174 | 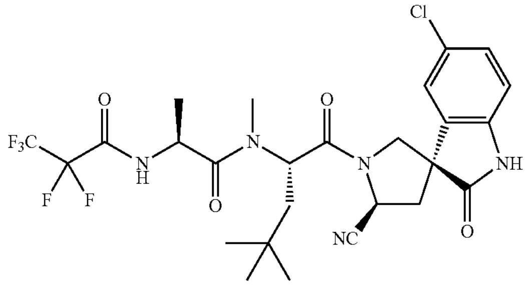 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccc(Cl)cc12] |
| 175 | 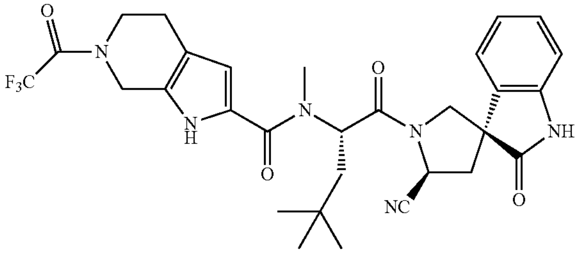 [SMILES: CN(C(=O)c1cc2c([nH]1)CN(C(=O)C(F)(F)F)CC2)[C@@H](CC(C)(C)C)C(=O)N1C[C@]2(C[C@H]1C#N)C(=O)Nc1ccccc12] |
| 176 | 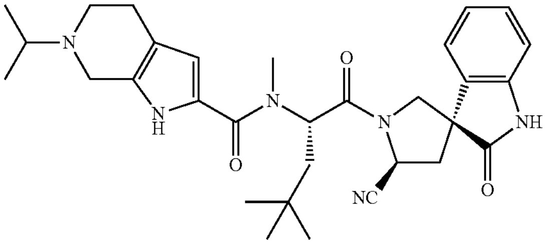 [SMILES: CC(C)N1CCc2cc(C(=O)N(C)[C@@H](CC(C)(C)C)C(=O)N3C[C@]4(C[C@H]3C#N)C(=O)Nc3ccccc34)[nH]c2C1] |
| 177 | 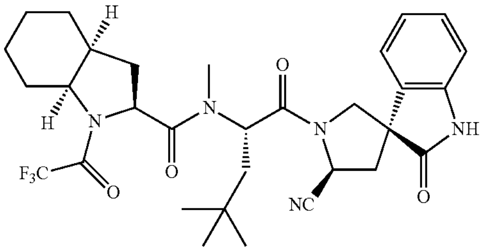 [SMILES: CN(C(=O)[C@@H]1C[C@@H]2CCCC[C@@H]2N1C(=O)C(F)(F)F)[C@@H](CC(C)(C)C)C(=O)N1C[C@]2(C[C@H]1C#N)C(=O)Nc1ccccc12] |
| 178 | 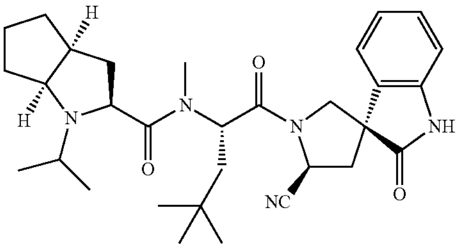 [SMILES: CC(C)N1[C@H](C(=O)N(C)[C@@H](CC(C)(C)C)C(=O)N2C[C@]3(C[C@H]2C#N)C(=O)Nc2ccccc23)C[C@@H]2CCC[C@@H]21] |
| 179 | 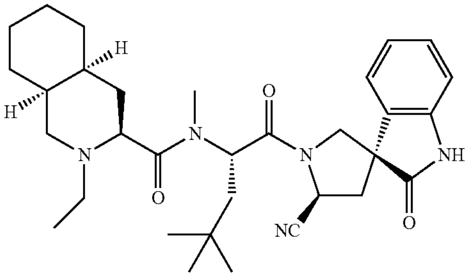 [SMILES: CCN1C[C@H]2CCCC[C@H]2C[C@H]1C(=O)N(C)[C@@H](CC(C)(C)C)C(=O)N1C[C@]2(C[C@H]1C#N)C(=O)Nc1ccccc12] |

-continued
| Compound | Structure |
|---|---|
| 180 | 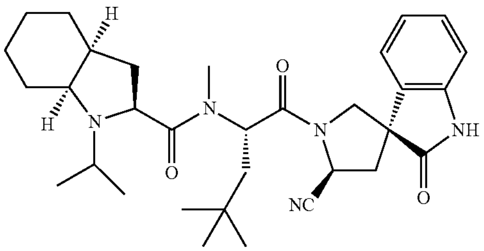 [SMILES: CC(C)N1[C@H](C(=O)N(C)[C@@H](CC(C)(C)C)C(=O)N2C[C@]3(C[C@H]2C#N)C(=O)Nc2ccccc23)C[C@@H]2CCCC[C@@H]21] |
| 181 | 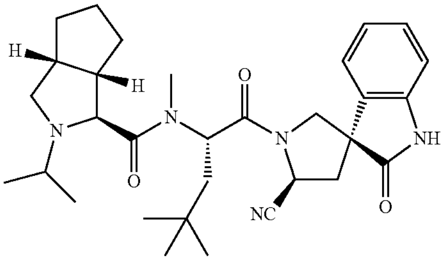 [SMILES: CC(C)N1C[C@@H]2CCC[C@@H]2[C@H]1C(=O)N(C)[C@@H](CC(C)(C)C)C(=O)N1C[C@]2(C[C@H]1C#N)C(=O)Nc1ccccc12] |
| 182 | 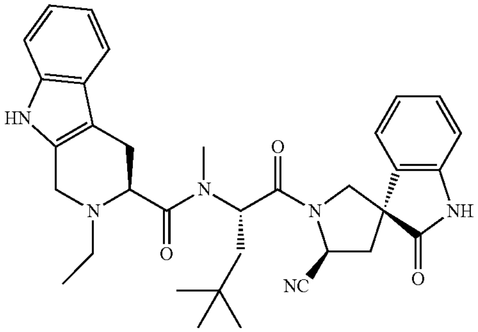 [SMILES: CCN1Cc2[nH]c3ccccc3c2C[C@H]1C(=O)N(C)[C@@H](CC(C)(C)C)C(=O)N1C[C@]2(C[C@H]1C#N)C(=O)Nc1ccccc12] |
| 183 | 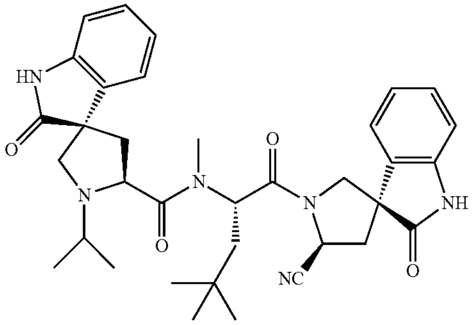 [SMILES: CC(C)N1C[C@]2(C[C@H]1C(=O)N(C)[C@@H](CC(C)(C)C)C(=O)N1C[C@]3(C[C@H]1C#N)C(=O)Nc1ccccc13)C(=O)Nc1ccccc12] |
| 184 | 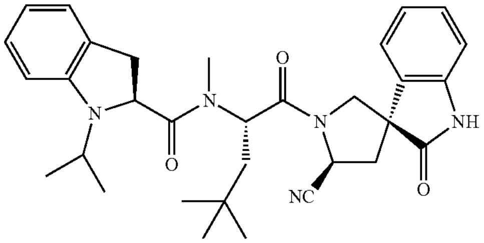 [SMILES: CC(C)N1c2ccccc2C[C@H]1C(=O)N(C)[C@@H](CC(C)(C)C)C(=O)N1C[C@]2(C[C@H]1C#N)C(=O)Nc1ccccc12] |

-continued
| Compound | Structure |
|---|---|
| 185 | 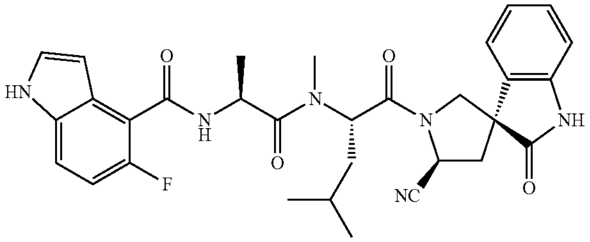 [SMILES: CC(C)C[C@@H](C(=O)N1C[C@]2(C[C@H]1C#N)C(=O)Nc1ccccc12)N(C)C(=O)[C@H](C)NC(=O)c1c(F)ccc2[nH]ccc12] |
| 186 | 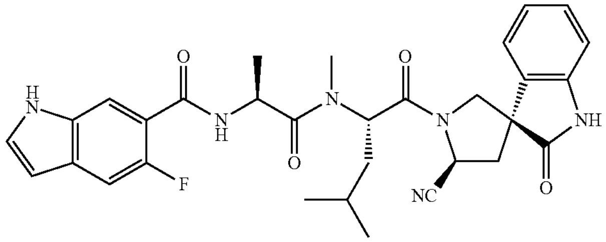 [SMILES: CC(C)C[C@@H](C(=O)N1C[C@]2(C[C@H]1C#N)C(=O)Nc1ccccc12)N(C)C(=O)[C@H](C)NC(=O)c1cc2[nH]ccc2cc1F] |
| 187 | 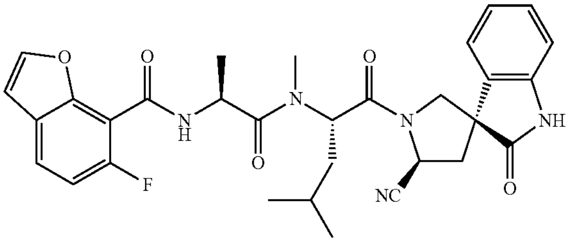 [SMILES: CC(C)C[C@@H](C(=O)N1C[C@]2(C[C@H]1C#N)C(=O)Nc1ccccc12)N(C)C(=O)[C@H](C)NC(=O)c1c(F)ccc2ccoc12] |
| 188 | 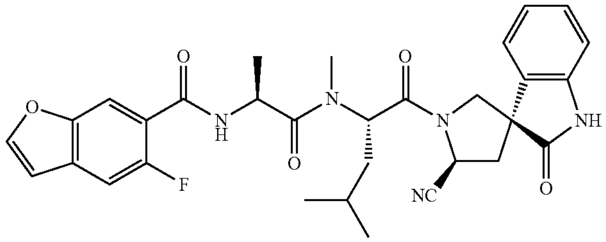 [SMILES: CC(C)C[C@@H](C(=O)N1C[C@]2(C[C@H]1C#N)C(=O)Nc1ccccc12)N(C)C(=O)[C@H](C)NC(=O)c1cc2occc2cc1F] |
| 189 | 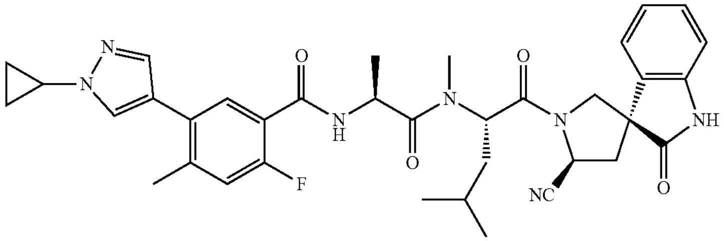 [SMILES: Cc1cc(F)c(C(=O)N[C@@H](C)C(=O)N(C)[C@@H](CC(C)C)C(=O)N2C[C@]3(C[C@H]2C#N)C(=O)Nc2ccccc23)cc1-c1cnn(C2CC2)c1] |
| 190 | 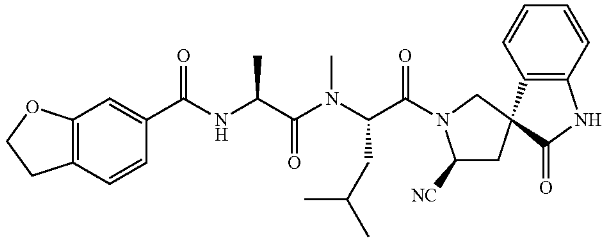 [SMILES: CC(C)C[C@@H](C(=O)N1C[C@]2(C[C@H]1C#N)C(=O)Nc1ccccc12)N(C)C(=O)[C@H](C)NC(=O)c1ccc2c(c1)OCC2] |

-continued
| Compound | Structure |
| --- | --- |
| 191 | 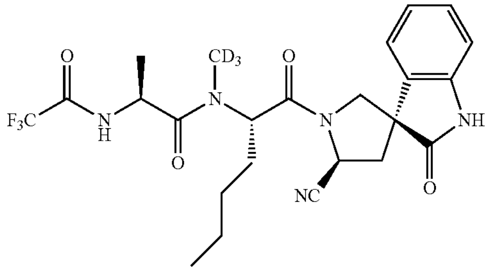 [SMILES: [2H]C([2H])([2H])N(C(=O)[C@H](C)NC(=O)C(F)(F)F)[C@@H](CCCC)C(=O)N1C[C@]2(C[C@H]1C#N)C(=O)Nc1ccccc12] |
| 192 | 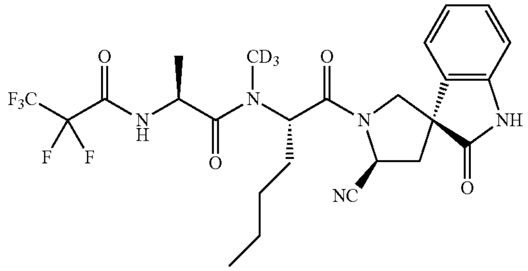 [SMILES: [2H]C([2H])([2H])N(C(=O)[C@H](C)NC(=O)C(F)(F)C(F)(F)F)[C@@H](CCCC)C(=O)N1C[C@]2(C[C@H]1C#N)C(=O)Nc1ccccc12] |
| 193 | 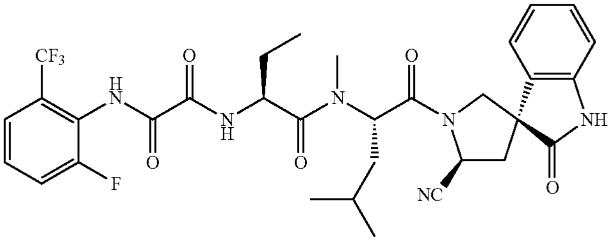 [SMILES: CC[C@H](NC(=O)C(=O)Nc1c(F)cccc1C(F)(F)F)C(=O)N(C)[C@@H](CC(C)C)C(=O)N1C[C@]2(C[C@H]1C#N)C(=O)Nc1ccccc12] |
| 194 | 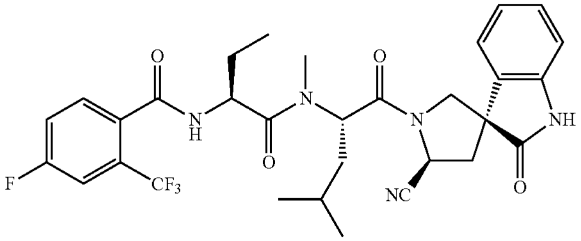 [SMILES: CC[C@H](NC(=O)c1ccc(F)cc1C(F)(F)F)C(=O)N(C)[C@@H](CC(C)C)C(=O)N1C[C@]2(C[C@H]1C#N)C(=O)Nc1ccccc12] |
| 195 | 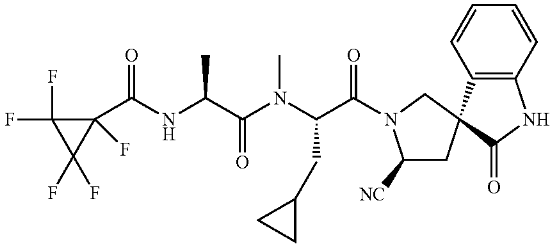 [SMILES: C[C@H](NC(=O)C1(F)C(F)(F)C1(F)F)C(=O)N(C)[C@@H](CC1CC1)C(=O)N1C[C@]2(C[C@H]1C#N)C(=O)Nc1ccccc12] |
| 196 | 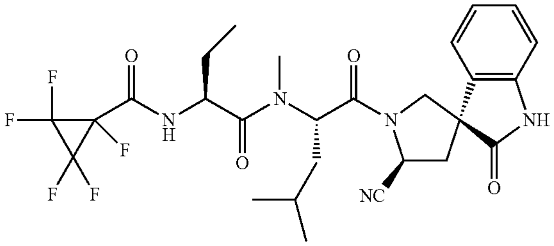 [SMILES: CC[C@H](NC(=O)C1(F)C(F)(F)C1(F)F)C(=O)N(C)[C@@H](CC(C)C)C(=O)N1C[C@]2(C[C@H]1C#N)C(=O)Nc1ccccc12] |

-continued
| Compound | Structure |
| --- | --- |
| 197 | 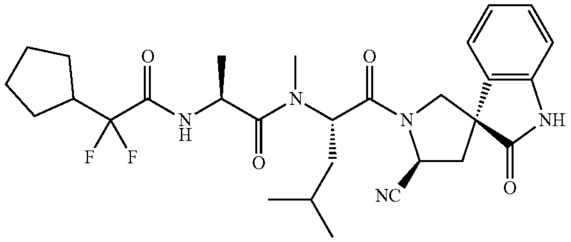 [SMILES: CC(C)C[C@@H](C(=O)N1C[C@]2(C[C@H]1C#N)C(=O)Nc1ccccc12)N(C)C(=O)[C@H](C)NC(=O)C(F)(F)C1CCCC1] |
| 198 | 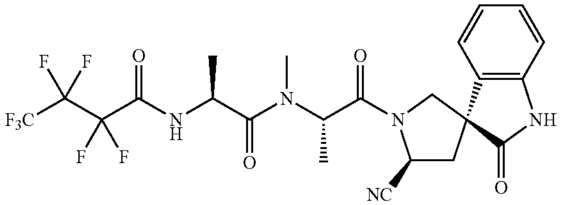 [SMILES: C[C@H](NC(=O)C(F)(F)C(F)(F)C(F)(F)F)C(=O)N(C)[C@@H](C)C(=O)N1C[C@]2(C[C@H]1C#N)C(=O)Nc1ccccc12] |
| 199 | 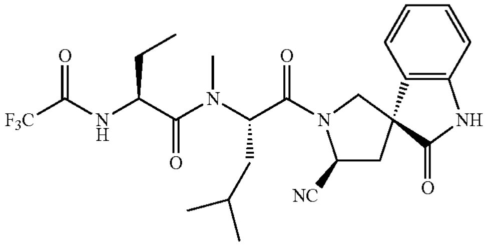 [SMILES: CC[C@H](NC(=O)C(F)(F)F)C(=O)N(C)[C@@H](CC(C)C)C(=O)N1C[C@]2(C[C@H]1C#N)C(=O)Nc1ccccc12] |
| 200 | 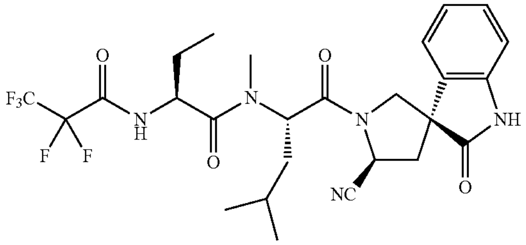 [SMILES: CC[C@H](NC(=O)C(F)(F)C(F)(F)F)C(=O)N(C)[C@@H](CC(C)C)C(=O)N1C[C@]2(C[C@H]1C#N)C(=O)Nc1ccccc12] |
| 201 | 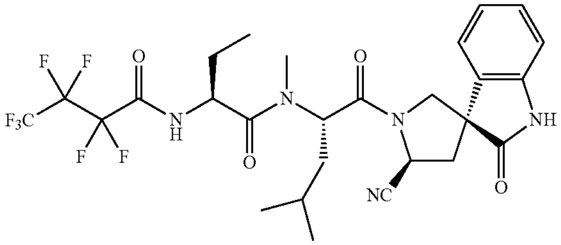 [SMILES: CC[C@H](NC(=O)C(F)(F)C(F)(F)C(F)(F)F)C(=O)N(C)[C@@H](CC(C)C)C(=O)N1C[C@]2(C[C@H]1C#N)C(=O)Nc1ccccc12] |
| 202 | 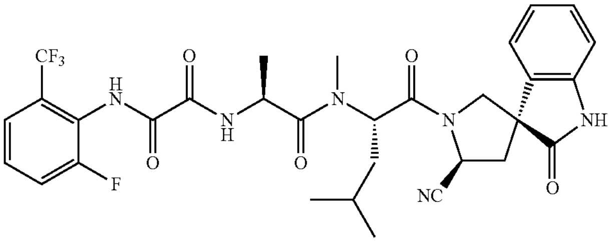 [SMILES: CC(C)C[C@@H](C(=O)N1C[C@]2(C[C@H]1C#N)C(=O)Nc1ccccc12)N(C)C(=O)[C@H](C)NC(=O)C(=O)Nc1c(F)cccc1C(F)(F)F] |

-continued
| Compound | Structure |
|---|---|
| 203 | 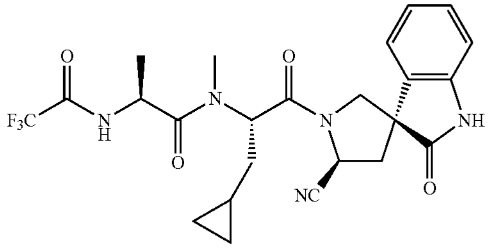 [SMILES: C[C@H](NC(=O)C(F)(F)F)C(=O)N(C)[C@@H](CC1CC1)C(=O)N1C[C@]2(C[C@H]1C#N)C(=O)Nc1ccccc12] |
| 204 | 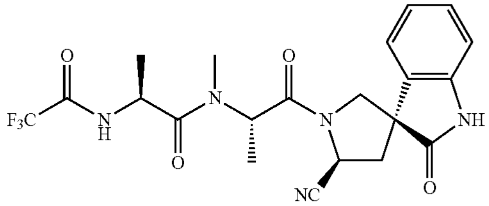 [SMILES: C[C@H](NC(=O)C(F)(F)F)C(=O)N(C)[C@@H](C)C(=O)N1C[C@]2(C[C@H]1C#N)C(=O)Nc1ccccc12] |
| 205 | 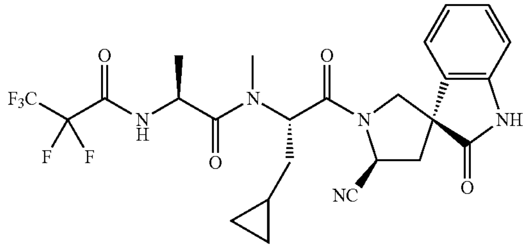 [SMILES: C[C@H](NC(=O)C(F)(F)C(F)(F)F)C(=O)N(C)[C@@H](CC1CC1)C(=O)N1C[C@]2(C[C@H]1C#N)C(=O)Nc1ccccc12] |
| 206 | 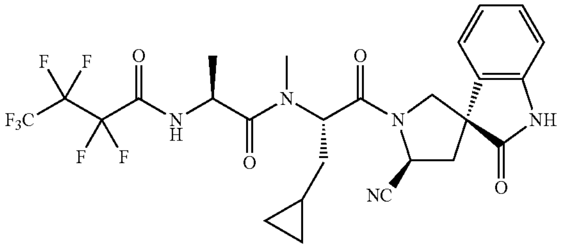 [SMILES: C[C@H](NC(=O)C(F)(F)C(F)(F)C(F)(F)F)C(=O)N(C)[C@@H](CC1CC1)C(=O)N1C[C@]2(C[C@H]1C#N)C(=O)Nc1ccccc12] |
| 207 | 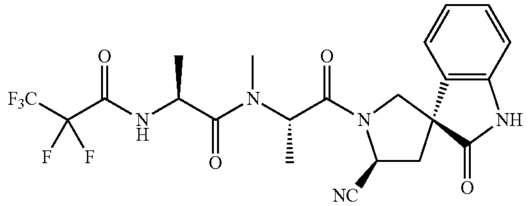 [SMILES: C[C@H](NC(=O)C(F)(F)C(F)(F)F)C(=O)N(C)[C@@H](C)C(=O)N1C[C@]2(C[C@H]1C#N)C(=O)Nc1ccccc12] |
| 208 | 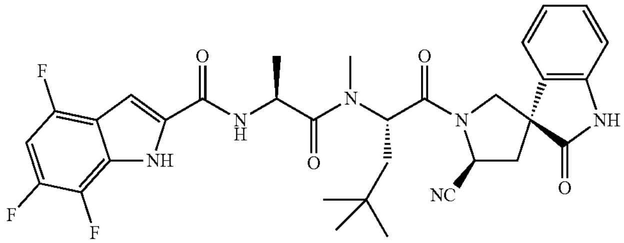 [SMILES: C[C@H](NC(=O)c1cc2c(F)cc(F)c(F)c2[nH]1)C(=O)N(C)[C@@H](CC(C)(C)C)C(=O)N1C[C@]2(C[C@H]1C#N)C(=O)Nc1ccccc12] |

-continued
| Compound | Structure |
|---|---|
| 209 | 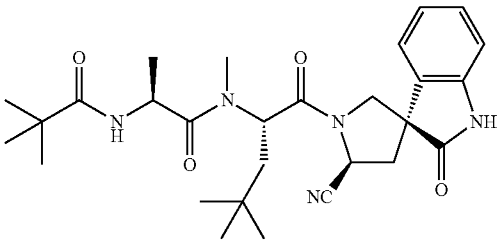 [SMILES: C[C@H](NC(=O)C(C)(C)C)C(=O)N(C)[C@@H](CC(C)(C)C)C(=O)N1C[C@]2(C[C@H]1C#N)C(=O)Nc1ccccc12] |
| 210 | 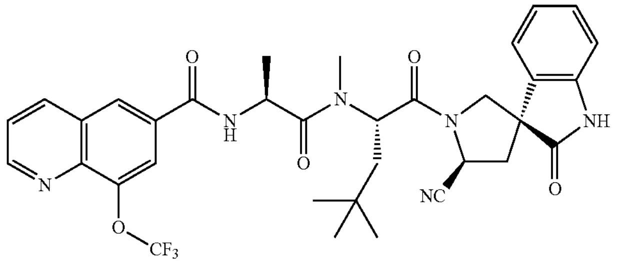 [SMILES: C[C@H](NC(=O)c1cc(OC(F)(F)F)c2ncccc2c1)C(=O)N(C)[C@@H](CC(C)(C)C)C(=O)N1C[C@]2(C[C@H]1C#N)C(=O)Nc1ccccc12] |
| 211 | 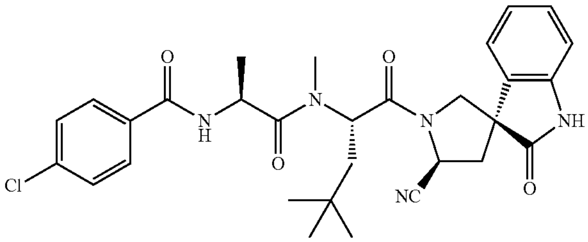 [SMILES: C[C@H](NC(=O)c1ccc(Cl)cc1)C(=O)N(C)[C@@H](CC(C)(C)C)C(=O)N1C[C@]2(C[C@H]1C#N)C(=O)Nc1ccccc12] |
| 212 | 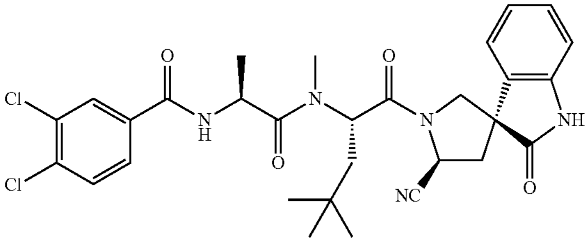 [SMILES: C[C@H](NC(=O)c1ccc(Cl)c(Cl)c1)C(=O)N(C)[C@@H](CC(C)(C)C)C(=O)N1C[C@]2(C[C@H]1C#N)C(=O)Nc1ccccc12] |
| 213 | 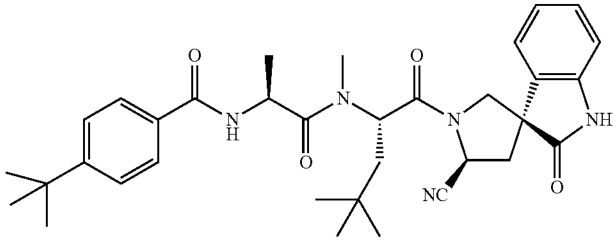 [SMILES: C[C@H](NC(=O)c1ccc(C(C)(C)C)cc1)C(=O)N(C)[C@@H](CC(C)(C)C)C(=O)N1C[C@]2(C[C@H]1C#N)C(=O)Nc1ccccc12] |
| 214 | 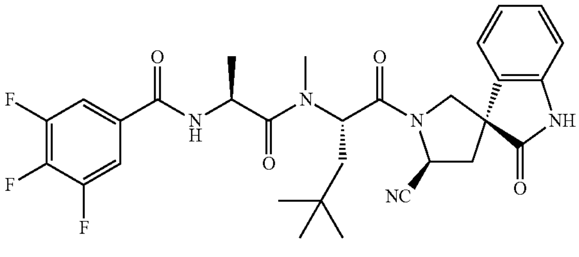 [SMILES: C[C@H](NC(=O)c1cc(F)c(F)c(F)c1)C(=O)N(C)[C@@H](CC(C)(C)C)C(=O)N1C[C@]2(C[C@H]1C#N)C(=O)Nc1ccccc12] |

-continued
| Compound | Structure |
|---|---|
| 215 | 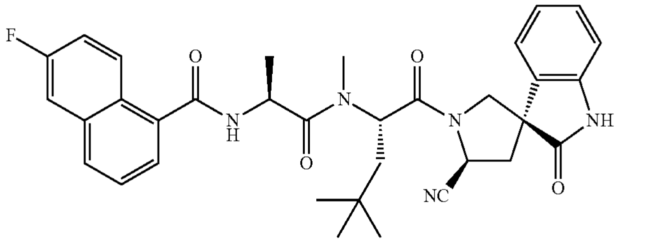 [SMILES: C[C@H](NC(=O)c1cccc2cc(F)ccc12)C(=O)N(C)[C@@H](CC(C)(C)C)C(=O)N1C[C@]2(C[C@H]1C#N)C(=O)Nc1ccccc12] |
| 216 | 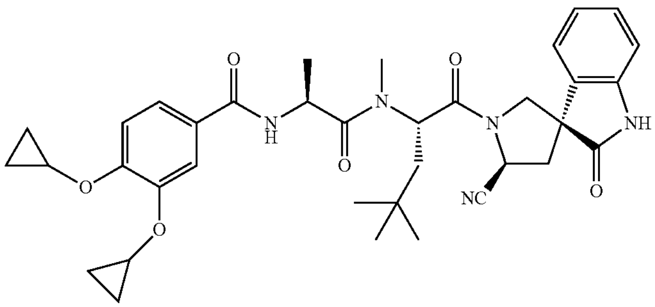 [SMILES: C[C@H](NC(=O)c1ccc(OC2CC2)c(OC2CC2)c1)C(=O)N(C)[C@@H](CC(C)(C)C)C(=O)N1C[C@]2(C[C@H]1C#N)C(=O)Nc1ccccc12] |
| 217 | 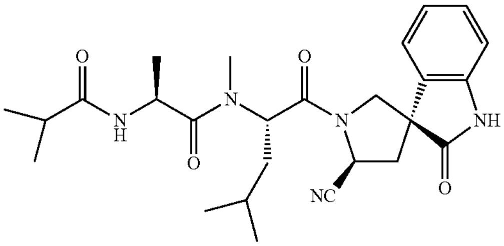 [SMILES: CC(C)C[C@@H](C(=O)N1C[C@]2(C[C@H]1C#N)C(=O)Nc1ccccc12)N(C)C(=O)[C@H](C)NC(=O)C(C)C] |
| 218 | 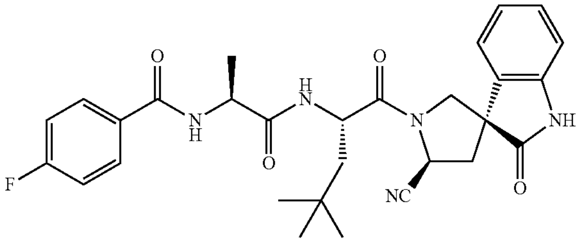 [SMILES: C[C@H](NC(=O)c1ccc(F)cc1)C(=O)N[C@@H](CC(C)(C)C)C(=O)N1C[C@]2(C[C@H]1C#N)C(=O)Nc1ccccc12] |
| 219 | 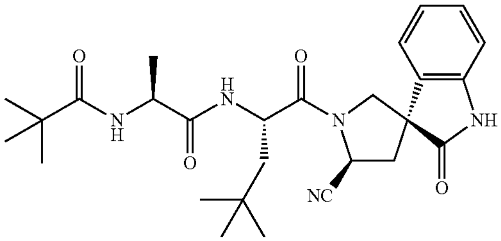 [SMILES: C[C@H](NC(=O)C(C)(C)C)C(=O)N[C@@H](CC(C)(C)C)C(=O)N1C[C@]2(C[C@H]1C#N)C(=O)Nc1ccccc12] |
| 220 | 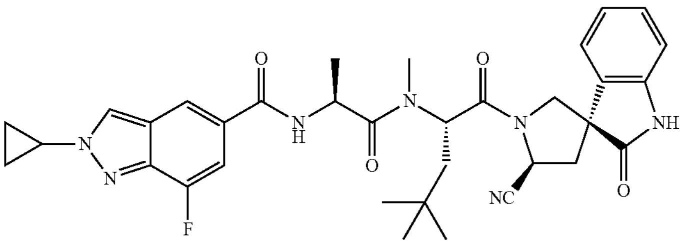 [SMILES: C[C@H](NC(=O)c1cc(F)c2nn(C3CC3)cc2c1)C(=O)N(C)[C@@H](CC(C)(C)C)C(=O)N1C[C@]2(C[C@H]1C#N)C(=O)Nc1ccccc12] |

-continued
| Compound | Structure |
| --- | --- |
| 221 | 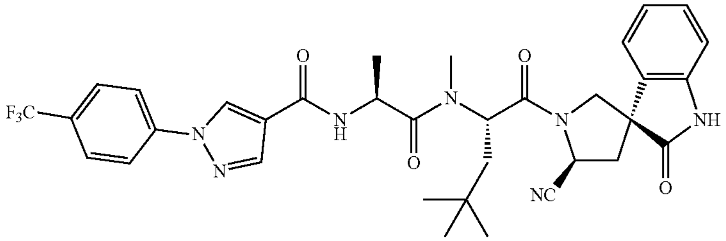 [SMILES: C[C@H](NC(=O)c1cnn(-c2ccc(C(F)(F)F)cc2)c1)C(=O)N(C)[C@@H](CC(C)(C)C)C(=O)N1C[C@]2(C[C@H]1C#N)C(=O)Nc1ccccc12] |
| 222 | 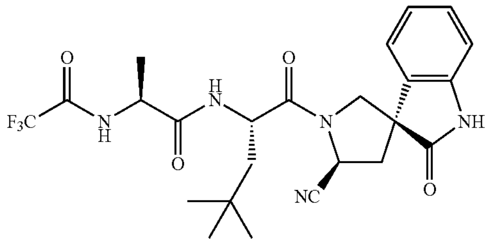 [SMILES: C[C@H](NC(=O)C(F)(F)F)C(=O)N[C@@H](CC(C)(C)C)C(=O)N1C[C@]2(C[C@H]1C#N)C(=O)Nc1ccccc12] |
| 223 | 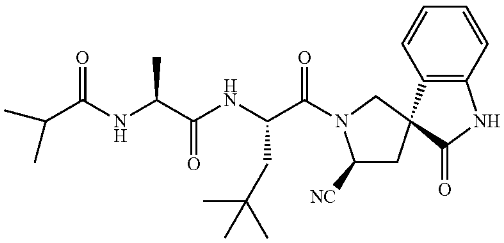 [SMILES: CC(C)C(=O)N[C@@H](C)C(=O)N[C@@H](CC(C)(C)C)C(=O)N1C[C@]2(C[C@H]1C#N)C(=O)Nc1ccccc12] |
| 224 | 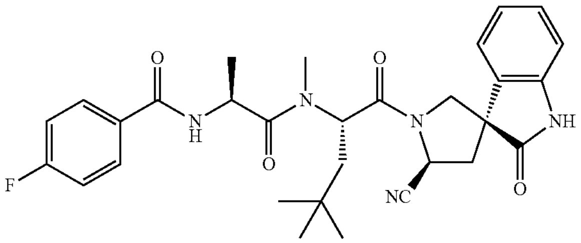 [SMILES: C[C@H](NC(=O)c1ccc(F)cc1)C(=O)N(C)[C@@H](CC(C)(C)C)C(=O)N1C[C@]2(C[C@H]1C#N)C(=O)Nc1ccccc12] |
| 225 | 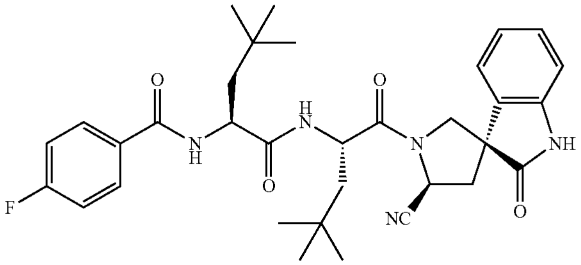 [SMILES: CC(C)(C)C[C@H](NC(=O)c1ccc(F)cc1)C(=O)N[C@@H](CC(C)(C)C)C(=O)N1C[C@]2(C[C@H]1C#N)C(=O)Nc1ccccc12] |
| 226 | 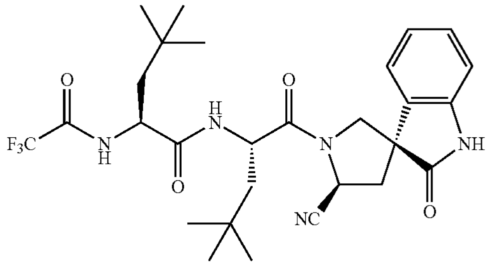 [SMILES: CC(C)(C)C[C@H](NC(=O)C(F)(F)F)C(=O)N[C@@H](CC(C)(C)C)C(=O)N1C[C@]2(C[C@H]1C#N)C(=O)Nc1ccccc12] |

-continued
| Compound | Structure |
|---|---|
| 227 | 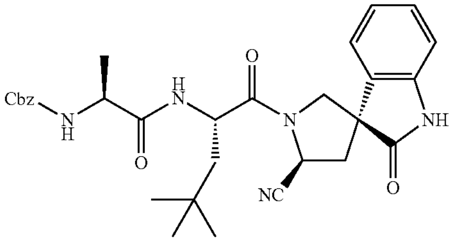 [SMILES: C[C@H](NC(=O)OCc1ccccc1)C(=O)N[C@@H](CC(C)(C)C)C(=O)N1C[C@]2(C[C@H]1C#N)C(=O)Nc1ccccc12] |
| 228 | 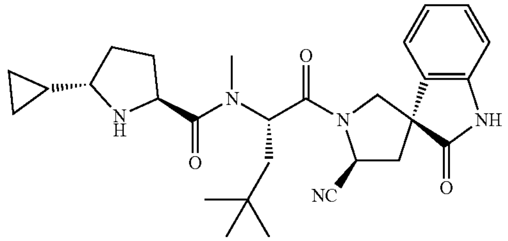 [SMILES: CN(C(=O)[C@@H]1CC[C@@H](C2CC2)N1)[C@@H](CC(C)(C)C)C(=O)N1C[C@]2(C[C@H]1C#N)C(=O)Nc1ccccc12] |
| 229 | 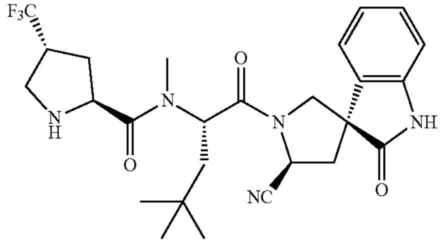 [SMILES: CN(C(=O)[C@@H]1C[C@@H](C(F)(F)F)CN1)[C@@H](CC(C)(C)C)C(=O)N1C[C@]2(C[C@H]1C#N)C(=O)Nc1ccccc12] |
| 230 | 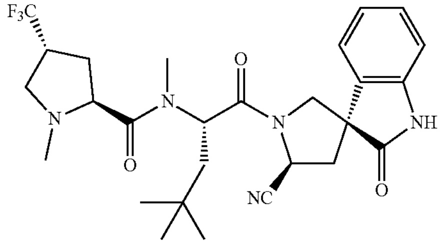 [SMILES: CN1C[C@H](C(F)(F)F)C[C@H]1C(=O)N(C)[C@@H](CC(C)(C)C)C(=O)N1C[C@]2(C[C@H]1C#N)C(=O)Nc1ccccc12] |
| 231 | 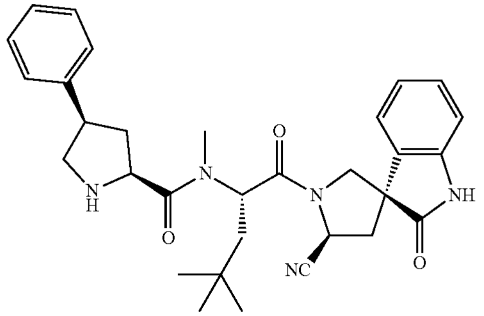 [SMILES: CN(C(=O)[C@@H]1C[C@H](c2ccccc2)CN1)[C@@H](CC(C)(C)C)C(=O)N1C[C@]2(C[C@H]1C#N)C(=O)Nc1ccccc12] |

-continued
| Compound | Structure |
|---|---|
| 232 | 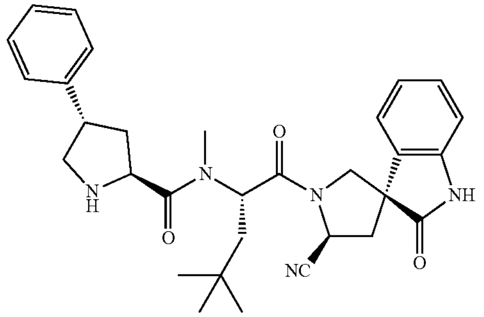 [SMILES: CN(C(=O)[C@@H]1C[C@@H](c2ccccc2)CN1)[C@@H](CC(C)(C)C)C(=O)N1C[C@]2(C[C@H]1C#N)C(=O)Nc1ccccc12] |
| 233 | 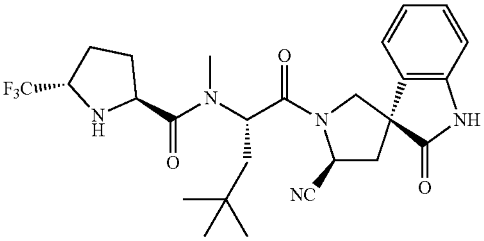 [SMILES: CN(C(=O)[C@@H]1CC[C@@H](C(F)(F)F)N1)[C@@H](CC(C)(C)C)C(=O)N1C[C@]2(C[C@H]1C#N)C(=O)Nc1ccccc12] |
| 234 | 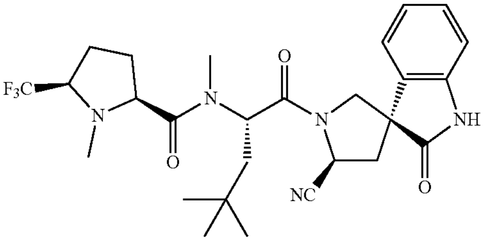 [SMILES: CN(C(=O)[C@@H]1CC[C@H](C(F)(F)F)N1C)[C@@H](CC(C)(C)C)C(=O)N1C[C@]2(C[C@H]1C#N)C(=O)Nc1ccccc12] |
| 235 | 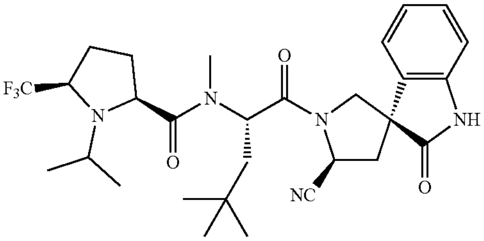 [SMILES: CC(C)N1[C@H](C(=O)N(C)[C@@H](CC(C)(C)C)C(=O)N2C[C@]3(C[C@H]2C#N)C(=O)Nc2ccccc23)CC[C@@H]1C(F)(F)F] |
| 236 | 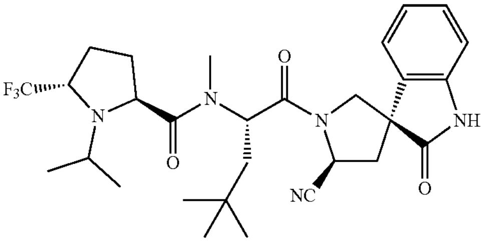 [SMILES: CC(C)N1[C@H](C(F)(F)F)CC[C@H]1C(=O)N(C)[C@@H](CC(C)(C)C)C(=O)N1C[C@]2(C[C@H]1C#N)C(=O)Nc1ccccc12] |
| 237 | 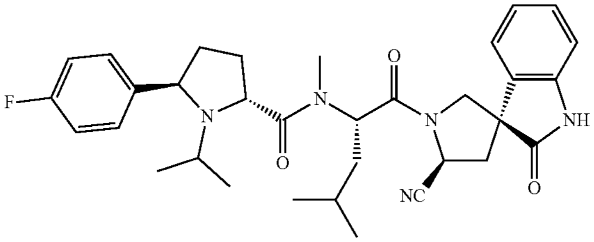 [SMILES: CC(C)C[C@@H](C(=O)N1C[C@]2(C[C@H]1C#N)C(=O)Nc1ccccc12)N(C)C(=O)[C@H]1CC[C@H](c2ccc(F)cc2)N1C(C)C] |

-continued
| Compound | Structure |
|---|---|
| 238 | 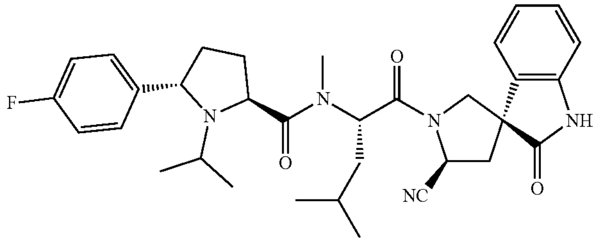 [SMILES: CC(C)C[C@@H](C(=O)N1C[C@]2(C[C@H]1C#N)C(=O)Nc1ccccc12)N(C)C(=O)[C@@H]1CC[C@@H](c2ccc(F)cc2)N1C(C)C] |
| 239 | 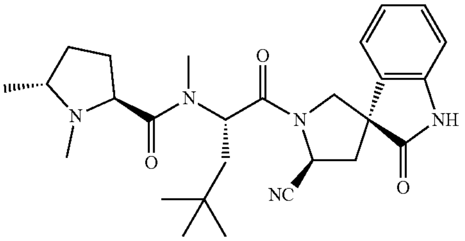 [SMILES: C[C@@H]1CC[C@@H](C(=O)N(C)[C@@H](CC(C)(C)C)C(=O)N2C[C@]3(C[C@H]2C#N)C(=O)Nc2ccccc23)N1C] |
| 240 | 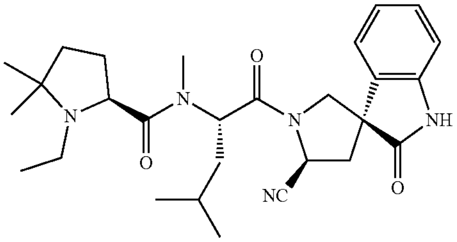 [SMILES: CCN1[C@H](C(=O)N(C)[C@@H](CC(C)C)C(=O)N2C[C@]3(C[C@H]2C#N)C(=O)Nc2ccccc23)CCC1(C)C] |
| 241 | 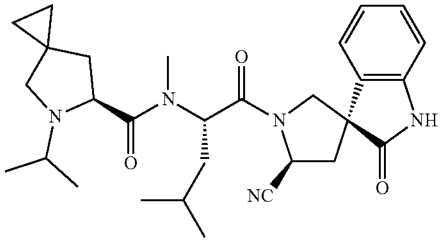 [SMILES: CC(C)C[C@@H](C(=O)N1C[C@]2(C[C@H]1C#N)C(=O)Nc1ccccc12)N(C)C(=O)[C@@H]1CC2(CC2)CN1C(C)C] |
| 242 | 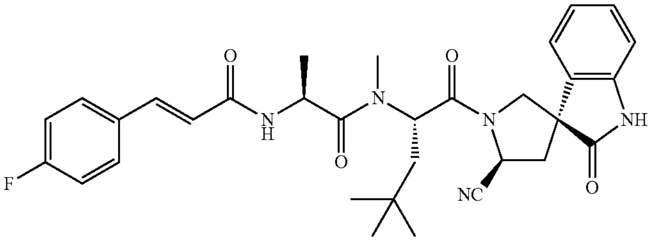 [SMILES: C[C@H](NC(=O)/C=C/c1ccc(F)cc1)C(=O)N(C)[C@@H](CC(C)(C)C)C(=O)N1C[C@]2(C[C@H]1C#N)C(=O)Nc1ccccc12] |
| 243 | 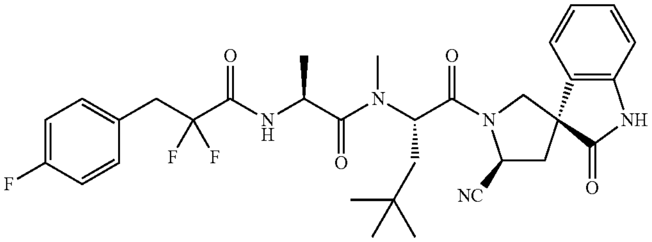 [SMILES: C[C@H](NC(=O)C(F)(F)Cc1ccc(F)cc1)C(=O)N(C)[C@@H](CC(C)(C)C)C(=O)N1C[C@]2(C[C@H]1C#N)C(=O)Nc1ccccc12] |

-continued
| Compound | Structure |
| --- | --- |
| 244 | 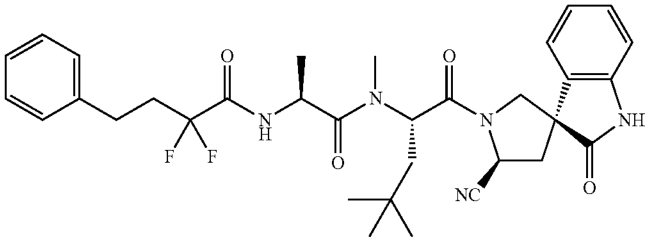 [SMILES: C[C@H](NC(=O)C(F)(F)CCc1ccccc1)C(=O)N(C)[C@@H](CC(C)(C)C)C(=O)N1C[C@]2(C[C@H]1C#N)C(=O)Nc1ccccc12] |
| 245 | 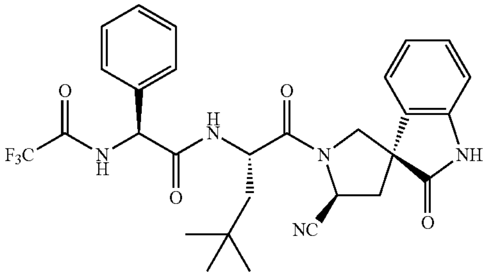 [SMILES: CC(C)(C)C[C@H](NC(=O)[C@@H](NC(=O)C(F)(F)F)c1ccccc1)C(=O)N1C[C@]2(C[C@H]1C#N)C(=O)Nc1ccccc12] |
| 246 | 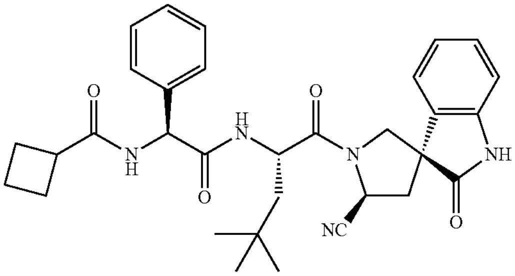 [SMILES: CC(C)(C)C[C@H](NC(=O)[C@@H](NC(=O)C1CCC1)c1ccccc1)C(=O)N1C[C@]2(C[C@H]1C#N)C(=O)Nc1ccccc12] |
| 247 | 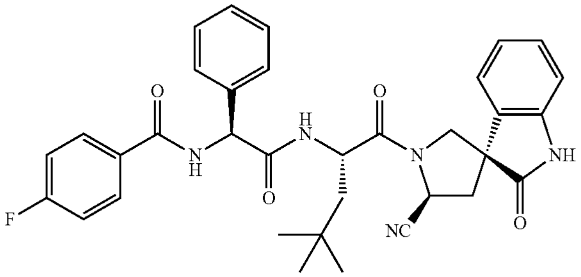 [SMILES: CC(C)(C)C[C@H](NC(=O)[C@@H](NC(=O)c1ccc(F)cc1)c1ccccc1)C(=O)N1C[C@]2(C[C@H]1C#N)C(=O)Nc1ccccc12] |
| 248 | 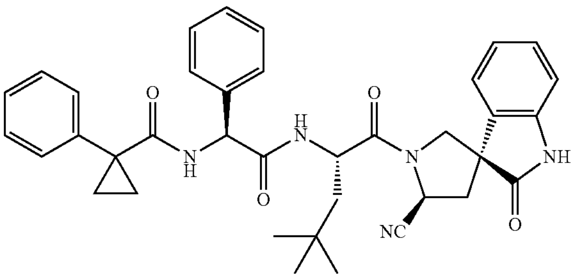 [SMILES: CC(C)(C)C[C@H](NC(=O)[C@@H](NC(=O)C1(c2ccccc2)CC1)c1ccccc1)C(=O)N1C[C@]2(C[C@H]1C#N)C(=O)Nc1ccccc12] |

-continued
| Compound | Structure |
|---|---|
| 249 | 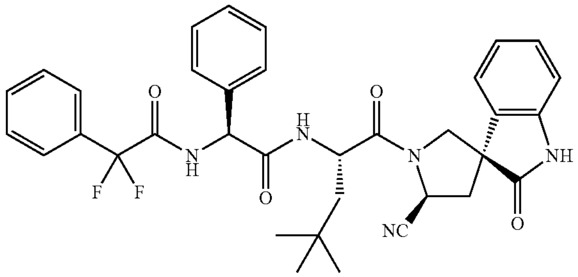 [SMILES: CC(C)(C)C[C@H](NC(=O)[C@@H](NC(=O)C(F)(F)c1ccccc1)c1ccccc1)C(=O)N1C[C@]2(C[C@H]1C#N)C(=O)Nc1ccccc12] |
| 250 | 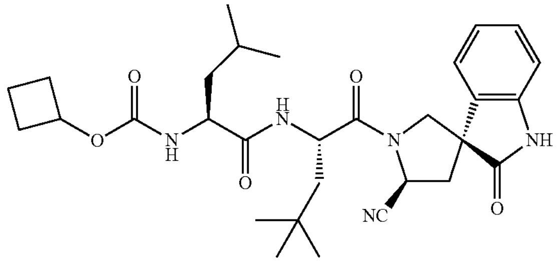 [SMILES: CC(C)C[C@H](NC(=O)OC1CCC1)C(=O)N[C@@H](CC(C)(C)C)C(=O)N1C[C@]2(C[C@H]1C#N)C(=O)Nc1ccccc12] |
| 251 | 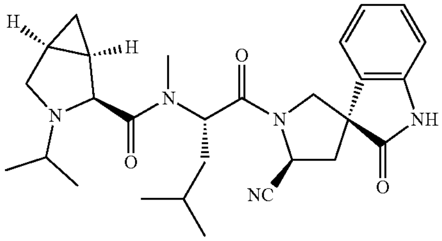 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C(C)C] |
| 252 | 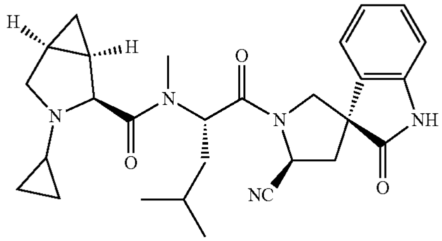 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C1CC1] |
| 253 | 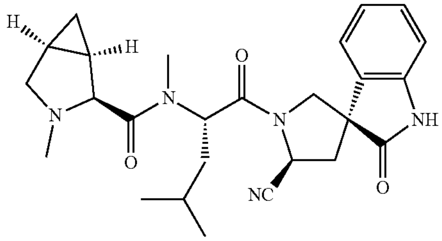 [SMILES: CC(C)C[C@@H](C(=O)N1C[C@]2(C[C@H]1C#N)C(=O)Nc1ccccc12)N(C)C(=O)[C@@H]1[C@@H]2C[C@@H]2CN1C] |
| 254 | 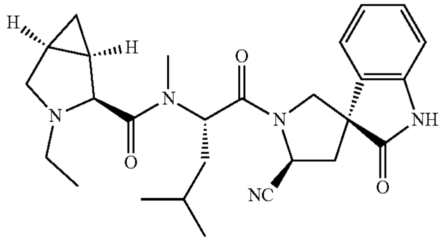 [SMILES: CCN1C[C@H]2C[C@H]2[C@H]1C(=O)N(C)[C@@H](CC(C)C)C(=O)N1C[C@]2(C[C@H]1C#N)C(=O)Nc1ccccc12] |

-continued
| Compound | Structure |
|---|---|
| 255 | 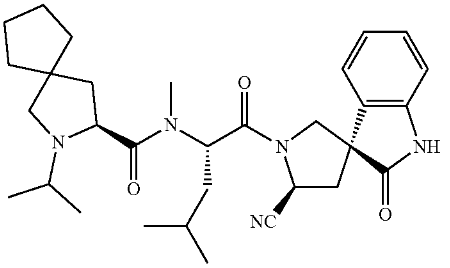 [SMILES: CC(C)C[C@@H](C(=O)N1C[C@]2(C[C@H]1C#N)C(=O)Nc1ccccc12)N(C)C(=O)[C@@H]1CC2(CCCC2)CN1C(C)C] |
| 256 | 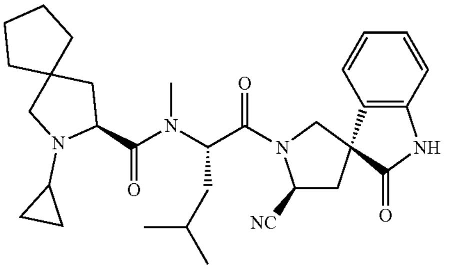 [SMILES: CC(C)C[C@@H](C(=O)N1C[C@]2(C[C@H]1C#N)C(=O)Nc1ccccc12)N(C)C(=O)[C@@H]1CC2(CCCC2)CN1C1CC1] |
| 257 | 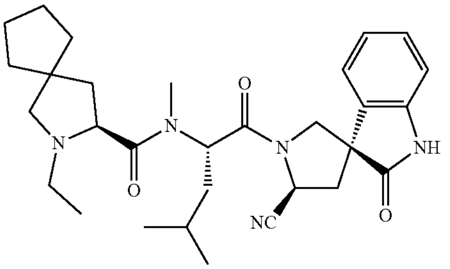 [SMILES: CCN1CC2(CCCC2)C[C@H]1C(=O)N(C)[C@@H](CC(C)C)C(=O)N1C[C@]2(C[C@H]1C#N)C(=O)Nc1ccccc12] |
| 258 | 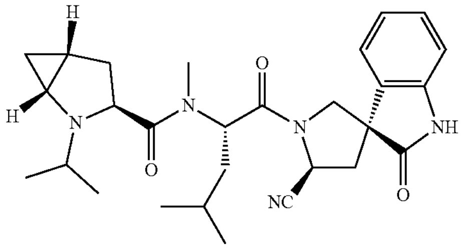 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C(C)C] |
| 259 | 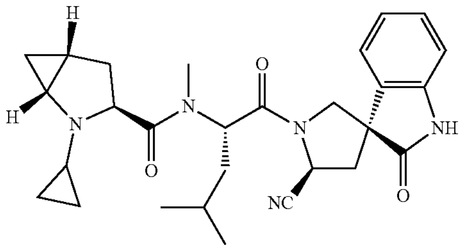 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C1CC1] |
| 260 | 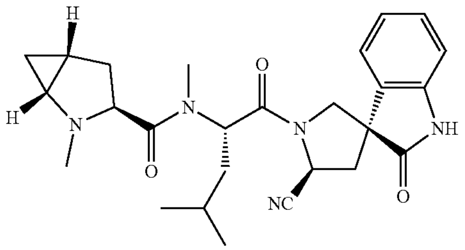 [SMILES: CC(C)C[C@@H](C(=O)N1C[C@]2(C[C@H]1C#N)C(=O)Nc1ccccc12)N(C)C(=O)[C@@H]1C[C@H]2C[C@H]2N1C] |

-continued
| Compound | Structure |
|---|---|
| 261 | 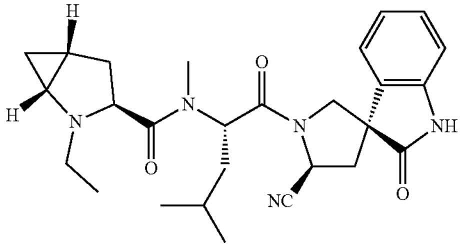 [SMILES: CCN1[C@@H]2C[C@@H]2C[C@H]1C(=O)N(C)[C@@H](CC(C)C)C(=O)N1C[C@]2(C[C@H]1C#N)C(=O)Nc1ccccc12] |
| 262 | 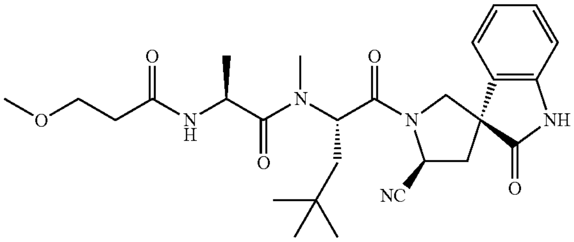 [SMILES: COCCC(=O)N[C@@H](C)C(=O)N(C)[C@@H](CC(C)(C)C)C(=O)N1C[C@]2(C[C@H]1C#N)C(=O)Nc1ccccc12] |
| 263 | 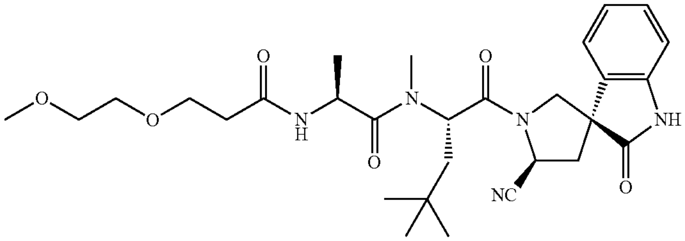 [SMILES: COCCOCCC(=O)N[C@@H](C)C(=O)N(C)[C@@H](CC(C)(C)C)C(=O)N1C[C@]2(C[C@H]1C#N)C(=O)Nc1ccccc12] |
| 264 | 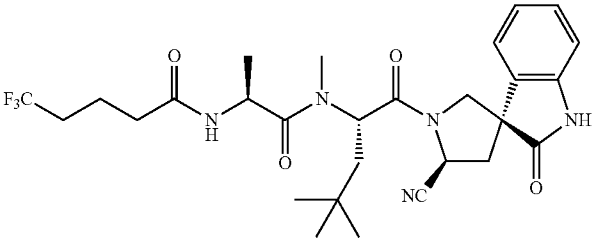 [SMILES: C[C@H](NC(=O)CCCC(F)(F)F)C(=O)N(C)[C@@H](CC(C)(C)C)C(=O)N1C[C@]2(C[C@H]1C#N)C(=O)Nc1ccccc12] |
| 265 | 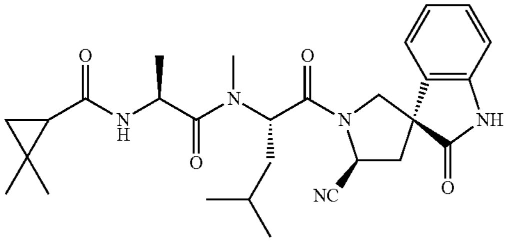 [SMILES: CC(C)C[C@@H](C(=O)N1C[C@]2(C[C@H]1C#N)C(=O)Nc1ccccc12)N(C)C(=O)[C@H](C)NC(=O)C1CC1(C)C] |
| 266 | 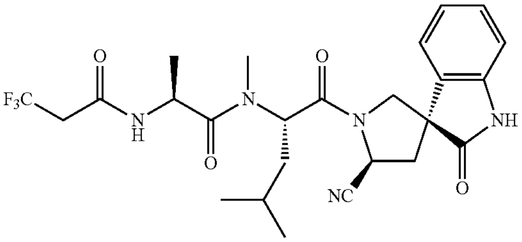 [SMILES: CC(C)C[C@@H](C(=O)N1C[C@]2(C[C@H]1C#N)C(=O)Nc1ccccc12)N(C)C(=O)[C@H](C)NC(=O)CC(F)(F)F] |

-continued
| Compound | Structure |
|---|---|
| 267 | 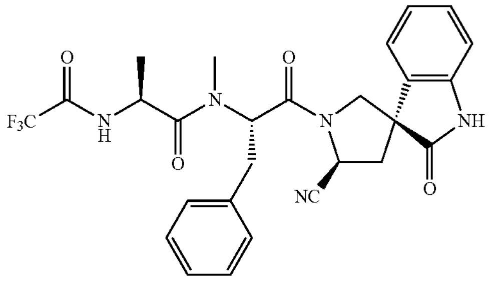 [SMILES: C[C@H](NC(=O)C(F)(F)F)C(=O)N(C)[C@@H](Cc1ccccc1)C(=O)N1C[C@]2(C[C@H]1C#N)C(=O)Nc1ccccc12] |
| 268 | 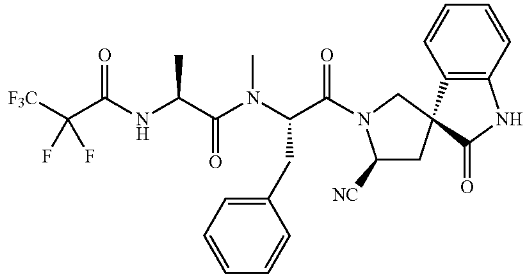 [SMILES: C[C@H](NC(=O)C(F)(F)C(F)(F)F)C(=O)N(C)[C@@H](Cc1ccccc1)C(=O)N1C[C@]2(C[C@H]1C#N)C(=O)Nc1ccccc12] |
| 269 | 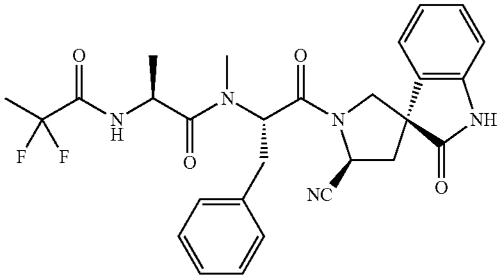 [SMILES: C[C@H](NC(=O)C(C)(F)F)C(=O)N(C)[C@@H](Cc1ccccc1)C(=O)N1C[C@]2(C[C@H]1C#N)C(=O)Nc1ccccc12] |
| 270 | 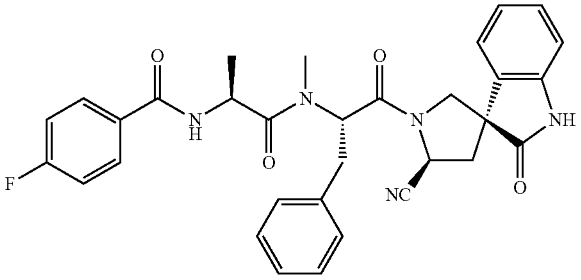 [SMILES: C[C@H](NC(=O)c1ccc(F)cc1)C(=O)N(C)[C@@H](Cc1ccccc1)C(=O)N1C[C@]2(C[C@H]1C#N)C(=O)Nc1ccccc12] |
| 271 | 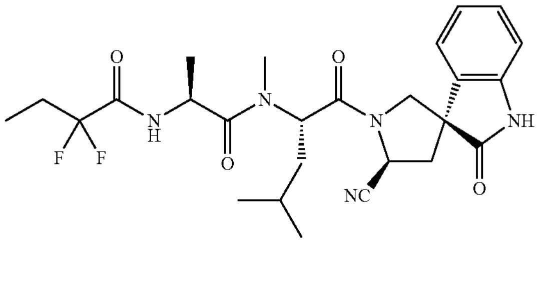 [SMILES: CCC(F)(F)C(=O)N[C@@H](C)C(=O)N(C)[C@@H](CC(C)C)C(=O)N1C[C@]2(C[C@H]1C#N)C(=O)Nc1ccccc12] |

-continued
| Compound | Structure |
|---|---|
| 272 | 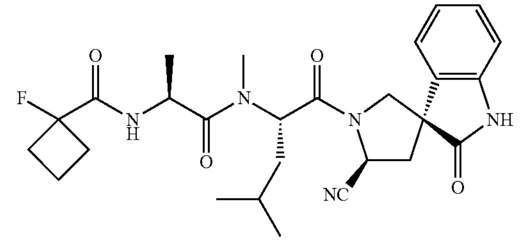 [SMILES: CC(C)C[C@@H](C(=O)N1C[C@]2(C[C@H]1C#N)C(=O)Nc1ccccc12)N(C)C(=O)[C@H](C)NC(=O)C1(F)CCC1] |
| 273 | 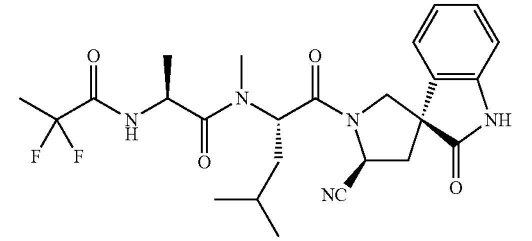 [SMILES: CC(C)C[C@@H](C(=O)N1C[C@]2(C[C@H]1C#N)C(=O)Nc1ccccc12)N(C)C(=O)[C@H](C)NC(=O)C(C)(F)F] |
| 274 | 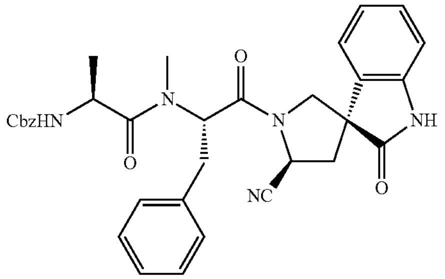 [SMILES: C[C@H](NC(=O)OCc1ccccc1)C(=O)N(C)[C@@H](Cc1ccccc1)C(=O)N1C[C@]2(C[C@H]1C#N)C(=O)Nc1ccccc12] |
| 275 | 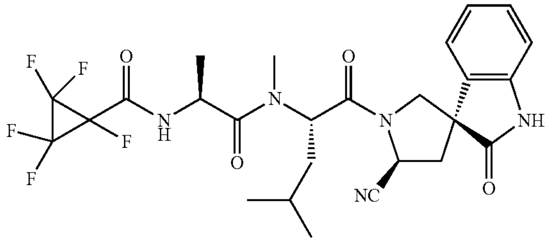 [SMILES: CC(C)C[C@@H](C(=O)N1C[C@]2(C[C@H]1C#N)C(=O)Nc1ccccc12)N(C)C(=O)[C@H](C)NC(=O)C1(F)C(F)(F)C1(F)F] |
| 276 | 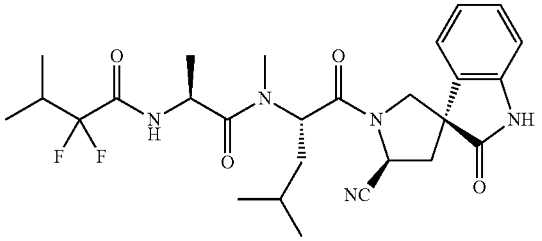 [SMILES: CC(C)C[C@@H](C(=O)N1C[C@]2(C[C@H]1C#N)C(=O)Nc1ccccc12)N(C)C(=O)[C@H](C)NC(=O)C(F)(F)C(C)C] |
| 277 | 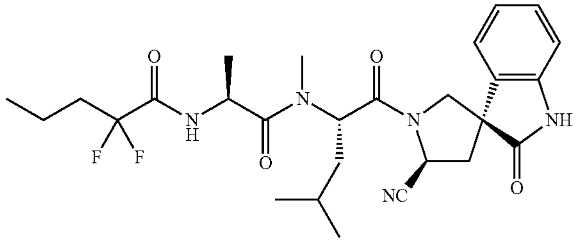 [SMILES: CCCC(F)(F)C(=O)N[C@@H](C)C(=O)N(C)[C@@H](CC(C)C)C(=O)N1C[C@]2(C[C@H]1C#N)C(=O)Nc1ccccc12] |

-continued
| Compound | Structure |
|---|---|
| 278 | 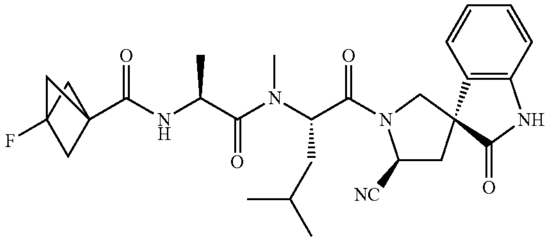 [SMILES: CC(C)C[C@@H](C(=O)N1C[C@]2(C[C@H]1C#N)C(=O)Nc1ccccc12)N(C)C(=O)[C@H](C)NC(=O)C12CC(F)(C1)C2] |
| 279 | 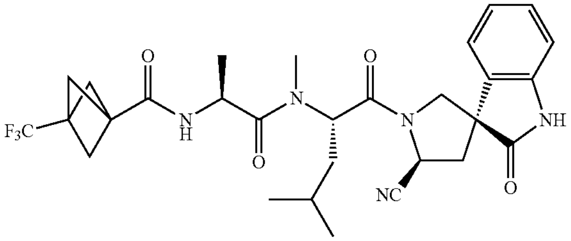 [SMILES: CC(C)C[C@@H](C(=O)N1C[C@]2(C[C@H]1C#N)C(=O)Nc1ccccc12)N(C)C(=O)[C@H](C)NC(=O)C12CC(C(F)(F)F)(C1)C2] |
| 280 | 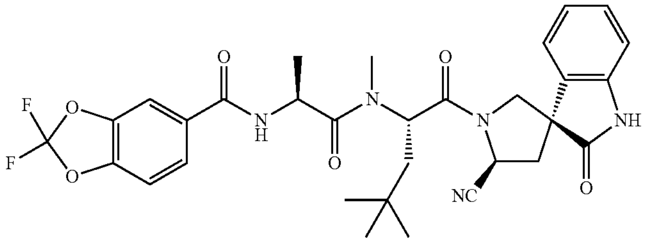 [SMILES: C[C@H](NC(=O)c1ccc2c(c1)OC(F)(F)O2)C(=O)N(C)[C@@H](CC(C)(C)C)C(=O)N1C[C@]2(C[C@H]1C#N)C(=O)Nc1ccccc12] |
| 281 | 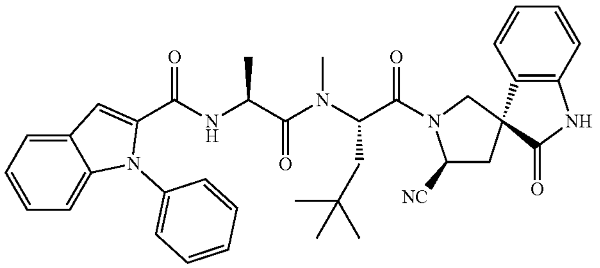 [SMILES: C[C@H](NC(=O)c1cc2ccccc2n1-c1ccccc1)C(=O)N(C)[C@@H](CC(C)(C)C)C(=O)N1C[C@]2(C[C@H]1C#N)C(=O)Nc1ccccc12] |
| 282 | 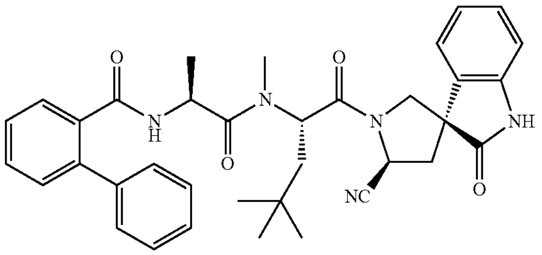 [SMILES: C[C@H](NC(=O)c1ccccc1-c1ccccc1)C(=O)N(C)[C@@H](CC(C)(C)C)C(=O)N1C[C@]2(C[C@H]1C#N)C(=O)Nc1ccccc12] |
| 283 | 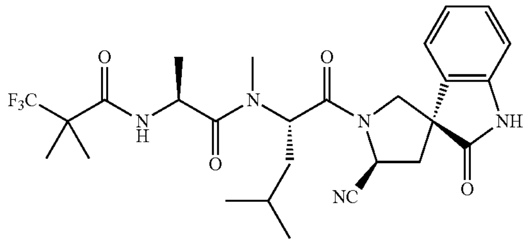 [SMILES: CC(C)C[C@@H](C(=O)N1C[C@]2(C[C@H]1C#N)C(=O)Nc1ccccc12)N(C)C(=O)[C@H](C)NC(=O)C(C)(C)C(F)(F)F] |

-continued
| Compound | Structure |
| --- | --- |
| 284 | 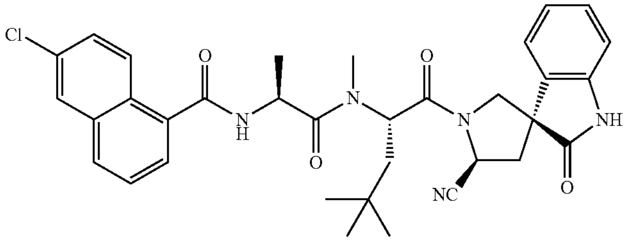 [SMILES: C[C@H](NC(=O)c1cccc2cc(Cl)ccc12)C(=O)N(C)[C@@H](CC(C)(C)C)C(=O)N1C[C@]2(C[C@H]1C#N)C(=O)Nc1ccccc12] |
| 285 | 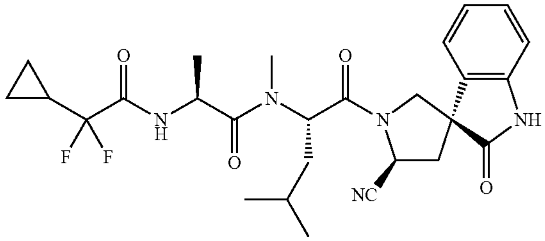 [SMILES: CC(C)C[C@@H](C(=O)N1C[C@]2(C[C@H]1C#N)C(=O)Nc1ccccc12)N(C)C(=O)[C@H](C)NC(=O)C(F)(F)C1CC1] |
| 286 | 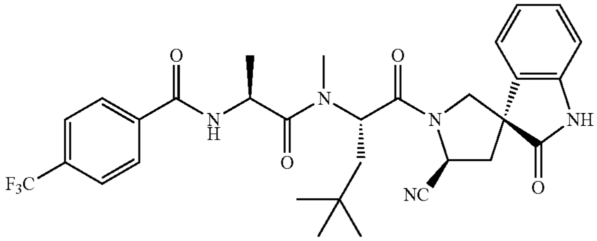 [SMILES: C[C@H](NC(=O)c1ccc(C(F)(F)F)cc1)C(=O)N(C)[C@@H](CC(C)(C)C)C(=O)N1C[C@]2(C[C@H]1C#N)C(=O)Nc1ccccc12] |
| 287 | 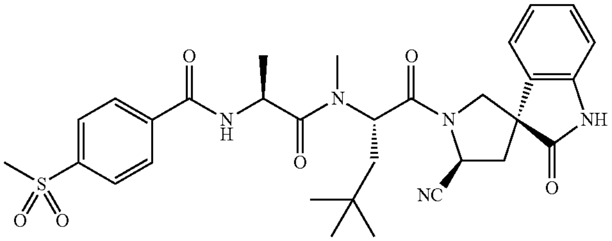 [SMILES: C[C@H](NC(=O)c1ccc(S(C)(=O)=O)cc1)C(=O)N(C)[C@@H](CC(C)(C)C)C(=O)N1C[C@]2(C[C@H]1C#N)C(=O)Nc1ccccc12] |
| 288 | 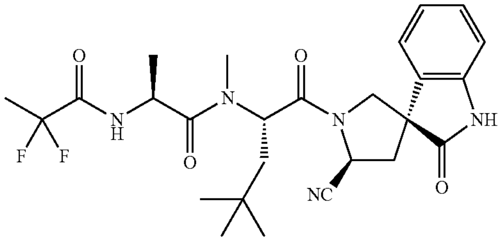 [SMILES: C[C@H](NC(=O)C(C)(F)F)C(=O)N(C)[C@@H](CC(C)(C)C)C(=O)N1C[C@]2(C[C@H]1C#N)C(=O)Nc1ccccc12] |
| 289 | 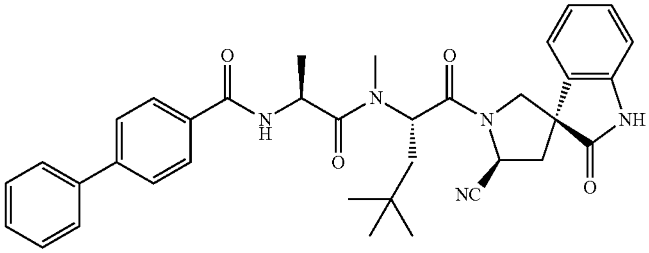 [SMILES: C[C@H](NC(=O)c1ccc(-c2ccccc2)cc1)C(=O)N(C)[C@@H](CC(C)(C)C)C(=O)N1C[C@]2(C[C@H]1C#N)C(=O)Nc1ccccc12] |

-continued
| Compound | Structure |
|---|---|
| 290 | 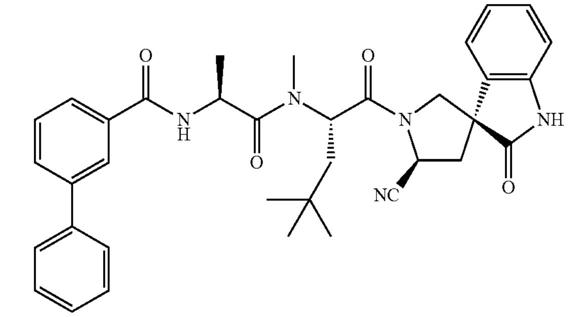 [SMILES: C[C@H](NC(=O)c1cccc(-c2ccccc2)c1)C(=O)N(C)[C@@H](CC(C)(C)C)C(=O)N1C[C@]2(C[C@H]1C#N)C(=O)Nc1ccccc12] |
| 291 | 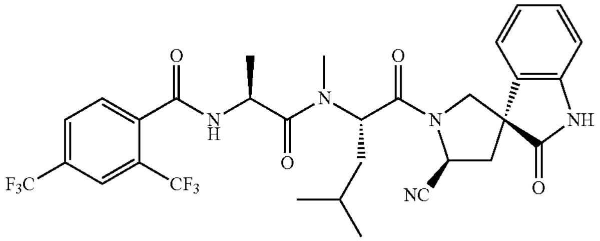 [SMILES: CC(C)C[C@@H](C(=O)N1C[C@]2(C[C@H]1C#N)C(=O)Nc1ccccc12)N(C)C(=O)[C@H](C)NC(=O)c1ccc(C(F)(F)F)cc1C(F)(F)F] |
| 292 | 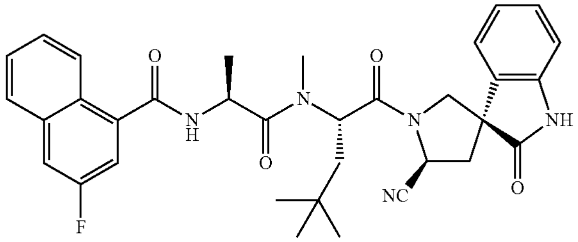 [SMILES: C[C@H](NC(=O)c1cc(F)cc2ccccc12)C(=O)N(C)[C@@H](CC(C)(C)C)C(=O)N1C[C@]2(C[C@H]1C#N)C(=O)Nc1ccccc12] |
| 293 | 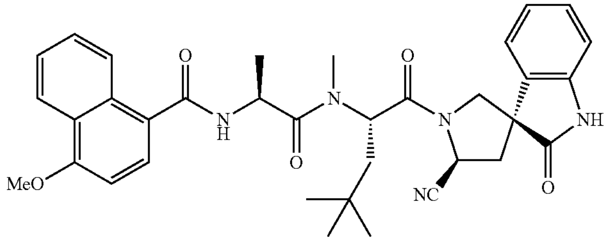 [SMILES: COc1ccc(C(=O)N[C@@H](C)C(=O)N(C)[C@@H](CC(C)(C)C)C(=O)N2C[C@]3(C[C@H]2C#N)C(=O)Nc2ccccc23)c2ccccc12] |
| 294 | 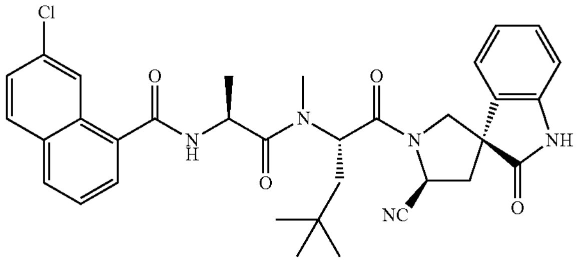 [SMILES: C[C@H](NC(=O)c1cccc2ccc(Cl)cc12)C(=O)N(C)[C@@H](CC(C)(C)C)C(=O)N1C[C@]2(C[C@H]1C#N)C(=O)Nc1ccccc12] |
| 295 | 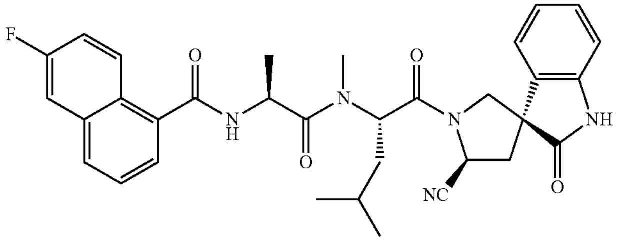 [SMILES: CC(C)C[C@@H](C(=O)N1C[C@]2(C[C@H]1C#N)C(=O)Nc1ccccc12)N(C)C(=O)[C@H](C)NC(=O)c1cccc2cc(F)ccc12] |

-continued
| Compound | Structure |
|---|---|
| 296 | 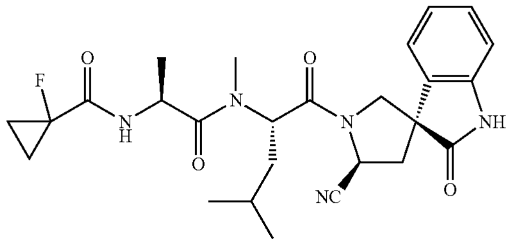 [SMILES: CC(C)C[C@@H](C(=O)N1C[C@]2(C[C@H]1C#N)C(=O)Nc1ccccc12)N(C)C(=O)[C@H](C)NC(=O)C1(F)CC1] |
| 297 | 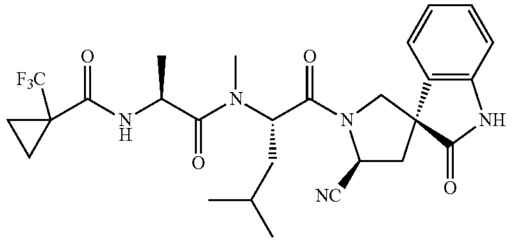 [SMILES: CC(C)C[C@@H](C(=O)N1C[C@]2(C[C@H]1C#N)C(=O)Nc1ccccc12)N(C)C(=O)[C@H](C)NC(=O)C1(C(F)(F)F)CC1] |
| 298 | 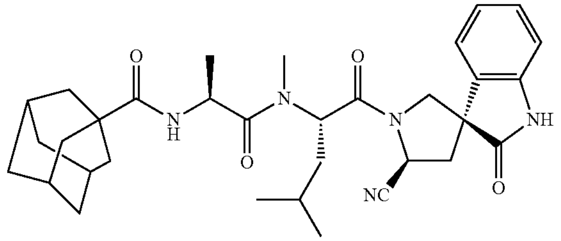 [SMILES: CC(C)C[C@@H](C(=O)N1C[C@]2(C[C@H]1C#N)C(=O)Nc1ccccc12)N(C)C(=O)[C@H](C)NC(=O)C12CC3CC(CC(C3)C1)C2] |
| 299 | 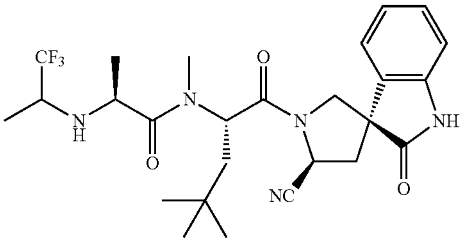 [SMILES: CC(N[C@@H](C)C(=O)N(C)[C@@H](CC(C)(C)C)C(=O)N1C[C@]2(C[C@H]1C#N)C(=O)Nc1ccccc12)C(F)(F)F] |
| 300 | 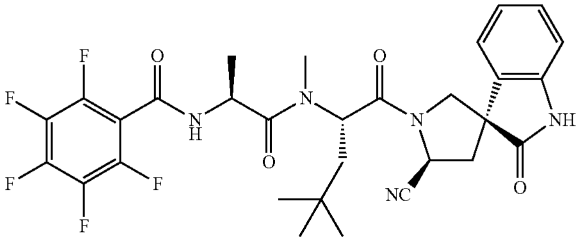 [SMILES: C[C@H](NC(=O)c1c(F)c(F)c(F)c(F)c1F)C(=O)N(C)[C@@H](CC(C)(C)C)C(=O)N1C[C@]2(C[C@H]1C#N)C(=O)Nc1ccccc12] |
| 301 | 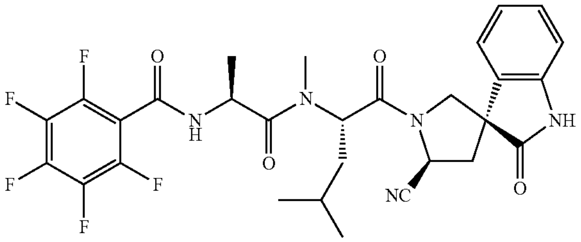 [SMILES: CC(C)C[C@@H](C(=O)N1C[C@]2(C[C@H]1C#N)C(=O)Nc1ccccc12)N(C)C(=O)[C@H](C)NC(=O)c1c(F)c(F)c(F)c(F)c1F] |

-continued
| Compound | Structure |
|---|---|
| 302 | 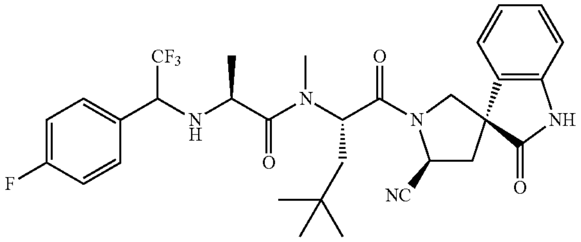 [SMILES: C[C@H](NC(c1ccc(F)cc1)C(F)(F)F)C(=O)N(C)[C@@H](CC(C)(C)C)C(=O)N1C[C@]2(C[C@H]1C#N)C(=O)Nc1ccccc12] |
| 303 | 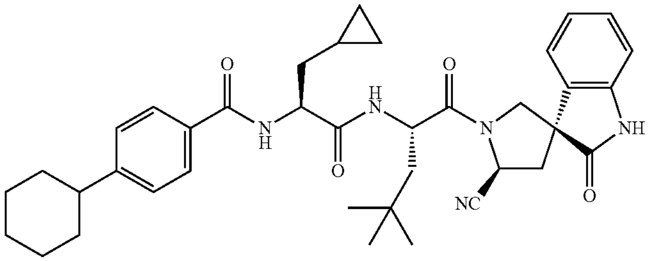 [SMILES: CC(C)(C)C[C@H](NC(=O)[C@H](CC1CC1)NC(=O)c1ccc(C2CCCCC2)cc1)C(=O)N1C[C@]2(C[C@H]1C#N)C(=O)Nc1ccccc12] |
| 304 | 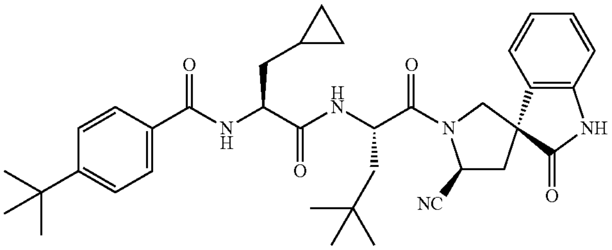 [SMILES: CC(C)(C)C[C@H](NC(=O)[C@H](CC1CC1)NC(=O)c1ccc(C(C)(C)C)cc1)C(=O)N1C[C@]2(C[C@H]1C#N)C(=O)Nc1ccccc12] |
| 305 | 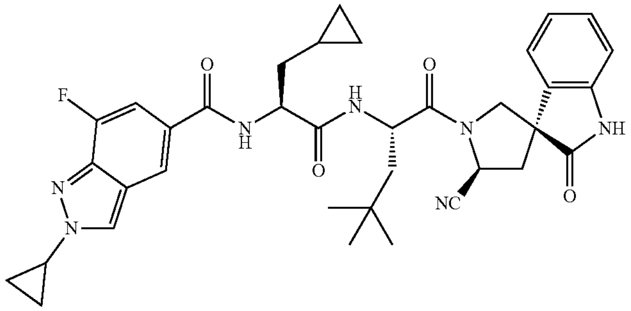 [SMILES: CC(C)(C)C[C@H](NC(=O)[C@H](CC1CC1)NC(=O)c1cc(F)c2nn(C3CC3)cc2c1)C(=O)N1C[C@]2(C[C@H]1C#N)C(=O)Nc1ccccc12] |
| 306 | 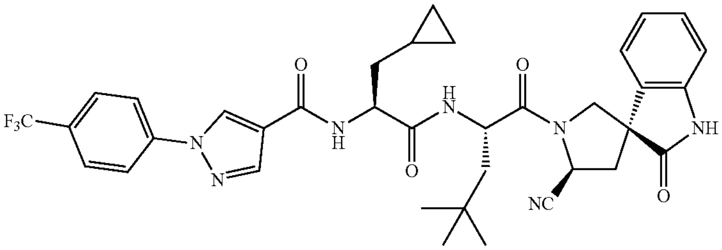 [SMILES: CC(C)(C)C[C@H](NC(=O)[C@H](CC1CC1)NC(=O)c1cnn(-c2ccc(C(F)(F)F)cc2)c1)C(=O)N1C[C@]2(C[C@H]1C#N)C(=O)Nc1ccccc12] |
| 307 | 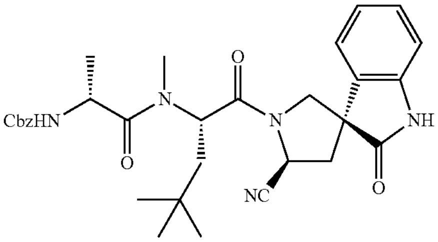 [SMILES: C[C@@H](NC(=O)OCc1ccccc1)C(=O)N(C)[C@@H](CC(C)(C)C)C(=O)N1C[C@]2(C[C@H]1C#N)C(=O)Nc1ccccc12] |

-continued
| Compound | Structure |
|---|---|
| 308 | 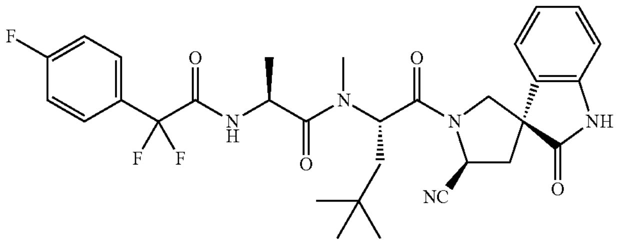 [SMILES: C[C@H](NC(=O)C(F)(F)c1ccc(F)cc1)C(=O)N(C)[C@@H](CC(C)(C)C)C(=O)N1C[C@]2(C[C@H]1C#N)C(=O)Nc1ccccc12] |
| 309 | 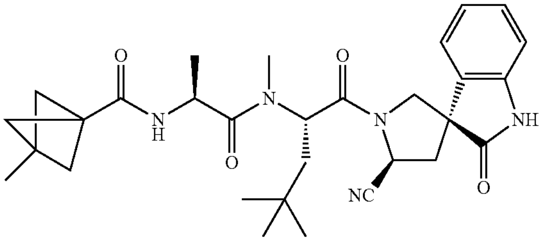 [SMILES: C[C@H](NC(=O)C12CC(C)(C1)C2)C(=O)N(C)[C@@H](CC(C)(C)C)C(=O)N1C[C@]2(C[C@H]1C#N)C(=O)Nc1ccccc12] |
| 310 | 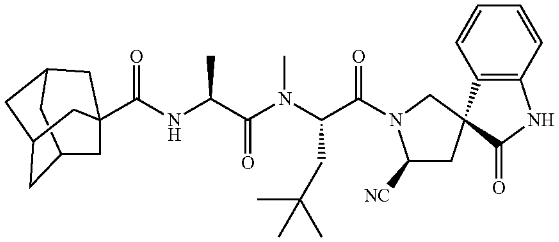 [SMILES: C[C@H](NC(=O)C12CC3CC(CC(C3)C1)C2)C(=O)N(C)[C@@H](CC(C)(C)C)C(=O)N1C[C@]2(C[C@H]1C#N)C(=O)Nc1ccccc12] |
| 311 | 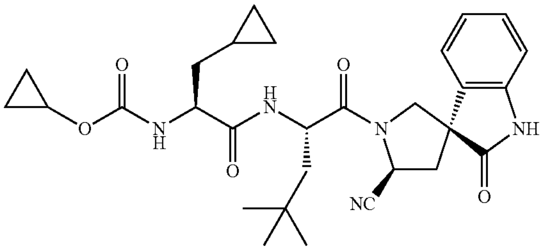 [SMILES: CC(C)(C)C[C@H](NC(=O)[C@H](CC1CC1)NC(=O)OC1CC1)C(=O)N1C[C@]2(C[C@H]1C#N)C(=O)Nc1ccccc12] |
| 312 | 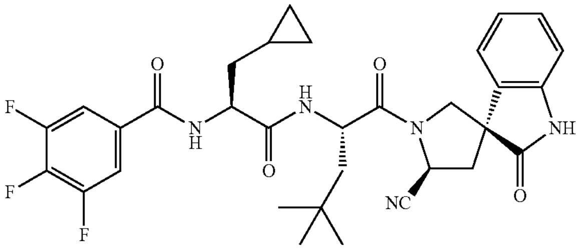 [SMILES: CC(C)(C)C[C@H](NC(=O)[C@H](CC1CC1)NC(=O)c1cc(F)c(F)c(F)c1)C(=O)N1C[C@]2(C[C@H]1C#N)C(=O)Nc1ccccc12] |
| 313 | 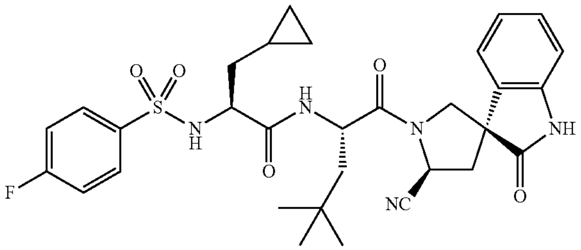 [SMILES: CC(C)(C)C[C@H](NC(=O)[C@H](CC1CC1)NS(=O)(=O)c1ccc(F)cc1)C(=O)N1C[C@]2(C[C@H]1C#N)C(=O)Nc1ccccc12] |

-continued
| Compound | Structure |
| --- | --- |
| 314 | 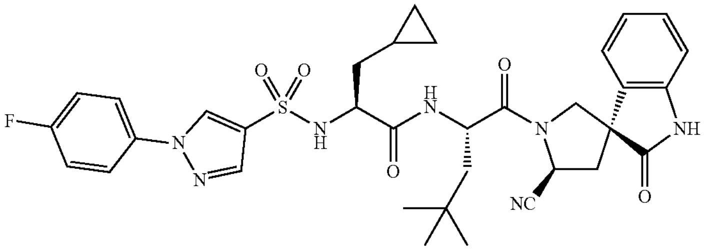 [SMILES: CC(C)(C)C[C@H](NC(=O)[C@H](CC1CC1)NS(=O)(=O)c1cnn(-c2ccc(F)cc2)c1)C(=O)N1C[C@]2(C[C@H]1C#N)C(=O)Nc1ccccc12] |
| 315 | 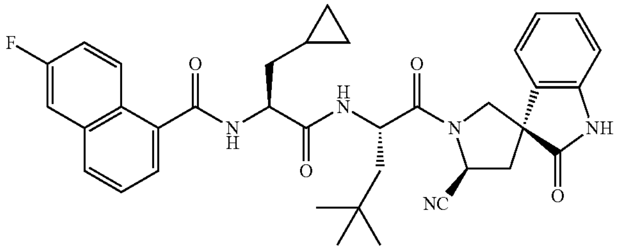 [SMILES: CC(C)(C)C[C@H](NC(=O)[C@H](CC1CC1)NC(=O)c1cccc2cc(F)ccc12)C(=O)N1C[C@]2(C[C@H]1C#N)C(=O)Nc1ccccc12] |
| 316 | 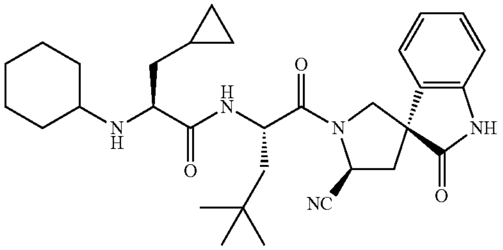 [SMILES: CC(C)(C)C[C@H](NC(=O)[C@H](CC1CC1)NC1CCCCC1)C(=O)N1C[C@]2(C[C@H]1C#N)C(=O)Nc1ccccc12] |
| 317 | 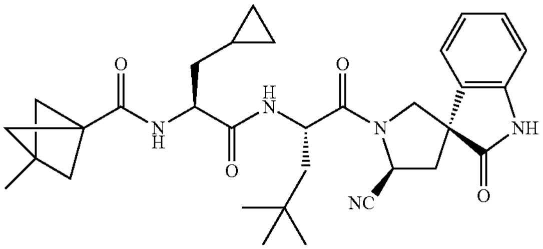 [SMILES: CC(C)(C)C[C@H](NC(=O)[C@H](CC1CC1)NC(=O)C12CC(C)(C1)C2)C(=O)N1C[C@]2(C[C@H]1C#N)C(=O)Nc1ccccc12] |
| 318 | 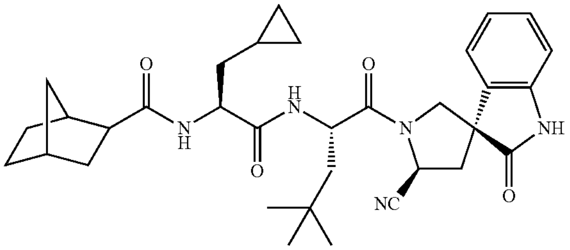 [SMILES: CC(C)(C)C[C@H](NC(=O)[C@H](CC1CC1)NC(=O)C1CC2CCC1C2)C(=O)N1C[C@]2(C[C@H]1C#N)C(=O)Nc1ccccc12] |
| 319 | 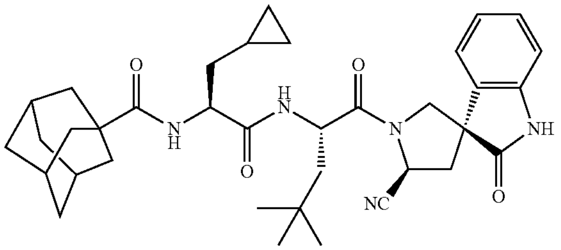 [SMILES: CC(C)(C)C[C@H](NC(=O)[C@H](CC1CC1)NC(=O)C12CC3CC(CC(C3)C1)C2)C(=O)N1C[C@]2(C[C@H]1C#N)C(=O)Nc1ccccc12] |

-continued
| Compound | Structure |
|---|---|
| 320 | 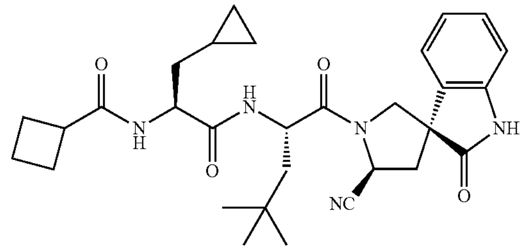 [SMILES: CC(C)(C)C[C@H](NC(=O)[C@H](CC1CC1)NC(=O)C1CCC1)C(=O)N1C[C@]2(C[C@H]1C#N)C(=O)Nc1ccccc12] |
| 321 | 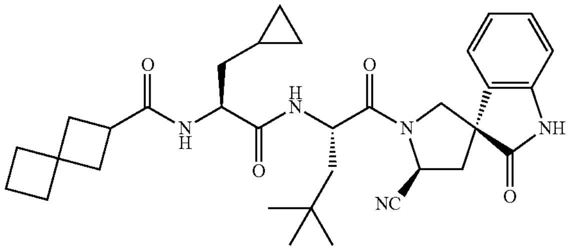 [SMILES: CC(C)(C)C[C@H](NC(=O)[C@H](CC1CC1)NC(=O)C1CC2(CCC2)C1)C(=O)N1C[C@]2(C[C@H]1C#N)C(=O)Nc1ccccc12] |
| 322 | 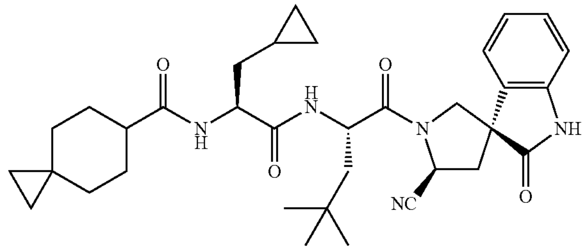 [SMILES: CC(C)(C)C[C@H](NC(=O)[C@H](CC1CC1)NC(=O)C1CCC2(CC1)CC2)C(=O)N1C[C@]2(C[C@H]1C#N)C(=O)Nc1ccccc12] |
| 323 | 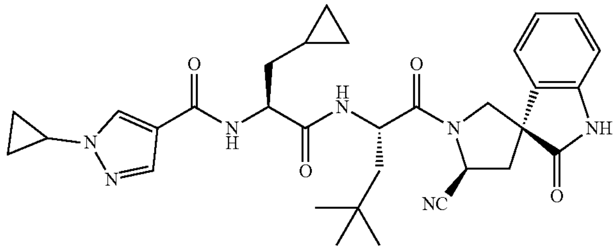 [SMILES: CC(C)(C)C[C@H](NC(=O)[C@H](CC1CC1)NC(=O)c1cnn(C2CC2)c1)C(=O)N1C[C@]2(C[C@H]1C#N)C(=O)Nc1ccccc12] |
| 324 | 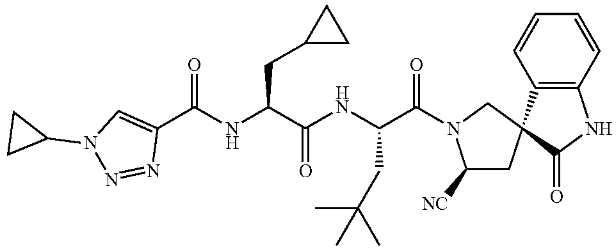 [SMILES: CC(C)(C)C[C@H](NC(=O)[C@H](CC1CC1)NC(=O)c1cn(C2CC2)nn1)C(=O)N1C[C@]2(C[C@H]1C#N)C(=O)Nc1ccccc12] |
| 325 | 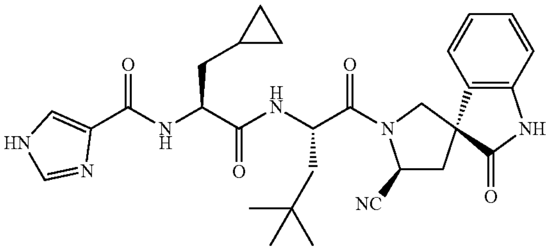 [SMILES: CC(C)(C)C[C@H](NC(=O)[C@H](CC1CC1)NC(=O)c1c[nH]cn1)C(=O)N1C[C@]2(C[C@H]1C#N)C(=O)Nc1ccccc12] |

-continued
| Compound | Structure |
| --- | --- |
| 326 | 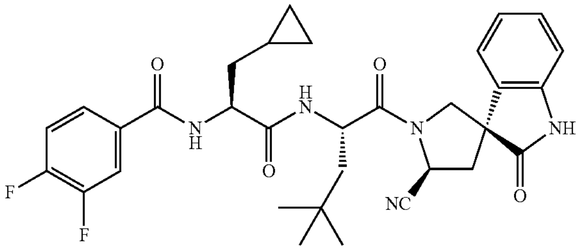 [SMILES: CC(C)(C)C[C@H](NC(=O)[C@H](CC1CC1)NC(=O)c1ccc(F)c(F)c1)C(=O)N1C[C@]2(C[C@H]1C#N)C(=O)Nc1ccccc12] |
| 327 | 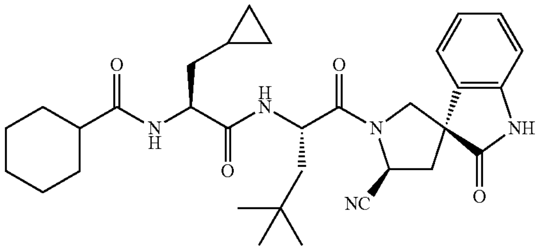 [SMILES: CC(C)(C)C[C@H](NC(=O)[C@H](CC1CC1)NC(=O)C1CCCCC1)C(=O)N1C[C@]2(C[C@H]1C#N)C(=O)Nc1ccccc12] |
| 328 | 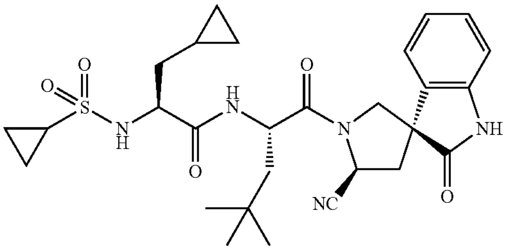 [SMILES: CC(C)(C)C[C@H](NC(=O)[C@H](CC1CC1)NS(=O)(=O)C1CC1)C(=O)N1C[C@]2(C[C@H]1C#N)C(=O)Nc1ccccc12] |
| 329 | 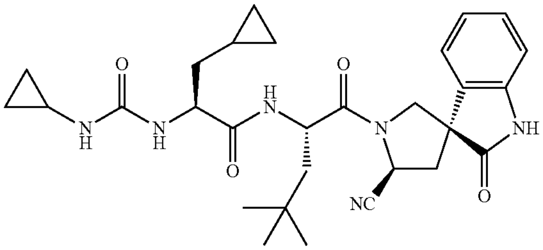 [SMILES: CC(C)(C)C[C@H](NC(=O)[C@H](CC1CC1)NC(=O)NC1CC1)C(=O)N1C[C@]2(C[C@H]1C#N)C(=O)Nc1ccccc12] |
| 330 | 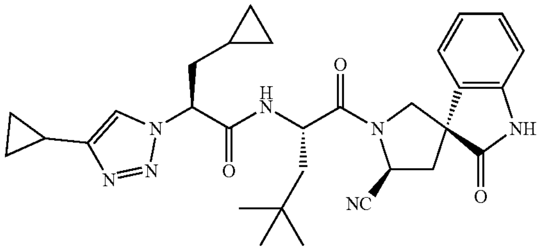 [SMILES: CC(C)(C)C[C@H](NC(=O)[C@H](CC1CC1)n1cc(C2CC2)nn1)C(=O)N1C[C@]2(C[C@H]1C#N)C(=O)Nc1ccccc12] |
| 331 | 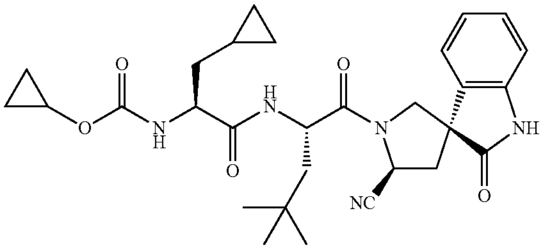 [SMILES: CC(C)(C)C[C@H](NC(=O)[C@H](CC1CC1)NC(=O)OC1CC1)C(=O)N1C[C@]2(C[C@H]1C#N)C(=O)Nc1ccccc12] |

-continued
| Compound | Structure |
|---|---|
| 332 | 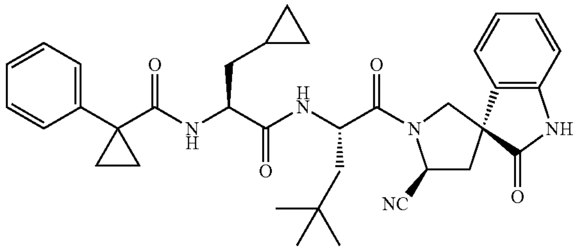 [SMILES: CC(C)(C)C[C@H](NC(=O)[C@H](CC1CC1)NC(=O)C1(c2ccccc2)CC1)C(=O)N1C[C@]2(C[C@H]1C#N)C(=O)Nc1ccccc12] |
| 333 | 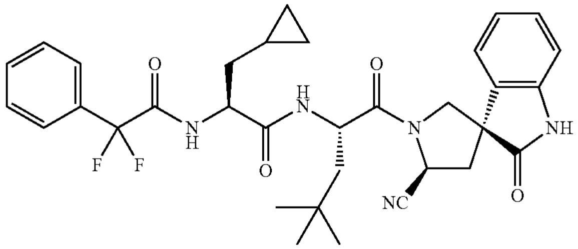 [SMILES: CC(C)(C)C[C@H](NC(=O)[C@H](CC1CC1)NC(=O)C(F)(F)c1ccccc1)C(=O)N1C[C@]2(C[C@H]1C#N)C(=O)Nc1ccccc12] |
| 334 | 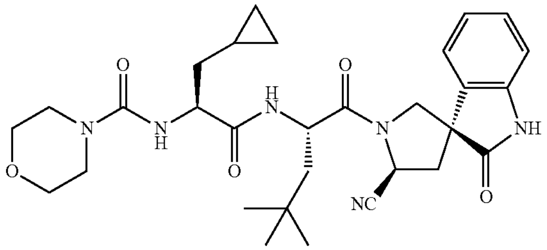 [SMILES: CC(C)(C)C[C@H](NC(=O)[C@H](CC1CC1)NC(=O)N1CCOCC1)C(=O)N1C[C@]2(C[C@H]1C#N)C(=O)Nc1ccccc12] |
| 335 | 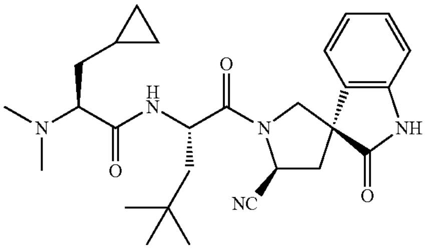 [SMILES: CN(C)[C@@H](CC1CC1)C(=O)N[C@@H](CC(C)(C)C)C(=O)N1C[C@]2(C[C@H]1C#N)C(=O)Nc1ccccc12] |
| 336 | 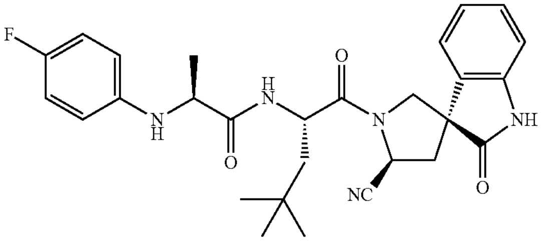 [SMILES: C[C@H](Nc1ccc(F)cc1)C(=O)N[C@@H](CC(C)(C)C)C(=O)N1C[C@]2(C[C@H]1C#N)C(=O)Nc1ccccc12] |
| 337 | 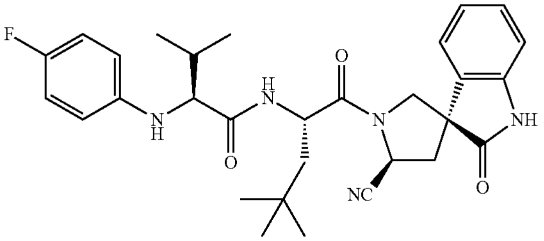 [SMILES: CC(C)[C@H](Nc1ccc(F)cc1)C(=O)N[C@@H](CC(C)(C)C)C(=O)N1C[C@]2(C[C@H]1C#N)C(=O)Nc1ccccc12] |

-continued
| Compound | Structure |
|---|---|
| 338 | 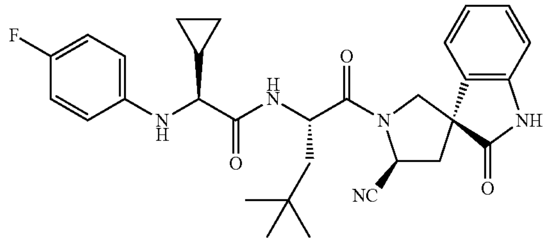 [SMILES: CC(C)(C)C[C@H](NC(=O)[C@@H](Nc1ccc(F)cc1)C1CC1)C(=O)N1C[C@]2(C[C@H]1C#N)C(=O)Nc1ccccc12] |
| 339 | 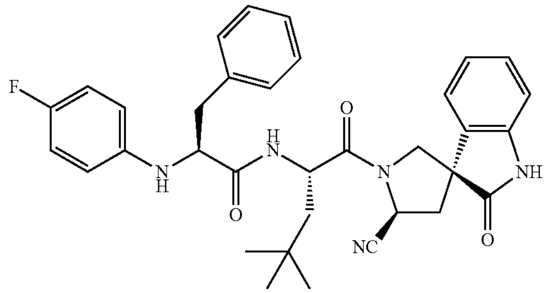 [SMILES: CC(C)(C)C[C@H](NC(=O)[C@H](Cc1ccccc1)Nc1ccc(F)cc1)C(=O)N1C[C@]2(C[C@H]1C#N)C(=O)Nc1ccccc12] |
| 340 | 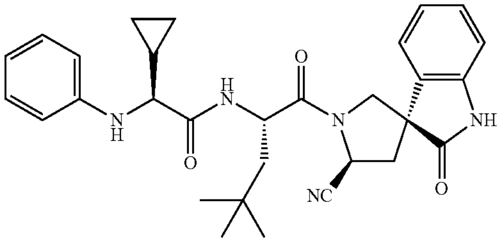 [SMILES: CC(C)(C)C[C@H](NC(=O)[C@@H](Nc1ccccc1)C1CC1)C(=O)N1C[C@]2(C[C@H]1C#N)C(=O)Nc1ccccc12] |
| 341 | 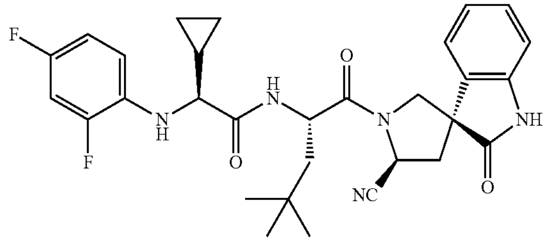 [SMILES: CC(C)(C)C[C@H](NC(=O)[C@@H](Nc1ccc(F)cc1F)C1CC1)C(=O)N1C[C@]2(C[C@H]1C#N)C(=O)Nc1ccccc12] |
| 342 | 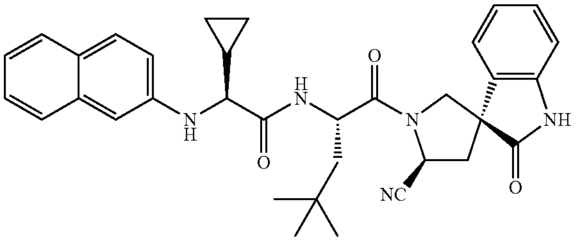 [SMILES: CC(C)(C)C[C@H](NC(=O)[C@@H](Nc1ccc2ccccc2c1)C1CC1)C(=O)N1C[C@]2(C[C@H]1C#N)C(=O)Nc1ccccc12] |
| 343 | 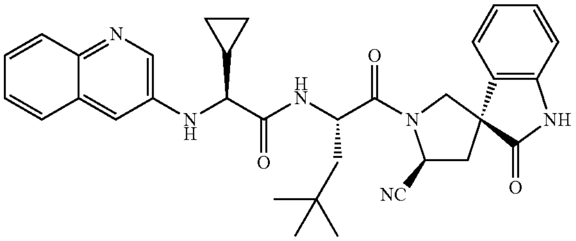 [SMILES: CC(C)(C)C[C@H](NC(=O)[C@@H](Nc1cnc2ccccc2c1)C1CC1)C(=O)N1C[C@]2(C[C@H]1C#N)C(=O)Nc1ccccc12] |

-continued
| Compound | Structure |
|---|---|
| 344 | 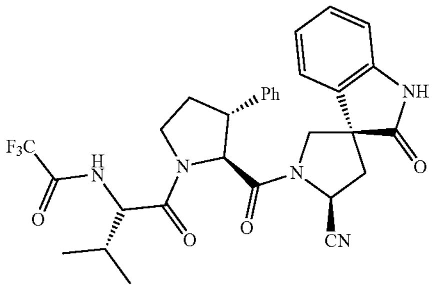 |
| 345 | 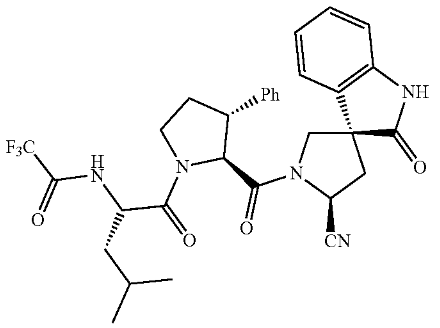 |
| 346 | 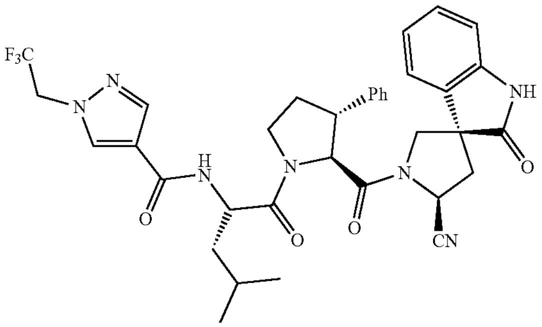 |
| 347 | 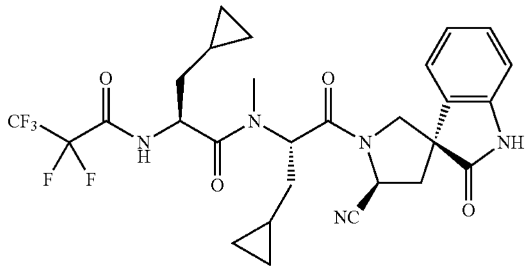 [SMILES: CN(C(=O)[C@H](CC1CC1)NC(=O)C(F)(F)C(F)(F)F)[C@@H](CC1CC1)C(=O)N1C[C@]2(C[C@H]1C#N)C(=O)Nc1ccccc12] |
| 348 | 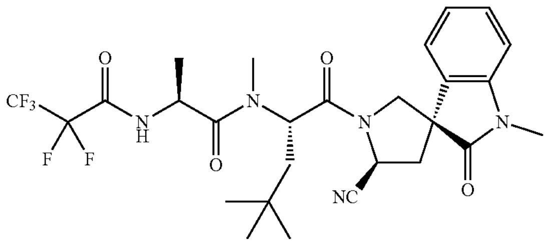 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)N(C)c1ccccc12] |

-continued
| Compound | Structure |
|---|---|
| 349 | 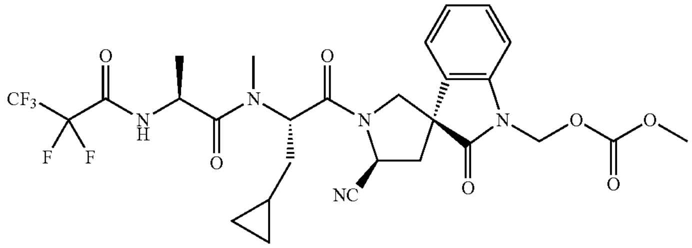 [SMILES: COC(=O)OCN1C(=O)[C@]2(C[C@@H](C#N)N(C(=O)[C@H](CC3CC3)N(C)C(=O)[C@H](C)NC(=O)C(F)(F)C(F)(F)F)C2)c2ccccc21] |
| 350 | 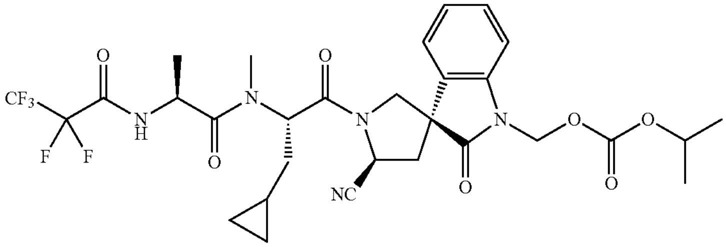 [SMILES: CC(C)OC(=O)OCN1C(=O)[C@]2(C[C@@H](C#N)N(C(=O)[C@H](CC3CC3)N(C)C(=O)[C@H](C)NC(=O)C(F)(F)C(F)(F)F)C2)c2ccccc21] |
| 351 | 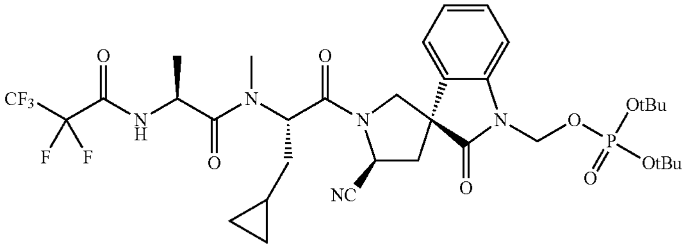 [SMILES: C[C@H](NC(=O)C(F)(F)C(F)(F)F)C(=O)N(C)[C@@H](CC1CC1)C(=O)N1C[C@]2(C[C@H]1C#N)C(=O)N(COP(=O)(OC(C)(C)C)OC(C)(C)C)c1ccccc12] |
| 352 | 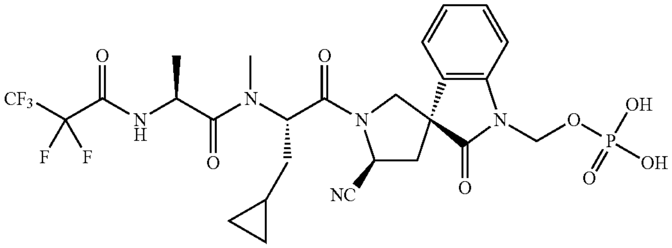 [SMILES: C[C@H](NC(=O)C(F)(F)C(F)(F)F)C(=O)N(C)[C@@H](CC1CC1)C(=O)N1C[C@]2(C[C@H]1C#N)C(=O)N(COP(=O)(O)O)c1ccccc12] |
| 353 | 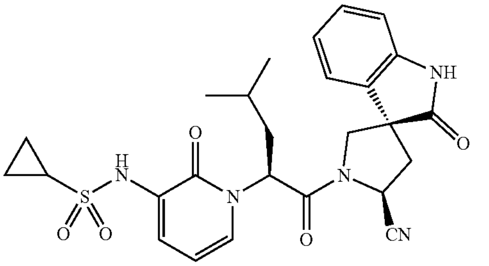 [SMILES: CC(C)C[C@@H](C(=O)N1C[C@]2(C[C@H]1C#N)C(=O)Nc1ccccc12)n1cccc(NS(=O)(=O)C2CC2)c1=O] |
| 354 | 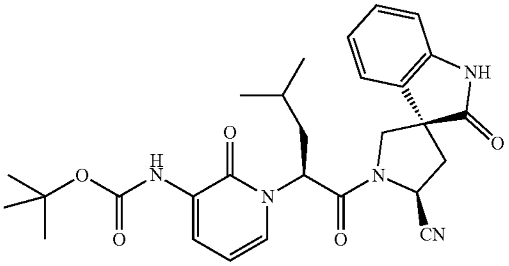 [SMILES: CC(C)C[C@@H](C(=O)N1C[C@]2(C[C@H]1C#N)C(=O)Nc1ccccc12)n1cccc(NC(=O)OC(C)(C)C)c1=O] |

-continued
| Compound | Structure |
|---|---|
| 355 | 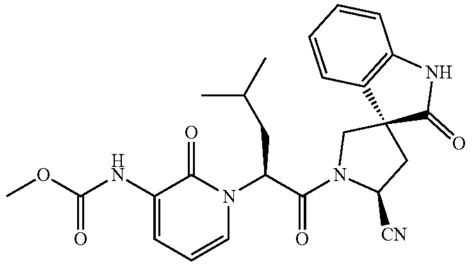 [SMILES: COC(=O)Nc1cccn([C@@H](CC(C)C)C(=O)N2C[C@]3(C[C@H]2C#N)C(=O)Nc2ccccc23)c1=O] |
| 356 | 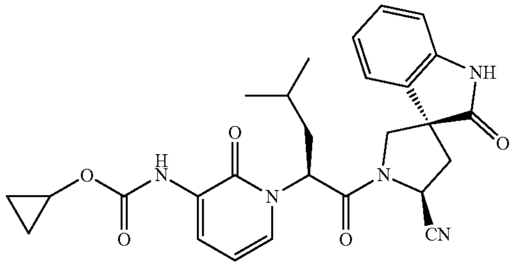 [SMILES: CC(C)C[C@@H](C(=O)N1C[C@]2(C[C@H]1C#N)C(=O)Nc1ccccc12)n1cccc(NC(=O)OC2CC2)c1=O] |
| 357 | 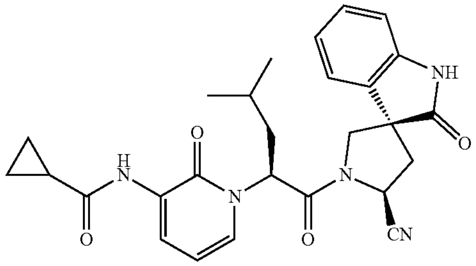 [SMILES: CC(C)C[C@@H](C(=O)N1C[C@]2(C[C@H]1C#N)C(=O)Nc1ccccc12)n1cccc(NC(=O)C2CC2)c1=O] |
| 358 | 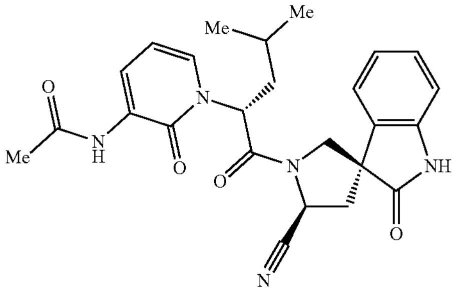 [SMILES: CC(=O)Nc1cccn([C@H](CC(C)C)C(=O)N2C[C@]3(C[C@H]2C#N)C(=O)Nc2ccccc23)c1=O] |
| 359 | 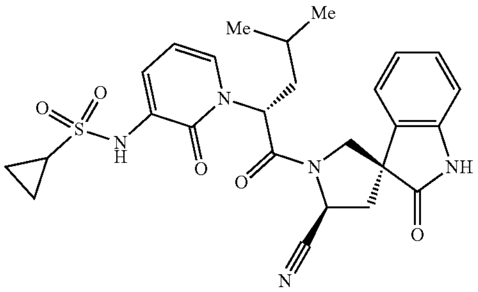 [SMILES: CC(C)C[C@H](C(=O)N1C[C@]2(C[C@H]1C#N)C(=O)Nc1ccccc12)n1cccc(NS(=O)(=O)C2CC2)c1=O] |

-continued
| Compound | Structure |
|---|---|
| 360 | 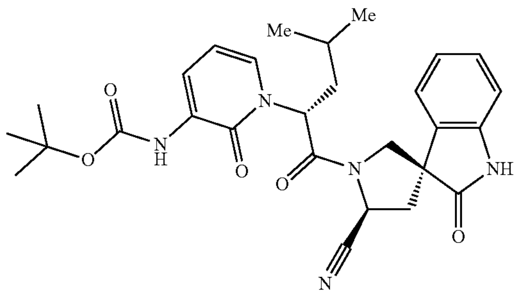 [SMILES: CC(C)C[C@H](C(=O)N1C[C@]2(C[C@H]1C#N)C(=O)Nc1ccccc12)n1cccc(NC(=O)OC(C)(C)C)c1=O] |
| 361 | 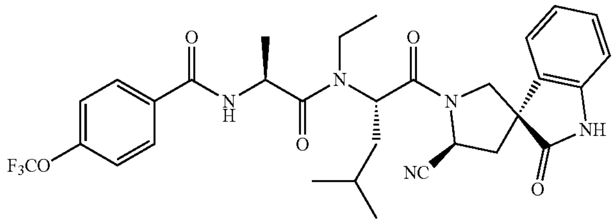 [SMILES: CCN(C(=O)[C@H](C)NC(=O)c1ccc(OC(F)(F)F)cc1)[C@@H](CC(C)C)C(=O)N1C[C@]2(C[C@H]1C#N)C(=O)Nc1ccccc12] |
| 362 | 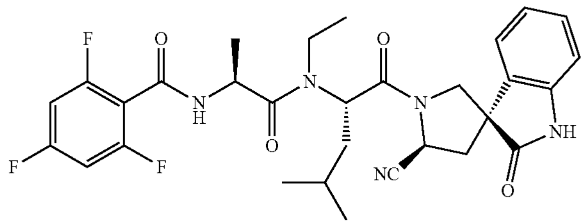 [SMILES: CCN(C(=O)[C@H](C)NC(=O)c1c(F)cc(F)cc1F)[C@@H](CC(C)C)C(=O)N1C[C@]2(C[C@H]1C#N)C(=O)Nc1ccccc12] |
| 363 | 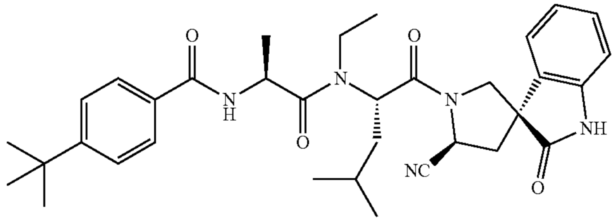 [SMILES: CCN(C(=O)[C@H](C)NC(=O)c1ccc(C(C)(C)C)cc1)[C@@H](CC(C)C)C(=O)N1C[C@]2(C[C@H]1C#N)C(=O)Nc1ccccc12] |
| 364 | 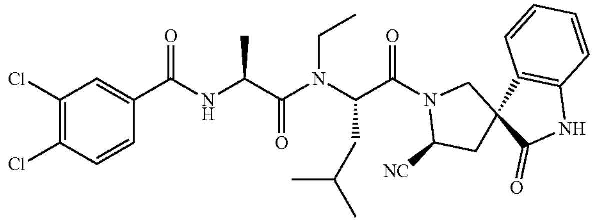 [SMILES: CCN(C(=O)[C@H](C)NC(=O)c1ccc(Cl)c(Cl)c1)[C@@H](CC(C)C)C(=O)N1C[C@]2(C[C@H]1C#N)C(=O)Nc1ccccc12] |
| 365 | 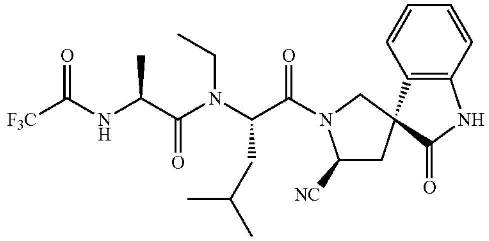 [SMILES: CCN(C(=O)[C@H](C)NC(=O)C(F)(F)F)[C@@H](CC(C)C)C(=O)N1C[C@]2(C[C@H]1C#N)C(=O)Nc1ccccc12] |

-continued
| Compound | Structure |
|---|---|
| 366 | 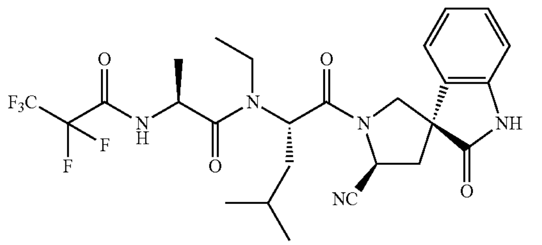 [SMILES: CCN(C(=O)[C@H](C)NC(=O)C(F)(F)C(F)(F)F)[C@@H](CC(C)C)C(=O)N1C[C@]2(C[C@H]1C#N)C(=O)Nc1ccccc12] |
| 367 | 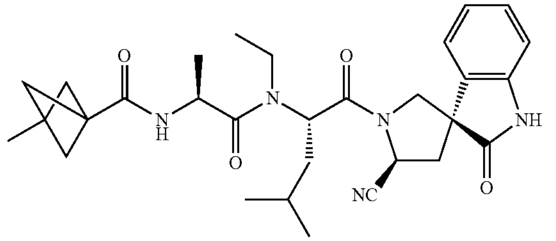 [SMILES: CCN(C(=O)[C@H](C)NC(=O)C12CCC(C)(C1)C2)[C@@H](CC(C)C)C(=O)N1C[C@]2(C[C@H]1C#N)C(=O)Nc1ccccc12] |
| 368 | 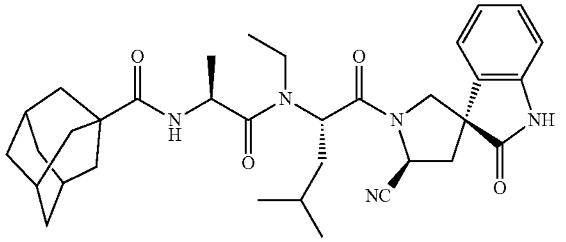 [SMILES: CCN(C(=O)[C@H](C)NC(=O)C12CC3CC(CC(C3)C1)C2)[C@@H](CC(C)C)C(=O)N1C[C@]2(C[C@H]1C#N)C(=O)Nc1ccccc12] |
| 369 | 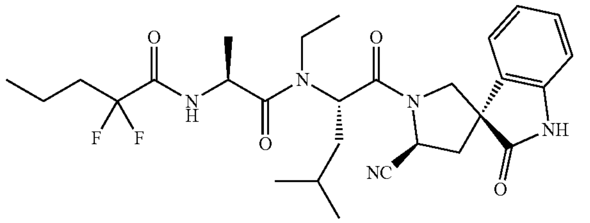 [SMILES: CCCC(F)(F)C(=O)N[C@@H](C)C(=O)N(CC)[C@@H](CC(C)C)C(=O)N1C[C@]2(C[C@H]1C#N)C(=O)Nc1ccccc12] |
| 370 | 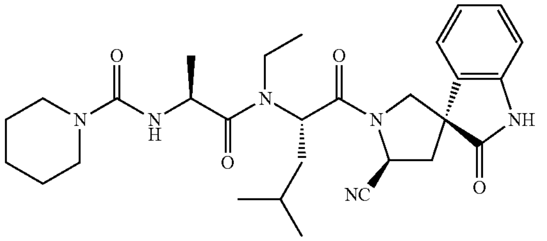 [SMILES: CCN(C(=O)[C@H](C)NC(=O)N1CCCCC1)[C@@H](CC(C)C)C(=O)N1C[C@]2(C[C@H]1C#N)C(=O)Nc1ccccc12] |
| 371 | 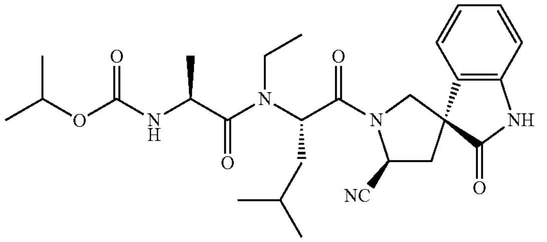 [SMILES: CCN(C(=O)[C@H](C)NC(=O)OC(C)C)[C@@H](CC(C)C)C(=O)N1C[C@]2(C[C@H]1C#N)C(=O)Nc1ccccc12] |

-continued
| Compound | Structure |
|---|---|
| 372 | 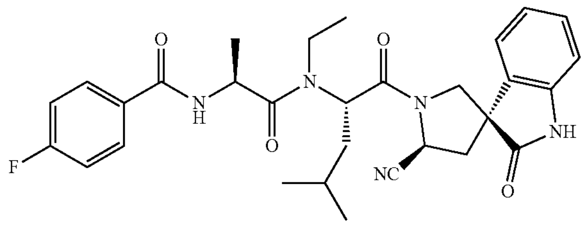 [SMILES: CCN(C(=O)[C@H](C)NC(=O)c1ccc(F)cc1)[C@@H](CC(C)C)C(=O)N1C[C@]2(C[C@H]1C#N)C(=O)Nc1ccccc12] |
| 373 | 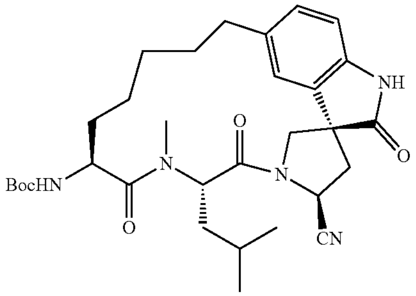 [SMILES: CC(C)C[C@H]1C(=O)N2C[C@]3(C[C@H]2C#N)C(=O)Nc2ccc(cc23)CCCCC[C@H](NC(=O)OC(C)(C)C)C(=O)N1C] |
| 374 | 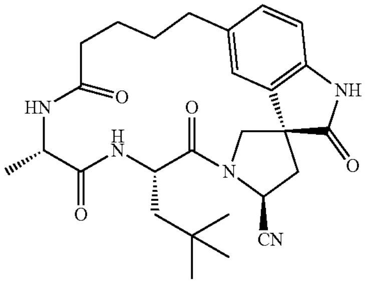 [SMILES: C[C@@H]1NC(=O)CCCCc2ccc3c(c2)[C@@]2(C[C@@H](C#N)N(C2)C(=O)[C@H](CC(C)(C)C)NC1=O)C(=O)N3] |
| 375 | 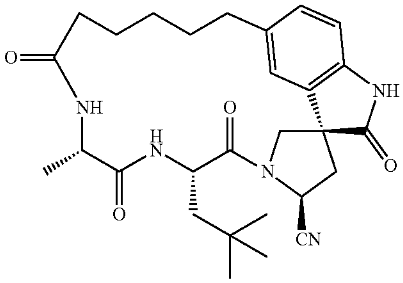 [SMILES: C[C@@H]1NC(=O)CCCCCc2ccc3c(c2)[C@@]2(C[C@@H](C#N)N(C2)C(=O)[C@H](CC(C)(C)C)NC1=O)C(=O)N3] |
| 376 | 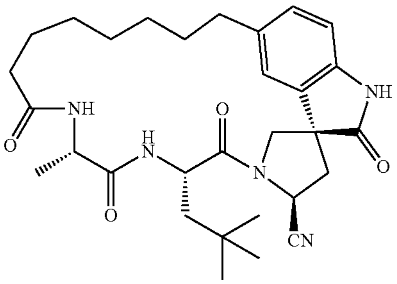 [SMILES: C[C@@H]1NC(=O)CCCCCCCc2ccc3c(c2)[C@@]2(C[C@@H](C#N)N(C2)C(=O)[C@H](CC(C)(C)C)NC1=O)C(=O)N3] |

-continued
| Compound | Structure |
| --- | --- |
| 377 | 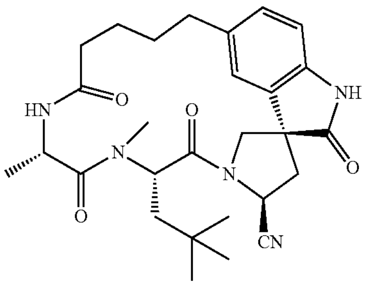 [SMILES: C[C@@H]1NC(=O)CCCCc2ccc3c(c2)[C@@]2(C[C@@H](C#N)N(C2)C(=O)[C@H](CC(C)(C)C)N(C)C1=O)C(=O)N3] |
| 378 | 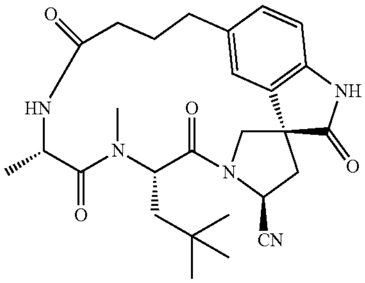 [SMILES: C[C@@H]1NC(=O)CCCc2ccc3c(c2)[C@@]2(C[C@@H](C#N)N(C2)C(=O)[C@H](CC(C)(C)C)N(C)C1=O)C(=O)N3] |
| 379 | 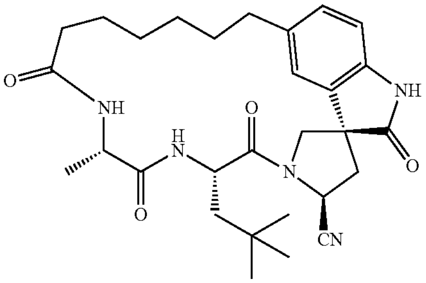 [SMILES: C[C@@H]1NC(=O)CCCCCCc2ccc3c(c2)[C@@]2(C[C@@H](C#N)N(C2)C(=O)[C@H](CC(C)(C)C)NC1=O)C(=O)N3] |
| 380 | 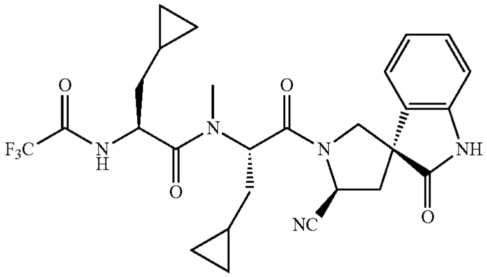 [SMILES: CN(C(=O)[C@H](CC1CC1)NC(=O)C(F)(F)F)[C@@H](CC1CC1)C(=O)N1C[C@]2(C[C@H]1C#N)C(=O)Nc1ccccc12] |
| 381 | 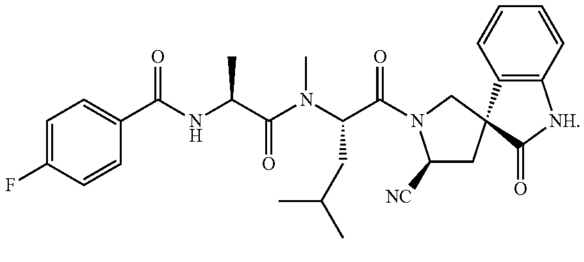 [SMILES: CC(C)C[C@@H](C(=O)N1C[C@]2(C[C@H]1C#N)C(=O)Nc1ccccc12)N(C)C(=O)[C@H](C)NC(=O)c1ccc(F)cc1] |

10. A pharmaceutical composition comprising a compound according to claim 1, or a pharmaceutically acceptable salt thereof, and a pharmaceutically acceptable carrier or excipient.

11. A method of treating or preventing a virus infection, wherein the virus is an RNA-based virus, a coronavirus, a rhinovirus or a norovirus, in a subject susceptible to or suffering from the virus infection, the method comprising administering to the subject an effective amount of a compound according to claim 1, or a pharmaceutically acceptable salt thereof.

12. A method of treating or preventing a coronavirus infection in a subject in need thereof, comprising administering to the subject a therapeutically effective amount of a compound according to claim 1, or a pharmaceutically acceptable salt thereof.

13. The method according to claim 12, wherein the coronavirus is a 229E, NL63, OC43, HKU1, SARS-CoV or MERS coronavirus.

14. A method of treating or preventing a virus infection in a subject susceptible to or suffering from the virus infection comprising administering to the subject an effective amount of a compound according to claim 1, or a pharmaceutically acceptable salt thereof.

15. A method of inhibiting viral 3C protease or viral 3CL protease in a subject, comprising administering to said subject an effective amount of a compound according to claim 1, or a pharmaceutically acceptable salt thereof.

16. A method of treating a respiratory disorder selected from the group consisting of acute asthma, lung disease secondary to environmental exposures, acute lung infection, and chronic lung infection in a subject in need thereof, comprising administering to the subject a therapeutically effective amount of a compound of claim 1, or a pharmaceutically acceptable salt thereof.

17. The method according to claim 12, wherein the compound or pharmaceutically acceptable salt thereof is administered orally, subcutaneously, intravenously or by inhalation.

18. The method according to claim 12, wherein the subject is a human.

19. The method of claim 12, wherein the coronavirus is SARS-CoV-2.

20. The compound of claim 9, wherein the compound is

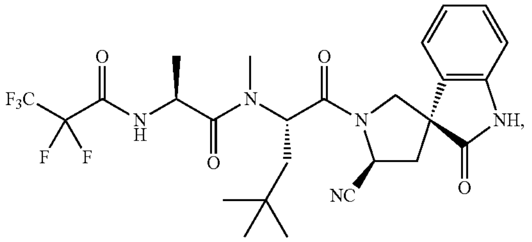 [SMILES: C[C@H](NC(=O)C(F)(F)C(F)(F)F)C(=O)N(C)[C@@H](CC(C)(C)C)C(=O)N1C[C@]2(C[C@H]1C#N)C(=O)Nc1ccccc12]

or a pharmaceutically acceptable salt thereof.

21. The compound of claim 9, wherein the compound is

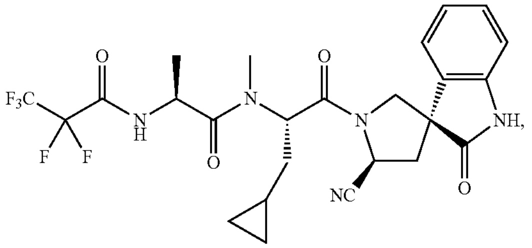 [SMILES: C[C@H](NC(=O)C(F)(F)C(F)(F)F)C(=O)N(C)[C@@H](CC1CC1)C(=O)N1C[C@]2(C[C@H]1C#N)C(=O)Nc1ccccc12]

or a pharmaceutically acceptable salt thereof.

22. The compound of claim 9, wherein the compound is

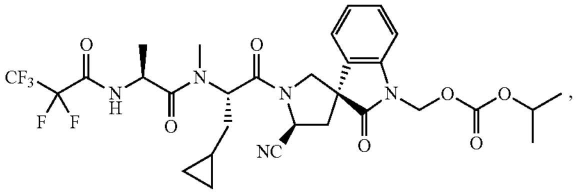 [SMILES: CC(C)OC(=O)OCN1C(=O)[C@]2(C[C@@H](C#N)N(C(=O)[C@H](CC3CC3)N(C)C(=O)[C@H](C)NC(=O)C(F)(F)C(F)(F)F)C2)c2ccccc21]

or a pharmaceutically acceptable salt thereof.

* * * * *